US012760030B2

(12) United States Patent
Mekonnen et al.

(10) Patent No.: US 12,760,030 B2
(45) Date of Patent: Oct. 13, 2026

(54) BENZAZEPINE DERIVATIVES, COMPOSITIONS, AND METHODS FOR TREATING COGNITIVE IMPAIRMENT

(71) Applicant: AGENEBIO, INC., Baltimore, MD (US)

(72) Inventors: Belew Mekonnen, Gilbertsville, PA (US); John A. Butera, Clarksburg, NJ (US); Jianxing Huang, Bethlehem, PA (US); Hemantbhai Patel, Piscataway, NJ (US)

(73) Assignee: AGENEBIO, INC., Baltimore, MD (US)

( * ) Notice: Subject to any disclaimer, the term of this patent is extended or adjusted under 35 U.S.C. 154(b) by 384 days.

(21) Appl. No.: 18/235,753

(22) Filed: Aug. 18, 2023

(65) Prior Publication Data

US 2024/0132513 A1 Apr. 25, 2024

Related U.S. Application Data

(60) Provisional application No. 63/399,509, filed on Aug. 19, 2022.

(51) Int. Cl.
*C07D 487/14* (2006.01)
*A61K 45/06* (2006.01)
(Continued)

(52) U.S. Cl.
CPC ............ *C07D 487/14* (2013.01); *A61K 45/06* (2013.01); *A61P 25/28* (2018.01); *C07D 413/14* (2013.01);
(Continued)

(58) Field of Classification Search
CPC .. C07D 487/14; C07D 413/14; C07D 487/04; C07D 498/14; C07D 519/00; A61K 45/06; A61P 25/28
See application file for complete search history.

(56) References Cited

U.S. PATENT DOCUMENTS

| | | |
|---|---|---|
| 3,391,142 A | 7/1968 | Mills |
| 3,539,573 A | 11/1970 | Schmutz |

(Continued)

FOREIGN PATENT DOCUMENTS

| | | |
|---|---|---|
| CA | 2817988 | 5/2012 |
| CN | 106068256 | 11/2016 |

(Continued)

OTHER PUBLICATIONS

Types of Isomers; Obtained from chem.libretexts.org [Retrieved on Nov. 2, 2025] <URL: https://chem.libretexts.org/Courses/Thompson_Rivers_University/CHEM_1500%3A_Chemical_Bonding_and_Organic_Chemistry/08%3A_Organic_Chemistry_II_-_Stereochemistry/8.01%3A_Types_of_Isomers>). (Year: 2025).*

(Continued)

*Primary Examiner* — Sarah Pihonak
*Assistant Examiner* — Jackson J Hernandez
(74) *Attorney, Agent, or Firm* — Leason Ellis LLP; Marcus J. Jellen; James F. Haley, Jr.

(57) ABSTRACT

Benzazepine derivatives, compositions comprising therapeutically effective amounts of those benzazepine derivatives and methods of using those derivatives or compositions in treating cognitive impairment associated with central nervous system (CNS) disorders or associated with risk factors for cognitive impairment. In particular, it relates to the use of a α5-containing $GABA_A$ R agonist (e.g., a α5-containing $GABA_A$ R positive allosteric modulator) in treating cognitive impairment associated with central nervous system (CNS) disorders or having a risk factor associated with cognitive impairment in a subject in need or at risk thereof, including, without limitation, subjects having or at risk for age-related cognitive impairment, Mild Cognitive Impairment (MCI), amnestic MCI (aMCI), Age-Associated Memory Impairment (AAMI), Age Related Cognitive
(Continued)

Figure 1:
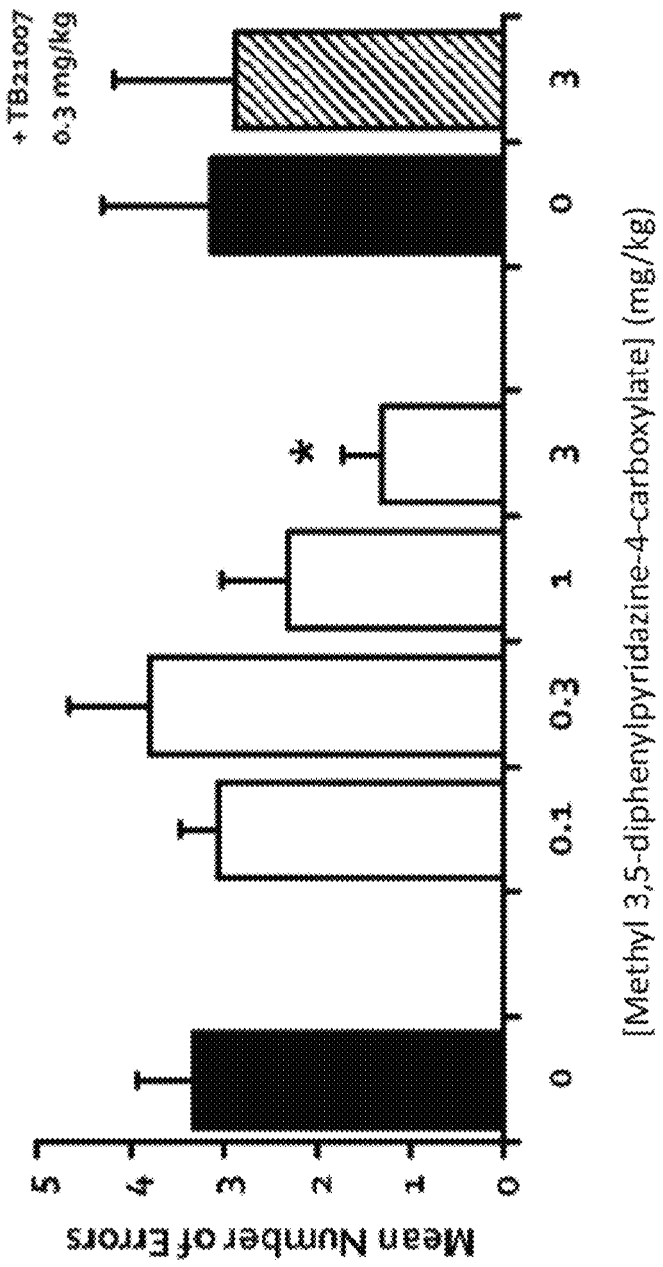

Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. It also relates to the use of a α5-containing $GABA_A$ R agonist (e.g., a α5-containing $GABA_A$ R positive allosteric modulator) as described herein in treating brain cancers (including brain tumors, e.g., medulloblastomas), and cognitive impairment associated therewith.

19 Claims, 10 Drawing Sheets

(51) Int. Cl.

| | |
|---|---|
| ***A61P 25/28*** | (2006.01) |
| ***C07D 413/14*** | (2006.01) |
| ***C07D 487/04*** | (2006.01) |
| ***C07D 498/14*** | (2006.01) |
| ***C07D 519/00*** | (2006.01) |

(52) U.S. Cl.
CPC ......... *C07D 487/04* (2013.01); *C07D 498/14* (2013.01); *C07D 519/00* (2013.01)

(56) References Cited

U.S. PATENT DOCUMENTS

| | | | |
|---|---|---|---|
| 4,122,193 | A | 10/1978 | Scherm |
| 4,145,434 | A | 3/1979 | Van Der Burg |
| 4,273,774 | A | 6/1981 | Scherm |
| 4,710,500 | A | 12/1987 | Perregaard |
| 4,734,416 | A | 3/1988 | Banno |
| 4,804,663 | A | 2/1989 | Kennis |
| 4,816,456 | A | 3/1989 | Summers |
| 4,831,031 | A | 5/1989 | Lowe, III |
| 4,879,288 | A | 11/1989 | Warawa |
| 4,895,841 | A | 1/1990 | Sugimoto |
| 5,006,528 | A | 4/1991 | Oshiro |
| 5,041,455 | A | 8/1991 | Sauerberg |
| 5,061,703 | A | 10/1991 | Bormann |
| 5,106,856 | A | 4/1992 | Kosley, Jr |
| 5,229,382 | A | 7/1993 | Chakrabarti |
| 5,312,925 | A | 5/1994 | Allen |
| 5,387,585 | A | 2/1995 | Borer |
| 5,500,438 | A | 3/1996 | Barnette |
| 5,532,372 | A | 7/1996 | Saji |
| 5,552,409 | A | 9/1996 | Michelotti |
| 5,602,176 | A | 2/1997 | Enz |
| 5,763,476 | A | 6/1998 | Delbressine |
| 6,677,330 | B1 | 1/2004 | Iimura |
| 6,689,816 | B2 | 2/2004 | Fogel |
| 6,743,789 | B2 | 6/2004 | Masciadri |
| 7,244,747 | B2 | 7/2007 | Kenda |
| 7,340,299 | B2 | 3/2008 | Puskas |
| 7,381,725 | B2 | 6/2008 | Fletcher |
| 7,432,256 | B2 | 10/2008 | Buettelmann |
| 7,498,361 | B2 | 3/2009 | Fogel |
| 7,507,728 | B2 | 3/2009 | Knust |
| 7,635,709 | B2 | 12/2009 | Korsten |
| 7,642,267 | B2 | 1/2010 | Li |
| 7,671,048 | B2 | 3/2010 | Knust |
| 8,058,268 | B2 | 11/2011 | Kovach |
| 8,510,055 | B2 | 8/2013 | Gallagher |
| 8,741,808 | B2 | 6/2014 | Li |
| 8,835,425 | B2 | 9/2014 | Gasser |
| 8,853,219 | B2 | 10/2014 | Hendrickson |
| 9,145,372 | B2 | 9/2015 | Lowe |
| 9,801,879 | B2 | 10/2017 | Lowe |
| 10,329,301 | B2 | 6/2019 | Mekonnen |
| 10,815,242 | B2 | 10/2020 | Mekonnen |
| 10,925,834 | B2 | 2/2021 | Gallagher |
| 11,142,529 | B2 | 10/2021 | Mekonnen |
| 11,312,721 | B2 | 4/2022 | MeKonnen |
| 11,414,425 | B2 | 8/2022 | Mekonnen et al. |
| 11,505,555 | B2 | 11/2022 | Mekonnen |
| 12,024,525 | B2 | 7/2024 | Mekonnen et al. |
| 2003/0125333 | A1 | 7/2003 | Bryant |
| 2004/0087658 | A1 | 5/2004 | Moebius |
| 2005/0113458 | A1 | 5/2005 | Gupta |
| 2006/0079507 | A1 | 4/2006 | Knust |
| 2006/0084642 | A1 | 4/2006 | Knust |
| 2006/0128691 | A1 | 6/2006 | Buettelmann |
| 2006/0167032 | A1 | 7/2006 | Galer |
| 2006/0205822 | A1 | 9/2006 | Jonas |
| 2006/0235021 | A1 | 10/2006 | Blackaby |
| 2007/0082890 | A1 | 4/2007 | Buettelmann |
| 2007/0112017 | A1 | 5/2007 | Barlow |
| 2008/0081832 | A1 | 4/2008 | Kenda |
| 2008/0269236 | A1 | 10/2008 | Ji |
| 2009/0081259 | A1 | 3/2009 | Jonas |
| 2009/0124659 | A1 | 5/2009 | Moebius |
| 2009/0143385 | A1 | 6/2009 | Buettelmann |
| 2010/0075954 | A1 | 3/2010 | Knust |
| 2010/0081648 | A1 | 4/2010 | Gallagher |
| 2010/0081723 | A1 | 4/2010 | Jonas |
| 2010/0099735 | A1 | 4/2010 | Gallagher |
| 2010/0227852 | A1 | 9/2010 | Moebius |
| 2011/0212928 | A1 | 9/2011 | Xia |
| 2012/0035139 | A9 | 2/2012 | Xu |
| 2012/0046336 | A1 | 2/2012 | Gallagher |
| 2012/0214859 | A1 | 8/2012 | Gallagher |
| 2013/0150351 | A1 | 6/2013 | Carmichael |
| 2013/0237530 | A1 | 9/2013 | Lowe |
| 2014/0057903 | A1 | 2/2014 | Gallagher |
| 2015/0374705 | A1 | 12/2015 | Zhang |
| 2016/0008357 | A1 | 1/2016 | Lowe |
| 2017/0022208 | A1 | 1/2017 | MeKonnen |
| 2018/0010183 | A1 | 1/2018 | Gallagher |
| 2018/0170941 | A1 | 6/2018 | MeKonnen |
| 2019/0055258 | A1 | 2/2019 | MeKonnen |
| 2019/0284196 | A1 | 9/2019 | MeKonnen |
| 2020/0048268 | A1 | 2/2020 | MeKonnen |
| 2021/0009602 | A1 | 1/2021 | MeKonnen |
| 2021/0253588 | A1 | 8/2021 | MeKonnen |
| 2022/0062296 | A1 | 3/2022 | Gallagher |
| 2022/0274996 | A1 | 9/2022 | Mekonnen |
| 2023/0098667 | A1 | 3/2023 | MeKonnen |
| 2023/0107032 | A1 | 4/2023 | MeKonnen |
| 2023/0134844 | A1 | 5/2023 | MeKonnen |
| 2023/0270753 | A1 | 8/2023 | Gallagher |
| 2023/0279021 | A1 | 9/2023 | Gandla |

FOREIGN PATENT DOCUMENTS

| | | |
|---|---|---|
| CN | 108567786 | 9/2018 |
| CN | 108567787 | 9/2018 |
| EP | 0368388 | 5/1990 |
| EP | 0402644 | 12/1990 |
| EP | 0468187 | 1/1992 |
| EP | 0481429 | 4/1992 |
| EP | 1682109 | 10/2008 |
| EP | 2260839 | 12/2010 |
| GB | 2352630 | 2/2001 |
| GB | 2352631 | 2/2001 |
| GB | 2352632 | 2/2001 |
| WO | WO199925353 | 5/1999 |
| WO | WO200027849 | 5/2000 |
| WO | WO200162726 | 8/2001 |
| WO | WO200232412 | 4/2002 |
| WO | WO200240487 | 5/2002 |
| WO | WO200269948 | 9/2002 |
| WO | WO200294834 | 11/2002 |
| WO | WO200325122 | 3/2003 |
| WO | WO2004014865 | 2/2004 |
| WO | WO2004014891 | 2/2004 |
| WO | WO2004048551 | 6/2004 |
| WO | WO2004087658 | 10/2004 |
| WO | WO2005079779 | 9/2005 |

(56) References Cited

FOREIGN PATENT DOCUMENTS

| | | |
|---|---|---|
| WO | WO2006045429 | 5/2006 |
| WO | WO2006063708 | 6/2006 |
| WO | WO2006128692 | 12/2006 |
| WO | WO2006128693 | 12/2006 |
| WO | WO2007018660 | 2/2007 |
| WO | WO2007019312 | 2/2007 |
| WO | WO2007042421 | 4/2007 |
| WO | WO2007065595 | 6/2007 |
| WO | WO2009071477 | 6/2009 |
| WO | WO2010036553 | 4/2010 |
| WO | WO2010044878 | 4/2010 |
| WO | WO2011100373 | 8/2011 |
| WO | WO2011153377 | 12/2011 |
| WO | WO2012059482 | 5/2012 |
| WO | WO2012068149 | 5/2012 |
| WO | WO2012068161 | 5/2012 |
| WO | WO2012109491 | 8/2012 |
| WO | WO2012161133 | 11/2012 |
| WO | WO2014144801 | 2/2014 |
| WO | WO2014039920 | 3/2014 |
| WO | WO2014078568 | 5/2014 |
| WO | WO2014144663 | 9/2014 |
| WO | WO2015095783 | 6/2015 |
| WO | WO2016191288 | 12/2016 |
| WO | WO2016205739 | 12/2016 |
| WO | WO2018130868 | 7/2018 |
| WO | WO2018130869 | 7/2018 |
| WO | WO2019246300 | 12/2019 |
| WO | WO2021127543 | 6/2021 |
| WO | WO2022011314 | 1/2022 |
| WO | WO2022011318 | 1/2022 |
| WO | WO200294787 | 11/2022 |

OTHER PUBLICATIONS

Black, "Flow Chart Determination of Isomer Relationships," Journal of Chemical Education, 67(2): 141-142 (1990).
Manoj et al., "Review of Brain and Brain Cancer Treatment," International Journal of Pharma and Bio Sciences, 2(1): p. 468-p. 477 (2011).
Abeu-Khalil, "Benefit-risk assessment of levetiracetam in the treatment of partial seizures," Drug Safety, 28(10):871-890 (2005).
Achermann et al., "Discovery of the imidazo[1,5-α][1,2,4]-triazolo[1,5-d][1,4] benzodiazepine scaffold as a novel, potent and selective $GABA_A$ α5 inverse agonist series," Aug. 2009, Bioorganic & Medicinal Chemistry Letters, vol. 19, pp. 5746-5752.
Adams et al., "Hippocampal dependent learning ability correlates with N-methyl-D-aspartate (NMDA) receptor levels in CA3 neurons of young and aged rats," The Journal of Comparative Neurology, 432:230-243 (2001).
Agam et al., "Levetiracetam does not interfere with attention to novel and targeted stimuli: An psychophysiological study," Neurology, 68(12), S1, p. 06.051 (2007) (Abstract).
Aisen et al., "Clinical core of the Alzheimer's Disease Neuroimaging Initiative: progress and plans," Alzheimers Dementia 6(3):239-246 (2010).
Akbarian et al., "Gene Expression for Glutamic Acid Decarboxylase is Reduced Without Loss of Neurons in Prefrontal Cortex of Schizophrenics," Archives of General Psychiatry, 52:258-266 (1995).
Alajarin et al., "A new modular and flexible approach to [1,2,3]triazolo[1,5-a][1,4]benzodiazepines," Tetrahedron Letters, 48(20):3495-3499 (2007).
Albert, "The ageing brain: normal and abnormal memory," Philosophical Transactions of the Royal Society B—Journals, 352:1703-1709 (1997).
Arcas et al., "Levetiracetaminn children and adolescents with refractory epilepsy: A clinical experience," Epilepsia, 47(S3):179 Absp696 (2006) (Abstract).
Ashe et al., "Probing the biology of Alzheimer's disease in mice," Neuron, 66(5): 631-645 (2010).
Auta et al., "Imidazenil: A Low Efficacy Agonist at al—but High Efficacy at a5-$GABA_A$ Receptors Fail to Show Anticonvulsant Cross Tolerance to Diazepam or Zolpidem," Neuropharmacology, 2008, 55(2): 148-153.
Bakker et al., "Pattern separation in the human hippocampal CA3 and dentate gyrus," Science, 319: 1640-1642 (2008).
Bakker et al., "Reduction of hippocampal hyperactivity improves cognition in amnestic mild cognitive impairment," Neuron, 74(3): 467-474 (2012).
Bakker et al., "Response of the medial temporal lobe network in amnestic mild cognitive impairment to therapeutic intervention assessed by fMRI and memory task performance," NeuroImage Clinical, 21(7):688-698 (2015).
Baldessarini et al., "Drugs and the Treatment of Psychiatric Disorders," (2001) Goodman & Gilman's The Pharmacological Basis of Therapeutics 10 Edition, 485-520.
Ballard et al., "RO4938581, a novel cognitive enhancer acting at $GABA_A$ α5 subunit-containing receptors," Psychopharmacology, 202:207-223 (2009).
Barker et al., "A Prevalence Study of Age-Associated Memory Impairment," British Journal of Psychiatry, 167:642-648 (1995).
Barnes et al., "Region-specific age effects on AMPA sensitivity: electrophysiological evidence for loss of synaptic contacts in hippocampal field CA1," Hippocampus, 2:457-468 (1992).
Bartus et al., "The cholinergic hypothesis of geriatric memory dysfunction," Science, 217:408-417 (1982).
Bassett et al., "Familial risk for Alzheimer's disease alters fMRI activation patterns," Brain, 129(5):1229-1239 (2006).
Baxter et al., "Neurobiological substrates of behavioral decline: models and data analytic strategies for individual differences in aging," Neurobiology of Aging, 17:491-495 (1996).
Becker et al., "Why Do So Many Drugs for Alzheimer's Disease Fail in Development? Time for New Methods and New Practices?" Journal of Alzheimer's Disease, 15(2):303-325 (2008).
Berezhnoy et al., "Pharmacological Properties of DOV 315,090, an ocinaplon metabolite," BMC Pharmacology, 8(11):1-10 (2008).
Berntsen, "The Unbidden Past: Involuntary Autobiographical Memories as a Basic Mode of Remembering," Current Directions in Psychological Science 19(3):138-142 (2010).
Berton et al., "Acamprosate Enhances N-Methyl-D-Apartate Receptor-Mediated Neurotransmission But Inhibits Presynaptic $GABA_B$ Receptors in Nucleus Accumbens Neurons," Alcohol, Clinical and Experimental Research, 22(1):183-191 (1998).
Betarbet et al., "Animal models of Parkinson's disease," BioEssays, 24:308-318 (2002).
Blalock et al., "Gene Microarrays in Hippocampal Aging: Statistical Profiling Identifies Novel Processes Correlated with Cognitive Impairment," Journal of Neuroscience, 23(9): 3807-3819 (2003).
Bontekoe et al., "Knockout mouse model for *Fxr2*: a model for mental retardation," Human Molecular Genetics, 11(5):487-498 (2002).
Bookheimer et al., "Patterns of Brain Activation in People at Risk for Alzheimer's Disease", New England Journal of Medicine, 343(7):450-456 (2000).
Bootsma et al., "The effect of antiepileptic drugs on cognition: patient perceived cognitive problem of topiramale versus leveliracetam in clinical practice," Epilepsia, 47(S2):24-27 (2006).
Brewer et al., "Optimized survival of hippocampal neurons in B27-supplemented Neurobasal, a new serum-free medium combination," Journal of Neuroscience Research, 35:567-576 (1993).
Brown et al., "Impact of levetiracetam on mood and cognition during prednisone therapy," European Psychiatry, 22(7):448-452 (2007).
Brunner et al., Neurocognitive effects of antiepileptic drugs frequently used in long term treatment of epilepsies: A review, Epileptologie, 25:118-130 (2008).
Buchanan et al., "The FDA-NIMH-MATRICS guidelines for clinical trial design of cognitive-enchanceing drugs: what do we know 5 years later?," Schizophrenia Bulletin, 37(6):1209-1217 (2011).
Buettelmann et al., "Imidazo[1,5-a][1,2,4]-triazolo[1,5-d][1,4]benzodiazepines as potent and highly selective GABAA

(56) References Cited

OTHER PUBLICATIONS alpha5 inverse agonists with potential for the treatment of cognitive dysfunction," Bioorganic & Medicinal Chemistry Letters, 19(20):5958-5961 (2009).
Busche et al., "Clusters of Hyperactive Neurons Near Amyloid Plaques in a Mouse Model of Alzheimer's Disease," Science, 321:1686-1689 (2008).
Buschke et al., "Evaluating storage, retention, and retrieval in disordered memory and learning," Neurology, 24:1019-1025 (1974).
Bustsamente et al., "A Modification of the Extended Hildebrand Approach to Predict the Solubility of Structurally Related Drugs in Solvent Mixtures," Journal of Pharmacy and Pharmacology, 45:253-257 (1993).
Carling et al., "7-(1,1-Dimethylethyl)-6-(2-ethy1-2H-1,2,4- triazol-3-ylmethoxy)-3-(2-fluoropheny1)-1,2,4-triazolo[4,3-b]pyridazine: A Functionally Selective γ-Aminobutyric Acid$_A$ (GABA$_A$) α2/α3-Subtype Selective Agonist That Exhibits Potent Anxiolytic Activity but Is Not Sedating in Animal Models", Journal of Medicinal Chemistry, 48(23): 7089-7092 (2005).
Celone et al., "Alterations in Memory Networks in Mild Cognitive Impairment and Alzheimer's Disease: An Independent Component Analysis," Journal of Neuroscience, 26(40): 10222-10231 (2006).
Chambers et al., "Identification of a novel, selective GABA$_A$ α5 receptor inverse agonist which enhances cognition," Journal of Medicinal Chemistry, 46:2227-2240 (2003).
Chambers, "An Orally Bioavailable, Functionally Selective Inverse Agonist at the Benzodiazepine Site of GABA$_A$ α5 Receptors with Cognition Enhancing Properties," Journal of Medicinal Chemistry, 47:5829-5832 (2004).
Chappell et al., "A re-examination of the role of basal forebrain cholinergic neurons in spatial working memory," Neuropharmacology, 37: 481-488 (1998).
Ciccocioppo et al., "Genetically selected Marchigian Sardinian alcohol-preferring (msP) rats; an animal model to study the neurobiology of alcoholism," Addiction Biology (2006), 11, 339-355.
Cicolin et al., "[Levetiracetam and cognitive functions: A single blind, crossover, placebo controlled study in healthy volunteers]," Bolletinno Lega Italiana contro I'Epilessia, No. 113-114:79-81 (2001) (English Abstract only).
Ciesielski et al., "Neuropsychological and psychiatric impact of add—On titration of pregabalin versus levetiracetam: a comparative short-term study," Epilepsy & Behavior, 9(3):424-431 (2006).
Ciesiel Ski et al., "Neuropsychological and psychiatric impact of add-on titration of pregabalin versus levetiracetam: A comparative short-term study," Epilepsia, 47(S3):135 (2006)(Abstract).
Colombo et al., "Spatial memory is related to hippocampal subcellular concentrations of calcium-dependent protein kinase C isoforms in young and aged rats," PNAS, 94:14195-14199 (1997).
Costa et al., "GABA$_A$ receptors and benzodiazepines: a role for dendritic resident subunit mRNAs," Neuropharmacology 43:925-937 (2002).
Crook et al., "Age-associated memory impairment: Proposed diagnostic criteria and measures of clinical change—report of a national institute of mental health work group," Developmental Neuropsychology, 2(4):261-276 (1986).
Cross et al., "Rules for the Nomenclature of Organic Chemistry: Section E: Stereochemistry," Pure and Applied Chemistry, 45:11-30 (1976).
Custer et al., "Synaptic vesicle protein 2 enhances release probability at quiescent synapses," Journal of Neuroscience, 26(4):1303-1313 (2006).
De Hoz et al., "Spatial learning with unilateral and bilateral hippocampal networks," European Journal of Neuroscience, 22(3):745-54 (2005).
De Smedt et al., "Levetiracetam: part II, the clinical profile of a novel anticonvulsant drug," CNS Drug Reviews, 13(1):57-78 (2007).
De Smedt et al., "Levetiracetam: the profile of a novel anticonvulsant dmg-part I: preclinical data," CNS Drug Review, 13(1):43-56 (2007).
Di Braccio et al., "1,5-Benzodiazepines XIV. Synthesis of new substituted 9H-bis-[1,2,4]triazolo[4,3-a:3',4'-d] [1,5]benzodiazepines and relate compounds endowed with in vitro cytotoxic properties," Farmaco, 60(2):113-125 (2005).
Dickerson et al. "Medial temporal lobe function and structure in mild cognitive impairment," Annals of Neurology, 56:27-35 (2004).
Dickerson et al., "Increased hippocampal activation in mild cognitive impairment compared to normal aging and AD," Neurology, 65: 404-411 (2005).
Dietrich et al., "Clinical Patterns and Biological Correlates of Cognitive Dysfunction Associated with Cancer Therapy," The Oncologist, 13:1285-1295 (2008).
Donald et al., "Application of a sequential multicomponent assembly process/huisgen cycloaddition strategy to the preparation of libraries of 1,2,3-triazole-fused 1,4-benzodiazepines," ACS Combinatorial Science, 14(2):135-143 (2012).
El Youssoufi et al., "Glycosylated benzocycloheptadipyrazoles: a new class of water-soluble heterocyclic compounds," Bulletin de la Societe Chimique de France, 134(6):571-581 (1997).
Ellison et al., "Beyond the "C" in MCI: Noncognitive Symptoms in Amnestic and Non-amnestic Mild Cognitive Impairment," CNS Spectrums, 13(1):66-72 (2008).
Enomoto et al., "Disruptions in spatial working memory, but not short-term memory, induced by repeated ketamine exposure," Progress in Neuro-Psychopharmacology & Biological Psychiatry, 33:668-675 (2009).
Essassi et al., "Research on 1,5-benzodiazepines. Synthesis of [4,3-a; 3,4-d]triazolo-1,5-benzodiazepines," Bulletin des Societes Chimiques Belges, 100(3):277-86 (1991).
Fauser et al., "Effect of levetiracetam in limbic encephalitis: A case report," Epilepsia, 44(S 8):111-112 p. 298 (2003) (Abstract).
Folstein et al., ""Mini-mental state". A practical method for grading the cognitive state of patients for the clinician," Journal of Psychiatric Research, 12(3):189-198 (1975).
Fritz et al., "Effects of add-on treatment with topiramate or levetiracetam on cognition and health related quality of life for patients with epilepsy," Epilepsia, 46(S6):106-107 (2005) (Abstract).
Fuks et al., "Localization and photoaffinity labelling of the levetiracetam binding site in rat brain and certain cell lines," European Journal of Pharmacology, 478(1):11-19 (2003).
Gallagher et al., "Severity of spatial learning impairment in aging: development of a learning index for performance in the Morris water maze," Behavioral Neuroscience, 107(4):618-626 (1993).
Gallagher et al., "Relationship of age-related decline across several behavioral domains," Neurobiology of Aging, 10:691-708 (1989).
Gallagher, "Animal models of memory impairment," Philosophical Transactions of the Royal Society B, 352:1711-1717 (1997).
Gaudenzi et al., "[Levetiracetam therapy in patients with epilepsy and dementia]," Bollettino—Lega Italiana contro l'Epilessia, 125-126:215-216 (2004) (English Abstract onlv).
Gerecke et al., "New tetracyclic Derivatives of Imidazo-[1,5-α] [1,4]benzodiazepines and of Imidazo[1,5-α]thieno[3,2-f][1,4]diazepines," Heterocycles, 39(2):693-721 *16/22 (1994).
Gharaghani et al., "A structure-based QSAR and docking study on imidazo[1,5-a][1,2,4]-triazolo[1,5-d][1,4,]benzodiazepines as Selective GABA(A) α5 inverse agonists," Chemical Biology & Drug Design, 78(4):612-621 (2011).
Gill et al., "A Novel α5GABA$_A$ R-Positive Allosteric Modulator Reverses Hyperactivation of the Dopamine System in the MAM Model of Schizophrenia," Neuropsychopharmacology , 36:1903-1911 (2011).
Gill et al., "The role of a5 GABAA receptor agonists in the treatment of cognitive deficits in schizophrenia," Current Pharmaceutical Design; 20(31):5069-5076 (2014).
Gillard et al., "Binding characteristics of levetiracetam to synaptic vesicle protein 2A (SV2A) in human brain and in CHO cells expressing the human recombinant protein," European Journal of Pharmacology, 536(1-2) : 102-108 (2006).
Giusti et al., "Imidazenil: A New Partial Positive Allosteric Modulator of γ-Aminobutyric Acid (GABA) Action at GABA$_A$ Receptors[1]," The Journal of Pharmacology and Experimental Therapeutics, 266(2):1018-1028 (1993).

(56) References Cited

OTHER PUBLICATIONS

Goldin et al., "Maintenance of Xenopus laevis and Oocyte Injection," Methods in Enzymology, 207:266-279 (1992).
Goodacre et al., "Imidazo[1,2-α]pyrimidines as Functionally Selective and Orally Bioavailable $GABAA_A\alpha2/\alpha3$ Binding Site Agonists for the Treatment of Anxiety Disorders," Journal of Medicinal Chemistry, 49:35-38 (2006).
Gotz et al., "Animal models of Alzheimer's disease and frontotemporal dementia," Nature Review, 9:532-544 (2008).
Gourevitch et al., "Working memory deficits in adult rats after prenatal disruption of neurogenesis," Behavioral Pharmacology, 15:287-292 (2004).
Grauer et al., "WAY-163909, a 5-HT2C agonist, enhances the preclinical potency of current antipsychotics," Psychopharmacology, 204(1):37-48 (2004).
Guido et al., "Event-related potentials (ERPs) in the evaluation of the effect of levetiracetam and carbamazepine on cognitive functions in adult patients with newly diagnosed epilepsy," European Journal of Neurology, 15(S3):305 (2008) (Abstract).
Guidotti et al., "GABAergic dysfunction in schizophrenia: new treatment strategies on the horizon," Psychopharmacology, 180:191-205 (2005).
Guo et al., "Effects of levetiracetam on quality of life in children with refractory epilepsy," Changjiang Daxue Xuebao, Ziran Kexueban, 8(1):151-155 (2011) (English Abstract only).
Haberman et al., "Rapid encoding of new information alters the profile of plasticity-related mRNA transcripts in the hippocampal CA3 region," PNAS, 105(30): 10601-10606 (2008).
Harvey et al., "Stress-restress evokes sustained iNOS activity and altered GABA levels and NMDA receptors in rat hippocampus," Psychopharmacology, 175: 494-502 (2004).
Hashimoto et al., "Alterations in GABA-related transcriptome in the dorsolateral prefrontal cortex of subjects with schizophrenia," Molecular Psychiatry, 13: 147-161 (2008).
Hashimoto et al., "Gene Expression Deficits in a Subclass of GABA Neurons in the Prefrontal Cortex of Subjects with Schizophrenia," Journal of Neuroscience, 23(15):6315-6326 (2003).
Helm et al., "GABAB receptor antagonist SGS742 improves spatial memory and reduces protein binding to the cAMP response element (CRE) in the hippocampus," Neuropharmacology, 48: 956-964 (2005).
Helmstaedter, "'Real life' cohort study on levetiracetam versus carbamazepine monotherapy: a controlled surveillance study," Epilepsia, 50(S10): 100, p. 465 (2009) (Abstract).
Herholz et al., "Discrimination between Alzheimer Dementia and Controls by Automated Analysis of Multicenter FDG PET," NeuroImage, 17:302-316 (2002).
Hill et al., "First Occurrence of Hippocampal Spatial Firing in a New Environment," Experimental Neurology, 62: 282-297 (1978).
Hines et al., "Functional regulation of GABAA receptors in nervous system pathologies," Current Opinion in Neurobiology, 22(3):552-558 (2012).
Huang et al., "Comparative cognitive effects of levetiracetam and topiramate in intractable epilepsy," Psychiatry and Clinical Neurosciences, 62(5):548-553 (2008).
Hughes et al., "Physiochemical drug properties associated with in vivo toxicological outcomes," Bioorganic & Medicinal Chemistry Letters, 18: 4872-4875 (2008).
Hussain et al., "Tandem C-2 Functionalization-Intramolecular Azide-Alkyne 1,3-Dipolar Cycloaddition Reaction: A Convenient Route to Highly Diversified 9H-Benzo[b]pyrrolo[1,2-g]triazolo[1,5-d][1,4]diazepines," Organic Letters, 16:560-563 (2014).
Jarrard, "On the role of the hippocampus in learning and memory in the rat," Behavioral and Neural Biology, 60(1):9-26 (1993).
Jonas et al., "First In Vivo Testing of Compounds Targeting Group 3 Medulloblastomas Using an Implantable Microdevice as a New Paradigm for Drug Development," Journal of Biomedical Nanotechnology, 12(6):1297-302 (2016).
Kamenetz et al. "APP processing and synaptic function," Neuron, 37: 925-37 (2003).
Kauer et al., "Synaptic plasticity and addiction," Nature. Reviews Neuroscience, 8:844-858 (2007).
Khan et al., "Topiramate attenuates exaggerated acoustic startle in an animal model of PTSD," Psychopharmacology 172(2):225-229 (2004).
Kim et al. "Transient Impairment of Hippocampus-dependent Learning and Memory in Relatively Low-Dose of Acute Radiation Syndrome is Associated with Inhibition of Hippocampal Neurogenesis," Journal of Radiation Research, 49:517-526 (2008).
Kluger et al., "Neuropsychological prediction of decline to dementia in nondemented elderly," Journal of Geriatric Psychiatry and Neurology, 12(4):168-79 (1999).
Knust et al., "The discovery and unique pharmacological profile of RO4938581 and RO4882224 as potent and selective GABAA alpha5 inverse agonists for the treatment of cognitive dysfunction," Bioorganic & Medicinal Chemistry Letters, 19(20):5940-5944 (2009).
Kobayashi et al., "Behavioral phenotypes of amyloid-based genetically modified mouse models of Alzheimer's disease," Genes, Brain, and Behavior, 4(3):173-196 (2005).
Koh et al., "664.17/YY12-BPN-27473: a novel GABAaa5 positive allosteric modulator that improves memory performance of rats with conditions of hippocampal hyperactivity," Neuorscience, 2022 (https://www.abstractsonline.com/pp8/#!/10619/presentation/79719) (2 pages).
Koh et al., "Selective GABA(A) a5 positive allosteric modulators improve cognitive function in aged rats with memory impairment," Neuropharmacology, 64(1):145-52. (2013).
Koh et al., "Treatment with selective $GABA_A$ α5 receptor agonists improves cognitive function in aged rats with memory impairment," Society for Neuroscience meeting, Handout, 1 page (Nov. 16, 2010).
Korakas et al., "Synthesis of novel pyrrolo[2,1-d][1,2,5]benzotriazepine, pyrrolo[2,1-e] [1,3,6] benzotriazocine and pyrrolo[1,2-a]tetrazolo[1,5-d][1,4] benzodiazepine ring systems. A new route to pyrrolo[1,2-a]quinoxaline via transamination of in situ generated 1-(2-aminophenyl)-2-iminomethylpyrroles," Tetrahedron, 52(32):10751-10760 (1996).
Larrabee, "Age-Associated Memory Impairment: Definition and psychometric characteristics," Aging, Neuropsychology, and Cognition, 3(2):118-131 (1996).
Lee et al., "Levetiracetam inhibits glutamate transmission through presynaptic P/Q-type calcium channels on the granule cells of the dentate gyms," British Journal of Pharmacology, 158:1753-1762 (2009).
Lein et al., "Defining a molecular atlas of the hippocampus using DNA microarrays and high-throughput in situ hybridization," Journal of Neuroscience, 24(15):3879-3889 (2004).
Leppik et al., "Extended-release antiepileptic drugs: a comparison of phannacokinetic parameters relative to original immediate-release formulations," Epilepsia, 54(1):28-35 (2013).
Leutgeb et al., "Independent Codes for Spatial and Episodic Memory in Hippocampal Neuronal Ensembles," Science, 309: 619-623 (2005).
Leutgeb et al., "Pattern Separation in the Dentate Gyrus and CA3 of the Hippocampus," Science, 315: 961-966 (2007).
Levetiracetam, American Journal of Health-System Pharmacy, AHFS for FAX mew drug review, vol. 57, p. 1484 (Aug. 15, 2000).
Liberzon et al., "Stress-Restress: Effects on ACTH and Fast Feedback," Psychoneuroendocrinology, 22(6):443-453 (1997).
Lingford-Hughes et al., "Imaging the GABA-Benzodiazepine Receptor Subtype Containing the a5-Subunit In Vivo With [11C]Ro15 4513 Positron Emission Tomography," Journal of Cerebral Blood Flow & Metabolism, 22(7): 878-889 (2002).
Lippa et al., "Selective anxiolysis produced by ocinaplon, a $GABA_A$ receptor modulator," PNAS, 102(20):7380-7385 (2005).
Liu et al., "Synthesis and Pharmacological Properties of Novel 8-Substituted Imidazobenzodiazepines: High-Affinity, Selective Probes for α5-Containing $GABA_A$ Receptors[1]," Journal of Medicinal Chemistry, 39:1928-1934 (1996).
Lodge et al., "A Loss of Parvalbumin-Containing Interneurons is Associated with Diminished Oscillatory Activity in an Animal Model of Schizophrenia," Journal of Neuroscience, 29(8):2344-2354 (2009).

(56) References Cited

OTHER PUBLICATIONS

Lodge et al., "Aberrant Hippocampal Activity Underlies the Dopamine Dysregulation in an Animal Model of Schizophrenia," Journal of Neuroscience, 27(42):11424-11430 (2007).
Loscher et al., "Profile of UCB L059, a novel anticonvulsant drug, in models of partial and generalized epilepsy in mice and rats," European Journal of Pharmacology, 232(2-3): 147-158 (1993).
Luciano et al., "Results of treatment changes in patients with apparently drug-resistant chronic epilepsy," Annals of Neurology, 62(4):375-381 (2007).
Lukyanetz et al., "Selective blockade of N-type calcium channels by levetiracetam," Epilepsia, 43(1):9-18 (2002).
Lupien et al., "Effects of stress throughout the lifespan on the brain, behaviour and cognition," Nature Review/Neuroscience, 10:434-445 (2009).
Lynch et al., "The synaptic vesicle protein SV2A is the binding site for the antiepileptic drug levetiracetam," PNAS, 101(26):9861-9866 (2004).
Maeda et al., "Visualization of $\alpha$5 Subunit of $GABA_A$/ Benzodiazepine Receptor by [$^{11}$C]Ro15-4513 Using Positron Emission Tomography," Synapse, 47: 200-208 (2003).
Marquis et al., "Independent predictors of cognitive decline in healthy elderly persons," Archives of Neurology, 59:601-606 (2002).
Masur et al., "Neuropsychological prediction of dementia and the absence of dementia in healthy elderly persons," Neurology, 44:1427-1432 (1994).
Meador et al., "Cognitive and behavioral effects of carbamazepine and levetiracetam in healthy volunteers: S09.002: 2:15 pm," Neurology, 66(S2) P. A72 (2006) (Abstract).
Meador et al., "Neurocognitive effects of brivaracetam, levetiracetam, and lorazepam," Epilepsia, 52(2):264-272 (2011).
Meador, "Cognitive effects of levetiracetam versus topiramate," Epilepsy Currents, 8(3):64-65 (2008).
Mecarelli et al., "Clinical cognitive, and neurophysiologic correlates of short-term treatment with carbamazepine, oxcarbazepine, and levetiracetam in healthy volunteers," Annual Pharmacotherapy, 38(11):1816-1822 (2004).
Medical College of Wiscnsin, "Network-Level Mechanisms for Preclinical Alzheimer's Disease Development," Clinicaltrials.gov, NCT03461861 version 13, retrieved from https://clinicaltrials.gov/ct2/show/NCT03461861?V 13, Mar. 12, 2018 (9 pages).
Meehan et al.; Levetiracetam has an activity-dependent effect on inhibitory transmission.; Epilepsia, 53(3):469-476 (2012).
Meguro, "Subjective Memory Complaints are not Sine Qua Non as Diagnostic Criteria for MCI: the Tajiri Project," Acta Neurologica Taiwanica, 15(1):55-57 (2006).
Mendez et al., "The brain GABA-benzodiazepine receptor alpha-5 subtype in autism spectrum disorder: A pilot [11C]Ro15-4513 position emission tomography study," Neuropharmacology, 68:195-201 (2013).
Meo et al., "Use of levetiracetam monotherapy in patients with post-traumatic epilepsy: Preliminary data," Epilepsia, 47(S4):162, p. 2135 (2006) (Abstract).
Meyers et al., "Neurocognitive Function," Symptoms Secondary to Cancer and its Treatment, pp. 557-571 (2002).
Miller et al., "Hippocampal activation in adults with mild cognitive impairment predicts subsequent cognitive decline," Journal of Neurology, Neurosurgery, and Psychiatry, 79: 630-635 (2008).
Mirza et al., "NS11394 [3'-[5-(1-hydroxy-1-methyl-ethyl)-benzoimidazol-1-y1]-bipheny1-2-carbonitrile], a unique subtype-selective $GABA_A$ receptor positive allosteric modulator: in vitro actions, pharmacokinetic properties and in vivo anxiolytic efficacy," Journal of Pharmacology and Experimental Therapeutics, 327(3): 954-68 (2008).
Mondadori et al., "Enhanced brain activity may precede the diagnosis of Alzheimer's disease by 30 years," Brain, 129:2908-22 (2006).
Mondadori et al., "The Effects of Nootropics on Memory: New Aspects for Basic Research," Pharmacopsychiatry, 22(S 2):102-106 (1989).
Morris, "Spatial Localization Does Not Require the Presence of Local Cues," Learning and Motivation 12:239-260 (1981).
Munro et al., "Comparison of the Novel Subtype-Selective $GABA_A$ Receptor-Positive Allosteric Modulator NS11394 [3'-[5-(1-Hydroxy-1-methyl-ethyl)-benzoimidazol-1-y1]- bipheny1-2-carbonitrile] with Diazepam, Zolpidem, Bretazenil, and Gaboxadol in Rat Models of Inflammatory and Neuropathic Pain," Journal of Pharmacology and Experimental Therapeutics, 327(3): 969-81 (2008).
Muscas et al., "[Efficacy and tolerability of Levetiracetam in epileptic patients with acquired progressive cognitive impairment]," Bollettino—Lega Italiana contro I'Epilessia, 129-130:233-234 (2005) (full text English translation).
Nguyen et al., "Facile one-pot assembly of imidazotriazolobenzodiazepines via indium(III)-catalyzed multicomponent reactions," Organic Letters, 15(17):4492-4495 (2013).
Nicholson, "Pharmacology of nootropics and metabolically active compounds in relation to their use in dementia," Psychopharmacology, 101(No. 2):147-159 (1990).
Nicolle et al., "In Vitro Autoradiography of lonolropic Glutamate Receptors In Hippocampus and Striatum of Aged Long-Evans Rais: Relationship to Spatial Learning," Neuroscience, 74(3):741-756 (1996).
Nicolle et al.," Metabotropic Glutamate Receptor-Mediated Hippocampal Phosphoinositide Turnover is Blunted in Spatial Learning-Impaired Aged Rats," Journal of Neuroscience, 19(21):9604-9610 (1999).
Nishio et al., "A Mouse Model Characterizing Features of Vascular Dementia With Hippocampal Atrophy," Stroke, 41:1278-84 (2010).
Noyer et al., "The novel antiepileptic drug levetiracetam (UCB L059) appears to act via a specific binding site in CNS membranes," European Journal of Pharmacology, 286:137-146 (1995).
Nyberg, "Cognitive Impairments in Drug Addicts," Chapter 9 from the book Brain Damage—Bridging Between Basic Research and Clinics, 221-245 (2012).
Oler et al., "Age-Related Deficits in the Ability to Encode Contextual Change: A Place Cell Analysis," Hippocampus, 10:338-350 (2000).
Owens et al., "Alternative Routes of Insulin Delivery," Diabetic Medicine, 20:886-898 (2003).
Palop et al., "Aberrant excitatory neuronal activity and compensatory remodeling of inhibitory hippocampal circuits in mouse models of Alzheimer's disease," Neuron, 55:697-711 (2007).
Patani et al., "Bioisosterism: A Rational Approach in Drug Design," Chemical Reviews, 96:3147-3176 (1996).
Patsalos, "Clinical pharmacokinetics of levetiracetam," Clinical Pharmacokinetics, 43(11):707-724 (2004).
Pepeu et al., "Mild cognitive impairment: animal models," Dialogues in Clinical Neuroscience, 6(4):369-77 (2004).
Petersen et al., "Mild cognitive impairment: clinical characterization and outcome," Archives of Neurology, 56:303-308 (1999).
Petersen, "Mild Cognitive Impairment: Current Research and Clinical Implications," Seminars in Neurology, 27(1): 22-31 (2007).
Peterson et al., "Mild Cognitive Impairment: An Overview," CNS Spectrums, 13(1):45-53 (2008).
Plassman et al., "Prevalence of cognitive impairment without dementia in the United States," Annals of Internal Medicine, 148(6):427-434 (2008).
Platt et al., "Contribution of $\alpha_1 GABA_A$ and $\alpha_5 GABA_A$ receptor subtypes to the discriminative stimulus effects of ethanol in squirrel monkeys," Journal of Pharmacology and Experimental Therapeutics, 313(2):658-667 (2005).
Poschel et al., "Pharmacologic therapeutic window of pramiracetam demonstrated in behavior, EEG, and single neuron firing rates," Experientia, 41(9):1153-1156 (1985).
Pugsley et al., "Some neurochemical properties of pramiracetam (CI-879) a new cognition enhancing agent," Drug Development Research, 3(5):407-420 (1983).
Pym et al., "Selective labelling of diazepam-insensitive $GABA_A$ receptors in vivo using [$^3$H]Ro 15-4513," British Journal of Pharmacology, 146: 817-825 (2005).
Qin et al., "Evaluation of methods for oligonucleotide array data via quantitative real-time PCR," BMC Bioinformatics, 7:23: 1-12 (2006).

(56) References Cited

OTHER PUBLICATIONS

Rapp et al., "Preserved neuron number in the hippocampus of aged rats with spatial learning deficits," PNAS, 93:9926-9930 (1996).
Rapp et al., "An Evaluation of Spatial Information Processing in Aged Rats," Behavioral Neuroscience, 101(1):3-12 (1987).
Rapp et al., "Memory systems in normal and pathological aging," Current Opinion in Neurology, 7:294-298 (1994).
Reilly et al., "Effects of Acamprosate on Neuronal Receptors and Ion Channels Expressed in Xenopus Oocytes," Alcoholism: Clinical and Experimental Research, 32(2):188-196 (2008).
Ried et al., "Syntheses of new 1,3-diazepines," Chemiker-Zeitung, 111(5):179-180 (1987).
Rinaldi et al., "Hyper-connectivity and hyper-plasticity in the medial prefrontal cortex in the valproic acid animal model of autism," Frontiers in Neural Circuits, 2:1-7 (2008).
Robbins et al., "Cambridge Neuropsychological Test Automated Battery (CANTAB): a factor analytic study of a large sample of normal elderly volunteers," Dementia, 5:266-281 (1994).
Rodier et al., "Linking etiologies in humans and animal models: studies of autism," Reproductive Toxicology, 11:417-422 (1997).
Ronald et al., "Mild cognitive impairment: Aging to Alzheimer's Disease," New England Journal of Medicine, 349(14):1393 (2003) (1 page).
Rosche et al. "Different cognitive effects of inducing levetiracetam or topiramate into an antiepileptic pharmacotherapy in patients with therapy refractory epilepsy," Neurology, Psychiatry and Brain Research, 11:109-114 (2004).
Rosenzweig-Lipson et al., "Antidepressant-like effects of the novel, selective, 5-$HT_{2C}$ receptor agonist WAY-163909 in rodents," Psychopharmacology, 192:159-170 (2007).
Rozzini et al., "Treatment of cognitive impairment secondary to degenerative dementia. Effectiveness of oxiracetam therapy," Acta. Neurologica. (Napoli), 15(1):44-52 (1993).
Rudakova et al., "Levetiracetam (keppra) in the treatment of different epileptic syndromes in adults," Zhumal nevrologii i psikhiatrii imeni S.S. Korsakova / Ministerstvo zdravookhraneniia i meditsinskoi promyshlennosti Rossiiskoi Federatsii, Vserossiiskoe obshchestvo nevrologov [ii Vserossiiskoe obshchestvo psikhiatrov, 109(10):25-29 (2009) (English Abstract only).
Ryzhkov, "Advantages of levetiracetam as monotherapy in treating epileptic syndromes of early childhood, characterized by psychological disorders," European Journal of Neurology, 14(S1):90, p. 1224 (2007) (Abstract).
Sankaranarayanan, "Genetically modified mice models for Alzheimer's disease," Current Topics in Medicinal Chemistry, 6(6):609-27 (2006).
Schneider et al., "Validity and reliability of the Alzheimer's Disease Cooperative Study—Clinical Global Impression of Change," The Alzheimer's Disease Cooperative Study, Alzheimer Disease and Associated Disorders, 11 SuDDL 2:S22-S32 (1997).
Schoenberg et al., "Results of a randomized double-blind placebo controlled cross-over study of the cognitive and mood effects of levetiracetam in healthy older adults," Epilepsia, 48(S6):339, p. 3.246 (2007) (Abstract).
Schoenberg, "A randomized, double-blind, placebo-controlled cross-over study of the effects of levetiracetam on cognition, mood, and balance in healthy older adults", Epilepsia, 58:(9) 1566-1574 (2017).
Sengupta et al., "α5-GABAA receptors negatively regulate MYC-amplified medulloblastoma growth.," Acta Neuropathologica, 127(4): 593-603 (2014).
Shorvon, "Pyrrolidone derivatives," Lancet, 358(9296):1885-1892 (2001).
Sil Verman et al., "Negative Allosteric Modulation of the mGluR5 Receptor Reduces Repetitive Behaviors and Rescues Social Deficits in Mouse Models of Autism," Science Translational Medicine, 4(131):1-9 (2012).
Small et al., "Imaging correlates of brain function in monkeys and rats isolates a hippocampal subregion differentially vulnerable to aging," PNAS, 101(18):7181-7186 (2004).
Smith et al., "Age-Associated Memory Impairment Diagnoses: Problems of Reliability and Concerns for Terminology," Psychology and Aging, 6(4):551-558 (1991).
Smith et al., "Circuit-specific alterations in hippocampal synaptophysin immunoreactivity predict spatial learning impairment in aged rats," Journal of Neuroscience, 20(17):6587-6593 (2000).
Soussain et al., "CNS complications of radiotherapy and chemotherapy," Lancet, 374:1639-51 (2009).
Specchio et al., "Event-related potentials (erps) in the evaluation of the effect of levetiracetam and carbamazepine on cognitive functions in adult newly diagnosed epileptic patients. preliminary results of a randomized open trial," Epilepsia, 50(54):98, T189 (2009) (Abstract).
Steele et al., "Delay-Dependent Impairment of a Matching-to-Place Task With Chronic and Intrahippocampal Infusion of the NMDA-Antagonist D-AP5," Hippocampus 9(2):118-36 (1999).
Sternfeld et al., "Selective, orally active γ-aminobutyric $acid_A$ α5 receptor inverse agonists as cognition enhancers," Journal of Medicinal Chemistry, 47:2176-2179 (2004).
Sur et al., "Rat and Human Hippocampal α5 Subunit-Containing γ-Aminobutyric $Acid_A$ Receptors Have α5β3γ2 Pharmacological Characteristics." Molecular Pharmacology, 54: 928-933 (1998).
Szekeres et al., "3,4-Dihydronaphthalen-1(2H)-ones: novel ligands for the benzodiazepine site of α5-containing $GABA_A$ receptors," Bioorganic & Medicinal Chemistry Letters, 14:2871-2875 (2004).
Tanila et al., "Discordance of Spatial Representation in Ensembles of Hippocampal Place Cells," Hippocampus, 7: 613-623 (1997).
Thomaes et al., "Increased activation of the left hippocampus region in Complex PTSD during encoding and recognition of emotional words: A pilot study," Psychiatry Research: Neuroimaging, 171:44-53 (2009).
Tozzi et al., "[Levetiracetam in children and adolescents: Generalised vs partial seizures]," Bollellino-Lega Italiana contro l'Epilessia, 133-134:257-258 (2006) (English Abstract only).
Tremolizzo et al., "An epigenetic mouse model for molecular and behavioral neuropathologies related to schizophrenia vulnerability," PNAS, 99(26):17095-17100 (2002).
Van Niel et al., "A New Pyridazine Series of $GABA_A$ α5 Ligands," Journal of Medicinal Chemistry, 48:6004-6011 (2005).
Van Spronsen et al., "Synapse Pathology in Psychiatric and Neurologic Disease," Current Neurology and Neuroscience Reports, 10(3):207-214 (2010).
Vecht et al., "Seizures in low- and high-grade gliomas: current management and future outlook," Expert Review Anticancer Therapy, 10(5):663-669 (2010).
Verloes et al., "Effects of nootropic drugs in a scopolamine-induced amnesia model in mice," Psychopharmacology, 95(2):226-230 (1988).
Vinkers et al., "The inhibitory GABA system as a therapeutic target for cognitive symptoms in schizophrenia: investigational agents in the pipeline," Expert Opinion on Investigational Drugs, 19(10):1217-1233 (2009).
Volk et al., "Decreased Glutamic Acid $Decarboxylase_{67}$ Messenger RNA Expression in a Subset of Prefrontal Cortical γ-Aminobutyric Acid Neurons in Subjects With Schizophrenia," Archives of General Psychiatry, 57:237-245 (2000).
Von Rosenstiel, "Brivaracetam (UCB 34714)," Neurotherapeutics: The Journal of the American Society for Experimental NeuroTherapeutics, 84-87 (2007).
Walsh et al., "Ionic currents in cultured rat suprachiasmatic neurons," Neuroscience, 69:915-929 (1995).
Wang et al., "Magnetic resonance imaging of hippocampal subfields in posttraumatic stress disorder," Archives of General Psychiatry, 67(3):296-30 (2010).
Whitehouse et al., "Alzheimer's disease and senile dementia: loss of neurons in the basal forebrain," Science, 215:1237-39 (1982).
Wilby et al., "Clinical effectiveness, tolerability and cost-effectiveness of newer drugs for epilepsy in adults: a systematic review and economic evaluation," Health Technology Assessment, Executive Summary—Newer drugs for epilepsy in adult, 9(15) (2005).
Wilson et al. "Age associated alterations of hippocampal place cells are subregion specific," Journal of Neuroscience, 25(29):6877-6886 (2005).

(56) References Cited

OTHER PUBLICATIONS

Wilson et al., "Cognitive Aging and the Hippocampus: How Old Rats Represent New Environments," Journal of Neuroscience, 24(15):3870-3878 (2004).
Wilson et al., "Place cell rigidity correlates with impaired spatial learning in aged rats," Neurobiology of Aging, 2003, 24: 297-305.
Winblad et al., "Mild cognitive impairment—beyond controversies, towards a consensus: report of the International Working Group on Mild Cognitive Impairment," Journal of Internal Medicine, 256: 240-246 (2004).
Wisden et al., "The Distribution of 13 $GABA_A$ Receptor Subunit mRNAs in the Rat Brain. I. Telencephalon, Diencephalon, Mesencephalon," The Journal of Neuroscience, Mar. 1992, 12(3): 1040-1062.
Wishart et al., "Increased Brain Activation During Working Memory in Cognitively Intact Adults With the APOE ϵ4 Allele," American Journal of Psychiatry 163:1603-1610 (2006).
Witt et al., "The impact of antiepileptic drug treatment on attention and executive functions," Epilepsia, 51(S4):20 (2010) (Abstract).
Wolthuis, "Experiments with UCB 6215, a drug which enhances acquisition in rats: its effects compared with those of metamphetamine," European Journal of Pharmacology, 16(3):283-297 (1971).
Wood et al., "Hippocampal pathology in individuals at ultra-high risk for psychosis: A multi-modal magnetic resonance study," NeuroImage, 52:62-68 (2010).
Woon et al., "Hippocampal volume deficits associated with exposure to psychological trauma and posttraumatic stress disorder in adults: A meta-analysis," Progress in Neuro-Psychopharmacology & Biological Psychiatry, 34:1181-1188 (2010).
Wu et al., "A Model Based Background Adjustment for Oligonucleotide Expression Arrays," Journal of American Statistical Association, 99:909-917 (2004).
Xiang et al., "Stereochemistry as a Tool in Deciphering the Processes of a Tandem Iminium Cyclization and Smiles Rearrangement," Journal of Organic Chemistry, 75(23), 8147-8154 (2010).
Yaffe et al., "Posttraumatic stress disorder and risk of dementia among US veterans," Archives of General Psychiatry, 6(6):608-613 (2010).
Yang et al., "Cyclophosphamide impairs hippocampus-dependent learning and memory in adult mice: Possible involvement of hippocampal neurogenesis in chemotherapy-induced memory deficits," Neurobiology of Learning and Memory 93:487-494 (2010).
Yang et al., "Prolonged exposure to levetiracetam reveals a presynaptic effect on neurotransmission," Epilespia, 48(10):1861-1869 (2007).
Yassa et al., "Ultrahigh-resolution microstructural diffusion tensor imaging reveals perforant path degradation in aged humans in vivo," PNAS 107:12687-12691 (2010).
Yehuda et al., "Longitudinal Assessment of Cognitive Performance in Holocaust Survivors with and without PTSD," Biological Psychiatry, 60(7):714-721 (2006).
Yoon et al., "GABA Concentration Is Reduced in Visual Cortex in Schizophrenia and Correlates with Orientation-Specific Surround Suppression," Journal of Neuroscience, 30(10):3777-3781 (2010).
Young et al., "Using the MATRICS to guide development of a preclinical cognitive test battery for research in schizophrenia," Pharmacology & Therapeutics, 122(2):150-202 (2009).
Youngjohn et al., "Stability of everyday memory in age-associated impairment: A longitudinal study," Neuropsychology, 7(3);406-416 (1993).
Zahodne et al., "Pathophysiology and treatment of psychosis in Parkinson's disease," Drugs Aging, 25(8):665-682 (2008).
Zierhut et al., "The role of hippocampus dysfunction in deficient memory encoding and positive symptoms in schizophrenia," Psychiatry Research, 183(3): 187-194 (2010).
Zoran et al., "Specific muscle contacts induce increased transmitter release and neuritic arborization in motoneuronal cultures," Developmental Biology, 179:212-22 (1996).

* cited by examiner

BENZAZEPINE DERIVATIVES, COMPOSITIONS, AND METHODS FOR TREATING COGNITIVE IMPAIRMENT

RELATED APPLICATION

This application claims the benefit of and priority from U.S. Provisional Application 63/399,509, filed Aug. 19, 2022, which is incorporated herein by reference in its entirety.

This disclosure was made with government support under Grant No. R44 AG063607 awarded by the National Institutes of Health (NIH), and in particular, its National Institute on Aging (NIA) division, an agency of the United States Government. The United States Government has certain rights in the described embodiments.

FIELD OF THE DISCLOSURE

The disclosure relates to compounds, compositions, combinations and methods for treating cognitive impairment associated with various risk factors, for example, aging and the APOE4 genetic mutation, cognitive impairment associated with central nervous system (CNS) disorders, cognitive impairment associated with brain cancers, and brain cancers themselves in a subject at risk of developing or presenting with those cognitive impairments or in need of treatment thereof.

BACKGROUND OF THE DISCLOSURE

Cognitive ability may decline as a normal consequence of aging or other risk factors, or as a consequence of a central nervous disorder or a brain cancer.

For example, a significant population of elderly adults experiences a decline in cognitive ability that exceeds what is typical in normal aging. Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and age-related MCI is estimated to affect 5.5-7 million in the U.S. over the age of 65 (Plassman et al., 2008). Risk factors for cognitive impairment, in addition to aging, include, for example, the APOE4 genetic mutation or cancer treatments.

Cognitive impairment is also associated with other central nervous system (CNS) disorders (some being age-related), such as MCI, amnestic mild cognitive impairment (aMCI), dementia, Alzheimer's Disease (AD), prodromal AD, post-traumatic stress disorder (PTSD), schizophrenia, bipolar disorder (in particular, mania), amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. Cognitive impairment may also be associated with various brain cancers.

There is, therefore, a need for effective treatment of cognitive impairment associated with both age-related and non-age-related cognitive impairments (i.e., being associated with one of more risk factors for cognitive impairment) and for the treatment of cognitive impairments associated with central nervous system (CNS) disorders and to improve cognitive function in patients diagnosed with or suffering from, for example, age-related cognitive impairment, MCI, amnestic MCI, AAMI, ARCD, dementia, AD, prodromal AD, PTSD, schizophrenia or bipolar disorder (in particular, mania), amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction and cognitive impairment associated with other central nervous system (CNS) disorders or at risk of developing such cognitive impairments.

$GABA_A$ receptors ($GABA_A$ Rs) are pentameric assemblies from a pool of different subunits (α1-6, β1-3, γ1-3, δ, ε, π, θ) that form a Cl-permeable channel that is gated by the neurotransmitter γ-aminobutyric acid (GABA). Various pharmacological effects, including anxiety disorders, epilepsy, insomnia, pre-anesthetic sedation, and muscle relaxation, are mediated by different $GABA_A$ subtypes.

Various studies have demonstrated that reduced GABA signaling is linked to cognitive impairments associated with various CNS disorders. In particular, the α5-containing $GABA_A$ Rs, which are relatively sparse in the mammalian brain, play a role in modifying learning and memory. Previous studies have demonstrated a reduction of hippocampal expression of the α5 subunit of the $GABA_A$ R in rats with age-related cognitive decline (see, International Patent Publication WO 2007/019312). Such results suggest that upregulation of α5-containing $GABA_AR$ function may be effective in the treatment of cognitive impairment associated with said CNS disorders or cognitive impairments associated with aging and other risk factors of cognitive decline.

Thus, there is a need for positive allosteric modulators of α5-containing $GABA_A$ R that are useful in therapeutic preparations and medicaments for the treatment of cognitive impairment associated with CNS disorders or cognitive impairment associated with aging and other risk factors of cognitive decline or the treatments of subjects at risk of developing those cognitive impairments.

SUMMARY

The present disclosure in some of its embodiments addresses the aforementioned needs by providing a compound of formula I:

(I)

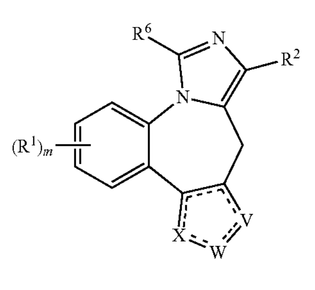

or a pharmaceutically acceptable salt, hydrate, solvate, polymorph, isomer, or combination thereof, wherein:

X is independently selected from O, N, —$NR^3$, or —$C(R^4)_{1-2}$;

W is O, N or $NR^3$;

V is O, $NR^3$ or —$C(R^4)_{1-2}$, wherein, when X is O, W is N and V is —$C(R^4)_{1-2}$;

when X is N, W is O or —$NR^3$, V is —$C(R^4)_{1-2}$;

when X is —$NR^3$, W is N, V is —$C(R^4)_{1-2}$;

when X is —$C(R^4)_{1-2}$, W is N, V is O or —$NR^3$;

each occurrence of the bond "$\overline{---}$" is either a single bond or a double bond;

m is an integer selected from 0-4;

each $R^1$ is independently selected from -halogen, —(C6-C10)aryl, —O(C1-C6)alkyl, —CN, —NCS, —$NO_2$, —$CHF_2$, —$CF_3$, —$OCF_3$, —$OCHF_2$, —CO(O)$R_7$, —$CH_2$—$OR^8$, —(C1-C6)alkyl-(C6-C10)aryl, -(5- to 10-membered)heteroaryl, —($C_1$-$C_6$)alkyl-(5- to 10-membered)heteroaryl, or —(C3-C6)cycloalkyl;

each $R^2$ is selected from —CO(O)$R_7$, —C≡C—$R^9$, —($C_1$-$C_6$)alkyl-C≡C—$R^9$, -(5- to 10-membered)heteroaryl, -(3- to 10-membered)heterocyclyl, or —($C_3$-$C_{10}$)cycloalkenyl; wherein each (5- to 6-membered) heteroaryl and (3- to 10-membered)heterocycle is substituted with 0-4 $R_7$;

wherein each $R_7$ is selected from —H, —$CF_3$, —(C1-C6)alkyl, —(C3-C6)cycloalkyl, -(5- to 10-membered)heteroaryl, —(C6-C10)aryl, —(C1-C6)alkyl-(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each $R^8$ is selected from —H, —(C1-C6)alkyl, -(5- to 10-membered)heteroaryl, -(3 to 10-membered)heterocyclyl, —(C3-C10)cycloalkenyl, —(C6-C10)aryl, —(C3-C6)cycloalkyl, —$CH_2$—(C3-C6)cycloalkyl, —$CH_2$—(C6-C10) aryl or —$CH_2$-(5- to 10-membered) heteroaryl, wherein each occurrence of $R^8$ is independently substituted by 0-5 R';

each $R^9$ is selected from —H, —(C1-C6)alkyl, -(5- to 10-membered)heteroaryl, -(3- to 10-membered)heterocyclyl, (C3-C10)cycloalkenyl, —(C6-C10)aryl, —(C3-C6)cycloalkyl, —(C1-C6)alkyl-(C6-C10)aryl, —(C1-C6)alkyl-(5- to 10-membered)heteroaryl, —(C1-C6) alkyl-(C3-C6)cycloalkyl, or —C(O)—(C6-C10)aryl, wherein each occurrence of $R^9$ is independently substituted by 0-5 R";

wherein each occurrence of R" is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl; wherein said heterocyclyl has 1-4 heteroatoms independently selected from N, NH, O, S, SO, or $SO_2$, and said heteroaryl has 1-4 heteroatoms independently selected from N, NH, O, or S;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-N($R^{12}$)$_2$, —(C1-C6)alkyl-(C6-C10)aryl, —(C1-C6)alkyl-(5- to 10-membered)heteroaryl, -(3- to 10-membered)heterocyclyl, -(5- to 10-membered)heteroaryl, —C(O)—(C6-C10)aryl, —C(O)—(C1-C6)alkyl, or —C(O)—(C3-C6) wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —C(O)N($R^o$)$_2$, —C(O)$OR^o$, —$NO_2$, —NCS, —CN, —$CF_3$, —$OCF_3$ or —N($R^o$)$_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl wherein said heterocyclyl has 1-4 heteroatoms independently selected from N, NH, O, S, SO, or $SO_2$, and said heteroaryl has 1-4 heteroatoms independently selected from N, NH, O, or S;

$R^4$ is selected from —H or —(C1-C6)alkyl;

$R^6$ is selected from —H or —(C1-C6)alkyl;

each $R^{13}$ and $R^{14}$ is independently selected from —H, —(C1-C3)aliphatic, or —(C3-C6)cycloalkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$;

wherein each occurrence of R" is independently selected from —H, —(C1-C6)aliphatic, —(C3-C6)cycloalkyl, -(3- to 6-membered)heterocyclyl, -(5- to 10-membered)heteroaryl, —(C6-C10)aryl, —(C1-C6)alkyl-(5- to 10-membered)heteroaryl, —(C1-C6)alkyl-(C6-C10) aryl, —(C1-C6)alkyl-O-(5- to 10-membered)heteroaryl, or —(C1-C6)alkyl-O—(C6-C10)aryl, wherein each occurrence of R" is independently substituted with 0-3 substituents, and in particular, in some aspects of the disclosure, R" is independently substituted with 1-3 substituents, wherein the substituents are selected from halogen, —$R^o$, —$OR^o$, oxo, —$CH_2OR^o$, —$CH_2N(R^o)$ 2, —C(O)N($R^o$)$_2$, —C(O)$OR^o$, —$NO_2$, —NCS, —CN, —$CF_3$, —$OCF_3$ or —N($R^o$)$_2$; and wherein each occurrence of $R^o$ is independently selected from —(C1-C6)aliphatic, —O(C1-C6)aliphatic, —(C3-C6)cycloalkyl, -(3- to 6-membered)heterocyclyl, -(5- to 10-membered)heteroaryl, or —(C6-C10) aryl, wherein said heterocyclyl has 1-4 heteroatoms independently selected from N, NH, O, S, SO, or $SO_2$, and said heteroaryl has 1-4 heteroatoms independently selected from N, NH, O, or S.

In another aspect, the present disclosure provides a compound of formula I-a:

I-a

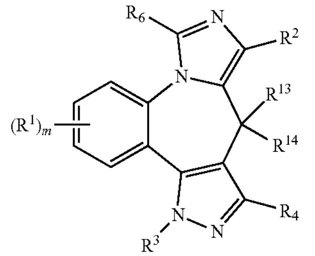

or a pharmaceutically acceptable salt, hydrate, solvate, polymorph, isomer, or combination thereof, wherein:

m is an integer selected from 0-4;

each $R^1$ is independently selected from -halogen, —(C6-C10)aryl, —O(C1-C6)alkyl, —CN, —$CHF_2$, —$CF_3$, —$OCF_3$, —$OCHF_2$, —CO(O)$R_7$, —$CH_2$—OR', —(C1-C6)alkyl-(C6-C10) aryl, -(5- to 10-membered) heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl, —(C3-C10)cycloalkenyl,

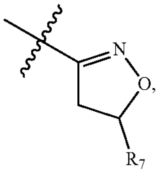
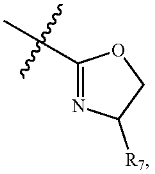
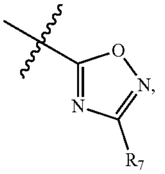
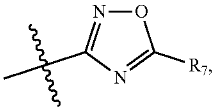
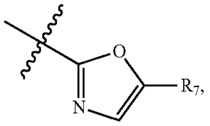
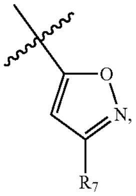
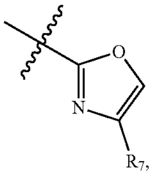
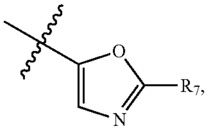
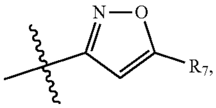
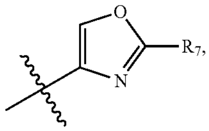
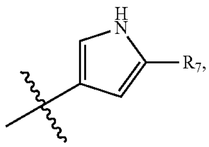
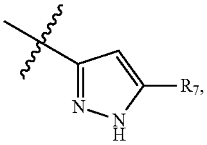
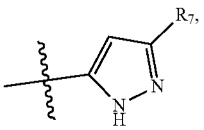
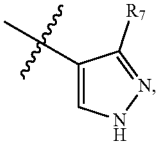
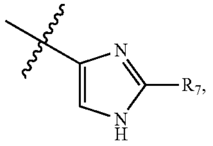
or
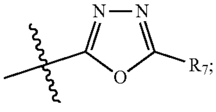

wherein each 5- to 6-membered heteroaryl and 3- to 10-membered heterocycle is substituted with 0-4 $R_7$;

each $R^9$ is selected from: —H, —(C1-C6)alkyl, -(5- to 10-membered)heteroaryl, -(3- to 10-membered)heterocyclyl, —(C6-C10)aryl, —(C1-C6)alkyl-(C6-C10)aryl,

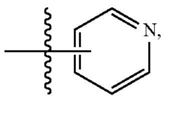
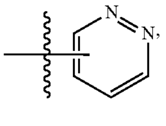
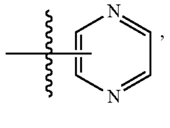

-continued

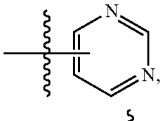
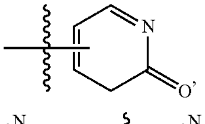
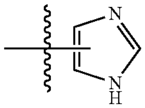
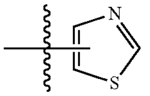
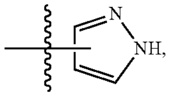
or
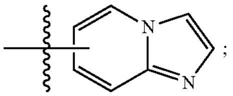

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —(C6-C10)aryl or -(5- to 10-membered)heteroaryl;

$R^3$ is independently selected from —H, —(C1-C6)alkyl, -(5- to 10-membered)heteroaryl, -(3- to 10-membered) heterocyclyl, —(C1-C6)alkyl-(C3-C6)cycloalkyl or —(C1-C6)alkyl-(C6-C10)aryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —$C(O)N(R^o)_2$, —$C(O)OR^o$, —$CF_3$, —$OCF_3$ or —$N(R^o)_2$, wherein each occurrence of $R^o$ is independently selected from —(C1-C6)aliphatic, —(C3-C6) cycloalkyl, -(3- to 10-membered)heterocyclyl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —$CH_2$—(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, —$CH_2OR''$, —$CH_2NR''_2$, —$C(O)N(R'')_2$, —$C(O)OR''$, —$NO_2$, —NCS, —CN, —$CF_3$, —$OCF_3$ or —$N(R'')_2$, wherein R" is selected from —Cl, —F, —(C1-C6)alkyl, —OMe, or —(C6-C10)aryl;

R" is independently substituted with 1-3 substituents wherein the substituents are selected from halogen, —$CF_3$, —$OCF_3$, —O—(C1-C6)aliphatic, or —(C1-C6)aliphatic;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-aa:

I-aa

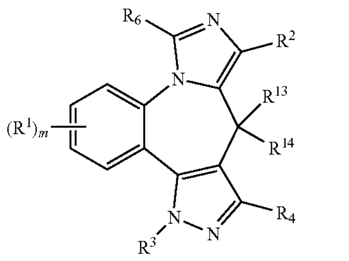

or a pharmaceutically acceptable salt, hydrate, solvate, polymorph, isomer, or combination thereof, wherein:

m is an integer selected from 0-4;

each $R^1$ is independently selected from halogen, —(C6-C10)aryl, —O(C1-C6)alkyl, —CN, —$CHF_2$, —$CF_3$, —$OCF_3$, —$OCHF_2$, CO(O)$R_7$, $CH_2$—$OR^8$, —(C1-C6) alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl, —(C3-C10)cycloalkenyl,

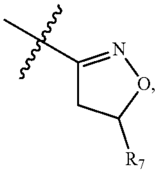 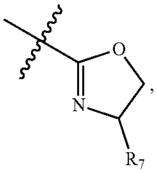, 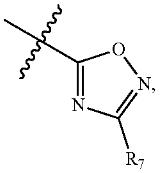

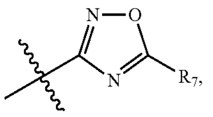 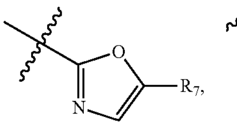 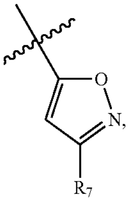

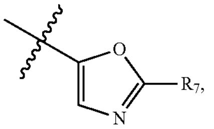 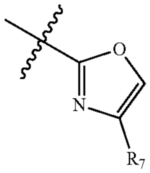,

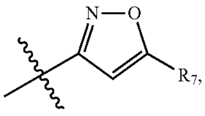 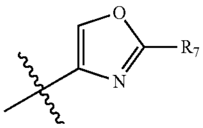,

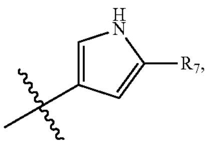 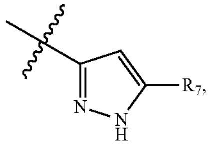

-continued

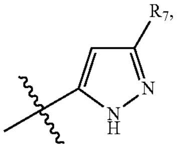 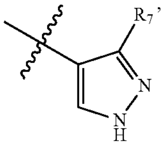

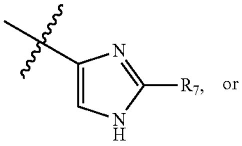 or 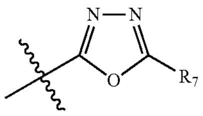;

wherein each 5- to 6-membered heteroaryl and 3- to 10-membered heterocycle is substituted with 0-4 $R_7$;

each $R^9$ is selected from: —H, —(C1-C6) alkyl, (5- to 10-membered)heteroaryl, -(3- to 10-membered)heterocyclyl, —(C6-C10) aryl, —(C1-C6) alkyl-(C6-C10) aryl,

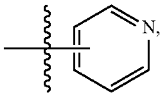 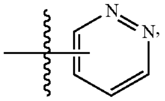 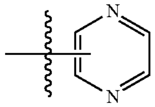,

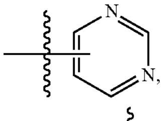 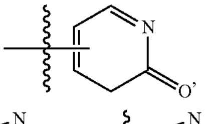 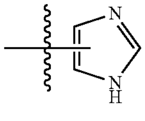,

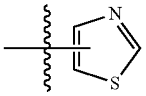, 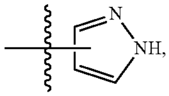 or

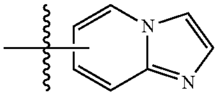;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —(C6-C10)aryl or -(5- to 10-membered)heteroaryl;

$R^3$ is independently selected from —H, —(C1-C6)alkyl, -(5- to 10-membered)heteroaryl, -(3- to 10-membered) heterocyclyl, —(C1-C6) alkyl-(C3-C6)cycloalkyl or —(C1-C6)alkyl-(C6-C10)aryl, wherein $R^3$ is independently substituted with 0-5 $R^{12}$;

wherein each $R^{12}$ is independently selected from: —H, -halogen, —$OR^o$, $R^o$, oxo, —$CH_2OR^o$, —$CH_2N(R^o)_2$, —C(O)N$(R^o)_2$, —C(O)$OR^o$, —$CF_3$, —$OCF_3$ or —N$(R^o)_2$, wherein each occurrence of $R^o$ is independently selected from —(C1-C6)aliphatic, —(C3-C6) cycloalkyl, -(3- to 10-membered)heterocyclyl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —$CH_2$—(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$, or —N(R")$_2$;

wherein R" is selected from —Cl, —F, —(C1-C6)alkyl, —OMe, -(3- to 6-membered)heterocyclyl, or —(C6-C10)aryl;

R" is independently substituted with 1-3 substituents wherein the substituents are selected from: halogen, —$CF_3$, —$OCF_3$, —O—(C1-C6)aliphatic, or —(C1-C6)aliphatic;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-b:

I-b

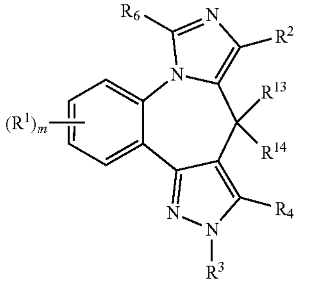

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—$OR^8$, —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

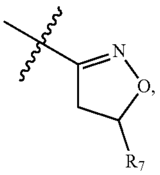
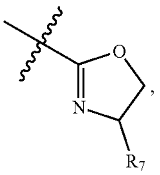
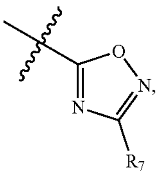

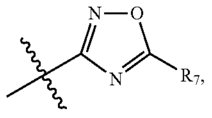
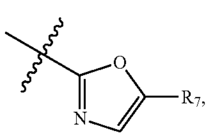
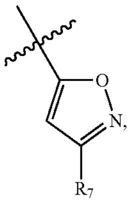

-continued

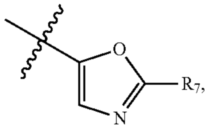
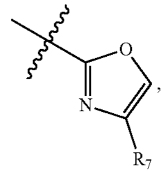

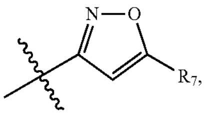
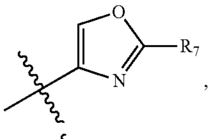

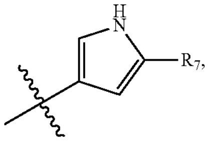
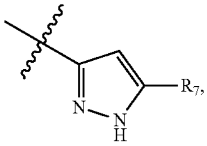

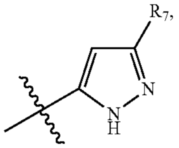
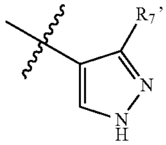

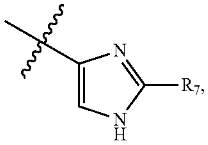
or
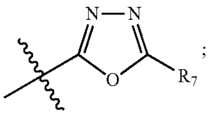

wherein each 5- to 6-membered heteroaryl or 3- to 10-membered heterocycle is substituted with 0-4$R_7$;

each $R^9$ is selected from —H, —(C1-C6)alkyl, -(5- to 10-membered)heteroaryl, -(3- to 10-membered)heterocyclyl, —(C6-C10)aryl, —(C1-C6)alkyl-(C6-C10)aryl,

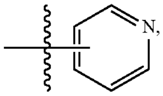
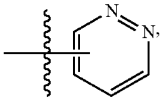
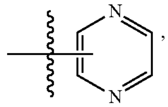

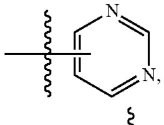
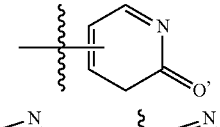
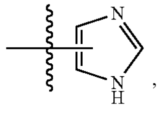

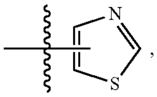
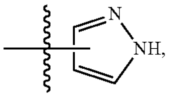
or

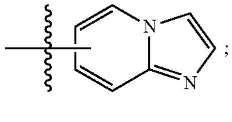

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-N($R^{12}$)$_2$, —(C1-C6)alkyl-(C6-C10)aryl, —(C1-C6)alkyl-(5- to 10-membered)heteroaryl, -(3- to 10-membered)heterocyclyl or -(5- to 10-membered)heteroaryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —$C(O)N(R^o)_2$, —$C(O)OR^o$, —$NO_2$, —NCS, —CN, —$CF_3$, —$OCF_3$ or —$N(R^o)_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —(C1-C6)alkyl-(C6-C10) aryl, —(C1-C6)alkyl-(5- to 10-membered)heteroaryl or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from -halogen, —R", —OR", oxo, —$CH_2OR"$, —$CH_2NR"_2$, —$C(O)N(R")_2$, —$C(O)OR"$, —$NO_2$, —NCS, —CN, —$CF_3$, —$OCF_3$ or —$N(R")_2$;

wherein R" is selected from —Cl, —F, —(C1-C6)alkyl, —OMe, —(C1-C6)alkyl-(5- to 10-membered)heteroaryl, -(5- to 10-membered)heteroaryl, -(3- to 10-membered)heterocyclyl, —(C3-C6)cycloalkyl or —(C6-C10)aryl;

R" is independently substituted with 1-3 substituents wherein the substituents are selected from halogen, —$CF_3$, —$OCF_3$, —O(C1-C6)aliphatic, —(C1-C6)aliphatic, or -(5- to 10 -membered)heteroaryl;

each $R^4$ and $R^6$ is independently selected from —H or —(C1-C6)alkyl; and each $R^{13}$ and $R^{14}$ is independently selected from H—, —(C1-C3)aliphatic, or —(C3-C6)cycloalkyl.

In another aspect, the present disclosure provides a compound of formula I-ba:

I-ba

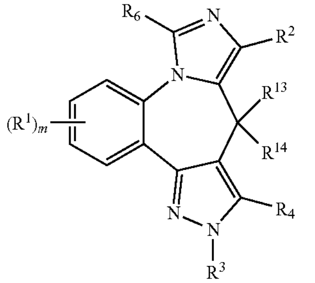

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —$CO(O)R_7$, —$CH_2$—$OR^8$, —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —$CO(O)R_7$, —C≡C—$R^9$, —(C1-C6)alkyl-C≡C—$R^9$, -(5- to 10-membered)heteroaryl, -(3- to 10-membered)heterocyclyl,

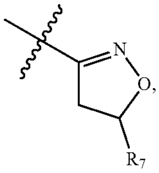
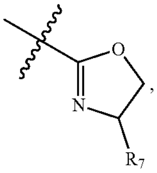
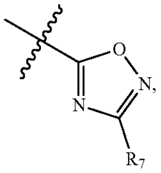
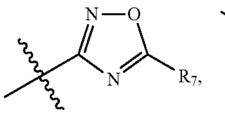
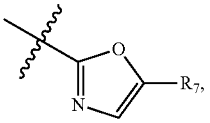
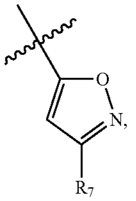
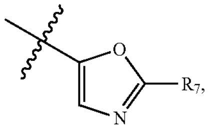
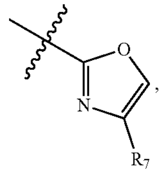
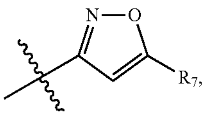
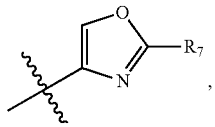
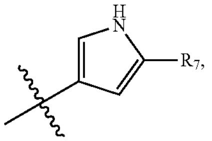
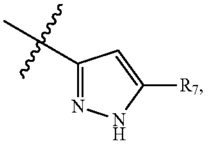
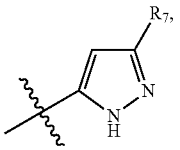
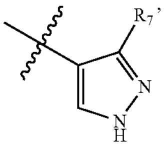
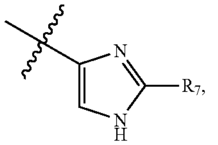
or
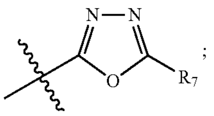
;

wherein each 5- to 6-membered heteroaryl or 3- to 10-membered heterocycle is substituted with 0-4$R_7$;

each $R^9$ is selected from —H, —(C1-C6)alkyl, -(5- to 10-membered)heteroaryl, -(3- to 10 -membered)heterocyclyl, —(C6-C10)aryl, —(C1-C6)alkyl-(C6-C10) aryl,

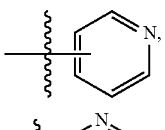, 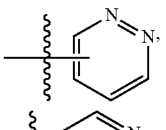, 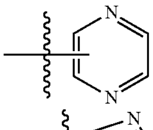, 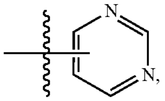, 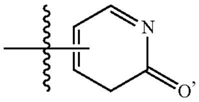, 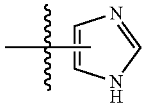, 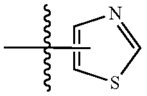, 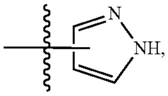, or 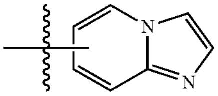;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-$N(R^{12})_2$, —(C1-C6)alkyl-(C6-C10) aryl, —(C1-C6 alkyl-(5- to 10-membered)heteroaryl, -(3- to 10-membered)heterocyclyl or -(5- to 10-membered)heteroaryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —$C(O)N(R^o)_2$, —$C(O)OR^o$, —$NO_2$, —NCS, —CN, —$CF_3$, —$OCF_3$, or —$N(R^o)_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)-aryl;

wherein each $R_7$ is selected from —H, —$CF_3$, —(C1-C6) alkyl, —(C3-C6)cycloalkyl, -5 to 10 membered heteroaryl, —(C6-C10)aryl, —(C1-C6)alkyl-(C6-C10) aryl, —(C1-C6)alkyl-(5- to 10-membered)heteroaryl or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, $CH_2OR"$, —$CH_2NR"_2$, —$C(O)N(R")_2$, —C(O)OR", —$NO_2$, —NCS, —CN, —$CF_3$, —$OCF_3$ or —$N(R")_2$;

wherein R" is selected from —Cl, —F, —(C1-C6)alkyl, —OMe, —(C1-C6)alkyl-(5- to 10-membered)heteroaryl, -(5- to 10-membered)heteroaryl, -(3- to 10-membered)heterocyclyl, —(C3-C6)cycloalkyl, —(C6-C10)aryl, —H, or —$C(O)CH_3$;

R" is independently substituted with 1-3 substituents wherein the substituents are selected from halogen, —$CF_3$, —$OCF_3$, —O(C1-C6)aliphatic, —(C1-C6)aliphatic, -(5- to 10-membered)heteroaryl, or oxo;

each $R^4$ and $R^6$ is independently selected from —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-c:

I-c

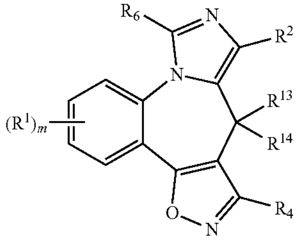

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —$CO(O)R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —$CO(O)R_7$, —C≡C—$R^9$, —(C1-C6)alkyl-C≡C—$R^9$, -(5- to 10-membered)heteroaryl, -(3- to 10-membered)heterocyclyl,

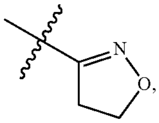, 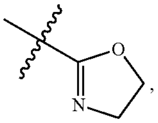, 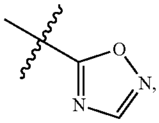, 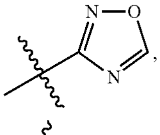, 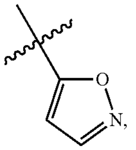, 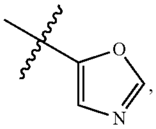, 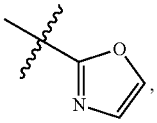, 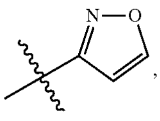, 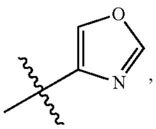, 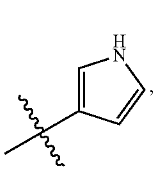, 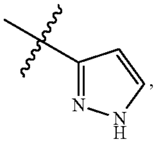, 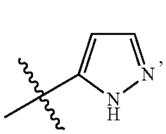, 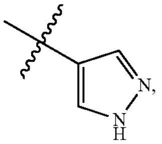, 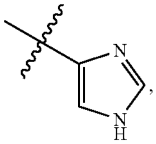, or 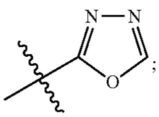;

wherein each 5-membered heterocycle or heteroaryl is substituted with 0-4 $R_7$;

each $R^9$ is selected from —H, —(C1-C6)alkyl, -(5- to 10-membered)heteroaryl, -(3- to 10-membered)heterocyclyl

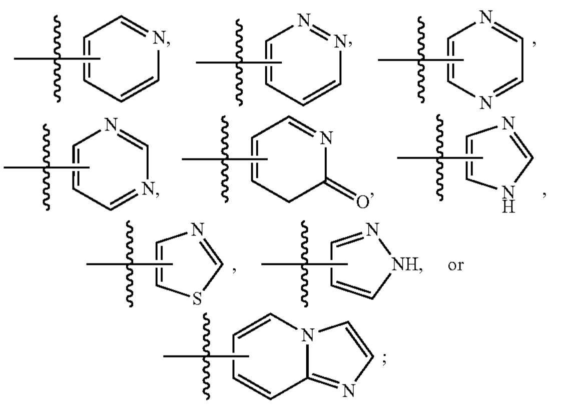

each occurrence of $R^9$ is independently substituted by 0-5 $R^{11}$;

each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

each occurrence of $R_7$ is selected from —$CF_3$, —(C1-C6) alkyl, —(C3-C6)cycloalkyl, -(5- to 10-membered)heteroaryl, —(C6-C10) aryl, —(C1-C6)alkyl-(C6-C10) aryl, —(C1-C6)alkyl-(5- to 10-membered)heteroaryl or -(3- to 10-membered)heterocyclyl, wherein each $R_7$ is independently substituted with 0-5 R';

each occurrence of R' is wherein each occurrence of R' is independently selected from halogen, —R'', —OR'', oxo, —$CH_2$OR'', —$CH_2NR''_2$, —C(O)N(R'')$_2$, —C(O) OR'', —$NO_2$, —NCS, —CN, —$CF_3$, —$OCF_3$ or —N(R'')$_2$, wherein each occurrence of R'' is selected from —Cl, —F, —(C1-C6)alkyl, —OMe, —(C1-C6)alkyl-(5- to 10-membered)heteroaryl, -(5- to 10-membered)heteroaryl, -(3- to 10-membered)heterocyclyl, —(C3-C6) cycloalkyl, or —(C6-C10)aryl, and R'' is independently substituted with 1-3 substituents wherein the substituents are selected from -halogen, —$CF_3$, —$OCF_3$, —(C1-C6)aliphatic, or -(5- to 10-membered)heteroaryl;

each $R^4$ and $R^6$ is independently selected from —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-d:

I-d

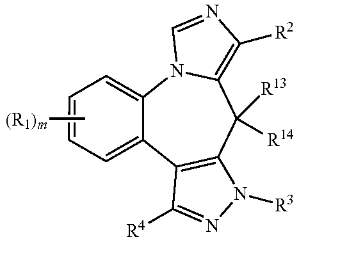

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—OR', —(C1-C6)alkyl-(C6-C10)aryl, -(5- to 10-membered)heteroaryl, —(C1-C6)alkyl-(5- to 10-membered)heteroaryl, or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

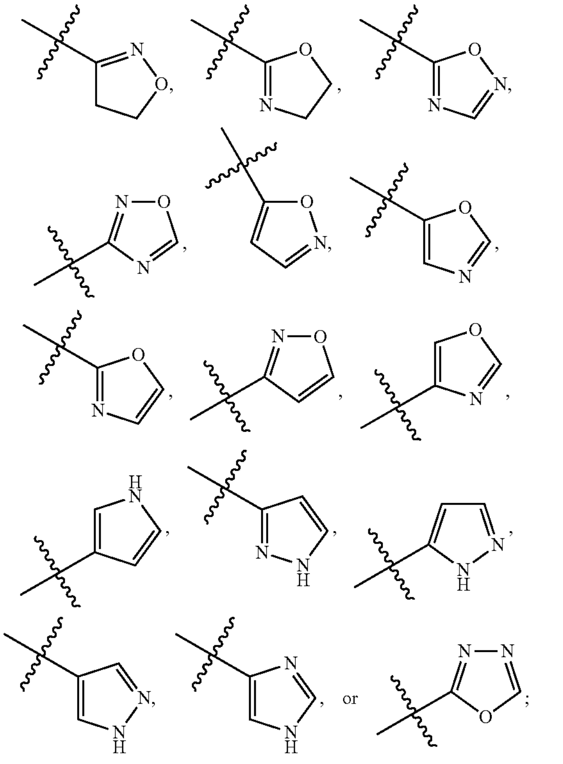

wherein each 5-membered heterocycle or heteroaryl is substituted with 0-4 $R_7$;

each $R^9$ is selected from —H, —(C1-C6)alkyl, -(5- to 10-membered)heteroaryl, -(3- to 10-membered)heterocyclyl, —(C6-C10)aryl, —(C1-C6)alkyl-(C6-C10) aryl,

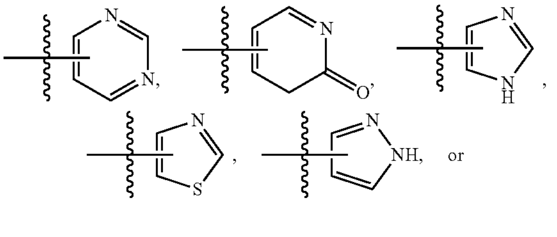

-continued

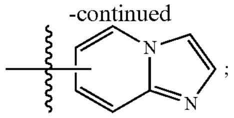

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl, or -(5- to 10-membered)heteroaryl;

$R^3$ is independently selected from: —H, —(C1-C6)alkyl, —(C1-C6)alkyl-(C3-C6)cycloalkyl, —(C1-C6)alkyl-$OR^{12}$, —(C1-C6)alkyl-$N(R^{12})_2$, —(C1-C6)alkyl-(C6-C10)aryl, or —(C1-C6) alkyl-(5- to 10-membered) heteroaryl wherein $R^3$ is independently substituted with 0-5 $R^{12}$;

wherein each $R^{12}$ is independently selected from —H, -halogen, —$OR^o$, —$R^o$, oxo, —$CH_2OR^o$, —$CH_2N(R^o)_2$, —$C(O)N(R^o)_2$, —$C(O)OR^o$, —$NO_2$, —NCS, —CN, —$CF_3$, —$OCF_3$ or —$N(R^o)_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl.

Wherein $R_7$ is selected from —$CF_3$, —(C1-C6)alkyl, —(C3-C6)cycloalkyl, -(5- to 10-membered)heteroaryl, —(C6-C10)aryl, —(C1-C6)alkyl-(C6-C10)aryl, —(C1-C6)alkyl-(5- to 10-membered)heteroaryl, or -(3- to 10-membered)heterocyclyl, wherein each $R_7$ is independently substituted with 0-5 R';

each occurrence of R' is wherein each occurrence of R' is independently selected from -halogen, —R", —OR", oxo, —$CH_2OR$", —$CH_2NR"_2$, —$C(O)N(R")_2$, —C(O)OR", —$NO_2$, —NCS, —CN, —$CF_3$, —$OCF_3$ or —$N(R")_2$;

wherein R" is selected from —Cl, —F, —(C1-C6)alkyl, —OMe, or —(C6-C10)aryl;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-e:

I-e

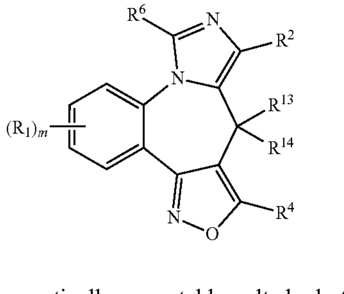

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —$CO(O)R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —$CO(O)R_7$, —C≡C—$R^9$, —(C1-C6)alkyl-C≡C—$R^9$, -(5- to 10-membered)heteroaryl, -(3- to 10-membered)heterocyclyl,

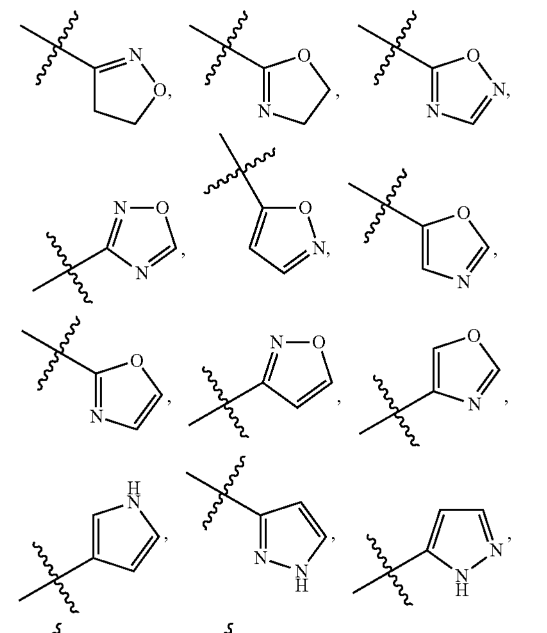

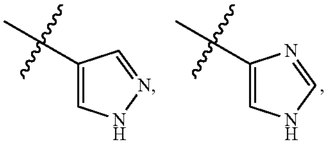

or

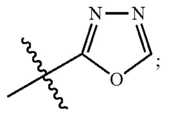

wherein each 5-membered heterocyclyl or heteroaryl is substituted with 0-4 $R_7$;

each $R^9$ is selected from —H, —(C1-C6)alkyl, -(5- to 10-membered)heteroaryl, -(3- to 10-membered)heterocyclyl,

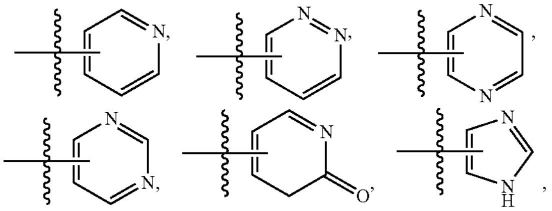

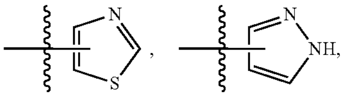

or

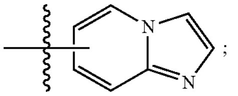

each occurrence of $R^9$ is independently substituted by 0-5 $R^{11}$, wherein each occurrence of $R^{11}$ is independently selected from —(C1-C6)alkyl, —O—(C1-C6)alkyl, -halogen, —$CF_3$, —$OCF_3$, —OMe, —(C6-C10) aryl or -(5- to 10-membered)heteroaryl;

wherein $R_7$ is selected from —(C1-C6)alkyl, —(C3-C6) cycloalkyl, -(5- to 10-membered)heteroaryl, —(C6-

C10)aryl, —(C1-C6)alkyl-(C6-C10)aryl, -(5- to 10-membered)heteroaryl-(C1-C6)alkyl, or -(3- to 10-membered)heterocyclyl, wherein each $R_7$ is independently substituted with 0-5 R';

each occurrence of R' is wherein each occurrence of R' is independently selected from -halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$, wherein each R' is independently substituted with 0-5 R";

wherein R" is selected from —Cl, —F, —(C1-C6)alkyl, —OMe, or —(C6-C10)aryl;

each $R^4$ is independently —H or —(C1-C6)alkyl;

each $R^6$ is independently —H or —(C1-C6)alkyl; and each $R^{13}$ and $R^{14}$ is independently selected from —H, —(C1-C3)aliphatic, or —(C3-C6)cycloalkyl.

In another aspect, the present disclosure provides a compound of formula I-f:

I-f

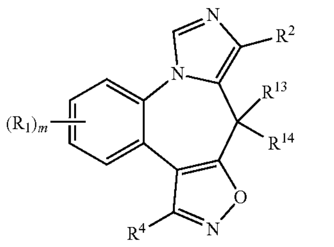

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

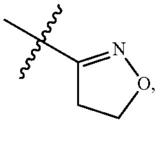,
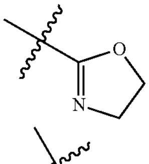,
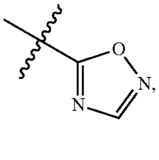,
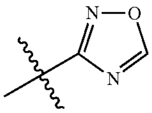,
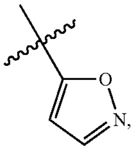,
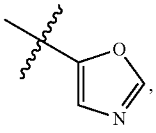,
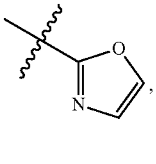,
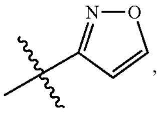,
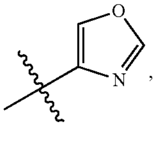, -continued

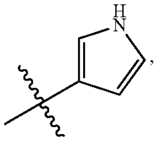,
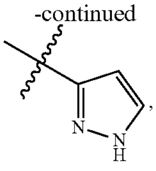,
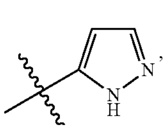,
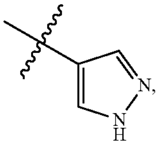,
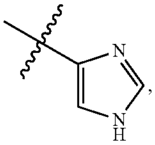, or
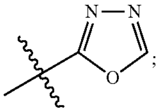;

wherein each 5-membered heterocycle or heteroaryl is substituted with 0-4 $R_7$;

each $R^9$ is selected from: —H, —(C1-C6) alkyl, -(5- to 10-membered)heteroaryl, -(3- to 10-membered)heterocyclyl

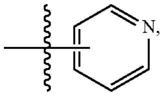,
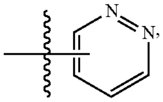,
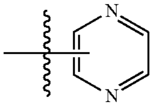,
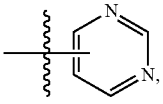,
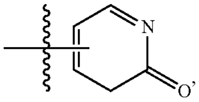,
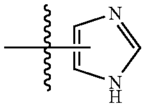,
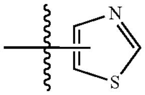,
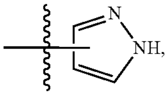, or
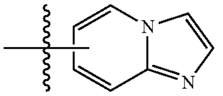;

each occurrence of $R^9$ is independently substituted by 0-5 $R^{11}$, wherein each occurrence of $R^{11}$ is independently selected from —(C1-C6)alkyl, —O—(C1-C6)alkyl, -halogen, —$CF_3$, —$OCF_3$, —OMe, —(C6-C10)aryl, or -(5- to 10-membered)heteroaryl;

wherein $R_7$ is selected from —(C1-C6)alkyl, —(C3-C6)cycloalkyl, -(5- to 10-membered)heteroaryl, —(C6-C10)aryl, —(C1-C6)alkyl-(C6-C10)aryl, or -(5- to 10-membered)heteroaryl-(C1-C6)alkyl, or -(3- to 10-membered)heterocyclyl, wherein each $R_7$ is independently substituted with 0-5 R';

each occurrence of R' is wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$;

wherein each R' is independently substituted with 0-5 R", wherein R" is selected from —Cl, —F, —(C1-C6)alkyl, —OMe, or —(C6-C10)aryl;

$R^4$ is —H or (C1-C6)alkyl;

$R^6$ is —H or —(C1-C6)alkyl; and each $R^{13}$ and $R^{14}$ is independently selected from —H, —(C1-C3)aliphatic, or —(C3-C6)cycloalkyl.

The in various aspects the present disclosure also provides pharmaceutical compositions that comprise a compound of formulae I, I-A, I-a, I-aa, I-B, I-b, I-ba, I-C, I-c, I-D, I-d, I-E, I-e, I-F and I-f or a pharmaceutically acceptable salt, hydrate, solvate, polymorph, isomer, or combinations thereof.

In some embodiments, compounds of formula I are $GABA_A$ α5 receptor positive allosteric modulators. In some embodiments, compounds of formula I-a are $GABA_A$ α5 receptor positive allosteric modulators. In some embodiments, compounds of formula I-aa are $GABA_A$ α5 receptor positive allosteric modulators. In some embodiments, compounds of formula I-b are $GABA_A$ α5 receptor positive allosteric modulators. In some embodiments, compounds of formula I-ba are $GABA_A$ α5 receptor positive allosteric modulators. In some embodiments, compounds of formula I-c are $GABA_A$ α5 receptor positive allosteric modulators. In some embodiments, compounds of formula I-d are $GABA_A$ α5 receptor positive allosteric modulators. In some embodiments, compounds of formula I-e are $GABA_A$ α5 receptor positive allosteric modulators. In some embodiments, compounds of formula I-f are $GABA_A$ α5 receptor positive allosteric modulators. In some aspects of this disclosure, one or more of the compounds of formula I, I-A, I-a, I-aa, I-B, I-b, I-ba, I-C, I-c, I-D, I-d, I-E, I-e, I-F and I-f are useful for treating the cognitive impairments and risk of those cognitive impairments described herein.

In some embodiments, the $GABA_A$ α5 receptor positive allosteric modulators described in this disclosure are used in combination with one or more of the $GABA_A$ α5 receptor positive allosteric modulators disclosed in PCT applications WO2015/095783A1, WO2016/205739A1, WO2018/130869A1, and WO2019/246300A1. In some embodiments, the $GABA_A$ α5 receptor positive allosteric modulators described in this disclosure or the combinations described above may be used in combination with one or more of the SV2a inhibitors as disclosed PCT application WO2022/011318 in the treatment of the cognitive impairments and risks of cognitive impairments described herein.

In another aspect of the disclosure, there is provided a method for treating cognitive impairment associated with a CNS disorder in a subject in need of treatment or at risk of said cognitive impairment, the method comprising the step of administering to said subject a therapeutically effective amount of a compound of the disclosure or a pharmaceutically acceptable salt, hydrate, solvate, polymorph, isomer, or combinations thereof. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In another aspect of the disclosure, there is provided a method of preserving or improving cognitive function in a subject in need thereof, the method comprising the step of administering to said subject a therapeutically effective amount of a compound of the disclosure or a pharmaceutically acceptable salt, hydrate, solvate, polymorph, isomer, or combinations thereof. In certain embodiments of the disclosure, a compound of the disclosure or a pharmaceutically acceptable salt, hydrate, solvate, polymorph, isomer, or combinations thereof is administered every 12 or 24 hours.

In another aspect of the disclosure, there is provided a method for treating cognitive impairment associated with aging or other risk of cognitive impairment in a subject in need of treatment or at risk of said cognitive impairment, the method comprising the step of administering to said subject a therapeutically effective amount of a compound of the disclosure or a pharmaceutically acceptable salt, hydrate, solvate, polymorph, isomer, or combinations thereof. In another aspect of the disclosure, there is provided a method of preserving or improving cognitive function in a subject in need thereof, the method comprising the step of administering to said subject a therapeutically effective amount of a compound of the disclosure or a pharmaceutically acceptable salt, hydrate, solvate, polymorph, isomer, or combinations thereof. In certain embodiments of the disclosure, a compound of the disclosure or a pharmaceutically acceptable salt, hydrate, solvate, polymorph, isomer, or combinations thereof is administered every 12 or 24 hours.

In another aspect of the disclosure, there is provided a method for treating α5-$GABA_A$R expressing pediatric and adult cancers, the method comprising the step of administering to said subject a therapeutically effective amount of a compound of the present disclosure or a pharmaceutically acceptable salt, hydrate, solvate, polymorph, isomer, or combinations thereof. In another aspect of the disclosure, there is provided a method for treating α5-$GABA_A$R expressing brain cancers (including brain tumors, e.g., medulloblastomas), the method comprising the step of administering to said subject a therapeutically effective amount of a compound of the present disclosure or a pharmaceutically acceptable salt, hydrate, solvate, polymorph, isomer, or combinations thereof. In another aspect of the disclosure, there is provided a method of preserving or improving cognitive function in a subject suffering from brain cancers (including brain tumors, e.g., medulloblastomas), the method comprising the step of administering to said subject a therapeutically effective amount of a compound of the disclosure or a pharmaceutically acceptable salt, hydrate, solvate, polymorph, isomer, or combinations thereof. In certain embodiments of the disclosure, a compound of the disclosure or a pharmaceutically acceptable salt, hydrate, solvate, polymorph, isomer, or combinations thereof is administered every 12 or 24 hours.

In some embodiments, the compounds, the compositions, or the combinations of the present disclosure are for use as a medicament or therapeutic agents. In some embodiments, the compounds, the compositions, or the combinations of the present disclosure and medicaments comprising them are useful to treat cognitive impairment associated with a CNS disorder in a subject in need of treatment or at risk of said cognitive impairment. In some embodiments, the CNS disorder that is associated with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, the compounds, the compositions, or the combinations of the present disclosure and the medicaments comprising them are useful to treat brain cancers (including brain tumors, e.g., medulloblastomas). In some embodiments, the compounds, the compositions, or the combinations of the present disclosure and the medicaments comprising them are useful for treating cognitive impairment associated with brain cancers (including brain tumors, e.g., medulloblastomas). In some embodiments the compounds, the compositions, or the combinations of this disclosure and the medicaments comprising them are useful for treating subjects at risk of developing cognitive impairment as the result of their having one or more rises factors for such impairment, one of such risk factors being aging.

In some embodiments, this disclosure provides the use of a compound or composition described herein in the preparation of a medicament for the treatment of cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, the compounds, the compositions, or the combinations of the present disclosure are for use in the preparation of a medicament for the treatment of brain cancers (including brain tumors, e.g., medulloblastomas). In some embodiments, the compounds, the compositions, or the combinations of the present disclosure are for use in the preparation of a medicament for the treatment of cognitive impairment associated with brain cancers (including brain tumors, e.g., medulloblastomas). In some embodiments the compounds, the compositions, or the combinations of this disclosure are for use in the preparation of a medicament for the treatment of subjects at risk of developing cognitive impairment as the result of their having one or more rises factors for such impairment, one of such risk factors being aging.

DETAILED DESCRIPTION OF THE FIGURES

FIG. 1 is a graph depicting the effects of administering methyl 3,5-diphenylpyridazine-4-carboxylate on the spatial memory retention of ten aged-impaired (AI) rats in an eight-arm Radial Arm Maze (RAM) test. The black bars refer to rats treated with vehicle alone; open bars refer to rats treated with methyl 3,5-diphenylpyridazine-4-carboxylate at different doses; hatched bar refers to rats treated with the combination of TB21007 and methyl 3,5-diphenylpyridazine-4-carboxylate.

Figure 2:
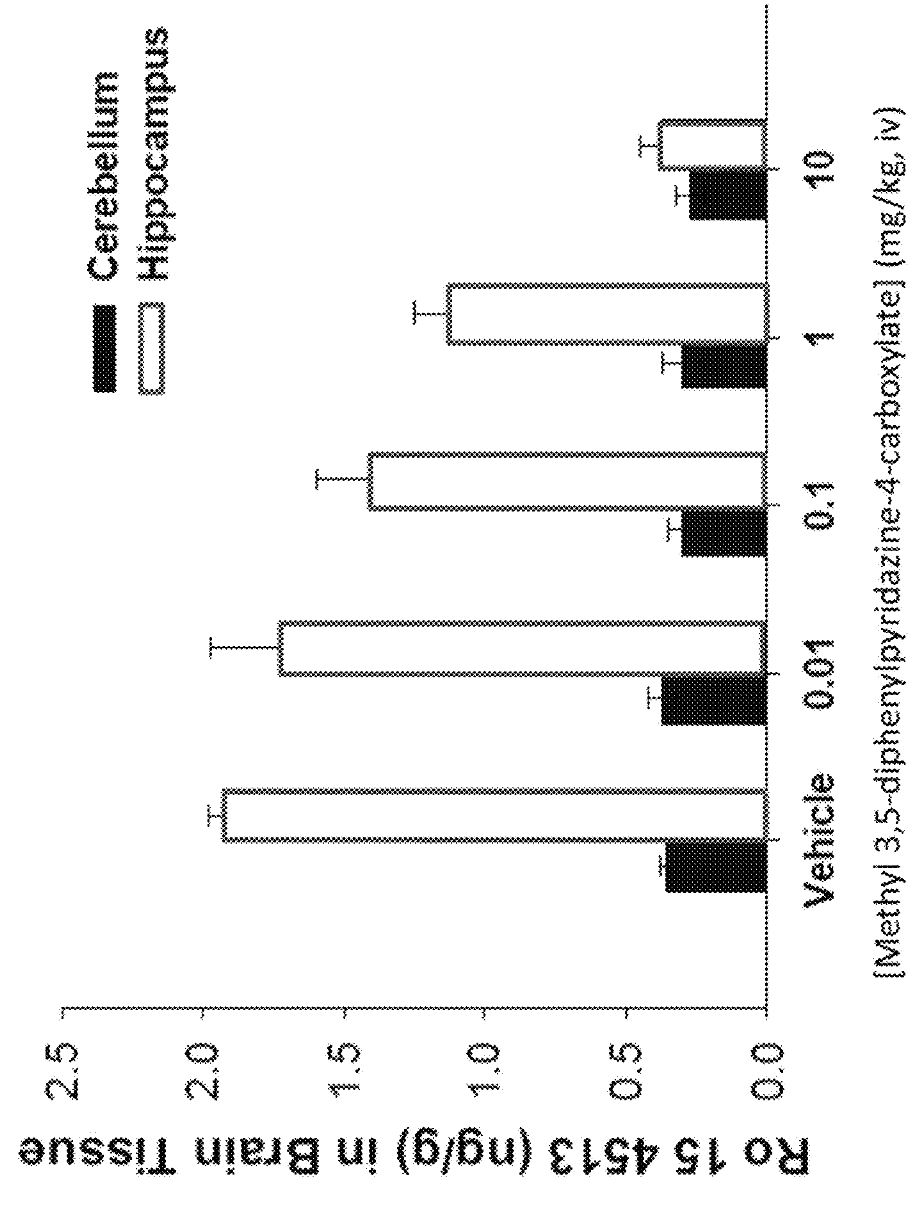

FIG. 2 is a graph showing the effect of methyl 3,5-diphenylpyridazine-4-carboxylate (administered intravenously) on the binding of Ro154513 in the hippocampus and cerebellum. Methyl 3,5-diphenylpyridazine-4-carboxylate blocked the binding of Ro154513 in the hippocampus but did not affect binding of Ro15413 in the cerebellum.

Figure 3:
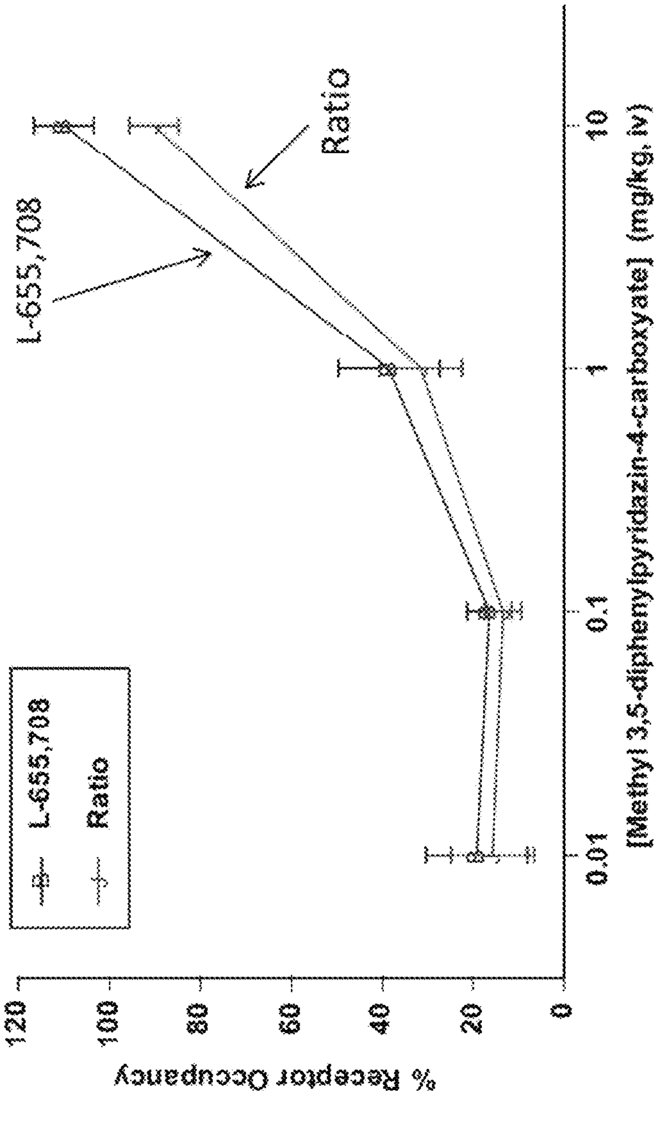

FIG. 3 is a graph showing dose-dependent $GABA_A$ α5 receptor occupancy by methyl 3,5-diphenylpyridazine-4-carboxylate administered intravenously, with receptor occupancy determined either by the ratio between hippocampus (a region of high $GABA_A$ α5 receptor density) exposure of RO 15-4513 and cerebellum (a region with low $GABA_A$ α5 receptor density) exposure of RO 15-4513, or by using the $GABA_A$ α5 selective compound L-655,708 (10 mg/kg, i.v.) to define full occupancy.

Figure 4:
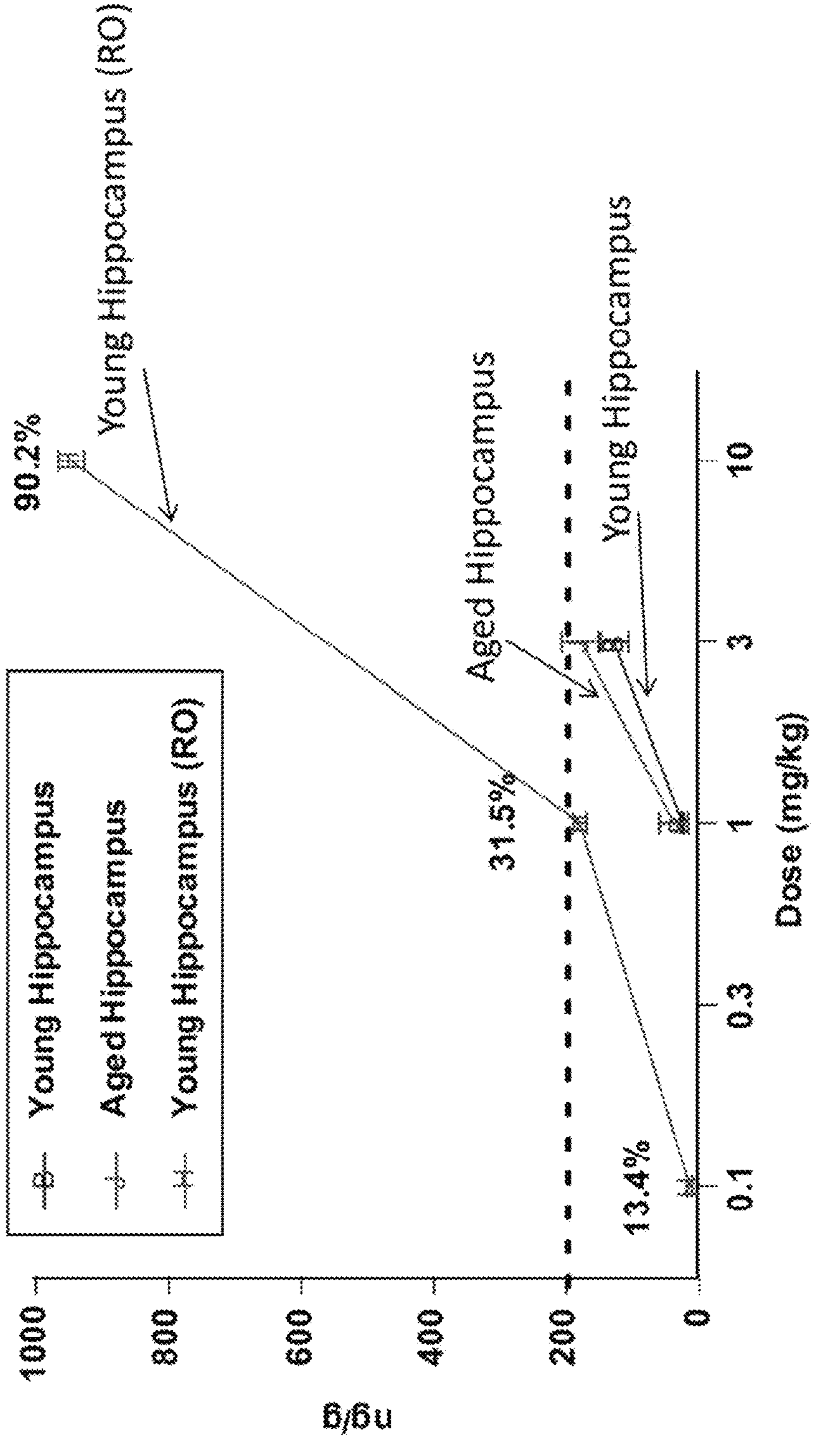

FIG. 4 is a graph showing exposure occupancy relationships for methyl 3,5-diphenylpyridazine-4-carboxylate in hippocampus. Methyl 3,5-diphenylpyridazine-4-carboxylate occupies about 32% of $GABA_A$ α5 receptors at exposures which are behaviorally active in aged-impaired rats.

Figure 5:
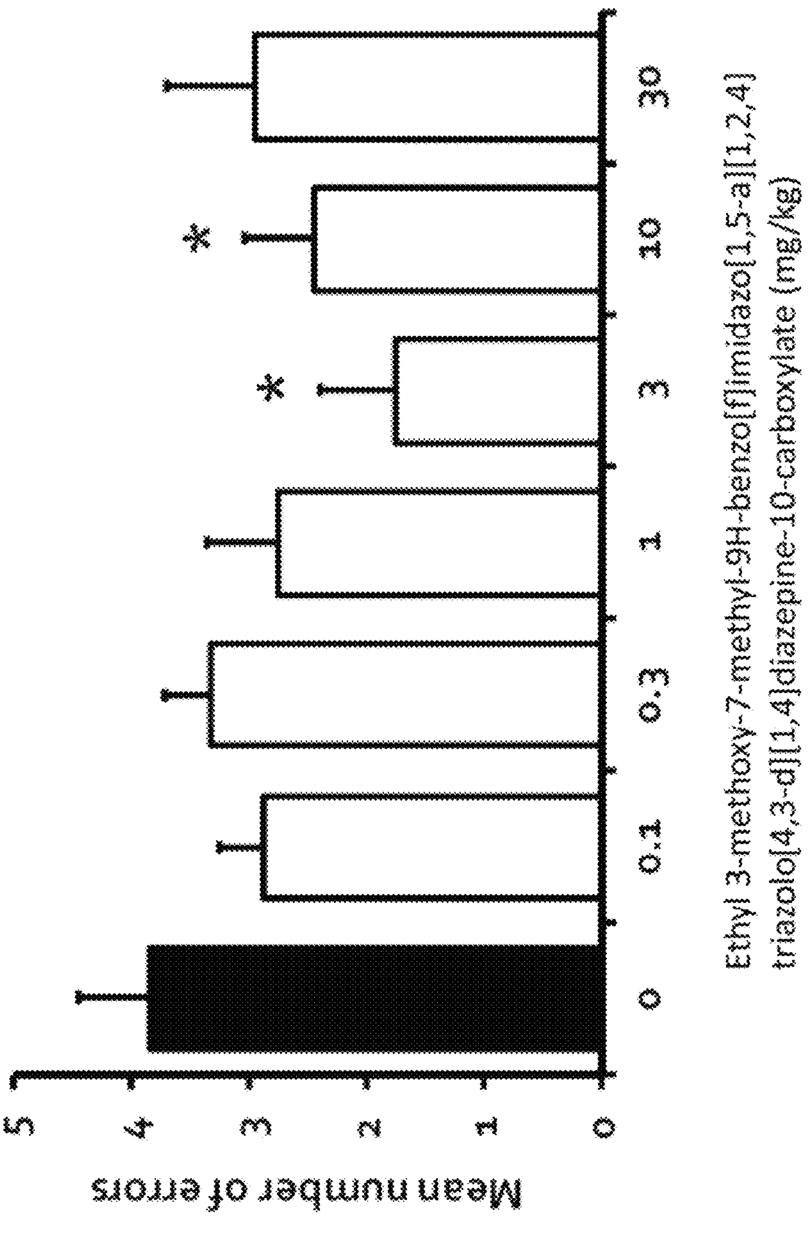

FIG. 5 is a graph depicting the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in an eight-arm Radial Arm Maze (RAM) test. FIG. 5 shows the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in the RAM test, where the vehicle control was tested 3 times, and the different doses of ethyl 3-methoxy-7-methyl-9H-benzo[f]imidazo[1,5-a][1,2,4]triazolo[4,3-d][1,4]diazepine-10-carboxylate were tested twice; In FIG. 5, black bars refer to rats treated with vehicle alone and open bars refer to rats treated with ethyl 3-methoxy-7-methyl-9H-benzo[f]imidazo[1,5-a][1,2,4]triazolo[4,3-d][1,4]diazepine-10-carboxylate at different doses.

Figure 6:
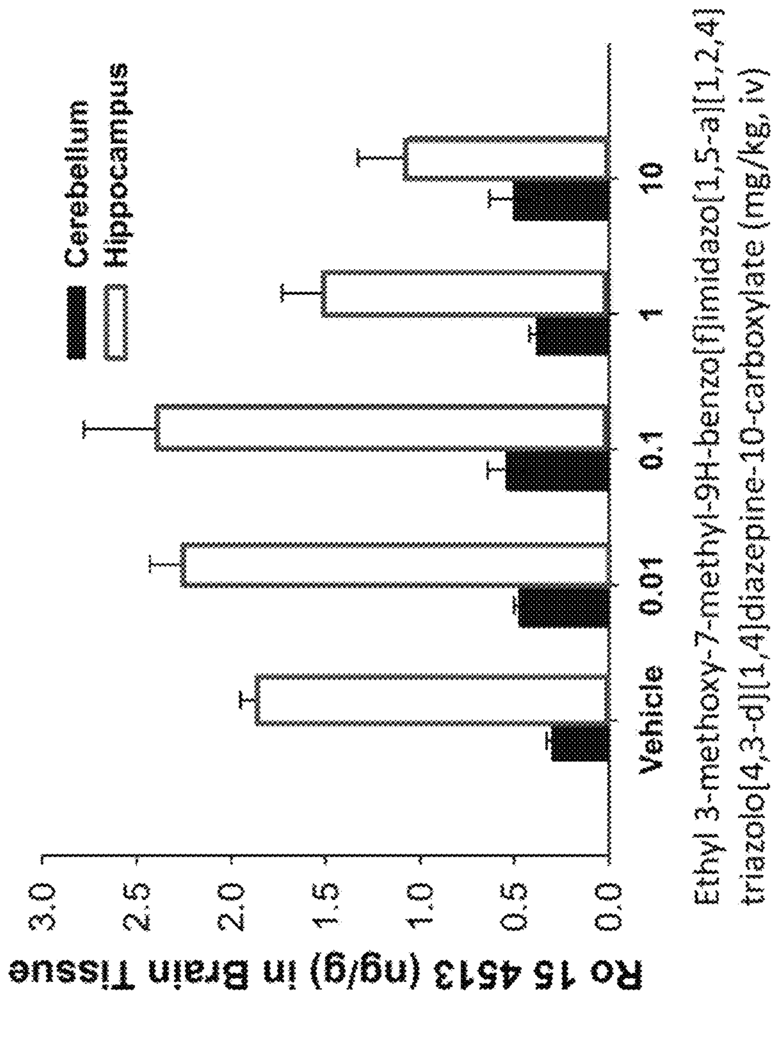

FIG. 6 is a graph showing the effect of ethyl 3-methoxy-7-methyl-9H-benzo[f]imidazo[1,5-a][1,2,4]triazolo[4,3-d][1,4]diazepine-10-carboxylate (administered intravenously) on the binding of Ro154513 in the hippocampus and cerebellum. Ethyl 3-methoxy-7-methyl-9H-benzo[f]imidazo[1,5-a][1,2,4]triazolo[4,3-d][1,4]diazepine-10-carboxylate blocked the binding of Ro154513 in the hippocampus but did not affect binding of Ro15413 in the cerebellum.

Figure 7:
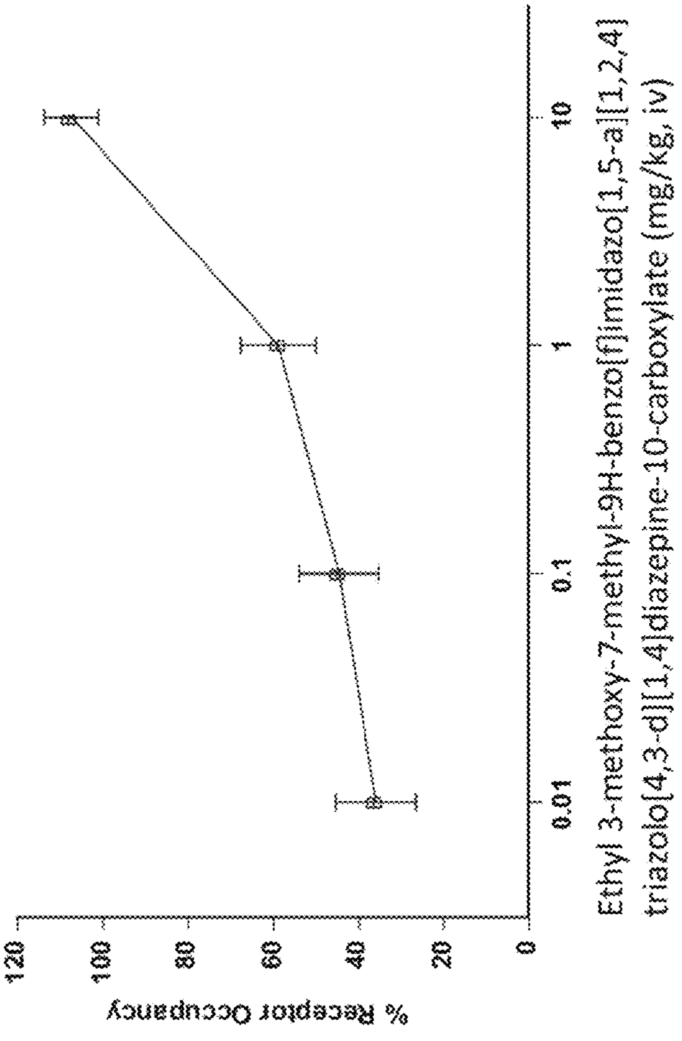

FIG. 7 is a graph showing dose-dependent $GABA_A$ α5 receptor occupancy by ethyl 3-methoxy-7-methyl-9H-benzo[f]imidazo[1,5-a][1,2,4]triazolo[4,3-d][1,4]diazepine-10-carboxylate administered intravenously, as calculated by the ratio between hippocampus (a region of high $GABA_A$a5 receptor density) exposure of RO 15-4513 and cerebellum (a region with low $GABA_A$a5 receptor density) exposure of RO 15-4513 to define full occupancy.

Figure 8A:
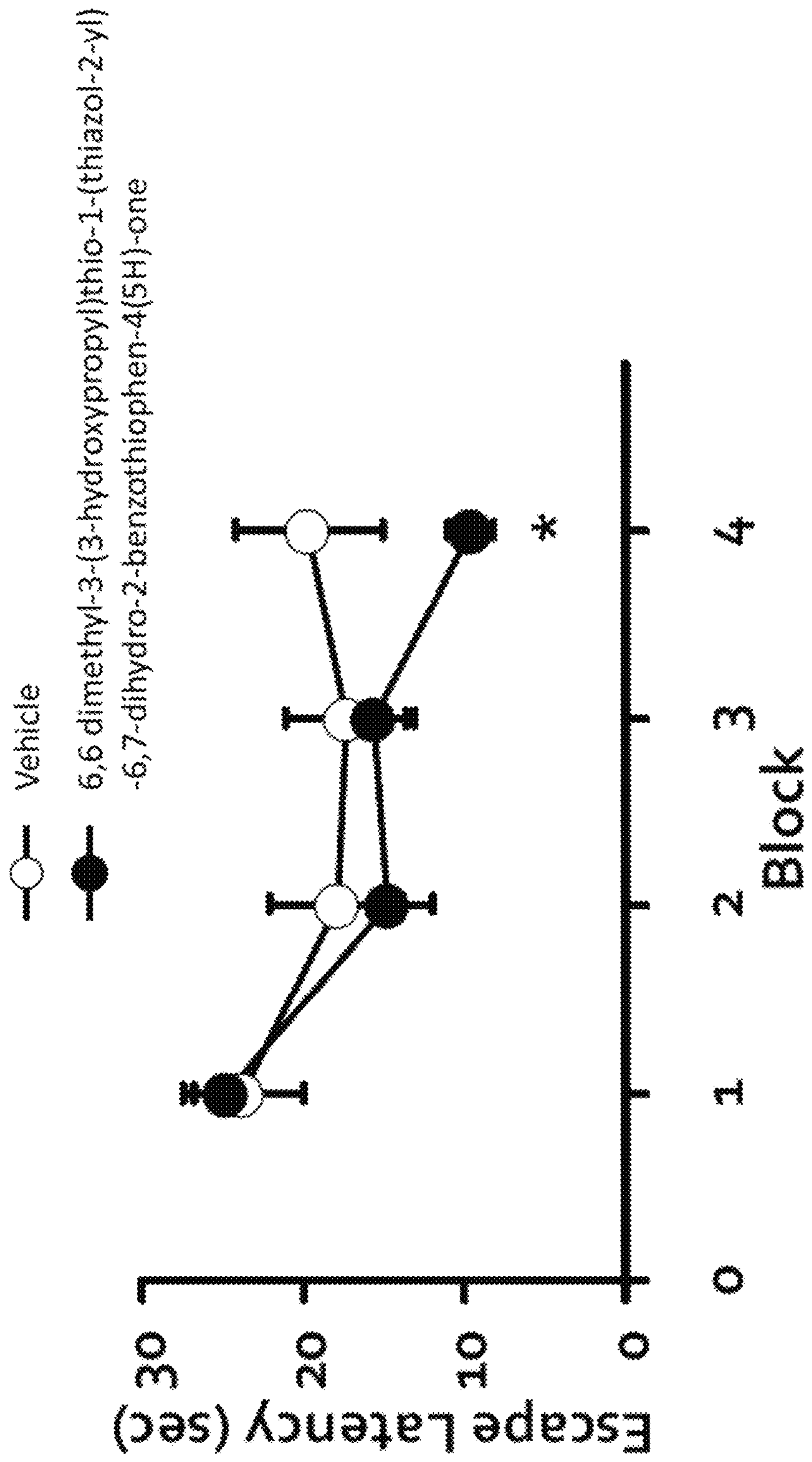
Figure 8B:
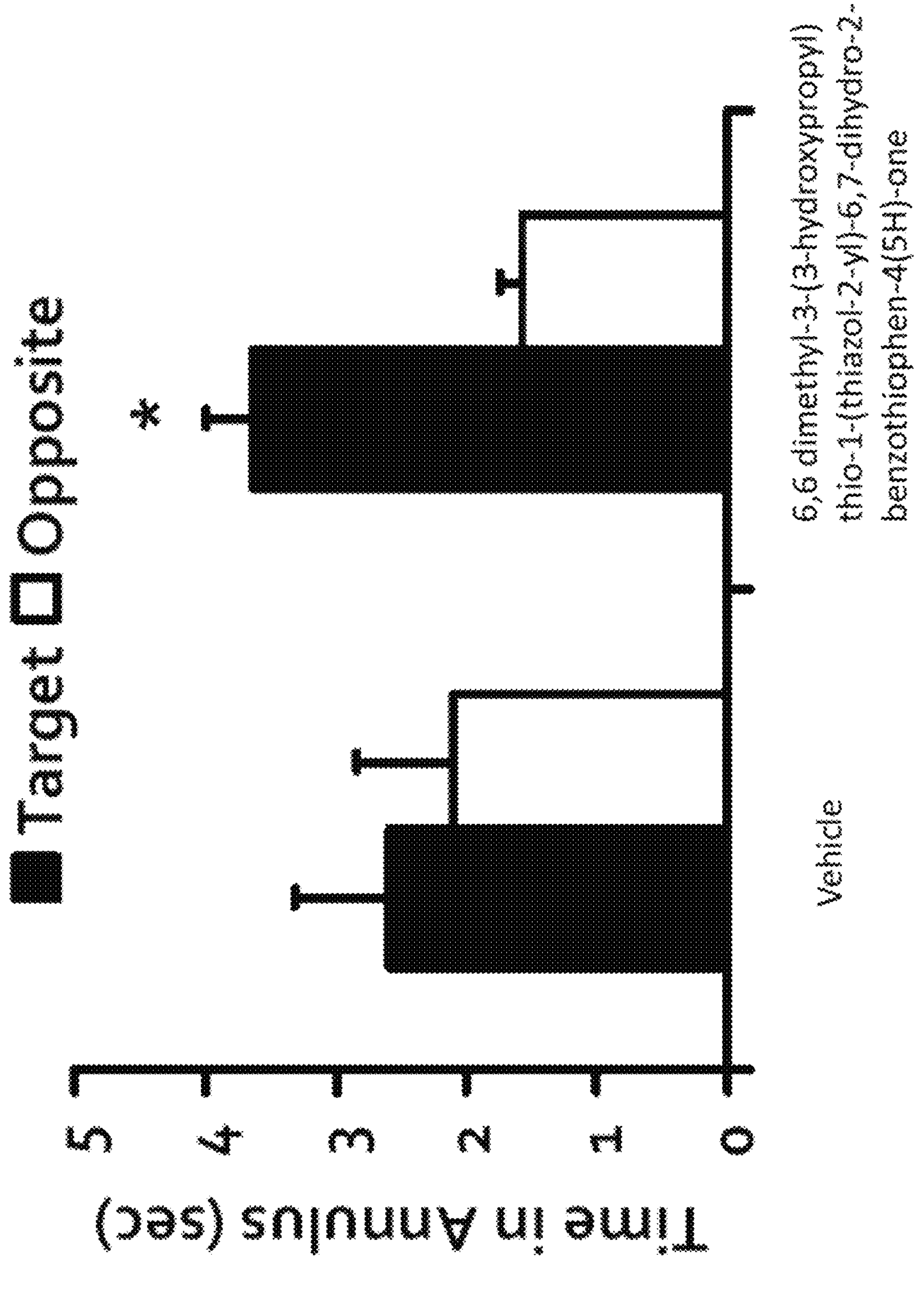
Figure 8C:
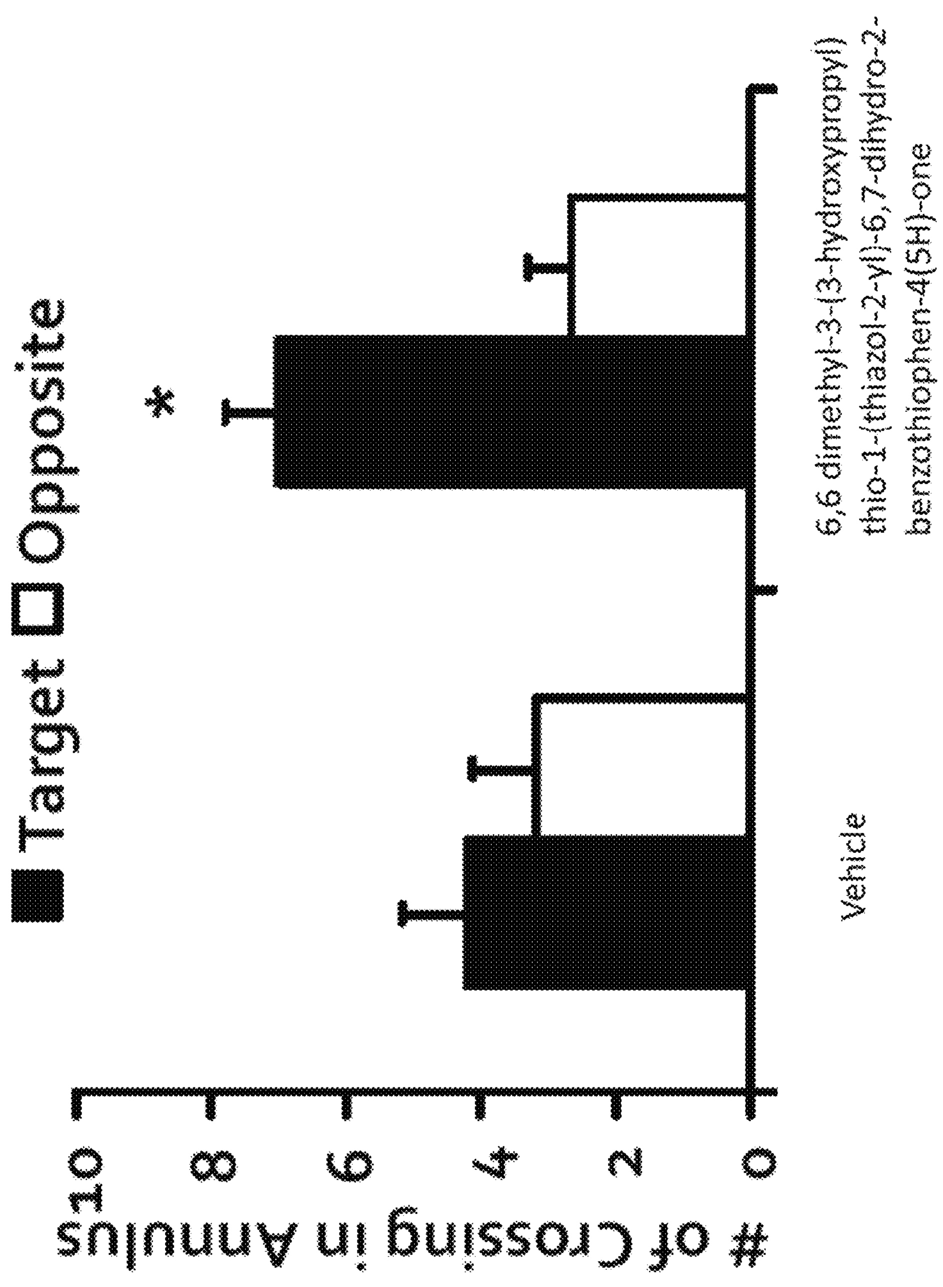

FIG. 8(A)-(C) are graphs showing the effect of 6,6 dimethyl-3-(3-hydroxypropyl)thio-1-(thiazol-2-yl)-6,7-dihydro-2-benzothiophen-4(5H)-one, as compared to vehicle dimethyl sulfoxide (DMSO), in aged-impaired rats using a Morris water maze behavioral task. FIG. 8(A) shows the escape latency (i.e., the average time in seconds rats took to find the hidden platform in the water pool) during training in rats received 6,6 dimethyl-3-(3-hydroxypropyl)thio-1-(thiazol-2-yl)-6,7-dihydro-2-benzothiophen-4(5H)-one and rats received vehicle DMSO; FIG. 8(B) shows the amount of time spent in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO; FIG. 8(C) shows number of crossing in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO.

DETAILED DESCRIPTION OF THE DISCLOSURE

Definitions

Unless otherwise defined herein, scientific and technical terms used in this disclosure shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science," McGraw-Hill Medical, New York, N.Y. (2000); Motulsky, "Intuitive Biostatistics," Oxford University Press, Inc. (1995); Lodish et al., "Molecular Cell Biology, $4^{th}$ ed.," W. H. Freeman & Co., New York (2000); Griffiths et al., "Introduction to Genetic Analysis, $7^{th}$ ed.," W. H. Freeman & Co., N.Y. (1999); and Gilbert et al., "Developmental Biology, $6^{th}$ ed.," Sinauer Associates, Inc., Sunderland, MA (2000).

Chemistry terms used herein are used according to conventional usage in the art, as exemplified by "The McGraw-Hill Dictionary of Chemical Terms," Parker S., Ed., McGraw-Hill, San Francisco, C.A. (1985).

All of the publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Recitation of ranges of values herein are merely intended to serve as a shorthand method of referring individually to each separate value falling within the range and including the endpoints, unless otherwise indicated herein, and each separate value is incorporated into the specification as if it were individually recited herein. For example, a range of 0-5 should be understood to encompass each value and subrange (i.e., 0, 1, 2, 3, 4, 5, 0-1, 0-2, 0-3, 0-4, 0-5, 1-2, 1-3, 1-4, 1-5, 2-3, 2-4, 2-5, 3-4, 3-5, or 4-5). All methods described herein can be performed in any suitable order unless otherwise indicated herein or otherwise clearly contradicted by context. Further, a disclosed 0-3 substitution means unsubstituted (0) or substituted with 1, 2 or 3 substituents (1, 2 or 3).

The singular forms "a," "an," and "the" include the plurals unless the context clearly dictates otherwise.

The term "including" is used to mean "including but not limited to". "Including" and "including but not limited to" are used interchangeably.

The term "agent" is used herein to denote a chemical compound (such as an organic or inorganic compound (including, such as, a compound of the present disclosure), a mixture of chemical compounds) Agents include, for example, agents which are known with respect to structure, and those which are not known with respect to structure. The α5-containing $GABA_A$ R agonist activity of such agents may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, expressing an interest in one's surroundings and self-care, speed of processing, reasoning and problem solving and social cognition.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or the explicit 3-alternative forced choice task, or MATRICS consensus neuropsychological test battery. See Folstein et al., *J Psychiatric Res* 12: 189-98, (1975); Robbins et al., Dementia 5: 266-81, (1994); Rey, L'examenppendor en psychologie, (1964); Kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later? Schizophr. *Bull.* 37, 1209-1217.

In animal model systems, cognitive function may be measured in various conventional ways known in the art, including using a Morris Water Maze (MWM), Barnes circular maze, elevated radial arm maze, T maze or any other mazes in which the animals use spatial information. Cognitive function can be assessed by reversal learning, extradimensional set shifting, conditional discrimination learning and assessments of reward expectancy. Other tests known in the art may also be used to assess cognitive function, such as novel object recognition and odor recognition tasks.

Cognitive function or impairment may be assessed by measuring the thickness of the cerebral cortex. The human cerebral cortex is a highly folded sheet of neurons and the thickness of which varies between 1 and 4.5 mm, with an overall average of approximately 2.5 mm. Cortical thinning in the temporal region is associated with the global cognition change. Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

In addition to assessing cognitive performance, the progression of cognitive impairment and dementia may be monitored by assessing surrogate changes in the brain of the subject. Surrogate changes include, without limitation, changes in regional brain volumes, perforant path degradation, and changes seen in brain function through resting state fMRI (R-fMRI), positron emission tomography (PET), single photon emission computed Tomography (SPECT), fluorodeoxyglucose positron emission tomography (FDG-PET), or any other imaging technique that allows one to measure brain function. Examples of regional brain volumes useful in monitoring the progression of age-related cognitive impairment and dementia include reduction of hippocampal volume and reduction in volume or thickness of entorhinal cortex. These volumes may be measured in a subject by, for example, MRI. Aisen et al., Alzheimer's & Dementia 6:239-246 (2010). 186 Perforant path degradation has been shown to be linked to age, as well as reduced cognitive performance. For example, older adults with more perforant path degradation tend to perform worse in hippocampus-dependent memory tests. Perforant path degradation may be monitored in subjects through ultrahigh-resolution diffusion tensor imaging (DTI). Yassa et al., PNAS 107:12687-12691 (2010). Resting-state fMRI (R-fMRI) involves imaging the brain during rest and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, particularly those areas whose connectivity increase or decrease with age, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. Aisen et al., Alzheimer's & Dementia 6:239-246 (2010), Herholz et al., NeuroImage 17:302-316 (2002).

"Promoting" cognitive function refers to affecting impaired cognitive function so that it more closely resembles the function of a normal, unimpaired, or in some aspects, an age-matched subject. Cognitive function may be promoted to any detectable degree, but in humans in some embodiments of this disclosure is promoted sufficiently to allow an impaired subject to carry out daily activities of normal life at a level of proficiency as close as possible to a normal, unimpaired subject or an age-matched normal, unimpaired subject.

In some cases, "promoting" cognitive function in a subject affected by age-related cognitive refers to affecting impaired cognitive function so that it more closely resembles the function of an aged-matched normal, unimpaired subject, or the function of a young adult subject. Cognitive function of that subject may be promoted to any detectable degree, but in humans in some embodiments of this disclosure is promoted sufficiently to allow an impaired subject to carry out daily activities of normal life at a level of proficiency close as possible to a normal, unimpaired subject or a young adult subject or an age-matched normal unimpaired subject.

"Preserving" cognitive function refers to affecting normal or impaired cognitive function such that it does not decline or does not fall below that observed in the subject upon first presentation or diagnosis, or delays at least to some level decline in cognitive function.

"Improving" cognitive function includes promoting cognitive function and/or preserving cognitive function in a subject.

"Cognitive impairment" refers to cognitive function in subjects that is not as robust as that expected in a normal, unimpaired, or in some cases an age-matched, subject. In some cases, cognitive function is reduced by about 5%, about 10%, about 30%, or more, compared to cognitive function expected in a normal, unimpaired, or in some aspects, an age-matched subject.

"Age-related cognitive impairment" refers to cognitive impairment in aged subjects, wherein their cognitive function is not as robust as that expected in an age-matched normal subject (i.e., subjects with mean scores for a given age in a cognitive test) or in some cases, as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with, for example, Mild Cognitive Impairment (MCI) (including amnestic MCI and non-amnestic MCI), Age-Associated Memory Impairment (AAMI), and Age-related Cognitive Decline (ARCD).

"Cognitive impairment" associated with AD or related to AD or in AD refers to cognitive function in subjects that is not as robust as that expected in subjects who have not been diagnosed with AD using conventional methodologies and standards.

"Mild Cognitive Impairment" or "MCI" refers to a condition characterized by isolated memory impairment unaccompanied other cognitive abnormalities and relatively normal functional abilities. One set of criteria for a clinical characterization of MCI specifies the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV or related guidelines). Petersen et al., Srch. Neurol. 56: 303-308 (1999); Petersen, "Mild cognitive impairment: Aging to Alzheimer's Disease." Oxford University Press, N.Y. (2003). The cognitive deficit in subjects with MCI may involve any cognition area or mental process including memory, language, association, attention, perception, problem solving, executive function and visuospatial skills. See, e.g., Winbald et al., J. Intern. Med. 256:240-240, 2004; Meguro, Acta. Neurol. Taiwan. 15:55-57, 2008; Ellison et al., *CNS Spectr.* 13:66-72, 2008, Petersen, Semin. Neurol. 27:22-31, 2007. MCI is further subdivided into amnestic MCI (aMCI) and non-amnestic MCI, characterized by the impairment (or lack thereof) of memory in particular. MCI is defined as aMCI if memory is found to be impaired given the age and education level of the subject. If, on the other hand, the memory of the subject is found to be intact for age and education, but other non-memory cognitive domains are impaired, such as language, executive function, or visuospatial skills, MCI is defined as non-amnestic MCI. aMCI and non-amnestic MCI can both be further subdivided into single or multiple domain MCI. aMCI-single domain refers to a condition where memory, but not other cognitive areas are impaired. aMCI-multiple domain refers to a condition where memory and at least one other cognitive area are impaired. Non-amnestic MCI is single domain or multiple domain dependent on whether nor not more than one non-memory cognitive area is impaired. See, e.g., Peterson and Negash, *CNS Spectr.* 13:45-53, 2008.

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., J Psychiatric Res 12: 189-98 (1975); Robbins et al., Dementia 5: 266-81 (1994); Kluger et al., J Geriatric Psychiatry Neurol 12:168-79 (1999).

"Age-Associated Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

"Dementia" refers to a condition characterized by severe cognitive deficit that interferes in normal activities of daily living. Subjects with dementia also display other symptoms such as impaired judgment, changes in personality, disorientation, confusion, behavior changes, trouble speaking, and motor deficits. There are different types of dementias, such as Alzheimer's disease (AD), vascular dementia, dementia with Lewy bodies, and frontotemporal dementia.

Alzheimer's disease (AD) is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

Vascular dementia is caused by strokes. Symptoms overlap with those of AD, but without the focus on memory impairment.

Dementia with Lewy bodies is characterized by abnormal deposits of alpha-synuclein that form inside neurons in the brain. Cognitive impairment may be similar to AD, including impairments in memory and judgment and behavior changes.

Frontotemporal dementia is characterized by gliosis, neuronal loss, superficial spongiform degeneration in the frontal cortex and/or anterior temporal lobes, and Picks' bodies. Symptoms include changes in personality and behavior, including a decline in social skills and language expression/comprehension.

"Post-traumatic stress disorder (PTSD)" refers to an anxiety disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses produce anxiety and can have significant impact, both chronic and acute, on a patient's quality of life and physical and emotional health. PTSD is also associated with impaired cognitive performance, and older individuals with PTSD have greater decline in cognitive performance relative to control patients.

"Schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. While abnormalities in the brain are proposed to underlie the full spectrum of psychopathology in schizophrenia, currently available antipsychotics are largely ineffective in treating cognitive impairments in patients.

"Bipolar disorder" or "BP" or "manic depressive disorder" or "manic depressive illness" refers to a chronic psychological/mood disorder which can be characterized by significant mood changes including periods of depression and euphoric manic periods. BP may be diagnosed by a skilled physician based on personal and medical history, interview consultation and physical examinations. The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

"Amyotrophic lateral sclerosis," also known as ALS, refers to a progressive, fatal, neurodegenerative disease characterized by a degeneration of motor neurons, the nerve cells in the central nervous system that control voluntary muscle movement. ALS is also characterized by neuronal degeneration in the entorhinal cortex and hippocampus, memory deficits, and neuronal hyperexcitability in different brain areas such as the cortex.

"Cancer-therapy-related cognitive impairment" refers to cognitive impairment that develops in subjects that are treated with cancer therapies such as chemotherapy (e.g., chemobrain) and radiation. Cytotoxicity and other adverse side-effects on the brain of cancer therapies result in cognitive impairment in such functions as memory, learning and attention.

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

"Autism," as used herein, refers to an autism spectrum disorder characterized by a neural development disorder leading to impaired social interaction and communication by restricted and repetitive behavior. "Autism Spectrum Disorder" refers to a group of developmental disabilities that includes: autism; Asperger syndrome; pervasive developmental disorder not otherwise specified (PDD-NOS or atypical autism); Rett syndrome; and childhood disintegrative disorder.

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, Curr. Neurol. Neurosci. Rep. 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, $4^{th}$ edition text revision (DSM-IV-TR) (2000) diagnostic criteria that include characteristics of obsessions and compulsions.

Substance addiction (e.g., drug addiction, alcohol addiction) is a mental disorder. The addiction is not triggered instantaneously upon exposure to substance of abuse. Rather, it involves multiple, complex neural adaptations that develop with different time courses ranging from hours to days to months (Kauer J. A. *Nat. Rev. Neurosci.* 2007, 8, 844-858). The path to addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance (s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize addictions to other controlled substances. The craving for alcohol, as well as other controlled substances, often is as strong as the need for food or water. Thus, an alcoholic may continue to drink despite serious family, health and/or legal ramifications.

The term "brain cancer" as used herein refers to neoplasms, which initiate in the brain or metastatic brain cancer, which starts somewhere else in the body and moves to the brain. The term "brain cancer" as used herein include both benign and malignant cancer cells. The term "brain cancer expressing $\alpha$5-GABA$_A$R" (also referred to herein as "$\alpha$5-GABA$_A$R expressing brain cancer") refers to a brain cancer, wherein GABA pathway signaling is potentially upregulated due to the increased expression of $\alpha$5-GABA$_A$R. $\alpha$5-GABA$_A$R expressing brain cancer may include, medulloblastoma, glioblastoma multiforme, astrocytomas, oligodendrogliomas, ependymomas, meningiomas, and the like.

The term "medulloblastoma" refers to a highly malignant primary brain tumor that originates in the cerebellum or posterior fossa. It is one of the most common malignant brain tumors and is more frequent in people under than 20 years of age than in adults. Medulloblastomas can spread through the CNS and frequently metastasize to different locations in the brain and spine. Medulloblastomas are divided into four subgroups based on molecular features of tumor cells namely, wingless (WNT), sonic hedgehog (SHH), group 3, and group 4. Among those types, groups 3 and 4, account for ~60% of medulloblastomas. Group 3 tumors share high expression of $\alpha$5-GABA$_A$R. The symptoms of medulloblastoma are mainly due to increased intracranial pressure due to blockage of the fourth ventricle and are predominantly neurological, with other symptoms such as vomiting also occurring.

The term "risk factors for cognitive impairment" refers to one or more risks that are predictive of or associated with developing cognitive decline or cognitive impairment or the progression of the decline or impairment. Such risks are associated with aging, with one or more genetic risks selected from the group of genomic variants, mutations, or polymorphs associated with a change in the expression of genes selected from the group consisting of ATP-binding cassette sub-family A member 7 (ABCA7), Clusterin (CLU), Complement receptor type 1 (CR1), Phosphatidylinositol binding clathrin assembly protein (PICALM), Phospholipase D3 (PLD3), Triggering receptor expressed on myeloid cells (TREM2), and sortilin related receptor 1 (SORL1) in the genome of the subject; with the presence of at least one allele of the APOE4 gene in the genome of the subject, with the presence of one of more biofluid biomarkers selected from the group consisting of p-tau, t-tau, and amyloid β in the subject, or with the presence of altered hippocampal functional connectivity in the subject.

"Treating" a condition or patient refers to taking steps to obtain beneficial or desired results, including, but not limited to, clinical results. Beneficial or desired clinical results include, but are not limited to, preventing or slowing the progression of the disease or disorder, or alleviation, amelioration, or slowing the progression, of one or more symptoms of cognitive impairment associated with the CNS disorders or risk factors of this disclosure, such as age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, treatment comprises preventing or slowing the progression, of cognitive impairment associated with a CNS disorder or risk factor (such as one as described herein). In certain embodiments, treatment comprises alleviation, amelioration, or slowing the progression of one or more symptoms of cognitive impairment associated with that CNS disorder or risk factor. In certain embodiments, the symptom to be treated is cognitive impairment or cognitive deficit. Treating age-related cognitive impairment further comprises slowing or delaying the conversion of age-related cognitive impairment (including, but not limited to age-related MCI, ARCD and AAMI) into dementia (e.g., AD).

"Treating cognitive impairment" refers to taking steps to improve cognitive function in a subject with cognitive impairment so that the subject's performance in one or more cognitive tests is improved to any detectable degree, or is prevented from further decline or whose progression to such decline is slowed. In some embodiments of this disclosure, a subject's cognitive function, after treatment as described in this disclosure, more closely resembles the function of a normal, unimpaired, or in some aspects, an age-matched, subject. Treatment of cognitive impairment in humans may improve cognitive function to any detectable degree, but in some embodiments is improved sufficiently to allow the impaired subject to carry out daily activities of normal life at the same level of proficiency as a normal, unimpaired subject. In some cases, "treating cognitive impairment" refers to taking steps to improve cognitive function in a subject with cognitive impairment so that the subject's performance in one or more cognitive tests is improved to any detectable degree, or is prevented from further decline or such decline is delayed. Preferably, that subject's cognitive function, after treatment as described in this disclosure more closely resembles the function of a normal, unimpaired, or in some aspects, an age-matched, subject. In some cases, "treating cognitive impairment" in a subject affected by age-related cognitive impairment refers to takings steps to improve cognitive function in the subject so that the subject's cognitive function, after treatment of as described in this disclosure, more closely resembles the function of an age-matched normal, unimpaired subject, or in some aspects, the function of a young adult subject.

"Administering" or "administration of" a substance, a compound or an agent to a subject in accordance with this disclosure can be carried out using one of a variety of methods known to those skilled in the art. For example, a compound or an agent can be administered, intravenously, arterially, intradermally, intramuscularly, intraperitoneally, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. In some embodiments of this disclosure the agent or compound is administered orally. Administering can also be performed, for example, once, a plurality of times, and/or over one or more extended periods. In some embodiments, the agent or compound is administered once per day. In some embodiments, the agent or compound of this disclosure is administered in immediate release, delayed/slow release, or extended release form. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g., solubility, digestibility, bioavailability, stability and toxicity). In some embodiments, a compound or an agent is administered orally, e.g., to a subject by ingestion, or intravenously, e.g., to a subject by injection. In some embodiments, the orally administered compound or agent is in an extended release or slow-release formulation, or administered using a device for such slow or extended release.

As used herein, a "α5-containing $GABA_A$ R agonist," "α5-containing $GABA_A$ R agonist" or a "$GABA_A$ α5 receptor agonist" and other variations as used herein refer to a compound that enhances the function of α5-containing $GABA_A$ R, i.e., a compound that increase GABA-gated Cl-currents. In some embodiments, α5-containing $GABA_A$ R agonist as used herein refers to a positive allosteric modulator, which potentiates the activity of GABA. A5-containing $GABA_A$ R agonists, suitable for use in the present disclosure, include the α5-containing $GABA_A$ R agonists of all formulas and specific α5-containing $GABA_A$ R agonists described herein, and their hydrates, solvates, polymorphs, salts (e.g., pharmaceutically acceptable salts), isomers (e.g., stereoisomers, E/Z isomers, and tautomers), and combinations thereof.

"Antipsychotic", "antipsychotic agent", "antipsychotic drug", or "antipsychotic compound" refers to (1) a typical or an atypical antipsychotic; (2) an agent that is selected from dopaminergic agents, glutamatergic agents, NMDA receptor positive allosteric modulators, glycine reuptake inhibitors, glutamate reuptake inhibitor, metabotropic glutamate receptors (mGluRs) agonists or positive allosteric modulators (PAMs) (e.g., mGluR2/3 agonists or PAMs), glutamate receptor glur5 positive allosteric modulators (PAMs), M1 muscarinic acetylcholine receptor (mAChR) positive allosteric modulators (PAMs), histamine H3 receptor antagonists, AMPA/kainate receptor antagonists, ampakines (CX-516), glutathione prodrugs, noradrenergic agents, serotonin receptor modulators, cholinergic agents, cannabinoid CB1 antagonists, neurokinin 3 antagonists, neurotensin agonists, MAO B inhibitors, PDE10 inhibitors, nNOS inhibits, neurosteroids, and neurotrophic factors, alpha-7 agonists or positive allosteric modulators (PAMs) PAMs, serotonin 2C agonists; and/or (3) an agent that is useful in treating one or more signs or symptoms of schizophrenia or bipolar disorder (in particular, mania).

"Typical antipsychotics", as used herein, refer to conventional antipsychotics, which produce antipsychotic effects as well as movement related adverse effects related to disturbances in the nigrostriatal dopamine system. These extrapyramidal side effects (EPS) include Parkinsonism, akathisia, tardive dyskinesia and dystonia. See Baldessarini and Tarazi in Goodman & Gilman's The Pharmacological Basis of Therapeutics 10 Edition, 2001, pp. 485-520.

"Atypical antipsychotics", as used herein, refer to antipsychotic drugs that produce antipsychotic effects with little or no EPS and include, but are not limited to, aripiprazole, asenapine, clozapine, iloperidone, olanzapine, lurasidone, paliperidone, quetiapine, risperidone and ziprasidone. “Atypical” antipsychotics differ from conventional antipsychotics in their pharmacological profiles. While conventional antipsychotics are characterized principally by D2 dopamine receptor blockade, atypical antipsychotics show antagonist effects on multiple receptors including the 5Hta and 5HTc serotonin receptors and varying degrees of receptor affinities. Atypical antipsychotic drugs are commonly referred to as serotonin/dopamine antagonists, reflecting the influential hypothesis that greater affinity for the 5HT2 receptor than for the D2 receptor underlies “atypical” antipsychotic drug action or “second generation” antipsychotic drugs. However, the atypical antipsychotics often display side effects, including, but not limited to, weight gain, diabetes (e.g., type II diabetes mellitus), hyperlipidemia, QTc interval prolongation, myocarditis, sexual side effects, extrapyramidal side effects and cataract. Thus, atypical antipsychotics do not represent a homogeneous class, given their differences in the context of both alleviation of clinical symptoms and their potential for inducing side effects such as the ones listed above. Further, the common side effects of the atypical antipsychotics as described above often limit the antipsychotic doses that can be used for these agents.

Memantine is chemically known as 3,5-dimethyladamantan-1-amine or 3,5-dimethyltricyclo [3.3.1.13,7]decan-1-amine, which is an uncompetitive N-methyl-D-aspartate (NMDA) receptor antagonist with moderate affinity. The proprietary names for memantine include: Axura® and Akatinol® (Merz), Namenda® (Forest Laboratories), Ebixa® and Abixa® (Lundbeck), and Memox® (Unipharm). Memantine is approved for the treatment of moderate to severe Alzheimer’s disease (AD) in the United States at a dose of up to 28 mg/day. Derivatives or analogs of memantine, which include compounds that structurally or chemically resemble memantine, are also useful in the present disclosure. Such derivatives or analogs of memantine include, but are not limited to those compounds disclosed in U.S. Pat. Nos. 3,391,142; 4,122,193; 4,273,774; and 5,061,703; U.S. Patent Application Publication US20040087658, US20050113458, US20060205822, US20090081259, US20090124659, and US20100227852; EP Patent Application Publication EP2260839A2; EP Patent EP1682109B1; and PCT Application Publication WO2005079779, all of which are incorporated herein by reference. Memantine, as used in the present invention, includes memantine and its derivatives and analogs, as well as hydrates, polymorphs, prodrugs, salts, and solvates thereof. Memantine, as used herein, also includes a composition comprising memantine or a derivative or an analog or a pharmaceutically acceptable salt, hydrate, solvate, polymorph, or prodrug thereof, wherein the composition may optionally be used in combination with at least one additional therapeutic agent (such as a therapeutic agent useful for treating a CNS disorder or cognitive impairments associated thereof). In some embodiments, the memantine composition suitable for use in the present invention comprises memantine and a second therapeutic agent that is donepezil (under the trade name Aricept®).

“Acetylcholinesterase inhibitor” or “AchEI” as used herein refers to an agent that inhibits the ability of the cholinesterase enzyme to break down the neurotransmitter acetylcholine, thereby increasing the concentration and duration of acetylcholine, mainly in brain synapses or neuromuscular junctions. AchEIs suitable for use in this disclosure may include, for example, the subcategories of (i) reversible non-competitive inhibitors or reversible competitive inhibitors, (ii) irreversible, and (iii) quasi-irreversible inhibitors.

“SV2A inhibitor” as used herein refers to any compound that binds to SV2A and reduces synaptic function by reducing pre-synaptic vesicle release (See, e.g., Noyer et al. 1995; Fuks et al. 2003; Lynch et al. 2004; Gillard et al. 2006; Custer et al., 2006; Smedt et al., 2007; Yang et al., 2007; Meehan, “Levetiracetam has an activity-dependent effect on inhibitory transmission,” *Epilepsia,* 2012 Jan. 31; and Example 8 of WO 2001/62726, all of which are specifically incorporated herein by reference.) A compound may be an SV2A inhibitor even if it does not itself bind to SV2A, as long as it causes, or affects the ability of, another compound to bind SV2A or reduce synaptic function by reducing pre-synaptic vesicle release. SV2A inhibitors suitable for the methods, uses, pharmaceutical compositions, or combinations of the present disclosure include the specific SV2A inhibitors described herein (see also PCT application WO2022/011318), and pharmaceutically acceptable salts, hydrates, solvates, polymorphs, or isomers thereof.

The term “simultaneous administration,” as used herein, means that a α5-containing $GABA_A$ R agonist (e.g., a α5-containing $GABA_A$ R positive allosteric modulator) or combinations of and a second therapeutic agent (e.g., an antipsychotic, memantine AchEI or an SV2A inhibitor), or their pharmaceutically acceptable salts, hydrates, solvates, or polymorphs, are administered with a time separation of no more than about 15 minutes, and in some embodiments no more than about 10 minutes. When the drugs are administered simultaneously, the α5-containing $GABA_A$ R agonist (e.g., an α5-containing $GABA_A$ R positive allosteric modulator) and a second therapeutic agent (e.g., an antipsychotic, memantine, AchEI or an SV2A inhibitor), or their salts, hydrates, solvates, or polymorphs, may be contained in the same dosage (e.g., a unit dosage form comprising both the α5-containing $GABA_A$ R agonist (e.g., an α5-containing $GABA_A$ R positive allosteric modulator) and a second therapeutic agent (e.g., an antipsychotic, memantine, AchEI or an SV2A inhibitor) or in discrete dosages (e.g., the α5-containing $GABA_A$ R agonist (e.g., an α5-containing $GABA_A$ R positive allosteric modulator) or its salt, hydrate, solvate, or polymorph is contained in one dosage form and a second therapeutic agent (e.g., an antipsychotic, memantine, AchEI or an SV2A inhibitor), or its salt, hydrate, solvate, or polymorph) is contained in another dosage form.

The term “sequential administration” as used herein means that the α5-containing $GABA_A$ R agonist (e.g., a α5-containing $GABA_A$ R positive allosteric modulator) and a second therapeutic agent (e.g., an antipsychotic, memantine AchEI or an SV2A inhibitor), or their pharmaceutically acceptable salts, hydrates, solvates, polymorphs, are administered with a time separation of more than about 15 minutes, and in some embodiments more than about one hour, or up to 12-24 hours. Either the α5-containing $GABA_A$ R agonist (e.g., a α5-containing $GABA_A$ R positive allosteric modulator) or a second therapeutic agent (e.g., an antipsychotic, memantine, AchEI or an SV2A inhibitor) may be administered first. The α5-containing $GABA_A$ R agonist (e.g., a α5-containing $GABA_A$ R positive allosteric modulator) and a second therapeutic agent (e.g., an antipsychotic, memantine, AchEI or an SV2A inhibitor), or their salts, hydrates, solvents, or polymorphs, for sequential administration may be contained in discrete dosage forms, optionally contained in the same container or package.

A “therapeutically effective amount” of a drug or agent of this disclosure is an amount of a drug or an agent that, when administered to a subject will have the intended therapeutic effect, e.g. improving cognitive function in a subject, e.g., a patient having cognitive impairment associated with a CNS disorder. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment or other symptoms of the CNS disorder (such as age-related cognitive impairment, Mild Cognitive Impairment (MCI), dementia, Alzheimer's Disease (AD), prodromal AD, post-traumatic stress disorder (PTSD), schizophrenia, bipolar, ALS, cancer-therapy-related cognitive impairment, mental retardation, Parkinson's disease (PD), autism spectrum disorders, fragile X disorder, Rett syndrome, compulsive behavior, and substance addiction), and the therapeutics or combination of therapeutics selected for administration, and the mode of administration. The skilled worker can readily determine the effective amount for a given situation by routine experimentation.

The compounds of the present disclosure also include prodrugs, analogs or derivatives. The term "prodrug" is art-recognized and is intended to encompass compounds or agents which, under physiological conditions, are converted into α5-containing $GABA_A$ R positive allosteric modulators. A common method for making a prodrug is to select moieties which are hydrolyzed or metabolized under physiological conditions to provide the desired compound or agent. In other embodiments, the prodrug is converted by an enzymatic activity of the host animal to a α5-containing $GABA_A$ R positive allosteric modulator.

The term "aliphatic" as used herein refers to a straight chained or branched alkyl, alkenyl or alkynyl. It is understood that alkenyl or alkynyl embodiments need at least two carbon atoms in the aliphatic chain. Aliphatic groups typically contain from 1 (or 2) to 12 carbons, such as from 1 (or 2) to 4 carbons.

The term "aryl" as used herein refers to a monocyclic or bicyclic carbocyclic aromatic ring system. Aryl as used herein includes a (C6-C12)-aryl-. For example, aryl as used herein can be a C6-C10 monocyclic or C8-C12 bicyclic carbocyclic aromatic ring system. In some embodiments, aryl as used herein can be a (C6-C10)-aryl-. Phenyl (or Ph) is an example of a monocyclic aromatic ring system. Bicyclic aromatic ring systems include systems wherein both rings are aromatic, e.g., naphthyl, and systems wherein only one of the two rings is aromatic, e.g., tetralin.

The term "heterocyclic" as used herein refers to a monocyclic or bicyclic non-aromatic ring system having 1 to 4 heteroatom or heteroatom groups selected from O, N, NH, S, SO, or $SO_2$ in a chemically stable arrangement. Heterocyclic as used herein includes a 3- to 12-membered heterocyclyl-having 1-4 heteroatoms independently selected from O, N, NH, S, SO, or $SO_2$. For example, heterocyclic as used herein can be a 3- to 10-membered monocyclic or 8- to 12-membered bicyclic non-aromatic ring system having 1 to 4 heteroatom or heteroatom groups selected from O, N, NH, S, SO, or $SO_2$ in a chemically stable arrangement. In some embodiments, heterocyclic as used herein can be a 3- to 10-membered heterocyclyl-having 1-4 heteroatoms independently selected from O, N, NH, S, SO, or $SO_2$. In a bicyclic non-aromatic ring system embodiment of "heterocyclyl," one or both rings may contain said heteroatom or heteroatom groups. In another bicyclic "heterocyclyl" embodiment, one of the two rings may be aromatic. In yet another heterocyclic ring system embodiment, a non-aromatic heterocyclic ring may optionally be fused to an aromatic carbocycle.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2 -piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein refers to a monocyclic or bicyclic aromatic ring system having 1 to 4 heteroatom or heteroatom groups selected from O, N, NH or S in a chemically stable arrangement. Heteroaryl as used herein includes a 5- to 12-membered heteroaryl having 1-4 heteroatoms independently selected from O, N, NH or S. In some embodiments, heteroaryl as used herein can be a 5- to 10-membered heteroaryl having 1-4 heteroatoms independently selected from O, N, NH or S. For example, heteroaryl as used herein can be a 5- to 10-membered monocyclic or 8- to 12-membered bicyclic aromatic ring system having 1 to 4 heteroatom or heteroatom groups selected from O, N, NH or S in one or both rings in a chemically stable arrangement. In such a bicyclic aromatic ring system embodiment of "heteroaryl":

both rings are aromatic; and one or both rings may contain said heteroatom or heteroatom groups.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "cycloalkyl or cycloalkenyl" refers to a monocyclic or fused or bridged bicyclic carbocyclic ring system that is not aromatic. For example, cycloalkyl or cycloalkenyl as used herein can be a C3-C10 monocyclic or fused or bridged C8-C12 bicyclic carbocyclic ring system that is not aromatic. Cycloalkenyl rings have one or more units of unsaturation. Preferred cycloalkyl or cycloalkenyl groups include cyclopropyl, cyclobutyl, cyclopentyl, cyclohexyl, cyclohexenyl, cycloheptyl, cycloheptenyl, norbornyl, adamantyl and decalinyl.

The term "heteroaralkyl" refers to an alkyl in which a heteroaryl group is substituted for an alkyl H atom. For example, the alkyl group is any straight chain hydrocarbon, and can include from 1 to 12 carbon atoms (e.g., methyl, ethyl, propyl, butyl, pentyl, hexyl, heptyl, octyl, nonyl, decyl, undecyl and dodecyl), wherein said alkyl group can be substituted with any heteroaryl group, including but not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl.

When a substituted moiety is described without indicating the atom via which such moiety is bonded to a substituent, then the substituent may be bonded via any appropriate atom in such moiety. For example, for a substituted 5- to 10-membered heteroaryl, a substituent on the heteroaryl can be bonded to any of the ring-forming atoms of the heteroaryl ring that are substitutable (i.e., atoms bound to one or more hydrogen atoms).

When a bond to a substituent is shown to cross a bond connecting two atoms in a ring, then such substituent may be bonded to any of the ring-forming atoms in that ring that are substitutable (i.e., atoms bound to one or more hydrogen atoms), unless otherwise specified or otherwise implicit from the context. For example, when a R group is defined as a pyridine, and said pyridine is depicted as follows:

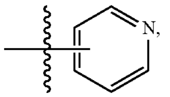

the pyridine ring may be bound to the benzodiazepine derivative through any one of the ring carbon atoms in the pyridine ring. As another example, when a R group is defined as a pyrazole, and said pyrazole is depicted as follows:

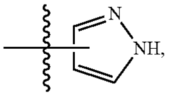

the pyrazole ring may be bound to the benzodiazepine derivative through any one of the ring carbon atoms of the pyrazole ring, or to the $sp^3$ N-atom.

As used herein, the carbon atom designations may have the indicated integer and any intervening integer. For example, the number of carbon atoms in a (C1-C4)alkyl group is 1, 2, 3, or 4. It should be understood that these designations refer to the total number of atoms in the appropriate group. For example, in a (3- to 10-membered) heterocyclyl the total number of carbon atoms and heteroatoms is 3 (as in aziridine), 4, 5, 6 (as in morpholine), 7, 8, 9, or 10.

"Pharmaceutically acceptable salt" is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid.

Compounds and their salts can be in the form of a solvate, which is included within the scope of the present invention. Such solvates include for example hydrates, alcoholates and the like. See, e.g., WO 01/062726.

As used herein, the term "hydrate" refers to a combination of water with a compound wherein the water retains its molecular state as water and is either absorbed, adsorbed or contained within a crystal lattice of the substrate compound.

As used herein, the term "polymorph" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore, X-ray powder diffraction can be used to identify different polymorphs, or a solid form that comprises more than one polymorph, in a reproducible and reliable way. Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since Impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The term "substituted with 0-X substituents" refer to the base moiety being unsubstituted (0) or independently substituted with 1, 2, 3 etc or more of X substituents, i.e. being substituted with, for example, 1 substituent, 2 substituents, 3 substituents etc.

This disclosure contemplates all the isomers of the compounds of formulae I, I-A, I-a, I-aa, I-B, I-b, I-ba, I-C, I-c, I-D, I-d, I-E, I-e, I-F and I-f "Isomer" as used herein includes optical isomers (such as stereoisomers, e.g., enantiomers and diastereoisomers), Z (zusammen) or E (entgegen) isomers, and tautomers. Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure also relates to all stereoisomeric forms such as enantiomeric and diastereoisomeric forms of the compounds or mixtures thereof (including all possible mixtures of stereoisomers). See, e.g., WO 01/062726. Furthermore, certain compounds which contain alkenyl groups may exist as Z (zusammen) or E (entgegen) isomers. In each instance, the disclosure includes both mixture and separate individual isomers. Multiple substituents on a piperidinyl or the azepanyl ring can also stand in either cis or trans relationship to each other with respect to the plane of the piperidinyl or the azepanyl ring. Some of the compounds may also exist in tautomeric forms. Such forms, although not explicitly indicated in the formulae described herein, are intended to be included within the scope of the present invention. With respect to the methods and compositions of the present disclosure, reference to a compound or compounds is intended to encompass that compound in each of its possible isomeric forms and mixtures thereof unless the particular isomeric form is referred to specifically. See, e.g., WO 01/062726.

The compounds of this disclosure enhance the function of α5-containing $GABA_A$ R, i.e., they are α5-containing $GABA_A$ R agonists (e.g., α5-containing $GABA_A$ R positive allosteric modulators) and are capable of increasing GABA-gated Cl-currents.

The disclosure further provides pharmaceutical compositions comprising one or more compounds of the disclosure together with a pharmaceutically acceptable carrier or excipient. In some embodiments, the pharmaceutical compositions of this disclosure may be used in combination with a second therapeutic agent, such as an antipsychotic, memantine, AChEI or an SV2A inhibitor.

In some aspects, this disclosure further provides methods for treating cognitive impairment associated with said CNS disorders or cognitive impairments associated with various risk factors of cognitive impairment that are responsive to positive allosteric modulators of α5-containing $GABA_A$ R, e.g., age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In certain embodiments, the method is a method of treating the age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In certain embodiments, treatment comprises preventing or slowing the progression of cognitive impairment associated with a CNS disorder or risk factor (such as those described herein). In certain embodiments, treatment comprises alleviation, amelioration, or slowing the progression of one or more impaired cognitive symptoms associated with the CNS disorder or risk factor. In certain embodiments, the symptom to be treated is cognitive impairment or cognitive deficit. In another aspect of the disclosure, there is provided a method of preserving or improving cognitive function in a subject in need thereof, the method comprising the step of administering to said subject a therapeutically effective amount of a compound of the disclosure or a pharmaceutically acceptable salt, hydrate, solvate, polymorph, isomer, or combinations thereof or a pharmaceutical composition of one or more of them.

The cognitive impairment treated in accordance with this disclosure may be associated with various CNS disorders or risks of cognitive impairment e.g., age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction These disorders may have a variety of etiologies. However, the cognitive impairment associated with each of the above-mentioned disorders or risks may have overlapping causes. Thus, a compound, composition or method of treatment that treats cognitive impairment associated with one CNS disorder or risk factor may also treat cognitive impairment in another.

Benzazepine Derivatives of the Disclosure

The present disclosure provides a compound of formula I:

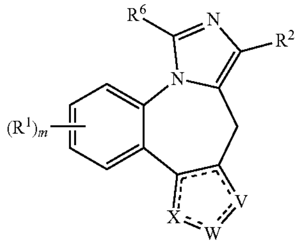

(I)

or a pharmaceutically acceptable salt, hydrate, solvate, polymorph, isomer, or combination thereof, wherein:

X is independently selected from O, N, —$NR^3$, or —$C(R^4)_{1-2}$;

W is O, N or $NR^3$;

V is O, $NR^3$ or —$C(R^4)_{1-2}$, wherein, when X is O, W is N and V is —$C(R^4)_{1-2}$;

when X is N, W is O or —$NR^3$, V is —$C(R^4)_{1-2}$;

when X is —$NR^3$, W is N, V is —$C(R^4)_{1-2}$;

when X is —$C(R^4)_{1-2}$, W is N, V is O or —$NR^3$;

each occurrence of the bond "⎓" is either a single bond or a double bond;

m is an integer selected from 0-4;

each $R^1$ is independently selected from -halogen, —(C6-C10)aryl, —O(C1-C6)alkyl, —CN, —NCS, —$NO_2$, —$CHF_2$, —$CF_3$, —$OCF_3$, —$OCHF_2$, —$CO(O)R_7$, —$CH_2$—$OR^8$, —(C1-C6)alkyl-(C6-C10)aryl, -(5- to 10-membered)heteroaryl, —(C1-C6)alkyl-(5- to 10-membered)heteroaryl, or —(C3-C6)cycloalkyl;

each $R^2$ is selected from —CO(O)$R_7$, —C≡C—$R^9$, —(C1-C6)alkyl-C≡C—$R^9$, -(5- to 10-membered) heteroaryl, -(3- to 10-membered)heterocyclyl, or —(C3-C10)cycloalkenyl; wherein each (5- to 6-membered)heteroaryl and (3- to 10-membered) heterocycle is substituted with 0-4 $R_7$;

wherein each $R_7$ is selected from —H, —$CF_3$, —(C1-C6)alkyl, —(C3-C6)cycloalkyl, -(5- to 10-membered)heteroaryl, —(C6-C10)aryl, —(C1-C6)alkyl-(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each $R^8$ is selected from —H, —(C1-C6)alkyl, -(5- to 10-membered)heteroaryl, -(3 to 10-membered)heterocyclyl, —(C3-C10)cycloalkenyl, —(C6-C10)aryl, —(C3-C6)cycloalkyl, —$CH_2$—(C3-C6)cycloalkyl, —$CH_2$—(C6-C10) aryl or —$CH_2$-(5- to 10-membered) heteroaryl, wherein each occurrence of $R^8$ is independently substituted by 0-5 R';

each $R^9$ is selected from —H, —(C1-C6)alkyl, -(5- to 10-membered)heteroaryl, -(3- to 10-membered)heterocyclyl, (C3-C10)cycloalkenyl, —(C6-C10)aryl, —(C3-C6)cycloalkyl, —(C1-C6)alkyl-(C6-C10)aryl, —(C1-C6)alkyl-(5- to 10-membered)heteroaryl, —(C1-C6) alkyl-(C3-C6)cycloalkyl, or —C(O)—(C6-C10)aryl, wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl; wherein said heterocyclyl has 1-4 heteroatoms independently selected from N, NH, O, S, SO, or $SO_2$, and said heteroaryl has 1-4 heteroatoms independently selected from N, NH, O, or S;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-N($R^{12}$)$_2$, —(C1-C6)alkyl-(C6-C10)aryl, —(C1-C6)alkyl-(5- to 10-membered)heteroaryl, -(3- to 10-membered)heterocyclyl, -(5- to 10-membered)heteroaryl, —C(O)—(C6-C10)aryl, —C(O)—(C1-C6)alkyl, or —C(O)—(C3-C6) wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —C(O)N($R^o$)$_2$, —C(O)$OR^o$, —$NO_2$, —NCS, —CN, —$CF_3$, —$OCF_3$ or —N($R^o$)$_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl wherein said heterocyclyl has 1-4 heteroatoms independently selected from N, NH, O, S, SO, or $SO_2$, and said heteroaryl has 1-4 heteroatoms independently selected from N, NH, O, or S;

$R^4$ is selected from —H or —(C1-C6)alkyl;

$R^6$ is selected from —H or —(C1-C6)alkyl;

each $R^{13}$ and $R^{14}$ is independently selected from —H, —(C1-C3)aliphatic, or —(C3-C6)cycloalkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$;

wherein each occurrence of R" is independently selected from —H, —(C1-C6)aliphatic, —(C3-C6)cycloalkyl, -(3- to 6-membered)heterocyclyl, -(5- to 10-membered)heteroaryl, —(C6-C10)aryl, —(C1-C6)alkyl-(5- to 10-membered)heteroaryl, —(C1-C6)alkyl-(C6-C10) aryl, —(C1-C6)alkyl-O-(5- to 10-membered)heteroaryl, or —(C1-C6)alkyl-O—(C6-C10)aryl, wherein each occurrence of R" is independently substituted with 0-3 substituents, and in particular, in some aspects of the disclosure, R" is independently substituted with 1-3 substituents, wherein the substituents are selected from halogen, —$R^o$, —$OR^o$, oxo, —$CH_2OR^o$, —$CH_2N(R^o)$ 2, —C(O)N($R^o$)$_2$, —C(O)$OR^o$, —$NO_2$, —NCS, —CN, —$CF_3$, —$OCF_3$ or —N($R^o$)$_2$; and wherein each occurrence of $R^o$ is independently selected from —(C1-C6)aliphatic, —O(C1-C6)aliphatic, —(C3-C6)cycloalkyl, -(3- to 6-membered)heterocyclyl, -(5- to 10-membered)heteroaryl, or —(C6-C10) aryl, wherein said heterocyclyl has 1-4 heteroatoms independently selected from N, NH, O, S, SO, or $SO_2$, and said heteroaryl has 1-4 heteroatoms independently selected from N, NH, O, or S.

In some embodiments of a compound of formula I, the compound has a structure of formula I-A:

I-A

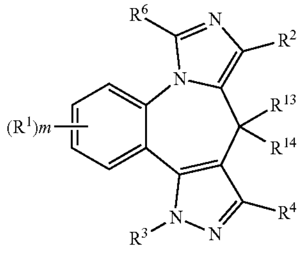

or a pharmaceutically acceptable salt, hydrate, solvate, polymorph, isomer, or combination thereof, wherein m, $R^1$, $R^2$, $R^3$, $R^4$, $R^6$, $R^{13}$ and $R^{14}$ are as defined in formula I.

In some embodiments of a compound of formula I-A, the compound has a structure of formula I-a:

I-a

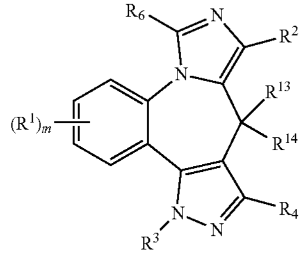

or a pharmaceutically acceptable salt, hydrate, solvate, polymorph, isomer, or combination thereof, wherein:

m is an integer selected from 0-4;

each $R^1$ is independently selected from -halogen, —(C6-C10)aryl, —O(C1-C6)alkyl, —CN, —$CHF_2$, —$CF_3$, —$OCF_3$, —$OCHF_2$, —CO(O)$R_7$, —$CH_2$—OR', —(C1-C6)alkyl-(C6-C10) aryl, -(5- to 10-membered) heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl, —(C3-C10)cycloalkenyl,

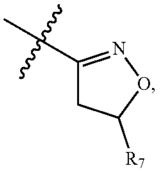 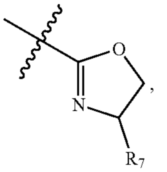 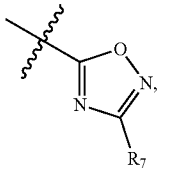

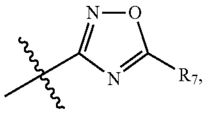 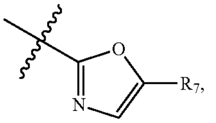 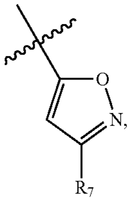

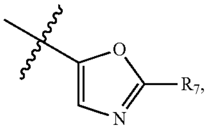 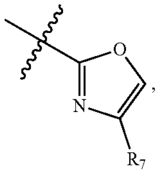

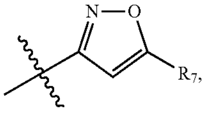 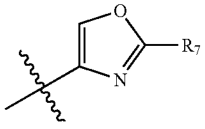 ,

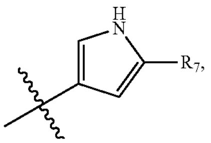 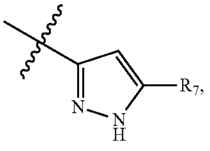

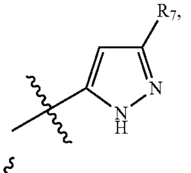 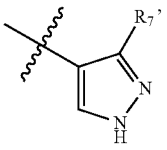

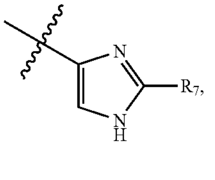 or 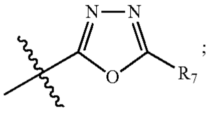 ;

wherein each 5- to 6-membered heteroaryl and 3- to 10-membered heterocycle is substituted with 0-4 $R_7$;

each $R^9$ is selected from: —H, —(C1-C6)alkyl, -(5- to 10-membered)heteroaryl, -(3- to 10-membered)heterocyclyl, —(C6-C10)aryl, —(C1-C6)alkyl-(C6-C10) aryl,

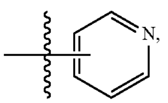 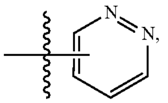 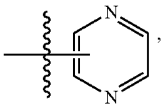 ,

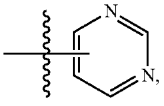 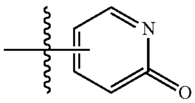 , 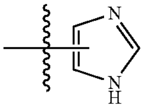 ,

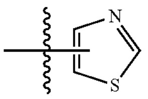 , 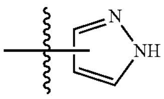 , or

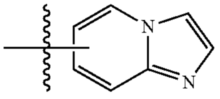 ;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —(C6-C10)aryl or -(5- to 10-membered)heteroaryl;

$R^3$ is independently selected from —H, —(C1-C6)alkyl, -(5- to 10-membered)heteroaryl, -(3- to 10-membered) heterocyclyl, —(C1-C6)alkyl-(C3-C6)cycloalkyl or —(C1-C6)alkyl-(C6-C10)aryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —$C(O)N(R^o)_2$, —$C(O)OR^o$, —$CF_3$, —$OCF_3$ or —$N(R^o)_2$, wherein each occurrence of $R^o$ is independently selected from —(C1-C6)aliphatic, —(C3-C6) cycloalkyl, -(3- to 10-membered)heterocyclyl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —$CH_2$—(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, —$CH_2OR"$, —$CH_2NR"_2$, —$C(O)N(R")_2$, —C(O)OR", —$NO_2$, —NCS, —CN, —$CF_3$, —$OCF_3$ or —$N(R")_2$, wherein R" is selected from —Cl, —F, —(C1-C6)alkyl, —OMe, or —(C6-C10)aryl;

R" is independently substituted with 1-3 substituents wherein the substituents are selected from halogen, —$CF_3$, —$OCF_3$, —O—(C1-C6)aliphatic, or —(C1-C6)aliphatic;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-a, or a pharmaceutically acceptable salt, hydrate, solvate, polymorph, isomer, or combination thereof, has the structure of formula I-a:

wherein: m is 0, 1 or 2;

when m is 1 or 2, at least one occurrence of $R^1$ is -halogen or —O—(C1-C6)alkyl;

each $R^1$ is independently selected from: -halogen and —O—(C1-C6)alkyl;

$R^2$ is selected from: —C≡C—$R^9$, —(C3-C10)cycloalkenyl,

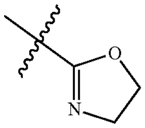, 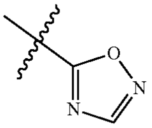, 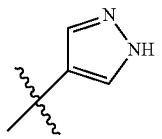, 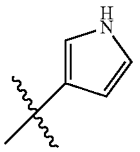, 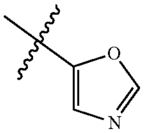, or 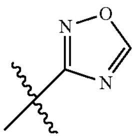;

wherein each 5-membered heterocycle or heteroaryl is substituted with 0-4 $R_7$;

each $R^9$ is selected from: —(C1-C6)alkyl,

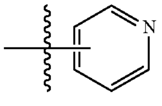 or 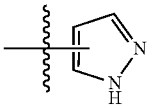;

wherein each occurrence of $R^9$ is independently substituted by 0-5 $R^{11}$;

wherein each occurrence of $R^{11}$ is independently selected from —(C1-C6)alkyl and —O—(C1-C6)alkyl;

$R^3$ is independently selected from: —H, —(C1-C6) alkyl, -(3- to 10-membered)heterocyclyl, —(C1-C6)alkyl-(C3-C6)cycloalkyl and —(C1-C6)alkyl-(C6-C10)aryl, wherein $R^3$ is independently substituted with 0-5 $R^{12}$;

wherein $R_7$ is selected from —$CF_3$, —(C1-C6)alkyl, —(C6-C10)aryl or —$CH_2$—(C6-C10)aryl, wherein each $R_7$ is independently substituted with 0-5 R';

each occurrence of $R^4$ and $R^6$ is —H; and wherein $R^{11}$, $R^{12}$, $R^{13}$ and $R^{14}$, R' and R" are as defined in Formula I-a.

In some embodiments of a compound of formula I-A, the compound has a structure of formula I-aa:

I-aa

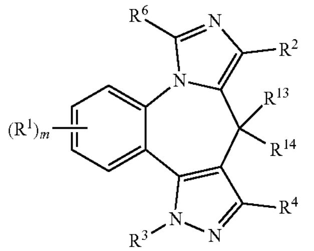

or a pharmaceutically acceptable salt, hydrate, solvate, polymorph, isomer, or combination thereof, wherein:

m is an integer selected from 0-4;

each $R^1$ is independently selected from halogen, —(C6-C10)aryl, —O(C1-C6)alkyl, —CN, —$CHF_2$, —$CF_3$, —$OCF_3$, —$OCHF_2$, CO(O)$R_7$, $CH_2$—$OR^8$, —(C1-C6) alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from CO(O)$R_7$, C≡C—$R^9$, —(C1-C6) alkyl-C≡C—$R^9$, -(5- to 10-membered)heteroaryl, -(3- to 10-membered)heterocyclyl, —(C3-C10)cycloalkenyl,

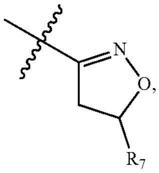 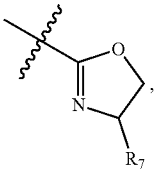, 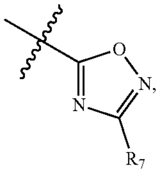

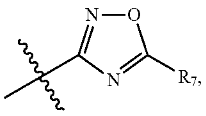 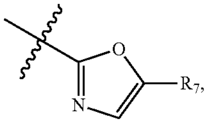 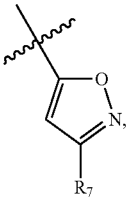

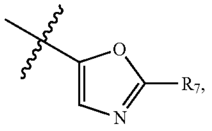 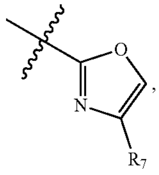

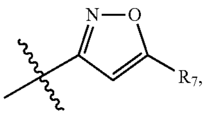 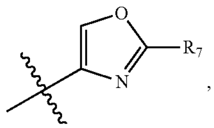,

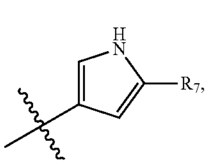 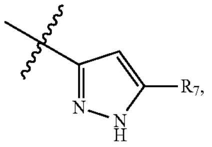

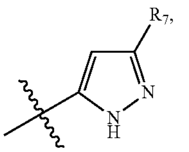 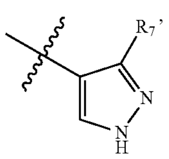

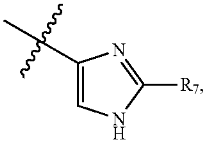 or 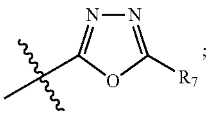;

wherein each 5- to 6-membered heteroaryl and 3- to 10-membered heterocycle is substituted with 0-4 $R_7$;

each $R^9$ is selected from: —H, —(C1-C6) alkyl, (5- to 10-membered)heteroaryl, -(3- to 10-membered)heterocyclyl, —(C6-C10) aryl, —(C1-C6) alkyl-(C6-C10) aryl,

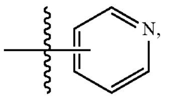, 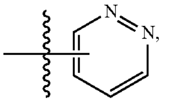, 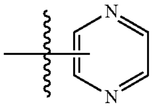,
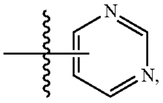, 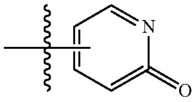, 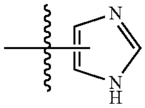,
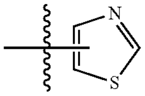, 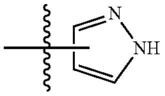, or
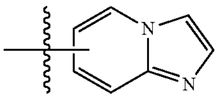;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —(C6-C10)aryl or -(5- to 10-membered)heteroaryl;

$R^3$ is independently selected from —H, —(C1-C6)alkyl, -(5- to 10-membered)heteroaryl, -(3- to 10-membered) heterocyclyl, —(C1-C6) alkyl-(C3-C6)cycloalkyl or —(C1-C6)alkyl-(C6-C10)aryl, wherein $R^3$ is independently substituted with 0-5 $R^{12}$;

wherein each $R^{12}$ is independently selected from: —H, -halogen, —$OR^o$, $R^o$, oxo, —$CH_2OR^o$, —$CH_2N(R^o)_2$, —$C(O)N(R^o)_2$, —$C(O)OR^o$, —$CF_3$, —$OCF_3$ or —$N(R^o)_2$, wherein each occurrence of $R^o$ is independently selected from —(C1-C6)aliphatic, —(C3-C6) cycloalkyl, -(3- to 10-membered)heterocyclyl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —$CH_2$—(C6-C10)aryl, -(5- to 10-membered)heteroaryl-(C1-C6)alkyl, or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, —$CH_2OR"$, —$CH_2NR"_2$, —$C(O)N(R")_2$, —$C(O)OR"$, —$NO_2$, —NCS, —CN, —$CF_3$, —$OCF_3$, or —$N(R")_2$;

wherein R" is selected from —Cl, —F, —(C1-C6)alkyl, —OMe, -(3- to 6-membered)heterocyclyl, or —(C6-C10)aryl;

R" is independently substituted with 1-3 substituents wherein the substituents are selected from: halogen, —$CF_3$, —$OCF_3$, —O—(C1-C6)aliphatic, or —(C1-C6)aliphatic;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-aa, or a pharmaceutically acceptable salt, hydrate, solvate, polymorph, isomer, or combination thereof, has the structure of formula I-aa:

wherein: m is 0, 1 or 2;

when m is 1 or 2, at least one occurrence of $R^1$ is -halogen or —O—(C1-C6)alkyl;

each $R^1$ is independently selected from: -halogen and —O—(C1-C6)alkyl;

$R^2$ is selected from: —C≡C—$R^9$, —(C3-C10)cycloalkenyl,

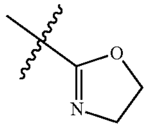, 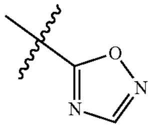, 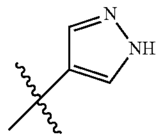,
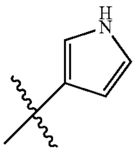, 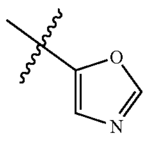, or 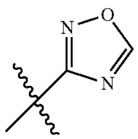;

wherein each 5-membered heterocycle or heteroaryl is substituted with 0-4 $R_7$;

each $R^9$ is selected from: —(C1-C6)alkyl,

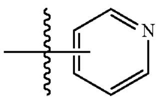 or 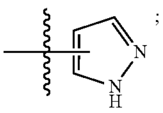;

wherein each occurrence of $R^9$ is independently substituted by 0-5 $R^{11}$;

wherein each occurrence of $R^{11}$ is independently selected from —(C1-C6)alkyl and —O—(C1-C6)alkyl;

$R^3$ is independently selected from: —H, —(C1-C6) alkyl, -(3- to 10-membered)heterocyclyl, —(C1-C6)alkyl-(C3-C6)cycloalkyl and —(C1-C6)alkyl-(C6-C10)aryl, wherein $R^3$ is independently substituted with 0-5 $R^{12}$;

wherein $R_7$ is selected from —$CF_3$, —(C1-C6)alkyl, —(C6-C10)aryl or —$CH_2$—(C6-C10)aryl, wherein each $R_7$ is independently substituted with 0-5 R';

each occurrence of $R^4$ and $R^6$ is —H; and wherein $R^{11}$, $R^{12}$, $R^{13}$ and $R^{14}$, R' and R" are as defined in Formula I-aa.

In some embodiments of a compound of formula I, the compound has a structure of formula I-B:

I-B

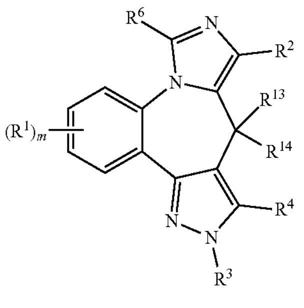

or a pharmaceutically acceptable salt, hydrate, solvate, polymorph, isomer, or combination thereof, wherein m, $R^1$, $R^2$, $R^3$, $R^4$, $R^6$, $R^{13}$ and $R^{14}$ are as defined in formula I.

In some embodiments of a compound of formula I-B, the compound has a structure of formula I-b:

I-b

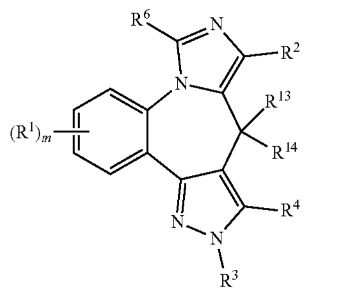

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—$OR^8$, —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

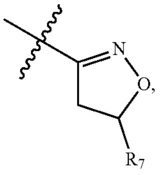 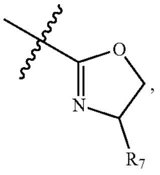, 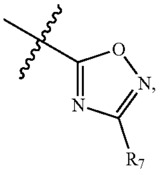

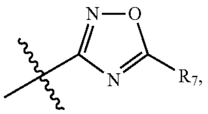 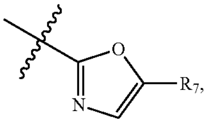 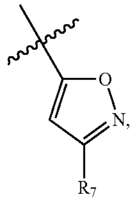

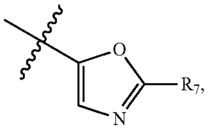 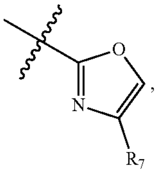,

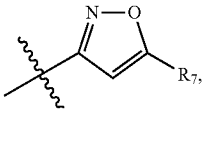 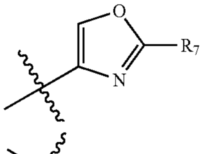,

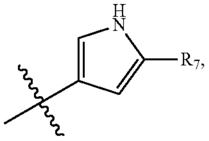 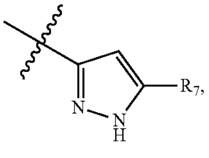

-continued

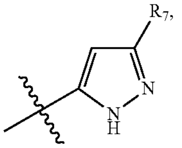 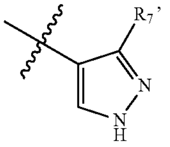

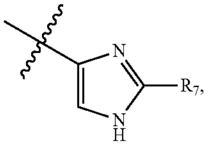 or 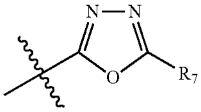 ;

wherein each 5- to 6-membered heteroaryl or 3- to 10-membered heterocycle is substituted with 0-4$R_7$;

each $R^9$ is selected from —H, —(C1-C6)alkyl, -(5- to 10-membered)heteroaryl, -(3- to 10-membered)heterocyclyl, —(C6-C10)aryl, —(C1-C6)alkyl-(C6-C10)aryl,

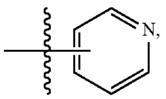 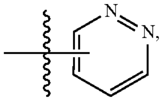 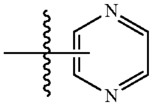,

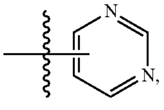 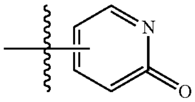, 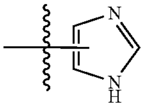,

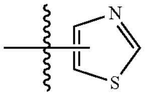, 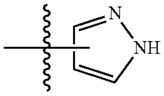, or

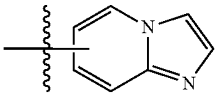 ;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-N($R^{12}$)$_2$, —(C1-C6)alkyl-(C6-C10)aryl, —(C1-C6)alkyl-(5- to 10-membered)heteroaryl, -(3- to 10-membered)heterocyclyl or -(5- to 10-membered)heteroaryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —C(O)N($R^o$)$_2$, —C(O)O$R^o$, —$NO_2$, —NCS, —CN, —$CF_3$, —$OCF_3$ or —N($R^o$)$_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl;

wherein each $R_7$ is selected from —H, —$CF_3$, —(C1-C6) alkyl, —(C3-C6)cycloalkyl, -(5- to 10-membered)heteroaryl, —(C6-C10)aryl, —(C1-C6)alkyl-(C6-C10) aryl, —(C1-C6)alkyl-(5- to 10 -membered)heteroaryl or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from -halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$;

wherein R" is selected from —Cl, —F, —(C1-C6)alkyl, —OMe, —(C1-C6)alkyl-(5- to 10-membered)heteroaryl, -(5- to 10-membered)heteroaryl, -(3- to 10-membered)heterocyclyl, —(C3-C6)cycloalkyl or —(C6-C10)aryl;

R" is independently substituted with 1-3 substituents wherein the substituents are selected from halogen, —$CF_3$, —$OCF_3$, —O(C1-C6)aliphatic, —(C1-C6)aliphatic, or -(5- to 10-membered)heteroaryl;

each $R^4$ and $R^6$ is independently selected from —H or —(C1-C6)alkyl; and each $R^{13}$ and $R^{14}$ is independently selected from H—, —(C1-C3)aliphatic, or —(C3-C6)cycloalkyl.

In some embodiments a compound of formula I-b or a pharmaceutically acceptable salt, hydrate, solvate, polymorph, isomer, or combination thereof has the structure of formula I-b:

wherein: m is 0, 1 or 2;

when m is 1 or 2, at least one occurrence of $R^1$ is -halogen or —O—(C1-C6)alkyl;

each $R^1$ is independently selected from: -halogen and —O—(C1-C6)alkyl; $R^2$ is selected from: —C≡C—$R^9$,

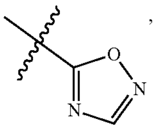, 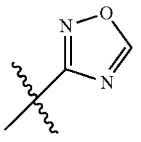, or 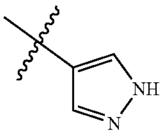;

wherein each 5-membered heterocycle or heteroaryl is substituted with 0-4 $R_7$;

each $R^9$ is selected from: —(C1-C6)alkyl, wherein each occurrence of $R^9$ is independently substituted by 0-5 $R^{11}$;

wherein each occurrence of $R^{11}$ is selected from —(C1-C6)alkyl;

$R^3$ is independently selected from: —H, —(C1-C6) alkyl or —$CH_2$—(C6-C10) aryl, and -(3 to 10-membered) heterocyclyl, wherein $R^3$ is independently substituted with 0-5 $R^{12}$;

wherein $R_7$ is selected from —(C1-C6)alkyl, —$CH_2$—(C6-C10)aryl, —(C3-C6)cycloalkyl, and -(3- to 10-membered)heterocyclyl, wherein each $R_7$ is independently substituted with 0-5 R';

each occurrence of $R^4$ and $R^6$ is —H; and wherein $R^{11}$, $R^{12}$, $R^{13}$, $R^{14}$ and R' are as defined in Formula I-b.

In some embodiments of a compound of formula I-B, the compound has a structure of formula I-ba:

I-ba

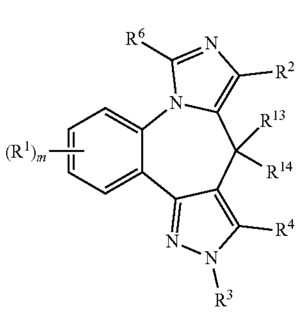

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—$OR^8$, —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

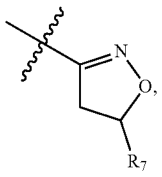 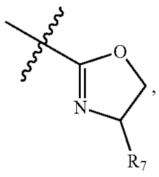, 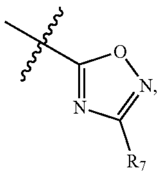

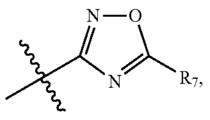 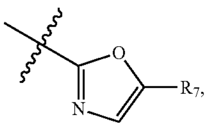 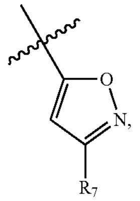

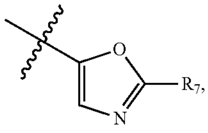 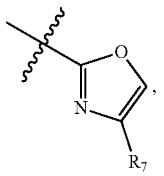,

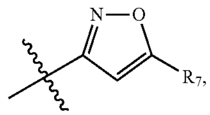 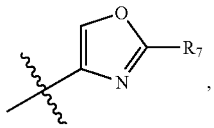,

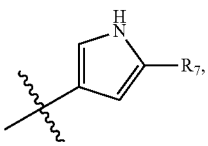 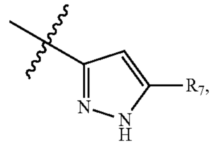

-continued

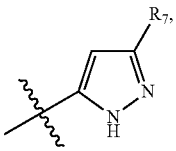

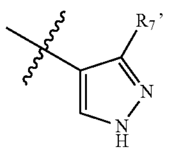

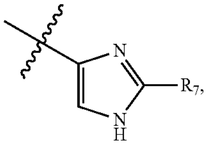

or

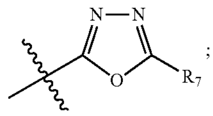

;

wherein each 5- to 6-membered heteroaryl or 3- to 10-membered heterocycle is substituted with 0-4$R_7$;

each $R^9$ is selected from —H, —(C1-C6)alkyl, -(5- to 10-membered)heteroaryl, -(3- to 10-membered)heterocyclyl, —(C6-C10)aryl, —(C1-C6)alkyl-(C6-C10) aryl,

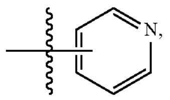

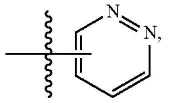

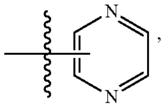

,

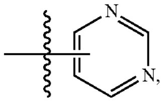

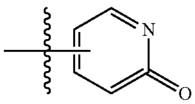

,

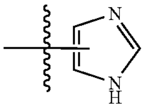

,

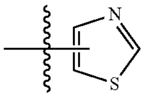

,

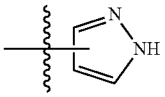

, or

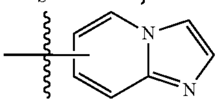

;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

$R^3$ is independently selected from —H, —(C1-C6)alkyl, —(C1-C6)alkyl-(C3-C6)cycloalkyl, —(C1-C6)alkyl-$OR^{12}$, —(C1-C6)alkyl-$N(R^{12})_2$, —(C1-C6)alkyl-(C6-C10) aryl, —(C1-C6 alkyl-(5- to 10-membered)heteroaryl, -(3- to 10-membered)heterocyclyl or -(5- to 10-membered)heteroaryl, wherein $R^3$ is independently substituted with 0-5 $R^{12}$;

wherein each $R^{12}$ is independently selected from —H, -halogen, —$OR^o$, $R^o$, oxo, —$CH_2OR^o$, —$CH_2N(R^o)_2$, —$C(O)N(R^o)_2$, —$C(O)OR^o$, —$NO_2$, —NCS, —CN, —$CF_3$, —$OCF_3$, or —$N(R^o)_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)-aryl;

wherein each $R_7$ is selected from —H, —$CF_3$, —(C1-C6) alkyl, —(C3-C6)cycloalkyl, -5 to 10 membered heteroaryl, —(C6-C10)aryl, —(C1-C6)alkyl-(C6-C10) aryl, —(C1-C6)alkyl-(5- to 10-membered)heteroaryl or -(3- to 10-membered)heterocyclyl, wherein each $R_7$ is independently substituted with 0-5 R';

or when two $R_7$ groups bound to the same atom, the two $R_7$ groups may be taken together with the atom to which they are bound to form a 3- to 10-membered aromatic or non-aromatic ring having 0-4 heteroatoms independently selected from N, NH, O, S, SO, or $SO_2$, wherein said ring is optionally substituted with 0-5 R';

each occurrence of R' is independently selected from halogen, —R", —OR", oxo, $CH_2OR"$, —$CH_2NR"_2$, —$C(O)N(R")_2$, —C(O)OR", —$NO_2$, —NCS, —CN, —$CF_3$, —$OCF_3$ or —$N(R")_2$;

wherein R" is selected from —Cl, —F, —(C1-C6)alkyl, —OMe, —(C1-C6)alkyl-(5- to 10 -membered)heteroaryl, -(5- to 10-membered)heteroaryl, -(3- to 10-membered)heterocyclyl, —(C3-C6)cycloalkyl, —(C6-C10)aryl, —H, or —$C(O)CH_3$;

R" is independently substituted with 1-3 substituents wherein the substituents are selected from halogen, —$CF_3$, —$OCF_3$, —O(C1-C6)aliphatic, —(C1-C6)aliphatic, -(5- to 10-membered)heteroaryl, or oxo;

each $R^4$ and $R^6$ is independently selected from —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-ba or a pharmaceutically acceptable salt, hydrate, solvate, polymorph, isomer, or combination thereof has the structure of formula I-ba:

wherein: m is 0, 1 or 2;

when m is 1 or 2, at least one occurrence of $R^1$ is -halogen or —O—(C1-C6)alkyl;

each $R^1$ is independently selected from: -halogen and —O—(C1-C6)alkyl; $R^2$ is selected from: —C≡C—$R^9$,

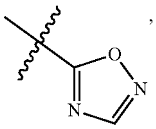

,

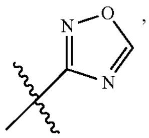

, or

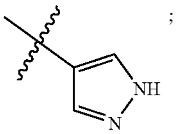

;

wherein each 5-membered heterocycle or heteroaryl is substituted with 0-4 $R_7$;

each $R^9$ is selected from: —(C1-C6)alkyl, wherein each occurrence of $R^9$ is independently substituted by 0-5 $R^{11}$;

wherein each occurrence of $R^{11}$ is selected from —(C1-C6)alkyl;

$R^3$ is independently selected from: —H, —(C1-C6) alkyl or —$CH_2$—(C6-C10) aryl, and -(3 to 10-membered) heterocyclyl, wherein $R^3$ is independently substituted with 0-5 $R^{12}$;

wherein $R_7$ is selected from —(C1-C6)alkyl, —$CH_2$—(C6-C10)aryl, —(C3-C6)cycloalkyl, and -(3- to 10-membered)heterocyclyl, wherein each $R_7$ is independently substituted with 0-5 R';

each occurrence of $R^4$ and $R^6$ is —H; and wherein $R^{11}$, $R^{12}$, $R^{13}$, $R^{14}$ and R' are as defined in Formula I-ba.

In some embodiments of a compound of formula I, the compound has a structure of formula I-C:

I-C

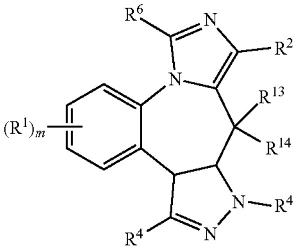

or a pharmaceutically acceptable salt, hydrate, solvate, polymorph, isomer, or combination thereof, wherein m, $R^1$, $R^2$, $R^3$, $R^4$, $R^6$, $R^{13}$ and $R^{14}$ are as defined in formula I.

In some embodiments of a compound of formula I-C, the compound has a structure of formula I-c:

I-c

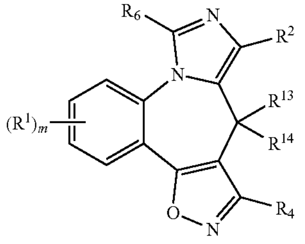

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

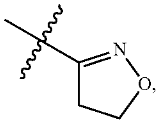, 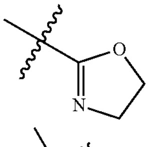, 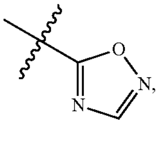, 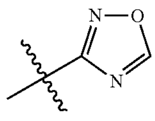, 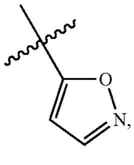, 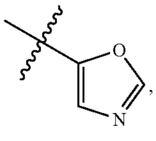, 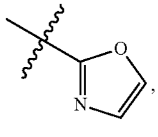, 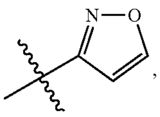, 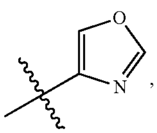, -continued

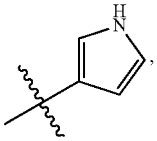, 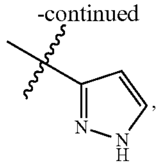, 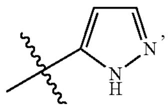, 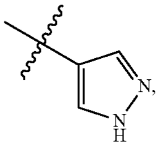, 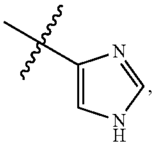, or 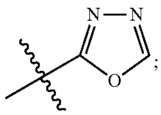;

wherein each 5-membered heterocycle or heteroaryl is substituted with 0-4 $R_7$;

each $R^9$ is selected from —H, —(C1-C6)alkyl, -(5- to 10-membered)heteroaryl, -(3- to 10-membered)heterocyclyl

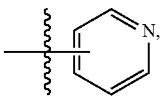, 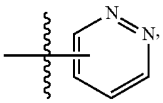, 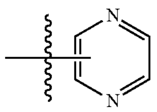, 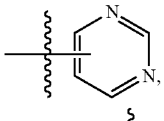, 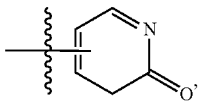, 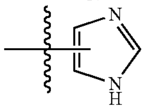, 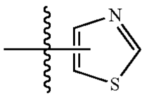, 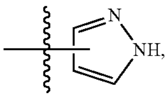, or 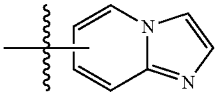;

each occurrence of $R^9$ is independently substituted by 0-5 $R^{11}$;

each occurrence of $R^{11}$ is independently selected from —(C1-C6)alkyl, —O—(C1-C6)alkyl, -halogen, —$CF_3$, —$OCF_3$, —OMe, —(C6-C10)aryl or -(5- to 10-membered)heteroaryl;

each occurrence of $R_7$ is selected from —$CF_3$, —(C1-C6) alkyl, —(C3-C6)cycloalkyl, -(5- to 10-membered)heteroaryl, —(C6-C10) aryl, —(C1-C6)alkyl-(C6-C10) aryl, —(C1-C6)alkyl-(5- to 10-membered)heteroaryl or -(3- to 10-membered)heterocyclyl, wherein each $R_7$ is independently substituted with 0-5 R';

each occurrence of R' is wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ or —N(R")$_2$, wherein each occurrence of R" is selected from —Cl, —F, —(C1-C6)alkyl, —OMe, —(C1-C6)alkyl-(5- to 10-membered)heteroaryl, -(5- to 10-membered)heteroaryl, -(3- to 10-membered)heterocyclyl, —(C3-C6) cycloalkyl, or —(C6-C10)aryl, and R" is independently substituted with 1-3 substituents wherein the substituents are selected from -halogen, —$CF_3$, —$OCF_3$, —(C1-C6)aliphatic, or -(5- to 10-membered)heteroaryl;

each $R^4$ and $R^6$ is independently selected from —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-c or a pharmaceutically acceptable salt, hydrate, solvate, polymorph, isomer, or combination thereof, has the structure of formula I-c:

wherein: m is 0, 1 or 2;

when m is 1 or 2, at least one occurrence of $R^1$ is -halogen or —O—(C1-C6)alkyl;

each $R^1$ is independently selected from: -halogen and —O(C1-C6)alkyl;

$R^2$ is selected from: —CO(O)$R_7$, —C≡C—$R^9$,

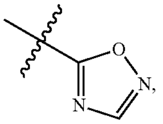 or 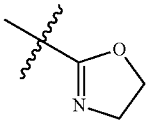;

wherein each 5-membered heterocycle or heteroaryl is substituted with 0-4 $R_7$;

each $R^9$ is selected from: —H or —(C1-C6)alkyl, wherein each occurrence of $R^9$ is independently substituted by 0-5 $R^{11}$;

each occurrence of $R^{11}$ is selected from —(C1-C6)alkyl;

each occurrence of $R^4$ and $R^6$ is —H; and wherein $R_7$, $R^{13}$, $R^{14}$, R' and R" are as defined in Formula I-c.

In some embodiments of a compound of formula I, the compound has a structure of formula I-D:

I-D

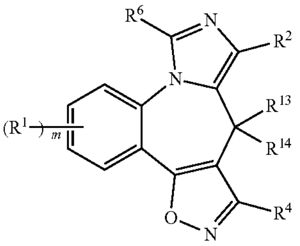

or a pharmaceutically acceptable salt, hydrate, solvate, polymorph, isomer, or combination thereof, wherein m, $R^1$, $R^2$, $R^4$, $R^6$, $R^{13}$ and $R^{14}$ are as defined in formula I.

In some embodiments of a compound of formula I-D, the compound has a structure of formula I-d:

I-d

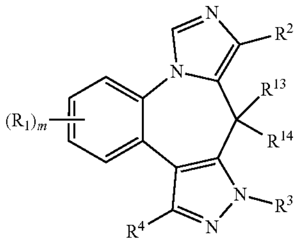

or a pharmaceutically acceptable salt, hydrate, solvate, polymorph, isomer, or combination thereof, m is an integer selected from 0-4;

wherein:

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—OR', —(C1-C6)alkyl-(C6-C10)aryl, -(5- to 10-membered)heteroaryl, —(C1-C6)alkyl-(5- to 10-membered)heteroaryl, or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

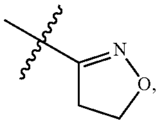 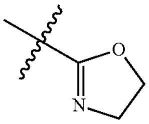, 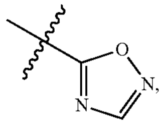

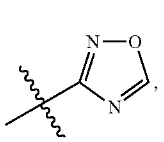, 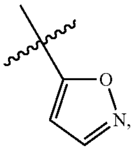, 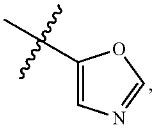,

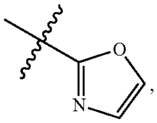, 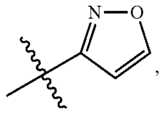, 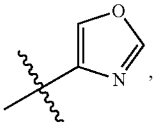,

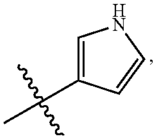, 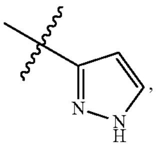, 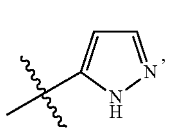,

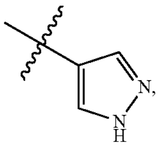 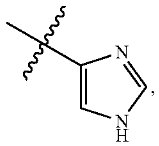, or 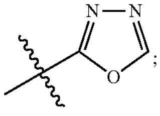;

wherein each 5-membered heterocycle or heteroaryl is substituted with 0-4 $R_7$;

each $R^9$ is selected from —H, —(C1-C6)alkyl, -(5- to 10-membered)heteroaryl, -(3- to 10-membered)heterocyclyl, —(C6-C10)aryl, —(C1-C6)alkyl-(C6-C10) aryl,

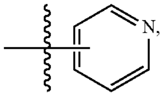 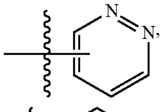 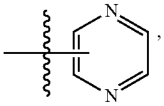,

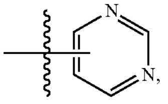 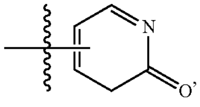 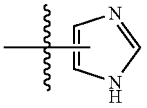,

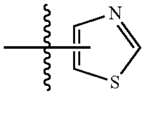, 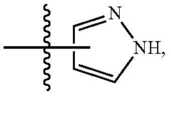 or

-continued

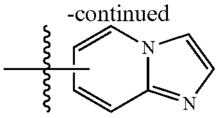;

wherein each occurrence of $R^9$ is independently substituted by 0-5 $R^{11}$;

wherein each occurrence of $R^{11}$ is independently selected from —(C1-C6)alkyl, —O—(C1-C6)alkyl, -halogen, —$CF_3$, —$OCF_3$, —OMe, —(C6-C10)aryl, or -(5- to 10-membered)heteroaryl;

$R^3$ is independently selected from: —H, —(C1-C6)alkyl, —(C1-C6)alkyl-(C3-C6)cycloalkyl, —(C1-C6)alkyl-$OR^{12}$, —(C1-C6)alkyl-$N(R^{12})_2$, —(C1-C6)alkyl-(C6-C10)aryl, or —(C1-C6) alkyl-(5- to 10-membered) heteroaryl wherein $R^3$ is independently substituted with 0-5 $R^{12}$;

wherein each $R^{12}$ is independently selected from —H, -halogen, —$OR^o$, —$R^o$, oxo, —$CH_2OR^o$, —$CH_2N(R^o)_2$, —$C(O)N(R^o)_2$, —$C(O)OR^o$, —$NO_2$, —NCS, —CN, —$CF_3$, —$OCF_3$ or —$N(R^o)_2$, wherein each occurrence of $R^o$ is independently selected from —(C1-C6)aliphatic, —(C3-C6)cycloalkyl, -(3- to 6-membered)heterocyclyl, -(5- to 10-membered)heteroaryl, or —(C6-C10)aryl.

Wherein $R_7$ is selected from —$CF_3$, —(C1-C6)alkyl, —(C3-C6)cycloalkyl, -(5- to 10-membered)heteroaryl, —(C6-C10)aryl, —(C1-C6)alkyl-(C6-C10)aryl, —(C1-C6)alkyl-(5- to 10-membered)heteroaryl, or -(3- to 10-membered)heterocyclyl, wherein each $R_7$ is independently substituted with 0-5 R';

each occurrence of R' is wherein each occurrence of R' is independently selected from -halogen, —R", —OR", oxo, —$CH_2OR"$, —$CH_2NR"_2$, —$C(O)N(R")_2$, —C(O)OR", —$NO_2$, —NCS, —CN, —$CF_3$, —$OCF_3$ or —$N(R")_2$;

wherein R" is selected from —Cl, —F, —(C1-C6)alkyl, —OMe, or —(C6-C10)aryl;

each $R^4$ is selected from —H or —(C1-C6)alkyl;

each $R^6$ is selected from —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-d or a pharmaceutically acceptable salt, hydrate, solvate, polymorph, isomer, or combination thereof has the structure of formula I-d:

wherein: m is 0, 1 or 2;

when m is 1 or 2, at least one occurrence of $R^1$ is halogen or —O—(C1-C6)alkyl;

each $R^1$ is independently selected from: -halogen and —O—(C1-C6)alkyl;

$R^2$ is selected from: —C≡C—$R^9$,

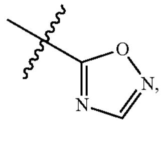 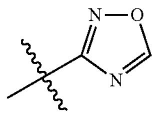, or 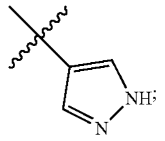

wherein each 5-membered heterocycle or heteroaryl is substituted with 0-4 $R_7$;

each $R^9$ is selected from: —(C1-C6)alkyl, wherein each occurrence of $R^9$ is independently substituted by 0-5 R", wherein each occurrence of R" is selected from —(C1-C6)alkyl;

$R^3$ is independently selected from: —H, —(C1-C6) alkyl or —$CH_2$—(C6-C10) aryl, wherein $R^3$ is independently substituted with 0-5 $R^{12}$, wherein each $R^{12}$ is independently selected from: —H or —F, wherein $R_7$ is selected from —(C1-C6)alkyl, —$CH_2$—(C6-C10)aryl, —(C3-C6)cycloalkyl, and -(3- to 10-membered)heterocyclyl, wherein each $R_7$ is independently substituted with 0-5 R';

each occurrence of $R^4$ and $R^6$ is —H; and wherein $R^{11}$, $R^{12}$ $R^{13}$, $R^{14}$ and R' are as defined in Formula I-d.

In some embodiments of a compound of formula I, the compound has a structure of formula I-E:

I-E

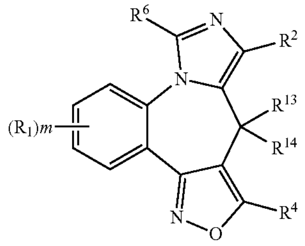

or a pharmaceutically acceptable salt, hydrate, solvate, polymorph, isomer, or combination thereof, wherein m, $R^1$, $R^2$, $R^4$, $R^6$, $R^{13}$ and $R^{14}$ are as defined in formula I.

In some embodiments of a compound of formula I-E, the compound has a structure of formula I-e:

I-e

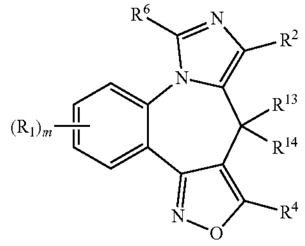

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —$CO(O)R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6)alkyl;

each $R^2$ is selected from —$CO(O)R_7$, —C≡C—$R^9$, —(C1-C6)alkyl-C≡C—$R^9$, -(5- to 10-membered)heteroaryl, -(3- to 10-membered)heterocyclyl,

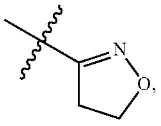 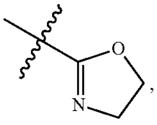, 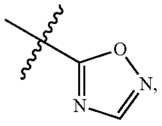

-continued

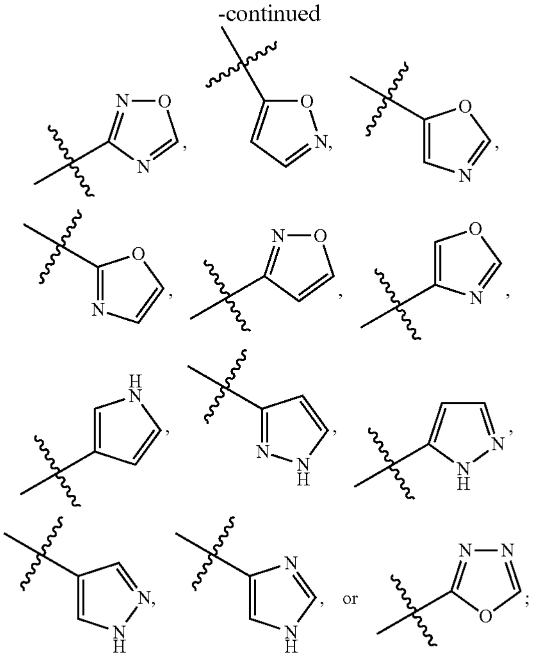

wherein each 5-membered heterocyclyl or heteroaryl is substituted with 0-4 $R_7$;

each $R^9$ is selected from —H, —(C1-C6)alkyl, -(5- to 10-membered)heteroaryl, -(3- to 10-membered)heterocyclyl,

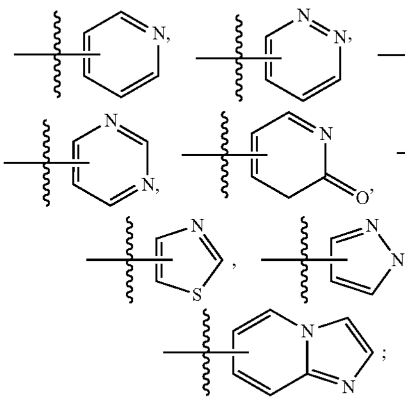

each occurrence of $R^9$ is independently substituted by 0-5 $R^{11}$, wherein each occurrence of $R^{11}$ is independently selected from —(C1-C6)alkyl, —O—(C1-C6)alkyl, -halogen, —$CF_3$, —$OCF_3$, —OMe, —(C6-C10) aryl or -(5- to 10-membered)heteroaryl;

wherein $R_7$ is selected from —(C1-C6)alkyl, —(C3-C6) cycloalkyl, -(5- to 10-membered)heteroaryl, —(C6-C10)aryl, —(C1-C6)alkyl-(C6-C10)aryl, -(5- to 10 -membered)heteroaryl-(C1-C6)alkyl, or -(3- to 10-membered)heterocyclyl, wherein each $R_7$ is independently substituted with 0-5 R';

each occurrence of R' is wherein each occurrence of R' is independently selected from -halogen, —R", —OR", oxo, —$CH_2$OR", —$CH_2NR"_2$, —C(O)N(R")$_2$, —C(O)OR", —$NO_2$, —NCS, —CN, —$CF_3$, —$OCF_3$ or —N(R")$_2$, wherein each R' is independently substituted with 0-5 R";

wherein R" is selected from —Cl, —F, —(C1-C6)alkyl, —OMe, or —(C6-C10)aryl;

each $R^4$ is independently —H or —(C1-C6)alkyl;

each $R^6$ is independently —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-e or a pharmaceutically acceptable salt, hydrate, solvate, polymorph, isomer, or combination thereof, has the structure of formula I-e:

wherein: m is 0, 1 or 2;

when m is 1 or 2, at least one occurrence of $R^1$ is halogen or —O—(C1-C6)alkyl;

each $R^1$ is independently selected from -halogen and —O—(C1-C6)alkyl;

$R^2$ is selected from: —CO(O)$R_7$, —C≡C—$R^9$,

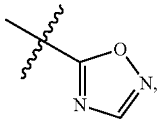 or 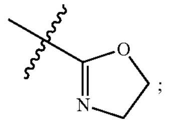;

wherein each 5-membered heterocycle or heteroaryl is substituted with 0-4 $R_7$;

each $R^9$ is selected from —H or —(C1-C6) alkyl, wherein each occurrence of $R^9$ is independently substituted by 0-5 $R^{11}$;

wherein each occurrence of $R^{11}$ is selected from —(C1-C6)alkyl;

$R^4$ and $R^6$ are both —H; and $R_7$, $R^{13}$, $R^{14}$ and R' are as defined in Formula I-e.

In some embodiments of a compound of formula I, the compound has a structure of formula I-F:

I-F

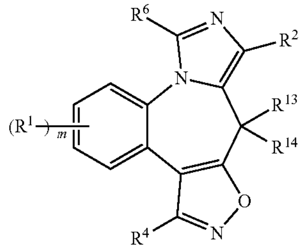

or a pharmaceutically acceptable salt, hydrate, solvate, polymorph, isomer, or combination thereof, wherein m, $R^1$, $R^2$, $R^4$, $R^6$, $R^{13}$ and $R^{14}$ are as defined in formula I.

In some embodiments of a compound of formula I-F, the compound has a structure of formula I-f:

I-f

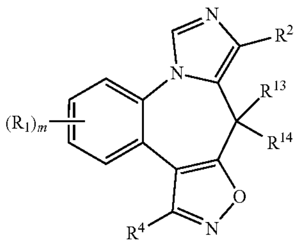

or a pharmaceutically acceptable salt, hydrate, solvate, polymorph, isomer, or combination thereof, m is an integer selected from 0-4;

each $R^1$ is independently selected from -halogen, —(C6-C10)aryl, —OMe, —CN, —$CHF_2$, —$CF_3$, —$OCF_3$, —$OCHF_2$, —CO(O)$R_7$, —$CH_2$—OR', —(C1-C6)alkyl-(C6-C10)aryl, -(5- to 10-membered)heteroaryl, —(C1-C6)alkyl-(5- to 10-membered)heteroaryl or —(C3-C6)cycloalkyl;

each $R^8$ is independently selected from —H or —(C1-C6 alkyl);

each $R^2$ is selected from —CO(O)$R_7$, —C≡C—$R^9$, —(C1-C6)alkyl-C≡C—$R^9$, -(5- to 10-membered)heteroaryl, -(3- to 10-membered)heterocyclyl,

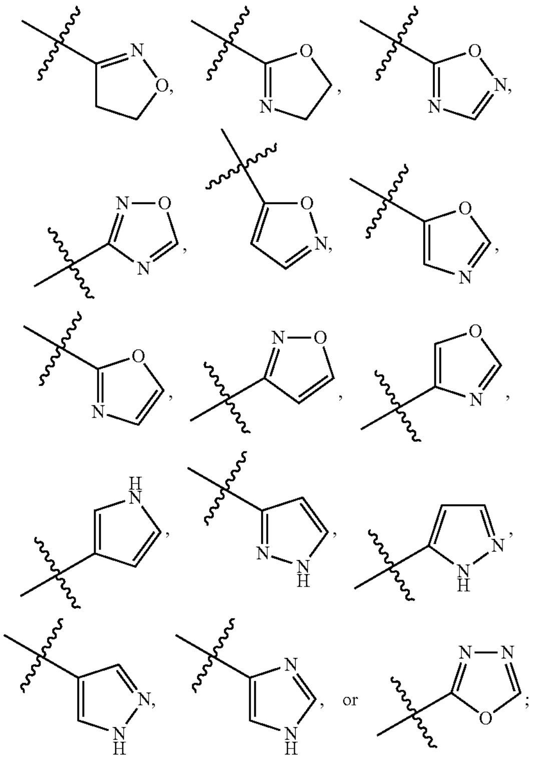

wherein each 5-membered heterocycle or heteroaryl is substituted with 0-4 $R_7$;

each $R^9$ is selected from: —H, —(C1-C6) alkyl, -(5- to 10-membered)heteroaryl, -(3- to 10-membered)heterocyclyl

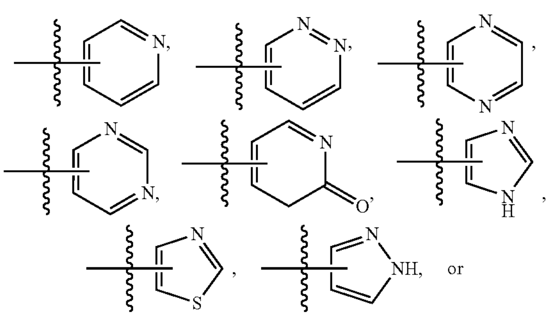

-continued

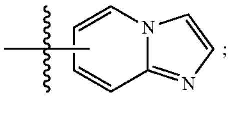

each occurrence of $R^9$ is independently substituted by 0-5 $R^{11}$, wherein each occurrence of $R^{11}$ is independently selected from —(C1-C6)alkyl, —O—(C1-C6)alkyl, -halogen, —$CF_3$, —$OCF_3$, —OMe, —(C6-C10)aryl, or -(5- to 10-membered)heteroaryl;

wherein $R_7$ is selected from —(C1-C6)alkyl, —(C3-C6) cycloalkyl, -(5- to 10-membered)heteroaryl, —(C6-C10)aryl, —(C1-C6)alkyl-(C6-C10)aryl, or -(5- to 10-membered)heteroaryl-(C1-C6)alkyl, or -(3- to 10-membered)heterocyclyl, wherein each $R_7$ is independently substituted with 0-5 R';

each occurrence of R' is wherein each occurrence of R' is independently selected from halogen, —R", —OR", oxo, —$CH_2$OR", —$CH_2$NR"$_2$, —C(O)N(R")$_2$, —C(O) OR", —$NO_2$, —NCS, —CN, —$CF_3$, —$OCF_3$ or —N(R")$_2$;

wherein each R' is independently substituted with 0-5 R", wherein R" is selected from —Cl, —F, —(C1-C6) alkyl, —OMe, or —(C6-C10)aryl;

$R^4$ is —H or (C1-C6)alkyl;

$R^6$ is —H or —(C1-C6)alkyl; and each $R^{13}$ and $R^{14}$ is independently selected from —H, —(C1-C3)aliphatic, or —(C3-C6)cycloalkyl.

In some embodiments a compound of formula I-f or a pharmaceutically acceptable salt, hydrate, solvate, polymorph, isomer, or combination thereof, has the structure of formula I-f:

wherein: m is 0, 1 or 2;

when m is 1 or 2, at least one occurrence of $R^1$ is halogen or —O—(C1-C6)alkyl;

each $R^1$ is independently selected from: -halogen and —O—(C1-C6)alkyl;

$R^2$ is selected from —CO(O)$R_7$, —C≡C—$R^9$,

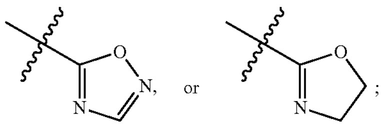 [SMILES: *c1ncno1 ; *C1=NCCO1]

wherein each 5-membered heterocycle or heteroaryl is substituted with 0-4 $R_7$;

each $R^9$ is selected from —H or —(C1-C6) alkyl, wherein each occurrence of $R^9$ is independently substituted by 0-5 R", and each occurrence of R" is selected from —(C1-C6)alkyl;

$R^4$ and $R^6$ are both —H; and wherein $R_7$, $R^{13}$, $R^{14}$ and R' are as defined in Formula I-f.

Examples of particular compounds of the present disclosure include:

| Compound | Structure |
|---|---|
| 1 | 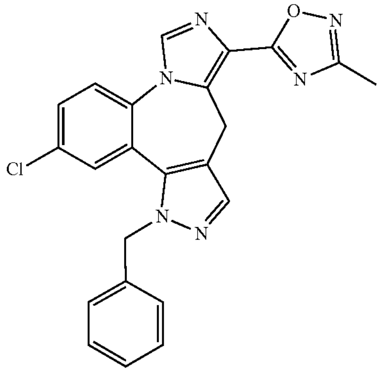 [SMILES: Cc1noc(-c2ncn3c2Cc2cnn(Cc4ccccc4)c2-c2cc(Cl)ccc2-3)n1] |
| 2 | 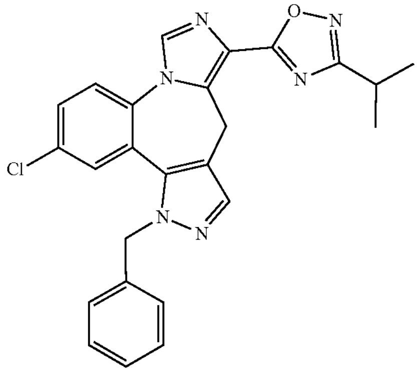 [SMILES: CC(C)c1noc(-c2ncn3c2Cc2cnn(Cc4ccccc4)c2-c2cc(Cl)ccc2-3)n1] |
| 3 | 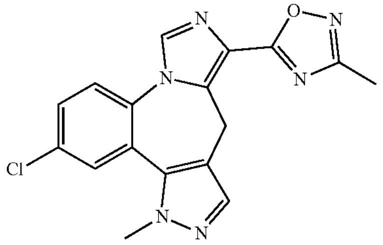 [SMILES: Cc1noc(-c2ncn3c2Cc2cnn(C)c2-c2cc(Cl)ccc2-3)n1] |
| 4 | 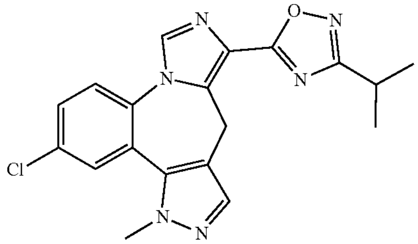 [SMILES: CC(C)c1noc(-c2ncn3c2Cc2cnn(C)c2-c2cc(Cl)ccc2-3)n1] |
| 5 | 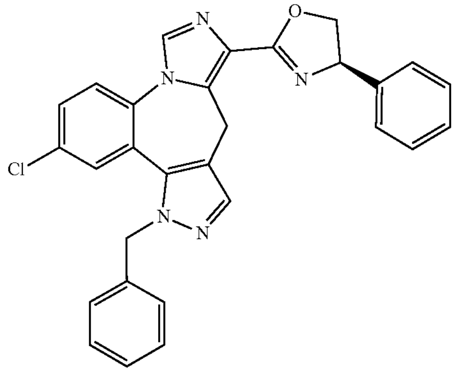 [SMILES: Clc1ccc2c(c1)-c1c(cnn1Cc1ccccc1)Cc1c(C3=N[C@H](c4ccccc4)CO3)ncn1-2] |

-continued
| Compound | Structure |
| --- | --- |
| 6 | 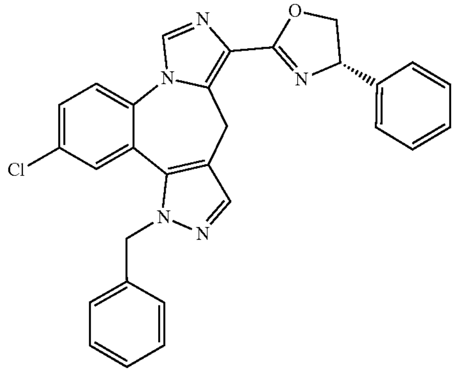 [SMILES: Clc1ccc2c(c1)-c1c(cnn1Cc1ccccc1)Cc1c(C3=N[C@@H](c4ccccc4)CO3)ncn1-2] |
| 7 | 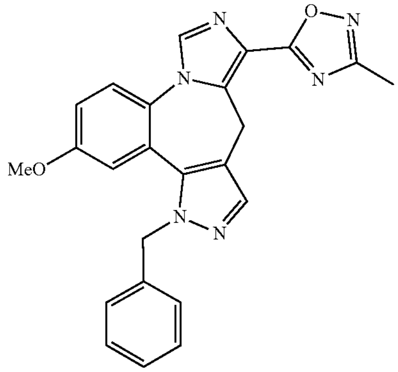 [SMILES: COc1ccc2c(c1)-c1c(cnn1Cc1ccccc1)Cc1c(-c3nc(C)no3)ncn1-2] |
| 8 | 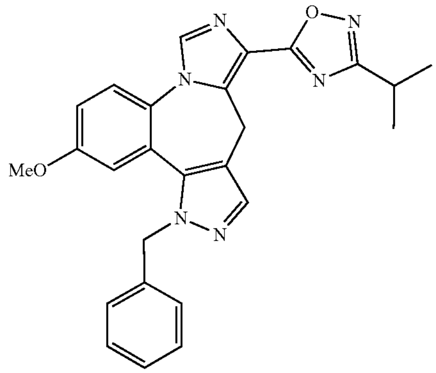 [SMILES: COc1ccc2c(c1)-c1c(cnn1Cc1ccccc1)Cc1c(-c3nc(C(C)C)no3)ncn1-2] |
| 9 | 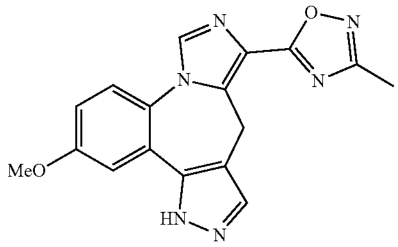 [SMILES: COc1ccc2c(c1)-c1[nH]ncc1Cc1c(-c3nc(C)no3)ncn1-2] |

-continued
| Compound | Structure |
| --- | --- |
| 10 | 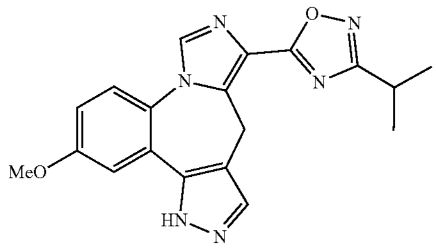 [SMILES: COc1ccc2c(c1)-c1[nH]ncc1Cc1c(-c3nc(C(C)C)no3)ncn1-2] |
| 11 | 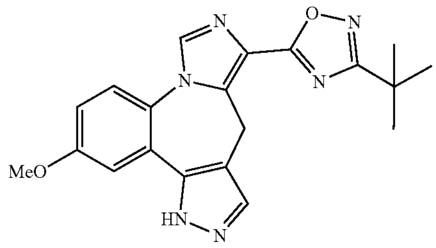 [SMILES: COc1ccc2c(c1)-c1[nH]ncc1Cc1c(-c3nc(C(C)(C)C)no3)ncn1-2] |
| 12 | 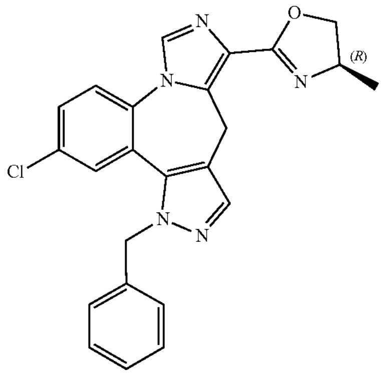 |
| 13 | 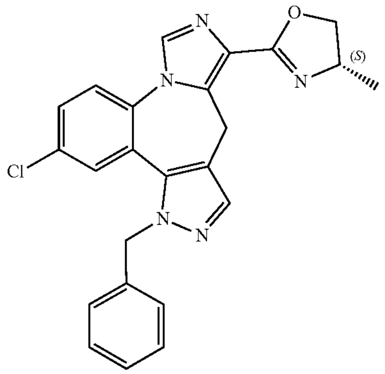 |
| 14 | 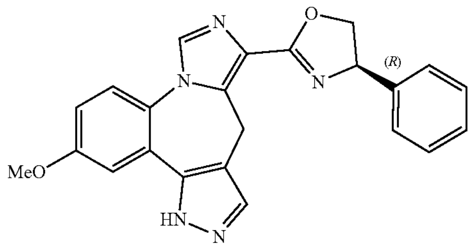 |

-continued
| Compound | Structure |
| --- | --- |
| 15 | 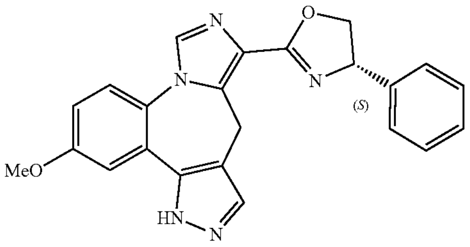 |
| 16 | 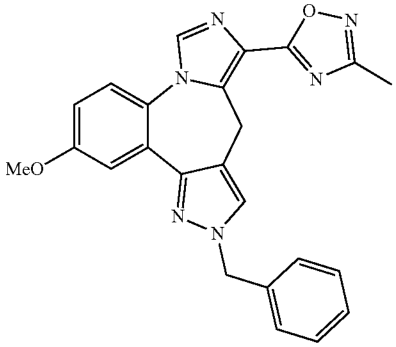 [SMILES: COc1ccc2c(c1)-c1nn(Cc3ccccc3)cc1Cc1c(-c3nc(C)no3)ncn1-2] |
| 17 | 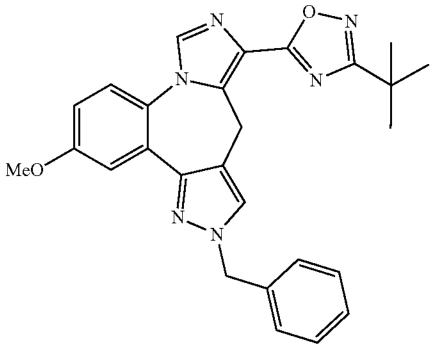 [SMILES: COc1ccc2c(c1)-c1nn(Cc3ccccc3)cc1Cc1c(-c3nc(C(C)(C)C)no3)ncn1-2] |
| 18 | 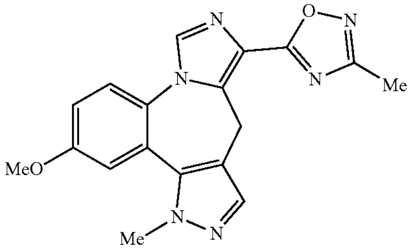 [SMILES: COc1ccc2c(c1)-c1c(cnn1C)Cc1c(-c3nc(C)no3)ncn1-2] |
| 19 | 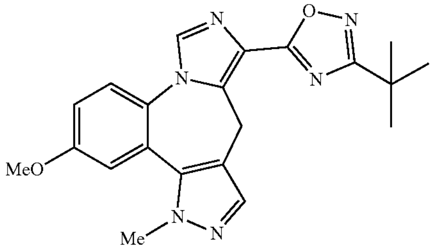 [SMILES: COc1ccc2c(c1)-c1c(cnn1C)Cc1c(-c3nc(C(C)(C)C)no3)ncn1-2] |

-continued
| Compound | Structure |
| --- | --- |
| 20 | 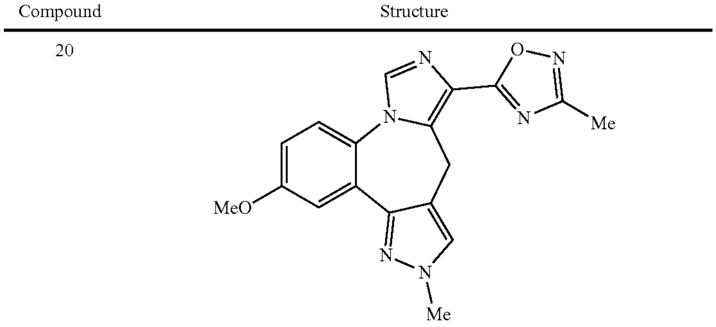 |
| 21 | 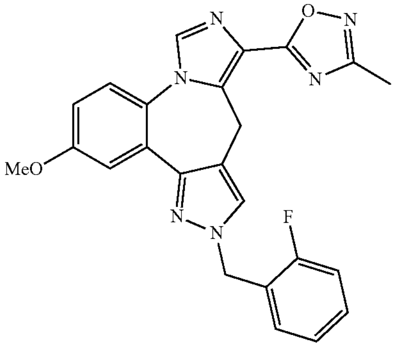 [SMILES: COc1ccc2c(c1)-c1nn(Cc3ccccc3F)cc1Cc1c(-c3nc(C)no3)ncn1-2] |
| 22 | 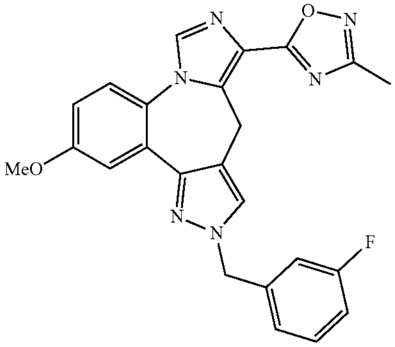 [SMILES: COc1ccc2c(c1)-c1nn(Cc3cccc(F)c3)cc1Cc1c(-c3nc(C)no3)ncn1-2] |
| 23 | 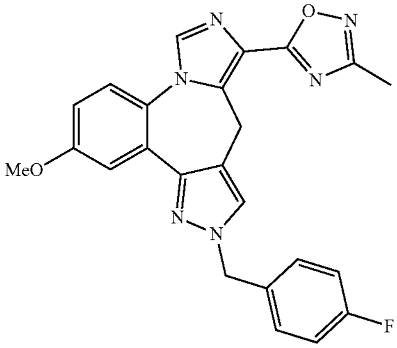 [SMILES: COc1ccc2c(c1)-c1nn(Cc3ccc(F)cc3)cc1Cc1c(-c3nc(C)no3)ncn1-2] |
| 24 | 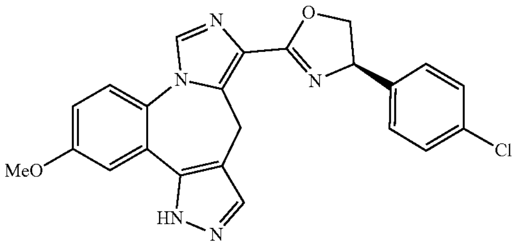 [SMILES: COc1ccc2c(c1)-c1[nH]ncc1Cc1c(C3=N[C@H](c4ccc(Cl)cc4)CO3)ncn1-2] |

-continued
| Compound | Structure |
| --- | --- |
| 25 | 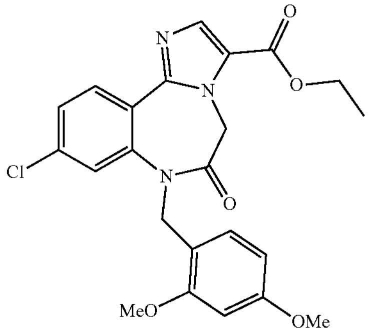 [SMILES: CCOC(=O)c1cnc2n1CC(=O)N(Cc1ccc(OC)cc1OC)c1cc(Cl)ccc1-2] |
| 26 | 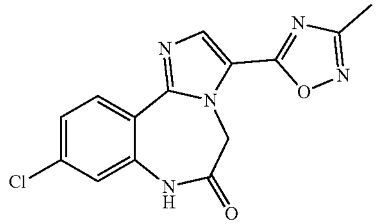 [SMILES: Cc1noc(-c2cnc3n2CC(=O)Nc2cc(Cl)ccc2-3)n1] |
| 27 | 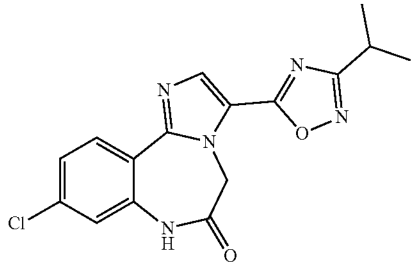 [SMILES: CC(C)c1noc(-c2cnc3n2CC(=O)Nc2cc(Cl)ccc2-3)n1] |
| 28 | 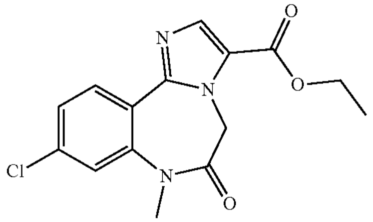 [SMILES: CCOC(=O)c1cnc2n1CC(=O)N(C)c1cc(Cl)ccc1-2] |
| 29 | 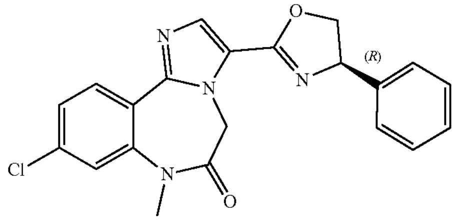 |
| 30 | 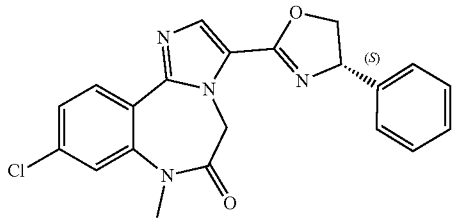 |

-continued
| Compound | Structure |
| --- | --- |
| 31 | 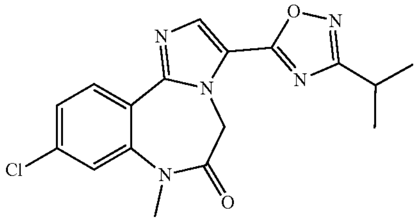 [SMILES: CC(C)c1noc(-c2cnc3n2CC(=O)N(C)c2cc(Cl)ccc2-3)n1] |
| 32 | 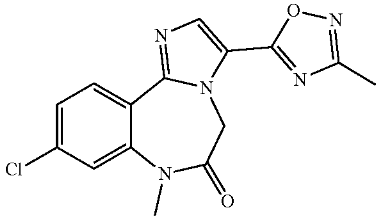 [SMILES: Cc1noc(-c2cnc3n2CC(=O)N(C)c2cc(Cl)ccc2-3)n1] |
| 33 | 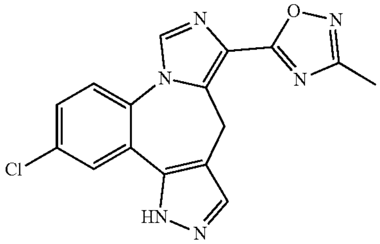 [SMILES: Cc1noc(-c2ncn3c2Cc2cn[nH]c2-c2cc(Cl)ccc2-3)n1] |
| 34 | 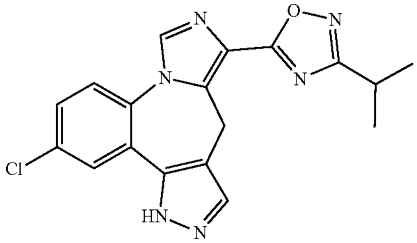 [SMILES: CC(C)c1noc(-c2ncn3c2Cc2cn[nH]c2-c2cc(Cl)ccc2-3)n1] |
| 35 | 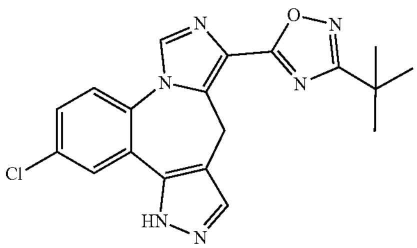 [SMILES: CC(C)(C)c1noc(-c2ncn3c2Cc2cn[nH]c2-c2cc(Cl)ccc2-3)n1] |

-continued
| Compound | Structure |
| --- | --- |
| 36 | 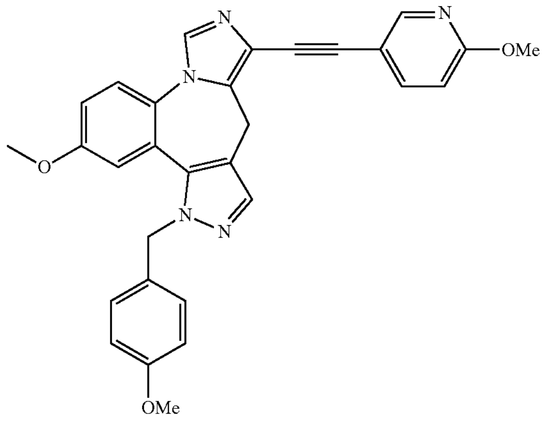 [SMILES: COc1ccc(Cn2ncc3c2-c2cc(OC)ccc2-n2cnc(C#Cc4ccc(OC)nc4)c2C3)cc1] |
| 37 | 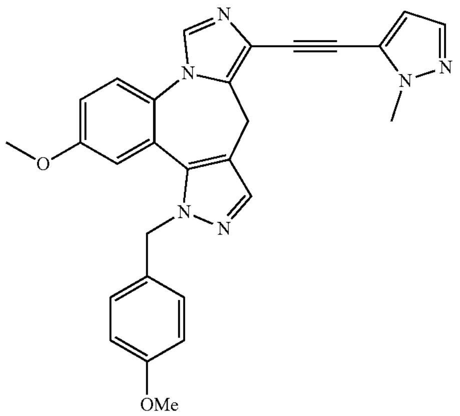 [SMILES: COc1ccc(Cn2ncc3c2-c2cc(OC)ccc2-n2cnc(C#Cc4ccnn4C)c2C3)cc1] |
| 38 | 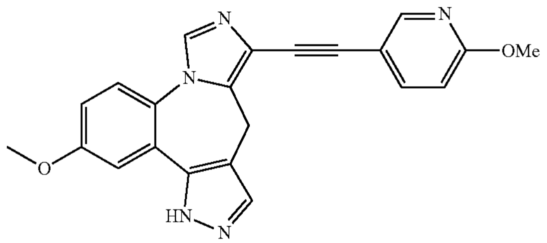 [SMILES: COc1ccc2c(c1)-c1[nH]ncc1Cc1c(C#Cc3ccc(OC)nc3)ncn1-2] |
| 39 | 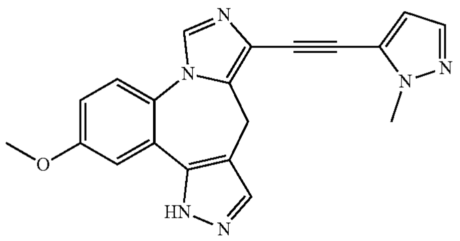 [SMILES: COc1ccc2c(c1)-c1[nH]ncc1Cc1c(C#Cc3ccnn3C)ncn1-2] |
| 40 | 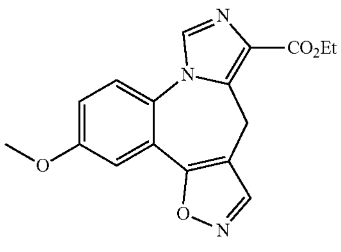 [SMILES: CCOC(=O)c1ncn2c1Cc1cnoc1-c1cc(OC)ccc1-2] |

-continued
| Compound | Structure |
|---|---|
| 41 | 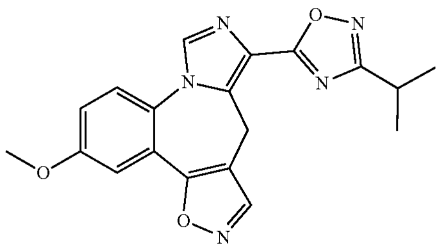 [SMILES: COc1ccc2c(c1)-c1oncc1Cc1c(-c3nc(C(C)C)no3)ncn1-2] |
| 42 | 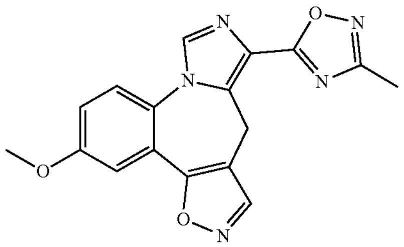 |
| 43 | 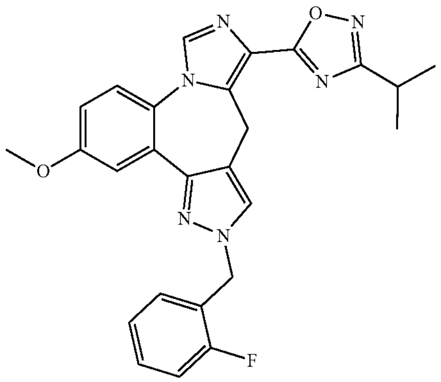 [SMILES: COc1ccc2c(c1)-c1nn(Cc3ccccc3F)cc1Cc1c(-c3nc(C(C)C)no3)ncn1-2] |
| 44 | 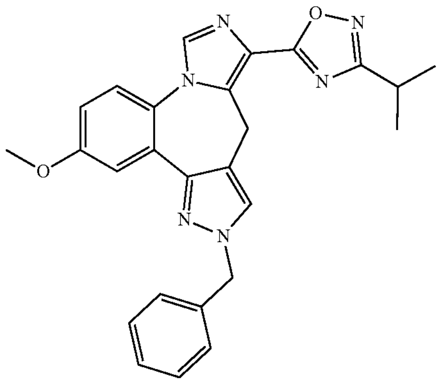 [SMILES: COc1ccc2c(c1)-c1nn(Cc3ccccc3)cc1Cc1c(-c3nc(C(C)C)no3)ncn1-2] |
| 45 | 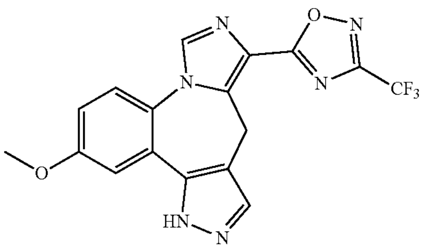 [SMILES: COc1ccc2c(c1)-c1[nH]ncc1Cc1c(-c3nc(C(F)(F)F)no3)ncn1-2] |

-continued
| Compound | Structure |
|---|---|
| 46 | 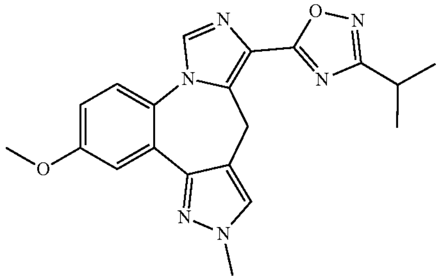 [SMILES: COc1ccc2c(c1)-c1nn(C)cc1Cc1c(-c3nc(C(C)C)no3)ncn1-2] |
| 47 | 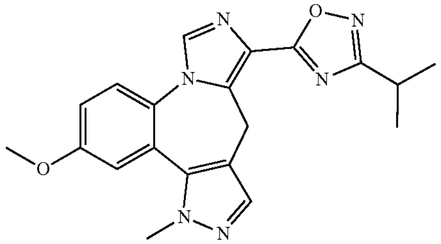 [SMILES: COc1ccc2c(c1)-c1c(cnn1C)Cc1c(-c3nc(C(C)C)no3)ncn1-2] |
| 48 | 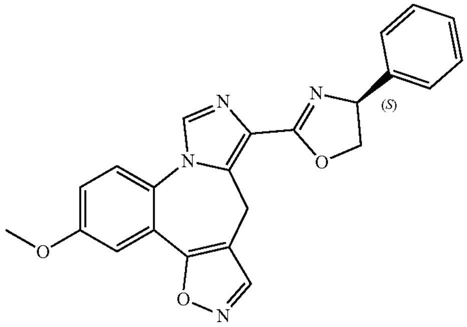 |
| 49 | 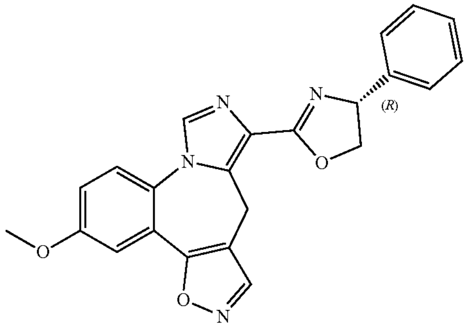 |
| 50 | 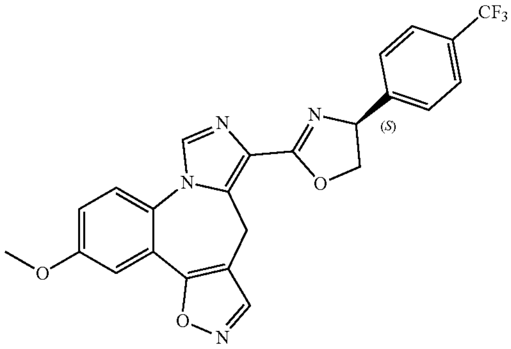 |

-continued
| Compound | Structure |
| --- | --- |
| 51 | 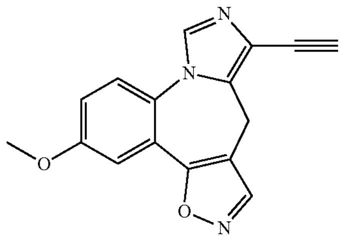 [SMILES: C#Cc1ncn2c1Cc1cnoc1-c1cc(OC)ccc1-2] |
| 52 | 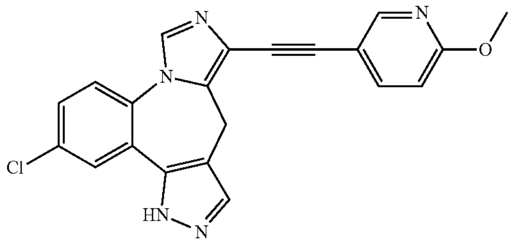 [SMILES: COc1ccc(C#Cc2ncn3c2Cc2cn[nH]c2-c2cc(Cl)ccc2-3)cn1] |
| 53 | 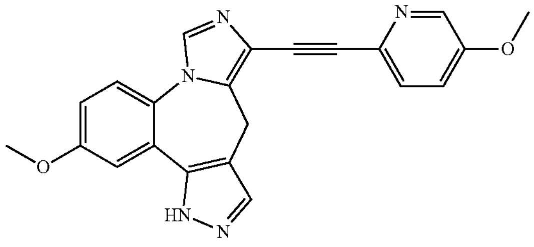 |
| 54 | 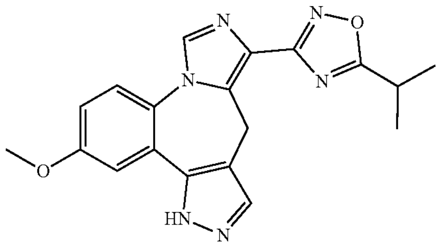 [SMILES: COc1ccc2c(c1)-c1[nH]ncc1Cc1c(-c3noc(C(C)C)n3)ncn1-2] |
| 55 | 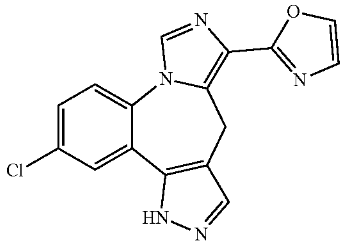 [SMILES: Clc1ccc2c(c1)-c1[nH]ncc1Cc1c(-c3ncco3)ncn1-2] |
| 56 | 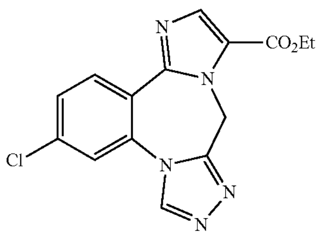 [SMILES: CCOC(=O)c1cnc2n1Cc1nncn1-c1cc(Cl)ccc1-2] |

-continued
| Compound | Structure |
|---|---|
| 57 | 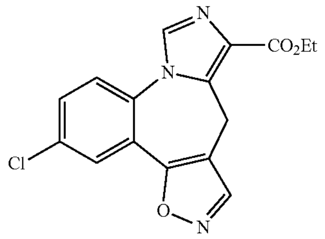 [SMILES: CCOC(=O)c1ncn2c1Cc1cnoc1-c1cc(Cl)ccc1-2] |
| 58 | 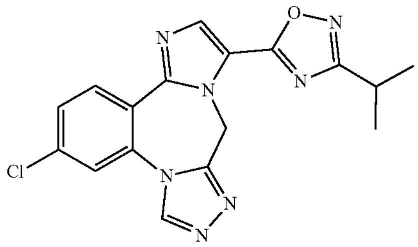 [SMILES: CC(C)c1noc(-c2cnc3n2Cc2nncn2-c2cc(Cl)ccc2-3)n1] |
| 59 | 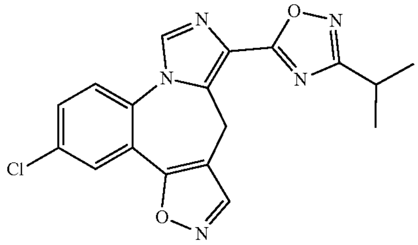 [SMILES: CC(C)c1noc(-c2ncn3c2Cc2cnoc2-c2cc(Cl)ccc2-3)n1] |
| 60 | 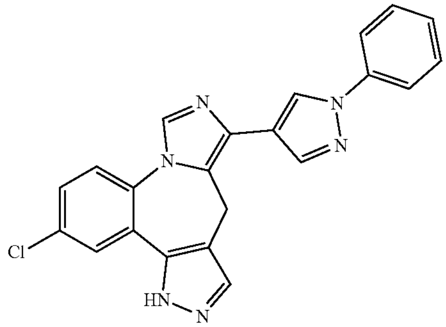 [SMILES: Clc1ccc2c(c1)-c1[nH]ncc1Cc1c(-c3cnn(-c4ccccc4)c3)ncn1-2] |
| 61 | 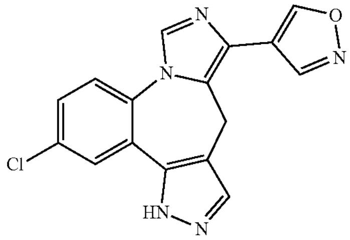 [SMILES: Clc1ccc2c(c1)-c1[nH]ncc1Cc1c(-c3cnoc3)ncn1-2] |
| 62 | 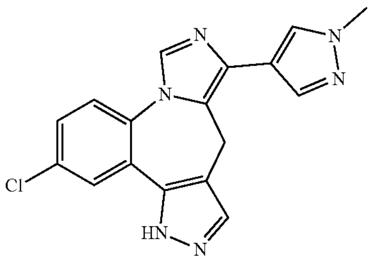 [SMILES: Cn1cc(-c2ncn3c2Cc2cn[nH]c2-c2cc(Cl)ccc2-3)cn1] |

-continued
| Compound | Structure |
|---|---|
| 63 | 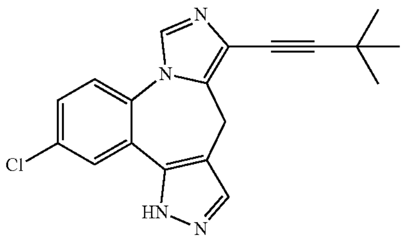 [SMILES: CC(C)(C)C#Cc1ncn2c1Cc1cn[nH]c1-c1cc(Cl)ccc1-2] |
| 64 | 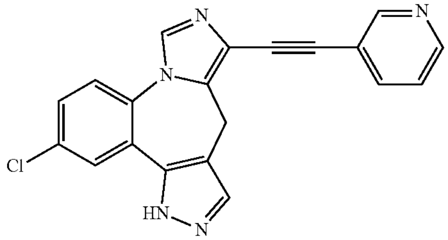 [SMILES: Clc1ccc2c(c1)-c1[nH]ncc1Cc1c(C#Cc3cccnc3)ncn1-2] |
| 65 | 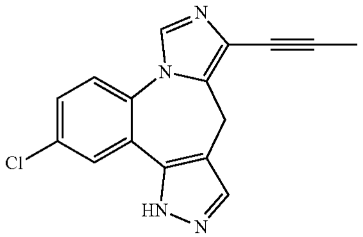 [SMILES: CC#Cc1ncn2c1Cc1cn[nH]c1-c1cc(Cl)ccc1-2] |
| 66 | 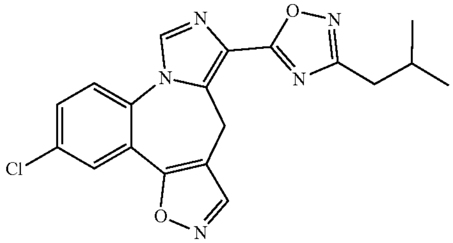 [SMILES: CC(C)Cc1noc(-c2ncn3c2Cc2cnoc2-c2cc(Cl)ccc2-3)n1] |
| 67 | 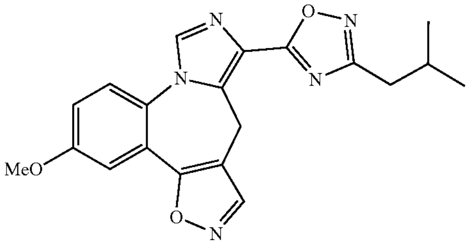 [SMILES: COc1ccc2c(c1)-c1oncc1Cc1c(-c3nc(CC(C)C)no3)ncn1-2] |
| 68 | 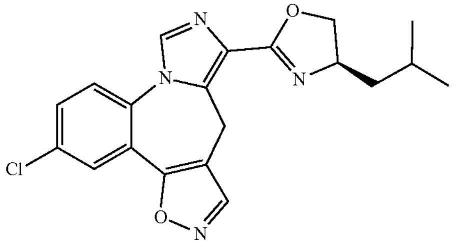 [SMILES: CC(C)C[C@@H]1COC(c2ncn3c2Cc2cnoc2-c2cc(Cl)ccc2-3)=N1] |

-continued
| Compound | Structure |
| --- | --- |
| 69 | 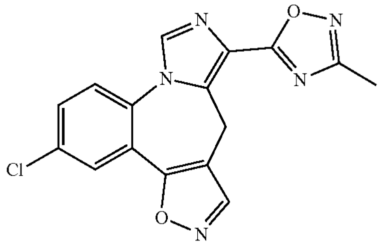 [SMILES: Cc1noc(-c2ncn3c2Cc2cnoc2-c2cc(Cl)ccc2-3)n1] |
| 70 | 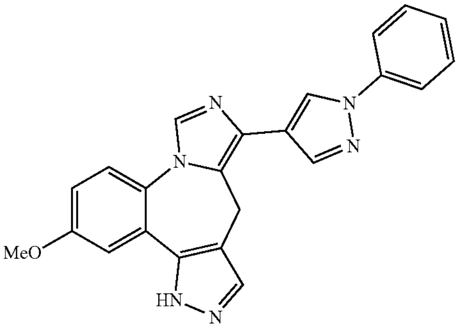 [SMILES: COc1ccc2c(c1)-c1[nH]ncc1Cc1c(-c3cnn(-c4ccccc4)c3)ncn1-2] |
| 71 | 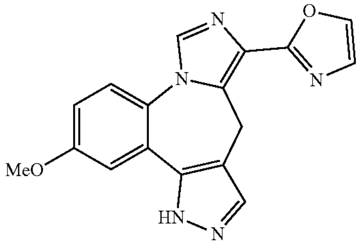 [SMILES: COc1ccc2c(c1)-c1[nH]ncc1Cc1c(-c3ncco3)ncn1-2] |
| 72 | 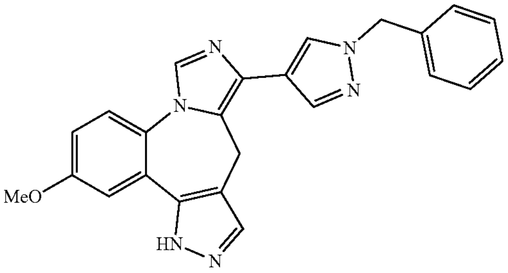 [SMILES: COc1ccc2c(c1)-c1[nH]ncc1Cc1c(-c3cnn(Cc4ccccc4)c3)ncn1-2] |
| 73 | 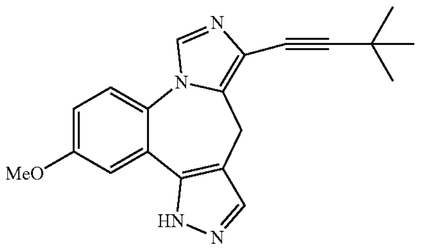 [SMILES: COc1ccc2c(c1)-c1[nH]ncc1Cc1c(C#CC(C)(C)C)ncn1-2] |

-continued
| Compound | Structure |
|---|---|
| 74 | 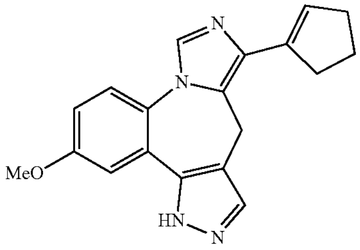 [SMILES: COc1ccc2c(c1)-c1[nH]ncc1Cc1c(C3=CCCC3)ncn1-2] |
| 75 | 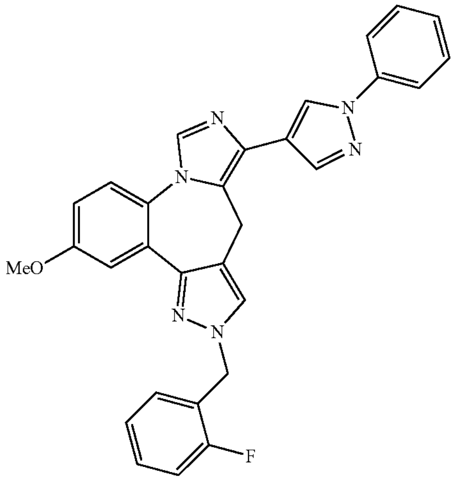 [SMILES: COc1ccc2c(c1)-c1nn(Cc3ccccc3F)cc1Cc1c(-c3cnn(-c4ccccc4)c3)ncn1-2] |
| 76 | 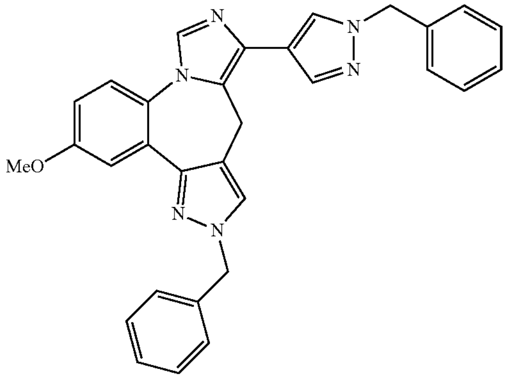 [SMILES: COc1ccc2c(c1)-c1nn(Cc3ccccc3)cc1Cc1c(-c3cnn(Cc4ccccc4)c3)ncn1-2] |
| 77 | 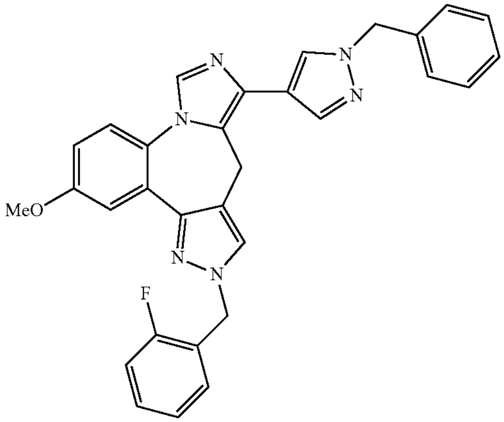 [SMILES: COc1ccc2c(c1)-c1nn(Cc3ccccc3F)cc1Cc1c(-c3cnn(Cc4ccccc4)c3)ncn1-2] |

-continued
| Compound | Structure |
| --- | --- |
| 78 | 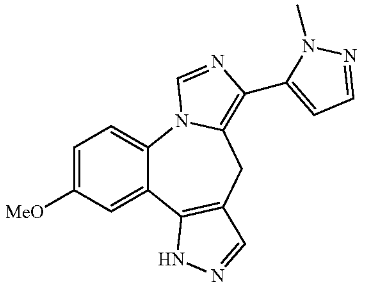 [SMILES: COc1ccc2c(c1)-c1[nH]ncc1Cc1c(-c3ccnn3C)ncn1-2] |
| 79 | 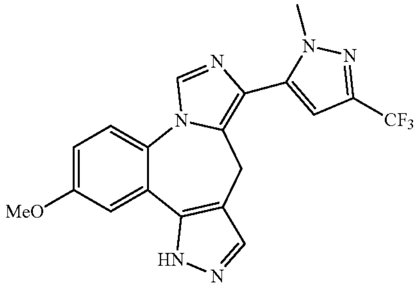 [SMILES: COc1ccc2c(c1)-c1[nH]ncc1Cc1c(-c3cc(C(F)(F)F)nn3C)ncn1-2] |
| 80 | 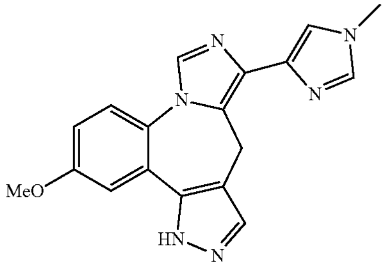 [SMILES: COc1ccc2c(c1)-c1[nH]ncc1Cc1c(-c3cn(C)cn3)ncn1-2] |
| 81 | 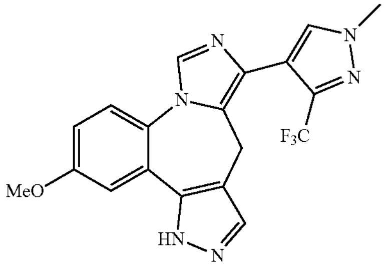 [SMILES: COc1ccc2c(c1)-c1[nH]ncc1Cc1c(-c3cn(C)nc3C(F)(F)F)ncn1-2] |
| 82 | 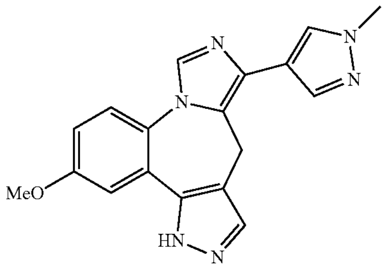 [SMILES: COc1ccc2c(c1)-c1[nH]ncc1Cc1c(-c3cnn(C)c3)ncn1-2] |

-continued
| Compound | Structure |
|---|---|
| 83 | 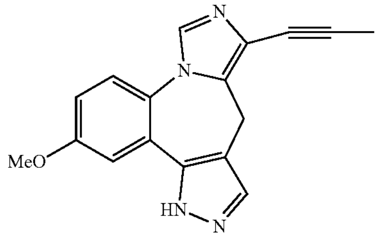 [SMILES: CC#Cc1ncn2c1Cc1cn[nH]c1-c1cc(OC)ccc1-2] |
| 84 | 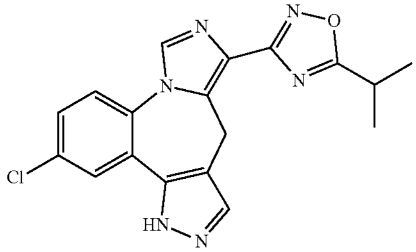 [SMILES: CC(C)c1nc(-c2ncn3c2Cc2cn[nH]c2-c2cc(Cl)ccc2-3)no1] |
| 85 | 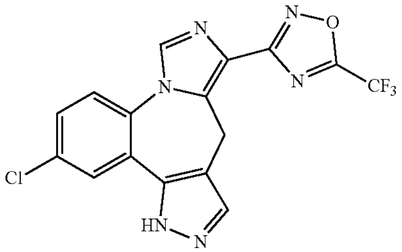 [SMILES: FC(F)(F)c1nc(-c2ncn3c2Cc2cn[nH]c2-c2cc(Cl)ccc2-3)no1] |
| 86 | 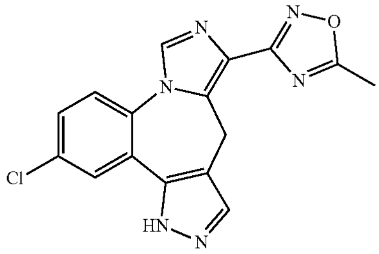 [SMILES: Cc1nc(-c2ncn3c2Cc2cn[nH]c2-c2cc(Cl)ccc2-3)no1] |
| 87 | 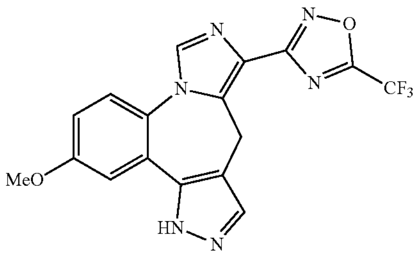 [SMILES: COc1ccc2c(c1)-c1[nH]ncc1Cc1c(-c3noc(C(F)(F)F)n3)ncn1-2] |
| 88 | 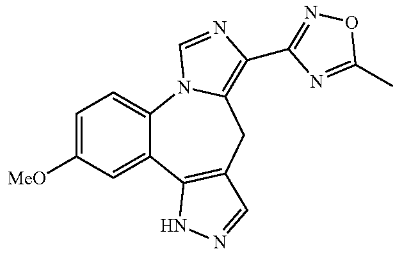 [SMILES: COc1ccc2c(c1)-c1[nH]ncc1Cc1c(-c3noc(C)n3)ncn1-2] |

-continued
| Compound | Structure |
| --- | --- |
| 89 | 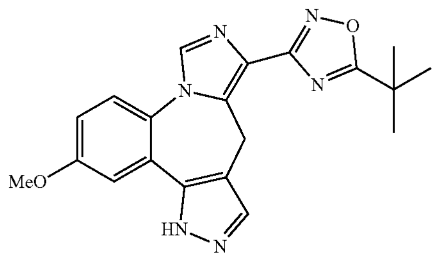 [SMILES: COc1ccc2c(c1)-c1[nH]ncc1Cc1c(-c3noc(C(C)(C)C)n3)ncn1-2] |
| 90 | 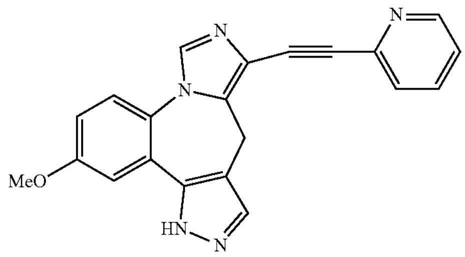 [SMILES: COc1ccc2c(c1)-c1[nH]ncc1Cc1c(C#Cc3ccccn3)ncn1-2] |
| 91 | 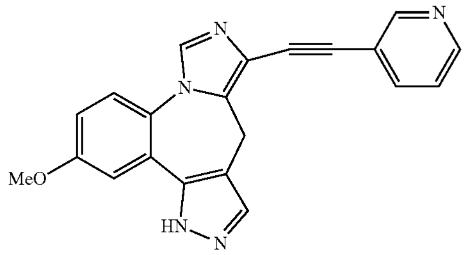 [SMILES: COc1ccc2c(c1)-c1[nH]ncc1Cc1c(C#Cc3cccnc3)ncn1-2] |
| 92 | 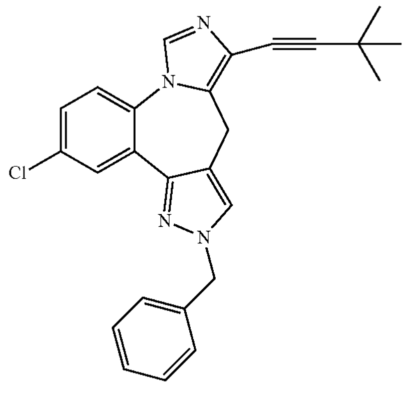 [SMILES: CC(C)(C)C#Cc1ncn2c1Cc1cn(Cc3ccccc3)nc1-c1cc(Cl)ccc1-2] |
| 93 | 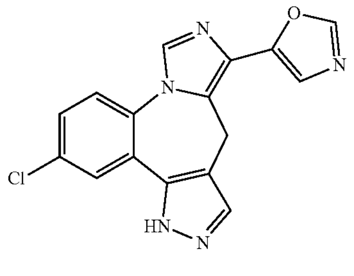 [SMILES: Clc1ccc2c(c1)-c1[nH]ncc1Cc1c(-c3cnco3)ncn1-2] |

-continued
| Compound | Structure |
| --- | --- |
| 94 | 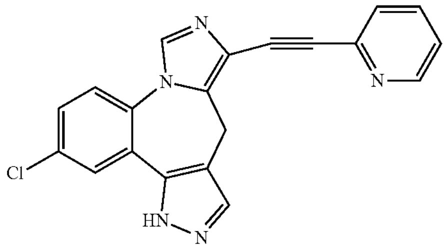 [SMILES: Clc1ccc2c(c1)-c1[nH]ncc1Cc1c(C#Cc3ccccn3)ncn1-2] |
| 95 | 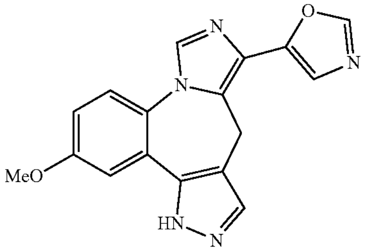 [SMILES: COc1ccc2c(c1)-c1[nH]ncc1Cc1c(-c3cnco3)ncn1-2] |
| 96 | 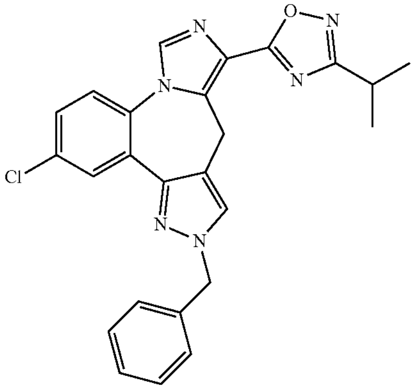 [SMILES: CC(C)c1noc(-c2ncn3c2Cc2cn(Cc4ccccc4)nc2-c2cc(Cl)ccc2-3)n1] |
| 97 | 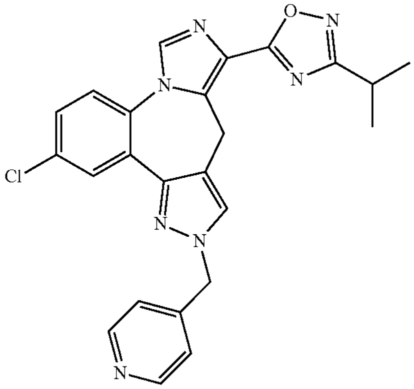 [SMILES: CC(C)c1noc(-c2ncn3c2Cc2cn(Cc4ccncc4)nc2-c2cc(Cl)ccc2-3)n1] |

-continued
| Compound | Structure |
|---|---|
| 98 | 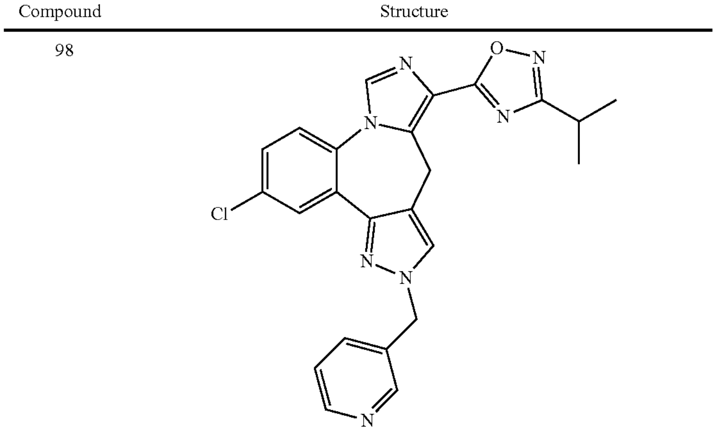 |
| 99 | 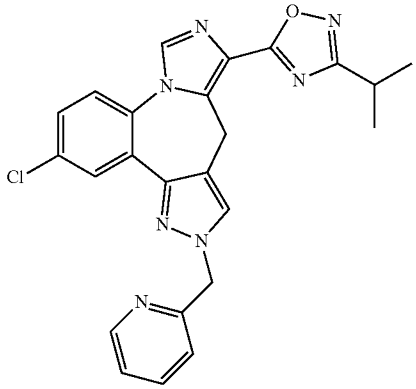 [SMILES: CC(C)c1noc(-c2ncn3c2Cc2cn(Cc4ccccn4)nc2-c2cc(Cl)ccc2-3)n1] |
| 100 | 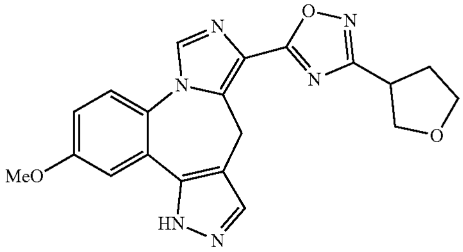 [SMILES: COc1ccc2c(c1)-c1[nH]ncc1Cc1c(-c3nc(C4CCOC4)no3)ncn1-2] |
| 101 | 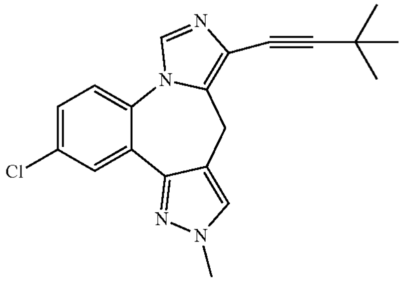 [SMILES: Cn1cc2c(n1)-c1cc(Cl)ccc1-n1cnc(C#CC(C)(C)C)c1C2] |
| 102 | 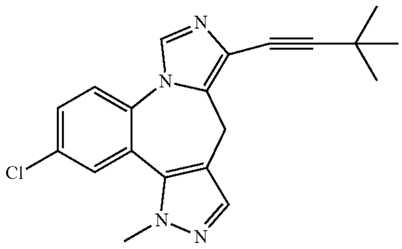 [SMILES: Cn1ncc2c1-c1cc(Cl)ccc1-n1cnc(C#CC(C)(C)C)c1C2] |

-continued
| Compound | Structure |
|---|---|
| 103 | 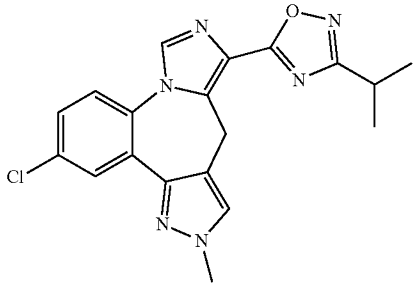 [SMILES: CC(C)c1noc(-c2ncn3c2Cc2cn(C)nc2-c2cc(Cl)ccc2-3)n1] |
| 104 | 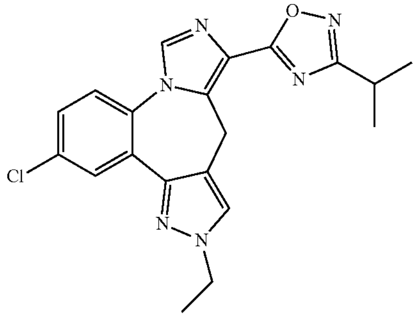 [SMILES: CCn1cc2c(n1)-c1cc(Cl)ccc1-n1cnc(-c3nc(C(C)C)no3)c1C2] |
| 105 | 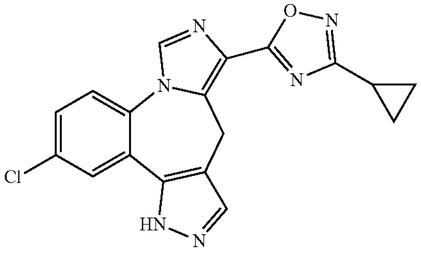 [SMILES: Clc1ccc2c(c1)-c1[nH]ncc1Cc1c(-c3nc(C4CC4)no3)ncn1-2] |
| 106 | 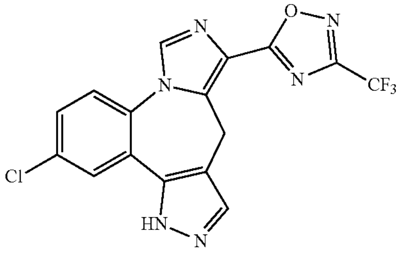 [SMILES: FC(F)(F)c1noc(-c2ncn3c2Cc2cn[nH]c2-c2cc(Cl)ccc2-3)n1] |
| 107 | 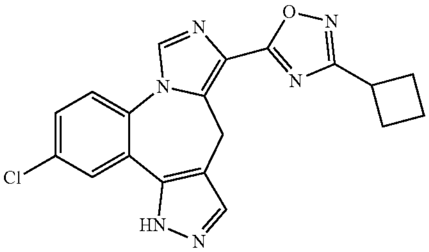 [SMILES: Clc1ccc2c(c1)-c1[nH]ncc1Cc1c(-c3nc(C4CCC4)no3)ncn1-2] |

-continued
| Compound | Structure |
| --- | --- |
| 108 | 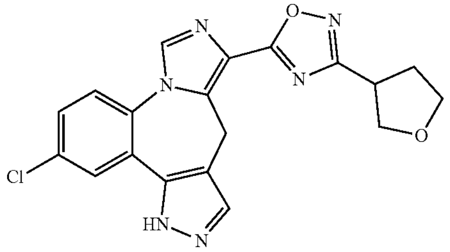 [SMILES: Clc1ccc2c(c1)-c1[nH]ncc1Cc1c(-c3nc(C4CCOC4)no3)ncn1-2] |
| 109 | 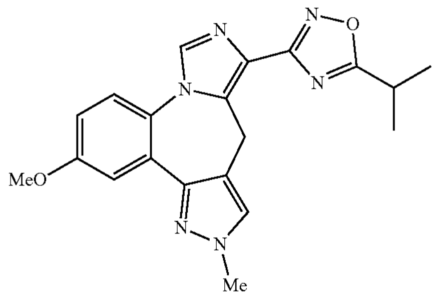 [SMILES: COc1ccc2c(c1)-c1nn(C)cc1Cc1c(-c3noc(C(C)C)n3)ncn1-2] |
| 110 | 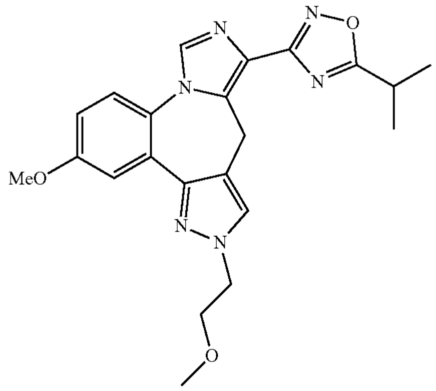 [SMILES: COCCn1cc2c(n1)-c1cc(OC)ccc1-n1cnc(-c3noc(C(C)C)n3)c1C2] |
| 111 | 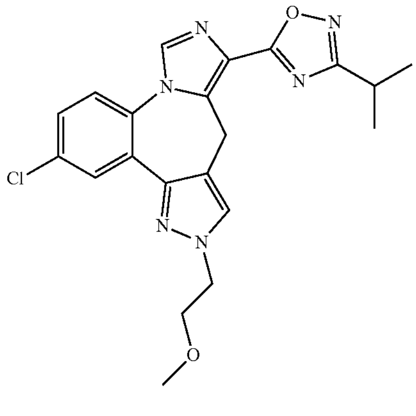 [SMILES: COCCn1cc2c(n1)-c1cc(Cl)ccc1-n1cnc(-c3nc(C(C)C)no3)c1C2] |

-continued
| Compound | Structure |
|---|---|
| 112 | 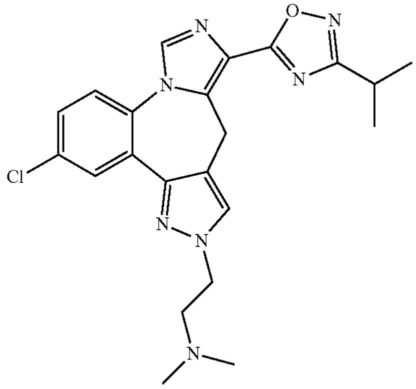 [SMILES: CC(C)c1noc(-c2ncn3c2Cc2cn(CCN(C)C)nc2-c2cc(Cl)ccc2-3)n1] |
| 113 | 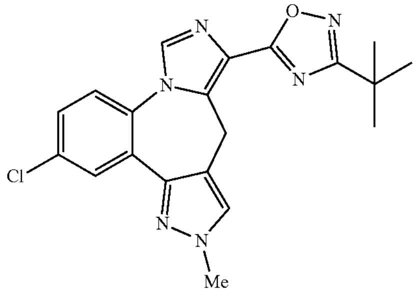 [SMILES: Cn1cc2c(n1)-c1cc(Cl)ccc1-n1cnc(-c3nc(C(C)(C)C)no3)c1C2] |
| 114 | 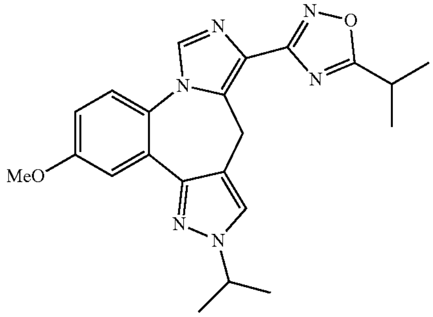 [SMILES: COc1ccc2c(c1)-c1nn(C(C)C)cc1Cc1c(-c3noc(C(C)C)n3)ncn1-2] |
| 115 | 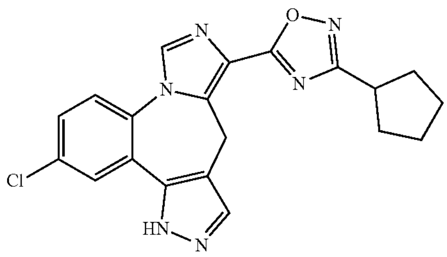 [SMILES: Clc1ccc2c(c1)-c1[nH]ncc1Cc1c(-c3nc(C4CCCC4)no3)ncn1-2] |

-continued
| Compound | Structure |
| --- | --- |
| 116 | 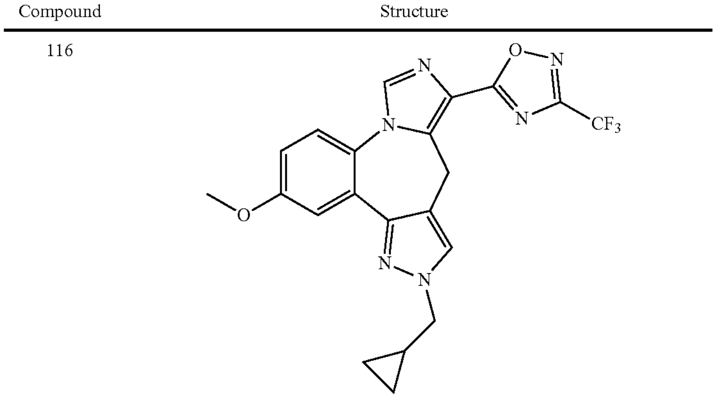 |
| 117 | 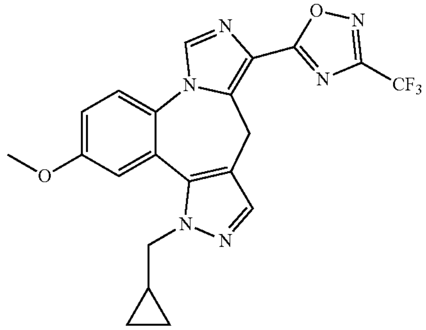 [SMILES: COc1ccc2c(c1)-c1c(cnn1CC1CC1)Cc1c(-c3nc(C(F)(F)F)no3)ncn1-2] |
| 118 | 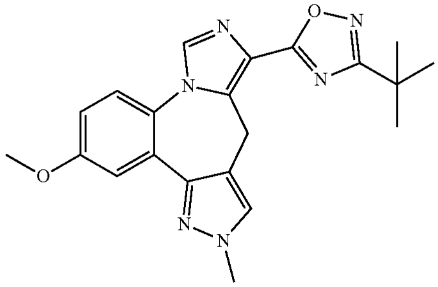 [SMILES: COc1ccc2c(c1)-c1nn(C)cc1Cc1c(-c3nc(C(C)(C)C)no3)ncn1-2] |
| 119 | 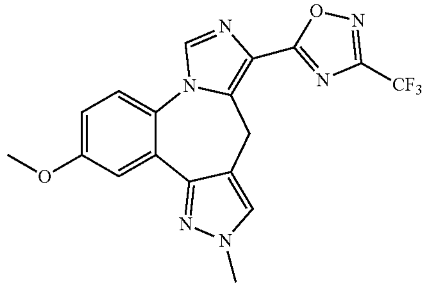 [SMILES: COc1ccc2c(c1)-c1nn(C)cc1Cc1c(-c3nc(C(F)(F)F)no3)ncn1-2] |
| 120 | 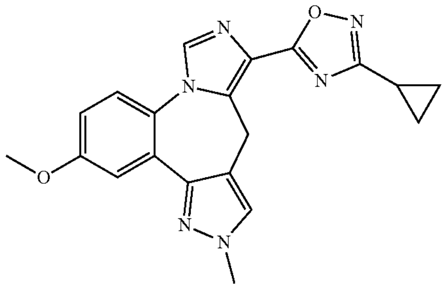 [SMILES: COc1ccc2c(c1)-c1nn(C)cc1Cc1c(-c3nc(C4CC4)no3)ncn1-2] |

-continued
| Compound | Structure |
|---|---|
| 121 | 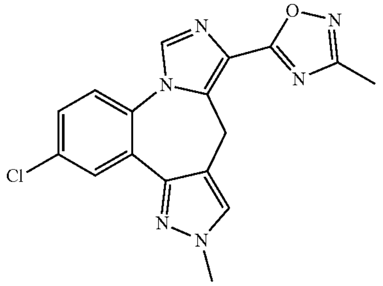 [SMILES: Cc1noc(-c2ncn3c2Cc2cn(C)nc2-c2cc(Cl)ccc2-3)n1] |
| 122 | 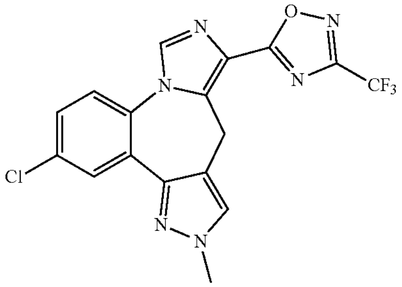 [SMILES: Cn1cc2c(n1)-c1cc(Cl)ccc1-n1cnc(-c3nc(C(F)(F)F)no3)c1C2] |
| 123 | 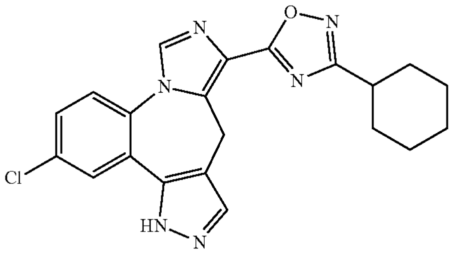 [SMILES: Clc1ccc2c(c1)-c1[nH]ncc1Cc1c(-c3nc(C4CCCCC4)no3)ncn1-2] |
| 124 | 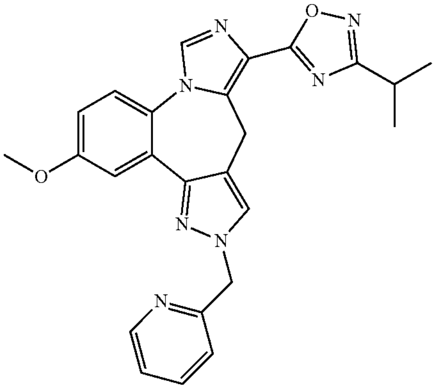 [SMILES: COc1ccc2c(c1)-c1nn(Cc3ccccn3)cc1Cc1c(-c3nc(C(C)C)no3)ncn1-2] |

-continued
| Compound | Structure |
| --- | --- |
| 125 | 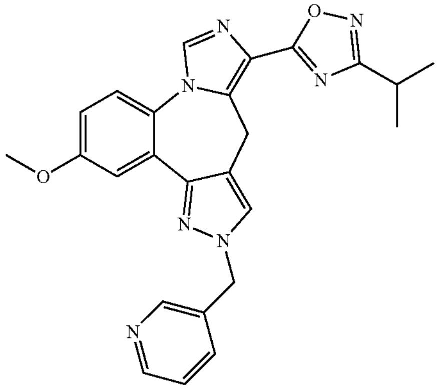 [SMILES: COc1ccc2c(c1)-c1nn(Cc3cccnc3)cc1Cc1c(-c3nc(C(C)C)no3)ncn1-2] |
| 126 | 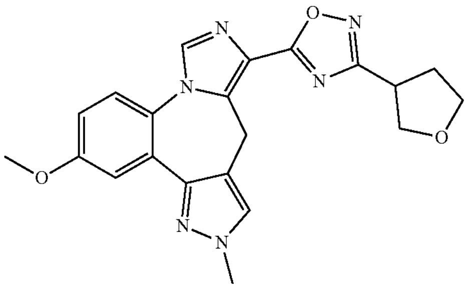 [SMILES: COc1ccc2c(c1)-c1nn(C)cc1Cc1c(-c3nc(C4CCOC4)no3)ncn1-2] |
| 127 | 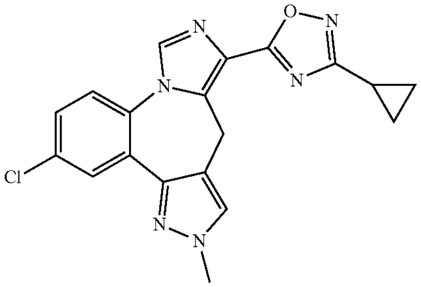 [SMILES: Cn1cc2c(n1)-c1cc(Cl)ccc1-n1cnc(-c3nc(C4CC4)no3)c1C2] |
| 128 | 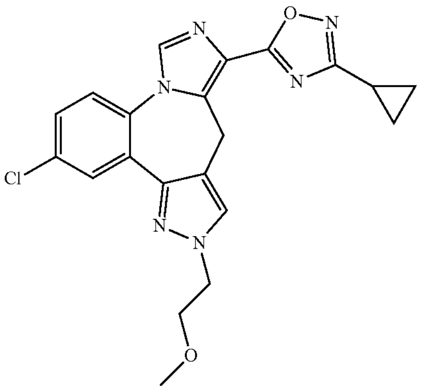 [SMILES: COCCn1cc2c(n1)-c1cc(Cl)ccc1-n1cnc(-c3nc(C4CC4)no3)c1C2] |

-continued
| Compound | Structure |
|---|---|
| 129 | 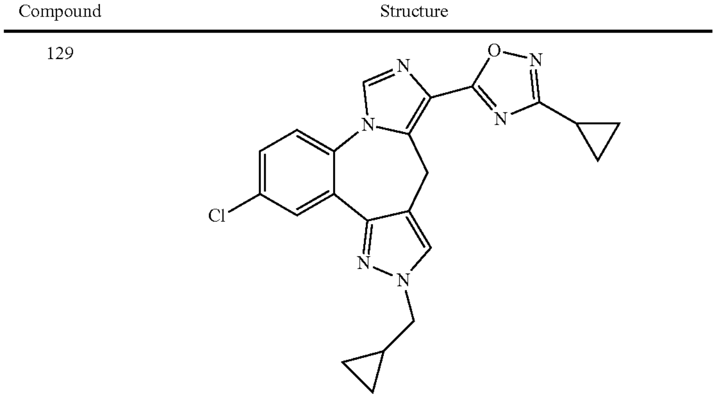 |
| 130 | 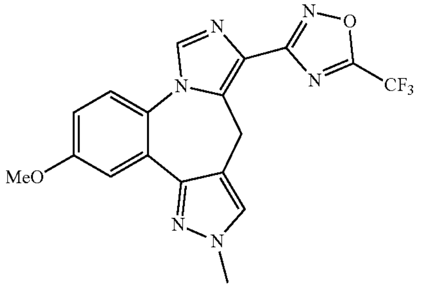 [SMILES: COc1ccc2c(c1)-c1nn(C)cc1Cc1c(-c3noc(C(F)(F)F)n3)ncn1-2] |
| 131 | 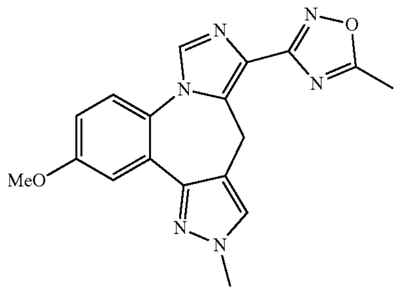 [SMILES: COc1ccc2c(c1)-c1nn(C)cc1Cc1c(-c3noc(C)n3)ncn1-2] |
| 132 | 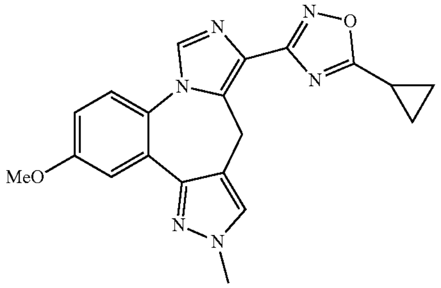 [SMILES: COc1ccc2c(c1)-c1nn(C)cc1Cc1c(-c3noc(C4CC4)n3)ncn1-2] |
| 133 | 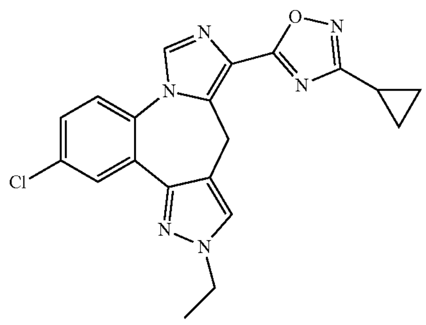 [SMILES: CCn1cc2c(n1)-c1cc(Cl)ccc1-n1cnc(-c3nc(C4CC4)no3)c1C2] |

-continued
| Compound | Structure |
|---|---|
| 134 | 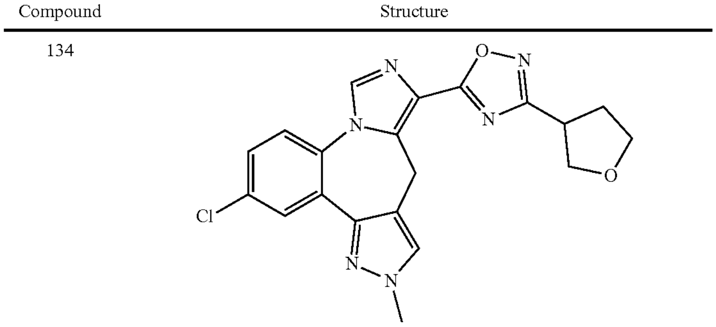 |
| 135 | 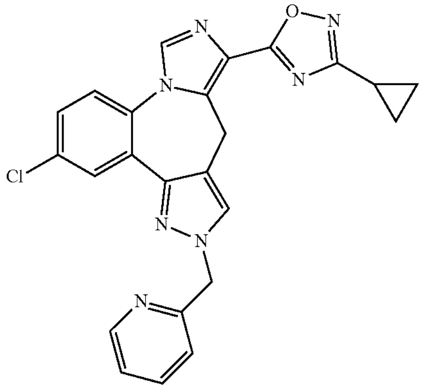 [SMILES: Clc1ccc2c(c1)-c1nn(Cc3ccccn3)cc1Cc1c(-c3nc(C4CC4)no3)ncn1-2] |
| 136 | 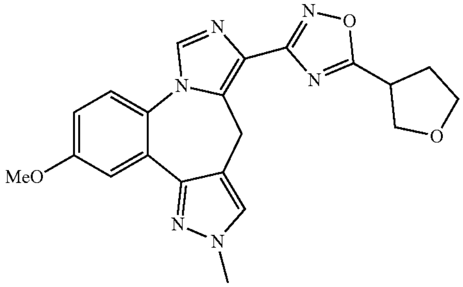 [SMILES: COc1ccc2c(c1)-c1nn(C)cc1Cc1c(-c3noc(C4CCOC4)n3)ncn1-2] |
| 137 | 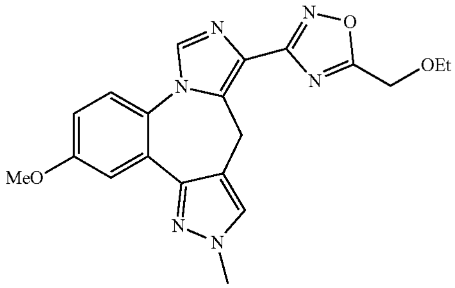 [SMILES: CCOCc1nc(-c2ncn3c2Cc2cn(C)nc2-c2cc(OC)ccc2-3)no1] |
| 138 | 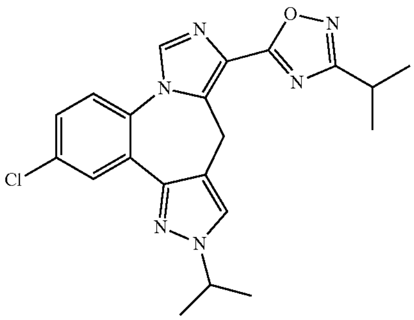 [SMILES: CC(C)c1noc(-c2ncn3c2Cc2cn(C(C)C)nc2-c2cc(Cl)ccc2-3)n1] |

-continued
| Compound | Structure |
|---|---|
| 139 | 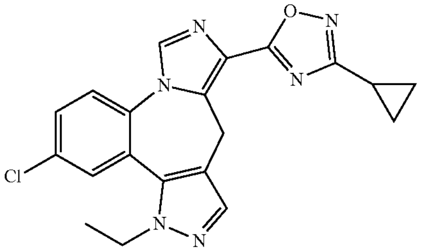 [SMILES: CCn1ncc2c1-c1cc(Cl)ccc1-n1cnc(-c3nc(C4CC4)no3)c1C2] |
| 140 | 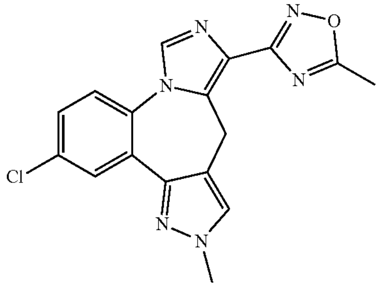 [SMILES: Cc1nc(-c2ncn3c2Cc2cn(C)nc2-c2cc(Cl)ccc2-3)no1] |
| 141 | 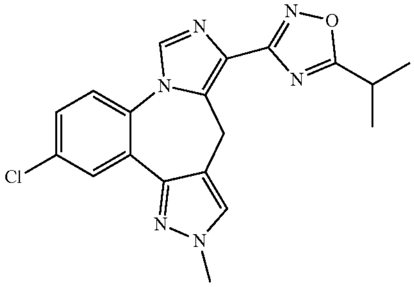 [SMILES: CC(C)c1nc(-c2ncn3c2Cc2cn(C)nc2-c2cc(Cl)ccc2-3)no1] |
| 142 | 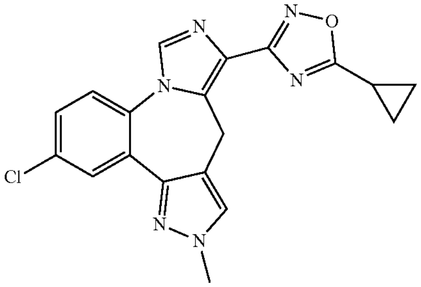 [SMILES: Cn1cc2c(n1)-c1cc(Cl)ccc1-n1cnc(-c3noc(C4CC4)n3)c1C2] |
| 143 | 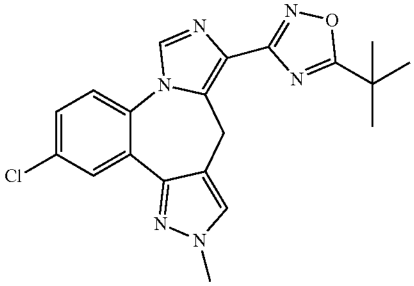 [SMILES: Cn1cc2c(n1)-c1cc(Cl)ccc1-n1cnc(-c3noc(C(C)(C)C)n3)c1C2] |

-continued
| Compound | Structure |
|---|---|
| 144 | 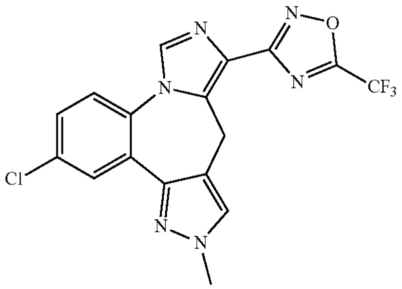 [SMILES: Cn1cc2c(n1)-c1cc(Cl)ccc1-n1cnc(-c3noc(C(F)(F)F)n3)c1C2] |
| 145 | 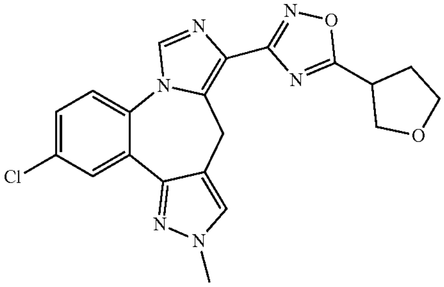 [SMILES: Cn1cc2c(n1)-c1cc(Cl)ccc1-n1cnc(-c3noc(C4CCOC4)n3)c1C2] |
| 146 | 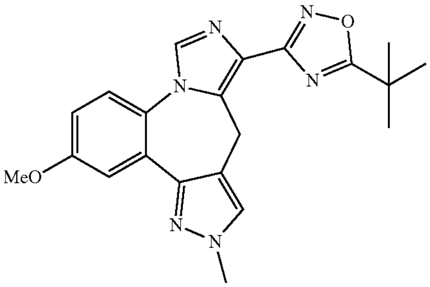 [SMILES: COc1ccc2c(c1)-c1nn(C)cc1Cc1c(-c3noc(C(C)(C)C)n3)ncn1-2] |
| 147 | 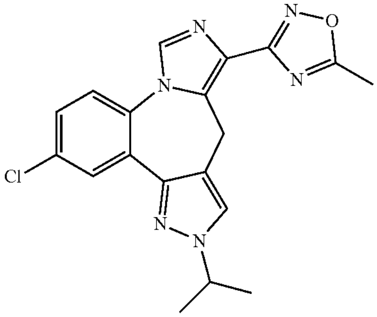 [SMILES: Cc1nc(-c2ncn3c2Cc2cn(C(C)C)nc2-c2cc(Cl)ccc2-3)no1] |
| 148 | 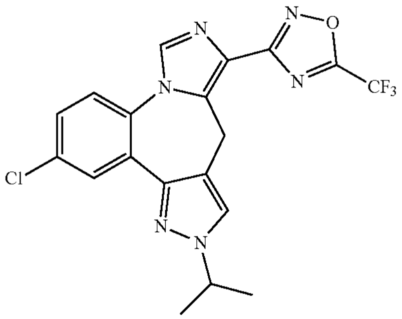 [SMILES: CC(C)n1cc2c(n1)-c1cc(Cl)ccc1-n1cnc(-c3noc(C(F)(F)F)n3)c1C2] |

-continued
| Compound | Structure |
|---|---|
| 149 | 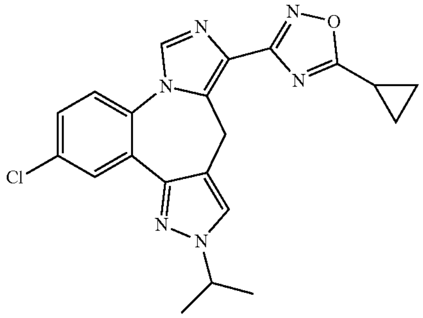 [SMILES: CC(C)n1cc2c(n1)-c1cc(Cl)ccc1-n1cnc(-c3noc(C4CC4)n3)c1C2] |
| 150 | 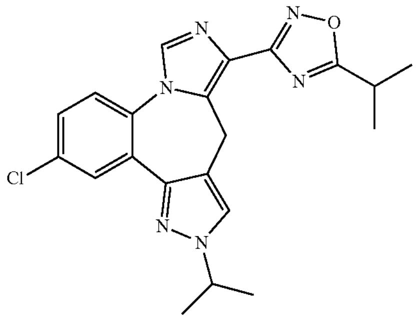 [SMILES: CC(C)c1nc(-c2ncn3c2Cc2cn(C(C)C)nc2-c2cc(Cl)ccc2-3)no1] |
| 151 | 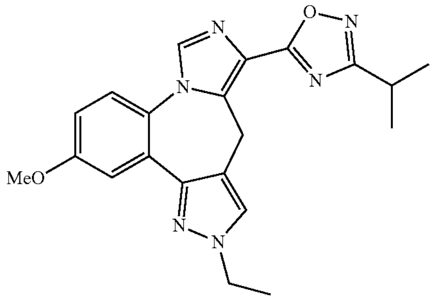 [SMILES: CCn1cc2c(n1)-c1cc(OC)ccc1-n1cnc(-c3nc(C(C)C)no3)c1C2] |
| 152 | 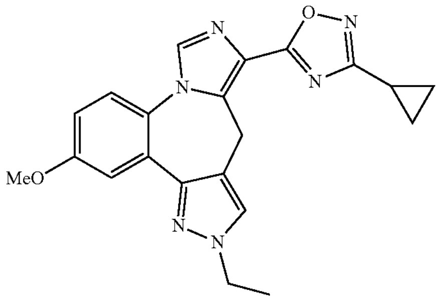 [SMILES: CCn1cc2c(n1)-c1cc(OC)ccc1-n1cnc(-c3nc(C4CC4)no3)c1C2] |
| 153 | 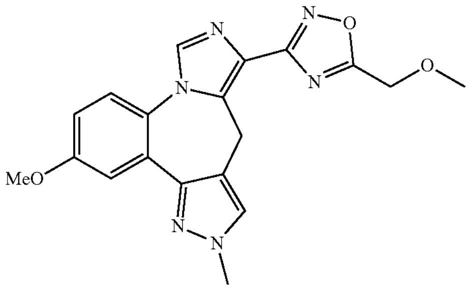 [SMILES: COCc1nc(-c2ncn3c2Cc2cn(C)nc2-c2cc(OC)ccc2-3)no1] |

-continued
| Compound | Structure |
| --- | --- |
| 154 | 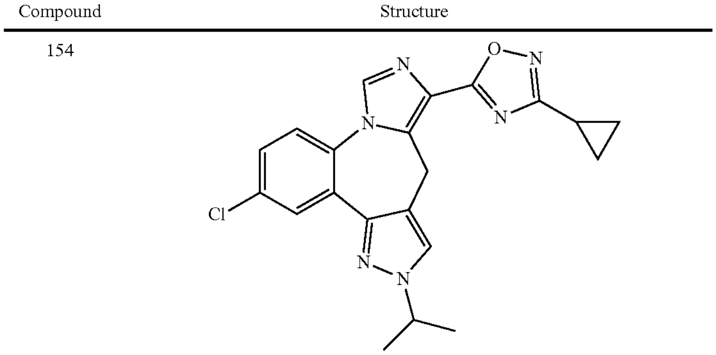 |
| 155 | 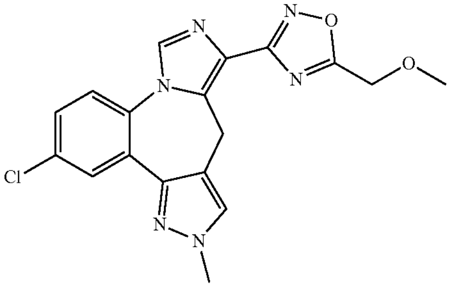 [SMILES: COCc1nc(-c2ncn3c2Cc2cn(C)nc2-c2cc(Cl)ccc2-3)no1] |
| 156 | 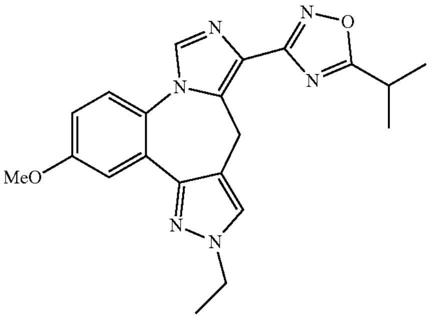 [SMILES: CCn1cc2c(n1)-c1cc(OC)ccc1-n1cnc(-c3noc(C(C)C)n3)c1C2] |
| 157 | 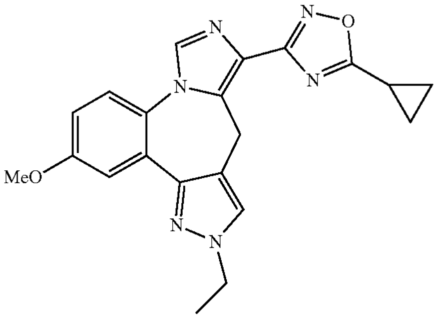 [SMILES: CCn1cc2c(n1)-c1cc(OC)ccc1-n1cnc(-c3noc(C4CC4)n3)c1C2] |
| 158 | 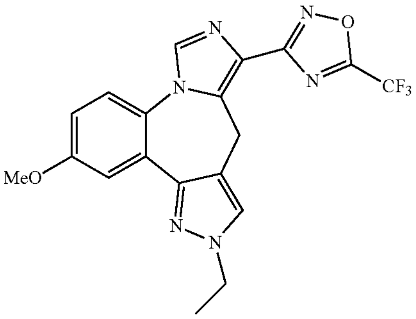 [SMILES: CCn1cc2c(n1)-c1cc(OC)ccc1-n1cnc(-c3noc(C(F)(F)F)n3)c1C2] |

-continued
| Compound | Structure |
|---|---|
| 159 | 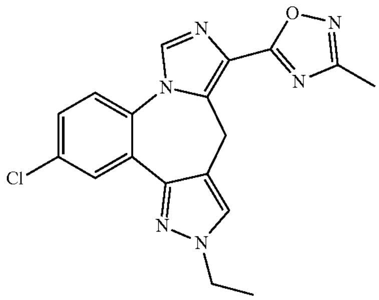 [SMILES: CCn1cc2c(n1)-c1cc(Cl)ccc1-n1cnc(-c3nc(C)no3)c1C2] |
| 160 | 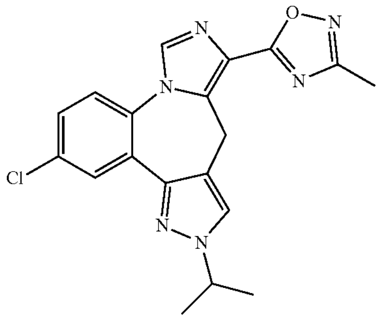 [SMILES: Cc1noc(-c2ncn3c2Cc2cn(C(C)C)nc2-c2cc(Cl)ccc2-3)n1] |
| 161 | 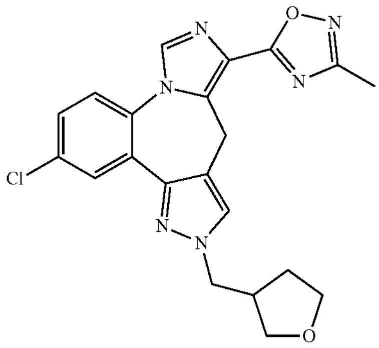 [SMILES: Cc1noc(-c2ncn3c2Cc2cn(CC4CCOC4)nc2-c2cc(Cl)ccc2-3)n1] |
| 162 | 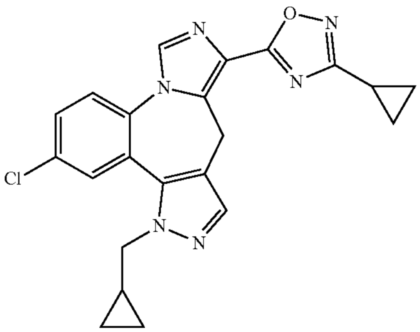 [SMILES: Clc1ccc2c(c1)-c1c(cnn1CC1CC1)Cc1c(-c3nc(C4CC4)no3)ncn1-2] |

-continued
| Compound | Structure |
| --- | --- |
| 163 | 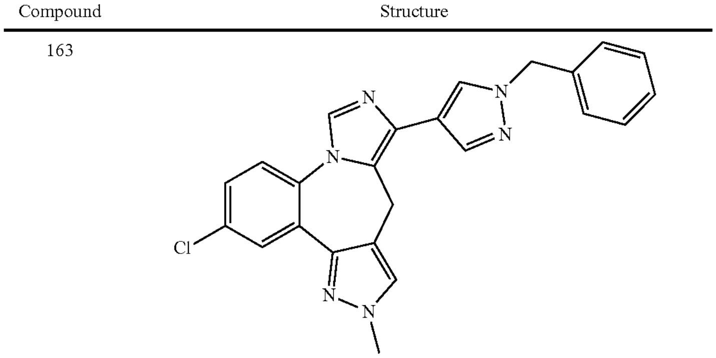 |
| 164 | 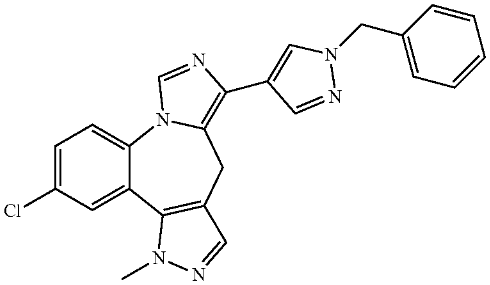 [SMILES: Cn1ncc2c1-c1cc(Cl)ccc1-n1cnc(-c3cnn(Cc4ccccc4)c3)c1C2] |
| 165 | 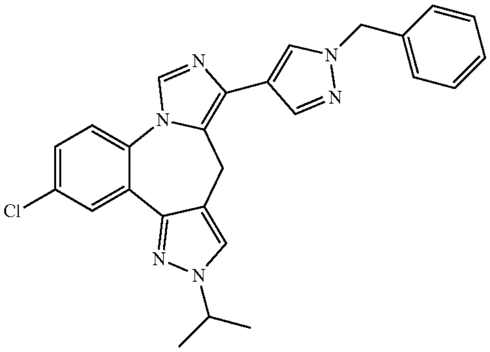 [SMILES: CC(C)n1cc2c(n1)-c1cc(Cl)ccc1-n1cnc(-c3cnn(Cc4ccccc4)c3)c1C2] |
| 166 | 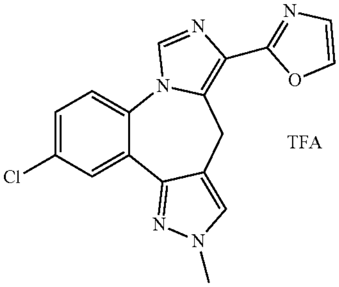 [SMILES: Cn1cc2c(n1)-c1cc(Cl)ccc1-n1cnc(-c3ncco3)c1C2] |
| 167 | 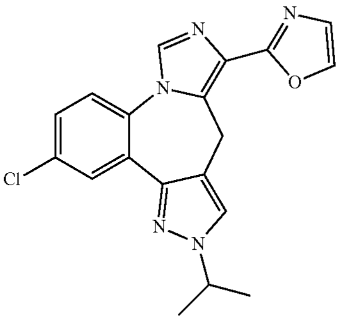 [SMILES: CC(C)n1cc2c(n1)-c1cc(Cl)ccc1-n1cnc(-c3ncco3)c1C2] |

-continued
| Compound | Structure |
|---|---|
| 168 | 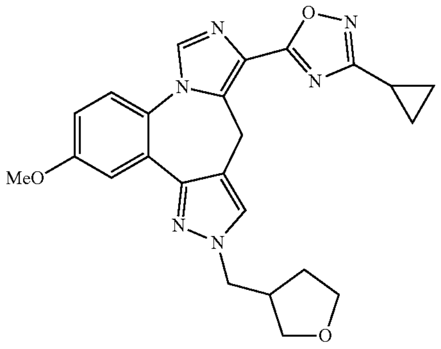 [SMILES: COc1ccc2c(c1)-c1nn(CC3CCOC3)cc1Cc1c(-c3nc(C4CC4)no3)ncn1-2] |
| 169 | 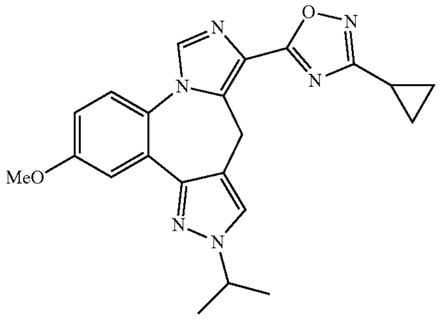 [SMILES: COc1ccc2c(c1)-c1nn(C(C)C)cc1Cc1c(-c3nc(C4CC4)no3)ncn1-2] |
| 170 | 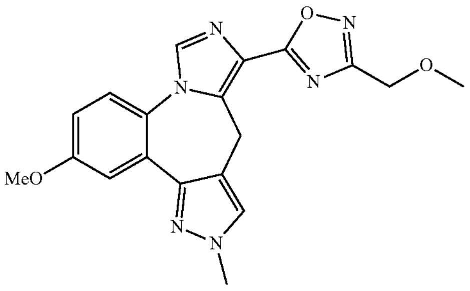 [SMILES: COCc1noc(-c2ncn3c2Cc2cn(C)nc2-c2cc(OC)ccc2-3)n1] |
| 171 | 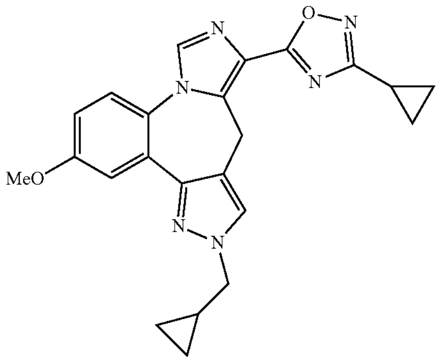 [SMILES: COc1ccc2c(c1)-c1nn(CC3CC3)cc1Cc1c(-c3nc(C4CC4)no3)ncn1-2] |

-continued
| Compound | Structure |
|---|---|
| 172 | 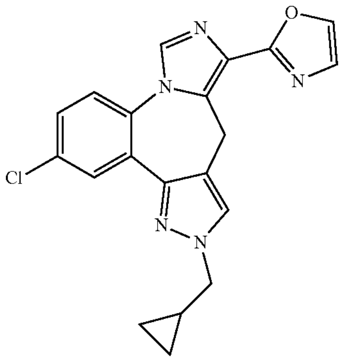 [SMILES: Clc1ccc2c(c1)-c1nn(CC3CC3)cc1Cc1c(-c3ncco3)ncn1-2] |
| 173 | 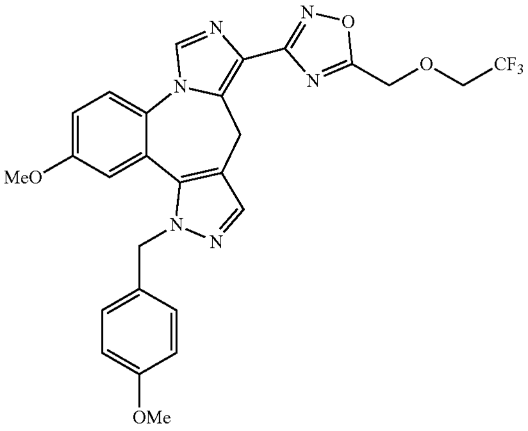 [SMILES: COc1ccc(Cn2ncc3c2-c2cc(OC)ccc2-n2cnc(-c4noc(COCC(F)(F)F)n4)c2C3)cc1] |
| 174 | 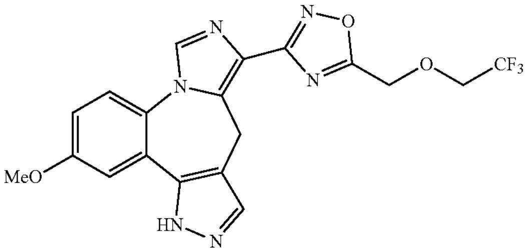 [SMILES: COc1ccc2c(c1)-c1[nH]ncc1Cc1c(-c3noc(COCC(F)(F)F)n3)ncn1-2] |
| 175 | 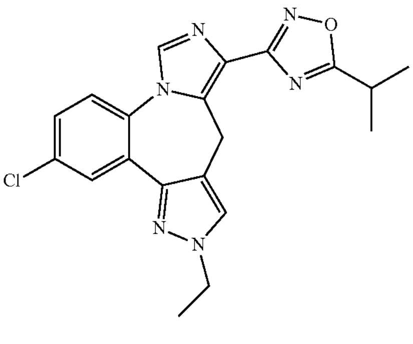 [SMILES: CCn1cc2c(n1)-c1cc(Cl)ccc1-n1cnc(-c3noc(C(C)C)n3)c1C2] |

-continued
| Compound | Structure |
| --- | --- |
| 176 | 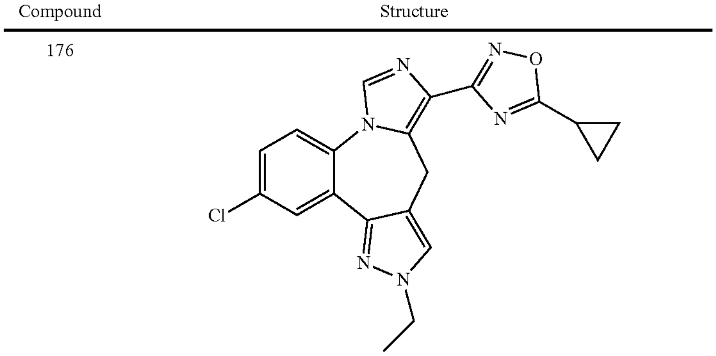 |
| 177 | 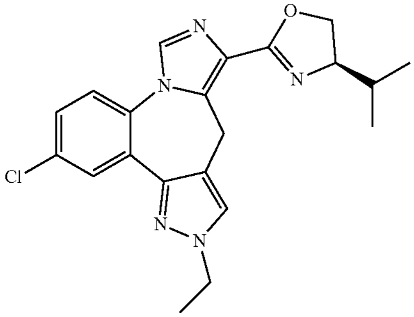 [SMILES: CCn1cc2c(n1)-c1cc(Cl)ccc1-n1cnc(C3=N[C@H](C(C)C)CO3)c1C2] |
| 178 | 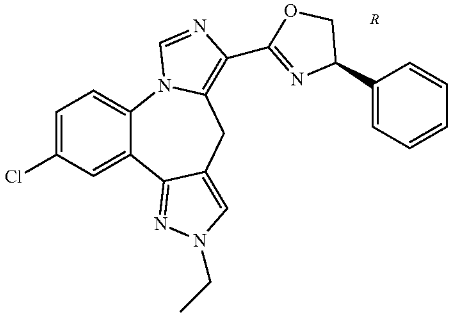 |
| 179 | 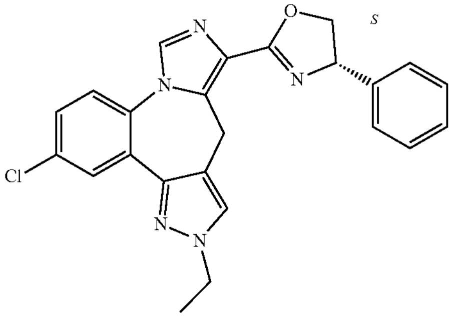 |
| 180 | 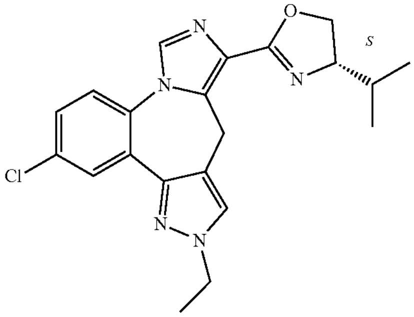 |

-continued
| Compound | Structure |
|---|---|
| 181 | 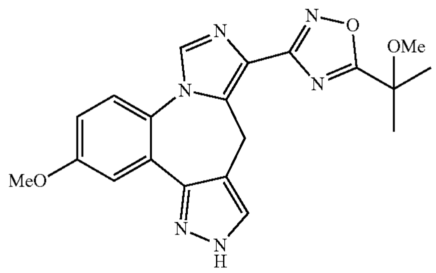 [SMILES: COc1ccc2c(c1)-c1n[nH]cc1Cc1c(-c3noc(C(C)(C)OC)n3)ncn1-2] |
| 182 | 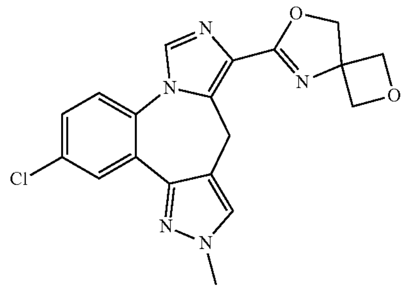 [SMILES: Cn1cc2c(n1)-c1cc(Cl)ccc1-n1cnc(C3=NC4(COC4)CO3)c1C2] |
| 183 | 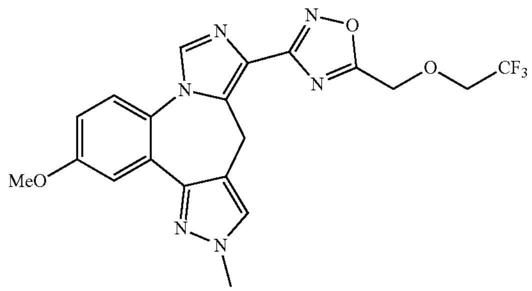 [SMILES: COc1ccc2c(c1)-c1nn(C)cc1Cc1c(-c3noc(COCC(F)(F)F)n3)ncn1-2] |
| 184 | 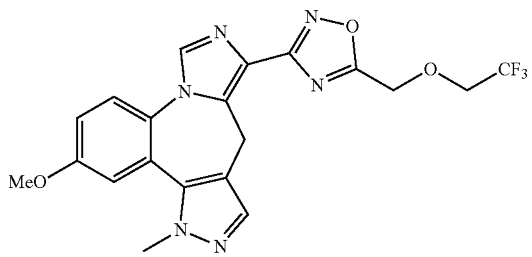 [SMILES: COc1ccc2c(c1)-c1c(cnn1C)Cc1c(-c3noc(COCC(F)(F)F)n3)ncn1-2] |
| 185 | 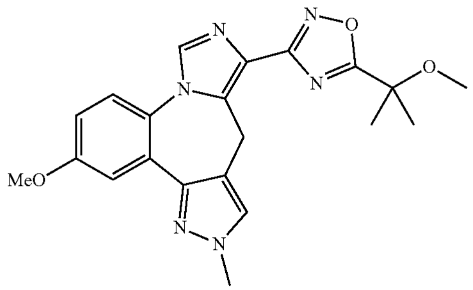 [SMILES: COc1ccc2c(c1)-c1nn(C)cc1Cc1c(-c3noc(C(C)(C)OC)n3)ncn1-2] |

-continued
| Compound | Structure |
| --- | --- |
| 186 | 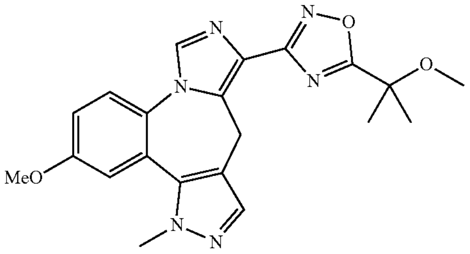 [SMILES: COc1ccc2c(c1)-c1c(cnn1C)Cc1c(-c3noc(C(C)(C)OC)n3)ncn1-2] |
| 187 | 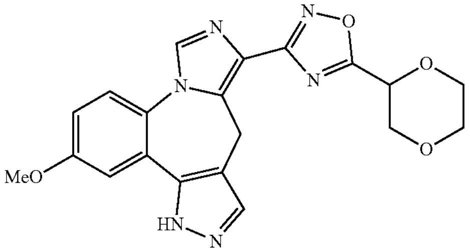 [SMILES: COc1ccc2c(c1)-c1[nH]ncc1Cc1c(-c3noc(C4COCCO4)n3)ncn1-2] |
| 188 | 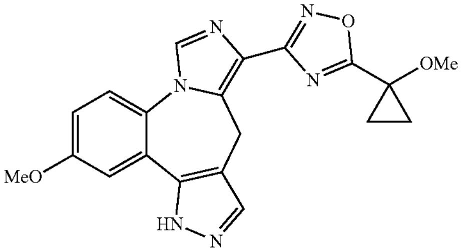 [SMILES: COc1ccc2c(c1)-c1[nH]ncc1Cc1c(-c3noc(C4(OC)CC4)n3)ncn1-2] |
| 189 | 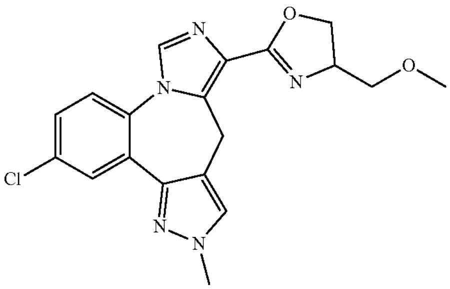 [SMILES: COCC1COC(c2ncn3c2Cc2cn(C)nc2-c2cc(Cl)ccc2-3)=N1] |
| 190 | 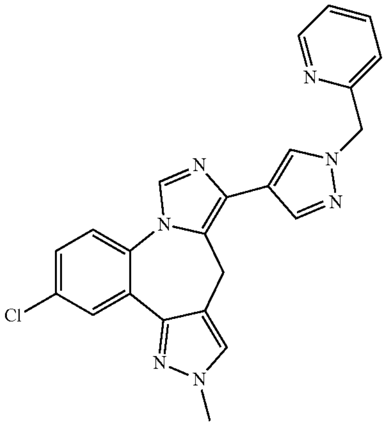 [SMILES: Cn1cc2c(n1)-c1cc(Cl)ccc1-n1cnc(-c3cnn(Cc4ccccn4)c3)c1C2] |

-continued
| Compound | Structure |
|---|---|
| 191 | 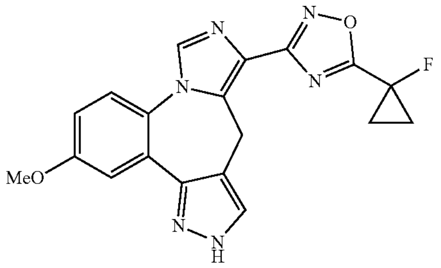 [SMILES: COc1ccc2c(c1)-c1n[nH]cc1Cc1c(-c3noc(C4(F)CC4)n3)ncn1-2] |
| 192 | 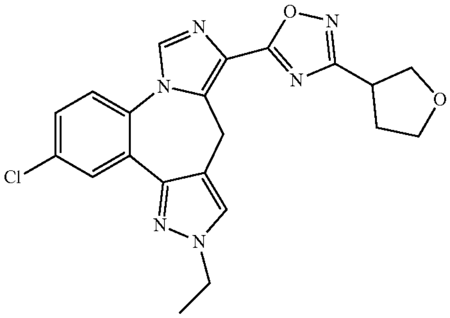 [SMILES: CCn1cc2c(n1)-c1cc(Cl)ccc1-n1cnc(-c3nc(C4CCOC4)no3)c1C2] |
| 193 | 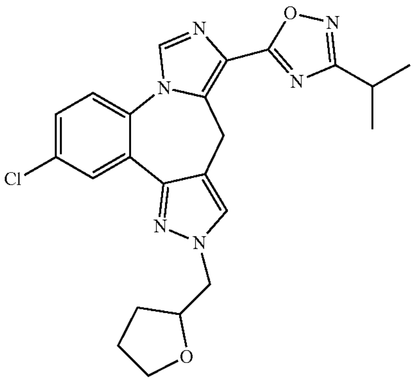 [SMILES: CC(C)c1noc(-c2ncn3c2Cc2cn(CC4CCCO4)nc2-c2cc(Cl)ccc2-3)n1] |
| 194 | 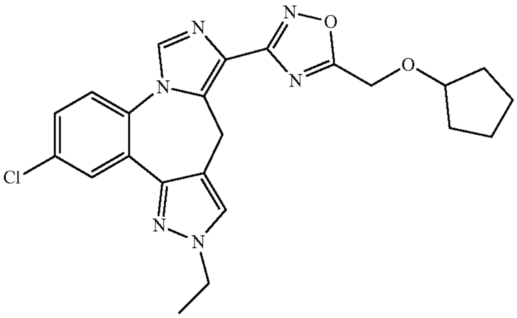 [SMILES: CCn1cc2c(n1)-c1cc(Cl)ccc1-n1cnc(-c3noc(COC4CCCC4)n3)c1C2] |

-continued
| Compound | Structure |
| --- | --- |
| 195 | 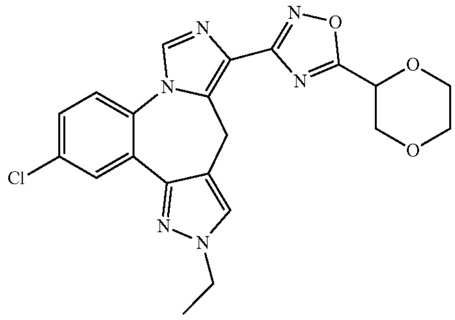 [SMILES: CCn1cc2c(n1)-c1cc(Cl)ccc1-n1cnc(-c3noc(C4COCCO4)n3)c1C2] |
| 196 | 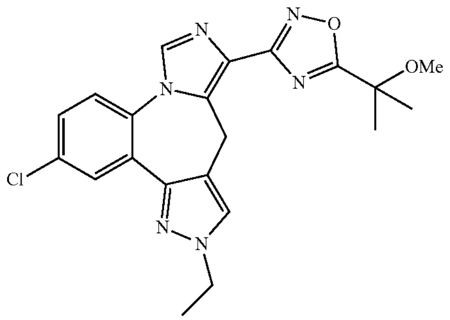 [SMILES: CCn1cc2c(n1)-c1cc(Cl)ccc1-n1cnc(-c3noc(C(C)(C)OC)n3)c1C2] |
| 197 | 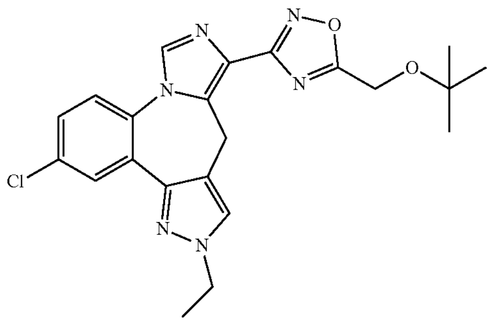 [SMILES: CCn1cc2c(n1)-c1cc(Cl)ccc1-n1cnc(-c3noc(COC(C)(C)C)n3)c1C2] |
| 198 | 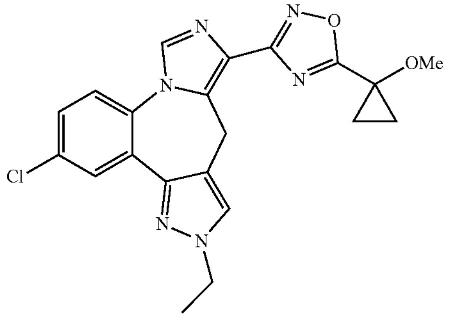 [SMILES: CCn1cc2c(n1)-c1cc(Cl)ccc1-n1cnc(-c3noc(C4(OC)CC4)n3)c1C2] |

-continued
| Compound | Structure |
| --- | --- |
| 199 | 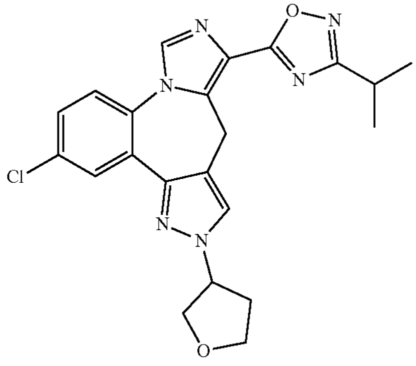 [SMILES: CC(C)c1noc(-c2ncn3c2Cc2cn(C4CCOC4)nc2-c2cc(Cl)ccc2-3)n1] |
| 200 | 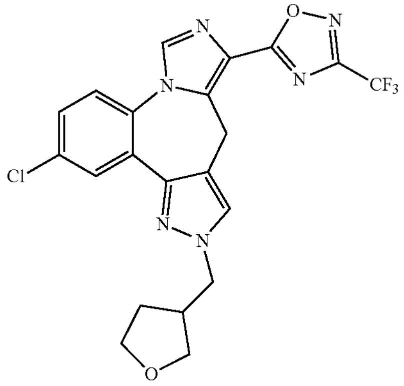 [SMILES: FC(F)(F)c1noc(-c2ncn3c2Cc2cn(CC4CCOC4)nc2-c2cc(Cl)ccc2-3)n1] |
| 201 | 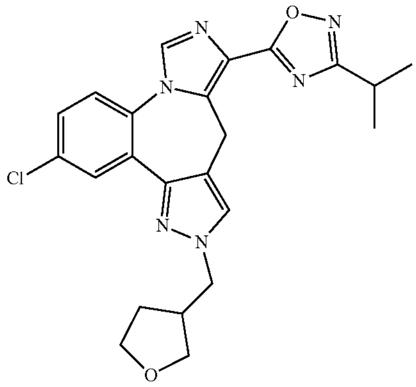 [SMILES: CC(C)c1noc(-c2ncn3c2Cc2cn(CC4CCOC4)nc2-c2cc(Cl)ccc2-3)n1] |
| 202 | 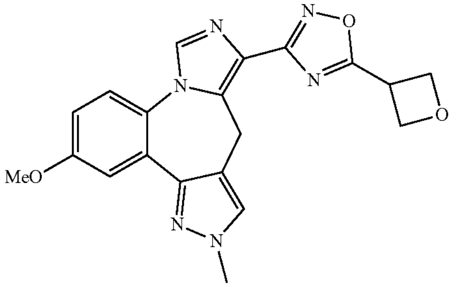 [SMILES: COc1ccc2c(c1)-c1nn(C)cc1Cc1c(-c3noc(C4COC4)n3)ncn1-2] |

-continued
| Compound | Structure |
|---|---|
| 203 | 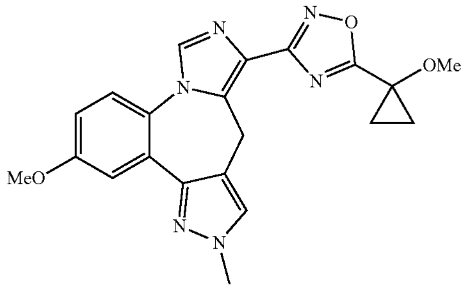 [SMILES: COc1ccc2c(c1)-c1nn(C)cc1Cc1c(-c3noc(C4(OC)CC4)n3)ncn1-2] |
| 204 | 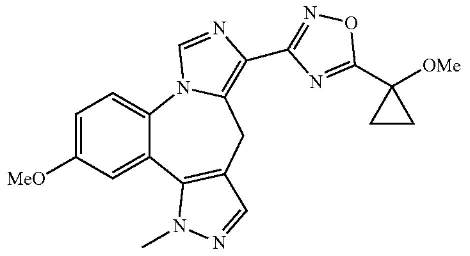 [SMILES: COc1ccc2c(c1)-c1c(cnn1C)Cc1c(-c3noc(C4(OC)CC4)n3)ncn1-2] |
| 205 | 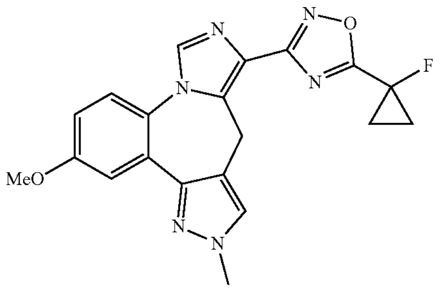 [SMILES: COc1ccc2c(c1)-c1nn(C)cc1Cc1c(-c3noc(C4(F)CC4)n3)ncn1-2] |
| 206 | 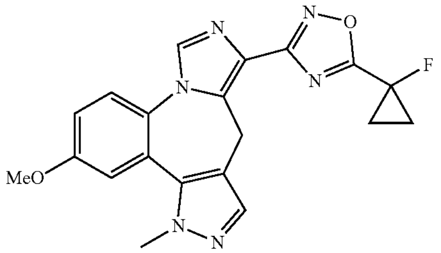 [SMILES: COc1ccc2c(c1)-c1c(cnn1C)Cc1c(-c3noc(C4(F)CC4)n3)ncn1-2] |
| 207 | 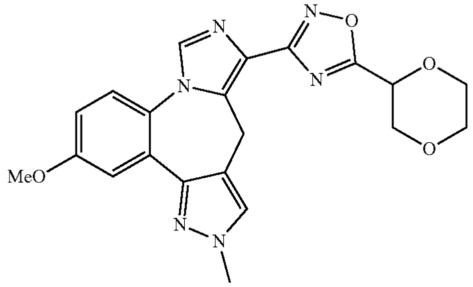 [SMILES: COc1ccc2c(c1)-c1nn(C)cc1Cc1c(-c3noc(C4COCCO4)n3)ncn1-2] |

-continued
| Compound | Structure |
|---|---|
| 208 | 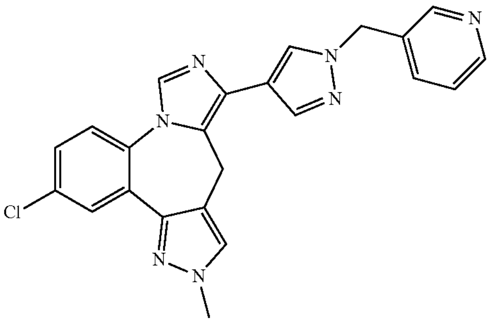 [SMILES: Cn1cc2c(n1)-c1cc(Cl)ccc1-n1cnc(-c3cnn(Cc4cccnc4)c3)c1C2] |
| 209 | 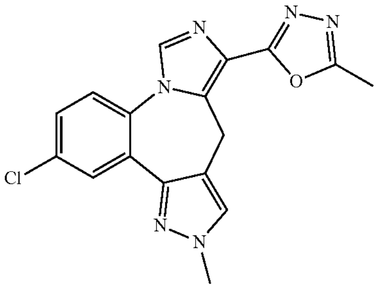 [SMILES: Cc1nnc(-c2ncn3c2Cc2cn(C)nc2-c2cc(Cl)ccc2-3)o1] |
| 210 | 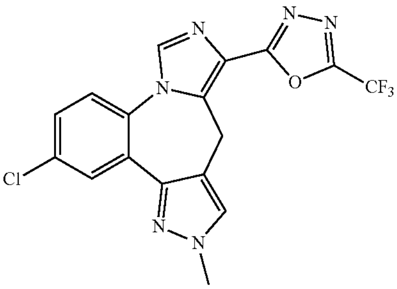 [SMILES: Cn1cc2c(n1)-c1cc(Cl)ccc1-n1cnc(-c3nnc(C(F)(F)F)o3)c1C2] |
| 211 | 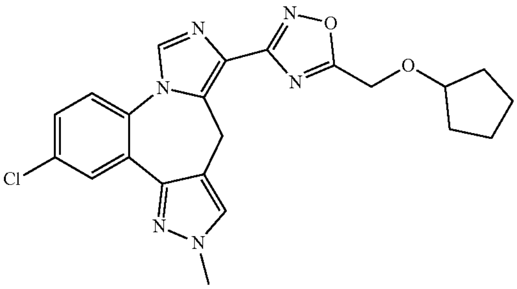 [SMILES: Cn1cc2c(n1)-c1cc(Cl)ccc1-n1cnc(-c3noc(COC4CCCC4)n3)c1C2] |
| 212 | 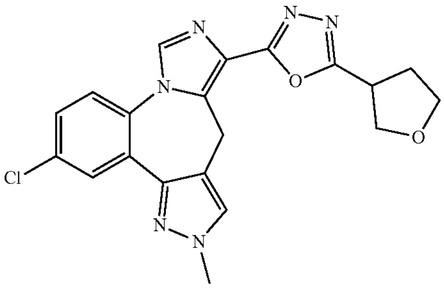 [SMILES: Cn1cc2c(n1)-c1cc(Cl)ccc1-n1cnc(-c3nnc(C4CCOC4)o3)c1C2] |

-continued
| Compound | Structure |
|---|---|
| 213 | 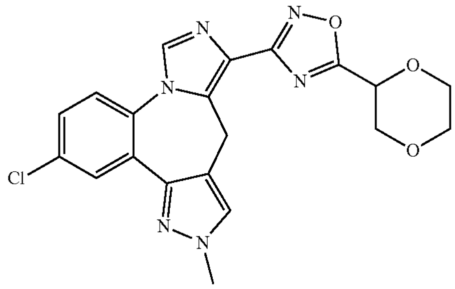 [SMILES: Cn1cc2c(n1)-c1cc(Cl)ccc1-n1cnc(-c3noc(C4COCCO4)n3)c1C2] |
| 214 | 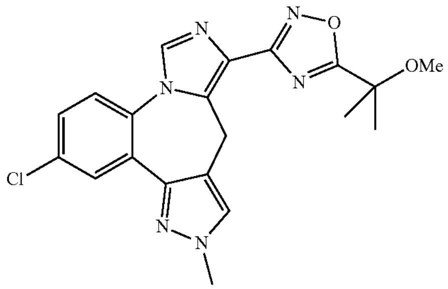 [SMILES: COC(C)(C)c1nc(-c2ncn3c2Cc2cn(C)nc2-c2cc(Cl)ccc2-3)no1] |
| 215 | 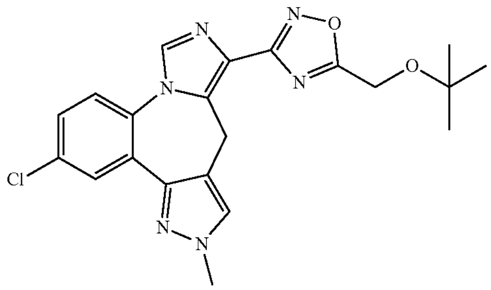 [SMILES: Cn1cc2c(n1)-c1cc(Cl)ccc1-n1cnc(-c3noc(COC(C)(C)C)n3)c1C2] |
| 216 | 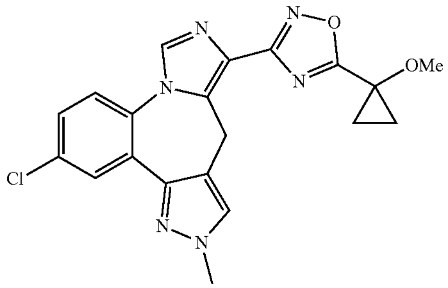 [SMILES: COC1(c2nc(-c3ncn4c3Cc3cn(C)nc3-c3cc(Cl)ccc3-4)no2)CC1] |
| 217 | 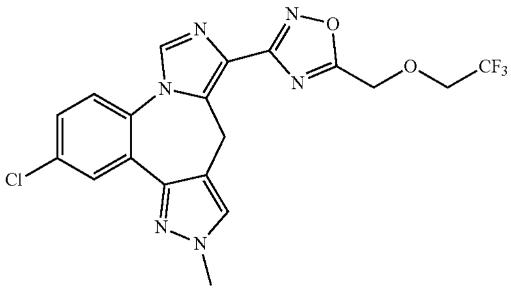 [SMILES: Cn1cc2c(n1)-c1cc(Cl)ccc1-n1cnc(-c3noc(COCC(F)(F)F)n3)c1C2] |

-continued
| Compound | Structure |
|---|---|
| 218 | 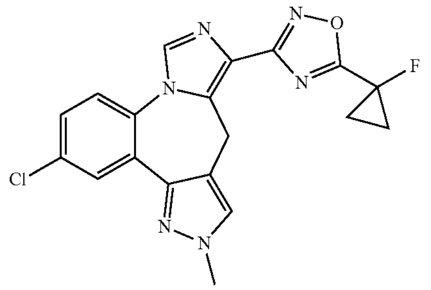 [SMILES: Cn1cc2c(n1)-c1cc(Cl)ccc1-n1cnc(-c3noc(C4(F)CC4)n3)c1C2] |
| 219 | 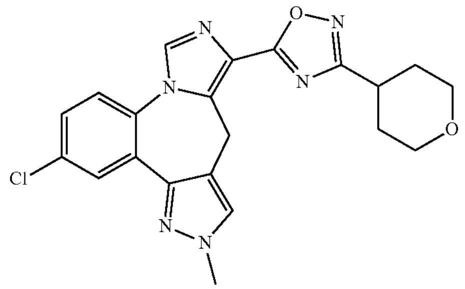 [SMILES: Cn1cc2c(n1)-c1cc(Cl)ccc1-n1cnc(-c3nc(C4CCOCC4)no3)c1C2] |
| 220 | 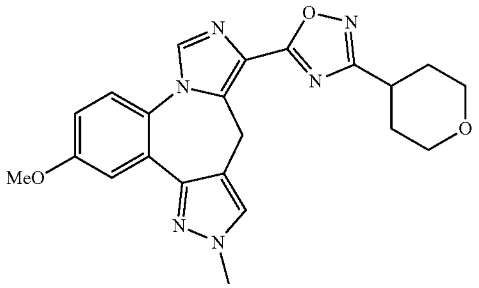 [SMILES: COc1ccc2c(c1)-c1nn(C)cc1Cc1c(-c3nc(C4CCOCC4)no3)ncn1-2] |
| 221 | 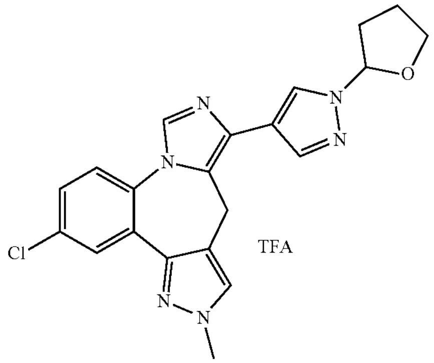 [SMILES: Cn1cc2c(n1)-c1cc(Cl)ccc1-n1cnc(-c3cnn(C4CCCO4)c3)c1C2] TFA |
| 222 | 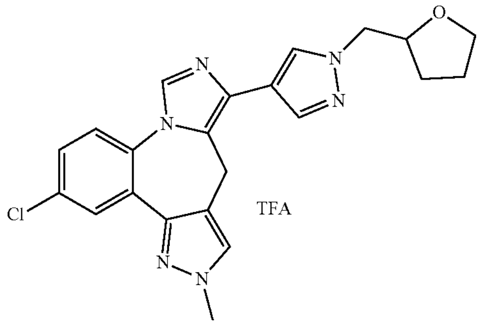 [SMILES: Cn1cc2c(n1)-c1cc(Cl)ccc1-n1cnc(-c3cnn(CC4CCCO4)c3)c1C2] TFA |

-continued
| Compound | Structure |
|---|---|
| 223 | 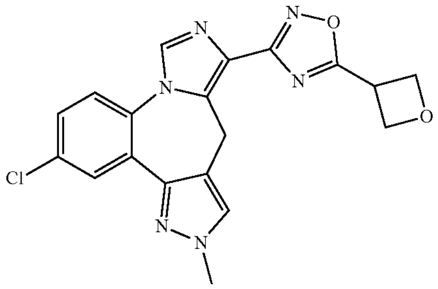 [SMILES: Cn1cc2c(n1)-c1cc(Cl)ccc1-n1cnc(-c3noc(C4COC4)n3)c1C2] |
| 224 | 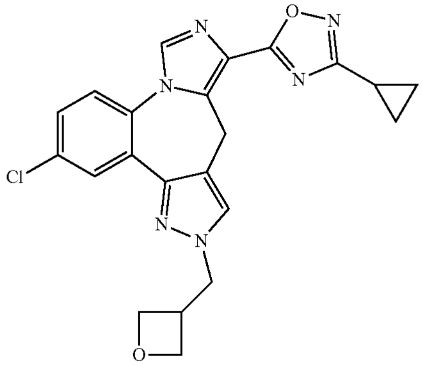 [SMILES: Clc1ccc2c(c1)-c1nn(CC3COC3)cc1Cc1c(-c3nc(C4CC4)no3)ncn1-2] |
| 225 | 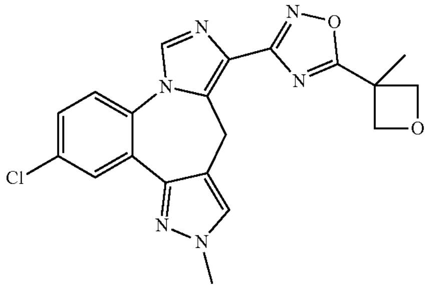 [SMILES: Cn1cc2c(n1)-c1cc(Cl)ccc1-n1cnc(-c3noc(C4(C)COC4)n3)c1C2] |
| 226 | 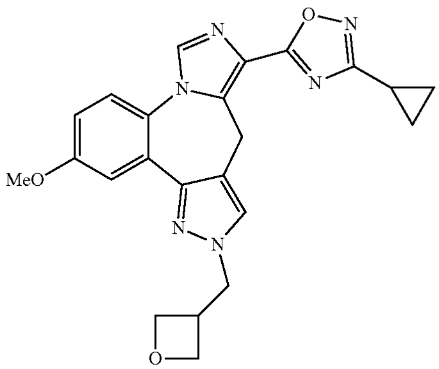 [SMILES: COc1ccc2c(c1)-c1nn(CC3COC3)cc1Cc1c(-c3nc(C4CC4)no3)ncn1-2] |

-continued
| Compound | Structure |
| --- | --- |
| 227 | 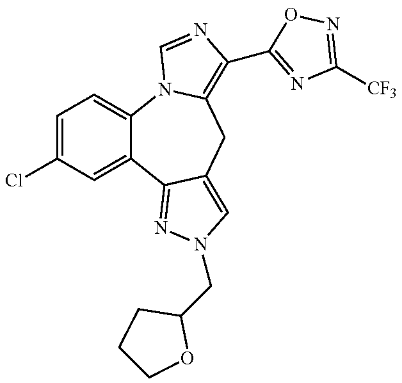 [SMILES: FC(F)(F)c1noc(-c2ncn3c2Cc2cn(CC4CCCO4)nc2-c2cc(Cl)ccc2-3)n1] |
| 228 | 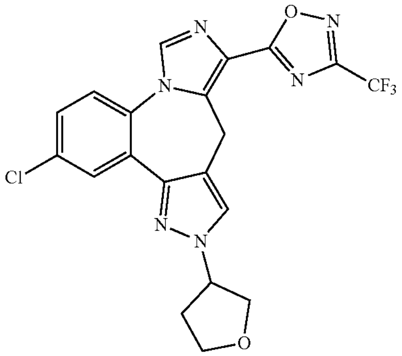 [SMILES: FC(F)(F)c1noc(-c2ncn3c2Cc2cn(C4CCOC4)nc2-c2cc(Cl)ccc2-3)n1] |
| 229 | 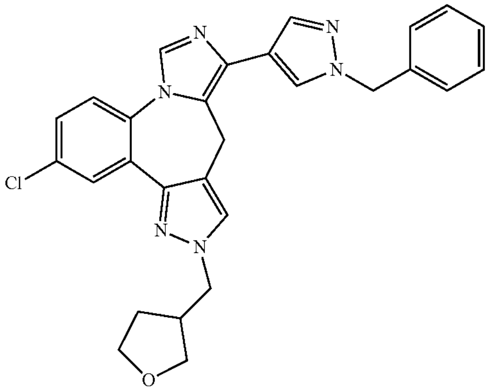 [SMILES: Clc1ccc2c(c1)-c1nn(CC3CCOC3)cc1Cc1c(-c3cnn(Cc4ccccc4)c3)ncn1-2] |
| 230 | 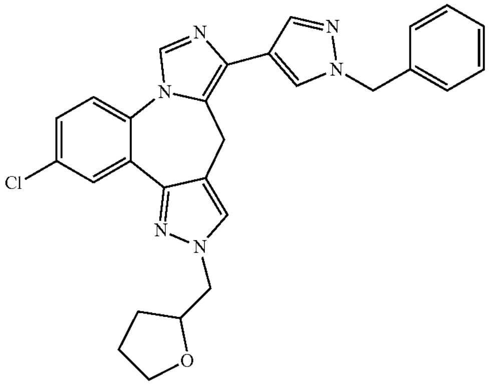 [SMILES: Clc1ccc2c(c1)-c1nn(CC3CCCO3)cc1Cc1c(-c3cnn(Cc4ccccc4)c3)ncn1-2] |

-continued
| Compound | Structure |
| --- | --- |
| 231 | 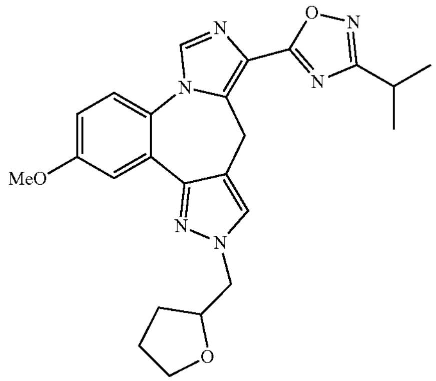 [SMILES: COc1ccc2c(c1)-c1nn(CC3CCCO3)cc1Cc1c(-c3nc(C(C)C)no3)ncn1-2] |
| 232 | 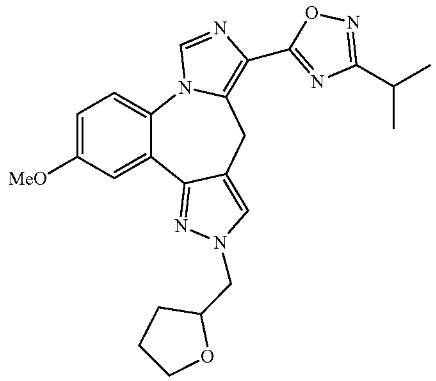 [SMILES: COc1ccc2c(c1)-c1nn(CC3CCCO3)cc1Cc1c(-c3nc(C(C)C)no3)ncn1-2] |
| 233 | 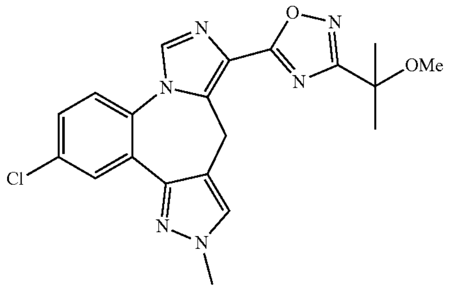 [SMILES: COC(C)(C)c1noc(-c2ncn3c2Cc2cn(C)nc2-c2cc(Cl)ccc2-3)n1] |
| 234 | 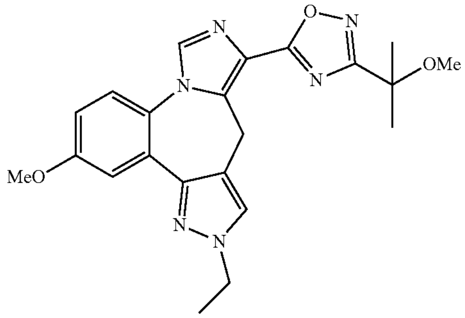 [SMILES: CCn1cc2c(n1)-c1cc(OC)ccc1-n1cnc(-c3nc(C(C)(C)OC)no3)c1C2] |

-continued
| Compound | Structure |
|---|---|
| 235 | 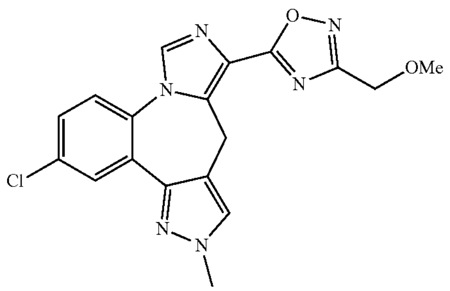 [SMILES: COCc1noc(-c2ncn3c2Cc2cn(C)nc2-c2cc(Cl)ccc2-3)n1] |
| 236 | 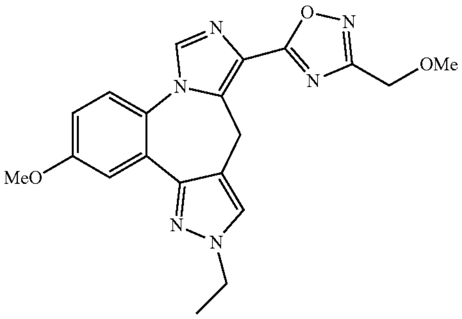 [SMILES: CCn1cc2c(n1)-c1cc(OC)ccc1-n1cnc(-c3nc(COC)no3)c1C2] |
| 237 | 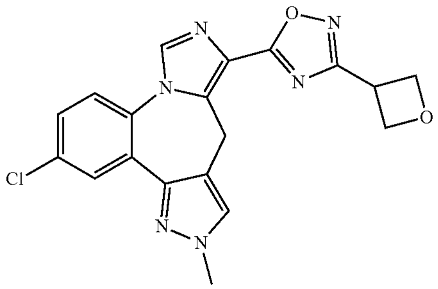 [SMILES: Cn1cc2c(n1)-c1cc(Cl)ccc1-n1cnc(-c3nc(C4COC4)no3)c1C2] |
| 238 | 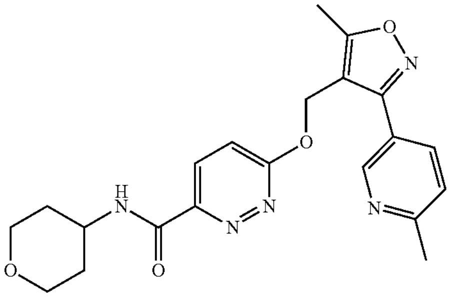 [SMILES: Cc1ccc(-c2noc(C)c2COc2ccc(C(=O)NC3CCOCC3)nn2)cn1] |
| 239 | 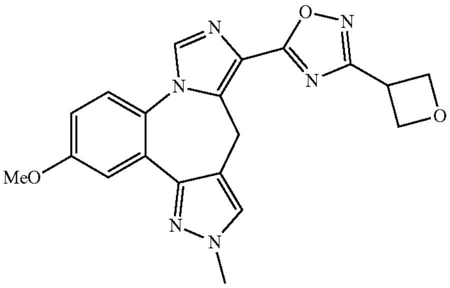 [SMILES: COc1ccc2c(c1)-c1nn(C)cc1Cc1c(-c3nc(C4COC4)no3)ncn1-2] |

-continued
| Compound | Structure |
| --- | --- |
| 240 | 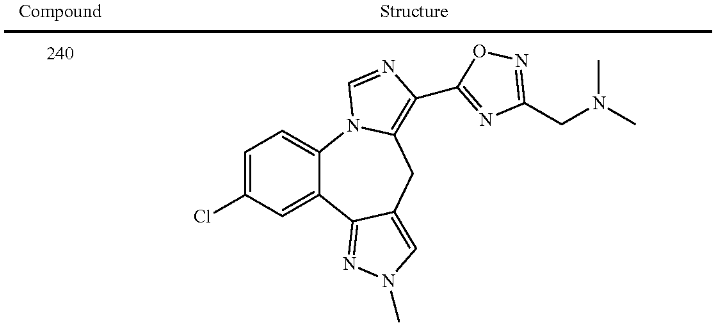 |
| 241 | 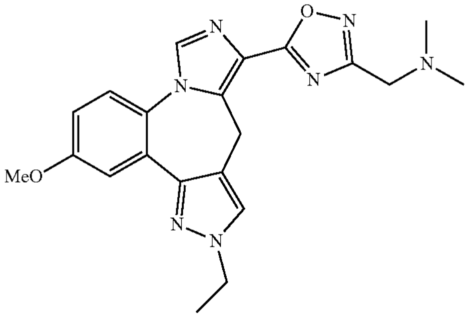 [SMILES: CCn1cc2c(n1)-c1cc(OC)ccc1-n1cnc(-c3nc(CN(C)C)no3)c1C2] |
| 242 | 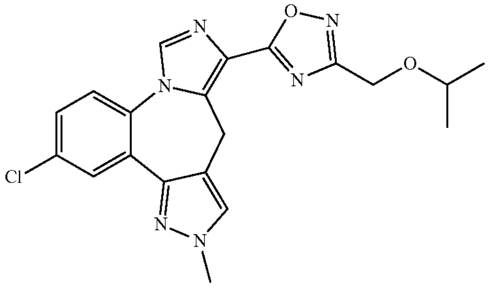 [SMILES: CC(C)OCc1noc(-c2ncn3c2Cc2cn(C)nc2-c2cc(Cl)ccc2-3)n1] |
| 243 | 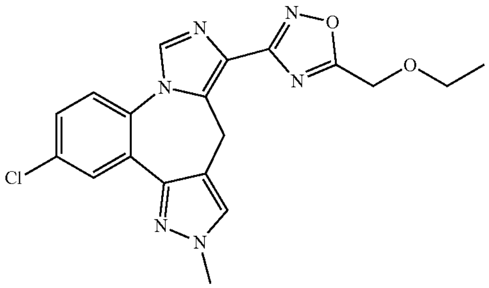 [SMILES: CCOCc1nc(-c2ncn3c2Cc2cn(C)nc2-c2cc(Cl)ccc2-3)no1] |
| 244 | 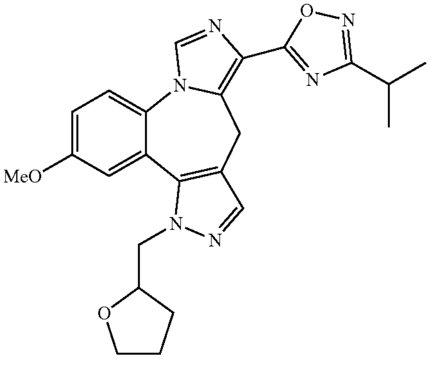 [SMILES: COc1ccc2c(c1)-c1c(cnn1CC1CCCO1)Cc1c(-c3nc(C(C)C)no3)ncn1-2] |

-continued
| Compound | Structure |
| --- | --- |
| 245 | 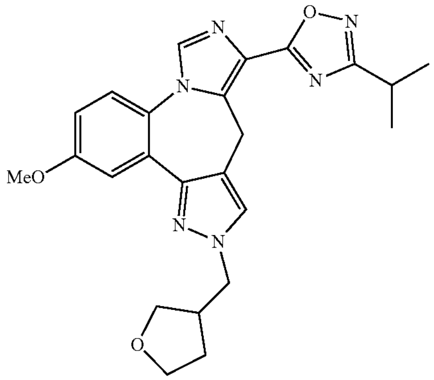 [SMILES: COc1ccc2c(c1)-c1nn(CC3CCOC3)cc1Cc1c(-c3nc(C(C)C)no3)ncn1-2] |
| 246 | 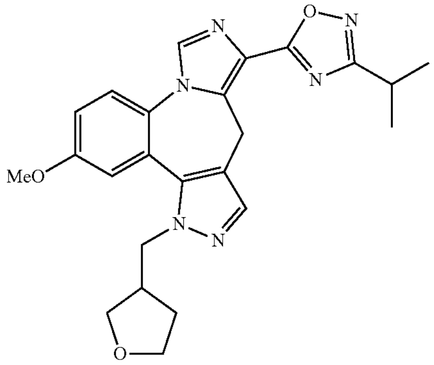 [SMILES: COc1ccc2c(c1)-c1c(cnn1CC1CCOC1)Cc1c(-c3nc(C(C)C)no3)ncn1-2] |
| 247 | 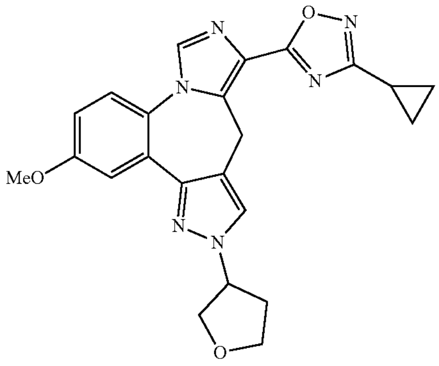 [SMILES: COc1ccc2c(c1)-c1nn(C3CCOC3)cc1Cc1c(-c3nc(C4CC4)no3)ncn1-2] |
| 248 | 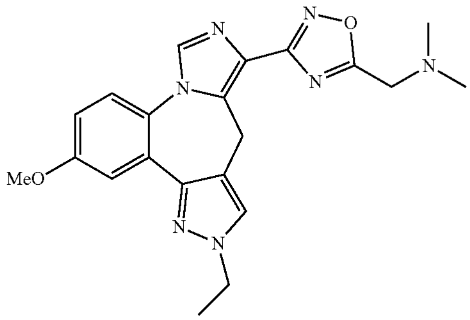 [SMILES: CCn1cc2c(n1)-c1cc(OC)ccc1-n1cnc(-c3noc(CN(C)C)n3)c1C2] |

-continued
| Compound | Structure |
| --- | --- |
| 249 | 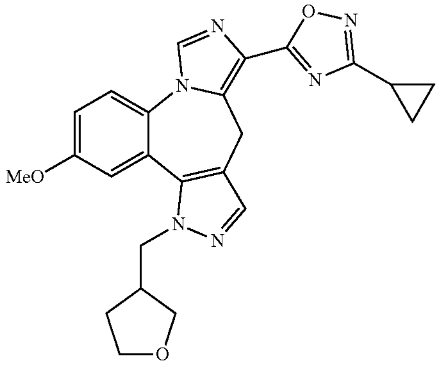 [SMILES: COc1ccc2c(c1)-c1c(cnn1CC1CCOC1)Cc1c(-c3nc(C4CC4)no3)ncn1-2] |
| 250 | 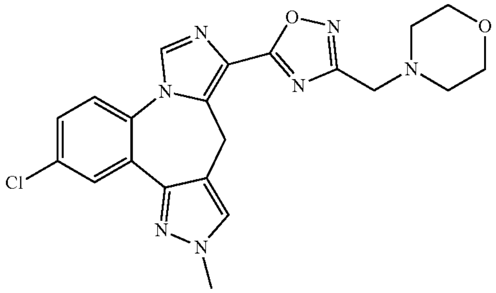 [SMILES: Cn1cc2c(n1)-c1cc(Cl)ccc1-n1cnc(-c3nc(CN4CCOCC4)no3)c1C2] |
| 251 | 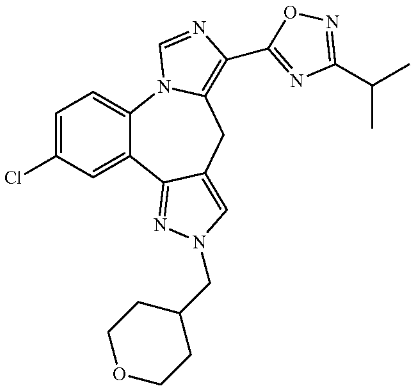 [SMILES: CC(C)c1noc(-c2ncn3c2Cc2cn(CC4CCOCC4)nc2-c2cc(Cl)ccc2-3)n1] |
| 252 | 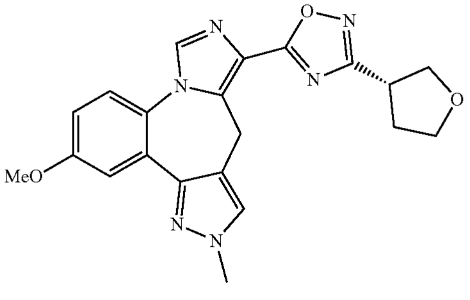 [SMILES: COc1ccc2c(c1)-c1nn(C)cc1Cc1c(-c3nc([C@H]4CCOC4)no3)ncn1-2] |

-continued
| Compound | Structure |
|---|---|
| 253 | 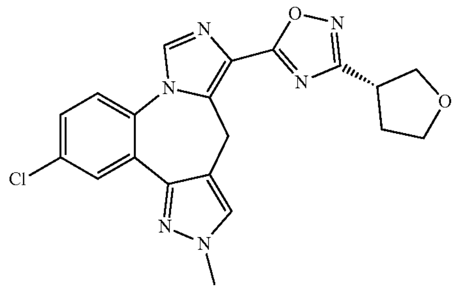 [SMILES: Cn1cc2c(n1)-c1cc(Cl)ccc1-n1cnc(-c3nc([C@H]4CCOC4)no3)c1C2] |
| 254 | 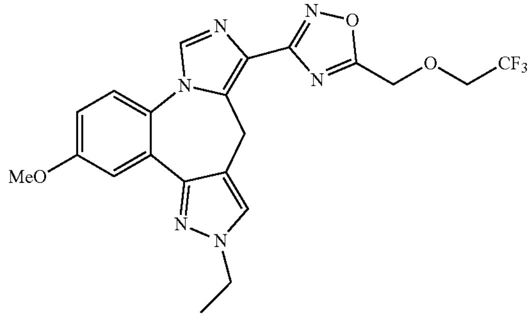 [SMILES: CCn1cc2c(n1)-c1cc(OC)ccc1-n1cnc(-c3noc(COCC(F)(F)F)n3)c1C2] |
| 255 | 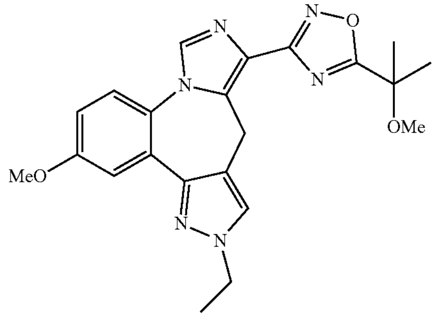 [SMILES: CCn1cc2c(n1)-c1cc(OC)ccc1-n1cnc(-c3noc(C(C)(C)OC)n3)c1C2] |
| 256 | 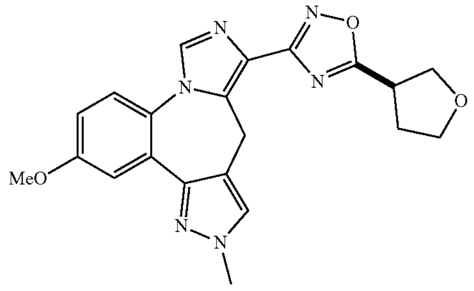 |
| 257 | 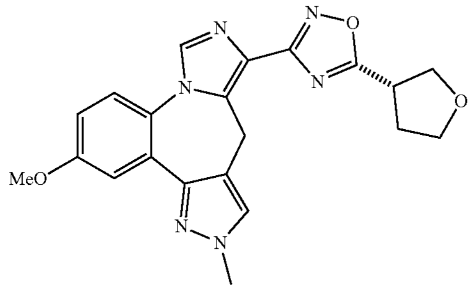 |

-continued
| Compound | Structure |
|---|---|
| 258 | 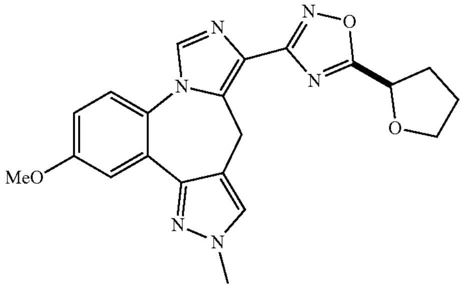 |
| 259 | 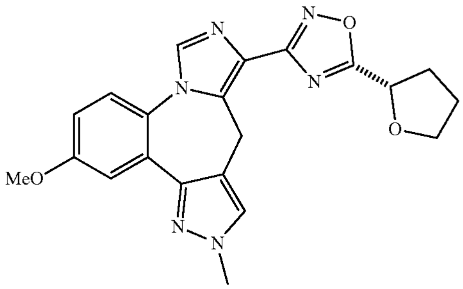 |
| 260 | 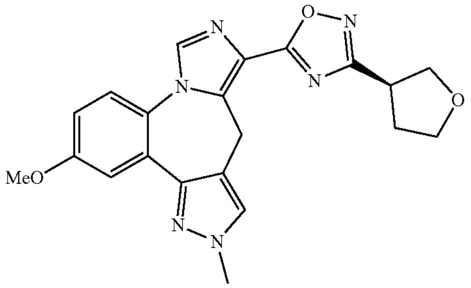 [SMILES: COc1ccc2c(c1)-c1nn(C)cc1Cc1c(-c3nc([C@@H]4CCOC4)no3)ncn1-2] |
| 261 | 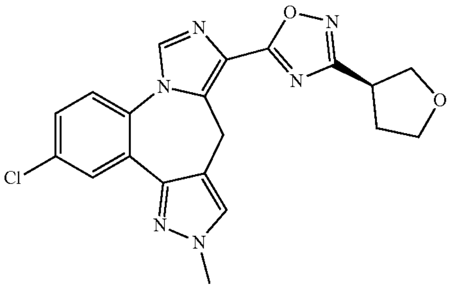 [SMILES: Cn1cc2c(n1)-c1cc(Cl)ccc1-n1cnc(-c3nc([C@@H]4CCOC4)no3)c1C2] |
| 262 | 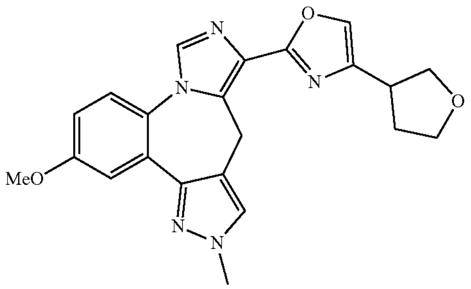 [SMILES: COc1ccc2c(c1)-c1nn(C)cc1Cc1c(-c3nc(C4CCOC4)co3)ncn1-2] |

-continued
| Compound | Structure |
|---|---|
| 263 | 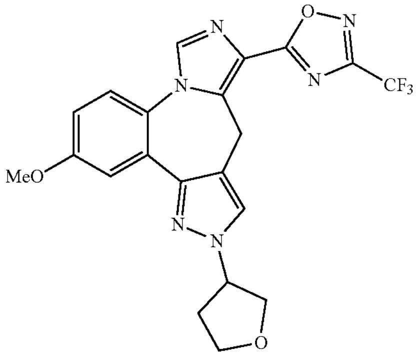 [SMILES: COc1ccc2c(c1)-c1nn(C3CCOC3)cc1Cc1c(-c3nc(C(F)(F)F)no3)ncn1-2] |
| 264 | 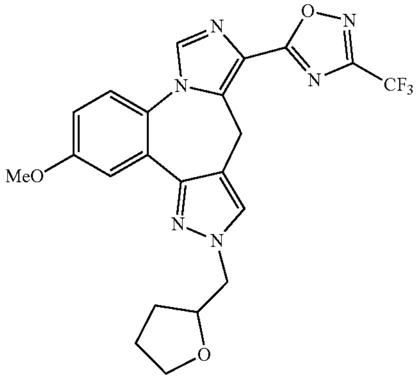 [SMILES: COc1ccc2c(c1)-c1nn(CC3CCCO3)cc1Cc1c(-c3nc(C(F)(F)F)no3)ncn1-2] |
| 265 | 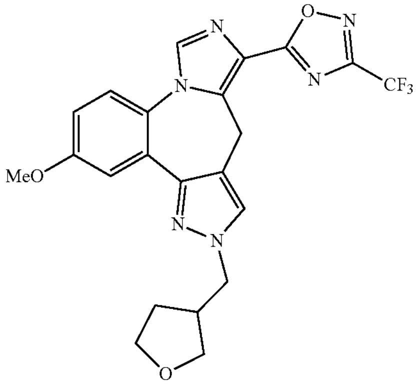 [SMILES: COc1ccc2c(c1)-c1nn(CC3CCOC3)cc1Cc1c(-c3nc(C(F)(F)F)no3)ncn1-2] |
| 266 | 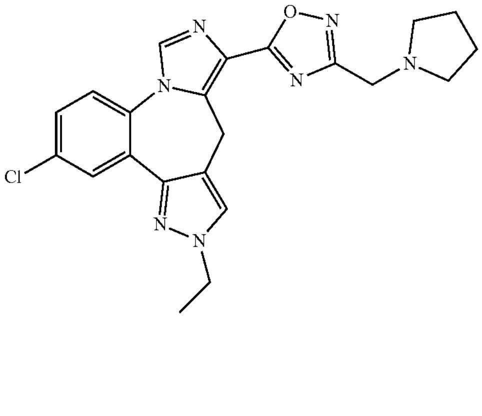 [SMILES: CCn1cc2c(n1)-c1cc(Cl)ccc1-n1cnc(-c3nc(CN4CCCC4)no3)c1C2] |

-continued
| Compound | Structure |
|---|---|
| 267 | 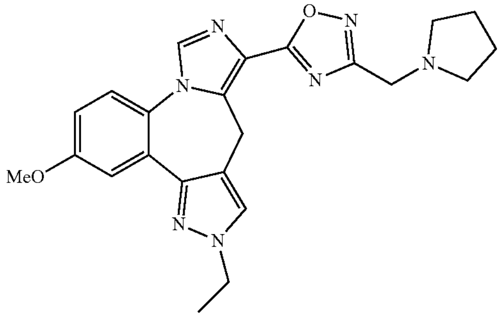 [SMILES: CCn1cc2c(n1)-c1cc(OC)ccc1-n1cnc(-c3nc(CN4CCCC4)no3)c1C2] |
| 268 | 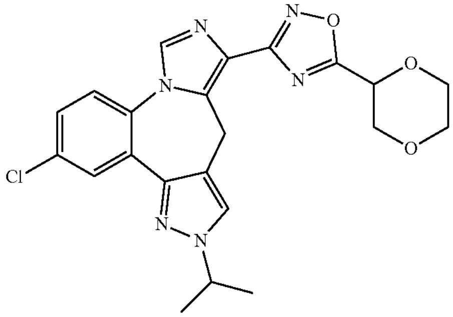 [SMILES: CC(C)n1cc2c(n1)-c1cc(Cl)ccc1-n1cnc(-c3noc(C4COCCO4)n3)c1C2] |
| 269 | 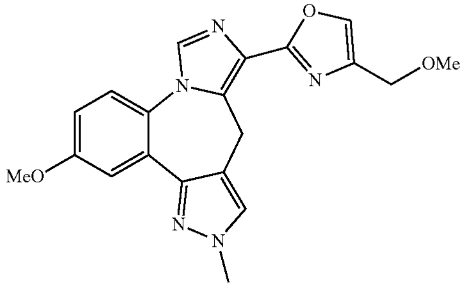 [SMILES: COCc1coc(-c2ncn3c2Cc2cn(C)nc2-c2cc(OC)ccc2-3)n1] |
| 270 | 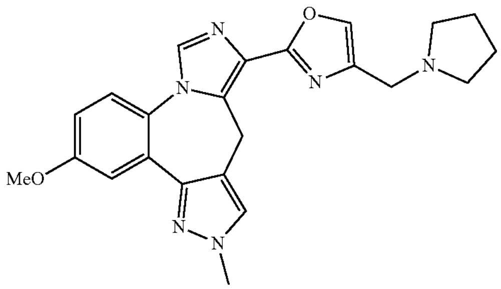 [SMILES: COc1ccc2c(c1)-c1nn(C)cc1Cc1c(-c3nc(CN4CCCC4)co3)ncn1-2] |
| 271 | 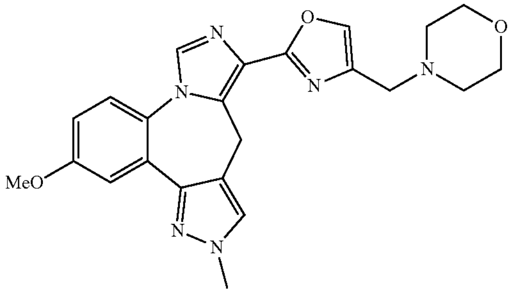 [SMILES: COc1ccc2c(c1)-c1nn(C)cc1Cc1c(-c3nc(CN4CCOCC4)co3)ncn1-2] |

-continued
| Compound | Structure |
|---|---|
| 272 | 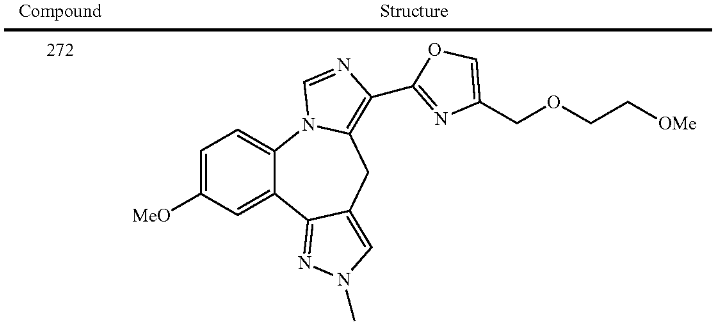 |
| 273 | 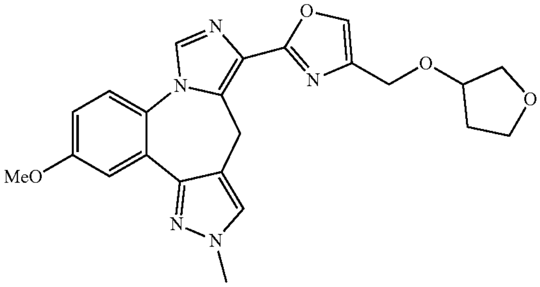 [SMILES: COc1ccc2c(c1)-c1nn(C)cc1Cc1c(-c3nc(COC4CCOC4)co3)ncn1-2] |
| 274 | 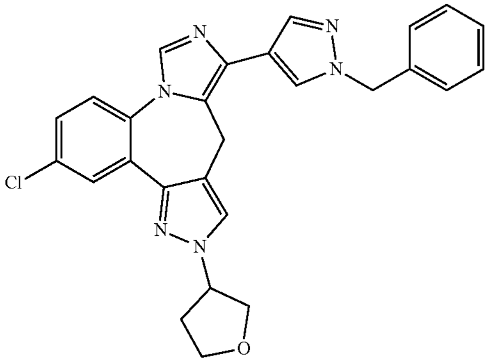 [SMILES: Clc1ccc2c(c1)-c1nn(C3CCOC3)cc1Cc1c(-c3cnn(Cc4ccccc4)c3)ncn1-2] |
| 275 | 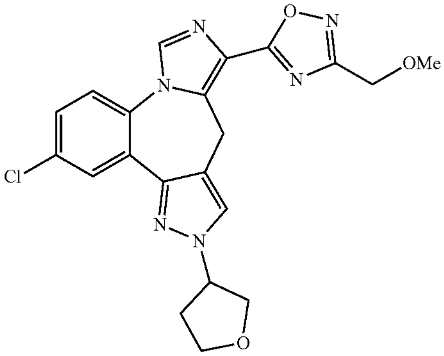 [SMILES: COCc1noc(-c2ncn3c2Cc2cn(C4CCOC4)nc2-c2cc(Cl)ccc2-3)n1] |
| 276 | 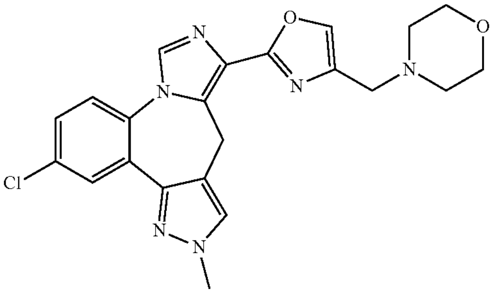 [SMILES: Cn1cc2c(n1)-c1cc(Cl)ccc1-n1cnc(-c3nc(CN4CCOCC4)co3)c1C2] |

-continued
| Compound | Structure |
|---|---|
| 277 | 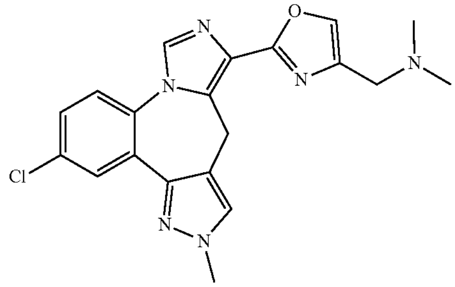 [SMILES: CN(C)Cc1coc(-c2ncn3c2Cc2cn(C)nc2-c2cc(Cl)ccc2-3)n1] |
| 278 | 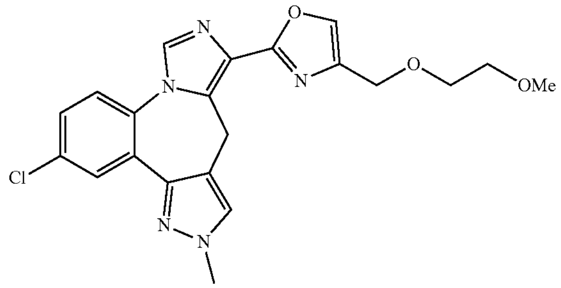 [SMILES: COCCOCc1coc(-c2ncn3c2Cc2cn(C)nc2-c2cc(Cl)ccc2-3)n1] |
| 279 | 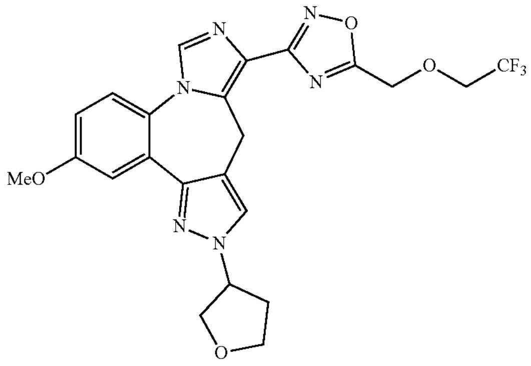 [SMILES: COc1ccc2c(c1)-c1nn(C3CCOC3)cc1Cc1c(-c3noc(COCC(F)(F)F)n3)ncn1-2] |
| 280 | 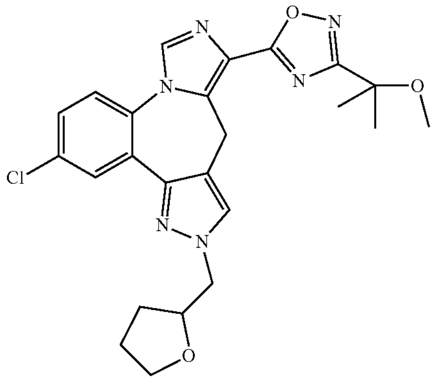 [SMILES: COC(C)(C)c1noc(-c2ncn3c2Cc2cn(CC4CCCO4)nc2-c2cc(Cl)ccc2-3)n1] |

-continued
| Compound | Structure |
|---|---|
| 281 | 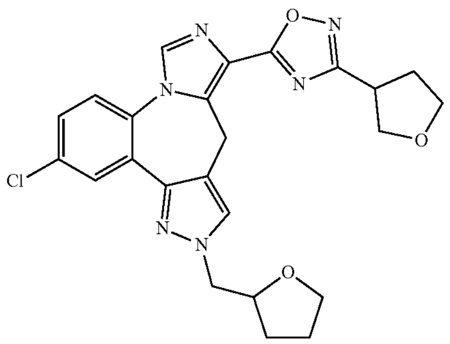 [SMILES: Clc1ccc2c(c1)-c1nn(CC3CCCO3)cc1Cc1c(-c3nc(C4CCOC4)no3)ncn1-2] |
| 282 | 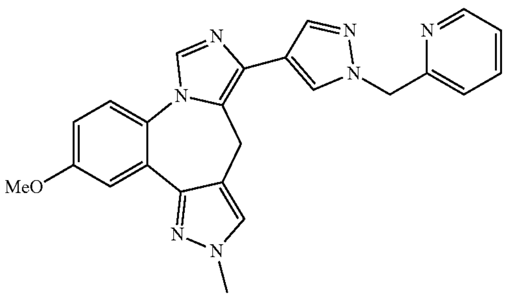 [SMILES: COc1ccc2c(c1)-c1nn(C)cc1Cc1c(-c3cnn(Cc4ccccn4)c3)ncn1-2] |
| 283 | 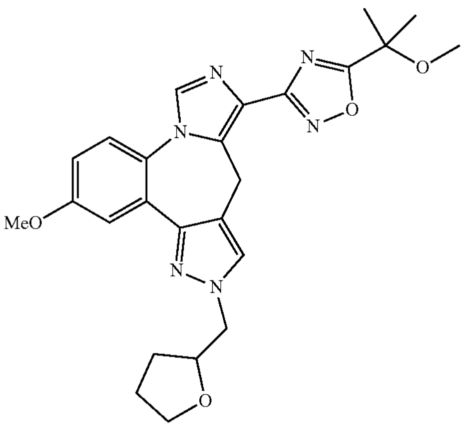 [SMILES: COc1ccc2c(c1)-c1nn(CC3CCCO3)cc1Cc1c(-c3noc(C(C)(C)OC)n3)ncn1-2] |
| 284 | 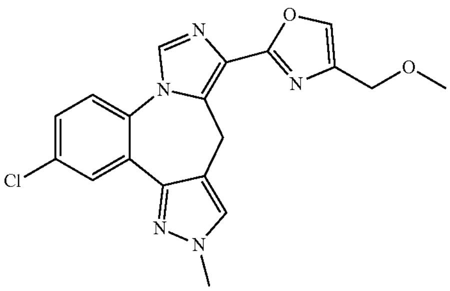 [SMILES: COCc1coc(-c2ncn3c2Cc2cn(C)nc2-c2cc(Cl)ccc2-3)n1] |

-continued
| Compound | Structure |
|---|---|
| 285 | 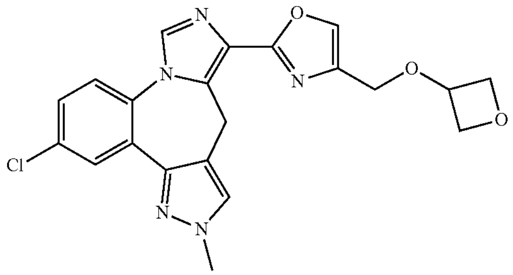 [SMILES: Cn1cc2c(n1)-c1cc(Cl)ccc1-n1cnc(-c3nc(COC4COC4)co3)c1C2] |
| 286 | 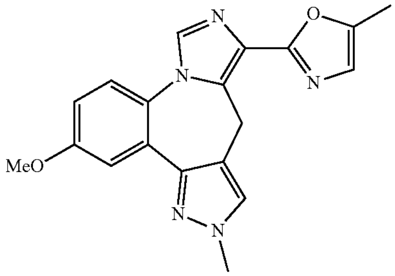 [SMILES: COc1ccc2c(c1)-c1nn(C)cc1Cc1c(-c3ncc(C)o3)ncn1-2] |
| 287 | 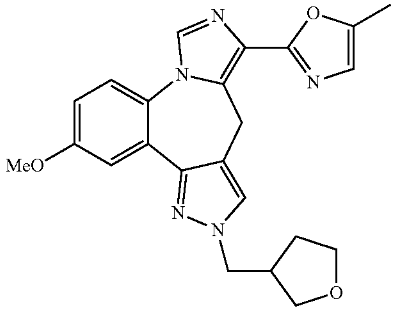 [SMILES: COc1ccc2c(c1)-c1nn(CC3CCOC3)cc1Cc1c(-c3ncc(C)o3)ncn1-2] |
| 288 | 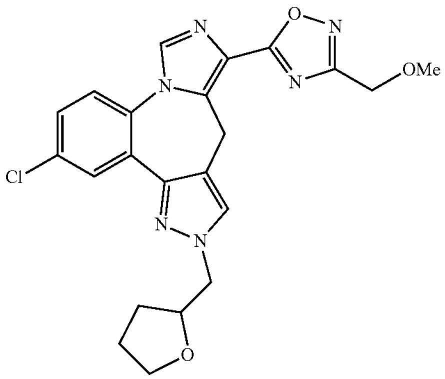 [SMILES: COCc1noc(-c2ncn3c2Cc2cn(CC4CCCO4)nc2-c2cc(Cl)ccc2-3)n1] |
| 289 | 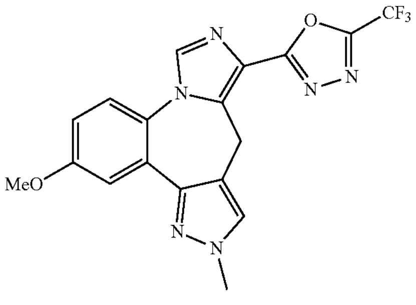 [SMILES: COc1ccc2c(c1)-c1nn(C)cc1Cc1c(-c3nnc(C(F)(F)F)o3)ncn1-2] |

-continued
| Compound | Structure |
| --- | --- |
| 290 | 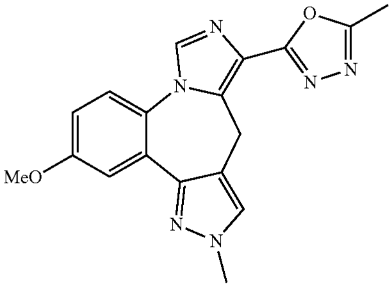 [SMILES: COc1ccc2c(c1)-c1nn(C)cc1Cc1c(-c3nnc(C)o3)ncn1-2] |
| 291 | 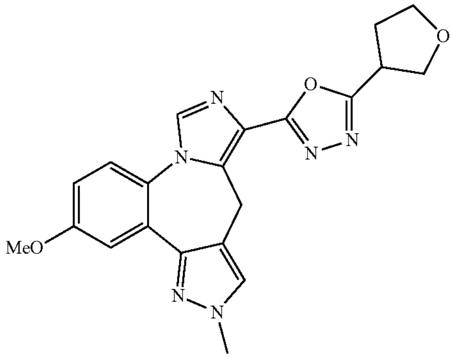 [SMILES: COc1ccc2c(c1)-c1nn(C)cc1Cc1c(-c3nnc(C4CCOC4)o3)ncn1-2] |
| 292 | 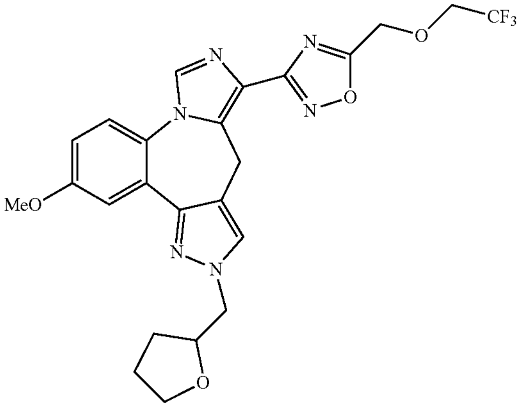 [SMILES: COc1ccc2c(c1)-c1nn(CC3CCCO3)cc1Cc1c(-c3noc(COCC(F)(F)F)n3)ncn1-2] |
| 293 | 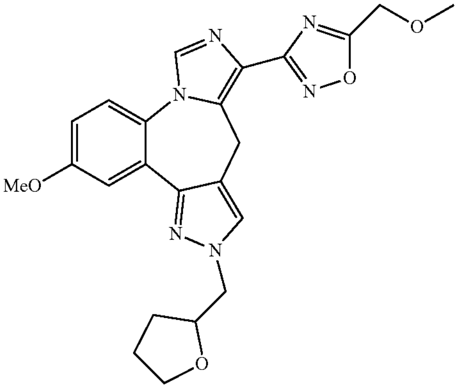 [SMILES: COCc1nc(-c2ncn3c2Cc2cn(CC4CCCO4)nc2-c2cc(OC)ccc2-3)no1] |

-continued
| Compound | Structure |
|---|---|
| 294 | 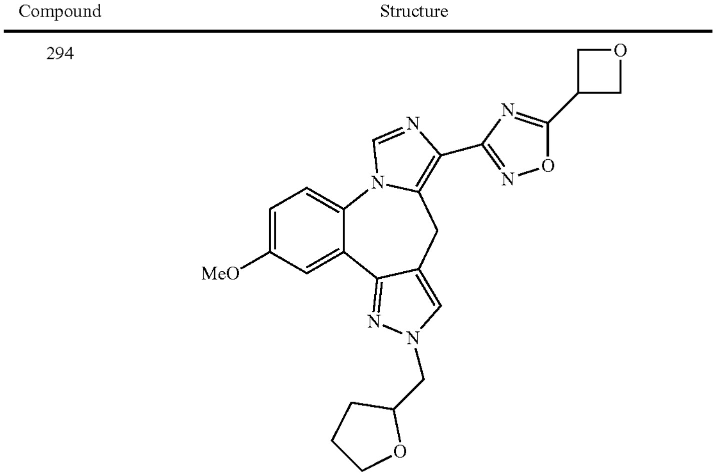 |
| 295 | 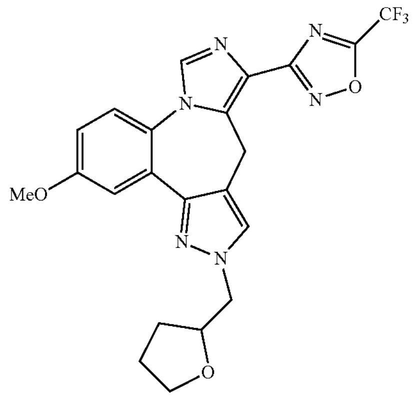 [SMILES: COc1ccc2c(c1)-c1nn(CC3CCCO3)cc1Cc1c(-c3noc(C(F)(F)F)n3)ncn1-2] |
| 296 | 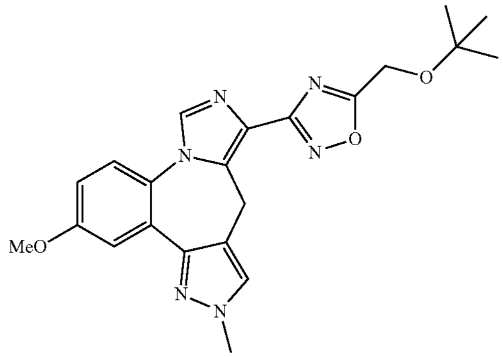 [SMILES: COc1ccc2c(c1)-c1nn(C)cc1Cc1c(-c3noc(COC(C)(C)C)n3)ncn1-2] |
| 297 | 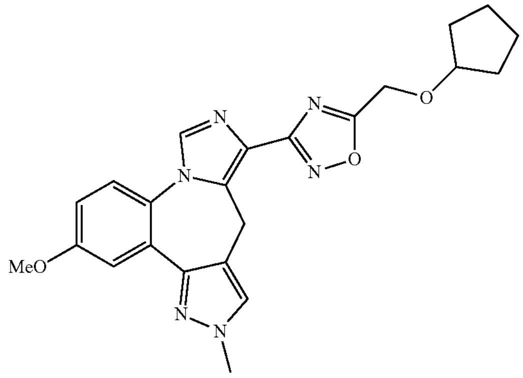 [SMILES: COc1ccc2c(c1)-c1nn(C)cc1Cc1c(-c3noc(COC4CCCC4)n3)ncn1-2] |

-continued
| Compound | Structure |
| --- | --- |
| 298 | 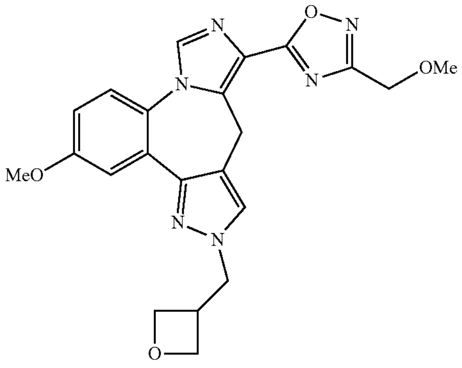 [SMILES: COCc1noc(-c2ncn3c2Cc2cn(CC4COC4)nc2-c2cc(OC)ccc2-3)n1] |
| 299 | 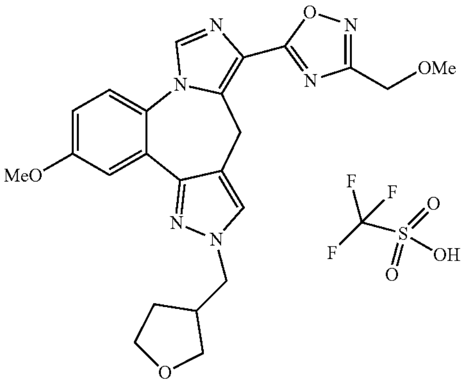 [SMILES: COCc1noc(-c2ncn3c2Cc2cn(CC4CCOC4)nc2-c2cc(OC)ccc2-3)n1 ; O=S(=O)(O)C(F)(F)F] |
| 300 | 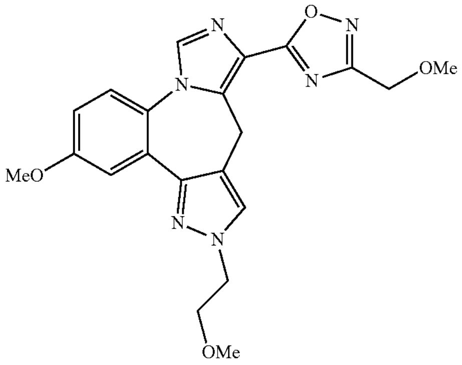 [SMILES: COCCn1cc2c(n1)-c1cc(OC)ccc1-n1cnc(-c3nc(COC)no3)c1C2] |
| 301 | 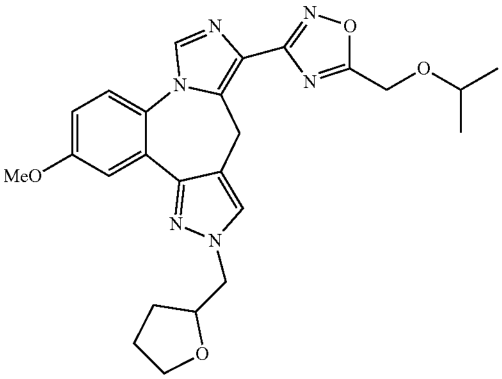 [SMILES: COc1ccc2c(c1)-c1nn(CC3CCCO3)cc1Cc1c(-c3noc(COC(C)C)n3)ncn1-2] |

-continued
| Compound | Structure |
| --- | --- |
| 302 | 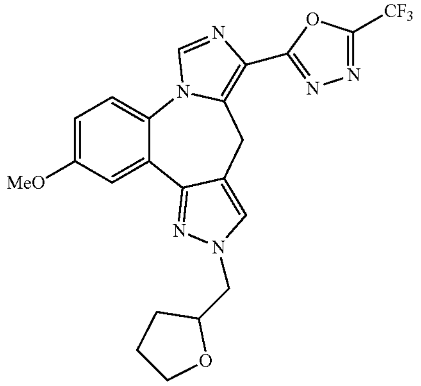 [SMILES: COc1ccc2c(c1)-c1nn(CC3CCCO3)cc1Cc1c(-c3nnc(C(F)(F)F)o3)ncn1-2] |
| 303 | 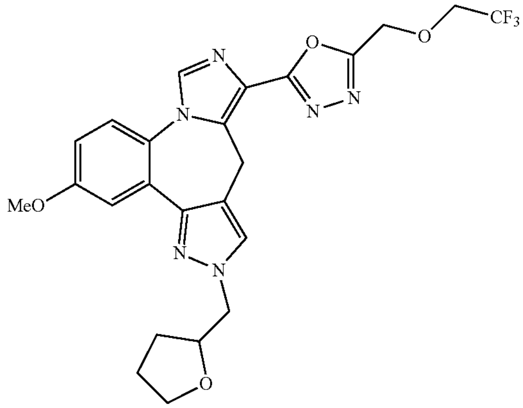 [SMILES: COc1ccc2c(c1)-c1nn(CC3CCCO3)cc1Cc1c(-c3nnc(COCC(F)(F)F)o3)ncn1-2] |
| 304 | 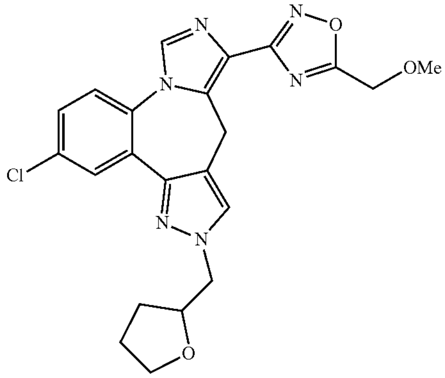 [SMILES: COCc1nc(-c2ncn3c2Cc2cn(CC4CCCO4)nc2-c2cc(Cl)ccc2-3)no1] |
| 305 | 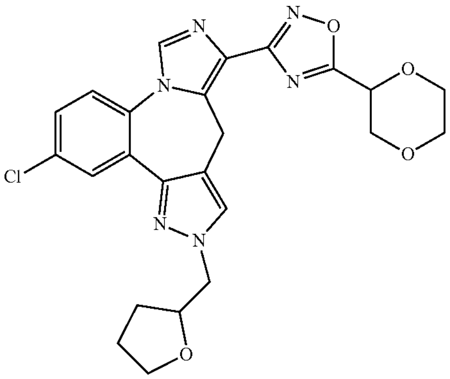 [SMILES: Clc1ccc2c(c1)-c1nn(CC3CCCO3)cc1Cc1c(-c3noc(C4COCCO4)n3)ncn1-2] |

-continued
| Compound | Structure |
|---|---|
| 306 | 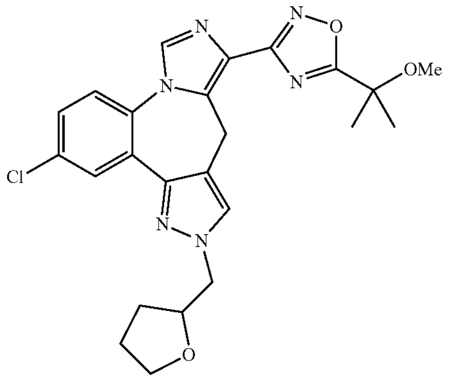 [SMILES: COC(C)(C)c1nc(-c2ncn3c2Cc2cn(CC4CCCO4)nc2-c2cc(Cl)ccc2-3)no1] |
| 307 | 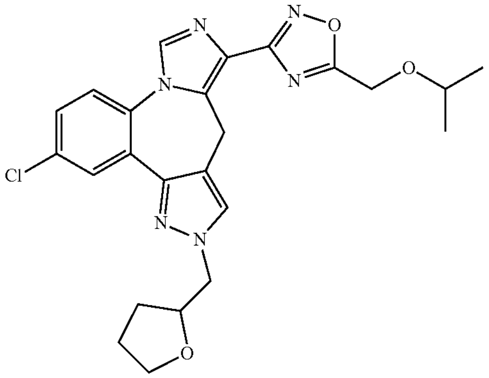 [SMILES: CC(C)OCc1nc(-c2ncn3c2Cc2cn(CC4CCCO4)nc2-c2cc(Cl)ccc2-3)no1] |
| 308 | 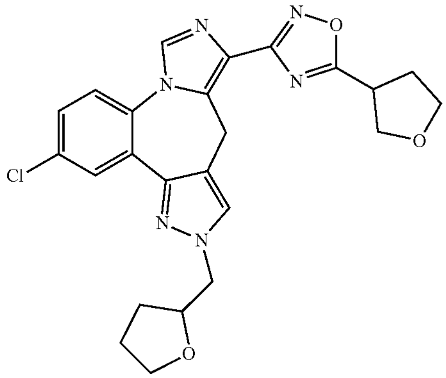 [SMILES: Clc1ccc2c(c1)-c1nn(CC3CCCO3)cc1Cc1c(-c3noc(C4CCOC4)n3)ncn1-2] |
| 309 | 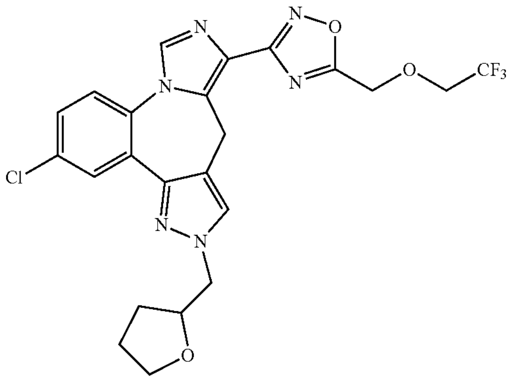 [SMILES: FC(F)(F)COCc1nc(-c2ncn3c2Cc2cn(CC4CCCO4)nc2-c2cc(Cl)ccc2-3)no1] |

-continued
| Compound | Structure |
| --- | --- |
| 310 | 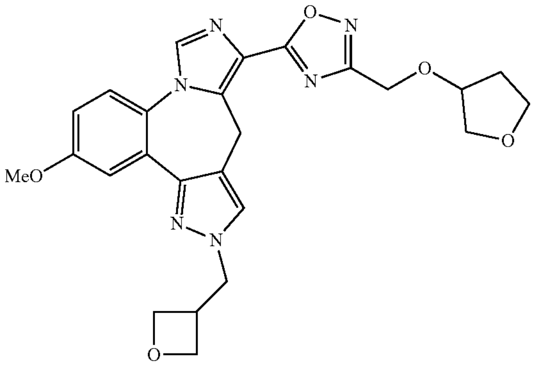 [SMILES: COc1ccc2c(c1)-c1nn(CC3COC3)cc1Cc1c(-c3nc(COC4CCOC4)no3)ncn1-2] |
| 311 | 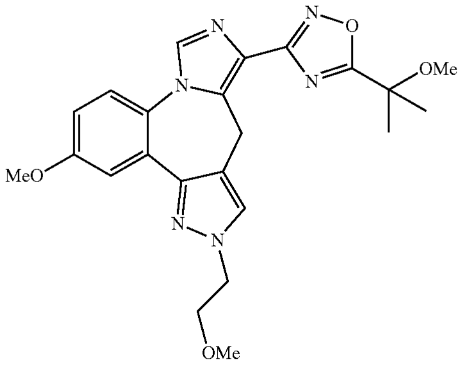 [SMILES: COCCn1cc2c(n1)-c1cc(OC)ccc1-n1cnc(-c3noc(C(C)(C)OC)n3)c1C2] |
| 312 | 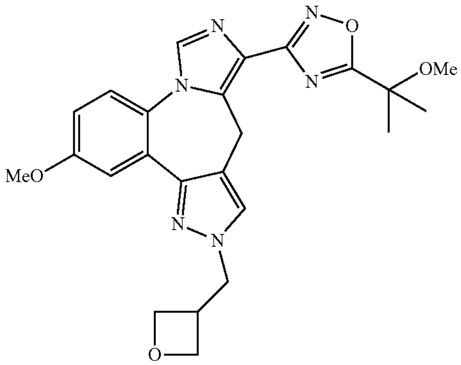 [SMILES: COc1ccc2c(c1)-c1nn(CC3COC3)cc1Cc1c(-c3noc(C(C)(C)OC)n3)ncn1-2] |
| 313 | 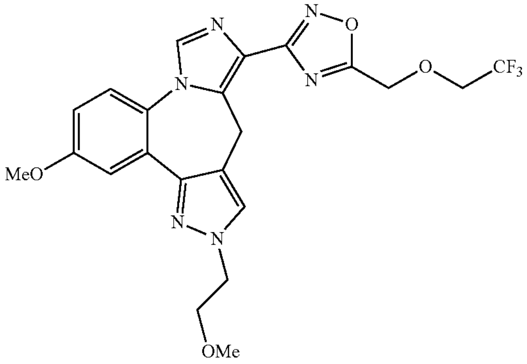 [SMILES: COCCn1cc2c(n1)-c1cc(OC)ccc1-n1cnc(-c3noc(COCC(F)(F)F)n3)c1C2] |

-continued
| Compound | Structure |
|---|---|
| 314 | 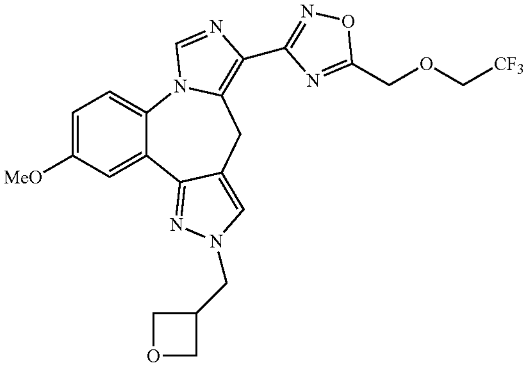 [SMILES: COc1ccc2c(c1)-c1nn(CC3COC3)cc1Cc1c(-c3noc(COCC(F)(F)F)n3)ncn1-2] |
| 315 | 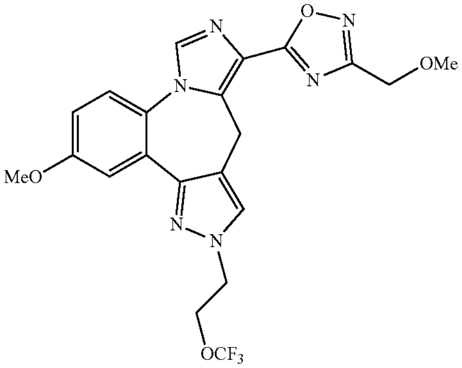 [SMILES: COCc1noc(-c2ncn3c2Cc2cn(CCOC(F)(F)F)nc2-c2cc(OC)ccc2-3)n1] |
| 316 | 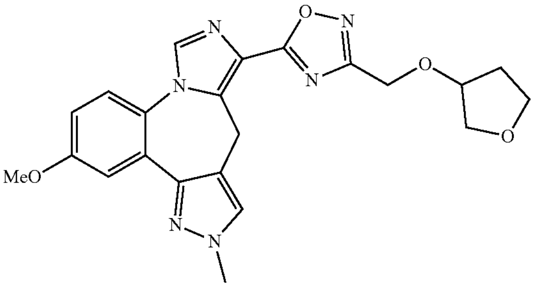 [SMILES: COc1ccc2c(c1)-c1nn(C)cc1Cc1c(-c3nc(COC4CCOC4)no3)ncn1-2] |
| 317 | 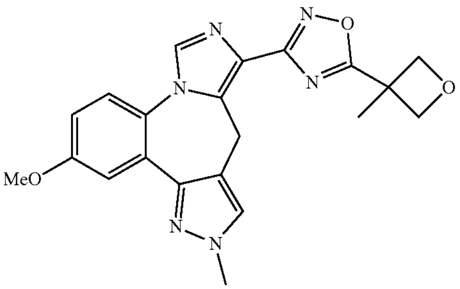 [SMILES: COc1ccc2c(c1)-c1nn(C)cc1Cc1c(-c3noc(C4(C)COC4)n3)ncn1-2] |

-continued
| Compound | Structure |
|---|---|
| 318 | 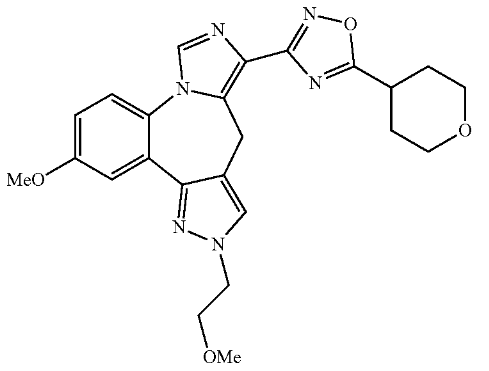 [SMILES: COCCn1cc2c(n1)-c1cc(OC)ccc1-n1cnc(-c3noc(C4CCOCC4)n3)c1C2] |
| 319 | 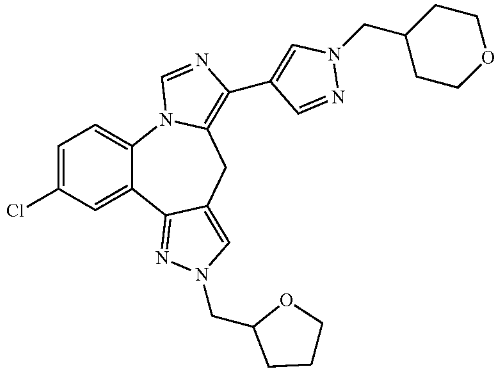 [SMILES: Clc1ccc2c(c1)-c1nn(CC3CCCO3)cc1Cc1c(-c3cnn(CC4CCOCC4)c3)ncn1-2] |
| 320 | 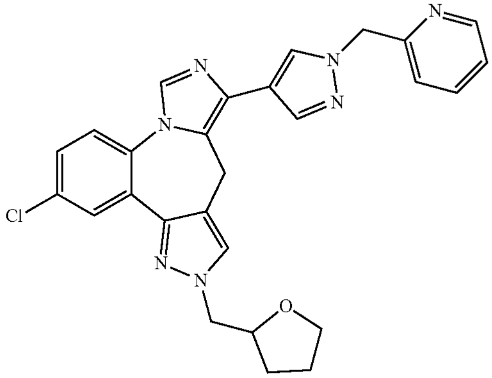 [SMILES: Clc1ccc2c(c1)-c1nn(CC3CCCO3)cc1Cc1c(-c3cnn(Cc4ccccn4)c3)ncn1-2] |
| 321 | 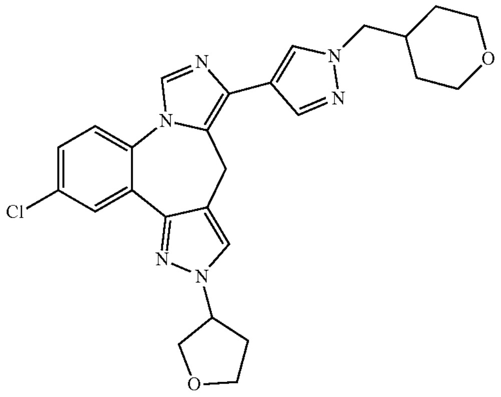 [SMILES: Clc1ccc2c(c1)-c1nn(C3CCOC3)cc1Cc1c(-c3cnn(CC4CCOCC4)c3)ncn1-2] |

-continued
| Compound | Structure |
| --- | --- |
| 322 | 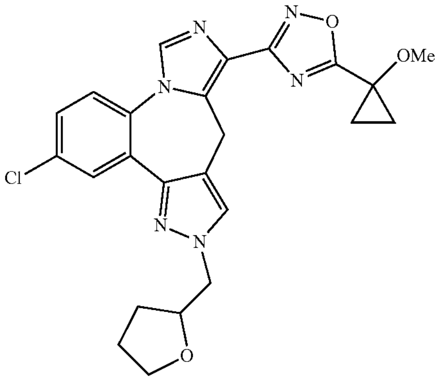 [SMILES: COC1(c2nc(-c3ncn4c3Cc3cn(CC5CCCO5)nc3-c3cc(Cl)ccc3-4)no2)CC1] |
| 323 | 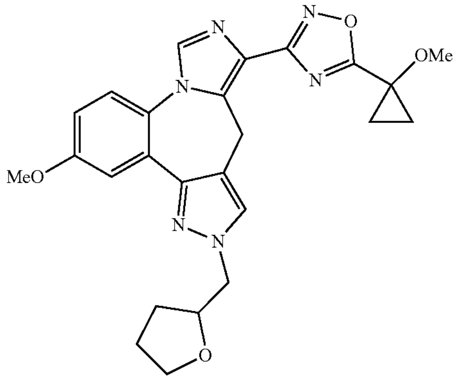 [SMILES: COc1ccc2c(c1)-c1nn(CC3CCCO3)cc1Cc1c(-c3noc(C4(OC)CC4)n3)ncn1-2] |
| 324 | 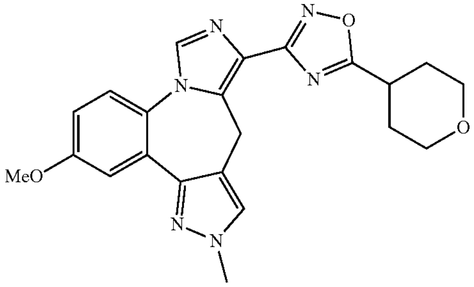 [SMILES: COc1ccc2c(c1)-c1nn(C)cc1Cc1c(-c3noc(C4CCOCC4)n3)ncn1-2] |
| 325 | 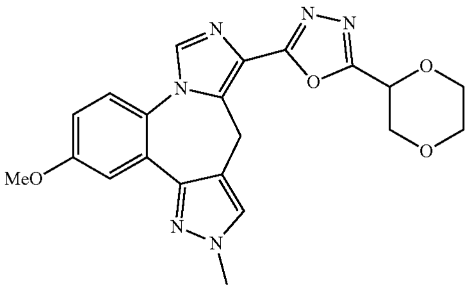 [SMILES: COc1ccc2c(c1)-c1nn(C)cc1Cc1c(-c3nnc(C4COCCO4)o3)ncn1-2] |

-continued
| Compound | Structure |
| --- | --- |
| 326 | 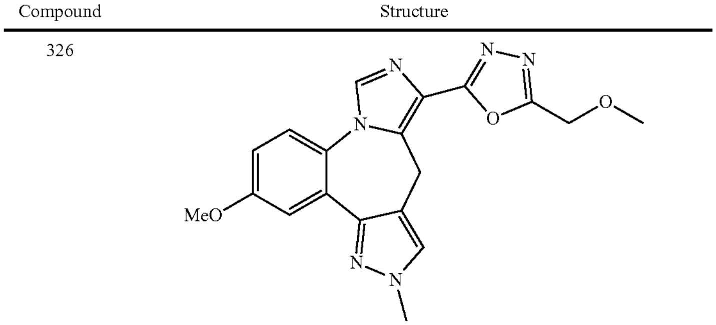 |
| 327 | 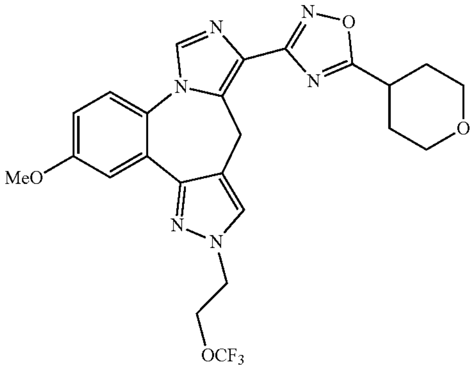 [SMILES: COc1ccc2c(c1)-c1nn(CCOC(F)(F)F)cc1Cc1c(-c3noc(C4CCOCC4)n3)ncn1-2] |
| 328 | 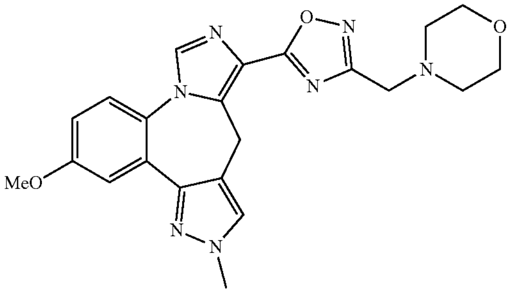 [SMILES: COc1ccc2c(c1)-c1nn(C)cc1Cc1c(-c3nc(CN4CCOCC4)no3)ncn1-2] |
| 329 | 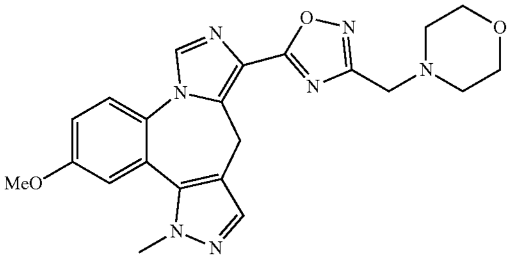 [SMILES: COc1ccc2c(c1)-c1c(cnn1C)Cc1c(-c3nc(CN4CCOCC4)no3)ncn1-2] |
| 330 | 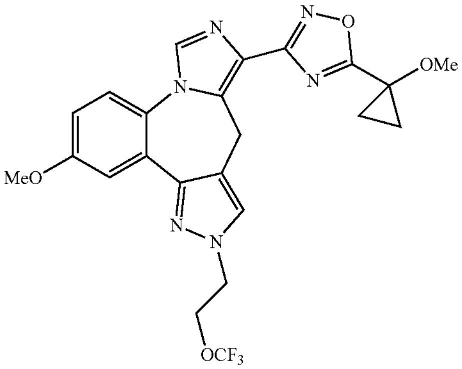 [SMILES: COc1ccc2c(c1)-c1nn(CCOC(F)(F)F)cc1Cc1c(-c3noc(C4(OC)CC4)n3)ncn1-2] |

-continued
| Compound | Structure |
| --- | --- |
| 331 | 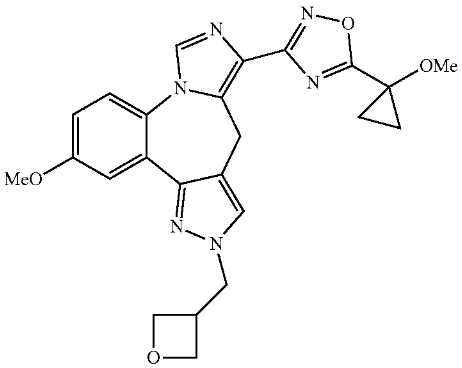 [SMILES: COc1ccc2c(c1)-c1nn(CC3COC3)cc1Cc1c(-c3noc(C4(OC)CC4)n3)ncn1-2] |
| 332 | 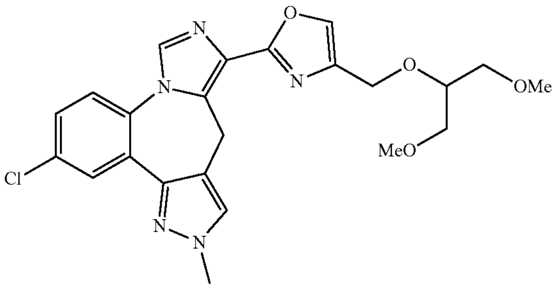 [SMILES: COCC(COC)OCc1coc(-c2ncn3c2Cc2cn(C)nc2-c2cc(Cl)ccc2-3)n1] |
| 333 | 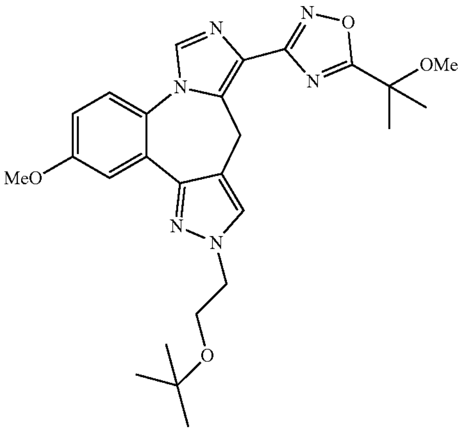 [SMILES: COc1ccc2c(c1)-c1nn(CCOC(C)(C)C)cc1Cc1c(-c3noc(C(C)(C)OC)n3)ncn1-2] |
| 334 | 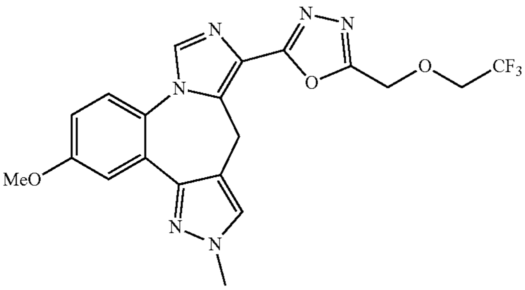 [SMILES: COc1ccc2c(c1)-c1nn(C)cc1Cc1c(-c3nnc(COCC(F)(F)F)o3)ncn1-2] |

-continued
| Compound | Structure |
|---|---|
| 335 | 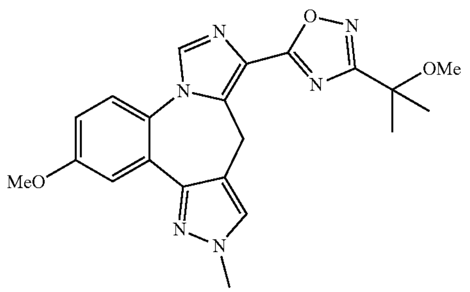 [SMILES: COc1ccc2c(c1)-c1nn(C)cc1Cc1c(-c3nc(C(C)(C)OC)no3)ncn1-2] |
| 336 | 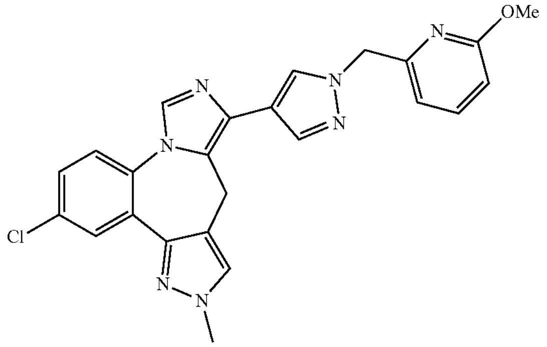 [SMILES: COc1cccc(Cn2cc(-c3ncn4c3Cc3cn(C)nc3-c3cc(Cl)ccc3-4)cn2)n1] |
| 337 | 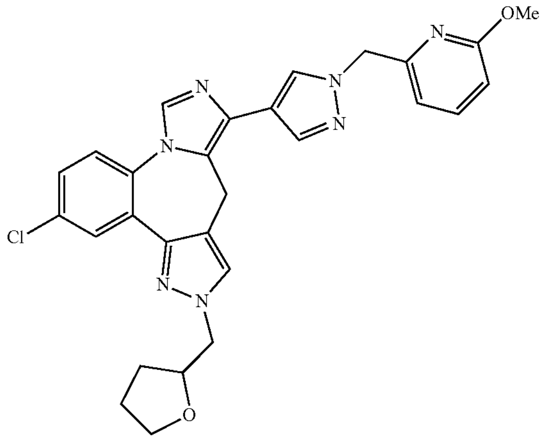 [SMILES: COc1cccc(Cn2cc(-c3ncn4c3Cc3cn(CC5CCCO5)nc3-c3cc(Cl)ccc3-4)cn2)n1] |
| 338 | 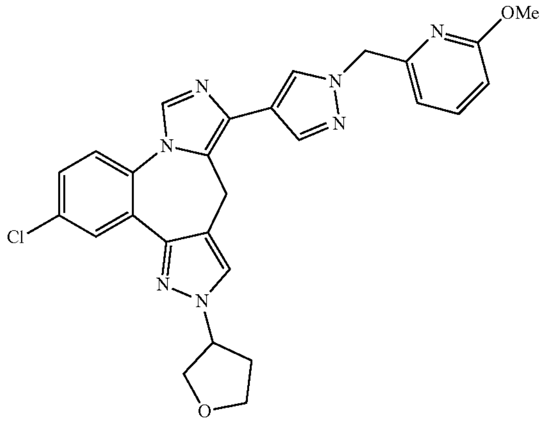 [SMILES: COc1cccc(Cn2cc(-c3ncn4c3Cc3cn(C5CCOC5)nc3-c3cc(Cl)ccc3-4)cn2)n1] |

-continued
| Compound | Structure |
| --- | --- |
| 339 | 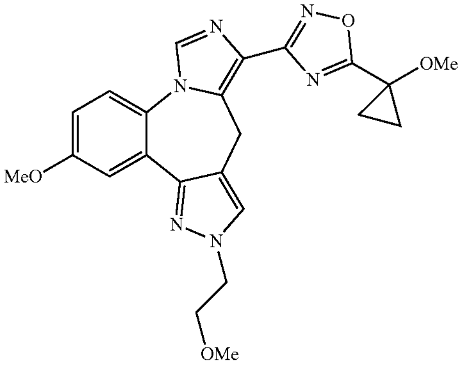 [SMILES: COCCn1cc2c(n1)-c1cc(OC)ccc1-n1cnc(-c3noc(C4(OC)CC4)n3)c1C2] |
| 340 | 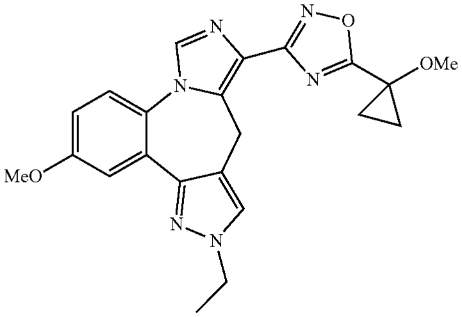 [SMILES: CCn1cc2c(n1)-c1cc(OC)ccc1-n1cnc(-c3noc(C4(OC)CC4)n3)c1C2] |
| 341 | 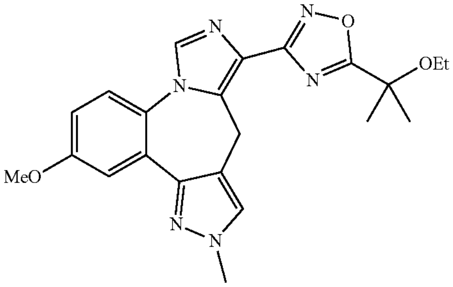 [SMILES: CCOC(C)(C)c1nc(-c2ncn3c2Cc2cn(C)nc2-c2cc(OC)ccc2-3)no1] |
| 342 | 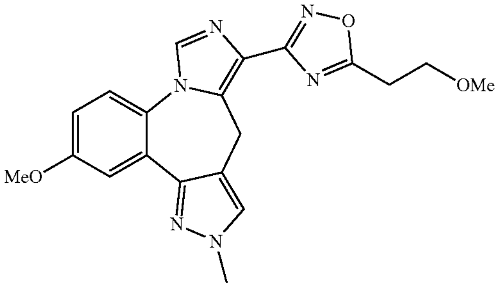 [SMILES: COCCc1nc(-c2ncn3c2Cc2cn(C)nc2-c2cc(OC)ccc2-3)no1] |

-continued
| Compound | Structure |
| --- | --- |
| 343 | 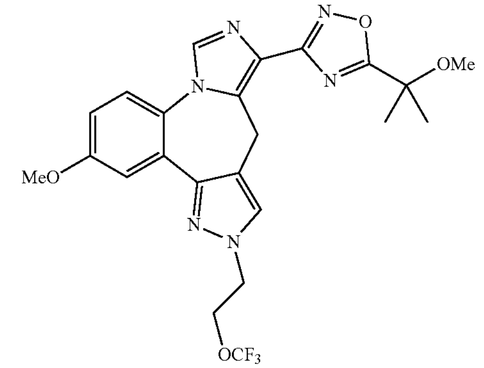 [SMILES: COc1ccc2c(c1)-c1nn(CCOC(F)(F)F)cc1Cc1c(-c3noc(C(C)(C)OC)n3)ncn1-2] |
| 344 | 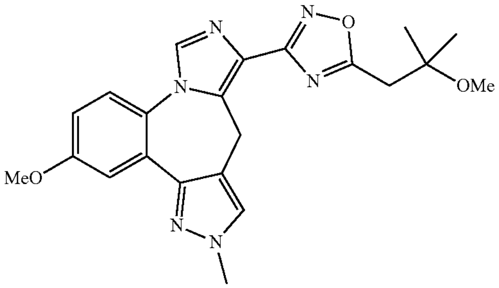 [SMILES: COc1ccc2c(c1)-c1nn(C)cc1Cc1c(-c3noc(CC(C)(C)OC)n3)ncn1-2] |
| 345 | 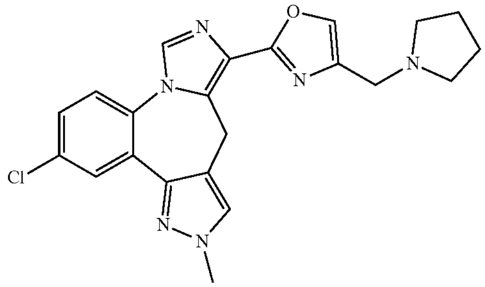 [SMILES: Cn1cc2c(n1)-c1cc(Cl)ccc1-n1cnc(-c3nc(CN4CCCC4)co3)c1C2] |
| 346 | 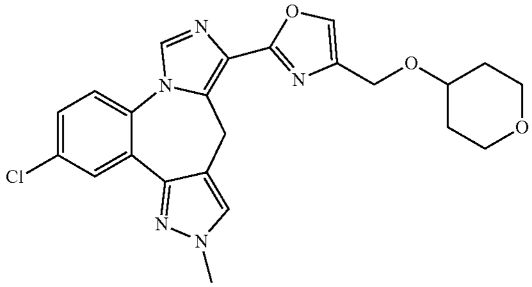 [SMILES: Cn1cc2c(n1)-c1cc(Cl)ccc1-n1cnc(-c3nc(COC4CCOCC4)co3)c1C2] |
| 347 | 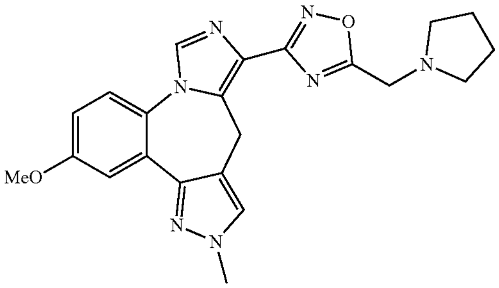 [SMILES: COc1ccc2c(c1)-c1nn(C)cc1Cc1c(-c3noc(CN4CCCC4)n3)ncn1-2] |

-continued
| Compound | Structure |
| --- | --- |
| 348 | 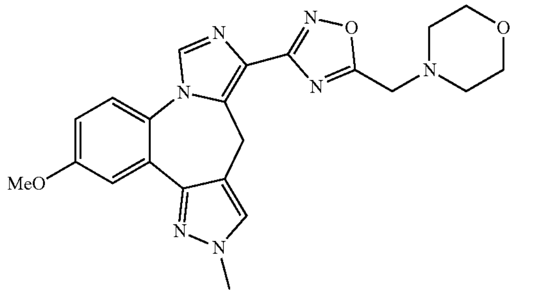 [SMILES: COc1ccc2c(c1)-c1nn(C)cc1Cc1c(-c3noc(CN4CCOCC4)n3)ncn1-2] |
| 349 | 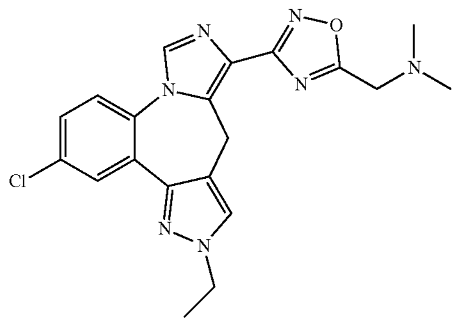 [SMILES: CCn1cc2c(n1)-c1cc(Cl)ccc1-n1cnc(-c3noc(CN(C)C)n3)c1C2] |
| 350 | 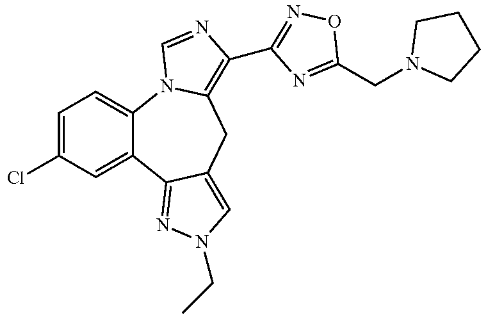 [SMILES: CCn1cc2c(n1)-c1cc(Cl)ccc1-n1cnc(-c3noc(CN4CCCC4)n3)c1C2] |
| 351 | 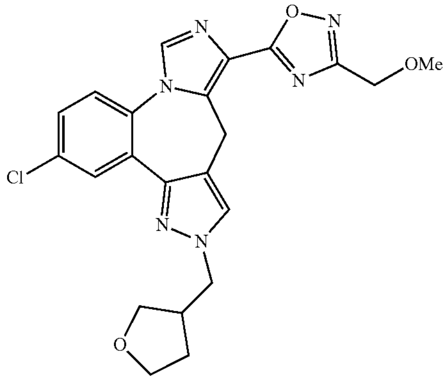 [SMILES: COCc1noc(-c2ncn3c2Cc2cn(CC4CCOC4)nc2-c2cc(Cl)ccc2-3)n1] |

-continued
| Compound | Structure |
|---|---|
| 352 | 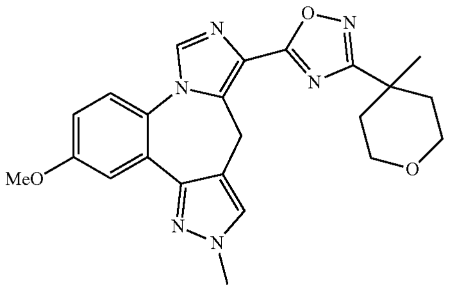 [SMILES: COc1ccc2c(c1)-c1nn(C)cc1Cc1c(-c3nc(C4(C)CCOCC4)no3)ncn1-2] |
| 353 | 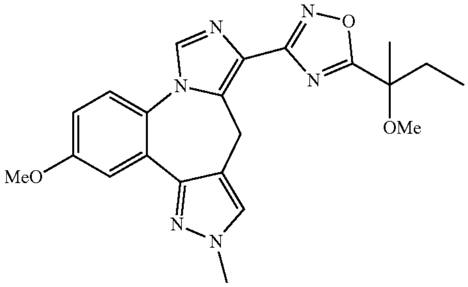 [SMILES: CCC(C)(OC)c1nc(-c2ncn3c2Cc2cn(C)nc2-c2cc(OC)ccc2-3)no1] |
| 354 | 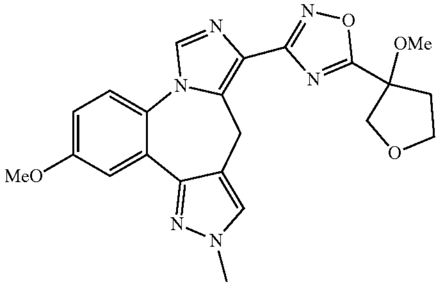 [SMILES: COc1ccc2c(c1)-c1nn(C)cc1Cc1c(-c3noc(C4(OC)CCOC4)n3)ncn1-2] |
| 355 | 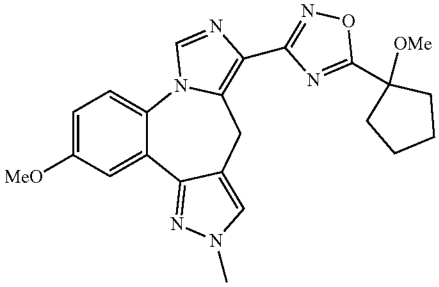 [SMILES: COc1ccc2c(c1)-c1nn(C)cc1Cc1c(-c3noc(C4(OC)CCCC4)n3)ncn1-2] |
| 356 | 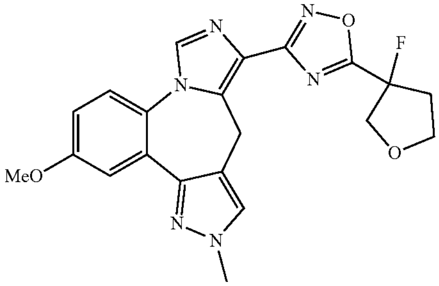 [SMILES: COc1ccc2c(c1)-c1nn(C)cc1Cc1c(-c3noc(C4(F)CCOC4)n3)ncn1-2] |

-continued
| Compound | Structure |
|---|---|
| 357 | 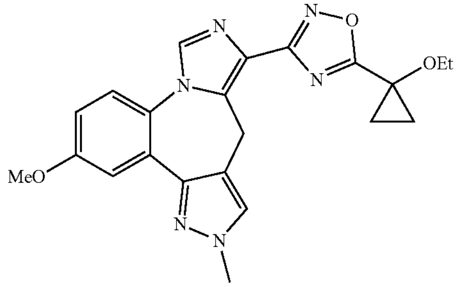 [SMILES: CCOC1(c2nc(-c3ncn4c3Cc3cn(C)nc3-c3cc(OC)ccc3-4)no2)CC1] |
| 358 | 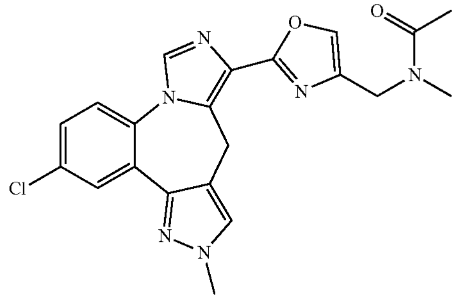 |
| 359 | 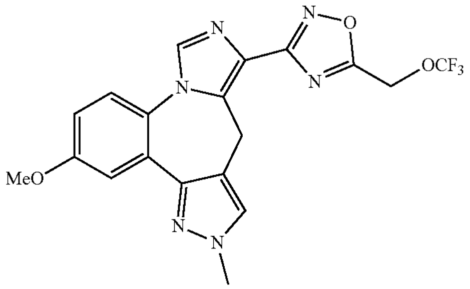 [SMILES: COc1ccc2c(c1)-c1nn(C)cc1Cc1c(-c3noc(COC(F)(F)F)n3)ncn1-2] |
| 360 | 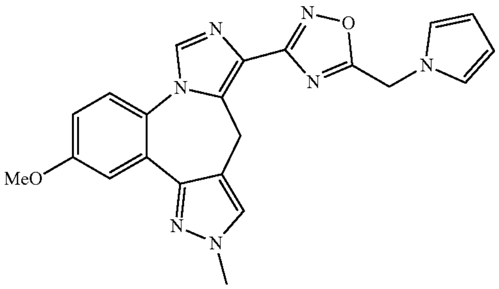 [SMILES: COc1ccc2c(c1)-c1nn(C)cc1Cc1c(-c3noc(Cn4cccc4)n3)ncn1-2] |
| 361 | 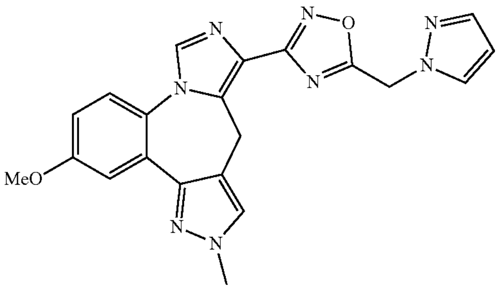 [SMILES: COc1ccc2c(c1)-c1nn(C)cc1Cc1c(-c3noc(Cn4cccn4)n3)ncn1-2] |

-continued
| Compound | Structure |
| --- | --- |
| 362 | 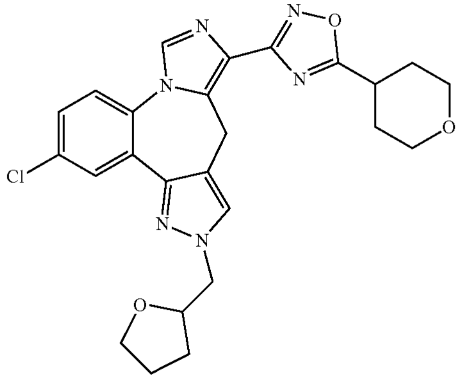 [SMILES: Clc1ccc2c(c1)-c1nn(CC3CCCO3)cc1Cc1c(-c3noc(C4CCOCC4)n3)ncn1-2] |
| 363 | 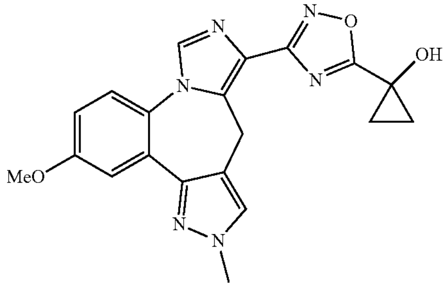 [SMILES: COc1ccc2c(c1)-c1nn(C)cc1Cc1c(-c3noc(C4(O)CC4)n3)ncn1-2] |
| 364 | 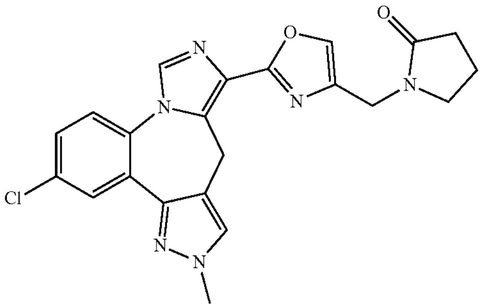 [SMILES: Cn1cc2c(n1)-c1cc(Cl)ccc1-n1cnc(-c3nc(CN4CCCC4=O)co3)c1C2] |
| 365 | 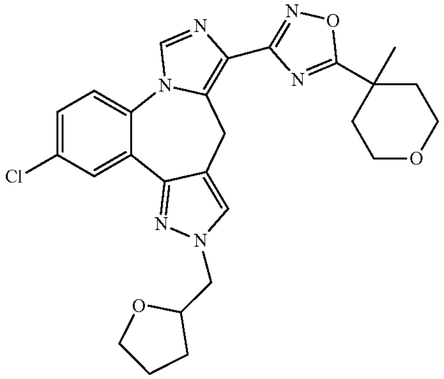 [SMILES: CC1(c2nc(-c3ncn4c3Cc3cn(CC5CCCO5)nc3-c3cc(Cl)ccc3-4)no2)CCOCC1] |

-continued
| Compound | Structure |
| --- | --- |
| 366 | 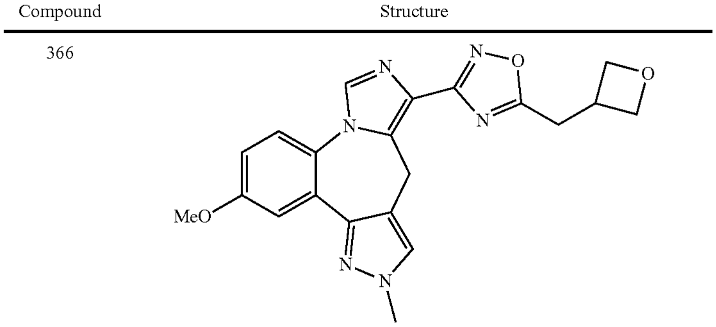 |
| 367 | 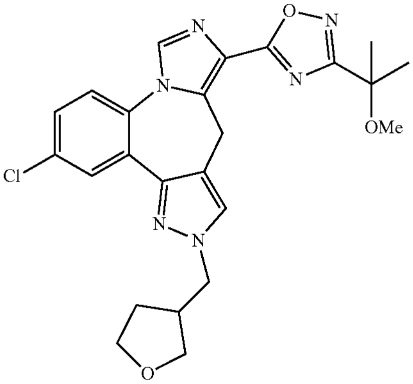 [SMILES: COC(C)(C)c1noc(-c2ncn3c2Cc2cn(CC4CCOC4)nc2-c2cc(Cl)ccc2-3)n1] |
| 368 | 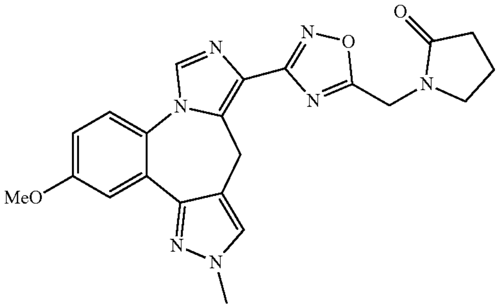 [SMILES: COc1ccc2c(c1)-c1nn(C)cc1Cc1c(-c3noc(CN4CCCC4=O)n3)ncn1-2] |
| 369 | 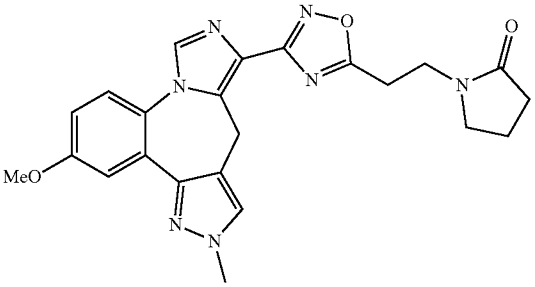 [SMILES: COc1ccc2c(c1)-c1nn(C)cc1Cc1c(-c3noc(CCN4CCCC4=O)n3)ncn1-2] |
| 370 | 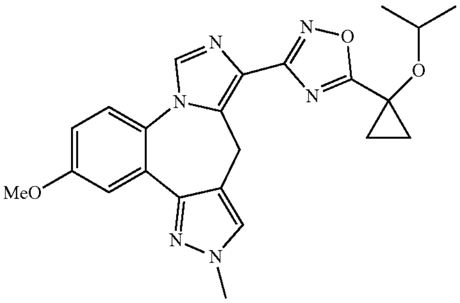 [SMILES: COc1ccc2c(c1)-c1nn(C)cc1Cc1c(-c3noc(C4(OC(C)C)CC4)n3)ncn1-2] |

-continued
| Compound | Structure |
| --- | --- |
| 371 | 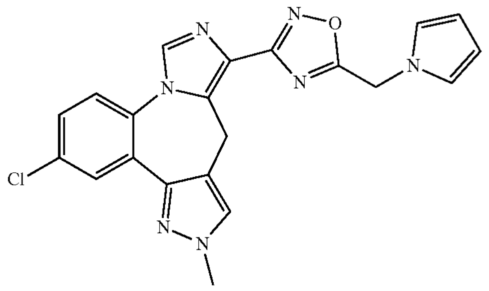 [SMILES: Cn1cc2c(n1)-c1cc(Cl)ccc1-n1cnc(-c3noc(Cn4cccc4)n3)c1C2] |
| 372 | 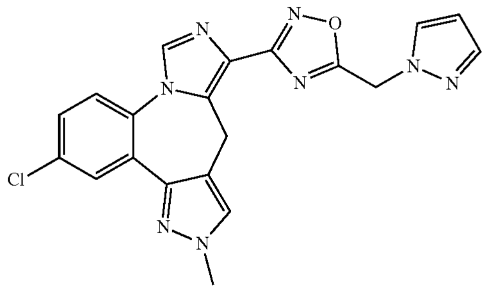 [SMILES: Cn1cc2c(n1)-c1cc(Cl)ccc1-n1cnc(-c3noc(Cn4cccn4)n3)c1C2] |
| 373 | 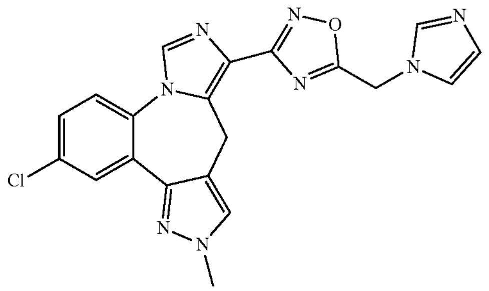 [SMILES: Cn1cc2c(n1)-c1cc(Cl)ccc1-n1cnc(-c3noc(Cn4ccnc4)n3)c1C2] |
| 374 | 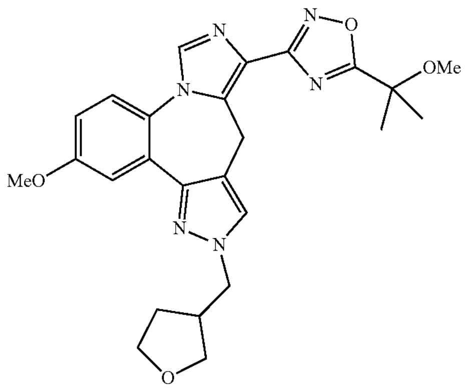 [SMILES: COc1ccc2c(c1)-c1nn(CC3CCOC3)cc1Cc1c(-c3noc(C(C)(C)OC)n3)ncn1-2] |

-continued
| Compound | Structure |
| --- | --- |
| 375 | 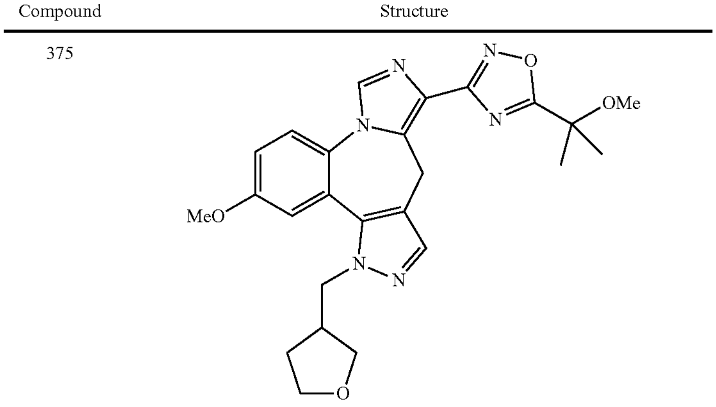 |
| 376 | 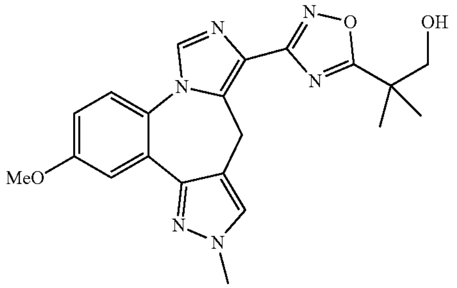 [SMILES: COc1ccc2c(c1)-c1nn(C)cc1Cc1c(-c3noc(C(C)(C)CO)n3)ncn1-2] |
| 377 | 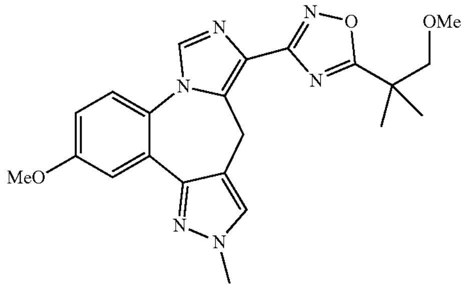 [SMILES: COCC(C)(C)c1nc(-c2ncn3c2Cc2cn(C)nc2-c2cc(OC)ccc2-3)no1] |
| 378 | 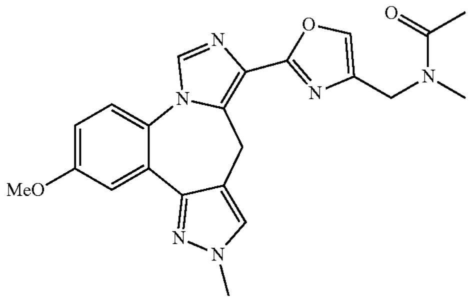 [SMILES: COc1ccc2c(c1)-c1nn(C)cc1Cc1c(-c3nc(CN(C)C(C)=O)co3)ncn1-2] |
| 379 | 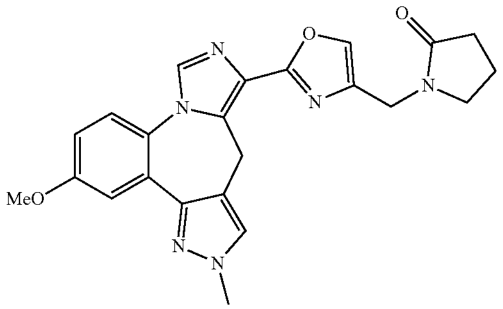 [SMILES: COc1ccc2c(c1)-c1nn(C)cc1Cc1c(-c3nc(CN4CCCC4=O)co3)ncn1-2] |

-continued
| Compound | Structure |
| --- | --- |
| 380 | 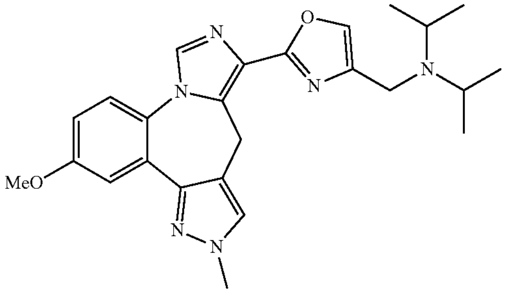 [SMILES: COc1ccc2c(c1)-c1nn(C)cc1Cc1c(-c3nc(CN(C(C)C)C(C)C)co3)ncn1-2] |
| 381 | 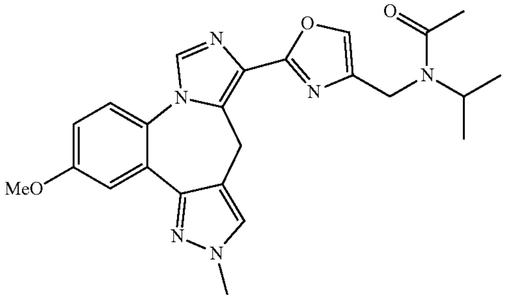 [SMILES: COc1ccc2c(c1)-c1nn(C)cc1Cc1c(-c3nc(CN(C(C)=O)C(C)C)co3)ncn1-2] |
| 382 | 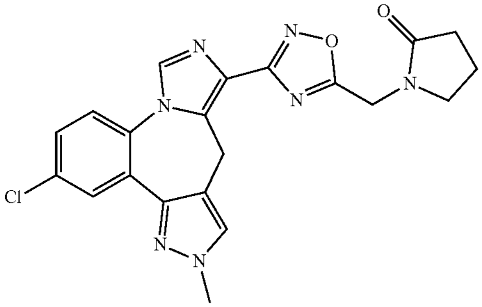 [SMILES: Cn1cc2c(n1)-c1cc(Cl)ccc1-n1cnc(-c3noc(CN4CCCC4=O)n3)c1C2] |
| 383 | 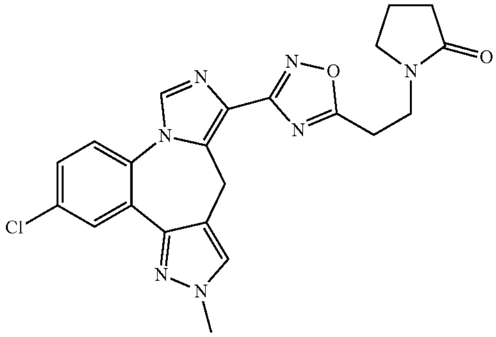 [SMILES: Cn1cc2c(n1)-c1cc(Cl)ccc1-n1cnc(-c3noc(CCN4CCCC4=O)n3)c1C2] |
| 384 | 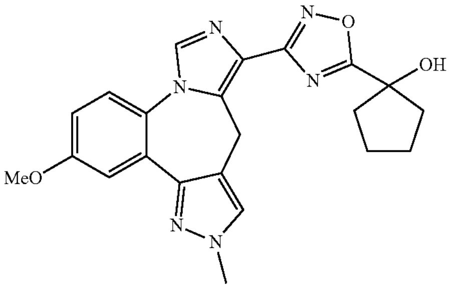 [SMILES: COc1ccc2c(c1)-c1nn(C)cc1Cc1c(-c3noc(C4(O)CCCC4)n3)ncn1-2] |

-continued

| Compound | Structure |
|---|---|
| 385 | 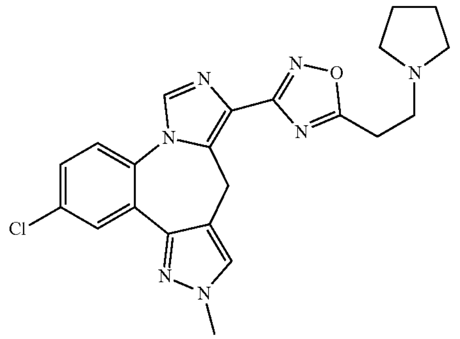 [SMILES: Cn1cc2c(n1)-c1cc(Cl)ccc1-n1cnc(-c3noc(CCN4CCCC4)n3)c1C2] |
| 386 | 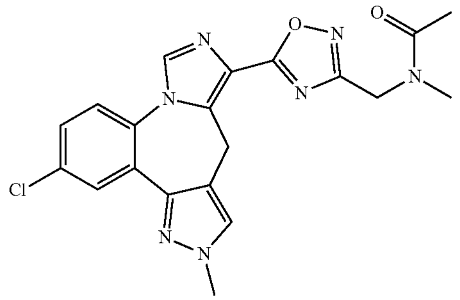 [SMILES: CC(=O)N(C)Cc1noc(-c2ncn3c2Cc2cn(C)nc2-c2cc(Cl)ccc2-3)n1] |
| 387 | 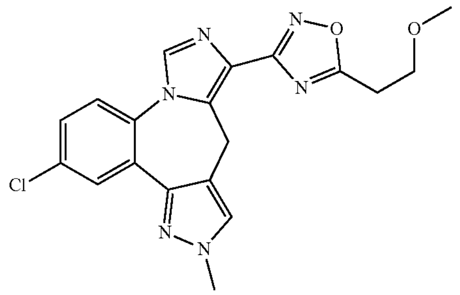 [SMILES: COCCc1nc(-c2ncn3c2Cc2cn(C)nc2-c2cc(Cl)ccc2-3)no1] |
| 388 | 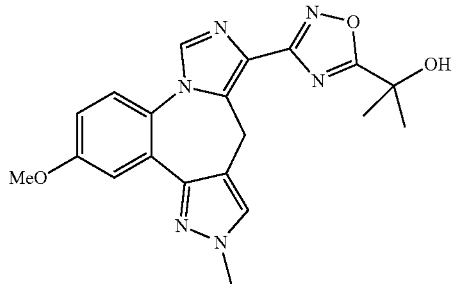 [SMILES: COc1ccc2c(c1)-c1nn(C)cc1Cc1c(-c3noc(C(C)(C)O)n3)ncn1-2] |

or a pharmaceutically acceptable salt, hydrate, solvate, polymorph, isomer, or combinations thereof.

The basic nitrogen-containing groups present in the compounds of the disclosure may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Any embodiment described herein is also intended to represent both unlabeled forms, as well as isotopically labeled forms of the compounds, unless otherwise indicated. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$, respectively. The invention includes various isotopically labeled compounds as defined herein, for example those into which radioactive isotopes, such as $^{3}H$, $^{13}C$, and $^{14}C$, are present. Such isotopically labeled compounds are useful in metabolic studies (preferably with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be, particularly preferred for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Any of the individual embodiments recited herein in the context of the generic formulas I, I-A, I-a, I-aa, I-B, I-b, I-ba, I-C, I-c, I-D, I-d, I-E, I-e, I-F and I-f are a part of this disclosure. Further, the various substituents recited at particular residues in those individual embodiments may be combined with one of the substituents recited at other of the particular residues without departing from the scope of this disclosure.

General Synthetic Methodology

The compounds of this disclosure may be prepared in general by methods known to those skilled in the art. Schemes 1-4 below provide general synthetic routes for the preparation of compounds of formulae I, I-A, I-a, I-aa, I-B, I-b, I-ba, I-C, I-c, I-D, I-d, I-E, I-e, I-F, and I-f. Other equivalent schemes, which will be readily apparent to the ordinary skilled organic chemist, may alternatively be used to synthesize various portions (or the entirety) of the molecules as illustrated by the general schemes below.

Scheme 1. General synthesis of a compound of formula I-A, I-a, and I-aa wherein X, W and V form a pyrazole ring.

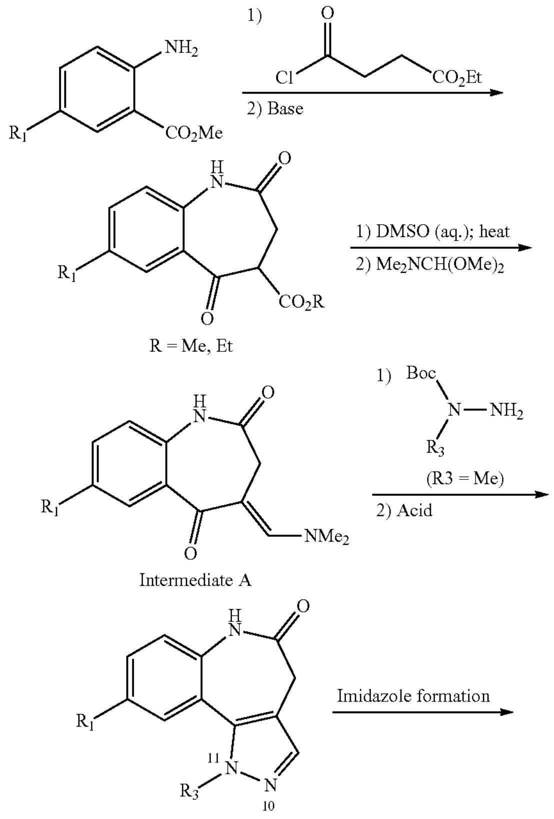

-continued

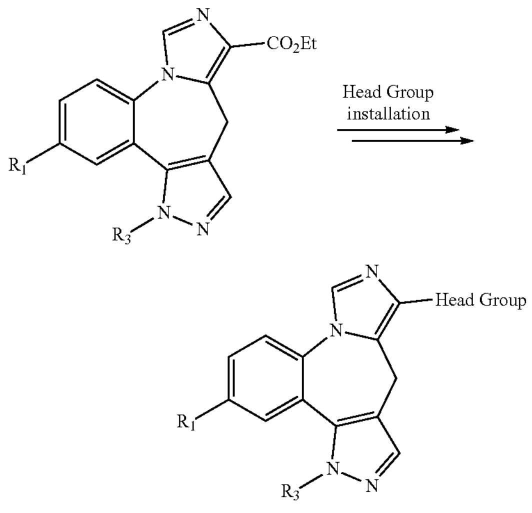

Scheme 2. General synthesis of a compound of formula I-B, I-b, and I-ba wherein X, W and V form a methyl ring.

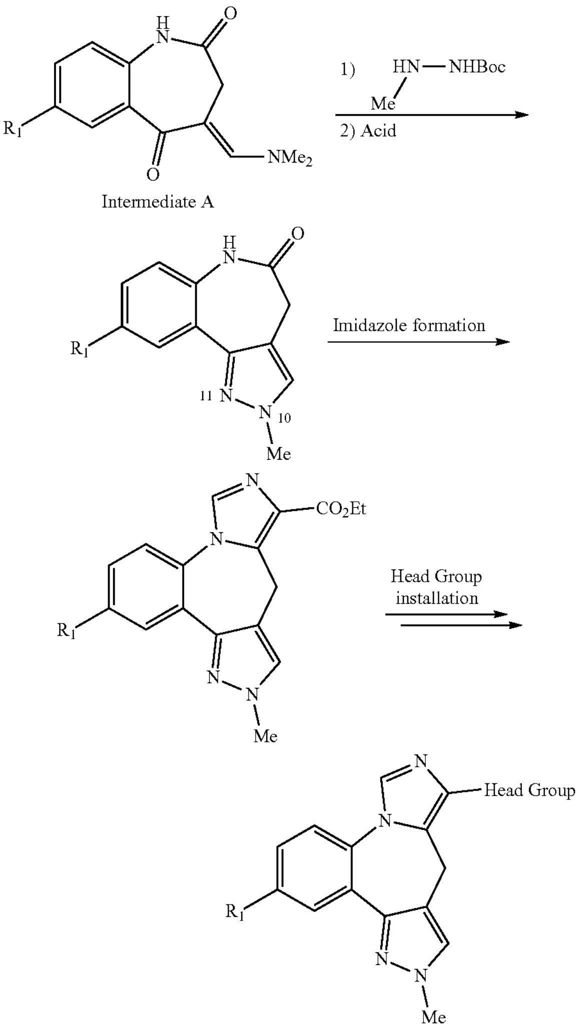

Scheme 3-A. General synthesis of a compound of formula I-B, I-b, and I-ba wherein X, W and V form a pyrazole ring.
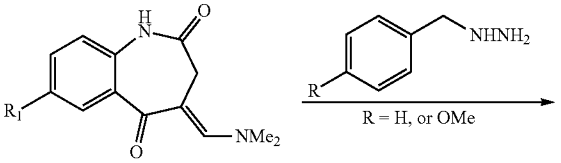
Intermediate A
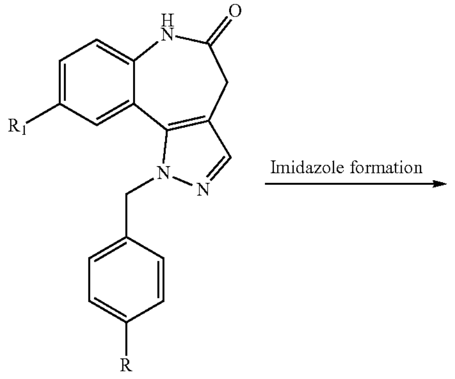
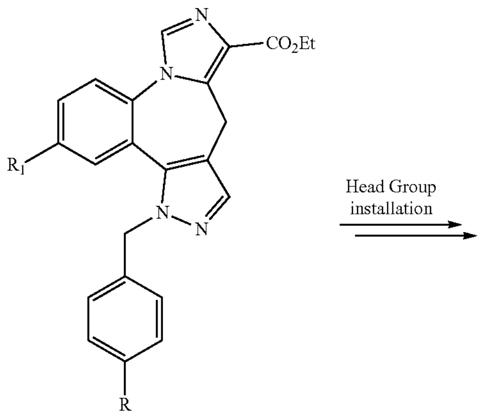
Intermediate B
(R = H, MeO)
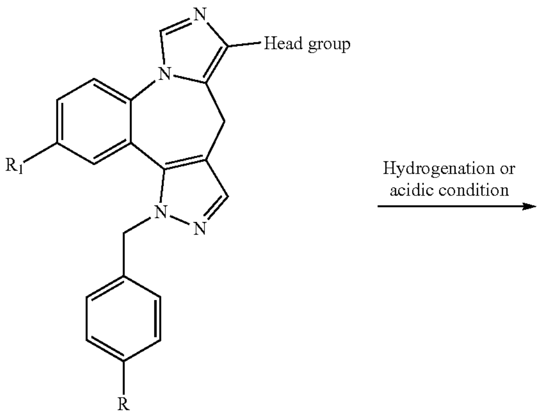
-continued
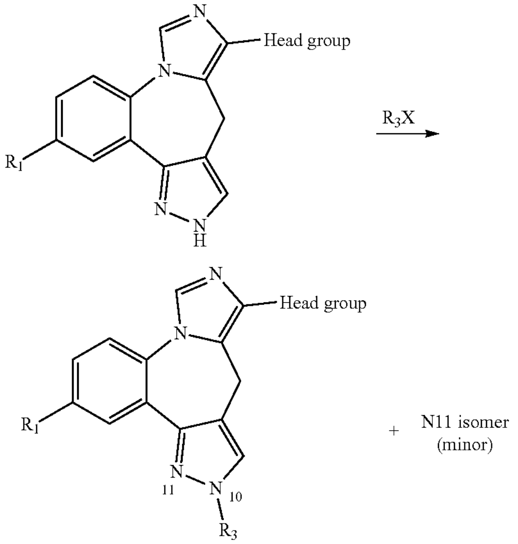
(major isomer)
Scheme 3-B. An alternative synthesis of a compound of formula I-B, I-b and I-ba (major) starting from intermediate A, wherein X, W, and V form a pyrazole ring.
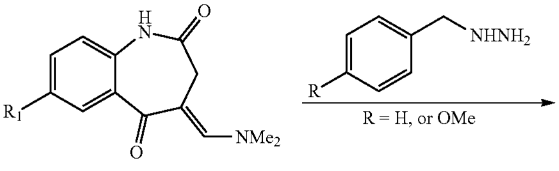
Intermediate A
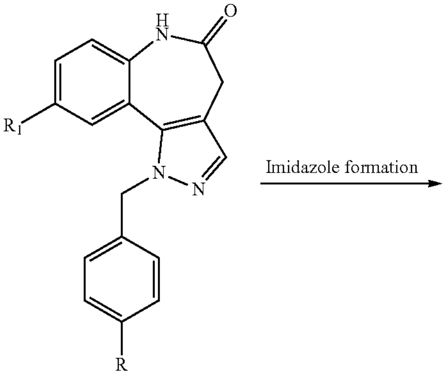

-continued

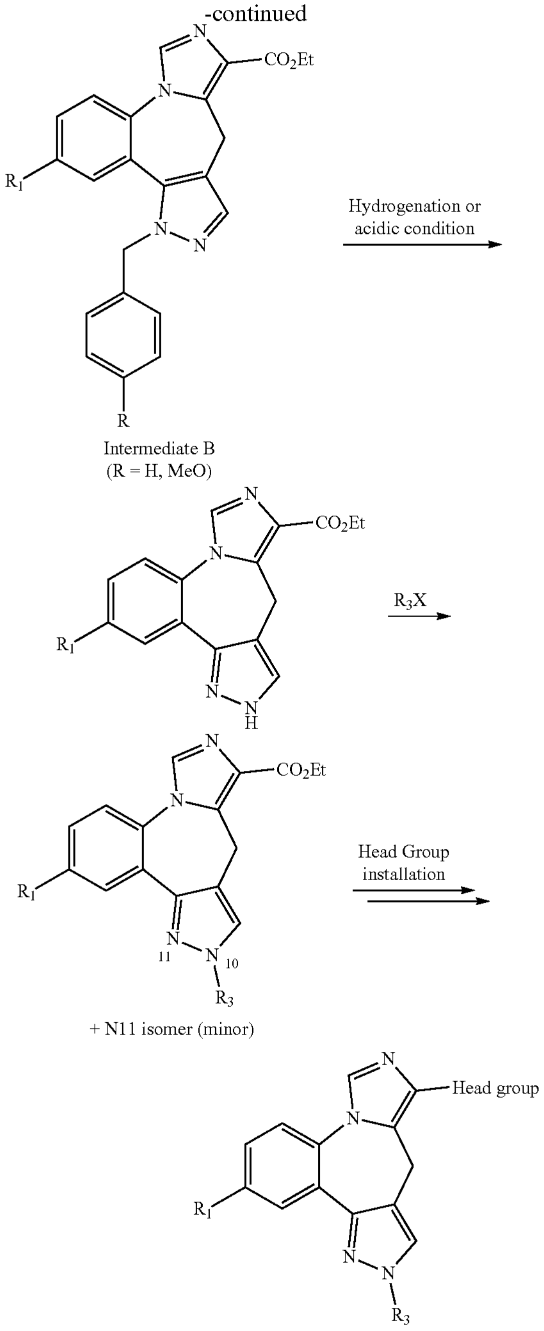

As would be recognized by skilled practitioners, compounds of formulae I, I-A, I-a, I-aa, I-B, I-b, I-ba, I-C, I-c, I-D, I-d, I-E, I-e, I-F and I-f with variables other than those depicted above may be prepared by varying the chemical reagents or the synthetic routes.

Pharmaceutical Compositions and Modes of Administration of this Disclosure

The present disclosure provides a pharmaceutical composition comprising a pharmaceutically acceptable carrier or excipient and one or more of a compound of formulae I, I-A, I-a, I-aa, I-B, I-b, I-ba, I-C, I-c, I-D, I-d, I-E, I-e, I-F and I-f or pharmaceutically acceptable salts, hydrates, solvates, polymorphs, isomers, or combinations thereof. In some embodiments, the $GABA_A$ α5 receptor positive allosteric modulators described in this disclosure are used in combination with one or more of the $GABA_A$ α5 receptor positive allosteric modulators disclosed in PCT applications WO2015/095783A1, WO2016/205739A1, WO2018/130869A1, and WO2019/246300A1. In some embodiments, the $GABA_A$ α5 receptor positive allosteric modulators described in this disclosure or the combinations described above may be used in combination with one or more of the SV2a inhibitors as disclosed PCT application WO2022/011318, and specifically levetiracetam or brivaracetam, in the treatment of such cognitive impairments and the other conditions described herein.

It will be appreciated that compounds and agents used in the compositions of this disclosure preferably should readily penetrate the blood-brain barrier when peripherally administered. Compounds which cannot penetrate the blood-brain barrier, however, can still be effectively administered directly into the central nervous system, e.g., by an intraventricular or other neuro-compatible route.

In some embodiments of this disclosure, the α5-containing $GABA_A$ R positive allosteric modulator or the combinations of this disclosure are formulated with a pharmaceutically acceptable carrier or excipient in a pharmaceutical composition. Pharmaceutically acceptable carriers that may be used in these compositions and combinations include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In other embodiments, no carrier is used. For example, the α5-containing $GABA_A$ R agonist (e.g., a α5-containing $GABA_A$ R positive allosteric modulator) can be administered alone or as a component of a pharmaceutical formulation (therapeutic composition). The α5-containing $GABA_A$ R agonist (e.g., a α5-containing $GABA_A$ R positive allosteric modulator) may be formulated for administration in any convenient way for use in human medicine.

In some embodiments, the therapeutic methods of the disclosure include administering a pharmaceutical composition of this disclosure or in some embodiments the combinations of this disclosure, or a compound or agent of this disclosure topically, systemically, or locally. For example, therapeutic compositions of compounds or agents of the disclosure may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds or agents or combinations described herein may also be formulated in some embodiments as part of an implant or device, or formulated for slow or extended release. When administered parenterally, the therapeutic compositions or the compounds or agents for use in this disclosure are preferably in a pyrogen-free, physiologically acceptable form. Techniques and formulations generally may be found in Remington's Pharmaceutical Sciences, Meade Publishing Co., Easton, PA.

In certain embodiments, pharmaceutical compositions suitable for parenteral administration may comprise the α5-containing $GABA_A$ R positive allosteric modulator in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a α5-containing $GABA_A$ R positive allosteric modulator may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the disclosure, compositions comprising a α5-containing $GABA_A$ R positive allosteric modulator can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the α5-containing $GABA_A$ R positive allosteric modulator as an active ingredient.

In solid dosage forms for oral administration (capsules, tablets, pills, dragees, powders, granules, and the like), one or more compositions comprising the α5-containing $GABA_A$ R positive allosteric modulator may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the α5 -containing $GABA_A$ R positive allosteric modulator, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

As described herein, the compounds, the compositions, or the combinations thereof of this disclosure may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g., greater than or equal to one hour. An extended-release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended-release dosage is administered in the form of a patch or a pump.

A person of ordinary skill in the art, such as a physician, is readily able to determine the required amount of α5-containing $GABA_A$ R positive allosteric modulator (s) to treat the subject using the compositions and methods of the disclosure. It is understood that the dosage regimen will be determined for an individual, taking into consideration, for example, various factors that modify the action of the selected α5-containing $GABA_A$ R positive allosteric modulator, the severity or stage of the disease, route of administration, and characteristics unique to the individual, such as age, weight, size, and extent of cognitive impairment.

In certain embodiments of the disclosure, the daily dose of the α5-containing $GABA_A$ R positive allosteric modulator or the pharmaceutically acceptable salt, hydrate, solvate, polymorph, or isomer thereof, is in an amount of 0.0015 mg to 5000 mg or 5 mg to 1000 mg. In some embodiments of the disclosure, the dose of the α5-containing $GABA_A$ R positive allosteric modulator or the pharmaceutically acceptable salt, hydrate, solvate, polymorph, or isomer thereof, is about 0.1-500 mg/day. Daily doses that may be used include, but are not limited to, 0.0015 mg/kg, 0.002 mg/kg, 0.0025 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.2 mg/kg, 1.4 mg/kg, 1.5 mg/kg, 1.6 mg/kg, 1.8 mg/kg, 2.0 mg/kg, 2.2 mg/kg, 2.4 mg/kg, 2.5 mg/kg, 2.6 mg/kg, 2.8 mg/kg, 3.0 mg/kg, 3.5 mg/kg, 4.0 mg/kg, 4.5 mg/kg, 5.0 mg/kg, 6.0 mg/kg, 7.0 mg/kg, 10 mg/kg, 14 mg/kg, 18 mg/kg, 36 mg/kg, 50 mg/kg, or 70 mg/kg.

In some embodiments of the disclosure, the daily dose of the α5-containing $GABA_A$ R positive allosteric modulator or the pharmaceutically acceptable salt, hydrate, solvate, polymorph, or isomer thereof is 0.1 mg, 0.15 mg, 0.18 mg, 0.35 mg, 0.7 mg, 1.5 mg, 2.0 mg, 2.5 mg, 2.8 mg, 3.0 mg, 3.5 mg, 4.2 mg, 5 mg, 5.5 mg, 6.0 mg, 7 mg, 8 mg, 9 mg, 10 mg, 12 mg, 15 mg, 20 mg, 25 mg, 28 mg, 30 mg, 35 mg, 40 mg, 45 mg, 50 mg, 55 mg, 60 mg, 70 mg, 75 mg, 80 mg, 85 mg, 90 mg, 95 mg, 100 mg, 110 mg, 120 mg, 125 mg, 140 mg, 150 mg, 170 mg, 175 mg, 180 mg, 190 mg, 200 mg, 210 mg, 225 mg, 250 mg, 280 mg, 300 mg, 350 mg, 400 mg, 500 mg, 750 mg, 1000 mg, 1250 mg, 2500 mg, 3500 mg, or 5000 mg. In some embodiments, the daily dose of the α5-containing $GABA_A$ R positive allosteric modulator or the pharmaceutically acceptable salt, hydrate, solvate, polymorph, or isomer thereof is in an amount of about 0.5 mg, about 5 mg, about 20 mg, about 50 mg, about 75 mg, about 100 mg, about 150 mg, about 250 mg, about 500 mg, about 750 mg, about 1000 mg, about 1250 mg, about 2500 mg, about 3500 mg, or 5000 mg of the α5-containing $GABA_A$ R positive allosteric modulator.

In certain embodiments of the disclosure, the dose of the α5-containing $GABA_A$ R positive allosteric modulator is 0.1 to 5 mg/kg/day (which, given a typical human subject of 70 kg, is 7 to 350 mg/day). In certain embodiments of the disclosure, the daily dose of the α5-containing $GABA_A$ R positive allosteric modulator is 7 to 350 mg. In some embodiments the daily doses of the α5-containing $GABA_A$ R positive allosteric modulator that may be used include, but are not limited to 0.1, 0.5, 1, 1.5, 2, 2.5, 3, 4, 5 mg/kg/day. In some embodiments the daily doses of the α5-containing $GABA_A$ R positive allosteric modulator that may be used include, but are not limited to 7, 35, 70, 110, 150, 180, 220, 300, 350 mg. In some embodiments of the disclosure, the dose of the α5-containing $GABA_A$ R positive allosteric modulator is 1-2 mg/kg/day. In some embodiments of the disclosure, the daily dose of the α5-containing $GABA_A$ R positive allosteric modulator is 70-140 mg. In other embodiments of the disclosure, the dose of the α5-containing $GABA_A$ R positive allosteric modulator is 0.1 to 0.2 mg/kg/day. In other embodiments of the disclosure, the daily dose of the α5-containing $GABA_A$ R positive allosteric modulator is 7 to 14 mg. Other doses higher than, intermediate to, or less than these daily doses may also be used and may be determined by one skilled in the art following the methods of this disclosure.

In certain embodiments of the disclosure, the interval of administration is 12 or 24 hours. Administration at less frequent intervals, such as once every 6 hours, may also be used. In some embodiments, the α5-containing $GABA_A$ R positive allosteric modulator is administered every 12 or 24 hours at a total daily dose of 0.1 to 5 mg/kg (e.g., in the case of administration every 12 hours of a daily dose of 2 mg/kg, each administration is 1 mg/kg). In some embodiments, the α5-containing $GABA_A$ R positive allosteric modulator is administered every 12 or 24 hours at a total daily dose of 7 to 350 mg. In some embodiments, the α5-containing $GABA_A$ R positive allosteric modulator is administered every 24 hours at a daily dose of 1 to 2 mg/kg. In some embodiments, the α5-containing $GABA_A$ R positive allosteric modulator is administered every 24 hours at a daily dose of 70 to 150 mg. In another embodiment, the α5-containing $GABA_A$ R positive allosteric modulator is administered every 24 hours at a daily dose of 0.1-0.2 mg/kg. In another embodiment, the α5-containing $GABA_A$ R positive allosteric modulator is administered every 24 hours at a daily dose of 7 to 15 mg. In some embodiments, the α5-containing $GABA_A$ R positive allosteric modulator is administered every 12 or 24 hours at a daily dose of 0.01 to 2.5 mg/kg (e.g., in the case of administration every 12 hours of a daily dose of 0.8 mg/kg, each administration is 0.4 mg/kg). In another embodiment, the α5-containing $GABA_A$ R positive allosteric modulator is administered every 24 hours at a daily dose of 0.7 to 15 mg. In some embodiments, the α5-containing $GABA_A$ R positive allosteric modulator is administered every 12 or 24 hours at a daily dose of 0.1 to 2.5 mg/kg. In another embodiment, the α5-containing $GABA_A$ R positive allosteric modulator is administered every 24 hours at a daily dose of 7 to 5 mg. In some embodiments, the α5-containing $GABA_A$ R positive allosteric modulator is administered every 12 or 24 hours at a daily dose of 25-180 mg. In some embodiments, the α5-containing $GABA_A$ R positive allosteric modulator is administered every 12 or 24 hours at a daily dose of 0.6 to 1.8 mg/kg. In some embodiments, the α5-containing $GABA_A$ R positive allosteric modulator is administered every 12 or 24 hours at a daily dose of 40 to 130 mg.

In some embodiments, the interval of administration of the $GABA_A$ α5 receptor agonist or the pharmaceutically acceptable salt, hydrate, solvate, polymorph, or isomer thereof, or a pharmaceutical composition comprising any of the foregoing, is once every 12 hours (twice daily) or 24 hours (once daily). Administration at less frequent intervals, such as once every 6 hours, may also be used. Other doses higher than, intermediate to, or less than these doses may also be used and may be determined by one skilled in the art following the methods of this disclosure. For repeated administrations over several days or weeks or longer, depending on the condition, the treatment is sustained until a sufficient level of cognitive function is achieved.

In certain embodiments of this disclosure, the interval of administration is once every 12 or 24 hours and, in some embodiments, once per day. Administration at less frequent intervals, such as once every 6 hours, may also be used.

If administered by an implant, a device or a slow or extended-release formulation, the α5-containing $GABA_A$ R positive allosteric modulator can be administered one time, or one or more times periodically throughout the lifetime of the patient as necessary. Other administration intervals intermediate to or shorter than these dosage intervals for clinical applications may also be used and may be determined by one skilled in the art following the methods of this invention.

Desired time of administration can be determined by routine experimentation by one skilled in the art. For example, the α5-containing $GABA_A$ R positive allosteric modulator may be administered for a period of 1-4 weeks, 1-3 months, 3-6 months, 6-12 months, 1-2 years, or more, up to the lifetime of the patient.

In addition to α5-containing $GABA_A$ R positive allosteric modulator, the compositions of this disclosure may be used in combination with other therapeutically useful agents but not limited to an antipsychotic, memantine AChEI or an SV2A inhibitor (e.g., levetiracetam or brivaracetam), or their pharmaceutically acceptable salts, hydrates, solvates, or polymorphs. These other therapeutically useful agents may be administered in a single formulation, or in separate formulations administered simultaneously or sequentially with the α5-containing $GABA_A$ R positive allosteric modulator according to the methods of the disclosure. In some embodiments, the two or more formulations are packaged together. In other embodiments, they are packaged separately.

It will be understood by one of ordinary skill in the art that the compositions described herein may be adapted and modified as is appropriate for the application being addressed and that the compositions described herein may be employed in other suitable applications. For example, the compositions of this disclosure may be used in combination with a second therapeutic agent. Such other additions and modifications will not depart from the scope hereof.

Pharmaceutical Compositions/Combinations with Antipsychotics

The compounds, the compositions, or the combinations of this disclosure may be used in combination with an antipsychotic in some embodiments for treating cognitive impairment associated with schizophrenia or bipolar disorder in a subject having or at risk of said schizophrenia or bipolar disorder (e.g., mania). The antipsychotic or a pharmaceutically acceptable salt, hydrate, solvate or polymorph thereof that is useful in the methods and compositions of these embodiments of this disclosure include both typical and atypical antipsychotics. In some embodiments, the compounds, the compositions, or the combinations of the present disclosure may be used to treat one or more positive and/or negative symptoms, as well as cognitive impairment, associated with schizophrenia. In some embodiments, the compounds, the compositions, or the combinations of the present disclosure may be used to treat one or more symptoms, as well as cognitive impairment, associated with bipolar disorder (in particular, mania). In some embodiments of this disclosure the compounds, the compositions, or the combinations of this invention prevent or slow the progression of cognitive impairment of schizophrenia or bipolar disorder (in particular, mania) in said subject.

In some embodiments, the antipsychotics suitable for use in the present disclosure are selected from atypical antipsychotics. Such atypical antipsychotics include, but are not limited to, those disclosed in, for example, U.S. Pat. Nos. 4,734,416; 5,006,528; 4,145,434; 5,763,476; 3,539,573; 5,229,382; 5,532,372; 4,879,288; 4,804,663; 4,710,500; 4,831,031; and 5,312,925, and EP Patents EP402644 and EP368388, and the pharmaceutically acceptable salts, hydrates, solvates, and polymorphs thereof.

In some embodiments, atypical antipsychotics suitable for use in the present disclosure include, but are not limited to, aripiprazole, asenapine, clozapine, iloperidone, olanzapine, lurasidone, paliperidone, quetiapine, risperidone and ziprasidone, and the pharmaceutically acceptable salts, hydrates, solvates, and polymorphs thereof. In some embodiments, the antipsychotic suitable for use herein is selected from aripiprazole (Bristol-Myers Squibb), olanzapine (Lilly) and ziprasidone (Pfizer), and the pharmaceutically acceptable salts, hydrates, solvates, and polymorphs thereof.

In some embodiments, the antipsychotics suitable for use in the present disclosure are typical antipsychotics, including, but not limited to, acepromazine, benperidol, bromazepam, bromperidol, chlorpromazine, chlorprothixene, clotiapine, cyamemazine, diazepam, dixyrazine, droperidol, flupentixol, fluphenazine, fluspirilene, haloperidol, heptaminol, isopropamide iodide, levomepromazine, levosulpiride, loxapine, melperone, mesoridazine, molindone, oxypertine, oxyprothepine, penfluridol, perazine, periciazine, perphenazine, pimozide, pipamperone, pipotiazine, prochlorperazine, promazine, promethazine, prothipendyl, pyridoxine, sulpiride, sultopride, tetrabenazine, thioproperazine, thioridazine, tiapride, tiotixene, trifluoperazine, triflupromazine, trihexyphenidyl, and zuclopenthixol, and the pharmaceutically acceptable salts, hydrates, solvates, and polymorphs thereof.

In some embodiments of the present disclosure, the antipsychotic or a pharmaceutically acceptable salt, hydrate, solvate or polymorph thereof may be selected from compounds that are dopaminergic agents (such as dopamine D1 receptor antagonists or agonists, dopamine $D_2$ receptor antagonists or partial agonists, dopamine D3 receptor antagonists or partial agonists, dopamine D4 receptor antagonists), glutamatergic agents, N-methyl-D-aspartate (NMDA) receptor positive allosteric modulators, glycine reuptake inhibitors, glutamate reuptake inhibitor, metabotropic glutamate receptors (mGluRs) agonists or positive allosteric modulators (PAMs) (e.g., mGluR2/3 agonists or PAMs), glutamate receptor glur5 positive allosteric modulators (PAMs), M1 muscarinic acetylcholine receptor (mAChR) positive allosteric modulators (PAMs), histamine H3 receptor antagonists, α-amino-3-hydroxy-5-methyl-isoxazole-4-propionic acid (AMPA)/kainate receptor antagonists, ampakines (CX-516), glutathione prodrugs, noradrenergic agents (such as alpha-2 adrenergic receptor agonists or antagonists and catechol-O-methyl transferase (COMT) inhibitors), serotonin receptor modulators (such as $5\text{-HT}_{2A}$ receptor antagonists, $5\text{-HT}_{1A}$ receptor partial agonists, $5\text{-HT}_{2C}$ agonists, and 5-HT6 antagonists, serotonin 2C agonists), cholinergic agents (such as alpha-7 nicotinic receptor agonists or PAMs, alpha4-beta2 nicotinic receptor agonists, allosteric modulators of nicotinic receptors and acetylcholinesterase inhibitors, muscarinic receptor agonists and antagonists), cannabinoid CB1 antagonists, neurokinin 3 antagonists, neurotensin agonists, monoamine oxidase (MAO) B inhibitors, PDE10 inhibitors, neuronal nitric oxide synthase (nNOS) inhibitors, neurosteroids, and neurotrophic factors.

In some embodiments, an α5-containing $GABA_A$ R positive allosteric modulator as described herein and an antipsychotic as described herein, or their pharmaceutically acceptable salts, hydrates, solvates or polymorphs, are administered simultaneously, or sequentially, or in a single formulation, or in separate formulations packaged together or in separate formulations in separate packages. In other embodiments, the α5-containing $GABA_A$ R positive allosteric modulator and the antipsychotic, or their pharmaceutically acceptable salts, hydrates, solvates or polymorphs, are administered via different routes. As used herein, "combination" includes packaging and administration by any of these formulations or routes of administration.

Pharmaceutical Compositions/Combinations with Memantine

The compounds, the compositions, or the combinations of the present disclosure may be used in combination with memantine or a derivative or an analog thereof in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI, Age-Associated Memory Impairment (AAMI), Age Related Cognitive Decline (ARCD), dementia, Alzheimer's Disease (AD), prodromal AD, post-traumatic stress disorder (PTSD), schizophrenia or bipolar disorder, amyotrophic lateral sclerosis (ALS) and cancer-therapy-related cognitive impairment.

Memantine, chemically also known as 3,5-dimethyladamantan-1-amine or 3,5-dimethyltricyclo[$3.3.1.1^{3,7}$]decan-1-amine, is an uncompetitive N-methyl-D-aspartate (NMDA)

receptor antagonist with moderate affinity. The proprietary names for memantine include: Axura® and Akatinol® (Merz), Namenda® (Forest Laboratories), Ebixa® and Abixa® (Lundbeck), and Memox® (Unipharm). Memantine is currently available in the U.S. and in over 42 countries worldwide. It is approved for the treatment of moderate to severe Alzheimer's disease (AD) in the United States at a dose of up to 28 mg/day. Memantine and some of its derivatives and analogs that are useful in the present disclosure are disclosed in U.S. Pat. Nos. 3,391,142; 4,122,193; 4,273,774; and 5,061,703, all of which are hereby incorporated by reference. Other memantine derivatives or analogs that are useful in the present disclosure include, but are not limited to, those compounds disclosed in U.S. Patent Application Publication US20040087658, US20050113458, US20060205822, US20090081259, US20090124659, and US20100227852; EP Patent Application Publication EP2260839A2; EP Patent EP1682109B1; and PCT Application Publication WO2005079779, all of which are incorporated herein by reference. Memantine, as used in the present disclosure, includes memantine and its derivatives and analogs, as well as hydrates, polymorphs, prodrugs, salts, and solvates thereof. Memantine, as used herein, also includes a composition comprising memantine or a derivative or an analog or a pharmaceutically acceptable salt, hydrate, solvate, polymorph, or prodrug thereof, wherein the composition may optionally be used in combination with at least one additional therapeutic agent (such as a therapeutic agent useful for treating a CNS disorder or cognitive impairments associated thereof). In some embodiments, the memantine composition suitable for use in the present disclosure comprises memantine and a second therapeutic agent that is donepezil (under the trade name Aricept).

In other embodiments of this disclosure, the α5-containing $GABA_A$ R positive allosteric modulator and memantine (or the memantine derivative/analog), or their pharmaceutically acceptable salts, hydrates, solvates, polymorphs, or prodrugs are administered simultaneously, or sequentially, or in a single formulation or in separate formulations packaged together or packaged separately. In other embodiments, the α5-containing $GABA_A$ R positive allosteric modulator and memantine (or the memantine derivative/analog), or their pharmaceutically acceptable salts, hydrates, solvates, polymorphs, or prodrugs are administered via different routes. As used herein, "combination" includes packaging or administration by any of these formulations or routes of administration.

Pharmaceutical Compositions/Combinations with Acetylcholine Esterase Inhibitors (AchEIs)

The compounds, the compositions, or the combinations of this disclosure may be used in combination with an acetylcholine esterase inhibitor ("AChEI") in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI, Age-Associated Memory Impairment (AAMI), Age Related Cognitive Decline (ARCD), dementia, Alzheimer's Disease (AD), prodromal AD, post-traumatic stress disorder (PTSD), schizophrenia or bipolar disorder, amyotrophic lateral sclerosis (ALS) and cancer-therapy-related cognitive impairment.

AChEIs known to a person of ordinary skill in the art may belong to the subcategories of (i) reversible non-competitive inhibitors or reversible competitive inhibitors, (ii) irreversible, and/or (iii) quasi-irreversible inhibitors.

In certain embodiments, AChEIs useful in the present disclosure include those described in PCT applications WO2014039920 and WO2002032412; EP patents Nos. 468187; 481429-A; and U.S. Pat. Nos. 4,816,456; 4,895,841; 5,041,455; 5,106,856; 5,602,176; 6,677,330; 7,340,299; 7,635,709; 8,058,268; 8,741,808; and 8,853,219, all of which are incorporated herein by reference.

In certain embodiment, typical AChEIs that may be used in accordance with this disclosure include, but are not limited to, ungeremine, ladostigil, demecarium, echothiophate (Phospholine), edrophonium (Tensilon), tacrine (Cognex), Pralidoxime (2-PAM), pyridostigmine (Mestinon), physostigmine (serine, Antilirium), abmenonium (Mytelase), galantamine (Reminyl, Razadyne), rivastigmine (Exelon, SZD-ENA-713), Huperzine A, Icopezil, neostigmine (Prostigmin, Vagostigmin), Aricept (Donepezil, E2020), Lactucopicrin, monoamine acridines and their derivatives, piperidine and piperazine derivatives, N-benzylpiperidine derivatives, piperidinyl-alkanoyl heterocyclic compounds, 4-(1-benzyl:piperidyl)-substituted fused quinoline derivatives and cyclic amide derivatives. Other typical AChEIs include carbamates and organophosphonate compounds such as Metrifonate (Trichlorfon). Benzazepinols such as galantamine are also useful AChEIs. In some embodiment, AChEIs suitable for use in combination with the compounds and compositions of this application include: Donepezil (aricept), Galantamine (razadyne), or Rivastigmine (exelons).

In other embodiments of this disclosure, the α5-containing $GABA_A$ R positive allosteric modulator and the AChEI, or their pharmaceutically acceptable salts, hydrates, solvates, polymorphs, or prodrugs are administered simultaneously, or sequentially, or in a single formulation or in separate formulations packaged together or packaged separately. In other embodiments, the α5-containing $GABA_A$ R positive allosteric modulator and the AChEI, or their pharmaceutically acceptable salts, hydrates, solvates, polymorphs, or prodrugs are administered via different routes. As used herein, "combination" includes packaging or administration by any of these formulations or routes of administration.

Pharmaceutical Compositions/Combinations with SV2A Inhibitors

The compounds, compositions, or combinations of this disclosure may be used in combination with an SV2A inhibitor in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI, Age-Associated Memory Impairment (AAMI), Age Related Cognitive Decline (ARCD), dementia, Alzheimer's Disease (AD), prodromal AD, post-traumatic stress disorder (PTSD), schizophrenia or bipolar disorder, amyotrophic lateral sclerosis (ALS) and cancer-therapy-related cognitive impairment.

In certain embodiments, SV2A inhibitors useful in the present disclosure include those described in PCT applications WO 2001/062726, WO 2002/094787, WO 2004/087658, WO 2007/065595, WO 2006/128692, WO 2006/128693, and WO 2022/011318. In certain embodiments, SV2A inhibitors useful in the present disclosure include those described in U.S. Pat. No. 7,244,747, US Patent Application 2008/0081832. In certain embodiments, SV2A inhibitors useful in the present disclosure include those described in British Patent No. 1,039,113 and British Patent No. 1,309,692 all of which are incorporated herein by reference.

In some embodiments of this disclosure, the SV2A inhibitor, or the pharmaceutically acceptable salt, hydrate, solvate, polymorph, or isomer thereof, is selected from the group consisting of levetiracetam, brivaracetam, and seletracetam, or pharmaceutically acceptable salts, solvates, hydrates, polymorphs, or isomers of any of the foregoing. In some embodiments of this disclosure, the SV2A inhibitor, or the pharmaceutically acceptable salt, hydrate, solvate, polymorph, or isomer thereof, is levetiracetam, or a pharmaceutically acceptable salt, hydrate, solvate, polymorph, or isomer thereof. In some embodiments of this disclosure, the SV2A inhibitor, or the pharmaceutically acceptable salt, hydrate, solvate, polymorph, or isomer thereof, is brivaracetam, or a pharmaceutically acceptable salt, hydrate, solvate, polymorph, or isomer thereof. Brivaracetam refers to the compound (2S)-2-[(4R)-2-oxo-4-propylpyrrolidin-1-yl]butanamide (IUPAC name). In some embodiments of this disclosure, the SV2A inhibitor, or the pharmaceutically acceptable salt, hydrate, solvate, polymorph, or isomer thereof, is seletracetam, or a pharmaceutically acceptable salt, hydrate, solvate, polymorph, or isomer thereof. Seletracetam refers to the compound (2S)-2-[(4S)-4-(2,2-difluoroethenyl)-2-oxopyrrolidin-1-yl]butanamide (IUPAC name). In certain embodiments of the invention, the SV2A inhibitor is selected from the group of levetiracetam, brivaracetam, and seletracetam or pharmaceutically acceptable salts thereof.

In certain embodiments, levetiracetam, brivaracetam, or seletracetam, or the pharmaceutically acceptable salt thereof, may be administered at doses as disclosed, for example, in U.S. patent application Ser. No. 12/580,464 (Pub. No. US-2010-0099735), U.S. patent application Ser. No. 13/287,531 (Pub. No. US-2012-0046336), U.S. patent application Ser. No. 13/370,253 (Pub. No. US-2012-0214859), WO 2010/044878, WO 2012/109491, WO 2014/144663, and WO 2022/011318. Each of these published documents is incorporated by reference herein in its entirety.

In certain embodiments of the disclosure, the dose of the SV2A inhibitor (e.g., levetiracetam, brivaracetam, or seletracetam), or the pharmaceutically acceptable salt, hydrate, solvate, polymorph, or isomer thereof, is 0.0015 to 7 mg/kg/day. In certain embodiments of the disclosure, the dose of the SV2A inhibitor (e.g., levetiracetam, brivaracetam, or seletracetam), or the pharmaceutically acceptable salt, hydrate, solvate, polymorph, or isomer thereof, is about 0.1-500 mg/day. Daily doses that may be used include, but are not limited to, 0.0015 mg/kg, 0.002 mg/kg, 0.0025 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.2 mg/kg, 1.4 mg/kg, 1.5 mg/kg, 1.6 mg/kg, 1.8 mg/kg, 2.0 mg/kg, 2.2 mg/kg, 2.4 mg/kg, 2.5 mg/kg, 2.6 mg/kg, 2.8 mg/kg, 3.0 mg/kg, 3.5 mg/kg, 4.0 mg/kg, 4.5 mg/kg, 5.0 mg/kg, 6.0 mg/kg, or 7.0 mg/kg; or 0.1 mg, 0.15 mg, 0.18 mg, 0.35 mg, 0.7 mg, 1.5 mg, 2.0 mg, 2.5 mg, 2.8 mg, 3.0 mg, 3.5 mg, 4.2 mg, 5 mg, 5.5 mg, 6.0 mg, 7 mg, 8 mg, 9 mg, 10 mg, 12 mg, 15 mg, 20 mg, 25 mg, 28 mg, 30 mg, 35 mg, 40 mg, 45 mg, 50 mg, 55 mg, 60 mg, 70 mg, 75 mg, 80 mg, 85 mg, 90 mg, 95 mg, 100 mg, 110 mg, 120 mg, 125 mg, 140 mg, 150 mg, 170 mg, 175 mg, 180 mg, 190 mg, 200 mg, 210 mg, 225 mg, 250 mg, 280 mg, 300 mg, 350 mg, 400 mg, or 500 mg.

In some embodiments, the daily dose of SV2A inhibitor (e.g., levetiracetam, brivaracetam, or seletracetam), or the pharmaceutically acceptable salt, hydrate, solvate, polymorph, or isomer thereof, that can be used in the methods, uses, pharmaceutical compositions for use, or combinations for use of this disclosure include, without limitation, 0.0015-5 mg/kg, 0.05-4 mg/kg, 0.05-2.0 mg/kg, 0.05-1.5 mg/kg, 0.1-1.0 mg/kg, 1-5 mg/kg, 1.5-4.0 mg/kg, 1.8-3.6 mg/kg, 0.01-0.8 mg/kg, 0.01-1 mg/kg, 0.01-1.5 mg/kg, 0.01-2 mg/kg, 0.01-2.5 mg/kg, 0.01-3 mg/kg, 0.01-3.5 mg/kg, 0.01-4 mg/kg, 0.01-5 mg/kg, 0.025-0.8 mg/kg, 0.025-1 mg/kg, 0.025-1.5 mg/kg, 0.025-2 mg/kg, 0.025-2.5 mg/kg, 0.025-3 mg/kg, 0.025-3.5 mg/kg, 0.025-4 mg/kg, 0.05-0.8 mg/kg, 0.05-1 mg/kg, 0.05-1.5 mg/kg, 0.05-2 mg/kg, 0.05-2.5 mg/kg, 0.05-3 mg/kg, 0.05-3.5 mg/kg, 0.05-4 mg/kg, 0.075-0.8 mg/kg, 0.075-1 mg/kg, 0.075-1.5 mg/kg, 0.075-2 mg/kg, 0.075-2.5 mg/kg, 0.075-3 mg/kg, 0.075-3.5 mg/kg, 0.075-4 mg/kg, 0.1-0.8 mg/kg, 0.1-1 mg/kg, 0.1-1.5 mg/kg, 0.1-2 mg/kg, 0.1-2.5 mg/kg, 0.1-3 mg/kg, 0.1-3.5 mg/kg, 0.1-4 mg/kg, 0.2-0.8 mg/kg, 0.2-1 mg/kg, 0.2-1.5 mg/kg, 0.2-2 mg/kg, 0.2-2.5 mg/kg, 0.2-3 mg/kg, 0.2-3.5 mg/kg, 0.2-4 mg/kg, 0.5-0.8 mg/kg, 0.5-1 mg/kg, 0.5-1.5 mg/kg, 0.5-2 mg/kg, 0.5-2.5 mg/kg, 0.5-3 mg/kg, 0.5-3.5 mg/kg, or 0.5-4 mg/kg; or 0.1-350 mg, 0.7-50 mg, 0.7-75 mg, 0.7-100 mg, 0.7-150 mg, 0.7-180 mg, 0.7-225 mg, 0.7-250 mg, 0.7-280 mg, 1.8-50 mg, 1.8-75 mg, 1.8-100 mg, 1.8-150 mg, 1.8-180 mg, 1.8-225 mg, 1.8-250 mg, 1.8-280 mg, 3.5-50 mg, 3.5-75 mg, 3.5-100 mg, 3.5-150 mg, 3.5-180 mg, 3.5 -225 mg, 3.5-250 mg, 3.5-280 mg, 5-50 mg, 5-75 mg, 5-100 mg, 5-150 mg, 5-180 mg, 5-225 mg, 5-250 mg, 5-280 mg, 7-50 mg, 7-75 mg, 7-100 mg, 7-150 mg, 7-180 mg, 7-225 mg, 7-250 mg, 7-280 mg, 15-50 mg, 15-75 mg, 15-100 mg, 15-150 mg, 15-180 mg, 15-225 mg, 15-250 mg, 15-280 mg, 35-50 mg, 35-75 mg, 35-100 mg, 35-150 mg, 35-180 mg, 35-225 mg, 35-250 mg, 35-280 mg, 0.1-500 mg, 3-300 mg, 3-150 mg, 3-110 mg, 7-70 mg, 70-350 mg, 100-300 mg, 190-220 mg, 190-240 mg, or 125-250 mg.

In certain embodiments of the invention, the SV2A inhibitor is selected from the group of levetiracetam, brivaracetam, and seletracetam or pharmaceutically acceptable salts thereof. In certain embodiments of the invention, the SV2A inhibitor or a pharmaceutically acceptable salt thereof is administered every 12 or 24 hours at a dose of about 0.1 to 5 mg/kg, or about 1 to 2 mg/kg, or about 0.1 to 0.2 mg/kg, or about 0.01 to 2.5 mg/kg, or about 0.1-2.5 mg/kg, or about 0.4-2.5 mg/kg, or about 0.6-1.8 mg/kg, or about 0.04-2.5 mg/kg or about 0.06-1.8 mg/kg.

In certain embodiments of the invention, the SV2A inhibitor is present in an amount of 5-140 mg. In other embodiments of the invention, the SV2A inhibitor is present in an amount of 0.7-180 mg. In certain embodiments of the invention, the SV2A inhibitor is present in an amount of 3-50 mg. In other embodiments of the invention, the SV2A inhibitor is present in an amount of 0.07-50 mg.

In some embodiments, the levetiracetam, brivaracetam or seletracetam, or a pharmaceutically acceptable salt thereof is administered at a daily dose of 0.7-350 mg or comprise administering to the subject a pharmaceutical composition comprising the daily dose of the levetiracetam, brivaracetam or seletracetam or pharmaceutical salt thereof, and a pharmaceutically acceptable carrier. In some embodiments, the daily dose of the levetiracetam or seletracetam, or a pharmaceutically acceptable salt thereof is 7-350 mg. In some embodiments, the daily dose of the brivaracetam, or pharmaceutically acceptable salt thereof is 0.7-180 mg. In other embodiments, the daily dose of the levetiracetam or seletracetam, or pharmaceutically acceptable salt thereof is 125-250 mg. In some embodiments, the daily dose of the levetiracetam or seletracetam, or pharmaceutically acceptable salt thereof is 220 mg. In some embodiments, the daily dose of the levetiracetam or seletracetam or pharmaceutically acceptable salt thereof is 190 mg.

In certain embodiments of the invention, levetiracetam or a pharmaceutically acceptable salt thereof is administered to said subject in a therapeutically effective amount. In certain embodiments of the invention, levetiracetam or a pharmaceutically acceptable salt thereof is administered every 12 or 24 hours at a daily dose of about 1-2 mg/kg. In certain embodiments of the invention, levetiracetam or a pharmaceutically acceptable salt thereof is administered every 12 or 24 hours at a daily dose of about 70-150 mg. In some embodiments of the invention, levetiracetam or a pharmaceutically acceptable salt thereof is administered every 12 or 24 hours at a daily dose of about 0.1-2.5 mg/kg. In some embodiments of the invention, levetiracetam or a pharmaceutically acceptable salt thereof is administered every 12 or 24 hours at a daily dose of about 7-180 mg. In some embodiments of the invention, levetiracetam or a pharmaceutically acceptable salt thereof is administered every 12 or 24 hours at a daily dose of about 0.4-2.5 mg/kg. In some embodiments of the invention, levetiracetam or a pharmaceutically acceptable salt thereof is administered every 12 or 24 hours at a daily dose of about 25-180 mg. In some embodiments of the invention, levetiracetam or a pharmaceutically acceptable salt thereof is administered every 12 or 24 hours at a daily dose of about 0.6-1.8 mg/kg. In some embodiments of the invention, levetiracetam or a pharmaceutically acceptable salt thereof is administered every 12 or 24 hours at a daily dose of about 40-130 mg.

In certain embodiments of the invention, brivaracetam or a pharmaceutically acceptable salt thereof is administered to said subject in a therapeutically effective amount. In certain embodiments of the invention, brivaracetam or a pharmaceutically acceptable salt thereof is administered every 12 or 24 hours at a daily dose of about 0.1-0.2 mg/kg. In certain embodiments of the invention, brivaracetam or a pharmaceutically acceptable salt thereof is administered every 12 or 24 hours at a daily dose of about 7-15 mg. In some embodiments of the invention, brivaracetam or a pharmaceutically acceptable salt thereof is administered every 12 or 24 hours at a daily dose of about 0.01-2.5 mg/kg. In some embodiments of the invention, brivaracetam or a pharmaceutically acceptable salt thereof is administered every 12 or 24 hours at a daily dose of about 0.7-180 mg. In some embodiments of the invention, brivaracetam or a pharmaceutically acceptable salt thereof is administered every 12 or 24 hours at a daily dose of about 0.04-2.5 mg/kg. In some embodiments of the invention, brivaracetam or a pharmaceutically acceptable salt thereof is administered every 12 or 24 hours at a daily dose of about 2.5-180 mg. In some embodiments of the invention, brivaracetam or a pharmaceutically acceptable salt thereof is administered every 12 or 24 hours at a daily dose of about 0.06-1.8 mg/kg. In some embodiments of the invention, brivaracetam or a pharmaceutically acceptable salt thereof is administered every 12 or 24 hours at a daily dose of about 4-130 mg.

In some embodiments, the daily dose of SV2A inhibitor (e.g., levetiracetam, brivaracetam, or seletracetam), or the pharmaceutically acceptable salt, hydrate, solvate, polymorph, or isomer thereof, that can be used in the methods, uses, pharmaceutical compositions for use, or combinations for use of this disclosure includes 0.1-350 mg/day. In some embodiments, the daily dose of SV2A inhibitor (e.g., levetiracetam, brivaracetam, or seletracetam), or the pharmaceutically acceptable salt, hydrate, solvate, polymorph, or isomer thereof, that can be used in the methods, uses, pharmaceutical compositions for use, or combinations for use of this disclosure includes about 220 mg/day. In some embodiments, the daily dose of levetiracetam is 220 mg in extended release form (See, e.g., U.S. Ser. No. 10/925,834B2). Other doses higher than, intermediate to, or less than these doses may also be used and may be determined by one skilled in the art following the methods of this disclosure.

In other embodiments of this disclosure, the α5-containing $GABA_A$ R positive allosteric modulator and the SV2A inhibitor, or their pharmaceutically acceptable salts, hydrates, solvates, polymorphs, or prodrugs are administered simultaneously, or sequentially, or in a single formulation or in separate formulations packaged together or packaged separately. In other embodiments, the α5-containing $GABA_A$ R positive allosteric modulator and the SV2A inhibitors, or their pharmaceutically acceptable salts, hydrates, solvates, polymorphs, or prodrugs are administered via different routes. As used herein, "combination" includes packaging or administration by any of these formulations or routes of administration.

Methods of Assessing Cognitive Impairment and Evaluating its Treatment

Animal models serve as an important resource for developing and evaluating treatments for cognitive impairment associated with CNS disorders. Features that characterize cognitive impairment in animal models typically extend to cognitive impairment in humans. Efficacy in such animal models is, thus, understood by the skilled worker to be reasonable predictive of efficacy in humans. The extent of cognitive impairment in an animal model for a CNS disorder, and the efficacy of a method of treatment for said CNS disorder may be tested and confirmed with the use of a variety of cognitive tests.

A Radial Arm Maze (RAM) behavioral task is one example of a cognitive test, specifically testing spatial memory (Chappell et al. *Neuropharmacology* 37: 481-487, 1998). The RAM apparatus consists of, e.g., eight equidistantly spaced arms. A maze arm projects from each facet of a center platform. A food well is located at the distal end of each arm. Food is used as a reward. Blocks can be positioned to prevent entry to any arm. Numerous extra maze cues surrounding the apparatus may also be provided. After habituation and training phases, spatial memory of the model animals may be tested in the RAM under control or test compound-treated conditions. As a part of the test, the animals are pretreated before trials with a vehicle control or one of a range of dosages of the test compound. At the beginning of each trial, a subset of the arms of the eight-arm maze is blocked. Animals are allowed to obtain food on the unblocked arms to which access is permitted during this initial "information phase" of the trial. Animals are then removed from the maze for a delay period, e.g., a 60 second delay, a 15-minute delay, a one-hour delay, a two-hour delay, a six-hour delay, a 24 hour delay, or longer) between the information phase and the subsequent "retention test," during which the barriers on the maze are removed, thus allowing access to all eight arms. After the delay period, the animals are placed back onto the center platform (with the barriers to the previously blocked arms removed) and allowed to obtain the remaining food rewards during this retention test phase of the trial. The identity and configuration of the blocked arms vary across trials. The number of "errors" the animal makes during the retention test phase is tracked. An error occurs in the trial if the animal entered an arm from which food had already been retrieved in the pre-delay component of the trial, or if the animal re-visits an arm in the post-delay session that had already been visited. A fewer number of errors indicates better spatial memory. The number of errors made by the test animal, under various test compound treatment regimes, can then be compared to assess the efficacy of the test compound in treating cognitive impairment associated with CNS disorders in the model.

Another cognitive test that may be used to assess the effects of a test compound on the cognitive impairment of a CNS disorder model animal is the Morris water maze. A water maze is a pool surrounded with a novel set of patterns relative to the maze. The training protocol for the water maze may be based on a modified water maze task that has been shown to be hippocampal-dependent (de Hoz et al., *Eur. J. Neurosci.,* 22:745-54, 2005; Steele and Morris, *Hippocampus* 9:118-36, 1999). A test animal is trained to locate a submerged escape platform hidden underneath the surface of the pool. During the training trial, the animal is released in the maze (pool) from random starting positions around the perimeter of the pool. The starting position varies from trial to trial. If the animal does not locate the escape platform within a set time, the experimenter guides and places the animal on the platform to "teach" the location of the platform. After a delay period following the last training trial, a retention test in the absence of the escape platform is given to assess spatial memory. An animal's level of preference for the location of the (now absent) escape platform, as measured by, e.g., the time spent in that location or the number of crossings of that location made by the animal, indicates better spatial memory, i.e., treatment of cognitive impairment. The preference for the location of the escape platform under different treatment conditions, can then be compared to assess the efficacy of the test compound in treating cognitive impairment associated with CNS disorders in the model.

There are various tests known in the art for assessing cognitive function in humans, for example and without limitation, the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or MATRICS consensus neuropsychological test battery which includes tests of working memory, speed of processing, attention, verbal learning, visual learning, reasoning and problem solving and social cognition. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011) The FDA-NIMH-MATRICS guidelines for clinical trial design of cognitive-enhancing drugs: what do we know 5 years later? Schizophr. Bull. 37, 1209-1217. Another example of a cognitive test in humans is the explicit 3-alternative forced choice task. In this test, subjects are presented with color photographs of common objects consisting of a mix of three types of image pairs: similar pairs, identical pairs and unrelated foils. The second of the pair of similar objects is referred to as the "lure". These image pairs are fully randomized and presented individually as a series of images. Subjects are instructed to make a judgment as to whether the objects seen are new, old or similar. A "similar" response to the presentation of a lure stimulus indicates successful memory retrieval by the subject. By contrast, calling the lure stimulus "old" or "new" indicates that correct memory retrieval did not occur.

In addition to assessing cognitive performance, the progression of age-related and other cognitive impairment and dementia, as well as the conversion of age-related and other cognitive impairment into dementia, may be monitored by assessing surrogate changes in the brain of the subject. Surrogate changes include, without limitation, changes in regional brain volumes, perforant path degradation, and changes seen in brain function through resting state fMRI (R-fMRI) and fluorodeoxyglucose positron emission tomography (FDG-PET). Examples of regional brain volumes useful in monitoring the progression of cognitive impairment and dementia include reduction of hippocampal volume and reduction in volume or thickness of entorhinal cortex. These volumes may be measured in a subject by, for example, MRI. Aisen et al., Alzheimer's & Dementia 6:239-246 (2010). Perforant path degradation has been shown to be linked to age, as well as reduced cognitive function. For example, older adults with more perforant path degradation tend to perform worse in hippocampus-dependent memory tests. Perforant path degradation may be monitored in subjects through ultrahigh-resolution diffusion tensor imaging (DTI). Yassa et al., PNAS 107:12687-12691 (2010). Resting-state fMRI (R-fMRI) involves imaging the brain during rest, and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, particularly those areas whose connectivity increase or decrease with age, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. Aisen et al., Alzheimer's & Dementia 6:239-246 (2010), Herholz et al., NeuroImage 17:302-316 (2002).

Risk Factors for Developing Cognitive Impairment

In some embodiments, the subject to be treated in the methods and uses of this disclosure (a subject displaying or presenting with cognitive performance within the normal range for the subject's age) is at risk of developing cognitive decline or cognitive impairment, where the risk is associated with aging.

In some embodiments of the methods of this disclosure, the subject to be treated is at risk of developing cognitive decline or cognitive impairment, wherein the risk is associated with the presence of altered hippocampal functional connectivity in the subject. In some embodiments of the methods of this disclosure, the subject to be treated is at risk of developing cognitive decline or cognitive impairment, wherein the risk is associated with the presence of increased hippocampal functional connectivity in the subject.

In some embodiments, the subject to be treated in the methods and uses of this disclosure (a subject displaying or presenting with cognitive performance within the normal range for the subject's age) is at risk of developing cognitive decline or cognitive impairment, wherein the risk is a genetic risk associated with the presence of one or more genomic variants, mutations, or polymorphs associated with a change in the expression of genes selected from the group consisting of ABCA7, CLU, CR1, PICALM, PLD3, TRFEM2, and SORL1 in the genome of the subject. In some embodiments, the subject is at risk of developing cognitive decline or cognitive impairment, wherein the risk is associated with the presence of one or more genomic variants, mutations, or polymorphs associated with ABCA7 in the genome of the subject. In some embodiments, the subject is at risk of developing cognitive decline or cognitive impairment, wherein the risk is associated with the presence of one or more genomic variants, mutations, or polymorphs associated with CLU in the genome of the subject. In some embodiments, the subject is at risk of developing cognitive decline or cognitive impairment, wherein the risk is associated with the presence of one or more genomic variants, mutations, or polymorphs associated with CR1 in the genome of the subject. In some embodiments, the subject is at risk of developing cognitive decline or cognitive impairment, wherein the risk is associated with the presence of one or more genomic variants, mutations, or polymorphs associated with PICALM in the genome of the subject. In some embodiments, the subject is at risk of developing cognitive decline or cognitive impairment, wherein the risk is associated with the presence of one or more genomic variants, mutations, or polymorphs associated with PLD3 in the genome of the subject. In some embodiments, the subject is at risk of developing cognitive decline or cognitive impairment, wherein the risk is associated with the presence of one or more genomic variants, mutations, or polymorphs associated with TREM2 in the genome of the subject. In some embodiments, the subject is at risk of developing cognitive decline or cognitive impairment, wherein the risk is associated with the presence of one or more genomic variants, mutations, or polymorphs associated with SORL1 in the genome of the subject.

In some embodiments, the subject is at risk of developing cognitive decline or cognitive impairment, wherein the risk is associated with the presence of at least one allele of the APOE4 gene in the genome of the subject. In some embodiments, the subject is at risk of developing cognitive decline or cognitive impairment, wherein the risk is associated with the presence of one allele of the APOE4 gene in the genome of the subject. In some embodiments, the subject is at risk of developing cognitive decline or cognitive impairment, wherein the risk is associated with the presence of both APOE4 alleles in the genome of the subject.

In some embodiments, the subject is at risk of developing cognitive decline or cognitive impairment, wherein the risk is associated with the presence of one or more biofluid biomarkers selected from the group consisting of p-tau, t-tau, and amyloid β in the subject. In some embodiments, the subject is at risk of developing cognitive decline or cognitive impairment, wherein the risk is associated with the presence of the biofluid biomarker p-tau in the subject. In some embodiments, the subject is at risk of developing cognitive decline or cognitive impairment, wherein the risk is associated with the presence of the biofluid biomarker t-tau in the subject. In some embodiments, the subject is at risk of developing cognitive decline or cognitive impairment, wherein the risk is associated with the presence of the biofluid biomarker amyloid β in the subject.

In some embodiments, the compounds, compositions, or combinations of the present disclosure are for use in treating cognitive impairment associated with a CNS disorder in a subject in need of treatment of said cognitive impairment. In some embodiments, the CNS disorder associated with the cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, the compounds, compositions, or combinations of the present disclosure are for use in treating cognitive impairment associated with a risk factor for cognitive impairment in a subject at risk of said cognitive impairment. In some embodiments, the cognitive impairment associated with the risk factor includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, the compounds, compositions, or combinations of the present disclosure are for use as a medicament for treating cognitive impairment associated with a CNS disorder in a subject in need of treatment of said cognitive impairment. In some embodiments, the CNS disorder associated with the cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, the compounds, compositions, or combinations of the present disclosure are for use as a medicament for treating cognitive impairment associated with a risk factor for cognitive impairment in a subject at risk of said cognitive impairment. In some embodiments, the cognitive impairment associated with the risk factor includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, this disclosure provides the use of a compound, composition, or combination described herein in the manufacture of a medicament for the treatment of cognitive impairment associated with a CNS disorder in a subject in need of treatment of said cognitive impairment. In some embodiments, the CNS disorder associated with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, this disclosure provides the use of a compound, composition, or combination described herein in the manufacture of a medicament for the treatment of cognitive impairment associated with a risk factor for cognitive impairment in a subject at risk of said cognitive impairment. In some embodiments, the cognitive impairment associated with the risk factor includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

Age-Related Cognitive Impairment

This disclosure provides methods and compositions for treating age-related cognitive impairment or the risk thereof using a α5-containing $GABA_A$ R positive allosteric modulator (i.e., a compound of this disclosure), such as one selected from the compounds or pharmaceutically acceptable salts, hydrates, solvates, polymorphs, isomers, or combinations thereof as described herein. In certain embodiments, treatment comprises preventing or slowing the progression, of age-related cognitive impairment. In certain embodiments, treatment comprises alleviation, amelioration or slowing the progression, of one or more symptoms associated with age-related cognitive impairment. In certain embodiments, treatment of age-related cognitive impairment comprises slowing the conversion of age-related cognitive impairment (including, but not limited to MCI, ARCD and AAMI) into dementia (e.g., AD). The methods and compositions may be used for human patients in clinical applications in the treating age-related cognitive impairment in conditions such as age-related MCI, ARCD and AAMI or for the risk thereof. The dose of the composition and dosage interval for the method is, as described herein, one that is safe and efficacious in those applications. In some embodiments of the disclosure, there is provided a method of preserving or improving cognitive function in a subject with age-related cognitive impairment, the method comprising the step of administering to said subject a therapeutically effective amount of a compound of the disclosure or a pharmaceutically acceptable salt, hydrate, solvate, polymorph, isomer, or combination thereof.

In some embodiments, a subject to be treated by the methods and compositions of this disclosure exhibits age-related cognitive impairment or is at risk of such impairment. In some embodiments, the age-related cognitive impairment includes, without limitation, Age-Associated Memory Impairment (AAMI), age-related Mild Cognitive Impairment (MCI) and Age-related Cognitive Decline (ARCD).

Animal models serve as an important resource for developing and evaluating treatments for such age-related cognitive impairments. Features that characterize age-related cognitive impairment in animal models typically extend to age-related cognitive impairment in humans. Efficacy in such animal models is, thus, reasonably predictive of efficacy in humans.

Various animal models of age-related cognitive impairment are known in the art. For example, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Gallagher et al. *Behav. Neurosci.* 107:618-626, (1993); Rapp and Gallagher, *Proc. Natl. Acad. Sci.* 93: 9926-9930, (1996); Nicolle et al., *Neuroscience* 74: 741-756, (1996); Nicolle et al., *J. Neurosci.* 19: 9604-9610, (1999); International Patent Publication WO2007/019312 and International Patent Publication WO 2004/048551. Such an animal model of age-related cognitive impairment may be used to assay the effectiveness of the methods and compositions this disclosure in treating age-related cognitive impairment.

The efficacy of the methods and compositions of this invention in treating age-related cognitive impairment may be assessed using a variety of cognitive tests, including the Morris water maze and the radial arm maze, as discussed herein.

Mild Cognitive Impairment

In some embodiments, a subject to be treated by the methods, uses, combinations, pharmaceutical compositions, combinations for use, or pharmaceutical compositions for use of this disclosure exhibits non-age-related MCI or is at risk of such impairment. The methods, uses, combinations, pharmaceutical compositions, combinations for use, or pharmaceutical compositions for use may be useful in human patients in clinical applications useful for treating non-age-related MCI (including amnestic MCI, and non-amnestic MC).

This disclosure provides methods, uses, combinations, pharmaceutical compositions, combinations for use, or pharmaceutical compositions for use useful for treating mild cognitive impairment or the risk thereof using a α5-containing $GABA_A$ R positive allosteric modulator (i.e., a compound of this disclosure), such as one selected from the compounds or pharmaceutically acceptable salts, hydrates, solvates, polymorphs, isomers, or combinations thereof as described herein. In certain embodiments, treatment comprises improving cognitive function in patients with mild cognitive impairment. In certain embodiments, treatment comprises slowing or delaying the progression of mild cognitive impairment. In certain embodiments, treatment comprises reducing the rate of decline of cognitive function associated with mild cognitive impairment. In certain embodiments, treatment comprises preventing or slowing the progression, of mild cognitive impairment. In certain embodiments, treatment comprises alleviation, amelioration or slowing the progression, of one or more symptoms associated with mild cognitive impairment.

Dementia

The disclosure also provides methods and compositions for treating cognitive impairment associated with dementia using a $\alpha 5$-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of cognitive impairment associated with dementia. In certain embodiments, treatment comprises alleviation, amelioration, or slowing the progression of one or more symptoms associated with dementia. In certain embodiments, the symptom to be treated is cognitive impairment. In some embodiments of this disclosure, there is provided a method of preserving or improving cognitive function in a subject with dementia, the method comprising the step of administering to said subject a therapeutically effective amount of a compound of this disclosure or a pharmaceutically acceptable salt, hydrate, solvate, polymorph, isomer, or combination thereof. In certain embodiments, the dementia is Alzheimer's disease (AD), prodromal AD, vascular dementia, dementia with Lewy bodies, or frontotemporal dementia. The methods and compositions may be used for human patients in clinical applications in treating cognitive impairment associate with dementia and these embodiments of it. The dose of the composition and dosage interval for the method is, as described herein, one that is safe and efficacious in those applications.

Animal models serve as an important resource for developing and evaluating treatments for dementia and the cognitive impairment associated with it. Features that characterize dementia and the cognitive impairment associated with it in animal models typically extend to dementia and the cognitive impairment associated with it in humans. Thus, efficacy in such animal models is reasonably predictive of efficacy in humans. Various animal models of, for example, dementia are known in the art, such as the PDAPP, Tg2576, APP23, TgCRND8, J20, hPS2 Tg, and APP+PS1 transgenic mice. Sankaranarayanan, *Curr. Top. Medicinal Chem.* 6: 609-627, 2006; Kobayashi et al. *Genes Brain Behav.* 4: 173-196. 2005; Ashe and Zahns, *Neuron.* 66: 631-45, 2010. Such animal models of dementia and the cognitive impairment associated with it may be used to assay the effectiveness of the methods and compositions of this invention of the disclosure in treating the cognitive impairment associated with dementia.

The efficacy of the methods and compositions of this disclosure in treating cognitive impairment associated with dementia, may be assessed in animal models of dementia, as well as human subjects with dementia, using a variety of cognitive tests known in the art, as discussed herein.

Post-Traumatic Stress Disorder

The invention also provides methods and compositions for treating cognitive impairment associated with post-traumatic stress disorder (PTSD) using a $\alpha 5$-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of cognitive impairment associated with PTSD. In certain embodiments, treatment comprises alleviation, amelioration, or slowing the progression of one or more symptoms associated with PTSD. In certain embodiments, the symptom to be treated is cognitive impairment. In some embodiments of the disclosure, there is provided a method of preserving or improving cognitive function in a subject with PTSD, the method comprising the step of administering to said subject a therapeutically effective amount of a compound of this disclosure or a pharmaceutically acceptable salt, hydrate, solvate, polymorph, isomer, or combination thereof. The methods and compositions may be used for human patients in clinical applications in treating cognitive impairment associated with PTSD. The dose of the composition and dosage interval for the method is, as described herein, one that is safe and efficacious in those applications.

Patients with PTSD (and, to a lesser degree trauma-exposed patients without PTSD) have smaller hippocampal volumes (Woon et al., Prog. *Neuro-Psychopharm. & Biological Psych.* 34, 1181-1188; Wang et al., *Arch. Gen. Psychiatry* 67:296-303, 2010). PTSD is also associated with impaired cognitive performance. Older individuals with PTSD have greater declines in cognitive performance relative to control patients (Yehuda et al., *Bio. Psych.* 60: 714-721, 2006) and have a greater likelihood of developing dementia (Yaffe et al., *Arch. Gen. Psych.* 678: 608-613, 2010).

Animal models serve as an important resource for developing and evaluating treatments for PTSD and the cognitive impairments associated with it. Features that characterize PTSD in animal models typically extend to PTSD in humans. Thus, efficacy in such animal models are reasonably predictive of efficacy in humans. Various animal models of PTSD are known in the art.

One rat model of PTSD is Time-dependent sensitization (TDS). TDS involves exposure of the animal to a severely stressful event followed by a situational reminder of the prior stress. The following is an example of TDS. Rats are placed in a restrainer, then placed in a swim tank and made to swim for a period of time, e.g., 20 min. Following this, each rat is then immediately exposed to a gaseous anesthetic until loss of consciousness, and finally dried. The animals are left undisturbed for a number of days, e.g., one week. The rats are then exposed to a "restress" session consisting of an initial stressor, e.g., a swimming session in the swim tank (Liberzon et al., *Psychoneuroendocrinology* 22: 443-453, 1997; Harvery et al., *Psychopharmacology* 175:494-502, 2004). TDS results in an enhancement of the acoustic startle response (ASR) in the rat, which is comparable to the exaggerated acoustic startle that is a prominent symptom of PTSD (Khan and Liberzon, Psychopharmacology 172: 225-229, 2004). Such animal models of PTSD may be used to assay the effectiveness of the methods and compositions of this invention of the invention in treating PTSD and the cognitive impairment associated with it The efficacy of the methods and compositions of this invention in treating, cognitive impairment associated with PTSD, may also be assessed in animal models of PTSD, as well as human subjects with PTSD, using a variety of cognitive tests known in the art, as discussed herein.

Schizophrenia and Bipolar Disorder

This disclosure additionally provides methods and compositions for treating cognitive impairment associated with schizophrenia or bipolar disorder (in particular, mania) using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of the cognitive impairment associated with schizophrenia or bipolar disorder (in particular, mania). Schizophrenia is characterized by a wide spectrum of psychopathology, including positive symptoms such as aberrant or distorted mental representations (e.g., hallucinations, delusions), or dopamine dysregulation-associated symptoms (e.g., hyperdopaminergic responses, hyperdopaminergic behavorial responses, dopaminergic hyperactivity, or hyperlocomotor activity, or psychosis), negative symptoms characterized by diminution of motivation and adaptive goal-directed action (e.g., anhedonia, affective flattening, avolition), and cognitive impairment. In certain embodiments, treatment comprises alleviation, amelioration or slowing the progression of one or more positive and/or negative symptoms, as well as cognitive impairment, associated with schizophrenia. Further, there are a number of other psychiatric diseases such as schizotypical and schizoaffective disorder, other acute- and chronic psychoses and bipolar disorder (in particular, mania), which have an overlapping symptomatology with schizophrenia, including cognitive impairment. In some embodiments, treatment comprises alleviation, amelioration or slowing the progression of one or more symptoms, e.g., cognitive impairment, associated with bipolar disorder (in particular, mania). In some embodiments of the disclosure, there is provided a method of preserving or improving cognitive function in a subject with schizophrenia or bipolar disorder, the method comprising the step of administering to said subject a therapeutically effective amount of a compound of the disclosure or a pharmaceutically acceptable salt, hydrate, solvate, polymorph, isomer, or combination thereof. The methods and compositions may be used for human patients in clinical applications in treating cognitive impairment associated with schizophrenia or bipolar disorder (in particular, mania). The dose of the composition and dosage interval for the method is, as described herein, one that is safe and efficacious in those applications.

Cognitive impairments are associated with schizophrenia. They precede the onset of psychosis and are present in non-affected relatives. The cognitive impairments associated with schizophrenia constitute a good predictor for functional outcome and are a core feature of the disorder. Cognitive features in schizophrenia reflect dysfunction in frontal cortical and hippocampal circuits. Patients with schizophrenia also present hippocampal pathologies such as reductions in hippocampal volume, reductions in neuronal size and dysfunctional hyperactivity. An imbalance in excitation and inhibition in these brain regions has also been documented in schizophrenic patients suggesting that drugs targeting inhibitory mechanisms could be therapeutic. See, e.g., Guidotti et al., *Psychopharmacology* 180: 191-205, 2005; Zierhut, *Psych. Res. Neuroimag.* 183:187-194, 2010; Wood et al., *NeuroImage* 52:62-63, 2010; Vinkers et al., *Expert Opin. Investig. Drugs* 19:1217-1233, 2009; Young et al., *Pharmacol. Ther.* 122:150-202, 2009.

Animal models serve as an important resource for developing and evaluating treatments for schizophrenia and the cognitive impairments associated with it. Features that characterize schizophrenia in animal models typically extend to schizophrenia in humans. Thus, efficacy in such animal models is reasonably predictive of efficacy in humans. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., *PNAS,* 99: 17095-17100, 2002). Another animal model of schizophrenia is methylaoxymethanol acetate (MAM)-treatment in rats. Pregnant female rats are administered MAM (20 mg/kg, intraperitoneal) on gestational day 17. MAM-treatment recapitulate a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning (see Lodge et al., J. Neurosci., 29:2344-2354, 2009). Such animal models of schizophrenia may be used to assay the effectiveness of the methods and compositions of the invention in treating cognitive impairments associate with schizophrenia or bipolar disorder (in particular, mania).

MAM-treated rats display a significantly enhanced locomotor response (or aberrant locomotor activity) to low dose D-amphetamine administration. The MAM-treated rats also display a significantly greater number of spontaneously firing ventral tegmental dopamine (DA) neurons. These results are believed to be a consequence of excessive hippocampal activity because in MAM-treated rats, the ventral hippocampus (vHipp) inactivation (e.g., by intra-vHipp administration of a sodium channel blocker, tetrodotoxin (TTX), to MAM rats) completely reversed the elevated DA neuron population activity and also normalized the augmented amphetamine-induced locomotor behavior. The correlation of hippocampal dysfunction and the hyper-responsivity of the DA system is believed to underlie the augmented response to amphetamine in MAM-treated animals and psychosis in schizophrenia patients. See Lodge D. J. et al. *Neurobiology of Disease* (2007), 27(42), 11424-11430. The use of MAM-treated rats in the above study may be suitable for use to assay the effectiveness of the methods and compositions of the present disclosure in treating schizophrenia or bipolar disorder (in particular, mania) and the cognitive impairment associated with them. For example, the methods and compositions of this invention maybe evaluated, using MAM-treated animals, for their effects on the central hippocampus (vHipp) regulation, on the elevated DA neuron population activity and on the hyperactive locomotor response to amphetamine in the MAM-treated animals.

In MAM-treated rats, hippocampal (HPC) dysfunction leads to dopamine system hyperactivity. A benzodiazepine-positive allosteric modulator (PAM), selective for the α5 subunit of the $GABA_A$ R, SH-053-2'F—R—$CH_3$, is tested for its effects on the output of the hippocampal (HPC). The effect of SH-053-2'F—R—$CH_3$ on the hyperactive locomotor response to amphetamine in MAM-treated animals is also examined. The α5-$GABA_A$R PAM reduces the number of spontaneously active DA neurons in the ventral tegmental area (VTA) of MAM rats to levels observed in saline-treated rats (control group), both when administered systemically and when directly infused into the ventral HPC. Moreover, HPC neurons in both saline-treated and MAM-treated animals show diminished cortical-evoked responses following the α5-$GABA_A$ R PAM treatment. In addition, the increased locomotor response to amphetamine observed in MAM-treated rats is reduced following the α5-$GABA_A$ R PAM treatment. See Gill K. M et al. *Neuropsychopharmacology* (2011), 1-9. The use of MAM-treated rats in the above study may be suitable for use in the present disclosure to assay the effectiveness of the methods and compositions of the invention in treating schizophrenia or bipolar disorder (in particular, mania) and the cognitive impairment associated with them. For example, the methods and compositions of this invention maybe evaluated, using MAM-treated animals, for their effects on the output of the hippocampal (HPC) and on the hyperactive locomotor response to amphetamine in the MAM-treated animals.

Administration of MAM to pregnant rats on embryonic day 15 (E15) severely impairs spatial memory or the ability to learn the spatial location of four items on an eight-arm radial maze in the offspring. In addition, embryonic day 17 (E17) MAM-treated rats are able to reach the level of performance of control rats at the initial stages of training, but are unable to process and retrieve spatial information when a 30-min delay is interposed, indicating a significant impairment in working memory. See Gourevitch R. et al. (2004). *Behav. Pharmacol,* 15, 287-292. Such animal models of schizophrenia may be used to assay the effectiveness of the methods and compositions of the invention in treating cognitive impairment associated with schizophrenia or bipolar disorder (in particular, mania).

Apomorphine-induced climbing (AIC) and stereotype (AIS) in mice is another animal model useful in this disclosure. Agents are administered to mice at a desired dose level (e.g., via intraperitoneal administration). Subsequently, e.g., thirty minutes later, experimental mice are challenges with apomorphine (e.g., with 1 mg/kg sc). Five minutes after the apomorphine injection, the sniffing-licking-gnawing syndrome (stereotyped behavior) and climbing behavior induced by apomorphine are scored and recorded for each animal. Readings can be repeated every 5 min during a 30-min test session. Scores for each animal are totaled over the 30-min test session for each syndrome (stereotyped behavior and climbing). If an effect reached at least of 50% inhibition, and $ID_{50}$ value (95% confidence interval) is calculated using a nonlinear least squares calculation with inverse prediction. Mean climbing and stereotype scores can be expressed as a percent of control values observed in vehicle treated (e.g., saline-treated) mice that receive apomorphine. See Grauer S. M. et al. *Psychopharmacology* (2009) 204, 37-48. This mouse model may be used to assay the effectiveness of the methods and compositions of the invention in treating cognitive impairments associated with schizophrenia or bipolar disorder (in particular, mania).

In another well-established preclinical model of schizophrenia, rats exposed chronically to ketamine, an uncompetitive N-methyl-D-aspartate (NMDA) receptor antagonist, produces positive and negative psychotic symptoms and cognitive impairment. Long-Evans male rats are injected intraperitoneally with ketamine (30 mg/kg, twice a day) for two weeks during adolescence (2 month-old). Rats are behaviorally tested when they reach adulthood (approximately 4-5 month-old) for the behavioral symptoms to ketamine exposure and for the efficacy of treatment to alleviate those symptoms. See, e.g., Enomoto et al. Progress in Neuro-Psychopharmacology & Biological Psychiatry 33 (2009) 668-675.

The efficacy of the methods and compositions of this disclosure in treating schizophrenia and cognitive impairment associated therewith may also be assessed in animal models of schizophrenia or bipolar disorder (in particular, mania), as well as human subjects with schizophrenia, using a variety of cognitive tests known in the art, as discussed herein.

Amyotrophic Lateral Sclerosis (ALS)

The disclosure additionally provides methods and compositions for treating cognitive impairment associated with ALS using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of the cognitive impairment associated with ALS. In certain embodiments, treatment comprises alleviation, amelioration or slowing the progression, of one or more symptoms associated with ALS. In certain embodiments, the symptom to be treated is cognitive impairment. In some embodiments of the disclosure, there is provided a method of preserving or improving cognitive function in a subject with ALS, the method comprising the step of administering to said subject a therapeutically effective amount of a compound of the disclosure or a pharmaceutically acceptable salt, hydrate, solvate, polymorph, isomer, or combination thereof. The methods and compositions may be used for human patients in clinical applications in treating cognitive impairment associated with ALS. The dose of the composition and dosage interval for the method is, as described herein, one that is safe and efficacious in those applications.

In addition to the degeneration of motor neurons, ALS is characterized by neuronal degeneration in the entorhinal cortex and hippocampus, memory deficits, and neuronal hyperexcitability in different brain areas such as the cortex.

The efficacy of the methods and compositions of this disclosure in treating cognitive impairment associated with ALS, may also be assessed in animal models of ALS, as well as human subjects with ALS, using a variety of cognitive tests known in the art, as discussed herein.

Cancer Therapy-Related Cognitive Impairment

The disclosure additionally provides methods and compositions for treating cancer therapy-related cognitive impairment using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of cancer therapy-related cognitive impairment. In certain embodiments, treatment comprises alleviation, amelioration or slowing the progression, of one or more symptoms associated with cancer therapy-related cognitive impairment. In some embodiments the symptom is cognitive impairment. In some embodiments of the invention, there is provided a method of preserving or improving cognitive function in a subject with cancer therapy-related cognitive impairment, the method comprising the step of administering to said subject a therapeutically effective amount of a compound of this disclosure or a pharmaceutically acceptable salt, hydrate, solvate, polymorph, isomer, or combination thereof. The methods and compositions may be used for human patients in clinical applications in treating cancer therapy-related cognitive impairment. The dose of the composition and dosage interval for the method is, as described herein, one that is safe and efficacious in those applications.

Therapies that are used in cancer treatment, including chemotherapy, radiation, or combinations thereof, can cause cognitive impairment in patients, in such functions as memory, learning and attention. Cytotoxicity and other adverse side-effects on the brain of cancer therapies are the basis for this form of cognitive impairment, which can persist for decades. (Dietrich et al., Oncologist 13:1285-95, 2008; Soussain et al., Lancet 374:1639-51, 2009).

Cognitive impairment following cancer therapies reflects dysfunction in frontal cortical and hippocampal circuits that are essential for normal cognition. In animal models, exposure to either chemotherapy or radiation adversely affects performance on tests of cognition specifically dependent on these brain systems, especially the hippocampus (Kim et al., J. Radiat. Res. 49:517-526, 2008; Yang et al., Neurobiol. Learning and Mem. 93:487-494, 2010). Thus, drugs targeting these cortical and hippocampal systems could be neuroprotective in patients receiving cancer therapies and efficacious in treating symptoms of cognitive impairment that may last beyond the interventions used as cancer therapies.

Animal models serve as an important resource for developing and evaluating treatments for cancer therapy-related cognitive impairment. Features that characterize cancer therapy-related cognitive impairment in animal models typically extend to cancer therapy-related cognitive impairment in humans. Thus, efficacy in such animal models is reasonably predictive of efficacy in humans. Various animal models of cancer therapy-related cognitive impairment are known in the art.

Examples of animal models of cancer therapy-related cognitive impairment include treating animals with anti-neoplastic agents such as cyclophosphamide (CYP) or with radiation, e.g., $^{60}Co$ gamma-rays. (Kim et al., *J. Radiat. Res.* 49:517-526, 2008; Yang et al., *Neurobiol. Learning and Mem.* 93:487-494, 2010). The cognitive function of animal models of cancer therapy-related cognitive impairment may then be tested with cognitive tests to assay the effectiveness of the methods and compositions of the invention in treating cancer therapy-related cognitive impairment. The efficacy of the methods and compositions of this disclosure in treating cancer therapy-related cognitive impairment, as well as human subjects with cancer therapy-related cognitive impairment, using a variety of cognitive tests known in the art, as discussed herein.

Parkinson's Disease (PD)

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

Parkinson's disease, the etiology of which is unknown, belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics. Nonetheless, it is believed that the inappropriate loss of synaptic stability may lead to the disruption of neuronal circuits and to brain diseases. Whether as the result of genetics, drug use, the aging process, viral infections, or other various causes, dysfunction in neuronal communication is considered the underlying cause for many neurologic diseases, such as PD (Myrrhe van Spronsen and Casper C. Hoogenraad, *Curr. Neurol. Neurosci. Rep.* 2010, 10, 207-214).

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

This disclosure provides methods and compositions for treating cognitive impairment associated with PD using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of cognitive impairment associated with PD. In certain embodiments, treatment comprises alleviation, amelioration, or slowing the progression of one or more symptoms associated with PD. In certain embodiments, the symptom to be treated is cognitive impairment. For example, methods and compositions of the disclosure can be used to improve the motor/cognitive impairments symptomatic of Parkinson's disease. Moreover, methods and compositions of the disclosure may be useful for treating the memory impairment symptomatic of Parkinson's disease. In some embodiments of this disclosure, there is provided a method of preserving or improving cognitive function in a subject with PD, the method comprising the step of administering to said subject a therapeutically effective amount of a compound of the disclosure or a pharmaceutically acceptable salt, hydrate, solvate, polymorph, isomer, or combination thereof.

There are a number of animal models for PD. Exemplary animal models for PD include the reserpine model, the methamphetamine model, the 6-hydroxydopamine (6-OHDA) model, the 1-methyl-4-phenyl-1,2,3,6-tetrahydropyridine (MPTP) model, [the] the paraquat (PQ)-Maneb model, the rotenone model, the 3-nitrotyrosine model and genetic models using transgenic mice. Transgenic models include mice that over express α-synuclein, express human mutant forms of α-synuclein, or mice that express LRRK2 mutations. See review of these models by Ranjita B. et al. (Ranjita B. et al. *BioEssays* 2002, 24, 308-318). Additional information regarding these animal models is readily available from Jackson Laboratories, as well as in numerous publications disclosing the use of these validated models.

The efficacy of the methods and compositions of this disclosure in treating PD, or cognitive impairment associated with PD, may be assessed in any of the above animal models of PD, as well as human subjects with PD, using a variety of cognitive tests known in the art, as discussed herein.

Autism

Autism is a neurodevelopmental disorder characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities. Autism and related autism spectrum disorders are disabling neurological disorders that affect thousands of Americans and encompass a number of subtypes, with various putative causes and few documented ameliorative treatments. The disorders of the autistic spectrum may be present at birth, or may have later onset, for example, at ages two or three. There are no clear-cut biological markers for autism. Diagnosis of the disorder is made by considering the degree to which the child matches the behavioral syndrome, which is characterized by poor communicative abilities, peculiarities in social and cognitive capacities, and maladaptive behavioral patterns. The dysfunction in neuronal communication is considered one of the underlying causes for autism (Myrrhe van Spronsen and Casper C. Hoogenraad, *Curr. Neurol. Neurosci. Rep.* 2010, 10, 207-214). Recent studies have shown that there is a $GABA_A$ α5 deficit in autism spectrum disorder (ASD) and support further investigations of the GABA system in this disorder (Mendez M A, et al. Neuropharmacology. 2013, 68:195-201).

This disclosure also provides methods and compositions for treating cognitive impairments associated with autism using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of autism or the cognitive impairments associated with it. In certain embodiments, treatment comprises alleviation, amelioration, or slowing the progression of one or more symptoms associated with autism. In certain embodiments, the symptom to be treated is cognitive impairment or cognitive deficit. For example, methods and compositions of the disclosure can be used to improve the motor/cognitive deficits symptomatic of autism. In some embodiments of this disclosure there is provided a method of preserving or improving cognitive function in a subject with autism, the method comprising the step of administering to said subject a therapeutically effective amount of a compound of the invention or a pharmaceutically acceptable salt, hydrate, solvate, polymorph, isomer, or combination thereof.

The valproic acid (VPA) rat model of autism using in vitro electrophysiological techniques, established by Rodier et al. (Rodier, P. M. et al. *Reprod. Toxicol.* 1997, 11, 417-422) is one of the most exhaustively established insult-based animal models of autism and is based on the observation that pregnant women treated with VPA in the 1960s, during a circumscribed time window of embryogenesis, had a much higher risk of giving birth to an autistic child than the normal population. Offspring of VPA-exposed pregnant rats show several anatomical and behavioral symptoms typical of autism, such as diminished number of cerebellar Purkinje neurons, impaired social interaction, repetitive behaviors as well as other symptoms of autism, including enhanced fear memory processing. See, Rinaldi T. et al. *Frontiers in Neural Circuits,* 2008, 2, 1-7. Another mouse model, BTBR T+tf/J (BTBR) mice, an established model with robust behavioral phenotypes relevant to the three diagnostic behavioral symptoms of autism-unusual social interactions, impaired communication, and repetitive behaviors—was used to probe the efficacy of a selective negative allosteric modulator of the mGluR5 receptor, GRN-529. See, e.g., Silverman J. L. et al. *Sci Transl. Med.* 2012, 4, 131. The efficacy of the methods and compositions of this disclosure in treating autism, or cognitive deficits associated with autism, may be assessed in the VPA-treated rat model of autism or the BTBR T+tf/J (BTBR) mouse model, as well as human subjects with autism, using a variety of cognitive tests known in the art, as discussed herein.

Mental Retardation

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, *Curr. Neurol. Neurosci. Rep.* 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

The present disclosure contemplates the treatment of cognitive impairments associated with mild mental retardation, moderate mental retardation, severe mental retardation, profound mental retardation, and mental retardation severity unspecified. Such mental retardation may be, but is not required to be, associated with chromosomal changes, (for example Down Syndrome due to trisomy 21), heredity, pregnancy and perinatal problems, and other severe mental disorders. This disclosure provides methods and compositions for treating cognitive impairments associated with mental retardation using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of cognitive impairments associated with mental retardation. In certain embodiments, treatment comprises alleviation, amelioration, or slowing the progression of one or more symptoms associated with mental retardation. In certain embodiments, the symptom to be treated is cognitive deficit/impairment. For example, methods and compositions of the disclosure can be used to improve the motor/cognitive impairments symptomatic of mental retardation. In some embodiments of the disclosure there is provided a method of preserving or improving cognitive function in a subject with mental retardation, the method comprising the step of administering to said subject a therapeutically effective amount of a compound of this disclosure or a pharmaceutically acceptable salt, hydrate, solvate, polymorph, isomer, or combination thereof.

Several animal models have been developed for mental retardation. For example, a knockout mouse model has been developed for Fragile X syndrome. Fragile X syndrome is a common form of mental retardation caused by the absence of the FMR1 protein, FMRP. Two homologs of FMRP have been identified, FXR1P and FXR2P. FXR2P shows high expression in brain and testis, like FMRP. Both Fxr2 and Fmr1 knockout mice, and Fmr1/Fxr2 double knockout mice are believed to be useful models for mental retardation such as Fragile X syndrome. See, Bontekoe C. J. M. et al. *Hum. Mol. Genet.* 2002, 11 (5): 487-498. The efficacy of the methods and compositions of this invention in treating mental retardation, or cognitive deficit/impairment associated with mental retardation, may be assessed in these mouse models and other animal models developed for mental retardation, as well as human subjects with mental retardation, using a variety of cognitive tests known in the art, as discussed herein.

Compulsive Behavior (Obsessive-Compulsive Disorder)

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, $4^{th}$ edition text revision (DSM-IV-TR) (2000) diagnostic criteria that include characteristics of obsessions and compulsions. Characteristics of obsession include: (1) recurrent and persistent thoughts, impulses, or images that are experienced as intrusive and that cause marked anxiety or distress; (2) the thoughts, impulses, or images are not simply excessive worries about real-life problems; and (3) the person attempts to ignore or suppress such thoughts, impulses, or images, or to neutralize them with some other thought or action. The person recognizes that the obsessional thoughts, impulses, or images are a product of his or her own mind, and are not based in reality. Characteristics of compulsion include: (1) repetitive behaviors or mental acts that the person feels driven to perform in response to an obsession, or according to rules that must be applied rigidly; (2) the behaviors or mental acts are aimed at preventing or reducing distress or preventing some dreaded event or situation; however, these behaviors or mental acts are not actually connected to the issue, or they are excessive.

Individuals with OCD typically perform tasks (or compulsion) to seek relief from obsession-related anxiety. Repetitive behaviors such as handwashing, counting, checking, or cleaning are often performed with the hope of preventing obsessive thoughts or making them go away. Performing these "rituals," however, only provides temporary relief People with OCD may also be diagnosed with a spectrum of other mental disorders, such as generalized anxiety disorder, anorexia nervosa, panic attack, or schizophrenia.

The dysfunction in neuronal communication is considered one of the underlying causes for obsession disorder (Myrrhe van Spronsen and Casper C. Hoogenraad, *Curr. Neurol. Neurosci. Rep.* 2010, 10, 207-214). Studies suggest that OCD may be related to abnormal levels of a neurotransmitter called serotonin. The first-line treatment of OCD consists of behavioral therapy, cognitive therapy, and medications. Medications for treatment include serotonin reuptake inhibitors (SRIs) such as paroxetine (Seroxat™, Paxil®, Xetanor™, ParoMerck™ Rexetin™), sertraline (Zoloft®, Stimuloton™), fluoxetine (Prozac®, Bioxetin™), escitalopram (Lexapro®), and fluvoxamine (Luvox®) as well as the tricyclic antidepressants, in particular clomipramine (Anafranil®). Benzodiazepines are also used in treatment. As much as 40 to 60% of the patients, however, fail to adequately respond to the SRI therapy and an even greater proportion of patients fail to experience complete remission of their symptoms.

This disclosure provides methods and compositions for treating OCD and the cognitive impairments associated with it using a α5-containing $GABA_A$ R agonist (e.g., a α5-containing $GABA_A$ R positive allosteric modulator), such as one selected from the compounds or pharmaceutically acceptable salts, hydrates, solvates, polymorphs, isomers, or combinations thereof as described herein. In certain embodiments, treatment comprises preventing or slowing the progression of OCD and the cognitive impairments associated with it. In certain embodiments, treatment comprises alleviation, amelioration, or slowing the progression of one or more symptoms associated with OCD. In certain embodiments, the symptom to be treated is cognitive impairment or cognitive deficit. For example, methods and compositions of the disclosure can be used to treat the cognitive deficits in OCD, and/or to improve cognitive function in patients with OCD. In some embodiments of this disclosure, there is provided a method of preserving or improving cognitive function in a subject with OCD, the method comprising the step of administering to said subject a therapeutically effective amount of a compound of this disclosure or a pharmaceutically acceptable salt, hydrate, solvate, polymorph, isomer, or combination thereof.

A quinpirole-sensitized rat model has been developed for OCD. The compulsive checking behavior of the quinpirole-sensitized rats is subject to interruption, which is an attribute characteristic of OCD compulsions. In addition, a schedule-induced polydipsia (SIP) rodent model of obsessive-compulsive disorder was used to evaluate the effects of the novel 5-HT2C receptor agonist WAY-163909. See, e.g., Rosenzweig-Lipson S. et al. Psychopharmacology (Berl) 2007, 192, 159-70. The efficacy of the methods and compositions of this disclosure in treating OCD, or cognitive impairment or cognitive deficits associated with OCD, may be assessed in the above animal models and other animal models developed for OCD, as well as human subjects with OCD, using a variety of cognitive tests known in the art, as discussed herein.

Substance Addiction

Substance addiction (e.g., drug substance addiction, alcohol substance addiction) is a mental disorder. The substance addiction is not triggered instantaneously upon exposure to substance of abuse. Rather, it involves multiple, complex neural adaptations that develop with different time courses ranging from hours to days to months (Kauer J. A. *Nat. Rev. Neurosci.* 2007, 8, 844-858). The path to substance addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize substance addictions to other controlled substances. The craving for alcohol, as well as other controlled substances, often is as strong as the need for food or water. Thus, an alcoholic may continue to drink despite serious family, health and/or legal ramifications.

Recent work exploring the effects of abusing alcohol, central stimulants, and opiates on the central nervous system (CNS) have demonstrated a variety of adverse effects related to mental health, including substance-induced impairments in cognition. See, Nyberg F. Cognitive Impairments in Drug Addicts, Chapter 9. In several laboratories and clinics substantial damages of brain function are seen to result from these drugs. Among the harmful effects of the abusing drugs on brain are those contributing to accelerated obsolescence. An observation that has received special attention during recent years is that chronic drug users display pronounced impairment in brain areas associated with executive and memory function. A remarked neuroadaptation caused by addictive drugs, such as alcohol, central stimulants and opiates involves diminished neurogenesis in the subgranular zone (SGZ) of the hippocampus. Indeed, it has been proposed that decreased adult neurogenesis in the SGZ could modify the hippocampal function in such a way that it contributes to relapse and a maintained addictive behavior. It also raises the possibility that decreased neurogenesis may contribute to cognitive deficits elicited by these abusing drugs.

This disclosure provides methods and compositions for treating the cognitive impairments associated with substance addiction using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of substance addiction and the cognitive impairments associated with it. In certain embodiments, treatment comprises alleviation, amelioration, or slowing the progression of one or more symptoms associated with substance addiction. In certain embodiments, the symptom to be treated is cognitive impairment. For example, methods and compositions of the disclosure can be used to treat the cognitive impairment and/or to improve cognitive function in patients with substance addiction. In some embodiments of this disclosure, there is provided a method of preserving or improving cognitive function in a subject with substance addiction, the method comprising the step of administering to said subject a therapeutically effective amount of a compound of this disclosure or a pharmaceutically acceptable salt, hydrate, solvate, polymorph, isomer, or combination thereof.

Several animal models have been developed to study substance addiction. For example, a genetically selected Marchigian Sardinian alcohol-preferring (msP) rat models was developed to study the neurobiology of alcoholism. See, Ciccocioppo R. et al. *Substance addiction Biology* 2006, 11, 339-355. The efficacy of the methods and compositions of this disclosure in treating substance addiction, or cognitive impairment associated with substance addiction, may also be assessed in animal models of substance addiction, as well as human subjects with substance addiction, using a variety of cognitive tests known in the art, as discussed herein.

Brain Cancers

Brain cancer is the growth of abnormal cells in the tissues of the brain usually related to the growth of malignant brain tumors. Brain tumors grow and press on the nearby areas of the brain which can stop that part of the brain from working the way it should. Brain cancer rarely spreads into other tissues outside of the brain. The grade of tumor, based on how abnormal the cancer cells look under a microscope, may be used to tell the difference between slow- and fast-growing tumors. Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors.

These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumorsthat may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, usually cerebral tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are highly malignant, primitive tumors that arise in the posterior fossa, primarily in children. Medulloblastoma is the most common childhood malignant brain tumor. Medulloblastomas can spread through the CNS and frequently metastasize to different locations in the brain and spine.

Meningiomas are common intracranial tumors that arise in the meninges and compress the underlying brain. Meningiomas are usually benign, but some "atypical" meningiomas may recur locally, and some meningiomas are frankly malignant and may invade the brain or metastasize. Atypical and malignant meningiomas are not as common as benign meningiomas. Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

Group 3 tumors share high expression of α5-containing $GABA_A$ R. α5-containing $GABA_A$ R is present in patient-derived group 3 cells and tumor tissue and contributed to assembly of a functional α5-containing $GABA_A$ R. The most lethal medulloblastoma subtype exhibits a high expression of the $GABA_A$ R α5 subunit gene and MYC amplification. See, e.g., *J. Biomed. Nanotechnol.* 2016 June; 12(6):1297-302.

This invention provides methods and compositions for treating α5-containing $GABA_A$R expressing brain cancers (for example, brain tumors as described herein) and the cognitive impairments associated with them using a α5-containing $GABA_A$ R positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of brain cancers and the cognitive impairments associated with them. In certain embodiments, treatment comprises alleviation, amelioration, or slowing the progression of one or more symptoms associated with brain cancers. In certain embodiments, the symptom to be treated is cognitive impairment. For example, methods and compositions of the disclosure can be used to treat the cognitive impairment and/or to improve cognitive function in patients with brain cancers. In some embodiments of this disclosure, there is provided a method of preserving or improving cognitive function in a subject with brain cancers, the method comprising the step of administering to said subject a therapeutically effective amount of a compound of this disclosure or a pharmaceutically acceptable salt, hydrate, solvate, polymorph, isomer, or combination thereof. In some embodiments, the brain tumor is medulloblastoma.

Research Domain Criteria (RdoC)

This disclosure further provides methods and compositions for treating cognitive impairment associated with neurological disorders and neuropsychiatric conditions using a α5-containing $GABA_A$ R positive allosteric modulator or a pharmaceutically acceptable salt, hydrate, solvate, polymorph, isomer, or combination thereof as described herein. In certain embodiments, treatment comprises alleviation, amelioration or slowing the progression, of one or more symptoms associated with such impairment. In another aspect of this disclosure, there is provided methods and compositions for preserving or improving cognitive function in a subject in need thereof using a compound of this disclosure or a pharmaceutically acceptable salt, hydrate, solvate, polymorph, isomer, or combination thereof.

Research Domain Criteria (RdoC) are used to augment clinical criteria, such as DSM and ICD, for diagnosis of disease and disorders affecting the nervous system (see, e.g., *Am. J. Psychiatry* 167:7 (2010)). The RdoC is intended to provide classification based on discoveries in genomics and neuroscience as well as clinical observation. The high level of expression of α5-containing $GABA_A$ R in specific neural circuits in the nervous system are therapeutic targets for neural circuit dysfunction identified under RdoC.

Assays for $GABA_A$ α5 Subunit Binding and Receptor Positive Allosteric Modulator Activity The affinity of test compounds for a $GABA_A$ R comprising the $GABA_A$ α5 subunit may be determined using any of the receptor binding assays that are known in the art. See, e.g., U.S. Pat. Nos. 7,642,267 and 6,743,789, which are incorporated herein by reference.

The activity of the test compounds as a α5-containing $GABA_A$ R positive allosteric modulator may be tested by electrophysiological methods known in the art. See, e.g., U.S. Pat. No. 7,642,267 and Guidotti et al., Psychopharmacology 180: 191-205, 2005. Positive allosteric modulator activity may be tested, for example, by assaying GABA-induced chloride ion conductance of $GABA_A$ R comprising the $GABA_A$ α5 subunit. Cells expressing such receptors may be exposed to an effective amount of a compound of this disclosure. Such cells may be contacted in vivo with compounds of the disclosure through contact with a body fluid containing the compound, for example through contact with cerebrospinal fluid. In vitro tests may be done by contacting cells with a compound of this disclosure in the presence of GABA. Increased GABA-induced chloride conductance in cells expressing $GABA_A$ R comprising the $GABA_A$ α5 subunit in the presence of the test compound would indicate positive allosteric modulator activity of said compound. Such changes in conductance may be detected by, e.g., using a voltage-clamp assay performed on *Xenopus* oocytes injected with $GABA_A$ R subunit mRNA (including $GABA_A$ α5 subunit RNA), HEK 293 cells transfected with plasmids encoding $GABA_A$ R subunits, or in vivo, ex vivo, or cultured neurons.

It will be understood by one of ordinary skill in the art that the methods described herein may be adapted and modified as is appropriate for the application being addressed and that the methods described herein may be employed in other suitable applications, and that such other additions and modifications will not depart from the scope hereof.

This disclosure will be better understood from the Examples which follow. However, one skilled in the art will readily appreciate that the specific methods and results discussed are merely illustrative of this disclosure as described more fully in the embodiments which follow thereafter.

Example 1: Synthesis of Compound 18

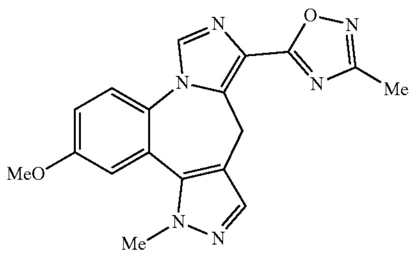 [SMILES: COc1ccc2c(c1)-c1c(cnn1C)Cc1c(-c3nc(C)no3)ncn1-2]

Scheme 4

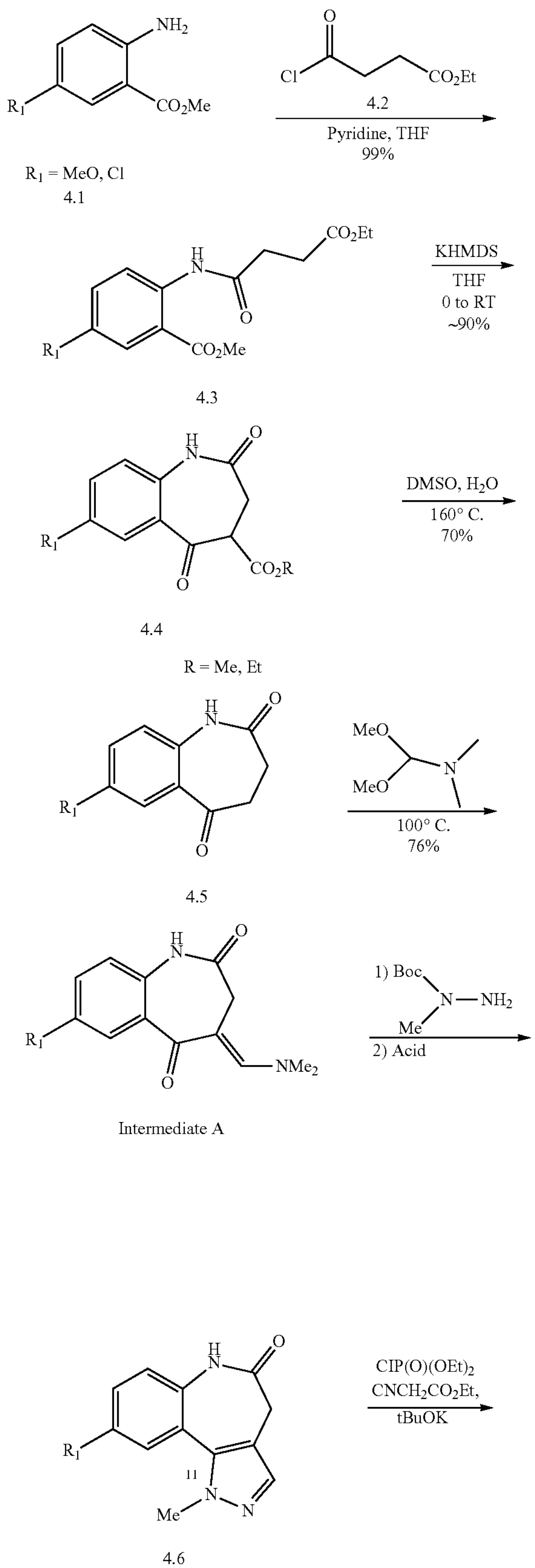

$R_1$ = MeO, Cl
4.1
4.2
4.3
4.4
R = Me, Et
4.5
Intermediate A
4.6

-continued

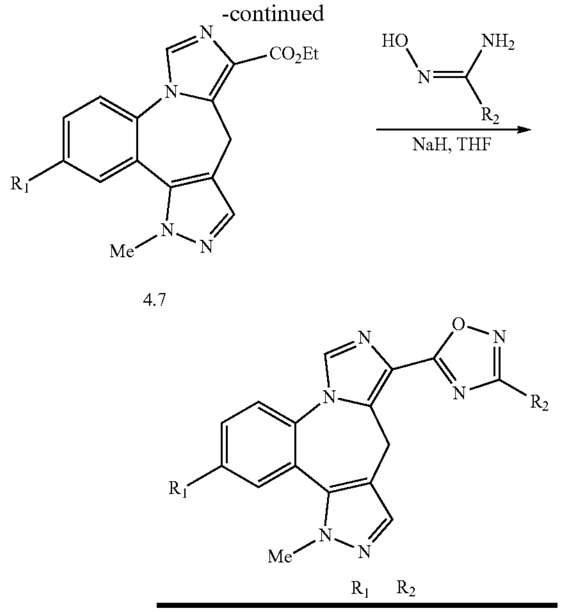

4.7

R1 R2

Ex. 1 Compound 18: OMe, Me
Ex. 2 Compound 19: OMe, tBu
Ex. 2a Compound 329: MeO, $O(CH_2CH_2)_2NCH_2$
Ex. 3 Compound 03: Cl, Me
Ex. 4 Compound 04: Cl, iPr To a stirring solution of methyl 2-amino-5-methoxybenzoate (12.7 g, 70.2 mmol) in pyridine (5.6 g) and THE (200 ml) at 0° C. was added acid chloride 4.2 (21.4 g, 130 mmol) dropwise. Ice bath was removed upon completion of the addition, and the reaction was allowed to proceed at ambient temperature for 20 h. The reaction mixture was concentrated to a thick slurry under reduced pressure, and sat. $NaHCO_3$ (120 ml) was added. After 30 min stirring, ppts was collected by filtration, washed with water, and dried to give 21.4 g product 4.3 as a pinkish solid.

To a stirring solution of methyl-ethyl-di ester 4.3 (10.6 g, 33.7 mmol) in THE (80 ml) at 0° C. was added potassium hexamethyldisilazide (1M THF; 74.1 ml) slowly. The reaction was allowed to proceed at ambient temperature overnight, then diluted with water (200 ml) and 1N HCl (150 ml). After 2 h stirring, ppts were collected by filtration, washed with water, and dried to give 8.1 g cyclization product 4.4 as a mixture of methyl and ethyl esters, about 1:1 ratio.

The ester 4.4 (2.54 g) from above was treated with DMSO (50 ml) and water (1 ml) at 160° C. for about 5 h, cooled to RT, and ice water mixture (~200 g) was added under stirring. Ppts was collected by filtration and washed with water. Filtrate was extracted with $Et_2O$ repeatedly; the combined ether solution was washed with water, brine, and dried over $MgSO_4$, filtered and solvent removed to give extra crude product. This was combined with the above ppts and purified by column chromatography (0 to 100% EtOAc in hexane gradient) to give 1.4 g of 4.5.

1.25 g of Compound 4.5 was treated with N,N-dimethylformamide dimethoxy acetal (10 ml) at 100° C. for 2 h, then cooled, and diluted with $Et_2O$ (20 ml) while stirring. Ppts was collected by filtration, washed with small amount of $Et_2O$, and dried to give 1.20 g keto enamine (Intermediate A, $R_1$=OMe).

A solution of the above Intermediate A (525.9 mg, 2.0 mmol) and 1-boc-1-methylhydrazine (886.2 mg, 6.0 mmol) in isopropanol (10 ml) was stirred at rt for 30 min, then heated to 80° C. for 16 h. Upon cooling, the reaction mixture was diluted with EtOAc, washed with sat. $NaHCO_3$, brine, and dried over $MgSO_4$. Filtration and concentration followed by silica gel column chromatography using 0 to 8% MeOH in DCM gradient as eluent gave a brownish foamy solid, which was dissolved in DCM (30 ml) and treated with TFA (20 ml) at RT for 16 h. The mixture was concentrated, diluted with EtOAc, and washed with sat. $NaHCO_3$; the aq. Layer was back extracted with EtOAc (2×), combined with the previous org. layer, and washed with brine before being dried over $MgSO_4$. Filtration and concentration followed by silica gel column chromatography using 0 to 100% EtOAc in hexane gradient gave 218.0 mg N11-methyl lactam (4.6).

To a stirring suspension of 4.6 (258.1 mg, 1.06 mmol) in an anhydrous solvent mixture of THE (6 ml) and DMF (1 ml) under nitrogen at −20° C. was added t-BuOK powder (192 mg). After 20 min stirring at −20° C., diethyl chlorophosphate (329.5 mg, 1.91 mmol) was added dropwise, and the reaction was allowed to slowly warm to about +5° C. in 2 h stirring.

The reaction mixture was cooled back to −20° C., isocyanoacetic acid ethyl ester (239.8 mg, 2.12 mmol) was added slowly. The reaction was further cooled to −78° C., and t-BuOK powder (192 mg) was added. The reaction was allowed to proceed to rt overnight. After quenching with sat. $NaHCO_3$ (50 ml), the reaction solution was further diluted with EtOAc (50 ml), and stirred. Ppts from the bi-phasic solution was collected by filtration, washed with water, and dried to give 141.2 mg desired product 4.7. Aq. Layer of the filtrate was separated and extracted with EtOAc, combined with the previous organic layer, washed with water (2×), brine (1×), and dried over $MgSO_4$. Silica gel column chromatography with 0 to 100% EtOAc in hexane gradient gave 121.1 mg additional product. Total product weight of 4.7 is 262.3 mg (73%).

Acetamide oxime ($R_2$=Me) was azeotroped three times in toluene before use. To a suspension of acetamide oxime (43.3 mg, 0.58 mmol) in THE (0.5 mL) at 0° C. was added NaH 60% in oil dispersion (11.7 mg, 0.293 mmol). The suspension was stirred for 10 min. The ester 4.7 from above (16.5 mg, 0.049 mmol) was added. Ice bath was removed and the resulting suspension was stirred at ambient temperature for 30 min, then heated at 70° C. for 40 min. The reaction mixture was quenched with sat. $NaHCO_3$, and extracted with EtOAc, which was then washed with brine and dried over $MgSO_4$. Prep. TLC using 80% EtOAc in hexanes gave 11.7 mg desired product Example 1, compound 18 as a yellowish solid. MS: [M+1]=349. $H^1$NMR ($CDCl_3$) δ 7.76 (1H, s), 7.51 (1H, br d, J=8 Hz), 7.47 (1H, s), 7.07 (2H, m), 4.92 (1H, d, J=16 Hz), 4.01 (3H, s), 3.91 (3H, s), 3.51 (1H, d, J=16 Hz), and 2.46 (3H, s).

Example 2: Synthesis of Compound 19

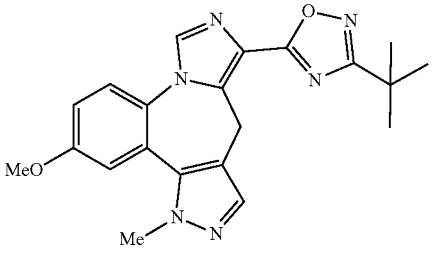 [SMILES: COc1ccc2c(c1)-c1c(cnn1C)Cc1c(-c3nc(C(C)(C)C)no3)ncn1-2]

Example 2 was prepared analogously as Example 1, using N'-hydroxypivalimidamide in the final oxadiazole ring formation step. MS: [M+1]=391. $H^1NMR$ ($CDCl_3$) Q 7.75 (1H, s), 7.50 (1H, d, J=12 Hz), 7.43 (1H, s), 7.07 (2H, m), 4.90 (1H, d, J=16 Hz), 4.00 (3H, s), 3.91 (3H, s), 3.50 (1H, d, J=16 Hz), and 1.43 (9H, s).

Example 2a: Synthesis of Compound 329

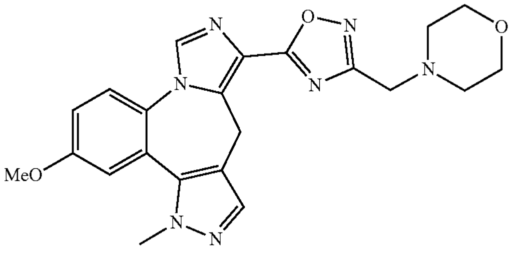 [SMILES: COc1ccc2c(c1)-c1c(cnn1C)Cc1c(-c3nc(CN4CCOCC4)no3)ncn1-2]

Example 2a was prepared analogously as Example 1, using N'-hydroxy-2-(4-morpholinyl)ethanimidamide in the final oxadiazole ring formation step. MS: [M+1]=434.

Example 3: Synthesis of Compound 03

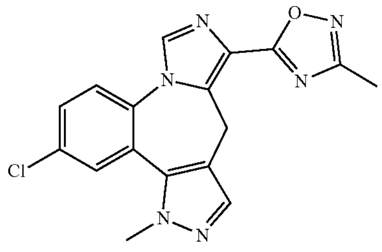 [SMILES: Cc1noc(-c2ncn3c2Cc2cnn(C)c2-c2cc(Cl)ccc2-3)n1]

Example 3 was prepared analogously as Example 1, starting with methyl 2-amino-5-chlorobenzoate in the first step of the synthetic sequence. MS: [M+1]=353.

Example 4: Synthesis of Compound 04

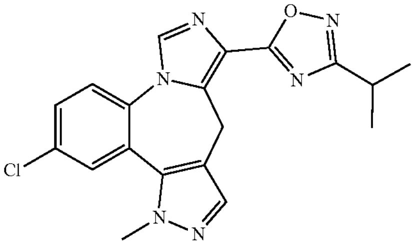 [SMILES: CC(C)c1noc(-c2ncn3c2Cc2cnn(C)c2-c2cc(Cl)ccc2-3)n1]

Example 4 was prepared analogously as Example 1, starting with methyl 2-amino-5-chlorobenzoate in the first step, and using isobutyramide oxime in the final oxadiazole formation step. MS: [M+1]=381.

Scheme 5

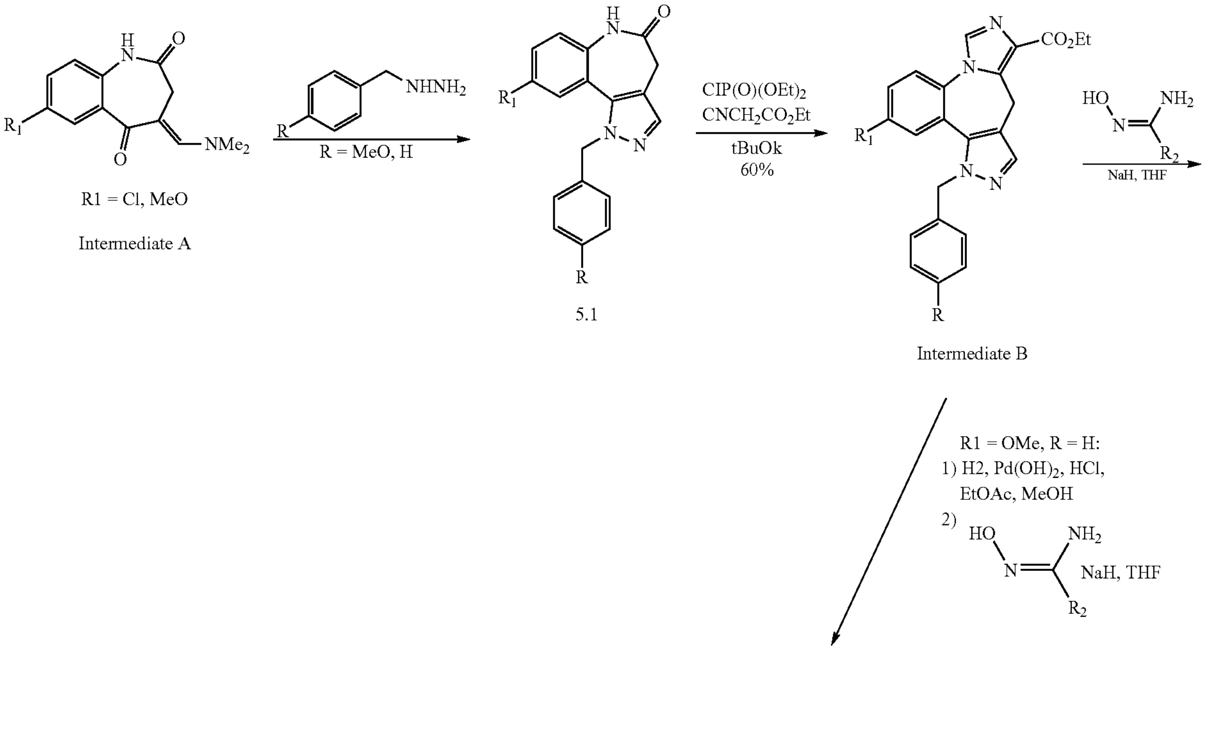

-continued

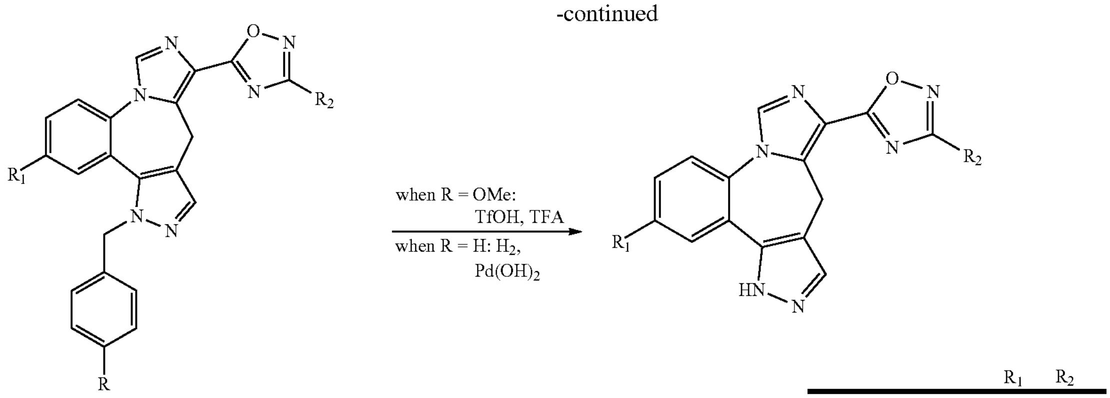

| $R_1$ $R_2$ R |
|---|
| Ex. 5 compound 07: OMe, Me, H |
| Ex. 6 compound 08: OMe, iPr, H |
| Ex. 7 compound 01: Cl, Me, H |
| Ex. 8 compound 02: Cl, iPr, H |

| $R_1$ $R_2$ |
|---|
| Ex. 9 compound 009: OMe, Me |
| Ex. 10 compound 10: OMe, iPr |
| Ex. 11 compound 11: OMe, tBu |
| Ex. 12 compound 100: OMe, tetrahydrofuan-3-yl |
| Ex. 13 compound 045: OMe, CF3 |
| Ex. 14 compound 033: Cl, Me |
| Ex. 15 compound 034: Cl, iPr |
| Ex. 16 compound 105: Cl, cPr |
| Ex. 17 compound 107: Cl, cBu |
| Ex. 18 compound 035: Cl, tBu |
| Ex. 19 compound 115: Cl, c-pentyl |
| Ex. 20 compound 123: Cl, c-hexyl |
| Ex. 21 compound 106: Cl, CF3 |
| Ex. 22 compound 108: Cl, tetrahydrofuan-3-yl |

Example 5: Synthesis of Compound 07

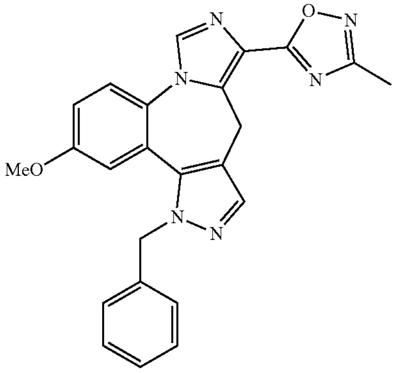 [SMILES: COc1ccc2c(c1)-c1c(cnn1Cc1ccccc1)Cc1c(-c3nc(C)no3)ncn1-2]

A solution of Intermediate A ($R_1$=OMe; 827 mg, 3.18 mmol) and benzylhydrazine di-HCl salt (2.48 g, 12.7 mmol) in isopropanol (20 ml) was stirred at rt for 30 min, then heated to 90° C. for 5 h. Upon cooling, the reaction mixture was diluted with EtOAc, washed with sat. $NaHCO_3$, brine, and dried over $MgSO_4$. Filtration and concentration followed by silica gel column chromatography using 0 to 100% EtOAc in hexane gradient as eluent gave 523 mg benzylpyrazolo lactam 5.1 as a yellowish solid.

To a stirring suspension of lactam 5.1 (505.1 mg, 1.58 mmol) in an anhydrous solvent mixture of THF (7 ml) and DMF (2 ml) under nitrogen at −20° C. was added tBuOK powder (284 mg). After 20 min stirring at −20° C., diethyl chlorophosphate (0.411 mL, 2.85 mmol) was added dropwise, and the reaction was allowed to slowly warm to about +50° C. in 2 h stirring. The reaction mixture was cooled back to −20° C., isocyanoacetic acid ethyl ester (357.5 mg, 3.16 mmol) was added slowly. The reaction was further cooled to −78° C., and tBuOK powder (284 mg) was added. The reaction was allowed to proceed to rt overnight. After quenching with sat. $NaHCO_3$, the reaction mixture was extracted with EtOAc, washed with water, and brine and dried over $MgSO_4$. Silica gel column chromatography with 0 to 100% EtOAc in hexane gradient gave 391.2 mg imidazole product Intermediate B ($R_1$=Ome, R=H).

Acetamide oxime ($R_2$=Me) was azeotroped three times in toluene before use. To a suspension of acetamide oxime (40.0 mg, 0.539 mmol) in THE (0.4 mL) at 0° C. was added NaH 60% in oil dispersion (9.0 mg, 0.225 mmol). The suspension was stirred for 10 min. The ester intermediate B from above (18.6 mg, 0.0449 mmol) was added. Ice bath was removed and the resulting suspension was stirred at ambient temperature for 30 mins, then heated at 70° C. for 30 min. The reaction mixture was quenched with sat. $NaHCO_3$, and extracted with EtOAc, which was then washed with brine and dried over $MgSO_4$. Prep. TLC using 5% MeOH in a pre-mixed solvents of EtOAc/DCM (1:1) gave 9.5 mg desired product Example 5, compound 07 as a yellowish solid. MS: [M+1]=425. $H^1$NMR ($CDCl_3$) δ 7.75 (1H, s), 7.61 (1H, s), 7.45 (1H, d, J=8 Hz), 7.35-7.25 (3H, m), 7.11 (2H, br d, J=8 Hz), 7.00 (1H, dd, J=4, 12 Hz), 6.85 (1H, d, J=4 Hz), 5.60 (1H, d, J=16 Hz), 5.37 (1H, d, J=16 Hz), 4.97 (1H, d, J=16 Hz), 3.55 (1H, d, J=16 Hz), 3.49 (3H, s), and 2.48 (3H, s).

Example 6: Synthesis of Compound 08

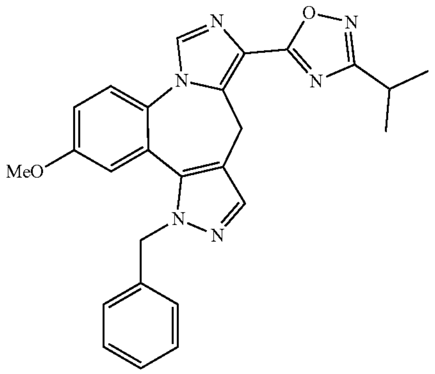 [SMILES: COc1ccc2c(c1)-c1c(cnn1Cc1ccccc1)Cc1c(-c3nc(C(C)C)no3)ncn1-2]

Example 6 was prepared analogously as Example 5, using isobutyramide oxime in the final oxadiazole formation step. MS: [M+1]=453.

Example 7: Synthesis of Compound 01

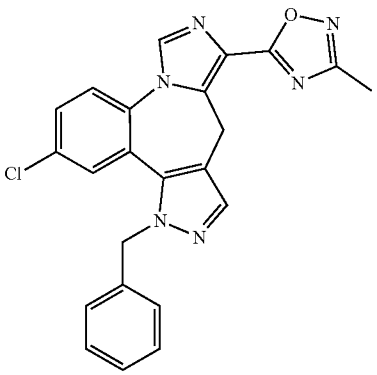 [SMILES: Cc1noc(-c2ncn3c2Cc2cnn(Cc4ccccc4)c2-c2cc(Cl)ccc2-3)n1]

Example 7 was prepared analogously as Example 5, starting with methyl 2-amino-5-chlorobenzoate in the first step. MS: [M+1]=429.

Example 8: Synthesis of Compound 02

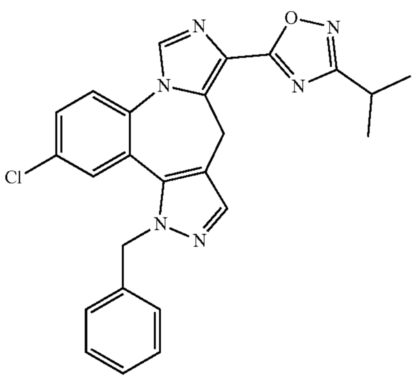 [SMILES: CC(C)c1noc(-c2ncn3c2Cc2cnn(Cc4ccccc4)c2-c2cc(Cl)ccc2-3)n1]

Example 8 was prepared analogously as Example 5, starting with methyl 2-amino-5-chlorobenzoate in the first step, and using isobutyramide oxime in the final oxadiazole formation step. MS: [M+1]=457.

Example 9: Synthesis of Compound 09

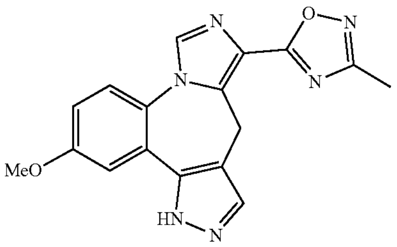 [SMILES: COc1ccc2c(c1)-c1[nH]ncc1Cc1c(-c3nc(C)no3)ncn1-2]

Step 1: 76.5 mg of Intermediate B ($R_1$=OMe, R=H) was stirred with $Pd(OH)_2$ (20% wt on carbon; cat. Amt.) in the presence of HCl (1N aq.; 50 ul) in EtOAc (2 ml) and MeOH (1 ml) under hydrogen atm. For 4 days. Catalyst was removed over Celite and rinsed with 5% MeOH in DCM; solvent of the filtrate was removed in vacuo to give 63.4 mg debenzylated pyrazolo ester as a yellowish solid.

Step 2: Acetamide oxime was azeotroped three times in toluene before use. A solution of acetamide oxime (41.0 mg; 0.553 mmol) and the above debenzylated ester (14.9 mg, 0.046 mmol) in THF (0.45 ml) was cooled to 0° C., NaH (60% mineral oil suspension; 11.0 mg) was added. Ice bath was removed and stirring continued at ambient temperature for 30 min, then the reaction was heated at 70° C. for 30 min. Upon cooling, the reaction was diluted with EtOAc, washed with sat. $NaHCO_3$, brine, and dried over $MgSO_4$. Prep. TLC with 7% MeOH in DCM as eluent gave Example 9 compound 09 as an off-white solid. Wt: 5.6 mg. MS: [M+1]=335. $H^1NMR$ ($CDCl_3$+ trace $CD_3OD$) δ 7.77 (1H, s), 7.51 (1H, s), 7.43 (1H, br d, J=8 Hz), 7.38 (1H, br s), 6.99 (1H, br d, J=12 Hz), 4.25 (2H, br s), 3.85 (3H, s), and 2.41 (3H, s).

Example 10: Synthesis of Compound 10

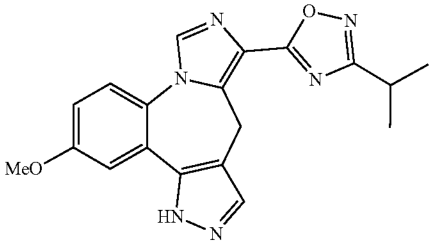 [SMILES: COc1ccc2c(c1)-c1[nH]ncc1Cc1c(-c3nc(C(C)C)no3)ncn1-2]

Example 10 was prepared analogously as Example 9, using isobutyramide oxime in the final oxadiazole formation step. MS: [M+1]=363.

Example 11: Synthesis of Compound 11

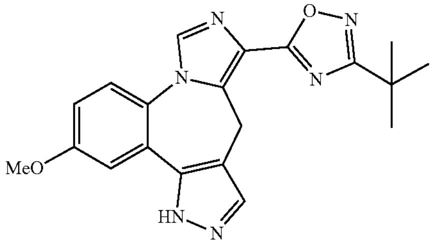 [SMILES: COc1ccc2c(c1)-c1[nH]ncc1Cc1c(-c3nc(C(C)(C)C)no3)ncn1-2]

Example 11 was prepared analogously as Example 9, using N'-hydroxypivalimidamide in Step 2. MS: [M+1]=377.

Example 12: Synthesis of Compound 100

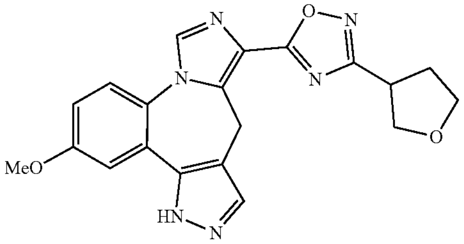 [SMILES: COc1ccc2c(c1)-c1[nH]ncc1Cc1c(-c3nc(C4CCOC4)no3)ncn1-2]

Example 12 was prepared analogously as Example 9, using N-hydroxytetrahydrofuran-3-carboxamidine in Step 2. MS: [M+1]=391.

Example 13: Synthesis of Compound 45

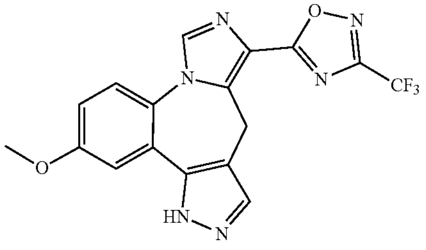 [SMILES: COc1ccc2c(c1)-c1[nH]ncc1Cc1c(-c3nc(C(F)(F)F)no3)ncn1-2]

2,2,2-trifluoro-N'-hydroxyethanimidaminde (~170 mg) was dried over $P_2O_5$ under vacuum for 24 h before being suspended in THE (0.7 ml), and Intermediate B ($R_1$=OMe, R=OMe; 30 mg) added. This mixture was cooled to 0° C., and NaH (60% mineral oil suspension; 28 mg) added. After 20 min stirring, the ice bath was removed, and the reaction mixture was heated to 60° C. for 16 h, and was quenched with sat. $NaHCO_3$, extracted with EtOAc (3×), the combined extracts washed with brine, and dried over $MgSO_4$. Following filtration and solvent removal, the 4-methoxy benzyl group was removed by treatment with TfOH (35 mg) in TFA (0.7 ml) and DCM (0.7 ml) at 40° C. for 5 h. Upon concentration, the reaction mixture was diluted with EtOAc, washed with sat. $NaHCO_3$, brine, and dried ($MgSO_4$). Example 13, compound 45 was isolated by prep. TLC using 5% MeOH in DCM/EtOAc (1:1), Wt: 8.6 mg. MS: [M+1]=389. $H^1$NMR ($CDCl_3$+ drops $CD_3OD$) δ 7.83 (1H, s), 7.54 (1H, s), 7.47 (1H, d, J=12 Hz), 7.42 (1H, br d, J=4 Hz), 7.03 (1H, dd, J=4, 12 Hz), 4.32 (2H, br s), and 3.89 (3H, s).

Example 14: Synthesis of Compound 33

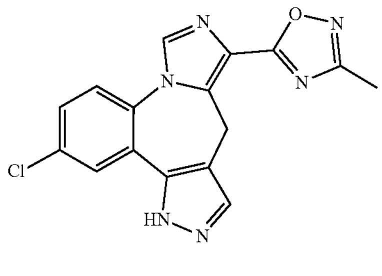 [SMILES: Cc1noc(-c2ncn3c2Cc2cn[nH]c2-c2cc(Cl)ccc2-3)n1]

Intermediate B ($R_1$=Cl, R=OMe) was prepared in the same way as Intermediate B ($R_1$=OMe, R=H) using methyl 2-amino-5-chlorobenzoate in the place of methyl 2-amino-5-methoxybenzoate and 4-methoxy benzylhydrazine HCl in the place of benzylhydrazine 2HCl in respective reaction steps. Step 1: Intermediate B ($R_1$=Cl, R=OMe; 100.8 mg) was treated with trifluoromethyl sulfonic acid (68 mg) in a mixture of trifluoroacetic acid (1.1 ml) and DCM (1.1 ml) at rt for 2 days, or until all 4-methoxy benzyl group was removed. The reaction mixture was concentrated, treated with sat. $NaHCO_3$, and extracted with EtOAc (3×). The combined organic extract was washed with water, brine, and dried over $MgSO_4$. Filtration and solvent removal gave 88.2 mg of the crude debenzylated ester as a yellowish solid. This is used without further purification.

Step 2: Acetamide oxime was azeotroped three times in toluene before use. A solution of acetamide oxime (51.8 mg; 0.699 mmol) and the above debenzylated ester (19.1 mg, 0.0583 mmol) in THF (0.40 ml) was cooled to 0° C., NaH (60% mineral oil suspension; 14.0 mg) was added. Ice bath was removed and stirring continued at ambient temperature for 30 min, then the reaction was heated at 70° C. for 30 min. Upon cooling, the reaction was diluted with EtOAc, washed with sat. $NaHCO_3$, brine, and dried over $MgSO_4$. Prep. TLC with 7% MeOH in DCM as eluent gave Example 14, compound 33 as an off-white solid, Wt: 5.8 mg. MS: [M+1]=339. $H^1$ NMR ($CDCl_3$+ trace $CD_3OD$) δ 7.95 (1H, br d, J=4 Hz), 7.88 (1H, s), 7.58 (1H, s), 7.54 (1H, br d, J=8 Hz), 7.49 (1H, br d, J=8 Hz), 4.35 (2H, br s), and 2.47 (3H, s).

Example 15: Synthesis of Compound 34

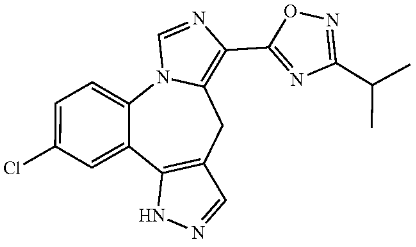 [SMILES: CC(C)c1noc(-c2ncn3c2Cc2cn[nH]c2-c2cc(Cl)ccc2-3)n1]

Example 15 was prepared analogously as Example 14 using isobutyramide oxime in Step 2. MS: [M+1]=367.

Example 16: Synthesis of Compound 105

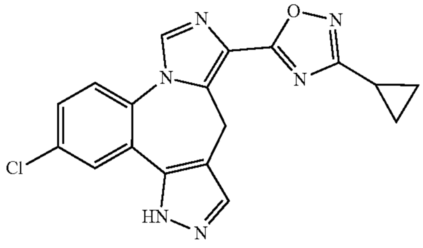 [SMILES: Clc1ccc2c(c1)-c1[nH]ncc1Cc1c(-c3nc(C4CC4)no3)ncn1-2]

Example 16 was prepared analogously as Example 14, using N'-hydroxycyclopropanecarboximidamide in Step 2. MS: [M+1]=365.

Example 17: Synthesis of Compound 107

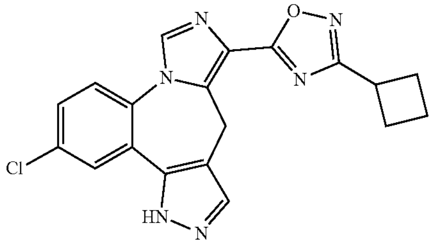 [SMILES: Clc1ccc2c(c1)-c1[nH]ncc1Cc1c(-c3nc(C4CCC4)no3)ncn1-2]

Example 17 was prepared analogously as Example 14, using N'-hydroxycyclobutanecarboximidamide in Step 2. MS: [M+1]=379.

Example 18: Synthesis of Compound 35

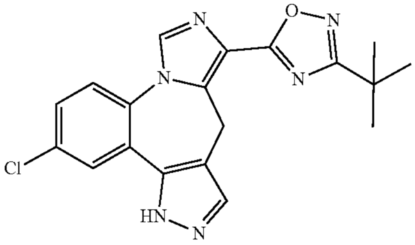 [SMILES: CC(C)(C)c1noc(-c2ncn3c2Cc2cn[nH]c2-c2cc(Cl)ccc2-3)n1]

Example 18 was prepared analogously as Example 14, using N'-hydroxy-2,2-dimethylpropanimidamide in Step 2. MS: [M+1]=381.

Example 19: Synthesis of Compound 115

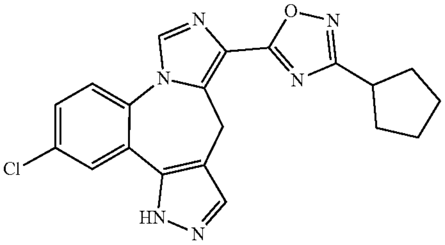 [SMILES: Clc1ccc2c(c1)-c1[nH]ncc1Cc1c(-c3nc(C4CCCC4)no3)ncn1-2]

Example 19 was prepared analogously as Example 14, using N'-hydroxycyclopentanecarboximidamide in Step 2. MS: [M+1]=393.

Example 20: Synthesis of Compound 123

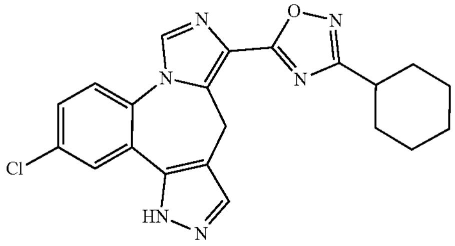 [SMILES: Clc1ccc2c(c1)-c1[nH]ncc1Cc1c(-c3nc(C4CCCCC4)no3)ncn1-2]

Example 20 was prepared analogously as Example 14, using N'-hydroxycyclohexanecarboximidamide in Step 2. MS: [M+1]=407.

Example 21: Synthesis of Compound 106

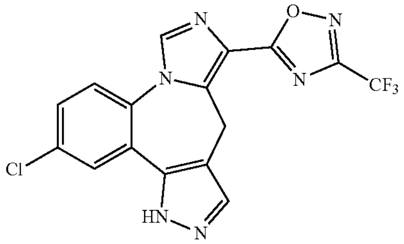 [SMILES: FC(F)(F)c1noc(-c2ncn3c2Cc2cn[nH]c2-c2cc(Cl)ccc2-3)n1]

Example 21 was prepared analogously as Example 13, starting with Intermediate B ($R_1$=Cl, R=OMe). MS: [M+1]=393.

Example 22: Synthesis of Compound 108

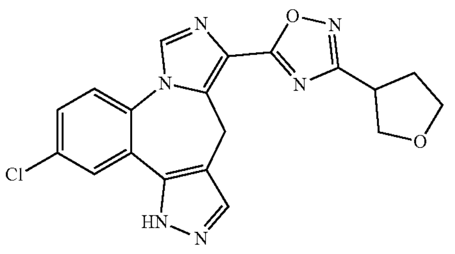 [SMILES: Clc1ccc2c(c1)-c1[nH]ncc1Cc1c(-c3nc(C4CCOC4)no3)ncn1-2]

Example 22 was prepared analogously as Example 14, using N'-hydroxyoxolane-3-carboximidamide in Step 2. MS: [M+1]=395.

-continued

| | |
|---|---|
| Ex. 29 Compound 125: | OMe, iPr, Pyr-3-$CH_2$ |
| Ex. 29-1 Compound 231: | OMe, iPr, THF-2-yl-$CH_2$ |
| Ex. 29-2 Compound 245: | OMe, iPr, THF-3-yl-$CH_2$ |
| Ex. 29-3 Compound 232: | OMe, iPr, THF-3-yl |
| Ex. 29-4 Compound 226: | OMe, cPr, OXT-3-yl-$CH_2$ |
| Ex. 29a Compound 298: | MeO, $MeOCH_2$, OXT-3-yl-$CH_2$ |
| Ex. 29b Compound 299: | MeO, $MeOCH_2$, THF-3-yl-$CH_2$ |
| Ex. 29c Compound 351: | Cl, $MeOCH_2$, THF-3-yl-$CH_2$ |
| Ex. 29d Compound 300: | MeO, $MeOCH_2$, $MeOCH_2CH_2$ |
| Ex. 29e Compound 315: | MeO, $MeOCH_2$, $CF_3OCH_2CH_2$ |
| Ex. 29-5 Compound 168: | OMe, cPr, THF-3-yl-$CH_2$ |
| Ex. 29-6 Compound 247: | OMe, cPr, THF-3-yl |
| Ex. 30 Compound 116: | OMe, CF3, cPr $CH_2$ |
| Ex. 30-1 Compound 263: | OMe, CF3, THF-3-yl |
| Ex. 30-2 Compound 264: | OMe, CF3, THF-2-yl-$CH_2$ |
| Ex. 30-3 Compound 265: | OMe, CF3, THF-3-yl-$CH_2$ |
| Ex. 31 Compound 103: | Cl, iPr, Me |
| Ex. 32 Compound 104: | Cl, iPr, Et |

Scheme 6

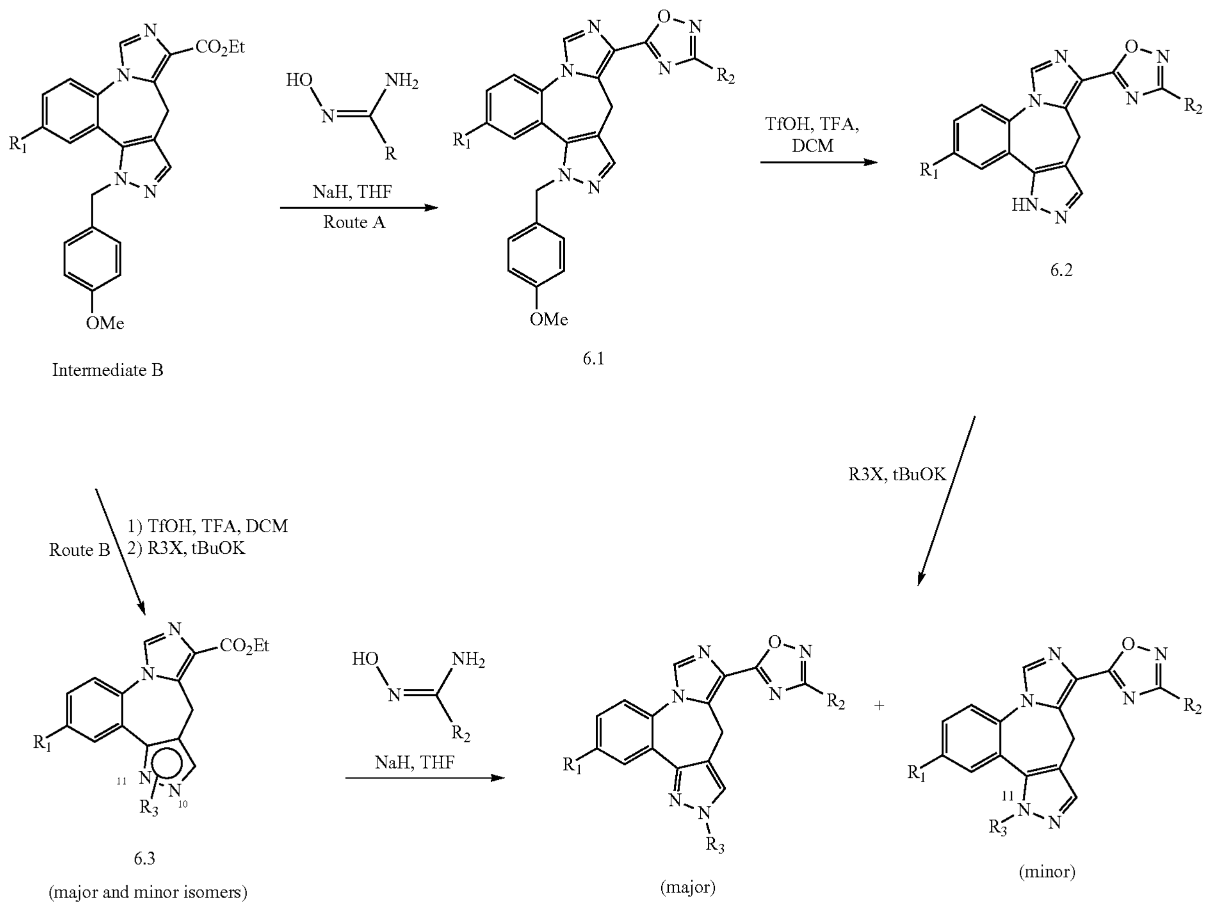

Intermediate B 6.1

6.2

6.3
(major and minor isomers)

(major)

(minor)

| Major N10 isomer (Route A) | |
|---|---|
| R1 R2 R3 | |
| Ex. 23 Compound 46: | OMe, iPr, Me |
| Ex. 24 Compound 21: | OMe, Me, 2-F Bn |
| Ex. 25 Compound 22: | OMe, Me, 3-F Bn |
| Ex. 26 Compound 23: | OMe, Me, 4-F Bn |
| Ex. 27 Compound 44: | OMe, iPr, Bn |
| Ex. 28 Compound 124: | OMe, iPr, Pyr-2-$CH_2$ |

-continued

| | |
|---|---|
| Ex. 33 Compound 138: | Cl, iPr, iPr |
| Ex. 34 Compound 096: | Cl, iPr, Bn |
| Ex. 35 Compound 111: | Cl, iPr, $MeO(CH_2)_2$ |
| Ex. 35-1 Compound 251: | Cl, iPr, THP-4-yl $CH_2$ |
| Ex. 36 Compound 112: | Cl, iPr, $Me_2N(CH_2)_2$ |
| Ex. 37 Compound 099: | Cl, iPr, Pyr-2-$CH_2$ |
| Ex. 38 Compound 098: | Cl, iPr, Pyr-3-$CH_2$ |
| Ex. 39 Compound 097: | Cl, iPr, Pyr-4-$CH_2$ |

-continued

| | |
|---|---|
| Ex. 40 Compound 127: | Cl, cPr, Me |
| Ex. 41 Compound 133: | Cl, cPr, Et |
| Ex. 42 Compound 154: | Cl, cPr, iPr |
| Ex. 43 Compound 129: | Cl, cPr, cPr-$CH_2$ |
| Ex. 44 Compound 128: | Cl, cPr, $MeO(CH_2)_2$ |
| Ex. 44-1 Compound 224: | Cl, cPr, OXT-3-yl-$CH_2$ |
| Ex. 45 Compound 135: | Cl, cPr, Pyr-2-$CH_2$ |
| Ex. 46 Compound 113: | Cl, tBu, Me |
| Ex. 46-1 Compound 227: | Cl, CF3, THF-2-yl-$CH_2$ |
| Ex. 46a Compound 367: | Cl, $C(Me)_2OMe$, THF-3-yl-$CH_2$ |
| Ex. 46-2 Compound 228: | Cl, CF3, THF-3-yl |
| Major N10 isomer (Route B) | |
| | R1 R2 R3 |
| Ex. 47 Compound 121: | Cl, Me, Me |
| Ex. 47-1 Compound 159: | Cl, Me, Et |
| Ex. 47-2 Compound 160: | Cl, Me, iPr |
| Ex. 47-3 Compound 161: | Cl, Me, THF-3-yl-$CH_2$ |
| Ex. 47-4 Compound 193: | Cl, iPr, THF-2-yl-$CH_2$ |
| Ex. 47a Compound 281: | Cl, THF-3-yl, THF-2-yl-$CH_2$ |
| Ex. 47-5 Compound 199: | Cl, iPr, THF-3-yl |
| Ex. 47b Compound 275: | Cl, $MeOCH_2$, THF-3-yl |
| Ex. 47c Compound 288: | Cl, $MeOCH_2$, THF-2-yl-$CH_2$ |
| Ex. 47-6 Compound 201: | Cl, iPr, THF-3-yl-$CH_2$ |
| Ex. 47-7 Compound 233: | Cl, $C(Me)_2OMe$, Me |
| Ex. 47d Compound 280: | Cl, $C(Me)_2OMe$, THF-2-yl-$CH_2$ |
| Ex. 47e Compound 335: | OMe, $C(Me)_2OMe$, Me |
| Ex. 47-8 Compound 234: | OMe, $C(Me)_2OMe$, Et |
| Ex. 48 Compound 134: | Cl, THF-3-yl, Me |
| Ex. 48-1 Compound 253: | Cl, THF-3-yl (R), Me |
| Ex. 48-2 Compound 261: | Cl, THF-3-yl (S) Me |
| Ex. 48-3 Compound 192: | Cl, THF-3-yl, Et |
| Ex. 48-4 Compound 219: | Cl, THP-4-yl, Me |
| Ex. 48-5 Compound 237: | Cl, $MeOCH_2$, Me |
| Ex. 48-7 Compound 242: | Cl, $iPrOCH_2$, Me |
| Ex. 48-8 Compound 250: | Cl, $O(CH_2)_2NCH_2$, Me |
| Ex. 48-9 Compound 240: | Cl, (Me)2$NCH_2$, Me |
| Ex. 48-10 Compound 266: | Cl, $(CH_2)_4NCH_2$, Et |
| Ex. 48-11 Compound 267: | OMe, $(CH_2)_4NCH_2$, Et |
| Ex. 48a Compound 328: | MeO, $O(CH_2CH_2)_2NCH_2$, Me |
| Ex. 48-12 Compound 239: | OMe, OXT-3-yl, Me |
| Ex. 49 Compound 122: | Cl, CF3, Me |
| Ex. 49-1 Compound 200: | Cl, CF3, THF-3-yl-$CH_2$ |
| Ex. 50 Compound 020: | OMe, Me, Me |
| Ex. 50-1 Compound 252: | OMe, THF-3-yl (R), Me |
| Ex. 50-2 Compound 260: | OMe, THF-3-yl (S), Me |
| Ex. 50-3 Compound 119: | OMe, CF3, Me |
| Ex. 51 Compound 016: | OMe, Me, Bn |
| Ex. 52 Compound 151: | OMe, iPr, Et |
| Ex. 53 Compound 043: | OMe, iPr, 2-F Bn |
| Ex. 54 Compound 120: | OMe, cPr, Me |
| Ex. 55 Compound 152: | OMe, cPr, Et |
| Ex. 55-1 Compound 169: | OMe, cPr, iPr |
| Ex. 55-2 Compound 171: | OMe, cPr, cPr$CH_2$ |
| Ex. 56 Compound 118: | OMe, tBu, Me |
| Ex. 56-1 Compound 170: | OMe, $MeOCH_2$, Me |
| Ex. 56-2 Compound 236: | OMe, $MeOCH_2$, Et |
| Ex. 56-3 Compound 241: | OMe, $(Me)_2NCH_2$, Et |
| Ex. 57 Compound 017: | OMe, tBu, Bn |
| Ex. 58 Compound 126: | OMe, THF-3-yl, Me |
| Ex. 58-1 Compound 220: | OMe, THP-4-yl, Me |
| Ex. 58a Compound 352: | OMe, $O(CH_2CH_2)_2MeC$, Me |
| Minor N11 isomer (Route A) | |
| | R1 R2 R3 |
| Ex. 60 Compound 047: | OMe, iPr, Me |
| Ex. 60-1 Compound 244: | OMe, iPr, THF-2-yl-CH2 |
| Ex. 60-2 Compound 246: | OMe, iPr, THF-3-yl-CH2 |
| Ex. 60-3 Compound 249: | OMe, cPr, THF-3-yl-CH2 |
| Ex. 61 Compound 139: | Cl, cPr, Et |
| Ex. 61-1 Compound 162: | Cl, cPr, cPr-CH2 |
| Ex. 62 Compound 117: | OMe, CF3, cPr CH2 |

Example 23 and Example 60: Synthesis of Compound 46 and Compound 47

Example 23 and Example 60 were prepared following Scheme 6, Route A. Intermediate B ($R_1$=OMe; 99.7 mg, 0.224 mmol) and isobutyramide oxime (275.0 mg, 2.69 mmol; dried over $P_2O_5$ under vacuum overnight) were stirred in THE (1.4 ml) at 0° C., NaH (60% oil suspension; 54.0 mg, 1.34 mmol) was added. After 20 min stirring at 0° C., the reaction was heated to 70° C. for 1 h. Upon cooling, the reaction was diluted with EtOAc, washed with sat. $NaHCO_3$, brine, and dried over $MgSO_4$. Filtration and concentration followed by silica gel column chromatography using 0 to 5% MeOH in DCM gradient gave 69.4 mg of methoxybenzylated pyrazole oxadiazole 6.1 as a yellowish solid.

Product 6.1 from above was treated with trifluoromethane sulfonic acid (45 mg) in a mixture of trifluoroacetic acid (0.7 ml) and DCM (0.7 ml) at rt for 3 days. The reaction mixture was concentrated, treated with sat. $NaHCO_3$, and extracted with EtOAc (3×). The combined organic extract was washed with water, brine, and dried over $MgSO_4$. Filtration and solvent removal followed by silica gel column chromatography using 0 to 5% MeOH in DCM gave 35.0 mg debenzylated oxadiazole 6.2 as a yellowish solid.

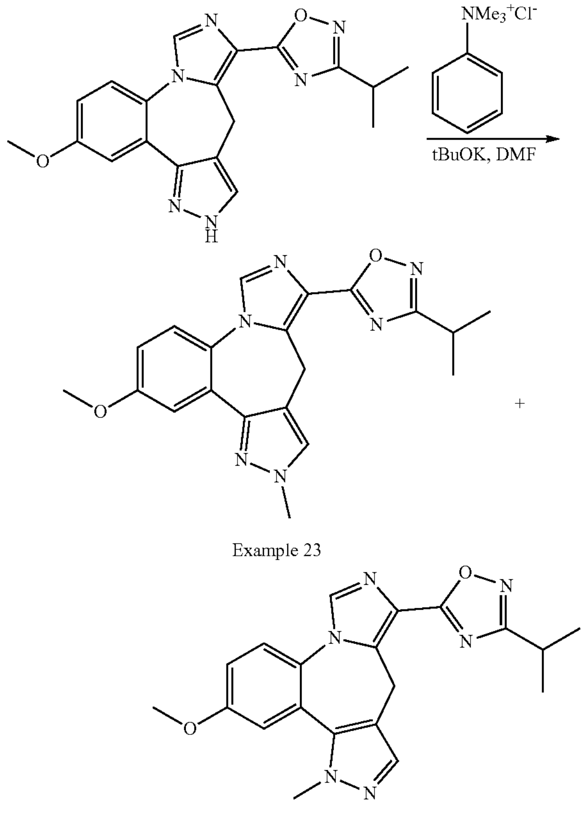

Example 23

Example 60

Trimethylphenylammonium chloride was azeotroped three times in toluene before use. Trimethylphenylammonium chloride (43.2 mg, 0.252 mmol) and the starting oxadiazole (22.8 mg, 0.0629 mmol) was stirred in DMF (0.4 ml) at 0° C., tBuOK (7.8 mg, 0.0692 mmol) was added. After 30 min stirring at 0° C., the reaction was heated at 60° C. for 16 h, quenched with sat. $NaHCO_3$, extracted with EtOAc (3×), the combined extracts washed with brine, and dried over $MgSO_4$. Prep. TLC using 10% MeOH in a mixed solvent of hexane/EtOAc (1:1) gave 7.7 mg of Example 23, compound 46 as the major product, MS: [M+1]=377. $H^1NMR$ ($CDCl_3$) δ 7.80 (1H, s), 7.49 (1H, d, J=4 Hz), 7.47 (1H, d, J=8 Hz), 7.38 (1H, s), 7.05 (1H, dd, J=4, 8 Hz), 4.35 (2H, br s), 3.96 (3H, s), 3.95 (3H, s), 3.20 (1H, m), and 1.44 (6H, d, J=4 Hz).

Also isolated was 1.4 mg of the minor isomer Example 60, compound 47, MS: [M+1]=377. $H^1NMR$ ($CDCl_3$) δ 7.81 (1H, s), 7.55 (1H, d, J=8 Hz), 7.50 (1H, s), 7.12 (1H, s), 7.11 (1H, br d, J=8 Hz), 4.96 (1H, d, J=16 Hz), 4.06 (3H, s), 3.96 (3H, s), 3.56 (1H, d, J=16 Hz), 3.21 (1H, m), and 1.45 (6H, d, J=4 Hz).

Example 24: Synthesis of Compound 21

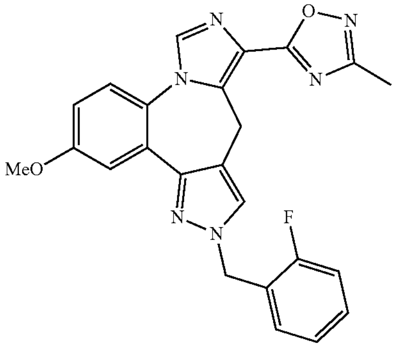 [SMILES: COc1ccc2c(c1)-c1nn(Cc3ccccc3F)cc1Cc1c(-c3nc(C)no3)ncn1-2]

Example 24 was synthesized analogously as Example 23, using acetamide oxime in the oxadiazole ring formation and 2-fluoro benzylbromide in the final pyrazole N-alkylation steps. MS: [M+1]=443. $H^1NMR$ ($CDCl_3$) δ 7.76 (1H, s), 7.49 (1H, d, J=4 Hz), 7.42 (1H, d, J=8 Hz), 7.40 (1H, s), 7.30 (1H, m), 7.17 (1H, m), 7.09 (2H, m), 7.00 (1H, dd, J=4, 12 Hz), 5.36 (2H, s), 4.26 (2H, br s), 3.91 (3H, s), and 2.44 (3H, s).

Example 25: Synthesis of Compound 22

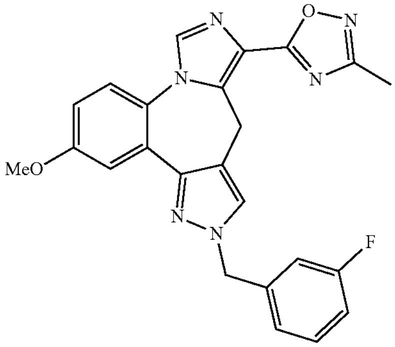 [SMILES: COc1ccc2c(c1)-c1nn(Cc3cccc(F)c3)cc1Cc1c(-c3nc(C)no3)ncn1-2]

Example 25 was synthesized analogously as Example 23, using acetamide oxime in the oxadiazole formation and 3-fluoro benzyl bromide in the final pyrazole N-alkylation steps. MS: [M+1]=443.

Example 26: Synthesis of Compound 23

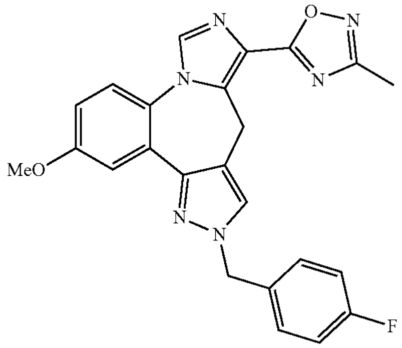 [SMILES: COc1ccc2c(c1)-c1nn(Cc3ccc(F)cc3)cc1Cc1c(-c3nc(C)no3)ncn1-2]

Example 26 was synthesized analogously as Example 23, using acetamide oxime in the oxadiazole formation and 4-fluoro benzylbromide in the final pyrazole N-alkylation steps. MS: [M+1]=443.

Example 27: Synthesis of Compound 44

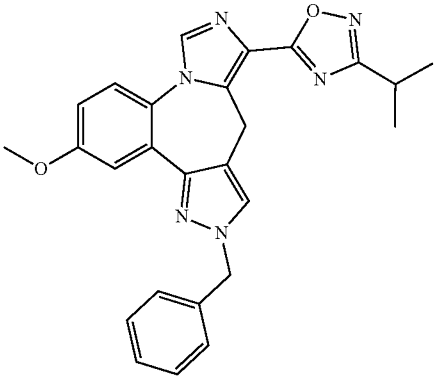 [SMILES: COc1ccc2c(c1)-c1nn(Cc3ccccc3)cc1Cc1c(-c3nc(C(C)C)no3)ncn1-2]

Example 27 was synthesized analogously as Example 23, using benzylbromide in the final pyrazole N-alkylation steps. MS: [M+1]=453.

Example 28: Synthesis of Compound 124

Example 28 was synthesized analogously as Example 23, with slight modification on the final N-alkylation step when 2-(bromomethyl)pyridine hydrobromide was used as the alkylating agent.

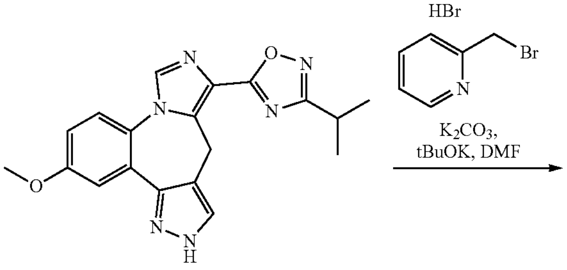

-continued

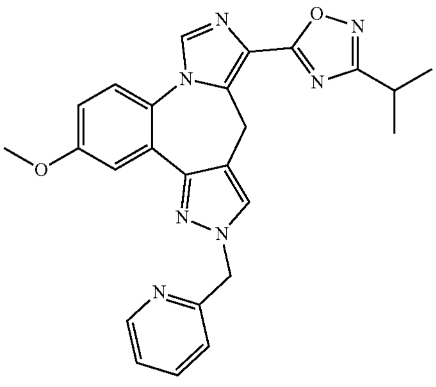

Example 28

2-(Bromomethyl)pyridine hydrobromide (138.4 mg, 0.547 mmol; dried over $P_2O_5$ under vacuum overnight before use) and the starting oxadiazole (24.8 mg, 0.0684 mmol) were stirred in DMF (0.8 ml) at 0° C., $K_2CO_3$ (75.6 mg, 0.547 mmol) was added, followed by tBuOK (61.4 mg, 03547 mmol). Ice bath was removed and the reaction was allowed to proceed at rt. Progress of the reaction was monitored by LCMS, with more 2-(Bromomethyl)pyridine hydrobromide and tBuOK added when needed to drive the reaction. Work-up by diluting with EtOAc, washed with sat. $NaHCO_3$, brine, and dried over $MgSO_4$. Example 28 was isolated by prep. TLC using 7% MeOH in EtOAc/DCM (1:1) as eluent, Wt: 2.3 mg. MS: [M+1]=454.

Example 29: Synthesis of Compound 125

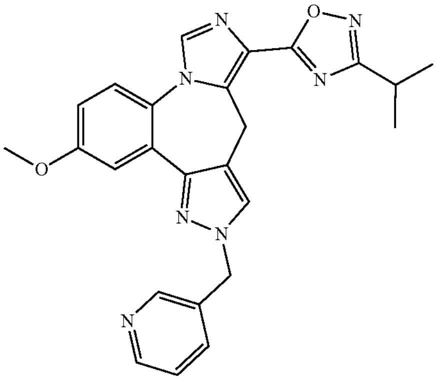 [SMILES: COc1ccc2c(c1)-c1nn(Cc3cccnc3)cc1Cc1c(-c3nc(C(C)C)no3)ncn1-2]

Example 29 was synthesized analogously as Example 28, using 3-(Bromomethyl)pyridine hydrobromide as the alkylating agent in the final pyrazole N-alkylation steps. MS: [M+1]=454.

Example 29-1 and Example 60-1: Synthesis of Compound 231 and Compound 244

Compound 231

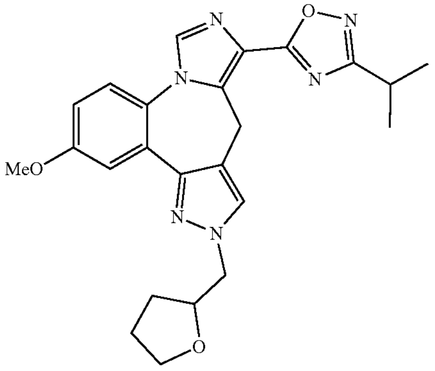

Compound 244

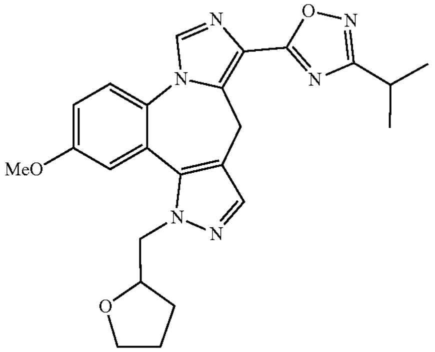

Compound 231 was prepared analogously as Example 29, using tetrahydrofurfuryl bromide as the N-alkylating agent in the pyrazole alkylation step. MS: [M+1]=447. Also isolated from the preparation was small amount of the N11 minor isomer Example 60-1 compound 244. MS: [M+1]=447.

Example 29-2 and Example 60-2: Synthesis of Compound 245 and Compound 246

Compound 245

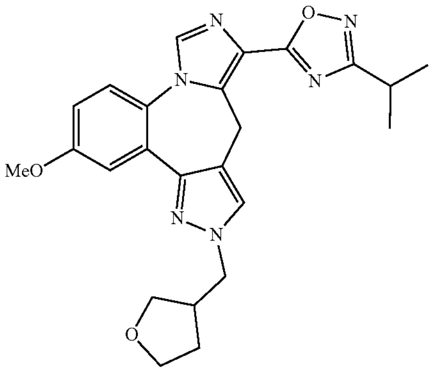

-continued

Compound 246

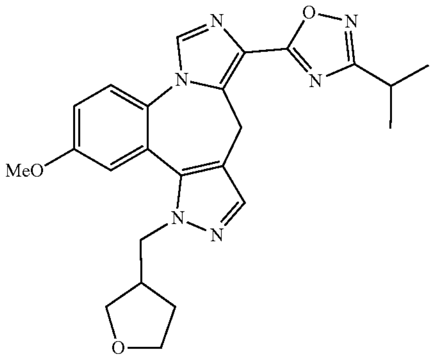

Compound 245 was prepared analogously as Example 29, using 3-bromomethyl oxolane as the N-alkylating agent in the pyrazole alkylation step. MS: [M+1]=447. Also isolated from the preparation was small amount of the N11 minor isomer Example 60-2 compound 246. MS: [M+1]=447.

Example 29-3: Synthesis of Compound 232

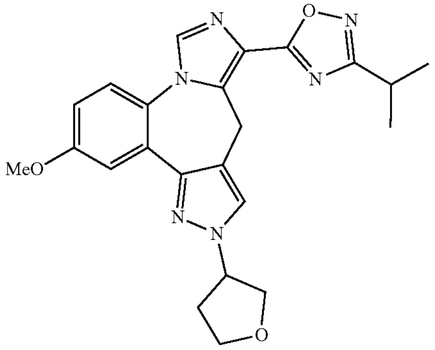 [SMILES: COc1ccc2c(c1)-c1nn(C3CCOC3)cc1Cc1c(-c3nc(C(C)C)no3)ncn1-2]

Compound 232 was prepared analogously as Example 29, using 3-bromotetrahydrofuran as the N-alkylating agent in the pyrazole alkylation step. MS: [M+1]=433.

Example 29-4: Synthesis of Compound 226

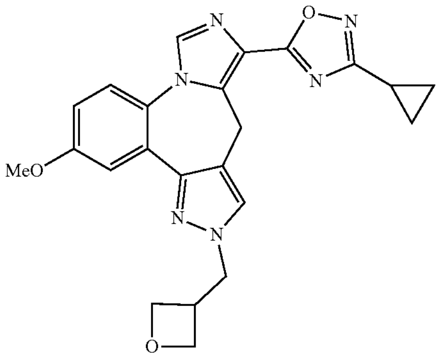 [SMILES: COc1ccc2c(c1)-c1nn(CC3COC3)cc1Cc1c(-c3nc(C4CC4)no3)ncn1-2]

Compound 226 was synthesized analogously as Example 23, using N'-hydroxycyclopropanecarboximidamide in the oxadiazole ring formation and toluene-4-sulfonic acid-oxetan-3-yl-methyl ester in the pyrazole N-alkylation steps. MS: [M+1]=431.

Example 29a: Synthesis of Compound 298

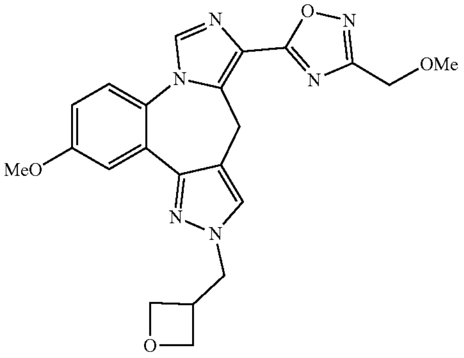 [SMILES: COCc1noc(-c2ncn3c2Cc2cn(CC4COC4)nc2-c2cc(OC)ccc2-3)n1]

Compound 298 was synthesized analogously as Compound 226, using methoxyacetamide oxime to form the oxadiazole ring. MS: [M+1]=435.

Example 29b: Synthesis of Compound 299

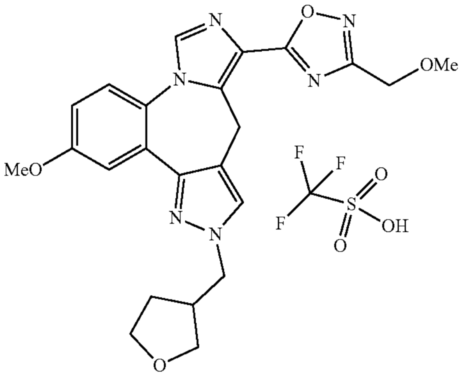

Compound 299 was synthesized analogously as Compound 298, using 3-iodomethyl tetrahydrofuran in the pyrazole N-alkylation steps. MS: [M+1]=450.

Example 29c: Synthesis of Compound 351

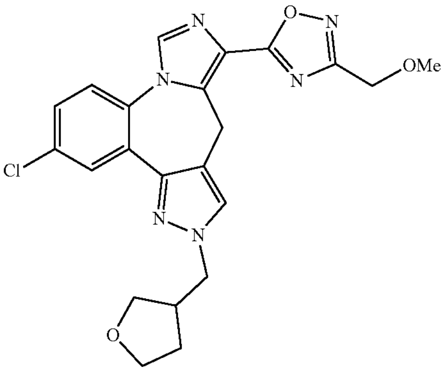 [SMILES: COCc1noc(-c2ncn3c2Cc2cn(CC4CCOC4)nc2-c2cc(Cl)ccc2-3)n1]

Compound 351 was synthesized analogously as Compound 299, starting with Intermediate B ($R_1$=Cl). MS: [M+1]=453.

Example 29d: Synthesis of Compound 300

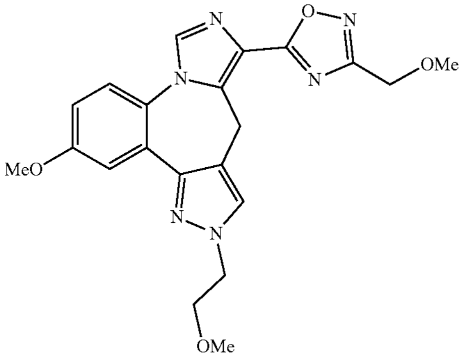 [SMILES: COCCn1cc2c(n1)-c1cc(OC)ccc1-n1cnc(-c3nc(COC)no3)c1C2]

Compound 300 was synthesized analogously as Compound 298, using 2-bromoethyl methyl ether in the pyrazole N-alkylation steps. MS: [M+1]=423.

Example 29e: Synthesis of Compound 315

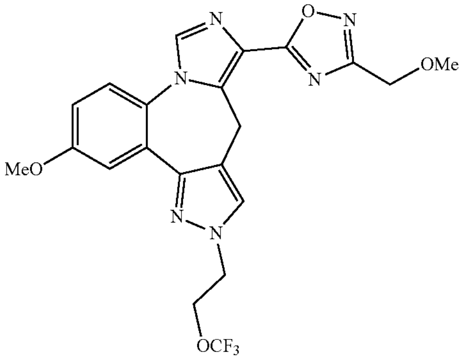 [SMILES: COCc1noc(-c2ncn3c2Cc2cn(CCOC(F)(F)F)nc2-c2cc(OC)ccc2-3)n1]

Compound 315 was synthesized analogously as Compound 298, using trifluoromethoxy ethyl bromide in the pyrazole N-alkylation steps. MS: [M+1]=477.

Example 29-5 and Example 60-3: Synthesis of Compound 168 and Compound 249

Compound 168

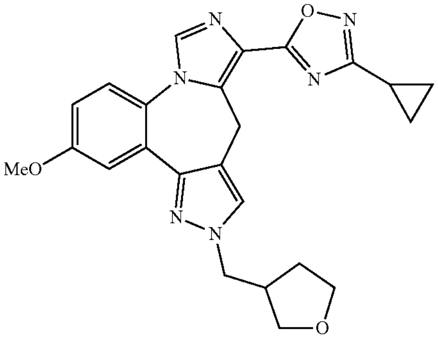

Compound 249

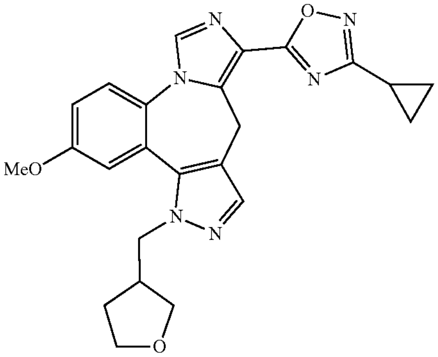

Compound 168 was prepared analogously as Example 29-4, using 3-bromomethyl oxolane as the N-alkylating agent in the pyrazole alkylation step. MS: [M+1]=445.

Also isolated from the preparation was small amount of the N11 minor isomer Example 60-3, Compound 249. MS: [M+1]=445.

Example 29-6 Synthesis of Compound 247

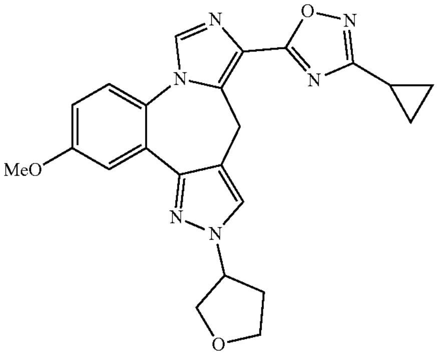 [SMILES: COc1ccc2c(c1)-c1nn(C3CCOC3)cc1Cc1c(-c3nc(C4CC4)no3)ncn1-2]

Compound 247 was synthesized analogously as Example 29-4, using 3-bromotetrahydrofuran in the pyrazole N-alkylation steps. MS: [M+1]=431.

Example 30 and Example 62: Synthesis of Compound 116 and Compound 117

Compound 116

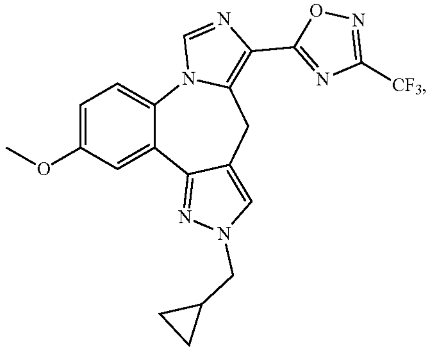

Example 37

Compound 117

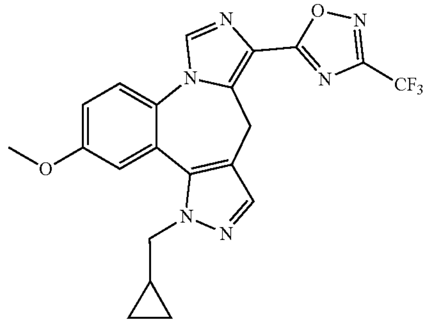

Example 62

Example 30 was prepared by N10-alkylation of Example 13 (Scheme 5) with iodomethyl cyclopropane under the same conditions described in Scheme 6 using tBuOK as the base. MS: [M+1]=443.

Also isolated was small amount of the N11 minor isomer Example 62, compound 117. MS: [M+1]=443.

Example 30-1: Synthesis of Compound 263

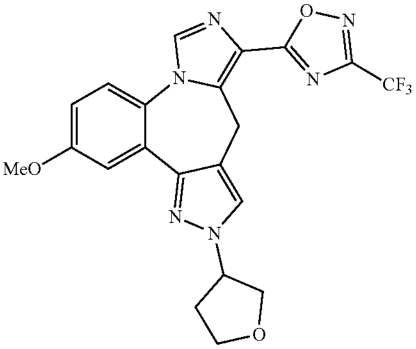 [SMILES: COc1ccc2c(c1)-c1nn(C3CCOC3)cc1Cc1c(-c3nc(C(F)(F)F)no3)ncn1-2]

Compound 263 was prepared analogously as Example 30, using 3-bromotetrahydrofuran as the N-alkylating agent in the pyrazole alkylation step. MS: [M+1]=459.

Example 30-2: Synthesis of Compound 264

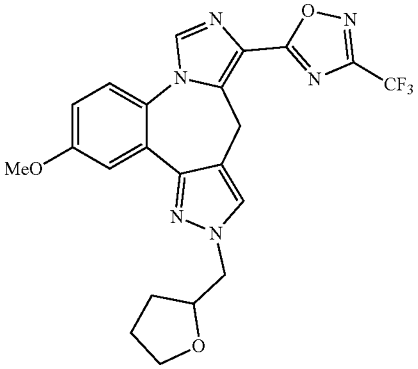 [SMILES: COc1ccc2c(c1)-c1nn(CC3CCCO3)cc1Cc1c(-c3nc(C(F)(F)F)no3)ncn1-2]

Compound 264 was prepared analogously as Example 30, using tetrahydrofurfuryl bromide as the N-alkylating agent in the pyrazole alkylation step. MS: [M+1]=473.

Example 30-3: Synthesis of Compound 265

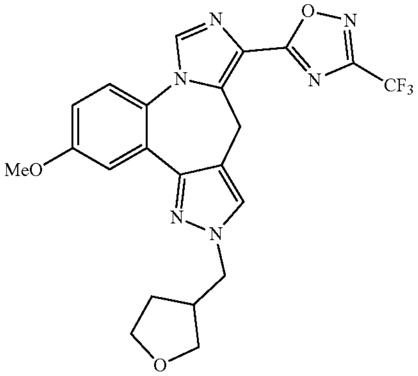 [SMILES: COc1ccc2c(c1)-c1nn(CC3CCOC3)cc1Cc1c(-c3nc(C(F)(F)F)no3)ncn1-2]

Compound 265 was prepared analogously as Example 30, using 3-bromomethyl oxolane as the N-alkylating agent in the pyrazole alkylation step. MS: [M+1]=473.

Example 31: Synthesis of Compound 103

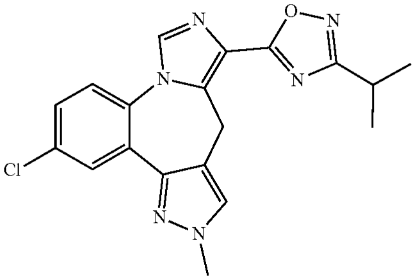 [SMILES: CC(C)c1noc(-c2ncn3c2Cc2cn(C)nc2-c2cc(Cl)ccc2-3)n1]

Example 31 was prepared analogously as Example 23, starting with Intermediate B ($R^1$=Cl). MS: [M+1]=381.

Example 32 Synthesis of Compound 104

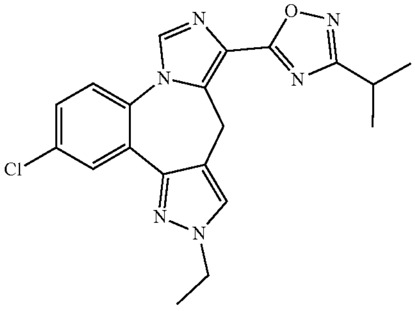 [SMILES: CCn1cc2c(n1)-c1cc(Cl)ccc1-n1cnc(-c3nc(C(C)C)no3)c1C2]

Example 32 was prepared analogously as Example 31, using ethyl iodide as the N-alkylating agent in the final pyrazole alkylation step. MS: [M+1]=395.

Example 33 Synthesis of Compound 138

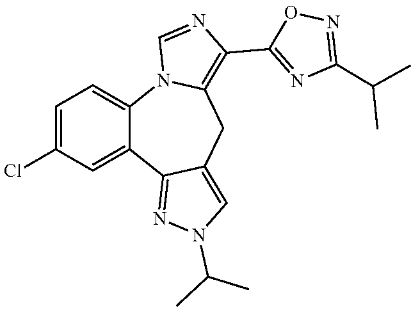 [SMILES: CC(C)c1noc(-c2ncn3c2Cc2cn(C(C)C)nc2-c2cc(Cl)ccc2-3)n1]

Example 33 was prepared analogously as Example 31, using 2-iodo propane as the N-alkylating agent in the final pyrazole alkylation step. MS: [M+1]=409.

Example 34: Synthesis of Compound 96

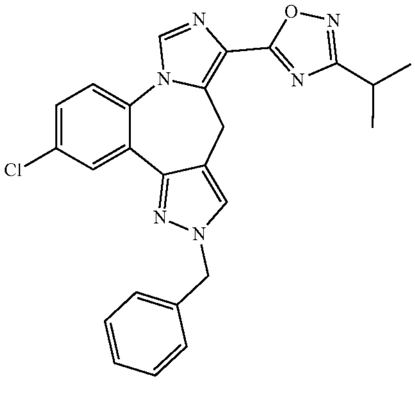 [SMILES: CC(C)c1noc(-c2ncn3c2Cc2cn(Cc4ccccc4)nc2-c2cc(Cl)ccc2-3)n1]

Example 34 was prepared analogously as Example 31, using benzyl bromide as the N-alkylating agent in the final pyrazole alkylation step. MS: [M+1]=457.

Example 35: Synthesis of Compound 111

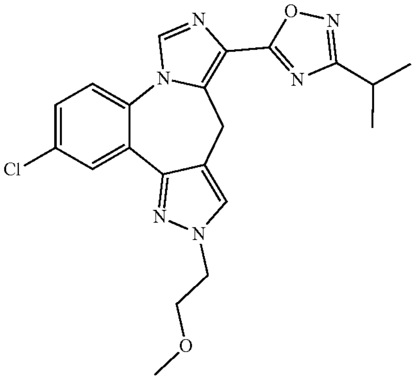 [SMILES: COCCn1cc2c(n1)-c1cc(Cl)ccc1-n1cnc(-c3nc(C(C)C)no3)c1C2]

Example 35 was prepared analogously as Example 31, using methoxy ethylbromide as the N-alkylating agent in the final pyrazole alkylation step. MS: [M+1]=425.

Example 35-1: Synthesis of Compound 251

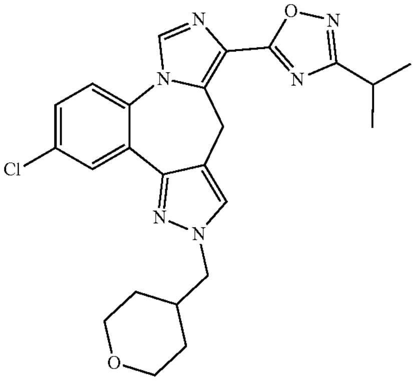 [SMILES: CC(C)c1noc(-c2ncn3c2Cc2cn(CC4CCOCC4)nc2-c2cc(Cl)ccc2-3)n1]

Compound 251 was prepared analogously as Example 31, using 4-bromomethyl tetrahydro-2H-pyran as the N-alkylating agent in the pyrazole alkylation step. MS: [M+1]=465.

Example 36: Synthesis of Compound 112

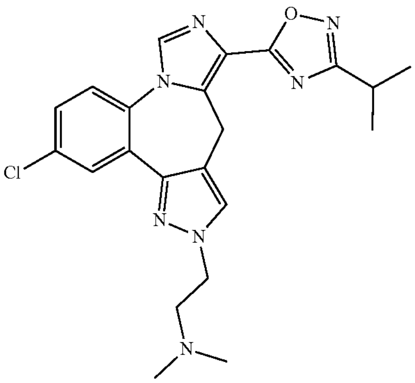 [SMILES: CC(C)c1noc(-c2ncn3c2Cc2cn(CCN(C)C)nc2-c2cc(Cl)ccc2-3)n1]

Example 36 was prepared analogously as Example 28, starting with Intermediate B ($R_1$=Cl), and using N,N-dimethylaminoethyl bromide hydrobromide as the N-alkylating agent in the final pyrazole alkylation step. MS: [M+1]=438.

Example 37: Synthesis of Compound 99

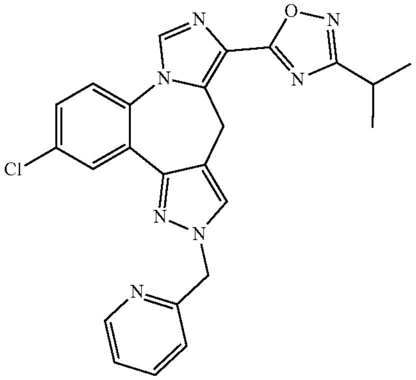 [SMILES: CC(C)c1noc(-c2ncn3c2Cc2cn(Cc4ccccn4)nc2-c2cc(Cl)ccc2-3)n1]

Example 37 was prepared analogously as Example 36, using 2-(bromomethyl)pyridine hydrobromide as the N-alkylating agent in the final pyrazole alkylation step. MS: [M+1]=458.

Example 38: Synthesis of Compound 98

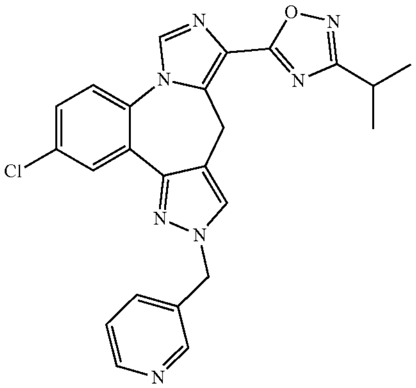 [SMILES: CC(C)c1noc(-c2ncn3c2Cc2cn(Cc4cccnc4)nc2-c2cc(Cl)ccc2-3)n1]

Example 38 was prepared analogously as Example 36, using 3-(bromomethyl)pyridine hydrobromide as the alkylating agent in the final pyrazole N-alkylation steps. MS: [M+1]=458.

Example 39: Synthesis of Compound 97

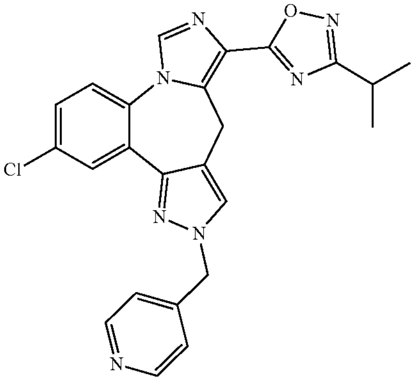 [SMILES: CC(C)c1noc(-c2ncn3c2Cc2cn(Cc4ccncc4)nc2-c2cc(Cl)ccc2-3)n1]

Example 39 was prepared analogously as Example 36, using 4-(bromomethyl)pyridine hydrobromide as the alkylating agent in the final pyrazole N-alkylation steps. MS: [M+1]=458.

Example 40: Synthesis of Compound 127

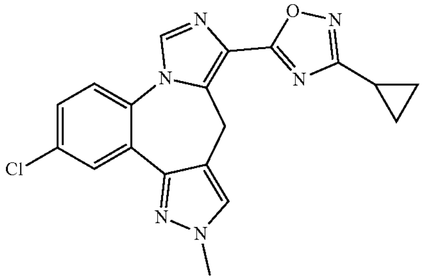 [SMILES: Cn1cc2c(n1)-c1cc(Cl)ccc1-n1cnc(-c3nc(C4CC4)no3)c1C2]

Example 40 was prepared analogously as Example 31, using N'-hydroxycyclopropanecarboximidamide in the oxadiazole formation step. MS: [M+1]=379.

Example 41 and Example 61: Synthesis of Compound 133 and Compound 139 compound 133

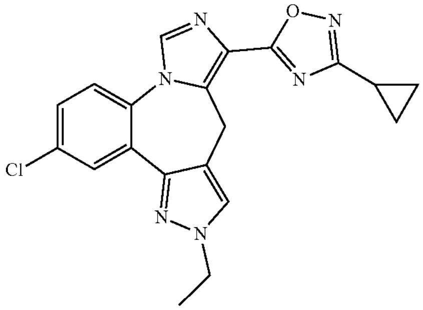

Example 41

-continued compound 139

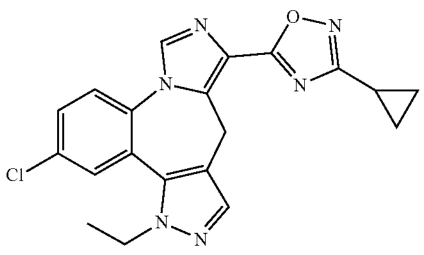

Example 61

Example 41 was prepared analogously as Example 40, using ethyl iodide as the N10-alkylating agent in the final pyrazole alkylation step. MS: [M+1]=393.

Also isolated was small amount of the N11 minor isomer Example 61, compound 139. MS: [M+1]=393.

Example 42: Synthesis of Compound 154

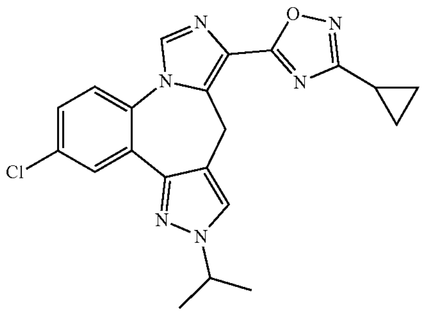 [SMILES: CC(C)n1cc2c(n1)-c1cc(Cl)ccc1-n1cnc(-c3nc(C4CC4)no3)c1C2]

Example 42 was prepared analogously as Example 40, using 2-iodo propane as the N-alkylating agent in the final pyrazole alkylation step. MS: [M+1]=407.

Example 43 and Example 61-1: Synthesis of Compound 129 and Compound 162

Compound 129

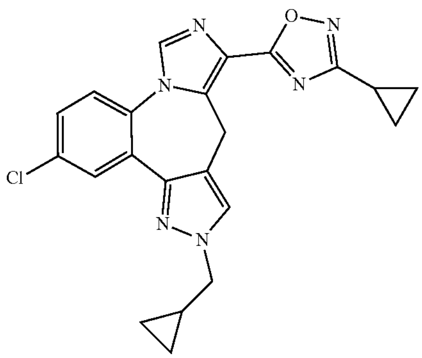

-continued

Compound 162

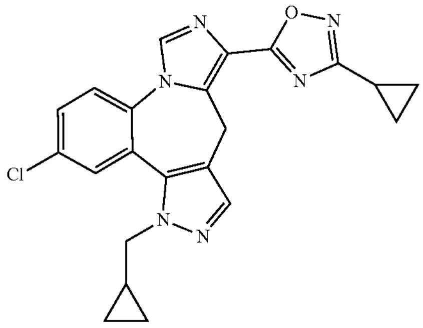

Example 43 was prepared analogously as Example 40, using cyclopropyl methyliodide as the N-alkylating agent in the final pyrazole alkylation step. MS: [M+1]=419.

Also isolated was small amount of the N11 minor isomer Example 61-1, compound 162. MS: [M+1]=419.

Example 44: Synthesis of Compound 128

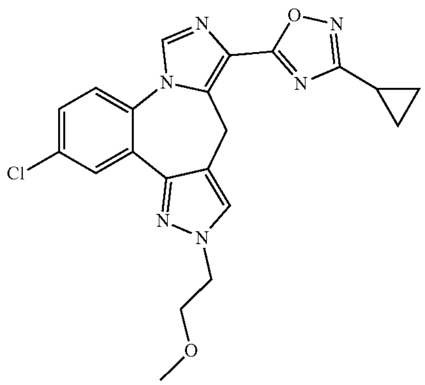 [SMILES: COCCn1cc2c(n1)-c1cc(Cl)ccc1-n1cnc(-c3nc(C4CC4)no3)c1C2]

Example 44 was prepared analogously as Example 40, using methoxyethylbromide as the N-alkylating agent in the final pyrazole alkylation step. MS: [M+1]=423.

Example 44-1: Synthesis of Compound 224

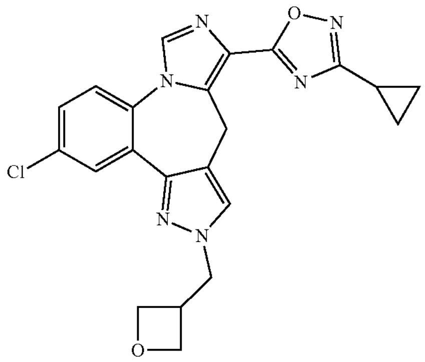 [SMILES: Clc1ccc2c(c1)-c1nn(CC3COC3)cc1Cc1c(-c3nc(C4CC4)no3)ncn1-2]

Compound 224 was prepared analogously as Example 44, using toluene-4-sulfonic acid oxetan-3-yl-methyl ester as the N-alkylating agent in the pyrazole alkylation step. MS: [M+1]=435.

Example 45: Synthesis of Compound 135

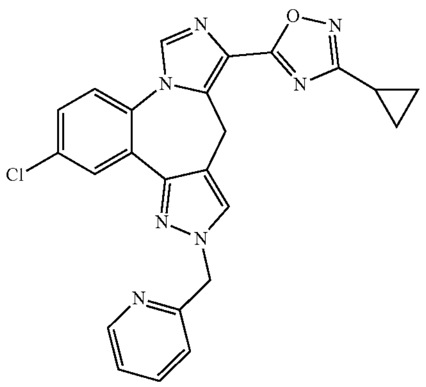 [SMILES: Clc1ccc2c(c1)-c1nn(Cc3ccccn3)cc1Cc1c(-c3nc(C4CC4)no3)ncn1-2]

Example 45 was prepared analogously as Example 37, using N'-hydroxycyclopropanecarboximidamide in the oxadiazole formation step. MS: [M+1]=456.

Example 46: Synthesis of Compound 113

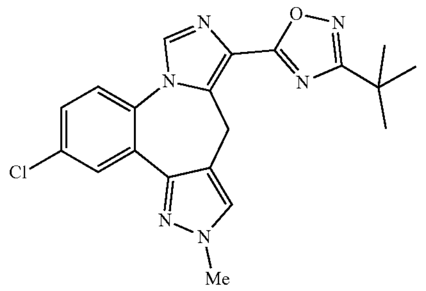 [SMILES: Cn1cc2c(n1)-c1cc(Cl)ccc1-n1cnc(-c3nc(C(C)(C)C)no3)c1C2]

Example 46 was prepared analogously as Example 40, using N'-hydroxy-2,2-dimethylpropanimidamide in the oxadiazole formation step. MS: [M+1]=395.

Example 46-1: Synthesis of Compound 227

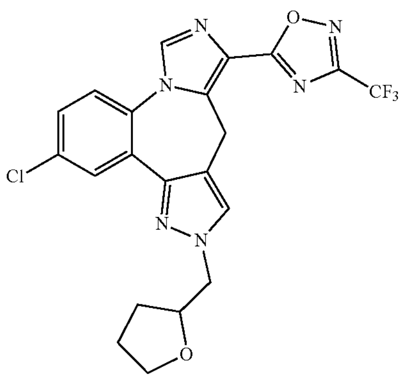 [SMILES: FC(F)(F)c1noc(-c2ncn3c2Cc2cn(CC4CCCO4)nc2-c2cc(Cl)ccc2-3)n1]

Compound 227 was prepared analogously as Example 30, starting with Intermediate B ($R_1$=Cl), and using tetrahydrofurfuryl bromide as the N-alkylating agent in the pyrazole alkylation step. MS: [M+1]=477.

Example 46a: Synthesis of Compound 367

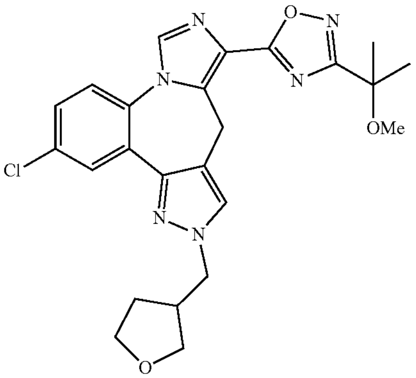 [SMILES: COC(C)(C)c1noc(-c2ncn3c2Cc2cn(CC4CCOC4)nc2-c2cc(Cl)ccc2-3)n1]

Compound 367 was synthesized analogously as Example 40, using N'-hydroxy-2-methoxy-2-methylpropanimidamide in the oxadiazole ring formation and 3-iodomethyl tetrahydrofuran in the pyrazole N-alkylation steps. MS: [M+1]=481.

Example 46-2: Synthesis of Compound 228

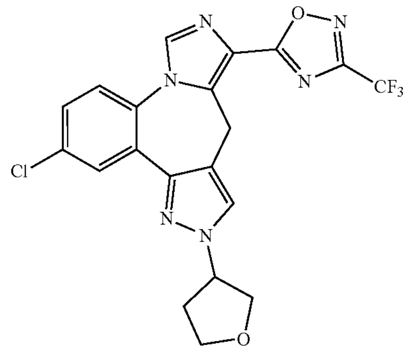 [SMILES: FC(F)(F)c1noc(-c2ncn3c2Cc2cn(C4CCOC4)nc2-c2cc(Cl)ccc2-3)n1]

Compound 228 was prepared analogously as Example 46-1, using 3-bromotetrahydrofuran as the N-alkylating agent in the pyrazole alkylation step. MS: [M+1]=463.

Example 47: Synthesis of Compound 121

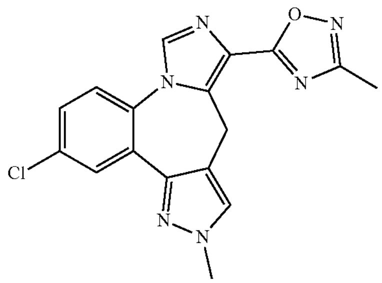 [SMILES: Cc1noc(-c2ncn3c2Cc2cn(C)nc2-c2cc(Cl)ccc2-3)n1]

Example 47 was prepared following Scheme 6, Route B.

Step 1: Intermediate B ($R_1$=Cl; 148.3 mg) was treated with trifluoromethane sulfonic acid (200 mg) in a mixture of trifluoroacetic acid (2 ml) and DCM (2 ml) at rt for 5 days. The reaction mixture was concentrated, treated with sat. $NaHCO_3$, and extracted with EtOAc (3×). The combined organic extract was washed with water, brine, and dried over $MgSO_4$. Filtration and solvent removal gave 145.5 mg crude debenzylated pyrazole ester as a yellowish solid.

Step 2: Trimethylphenylammonium chloride (303.7 mg; dried by azeotroping in tol. Repeatedly) and the starting pyrazole ester from above (145.5 mg) was stirred in DMF (2 ml) at 0° C., tBuOK (54 mg) was added. The reaction was allowed to proceed from 0° C. to rt overnight, and then heated at 60° C. for 2 h. The reaction mixture was diluted with EtOAc, washed with sat. $NaHCO_3$, brine, and dried over $MgSO_4$. Filtration and concentration followed by silica gel column chromatography using 0 to 10% MeOH in a pre-mixed solvent of hexanes/EtOAc (1:1) gradient gave 25.4 mg major N10 methylated isomer. MS: [M+1]=343.

Step 3: N10 methylated ester from above (10.0 mg, 0.0292 mmol) and acetamide oxime (26.0 mg, 0.350 mmol; dried by repeated azeotroping in tol.) was stirred in THE (0.25 ml) at 0° C., NaH (60% oil suspension; 7.0 mg, 0.175 mmol) was added. After 20 min stirring at 0° C., the reaction was heated to 70° C. for 1 h. Upon cooling, the reaction was diluted with EtOAc, washed with sat. $NaHCO_3$, brine, and dried over $MgSO_4$. Prep. TLC using 5% MeOH in EtOAc/DCM (1:1) as eluent gave Example 47, Compound 121 as an off-white solid, Wt: 6.1 mg. MS: [M+1]=353.

Example 47-1: Synthesis of Compound 159

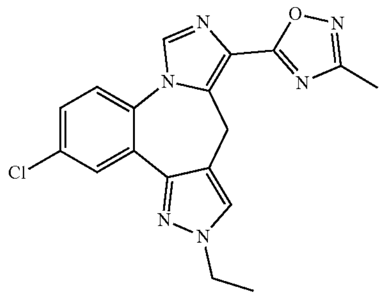 [SMILES: CCn1cc2c(n1)-c1cc(Cl)ccc1-n1cnc(-c3nc(C)no3)c1C2]

Compound 159 was prepared analogously as Example 47, using ethyl iodide as the N-alkylating agent in the pyrazole alkylation step. MS: [M+1]=367.

Example 47-2: Synthesis of Compound 160

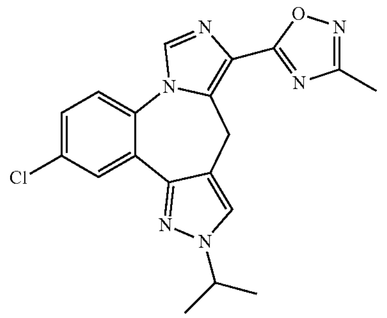 [SMILES: Cc1noc(-c2ncn3c2Cc2cn(C(C)C)nc2-c2cc(Cl)ccc2-3)n1]

Compound 160 was prepared analogously as Example 47, using 2-iodopropane as the N-alkylating agent in the pyrazole alkylation step. MS: [M+1]=381.

Example 47-3: Synthesis of Compound 161

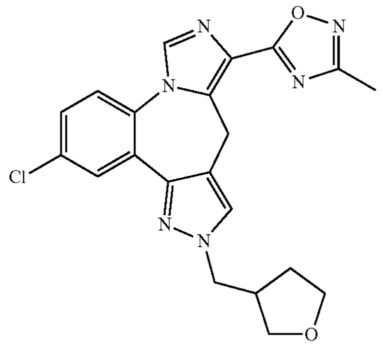 [SMILES: Cc1noc(-c2ncn3c2Cc2cn(CC4CCOC4)nc2-c2cc(Cl)ccc2-3)n1]

Compound 161 was prepared analogously as Example 47, using 3-bromomethyl oxolane as the N-alkylating agent in the pyrazole alkylation step. MS: [M+1]=423.

Example 47-4: Synthesis of Compound 193

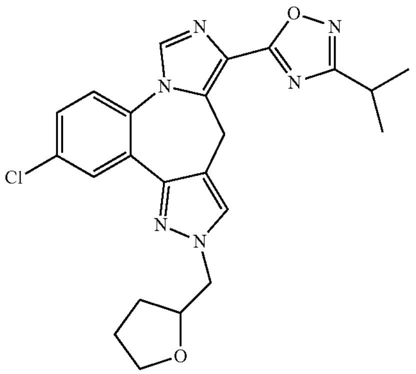 [SMILES: CC(C)c1noc(-c2ncn3c2Cc2cn(CC4CCCO4)nc2-c2cc(Cl)ccc2-3)n1]

Compound 193 was prepared analogously as Example 47, using tetrahydrofurfuryl bromide as the N-alkylating agent in the pyrazole alkylation, and isobutyramide oxime in the oxadiazole formation step. MS: [M+1]=451.

Example 47a: Synthesis of Compound 281

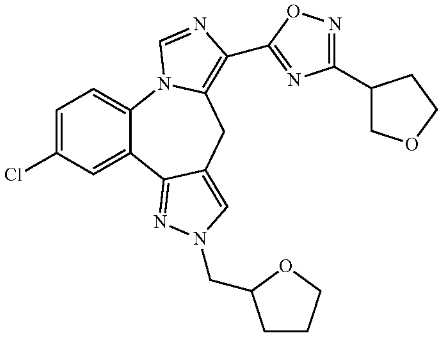 [SMILES: Clc1ccc2c(c1)-c1nn(CC3CCCO3)cc1Cc1c(-c3nc(C4CCOC4)no3)ncn1-2]

Compound 281 was prepared analogously as Compound 193, using N'-hydroxyoxolane-3-carboximidamide in the oxadiazole formation step, MS: [M+1]=479.

Example 47-5: Synthesis of Compound 199

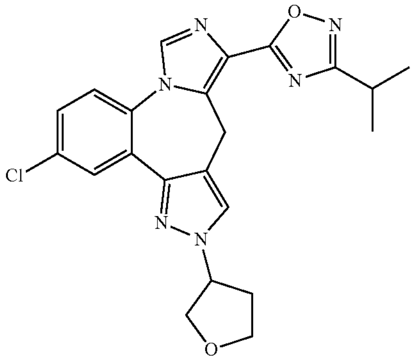 [SMILES: CC(C)c1noc(-c2ncn3c2Cc2cn(C4CCOC4)nc2-c2cc(Cl)ccc2-3)n1]

Compound 199 was prepared analogously as Example 47-4, using 3-bromo tetrahydrofuran as the N-alkylating agent in the pyrazole alkylation step, MS: [M+1]=437.

Example 47b: Synthesis of Compound 275

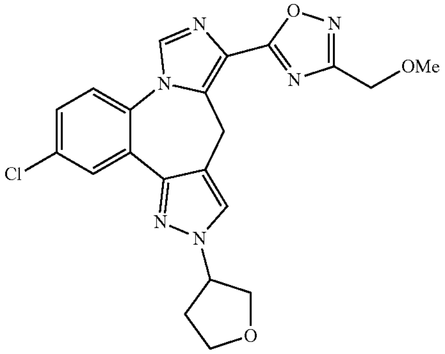 [SMILES: COCc1noc(-c2ncn3c2Cc2cn(C4CCOC4)nc2-c2cc(Cl)ccc2-3)n1]

Compound 275 was prepared analogously as Compound 199, using N'-hydroxy-2-methoxyethanimidamide in the oxadiazole formation step, MS: [M+1]=439.

Example 47c: Synthesis of Compound 288

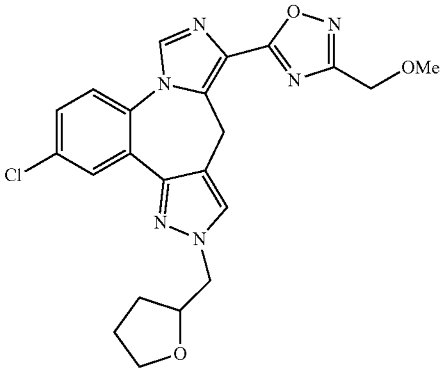 [SMILES: COCc1noc(-c2ncn3c2Cc2cn(CC4CCCO4)nc2-c2cc(Cl)ccc2-3)n1]

Compound 288 was prepared analogously as Compound 275, using tetrahydrofurfuryl bromide as the N-alkylating agent in the pyrazole alkylation. MS: [M+1]=453.

Example 47-6: Synthesis of Compound 201

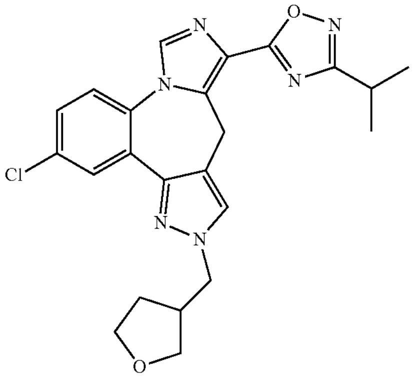 [SMILES: CC(C)c1noc(-c2ncn3c2Cc2cn(CC4CCOC4)nc2-c2cc(Cl)ccc2-3)n1]

Compound 201 was prepared analogously as Example 47-4, using 3-bromomethyl oxolane as the N-alkylating agent in the pyrazole alkylation step, MS: [M+1]=451.

Example 47-7: Synthesis of Compound 233

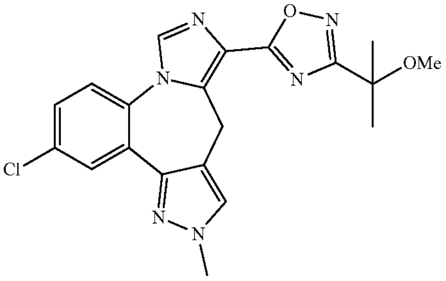 [SMILES: COC(C)(C)c1noc(-c2ncn3c2Cc2cn(C)nc2-c2cc(Cl)ccc2-3)n1]

Compound 233 was prepared analogously as Example 47, using N'-hydroxy-2-methoxy-2-methylpropanimidamide in the oxadiazole formation step. MS: [M+1]=411.

Example 47d: Synthesis of Compound 280

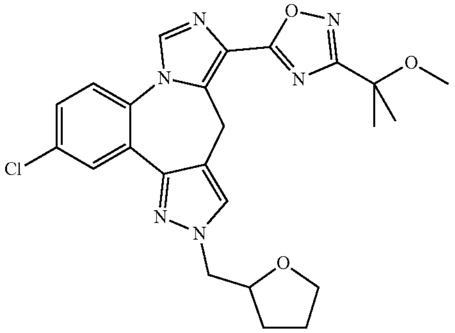 [SMILES: COC(C)(C)c1noc(-c2ncn3c2Cc2cn(CC4CCCO4)nc2-c2cc(Cl)ccc2-3)n1]

Compound 280 was prepared analogously as Compound 233, using tetrahydrofurfuryl bromide as the N-alkylating agent in the pyrazole alkylation step, MS: [M+1]=481.

Example 47e: Synthesis of Compound 335

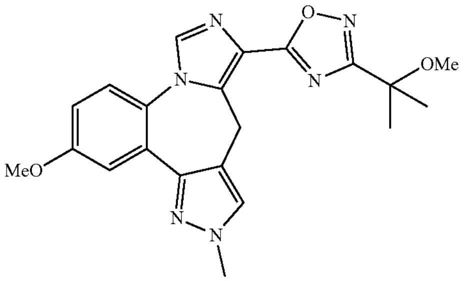 [SMILES: COc1ccc2c(c1)-c1nn(C)cc1Cc1c(-c3nc(C(C)(C)OC)no3)ncn1-2]

Compound 335 was prepared analogously as Example 47-7, starting with Intermediate B ($R_1$=OMe). MS: [M+1] =407.

Example 47-8: Synthesis of Compound 234

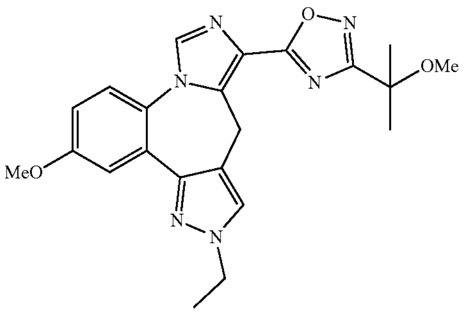 [SMILES: CCn1cc2c(n1)-c1cc(OC)ccc1-n1cnc(-c3nc(C(C)(C)OC)no3)c1C2]

Compound 234 was prepared analogously as Example 47-7, starting with Intermediate B ($R_1$=OMe), and using ethyl iodide as the N-alkylating agent in the pyrazole alkylation step. MS: [M+1]=421.

Example 48: Synthesis of Compound 134

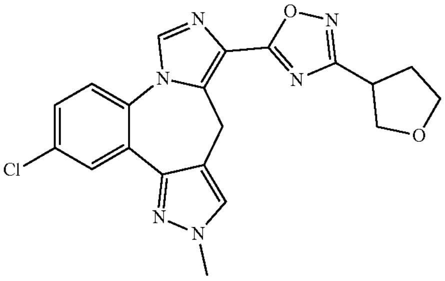 [SMILES: Cn1cc2c(n1)-c1cc(Cl)ccc1-n1cnc(-c3nc(C4CCOC4)no3)c1C2]

Example 48 was prepared analogously as Example 47, using N-hydroxytetrahydrofuran-3-carboxamidine in the final oxadiazole formation step. MS: [M+1]=409.

Example 48-1: Synthesis of Compound 253

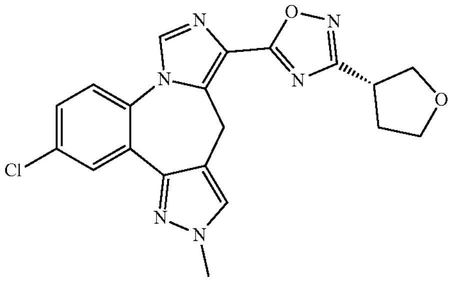 [SMILES: Cn1cc2c(n1)-c1cc(Cl)ccc1-n1cnc(-c3nc([C@H]4CCOC4)no3)c1C2]

Compound 253 was prepared analogously as Example 47, using (3R)—N'-hydroxyoxolane-3-carboximidamide in the final oxadiazole formation step. MS: [M+1]=409. (3R)—N'-hydroxyoxolane-3-carboximidamide was prepared as follows: To®-tetrahydrofuran-3-carbonitrile (229.5 mg, 2.36 mmol) in isopropanol (6 ml) and $H_2O$ (2 ml) was added hydroxylamine HCl (164.1 mg, 2.36 mmol) and potassium carbonate (326.2 mg, 2.36 mmol). The reaction mixture was heated at 80° C. for 16 h, cooled to rt, and all solvents removed in vacuo. The resulting solid was stirred in isopropanol (3 ml) and ethanol (1 ml) for about one hr, and filtered over a sintered glass filter. Solid was rinsed with isopropanol several times. Solvent of the filtrate was completely removed under vacuum to give 199.6 mg (65%) of the product as a clear oil.

Example 48-2: Synthesis of Compound 261

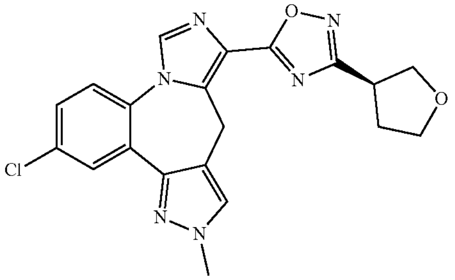 [SMILES: Cn1cc2c(n1)-c1cc(Cl)ccc1-n1cnc(-c3nc([C@@H]4CCOC4)no3)c1C2]

Compound 261 was prepared analogously as Example 48-1, using (3S)—N'-hydroxyoxolane-3-carboximidamide in the final oxadiazole formation step. MS: [M+1]=409. (3S)—N'-hydroxyoxolane-3-carboximidamide was prepared similarly as its R isomer, starting with (S)-tetrahydrofuran-3-carbonitrile.

Example 48-3: Synthesis of Compound 192

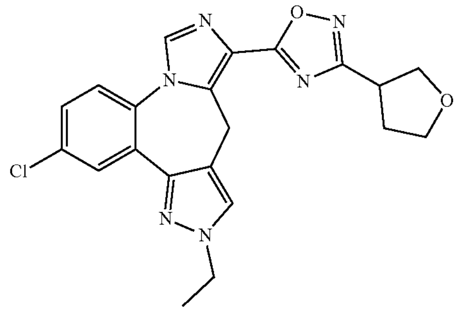 [SMILES: CCn1cc2c(n1)-c1cc(Cl)ccc1-n1cnc(-c3nc(C4CCOC4)no3)c1C2]

Compound 192 was prepared analogously as Example 48, using iodoethane as the N-alkylating agent in the pyrazole alkylation step. MS: [M+1]=423.

Example 48-4: Synthesis of Compound 219

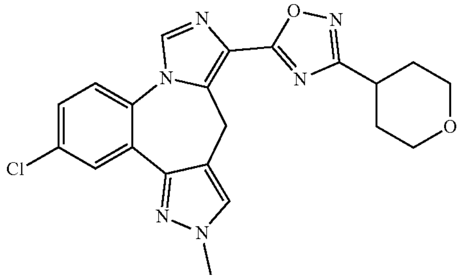 [SMILES: Cn1cc2c(n1)-c1cc(Cl)ccc1-n1cnc(-c3nc(C4CCOCC4)no3)c1C2]

Compound 219 was prepared analogously as Example 48, using N'-hydroxytetrahydro-2H-pyran-4-carboximidamide in the oxadiazole formation step. MS: [M+1]=423.

Example 48-5: Synthesis of Compound 237

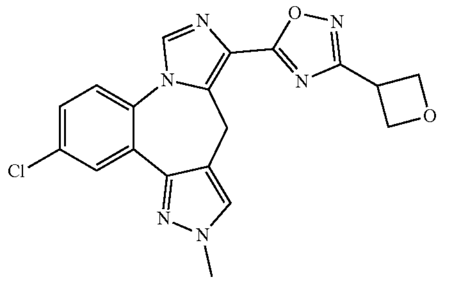 [SMILES: Cn1cc2c(n1)-c1cc(Cl)ccc1-n1cnc(-c3nc(C4COC4)no3)c1C2]

Compound 237 was prepared analogously as Example 48, using N'-hydroxyoxetane-3-carboximidamide in the oxadiazole formation step. MS: [M+1]=395. N'-hydroxyoxetane-3-carboximidamide was prepared as follows: To oxetane-3-carbonitrile (85.1 mg, 1.0 mmol) in isopropanol (3 ml) and $H_2O$ (1 ml) was added hydroxylamine HCl (71.2 mg, 1.0 mmol) and potassium carbonate (141.0 mg, 1 mmol). The reaction mixture was heated at 80° C. for 16 h, cooled to rt, and all solvents removed in vacuo. The resulting brownish solid was stirred in isopropanol (1.5 ml) and ethanol (0.5 ml) for about one hr, and filtered over a sintered glass filter. Solid was rinsed with isopropanol several times. Solvent of the filtrate was completely removed under vacuum to give 81.2 mg (69%) of the product as an off white waxy solid.

Example 48-6: Synthesis of Compound 235

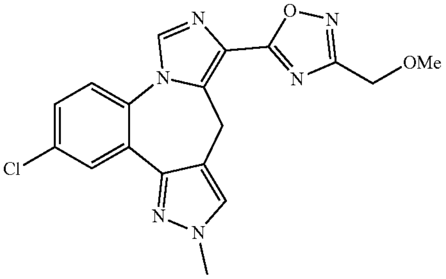 [SMILES: COCc1noc(-c2ncn3c2Cc2cn(C)nc2-c2cc(Cl)ccc2-3)n1]

Compound 235 was prepared analogously as Example 48, using N'-hydroxy-2-methoxyethanimidamide in the oxadiazole formation step. MS: [M+1]=383.

Example 48-7: Synthesis of Compound 242

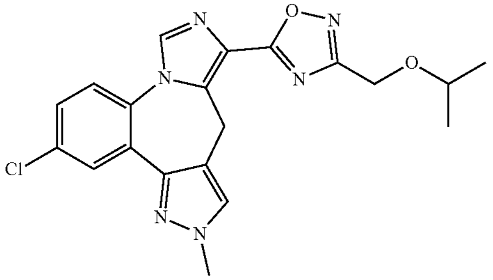 [SMILES: CC(C)OCc1noc(-c2ncn3c2Cc2cn(C)nc2-c2cc(Cl)ccc2-3)n1]

Compound 242 was prepared analogously as Example 48, using N'-hydroxy-2-propan-2-yloxyethanimidamide in the oxadiazole formation step. MS: [M+1]=411.

N'-hydroxy-2-propan-2-yloxyethanimidamide was prepared as follows: To isopropoxy acetonitrile (229.5 mg, 2.32 mmol) in isopropanol (6 ml) and $H_2O$ (2 ml) was added hydroxylamine HCl (160.9 mg, 2.32 mmol) and potassium carbonate (320.6 mg, 2.32 mmol). The reaction mixture was heated at 80° C. for 16 h, cooled to rt, and all solvents removed in vacuo. The resulting solid was stirred in isopropanol (3 ml) and ethanol (1 ml) for about one hr, and filtered over a sintered glass filter. Solid was rinsed with isopropanol several times. Solvent of the filtrate was completely removed under vacuum to give 272.9 mg (89%) of the product as a lightly yellowish oil.

Example 48-8: Synthesis of Compound 250

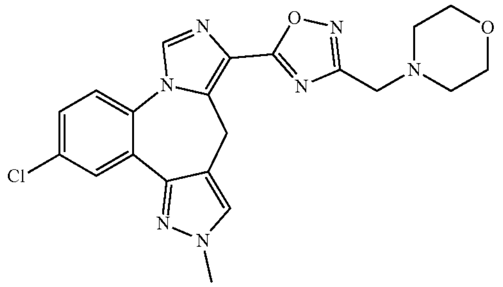 [SMILES: Cn1cc2c(n1)-c1cc(Cl)ccc1-n1cnc(-c3nc(CN4CCOCC4)no3)c1C2]

Compound 250 was prepared analogously as Example 48, using N-hydroxy-2-(4-morpholinyl)ethanimidamide in the oxadiazole formation step. MS: [M+1]=438.

Example 48-9: Synthesis of Compound 240

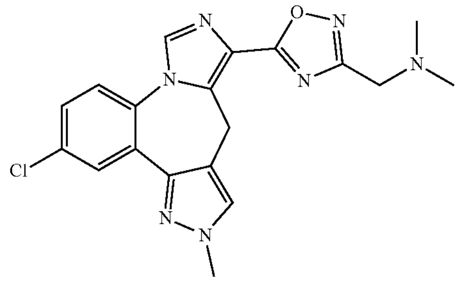 [SMILES: CN(C)Cc1noc(-c2ncn3c2Cc2cn(C)nc2-c2cc(Cl)ccc2-3)n1]

Compound 240 was prepared analogously as Example 48, using 2-dimethylamino-acetamide oxime in the oxadiazole formation step. MS: [M+1]=396.

Example 48-10: Synthesis of Compound 266

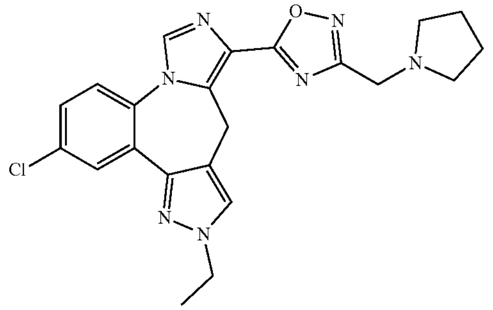 [SMILES: CCn1cc2c(n1)-c1cc(Cl)ccc1-n1cnc(-c3nc(CN4CCCC4)no3)c1C2]

Compound 266 was prepared analogously as Example 48-3, using N'-hydroxy-2-pyrrolidin-1-ylethanimidamide in the oxadiazole formation step. MS: [M+1]=436.

N'-hydroxy-2-pyrrolidin-1-ylethanimidamide was prepared as follows: To N-cyanomethyl pyrrolidine (916.1 mg, 8.32 mmol) in isopropanol (15 ml) and $H_2O$ (5 ml) was added hydroxylamine HCl (577.9 mg, 8.32 mmol) and potassium carbonate (1150.0 mg, 8.32 mmol). The reaction mixture was heated at 80° C. for 5 h, cooled to rt, and all solvents removed in vacuo. The resulting solid was stirred in isopropanol (12 ml) and ethanol (3 ml) for about one hr, and filtered over a sintered glass filter. Solid was rinsed with isopropanol several times. Solvent of the filtrate was completely removed under vacuum to give the desired product. Wt: 792.3 mg (66%).

Example 48-11: Synthesis of Compound 267

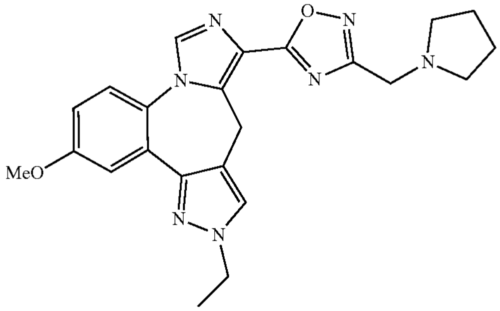 [SMILES: CCn1cc2c(n1)-c1cc(OC)ccc1-n1cnc(-c3nc(CN4CCCC4)no3)c1C2]

Compound 267 was prepared analogously as Example 48-10, starting with Intermediate B ($R_1$=OMe). MS: [M+1]=432.

Example 48a: Synthesis of Compound 328

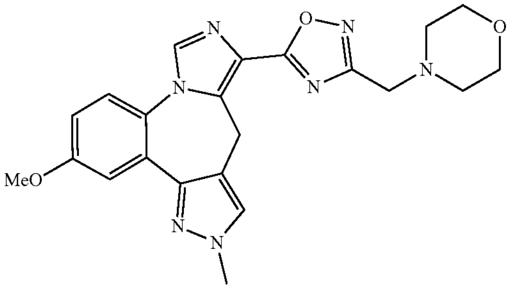 [SMILES: COc1ccc2c(c1)-c1nn(C)cc1Cc1c(-c3nc(CN4CCOCC4)no3)ncn1-2]

Compound 328 was prepared analogously as Compound 267, using N'-hydroxy-2-(4-morpholinyl)ethanimidamide for oxadiazole ring formation. MS: [M+1]=434.

Example 49: Synthesis of Compound 122

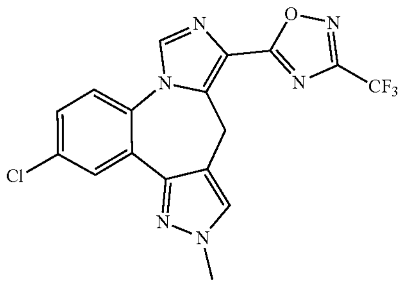 [SMILES: Cn1cc2c(n1)-c1cc(Cl)ccc1-n1cnc(-c3nc(C(F)(F)F)no3)c1C2]

Example 49 was prepared analogously as Example 47, using 2,2,2-trifluoro-N'-hydroxyethanimidaminde (dried over $P_2O_5$ under vacuum overnight before use) in the final oxadiazole formation step. MS: [M+1]=407.

Example 49-1: Synthesis of Compound 200

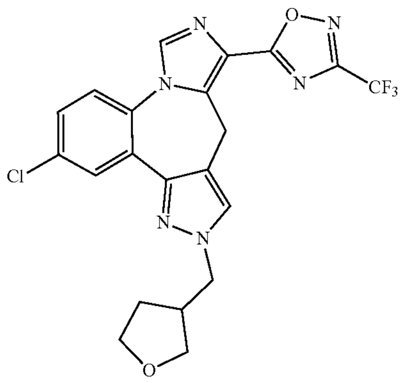 [SMILES: FC(F)(F)c1noc(-c2ncn3c2Cc2cn(CC4CCOC4)nc2-c2cc(Cl)ccc2-3)n1]

Compound 200 was prepared analogously as Example 49, using 3-bromomethyl oxolane as the N-alkylating agent in the pyrazole alkylation step. MS: [M+1]=477.

Example 50: Synthesis of Compound 20

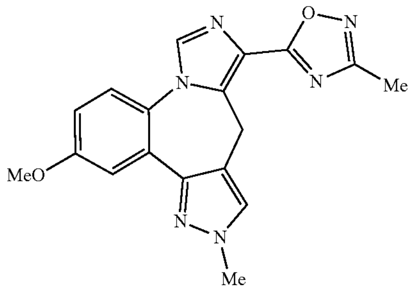 [SMILES: COc1ccc2c(c1)-c1nn(C)cc1Cc1c(-c3nc(C)no3)ncn1-2]

Example 50 was prepared analogously as Example 47, starting with Intermediate B ($R_1$=OMe). MS: [M+1]=349. $H^1$NMR ($CDCl_3$) δ 7.76 (1H, s), 7.46 (1H, d, J=4 Hz), 7.42 (1H, d, J=12 Hz), 7.37 (1H, s), 7.00 (1H, dd, J=4, 12 Hz), 4.28 (2H, br s), 3.92 (3H, s), 3.91 (3H, s), and 2.45 (3H, s).

Example 50-1: Synthesis of Compound 252

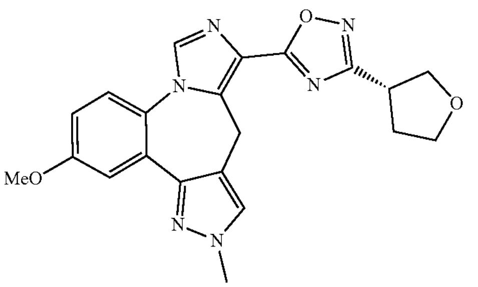 [SMILES: COc1ccc2c(c1)-c1nn(C)cc1Cc1c(-c3nc([C@H]4CCOC4)no3)ncn1-2]

Compound 252 was prepared analogously as Example 50, using (3R)—N'-hydroxyoxolane-3-carboximidamide in the final oxadiazole formation step. MS: [M+1]=405.

(3R)—N'-hydroxyoxolane-3-carboximidamide was prepared as follows: To @-tetrahydrofuran-3-carbonitrile (229.5 mg, 2.36 mmol) in isopropanol (6 ml) and $H_2O$ (2 ml) was added hydroxylamine HCl (164.1 mg, 2.36 mmol) and potassium carbonate (326.2 mg, 2.36 mmol). The reaction mixture was heated at 80° C. for 16 h, cooled to rt, and all solvents removed in vacuo. The resulting solid was stirred in isopropanol (3 ml) and ethanol (1 ml) for about one hr, and filtered over a sintered glass filter. Solid was rinsed with isopropanol several times. Solvent of the filtrate was completely removed under vacuum to give 199.6 mg (65%) of the product as a clear oil.

Example 51: Synthesis of Compound 16

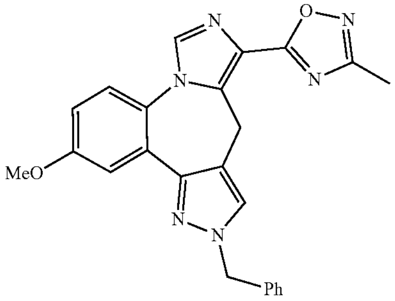 [SMILES: COc1ccc2c(c1)-c1nn(Cc3ccccc3)cc1Cc1c(-c3nc(C)no3)ncn1-2]

Example 51 was prepared analogously as Example 50, using benzyl bromide as the N-alkylating agent in the pyrazole alkylation step. MS: [M+1]=425.

Example 52: Synthesis of Compound 151

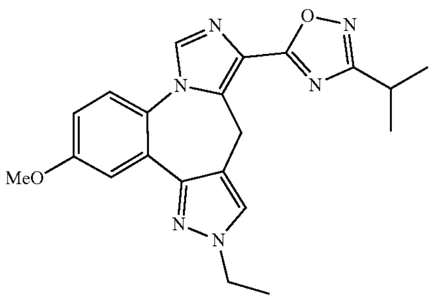 [SMILES: CCn1cc2c(n1)-c1cc(OC)ccc1-n1cnc(-c3nc(C(C)C)no3)c1C2]

Example 52 was prepared analogously as Example 50, using ethyl iodide as the N-alkylating agent in the pyrazole alkylation, and isobutyramide oxime in the final oxadiazole formation step. MS: [M+1]=391.

Example 53: Synthesis of Compound 43

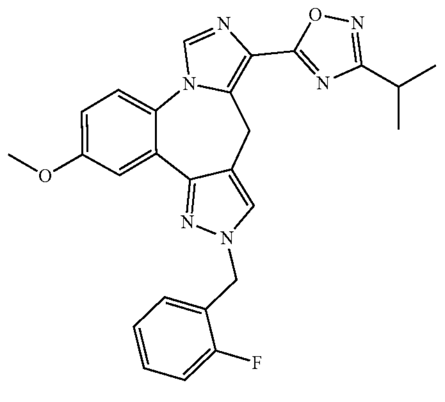 [SMILES: COc1ccc2c(c1)-c1nn(Cc3ccccc3F)cc1Cc1c(-c3nc(C(C)C)no3)ncn1-2]

Example 53 was prepared analogously as Example 50, using 2-fluorobenzyl bromide as the N-alkylating agent in the pyrazole alkylation, and isobutyramide oxime in the final oxadiazole formation step. MS: [M+1]=471.

Example 54: Synthesis of Compound 120

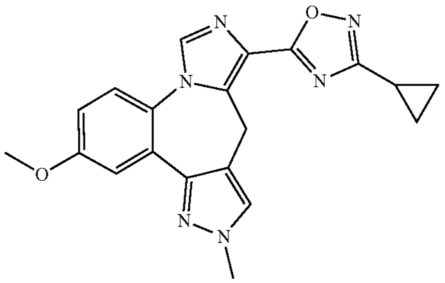 [SMILES: COc1ccc2c(c1)-c1nn(C)cc1Cc1c(-c3nc(C4CC4)no3)ncn1-2]

Example 54 was prepared analogously as Example 50, using N'-hydroxycyclopropanecarboximidamide in the final oxadiazole formation step. MS: [M+1]=375.

Example 55: Synthesis of Compound 152

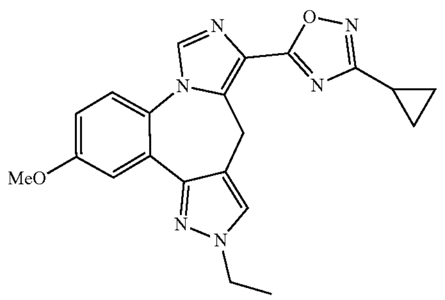 [SMILES: CCn1cc2c(n1)-c1cc(OC)ccc1-n1cnc(-c3nc(C4CC4)no3)c1C2]

Example 55 was prepared analogously as Example 50, using ethyl iodide as the N-alkylating agent in the pyrazole alkylation, and N'-hydroxycyclopropanecarboximidamide in the final oxadiazole formation step. MS: [M+1]=389.

Example 55-1: Synthesis of Compound 169

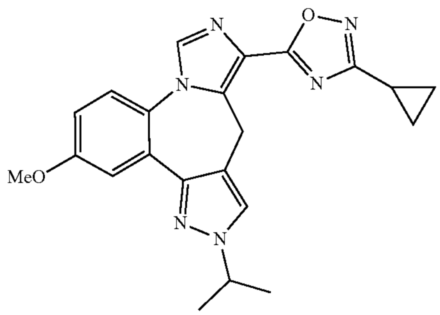 [SMILES: COc1ccc2c(c1)-c1nn(C(C)C)cc1Cc1c(-c3nc(C4CC4)no3)ncn1-2]

Compound 169 was prepared analogously as Example 55, using 2-iodo propane as the N-alkylating agent in the pyrazole alkylation step. MS: [M+1]=403.

Example 55-2: Synthesis of Compound 171

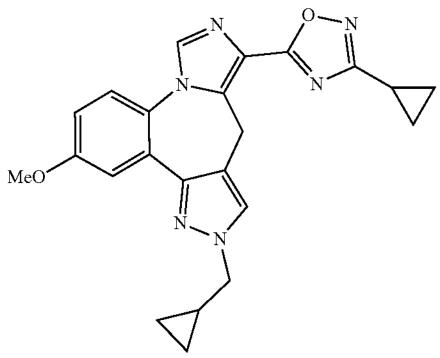 [SMILES: COc1ccc2c(c1)-c1nn(CC3CC3)cc1Cc1c(-c3nc(C4CC4)no3)ncn1-2]

Compound 171 was prepared analogously as Example 55, using cyclopropyl methylbromide as the N-alkylating agent in the pyrazole alkylation step. MS: [M+1]=415.

Example 56: Synthesis of Compound 118

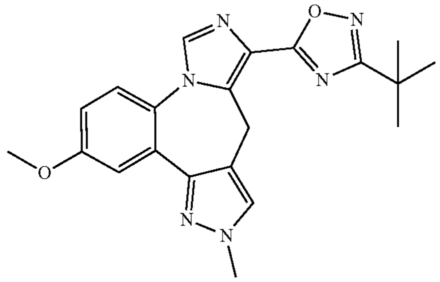 [SMILES: COc1ccc2c(c1)-c1nn(C)cc1Cc1c(-c3nc(C(C)(C)C)no3)ncn1-2]

Example 56 was prepared analogously as Example 50, using N'-hydroxy-2,2-dimethylpropanimidamide in the final oxadiazole formation step. MS: [M+1]=391.

Example 56-1: Synthesis of Compound 170

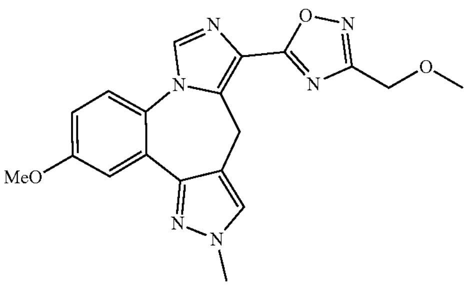 [SMILES: COCc1noc(-c2ncn3c2Cc2cn(C)nc2-c2cc(OC)ccc2-3)n1]

Compound 170 was prepared analogously as Example 56, using N'-hydroxy-2-methoxyethanimidamide in the final oxadiazole formation step. MS: [M+1]=379.

Example 56-2: Synthesis of Compound 236

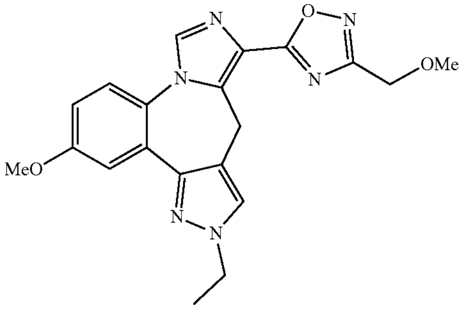 [SMILES: CCn1cc2c(n1)-c1cc(OC)ccc1-n1cnc(-c3nc(COC)no3)c1C2]

Compound 236 was prepared analogously as Example 56-2, using iodoethane as the N-alkylating agent in the pyrazole alkylation step. MS: [M+1]=393.

Example 56-3: Synthesis of Compound 241

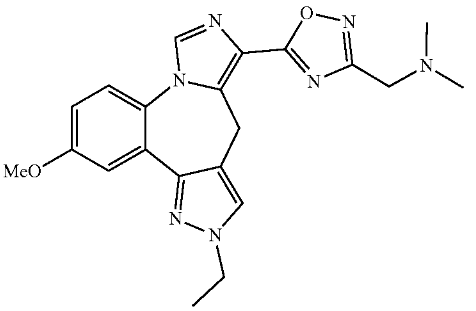 [SMILES: CCn1cc2c(n1)-c1cc(OC)ccc1-n1cnc(-c3nc(CN(C)C)no3)c1C2]

Compound 241 was prepared analogously as Example 56-2, using 2-dimethylamino-acetamide oxime in the oxadiazole formation step. MS: [M+1]=406.

Example 57: Synthesis of Compound 17

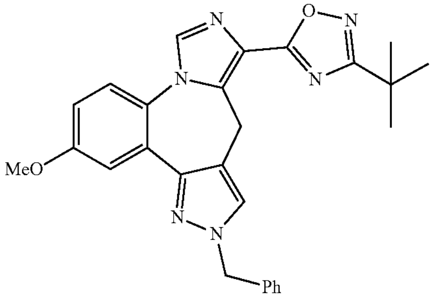 [SMILES: COc1ccc2c(c1)-c1nn(Cc3ccccc3)cc1Cc1c(-c3nc(C(C)(C)C)no3)ncn1-2]

Example 57 was prepared analogously as Example 50, using benzyl bromide as the N-alkylating agent in the pyrazole alkylation, and N'-hydroxy-2,2-dimethylpropanimidamide in the final oxadiazole formation step. MS: [M+1]=467.

Example 58: Synthesis of Compound 126

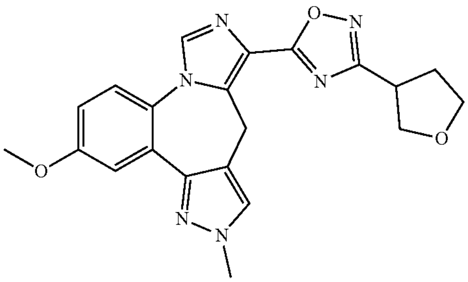 [SMILES: COc1ccc2c(c1)-c1nn(C)cc1Cc1c(-c3nc(C4CCOC4)no3)ncn1-2]

Example 58 was prepared analogously as Example 50, using N-hydroxytetrahydrofuran-3-carboxamidine in the final oxadiazole formation step. MS: [M+1]=405.

Example 50-2: Synthesis of Compound 260

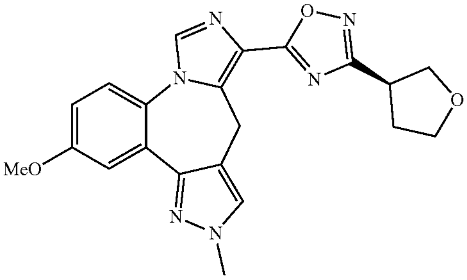 [SMILES: COc1ccc2c(c1)-c1nn(C)cc1Cc1c(-c3nc([C@@H]4CCOC4)no3)ncn1-2]

Compound 260 was prepared analogously as Example 50-1, using (3S)—N'-hydroxyoxolane-3-carboximidamide in the final oxadiazole formation step. MS: [M+1]=405.

(3S)—N'-hydroxyoxolane-3-carboximidamide was prepared similarly as its R isomer, starting with (S)-tetrahydrofuran-3-carbonitrile.

Example 58-1: Synthesis of Compound 220

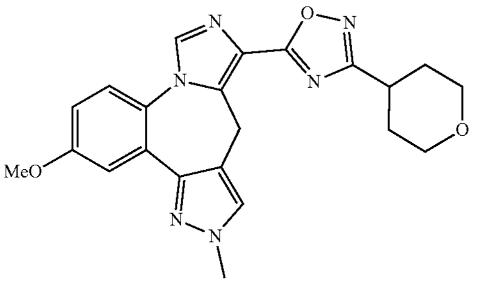 [SMILES: COc1ccc2c(c1)-c1nn(C)cc1Cc1c(-c3nc(C4CCOCC4)no3)ncn1-2]

Compound 220 was prepared analogously as Example 58, using N'-hydroxytetrahydro-2H-pyran-4-carboximidamide in the oxadiazole formation step. MS: [M+1]=419.

Example 58a: Synthesis of Compound 352

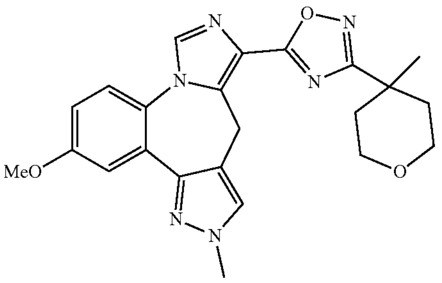 [SMILES: COc1ccc2c(c1)-c1nn(C)cc1Cc1c(-c3nc(C4(C)CCOCC4)no3)ncn1-2]

Compound 352 was prepared analogously as Example 58, using N'-hydroxy-4-methyltetrahydro-2H-pyran-4-carboximidamide in the oxadiazole formation step. MS: [M+1]=433.

Example 48-12: Synthesis of Compound 239

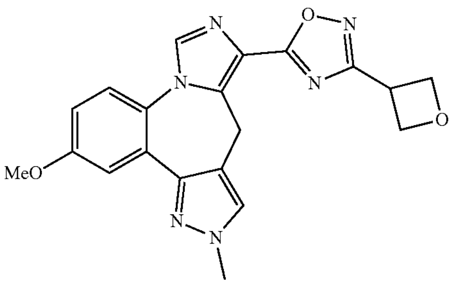 [SMILES: COc1ccc2c(c1)-c1nn(C)cc1Cc1c(-c3nc(C4COC4)no3)ncn1-2]

Compound 239 was prepared analogously as Example 48-5, starting with Intermediate B ($R_1$=OMe). MS: [M+1]=391.

Example 59: Synthesis of Compound 119

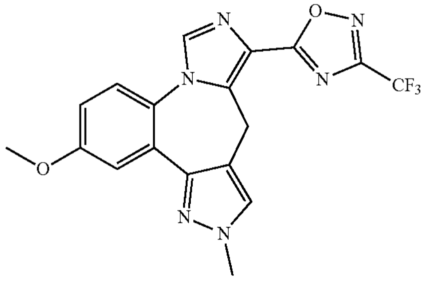 [SMILES: COc1ccc2c(c1)-c1nn(C)cc1Cc1c(-c3nc(C(F)(F)F)no3)ncn1-2]

Example 59 was prepared analogously as Example 50, using 2,2,2-trifluoro-N'-hydroxyethanimidaminde (dried over $P_2O_5$ under vacuum overnight before use) in the final oxadiazole formation step. MS: [M+1]=403.

Scheme 7-A

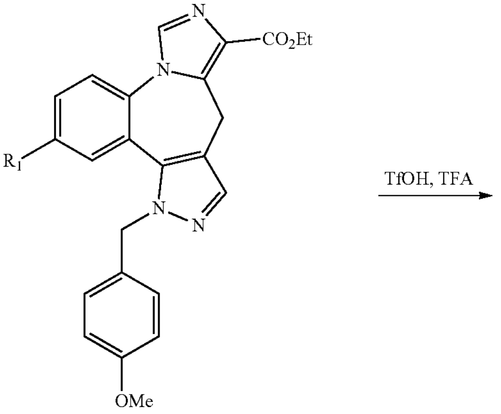

R1 = MeO, Cl

Intermediate B

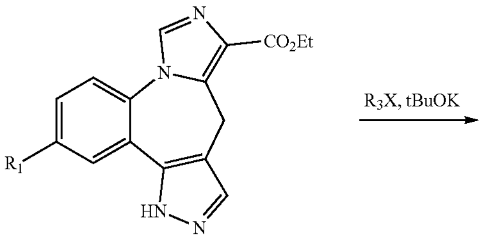

7A.1

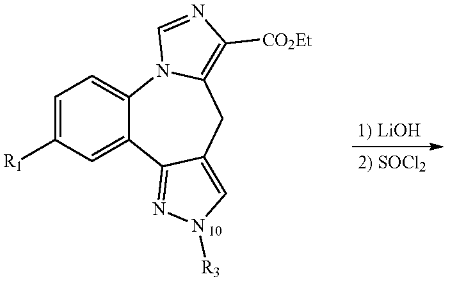

7A.2

(major isomer)

-continued

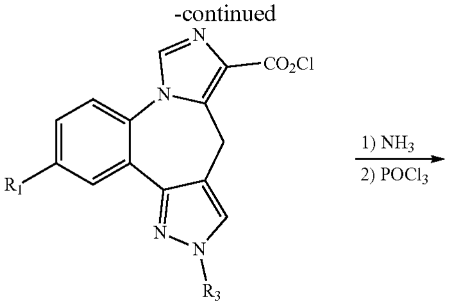

7A.3

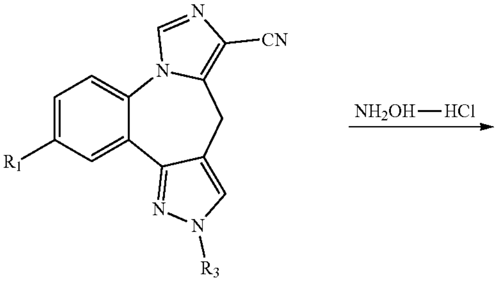

7A.4

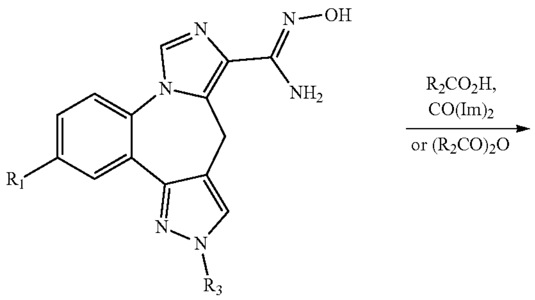

7A.5

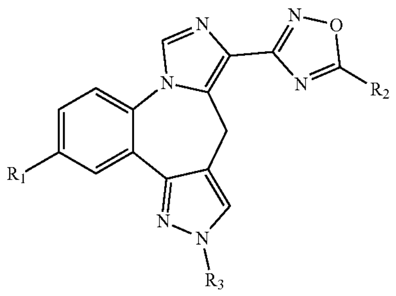

| | R1 R2 R3 |
|---|---|
| Ex. 63 Compound 131: | OMe, Me, Me |
| Ex. 64 Compound 132: | OMe, cPr, Me |
| Ex. 65 Compound 146: | OMe, tBu, Me |
| Ex. 65-1 Compound 248: | OMe, $(Me)_2NCH_2$, Et |
| Ex. 65a Compound 349: | Cl, $(Me)_2NCH_2$, Et |
| Ex. 65b Compound 347: | OMe, $(CH_2)_4NCH_2$, Me |
| Ex. 65c Compound 350: | Cl, $(CH_2)_4NCH_2$, Et |
| Ex. 65d Compound 348: | OMe, $O(CH_2CH_2)_2NCH_2$, Me |
| Ex. 65e Compound 363: | OMe, $OH(CH_2)_2C$, Me |
| Ex. 65f Compound 357: | OMe, $OEt(CH_2)_2C$, Me |
| Ex. 65g Compound 370: | OMe, $OiPr(CH_2)_2C$, Me |
| Ex. 65h Compound 376: | OMe, $OHCH_2(Me)_2C$, Me |
| Ex. 65i Compound 377: | OMe, $OMeCH_2(Me)_2C$, Me |
| Ex. 65j Compound 366: | OMe, OXT-3-yl-$CH_2$, Me |
| Ex. 65k Compound 388: | OMe, $OH(Me)_2C$, Me |

-continued

| | R1 R2 R3 |
|---|---|
| Ex. 65l Compound 384: | OMe, $OH(CH_2)_4C$, Me |
| Ex. 65m Compound 368: | OMe, 2-Prn-$CH_2$, Me |
| Ex. 65n Compound 369: | OMe, 2-Prn-$CH_2CH_2$, Me |
| Ex. 65o Compound 359: | OMe, $CF_3OCH_2$, Me |
| Ex. 65p Compound 360: | OMe, Pyr-$CH_2$, Me |
| Ex. 65q Compound 361: | OMe, Prz-$CH_2$, Me |
| Ex. 66 Compound 153: | OMe, $MeOCH_2$, Me |
| Ex. 67 Compound 137: | OMe, $EtOCH_2$, Me |
| Ex. 67a Compound 296: | OMe, $tBuOCH_2$, Me |
| Ex. 67b Compound 342: | OMe, $MeO(CH_2)_2$, Me |
| Ex. 67c Compound 297: | OMe, CPN-$OCH_2$, Me |
| Ex. 67-1 Compound 255: | OMe, $(Me)_2COMe$, Et |
| Ex. 67-2 Compound 202: | OMe, OXT-3-yl, Me |
| Ex. 67d Compound 317: | OMe, $O(CH_2)_2CMe$, Me |
| Ex. 67e Compound 353: | OMe, MeEtCOMe, Me |
| Ex. 67f Compound 354: | OMe, $O(CH_2)(CH_2CH_2)COMe$, Me |
| Ex. 67g Compound 355: | OMe, $(CH_2)_4COMe$, Me |
| Ex. 67h Compound 356: | OMe, $O(CH_2)(CH_2CH_2)CF$, Me |
| Ex. 67i Compound 344: | OMe, $MeO(Me)_2CCH_2$, Me |
| Ex. 67j Compound 323: | OMe, $(CH_2)_2COMe$, THF-2-yl-$CH_2$ |
| Ex. 68 Compound 136: | OMe, THF-3-yl, Me |
| Ex. 68-1 Compound 256: | OMe, THF-3-yl (R), Me |
| Ex. 68-2 Compound 257: | OMe, THF-3-yl (S), Me |
| Ex. 68-3 Compound 258: | OMe, THF-2-yl (R), Me |
| Ex. 68-4 Compound 259: | OMe, THF-2-yl (S), Me |
| Ex. 68-5 Compound 254: | OMe, $CF_3CH_2OCH_2$, Et |
| Ex. 68a Compound 279: | OMe, $CF_3CH_2OCH_2$, THF-3-yl |
| Ex. 68b Compound 292: | OMe, $CF_3CH_2OCH_2$, THF-2-yl-$CH_2$ |
| Ex. 69 Compound 130: | OMe, $CF_3$, Me |
| Ex. 70 Compound 140 | Cl, Me, Me |
| Ex. 71 Compound 147: | Cl, Me, iPr |
| Ex. 72 Compound 141: | Cl, iPr, Me |
| Ex. 72-1 Compound 175: | Cl, iPr, Et |
| Ex. 73 Compound 150: | Cl, iPr, iPr |
| Ex. 74 Compound 142: | Cl, cPr, Me |
| Ex. 74-1 Compound 176: | Cl, cPr, Et |
| Ex. 75 Compound 149: | Cl, cPr, iPr |
| Ex. 76 Compound 143: | Cl, tBu, Me |
| Ex. 76-1 Compound 243: | Cl, $EtOCH_2$, Me |
| Ex. 76-2 Compound 211: | Cl, CPN-$OCH_2$, Me |
| Ex. 76-3 Compound 194: | Cl, CPN-$OCH_2$, Et |
| Ex. 76-4 Compound 223: | Cl, OXT-3-yl, Me |
| Ex. 76-5 Compound 225: | Cl, 3-Me-OXT-3-yl, Me |
| Ex. 77 Compound 145: | Cl, THF-3-yl, Me |
| Ex. 77-1 Compound 214: | Cl, $(Me)_2COMe$, Me |
| Ex. 77-2 Compound 215: | Cl, $tBuOCH_2$, Me |
| Ex. 77a Compound 387: | Cl, $MeO(CH_2)_2$, Me |
| Ex. 77-3 Compound 216: | Cl, $(CH_2)_2COMe$, Me |
| Ex. 77b Compound 322: | Cl, $(CH_2)_2COMe$, THF-2-yl-$CH_2$ |
| Ex. 77-4 Compound 213: | Cl, DOX-2-yl, Me |
| Ex. 77-5 Compound 268: | Cl, DOX-2-yl, iPr |
| Ex. 77-6 Compound 217: | Cl, $CF_3CH_2OCH_2$, Me |
| Ex. 77-7 Compound 218: | Cl, $(CH_2)_2CF$, Me |
| Ex. 78 Compound 144: | Cl, $CF_3$, Me |
| Ex. 79 Compound 148: | Cl, $CF_3$, iPr |
| Ex. 80 Compound 155: | Cl, $MeOCH_2$ |
| Ex. 81 Compound 156: | OMe, iPr, Et |
| Ex. 82 Compound 157: | OMe, cPr, Et |
| Ex. 83 Compound 158: | OMe, $CF_3$, Et |
| Ex. 83a Compound 295: | MeO, $CF_3$, THF-2-yl-$CH_2$ |
| Ex. 83b Compound 371: | Cl, Pyr-$CH_2$, Me |
| Ex. 83c. Compound 372: | Cl, Pyz-$CH_2$, Me |
| Ex. 83d Compound 373: | Cl, Imd-$CH_2$, Me |
| Ex. 83e Compound 382: | Cl, 2-$PrnCH_2$, Me |
| Ex. 83f Compound 383: | Cl, 2-$PrnCH_2CH_2$, Me |
| Ex. 83g Compound 385: | Cl, 2-$PrrCH_2CH_2$, Me |
| Ex. 83h Compound 365: | Cl, $O(CH_2CH_2)_2MeC$, THF-2-yl-$CH_2$ |

Example 63: Synthesis of Compound 131

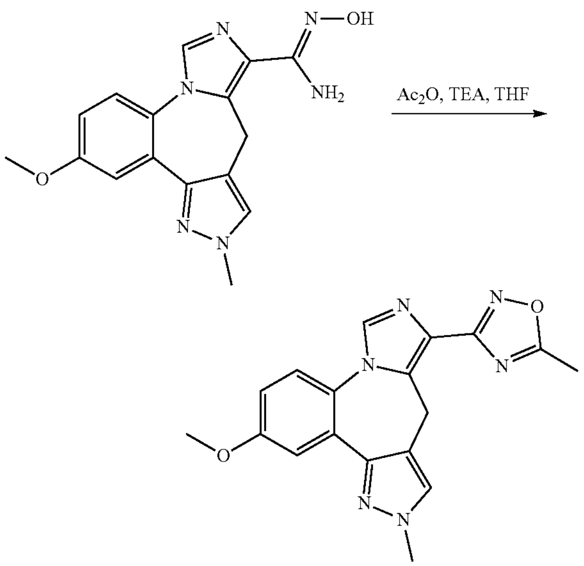

Example 63 Compound 131

Step 1: Intermediate B ($R_1$=OMe; 300 mg) was treated with trifluoromethane sulfonic acid (455 mg) in a mixture of trifluoroacetic acid (5 ml) and DCM (5 ml) at rt for 3 days, then warmed at 35° C. for 20 h. The reaction mixture was concentrated, treated with ammonium hydroxide (15% aq.; 10 ml) and stirred for 30 min. $Et_2O$ (5 ml) was then added and stirred for 10 min. Ppts was collected by filtration, washed with water, and dried to give the crude debenzylated pyrazole ester 7A.1 as a yellowish solid.

Step 2: Trimethylphenylammonium chloride (98.1 mg, 0.572 mmol; dried by repeated azeotroping in tol. Before use) and a previously obtained debenzylated pyrazole ester (61.8 mg, 0.191 mmol) were stirred in DMF (0.75 ml) at rt, tBuOK (30.4 mg, 0.270 mmol) was added. After 30 min stirring at rt, the reaction was heated at 60° C. for 16 h, quenched with sat. $NaHCO_3$, extracted with EtOAc (3×), combined extracts washed with brine, and dried over $MgSO_4$. Filtration and concentration followed by silica gel column chromatography using 0 to 10% MeOH in a pre-mixed solvent of hexanes/EtOAc (1:1) gradient gave 41.1 mg of the major N10 methylated ester isomer 7A.2.

Step 3: N10 methylated ester (58.7 mg, 0.173 mmol) was treated with LiOH (16.6 mg, 0.694 mmol) in a mixed solvents of THF (0.6 ml), water (0.5 ml) and MeOH (0.1 ml) for 16 h. The reaction mixture was concentrated, acidified to pH 3-4 with dil. HCl, and cooled to 0° C. Ppts was collected by filtration, washed with water and dried to give 41.2 mg of carboxylic acid.

Step 4: The carboxylic acid (129.1 mg) obtained following the above sequences was treated with thionyl chloride (1.5 ml) in a pre-heated oil bath of 80° C. for 30 min, cooled to rt, and excess reagent removed in vacuo. Residual thionyl chloride was removed by azeotroping with toluene repeatedly. The resulting crude acid chloride 7A.3 was dissolved in DCM (2 ml) and cooled to 0° C. Ammonia in 1,4-dioxane (0.5 M; 2 ml) was added, and the reaction was allowed to proceed to rt overnight. All solvent was removed in vacuo, and the solid residue was suspended and stirred in sat. $NaHCO_3$ and water (1:1, v/v) for 2 h. Ppts was collected by filtration, washed with water, and dried to give the N10 methylated primary carboxamide.

Step 5: The primary carboxamide from above was treated with $POCl_3$ (255.2 mg) in 1,2-dichloroethane (2 ml) at 80° C. for 3 h, cooled to rt, concentrated in vacuo, and further cooled down to 0° C. Sat. $NaHCO_3$ (10 ml) was stirred in, and the aq. Mixture was extracted with EtOAc (3×), the combined organic layer was washed with brine, and dried over $MgSO_4$. Filtration and concentration followed by silica gel column chromatography using 0 to 100% EtOAc in hexanes gradient gave 21.8 mg of nitrile 7A.4.

Step 6: The above nitrile 7A.4 (21.8 mg, 0.0748 mmol) was treated with hydroxylamine hydrochloride (15.6 mg, 0.224 mmol) in the presence of $K_2CO_3$ (20.7 mg, 0.150 mmol) in isopropanol (1.2 ml) and water (0.2 ml) at 80° C. for 1 h, then concentrated to a slurry. Water (3 ml) was added under stirring, and the mixture was cooled to 0° C. Ppts was collected by filtration and washed with water to give 17.4 mg amide oxime 7A.5. Filtrate from the above filtration was extracted with EtOAc (3×), washed with brine, and dried over $MgSO_4$. Filtration and solvent removal gave an additional 7.0 mg of the amide oxime 7A.5. Total Wt: 24.4 mg.

Step 7: The starting amide oxime 7A.5 (6.5 mg, 0.0203 mmol) was treated with acetic anhydride (10.4 mg, 0.102 mmol) and triethylamine (10.3 mg, 0.102 mmol) in THE (0.2 ml) at 0° C. for 1 h. THE was then removed and toluene (0.1 ml) added, and the reaction mixture was heated at 100° C. for 5 h. Upon cooling, the reaction was treated with sat. $NaHCO_3$, and extracted with EtOAc (3×), the combined extracts washed with brine, and dried over $MgSO_4$. Prep. TLC using 5% MeOH in EtOAc/DCM (1:1) as eluent gave Example 63, Compound 131 as an off-white solid, wt: 4.4 mg. MS: [M+1]=349.

Example 63: Compound 131

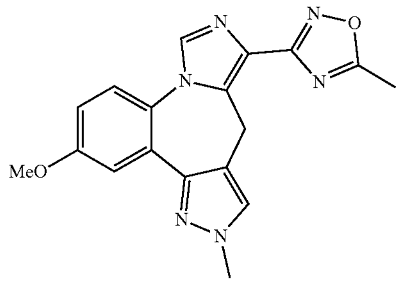 [SMILES: COc1ccc2c(c1)-c1nn(C)cc1Cc1c(-c3noc(C)n3)ncn1-2]

Example 64: Synthesis of Compound 132

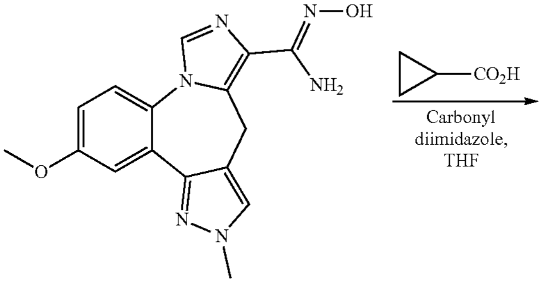

-continued

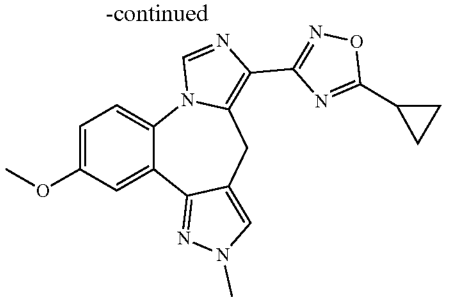

Cyclopropanecarboxylic acid (19.7 mg, 0.229 mmol) was stirred in THE (0.25 ml) at 0° C., carbonyl diimidazole (18.5 mg, 0.114 mmol) was added. Ice bath was subsequently removed and stirring continued at ambient temperature for 1 h. The thus obtained solution was added to the starting amide oxime (6.1 mg, 0.019 mmol), and the mixture was stirred for 30 min at rt. More cyclopropanecarboxylic acid (0.1 ml) was added, and the reaction mixture was heated at 100° C. for 1 h or until the oxadiazole ring cyclization had completed. Upon cooling, the reaction mixture was treated with sat. $NaHCO_3$, and extracted with EtOAc (3×), the combined extract was washed with brine, and dried over $MgSO_4$. Filtration and concentration followed by prep. TLC using 5% MeOH in EtOAc/DCM (1:1) gave 4.0 mg Example 64, Compound 132 as a yellowish solid. MS: [M+1]=375.

Example 65: Synthesis of Compound 146

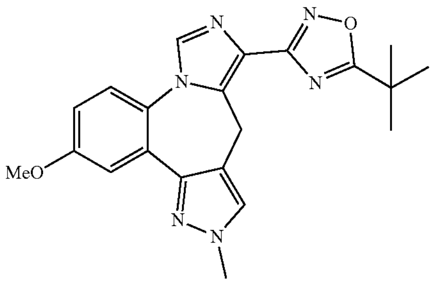 [SMILES: COc1ccc2c(c1)-c1nn(C)cc1Cc1c(-c3noc(C(C)(C)C)n3)ncn1-2]

Example 65 was prepared analogously as Example 64, using pivalic acid in the final oxadiazole formation step. MS: [M+1]=391.

Example 65-1: Synthesis of Compound 248

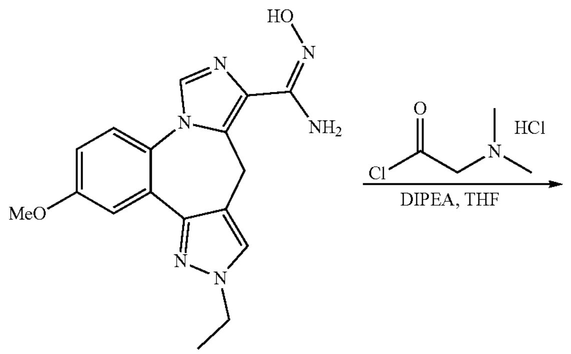

-continued

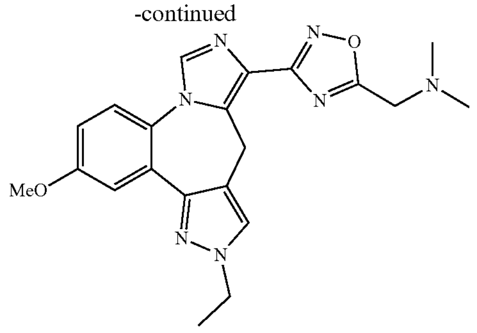

Compound 248 was prepared analogously as Example 63, using iodoethane as the N-alkylating agent for the pyrazole alkylation (step 2), and N,N-dimethylamino acetyl chloride HCl salt followed by heating to form and close up the oxadiazole ring in the final step, detailed below.

N,N-dimethylamino acetyl chloride HCl (13.1 mg, 0.0827 mmol) was added to a stirring solution of the amide oxime (7.0 mg, 0.0207 mmol) in THE (0.2 ml) at 0° C., DIPEA (21.4 mg, 0.166 mmol) was added. The reaction mixture was stirred to rt overnight. Toluene (0.5 ml) was added and the reaction mixture was heated at 100° C. for 4 hrs, and diluted with EtOAc, washed with sat. $NaHCO_3$, brine, and dried ($MgSO_4$). Prep TLC with 10% MeOH in DCM/EtOAc (1:1) of the concentrated filtrate gave 4.2 mg (50%) of the desired product as an off white solid. MS: [M+1]=406.

Example 65a: Synthesis of Compound 349

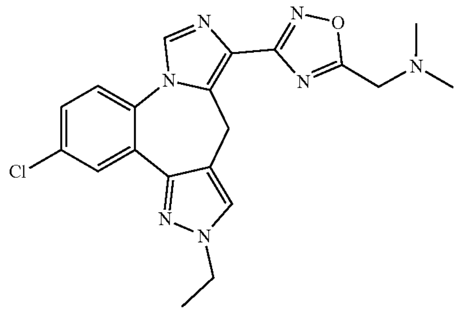 [SMILES: CCn1cc2c(n1)-c1cc(Cl)ccc1-n1cnc(-c3noc(CN(C)C)n3)c1C2]

Compound 349 was prepared analogously as Example 65-1, starting with Intermediate B ($R_1$=Cl). MS: [M+1]=410.

Example 65b: Synthesis of Compound 347

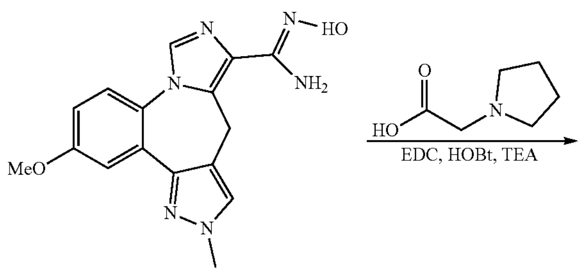

-continued

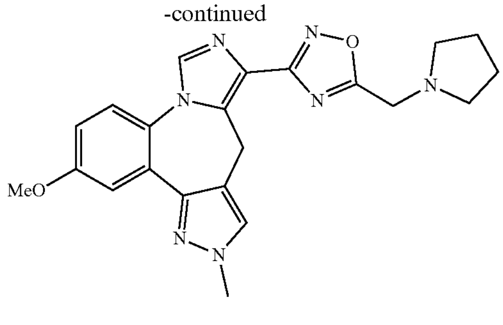

Compound 347 was prepared analogously as Example 63, using 2-(pyrrolidin-1-yl)acetic acid under amide formation conditions followed by heating to form and close up the oxadiazole ring in the final step, as detailed below.

2-(Pyrrolidin-1-yl)acetic acid (5 mg, 0.0386 mmol) was stirred in DCM (0.24 ml), EDC HCl (8.6 mg, 0.0448 mmol) and HOBt hydrate (5 mg) were added, followed by TEA (12 ul) and the starting amide oxime (7.8 mg, 0.0244 mmol). After 16 hr stirring, DCM was removed in vacuo, and toluene (1 ml) added. The reaction mixture was heated at 110° C. for 5 hr, cooled, and diluted with EtOAc, washed with sat. $NaHCO_3$, brine, and dried ($MgSO_4$). Prep TLC with 10% MeOH in DCM/EtOAc (1:1) of the concentrated filtrate gave 3.8 mg (34%) of the desired product as a clear filmy solid. MS: [M+1]=418.

Example 65c: Synthesis of Compound 348

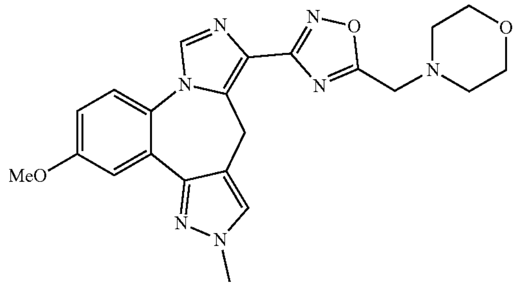 [SMILES: COc1ccc2c(c1)-c1nn(C)cc1Cc1c(-c3noc(CN4CCOCC4)n3)ncn1-2]

Compound 348 was prepared analogously as Compound 347, using morpholin-1-ylacetic acid in the final oxadiazole formation step. MS: [M+1]=434.

Example 65d: Synthesis of Compound 350

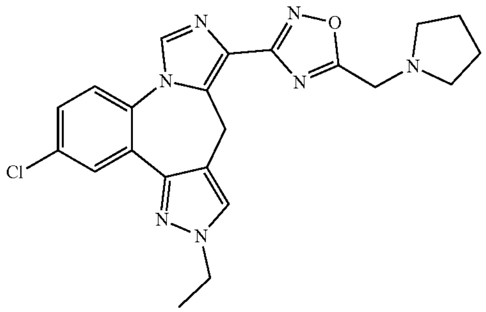 [SMILES: CCn1cc2c(n1)-c1cc(Cl)ccc1-n1cnc(-c3noc(CN4CCCC4)n3)c1C2]

Compound 350 was prepared analogously as Compound 347, starting with Intermediate B ($R_1$=Cl), and use ethyl iodide as the N-alkylating agent. MS: [M+1]=436.

Example 65e: Synthesis of Compound 363

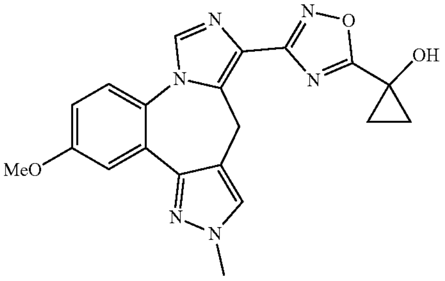 [SMILES: COc1ccc2c(c1)-c1nn(C)cc1Cc1c(-c3noc(C4(O)CC4)n3)ncn1-2]

Compound 363 was prepared analogously as Compound 347, using 1-hydroxypropane-1-carboxylic acid under EDC coupling conditions in the final oxadiazole formation step. MS: [M+1]=391.

Example 65f: Synthesis of Compound 357

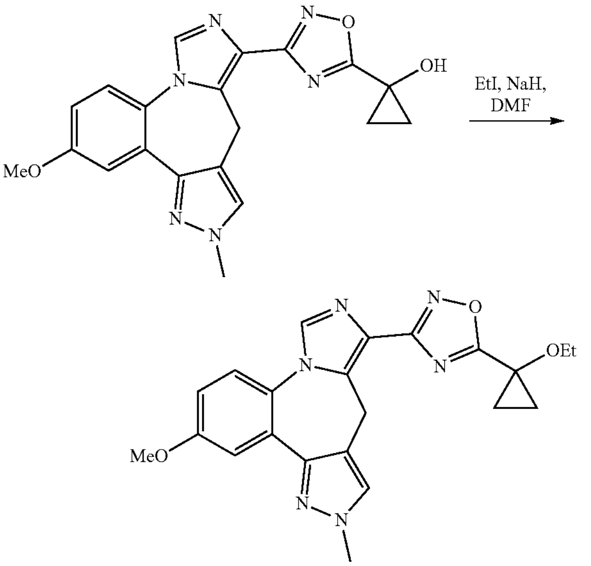

Compound 357 was prepared by O-alkylation of Compound 363 as detailed below:

The starting alcohol (10.5 mg, 0.0269 mmol) was stirred in DMF (0.13 ml) at 0° C., NaH (60% oil suspension; 3.0 mg) was added. After 30 min stirring at 0° C., ethyl iodide (21.0 mg, 0.134 mmol) was added, and the reaction was allowed to proceed to RT overnight, then diluted with EtOAc, washed with sat. $NaHCO_3$, brine, and dried over $MgSO_4$. Upon filtration and concentration, the mixture was purified by prep. TLC using 5% MeOH in hexanes/EtOAc (1:1) as eluting system to give 4.0 mg (36%) of the ether product as a clear filmy solid. MS: [M+1]=419.

Example 65g: Synthesis of Compound 370

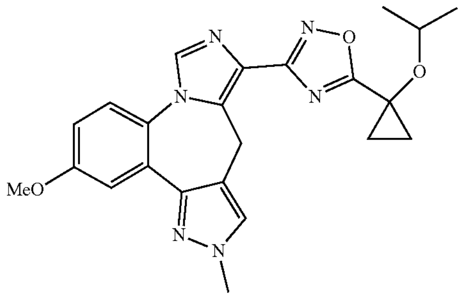 [SMILES: COc1ccc2c(c1)-c1nn(C)cc1Cc1c(-c3noc(C4(OC(C)C)CC4)n3)ncn1-2]

Compound 370 was prepared analogously as Compound 357, using 2-iodopropane in the final O-alkylation step. MS: [M+1]=433.

Example 65h: Synthesis of Compound 376

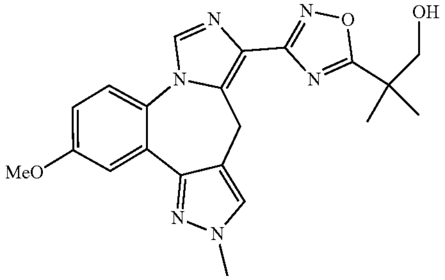 [SMILES: COc1ccc2c(c1)-c1nn(C)cc1Cc1c(-c3noc(C(C)(C)CO)n3)ncn1-2]

Compound 376 was prepared analogously as Compound 347, using 3-hydroxy-2,2-dimethylpropanoic acid under EDC coupling conditions in the final oxadiazole formation step. MS: [M+1]=407.

Example 65i: Synthesis of Compound 377

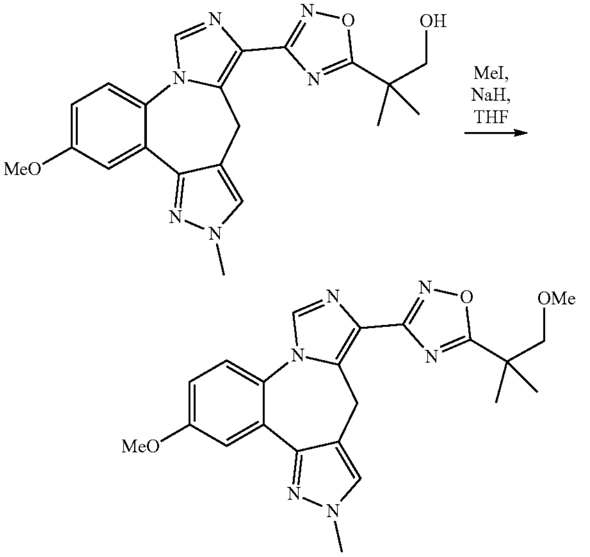

Compound 377 was prepared by O-alkylation of Compound 376 as detailed below:

The starting alcohol (5.9 mg, 0.0145 mmol) was stirred in THE (0.18 ml) at 0° C., MeI (4.1 mg, 0.0290 mmol) was added, followed by NaH (60% oil suspension; 2.5 mg). The reaction was allowed to proceed to RT overnight, then quenched with MeOH (0.5 ml), diluted with EtOAc, washed with sat. $NaHCO_3$, brine, and dried over $MgSO_4$. Upon filtration and concentration, the mixture was purified by prep. TLC using 7% MeOH in DCM/EtOAc (1:1) as eluting system to give 3.5 mg (59%) of the ether product as a yellowish solid. MS: [M+1]=421.

Example 65j: Synthesis of Compound 366

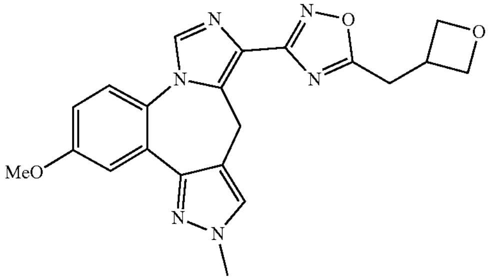 [SMILES: COc1ccc2c(c1)-c1nn(C)cc1Cc1c(-c3noc(CC4COC4)n3)ncn1-2]

Compound 366 was prepared analogously as Compound 347, using 2-(oxetan-3-yl)acetic acid in the final oxadiazole formation step. MS: [M+1]=405.

Example 65k: Synthesis of Compound 388

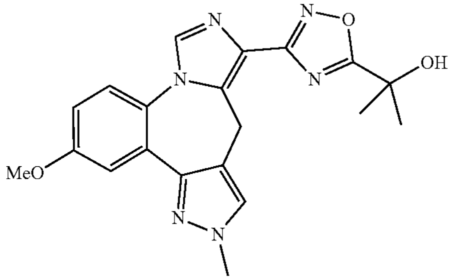 [SMILES: COc1ccc2c(c1)-c1nn(C)cc1Cc1c(-c3noc(C(C)(C)O)n3)ncn1-2]

Compound 388 was prepared analogously as Compound 347, using 2-hydroxyisobutyric acid in the final oxadiazole formation step. MS: [M+1]=393.

Example 65l: Synthesis of Compound 384

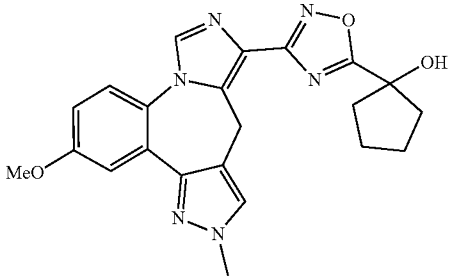 [SMILES: COc1ccc2c(c1)-c1nn(C)cc1Cc1c(-c3noc(C4(O)CCCC4)n3)ncn1-2]

Compound 384 was prepared analogously as Compound 347, using 1-hydroxycyclopentane carboxylic acid in the final oxadiazole formation step. MS: [M+1]=419.

Example 65m: Synthesis of Compound 368

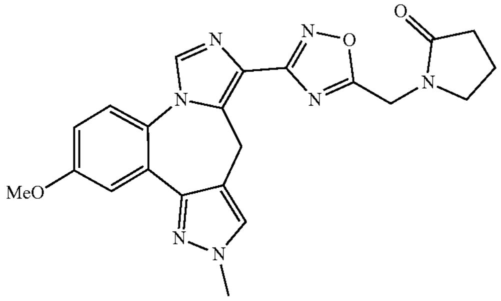 [SMILES: COc1ccc2c(c1)-c1nn(C)cc1Cc1c(-c3noc(CN4CCCC4=O)n3)ncn1-2]

Compound 368 was prepared analogously as Compound 347, using 2-oxo-1-pyrrolidineacetic acid in the final oxadiazole formation step. MS: [M+1]=432.

Example 65n: Synthesis of Compound 369

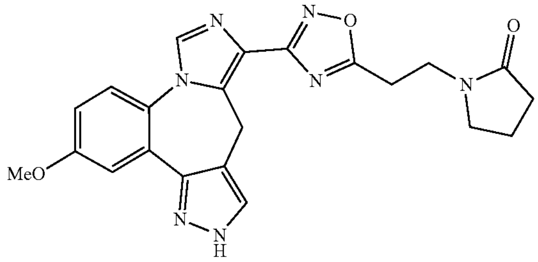 [SMILES: COc1ccc2c(c1)-c1n[nH]cc1Cc1c(-c3noc(CCN4CCCC4=O)n3)ncn1-2]

Compound 369 was prepared analogously as Compound 347, using 3-(2-oxopyrrolidin-1-yl)propionic acid in the final oxadiazole formation step. MS: [M+1]=446.

Example 65o: Synthesis of Compound 359

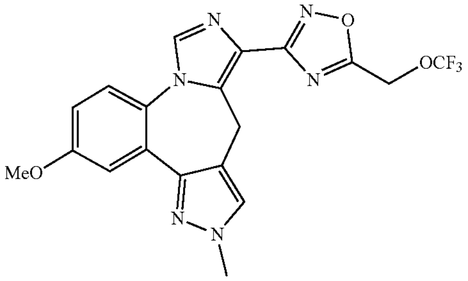 [SMILES: COc1ccc2c(c1)-c1nn(C)cc1Cc1c(-c3noc(COC(F)(F)F)n3)ncn1-2]

Compound 359 was prepared analogously as Compound 347, using 2-trifluoromethoxy acetic acid in the final oxadiazole formation step. MS: [M+1]=433.

Example 65p: Synthesis of Compound 360

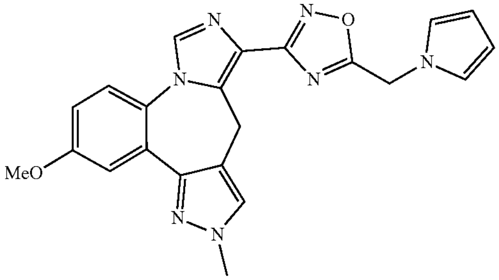 [SMILES: COc1ccc2c(c1)-c1nn(C)cc1Cc1c(-c3noc(Cn4cccc4)n3)ncn1-2]

Compound 360 was prepared analogously as Compound 347, using 1H-pyrrol-1-ylacetic acid in the final oxadiazole formation step. MS: [M+1]=414.

Example 65q: Synthesis of Compound 361

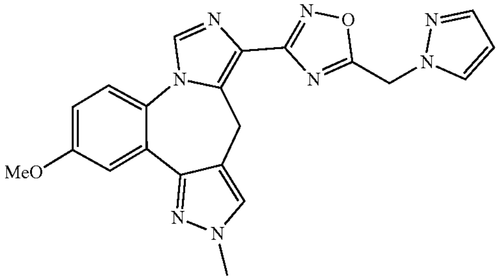 [SMILES: COc1ccc2c(c1)-c1nn(C)cc1Cc1c(-c3noc(Cn4cccn4)n3)ncn1-2]

Compound 361 was prepared analogously as Compound 347, using 1-pyrazoleacetic acid in the final oxadiazole formation step. MS: [M+1]=415.

Example 66: Synthesis of Compound 153

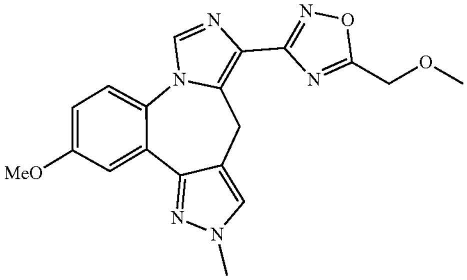 [SMILES: COCc1nc(-c2ncn3c2Cc2cn(C)nc2-c2cc(OC)ccc2-3)no1]

Example 66 was prepared analogously as Example 64, using methoxy acetic acid in the final oxadiazole formation step. MS: [M+1]=379.

Example 67: Synthesis of Compound 137

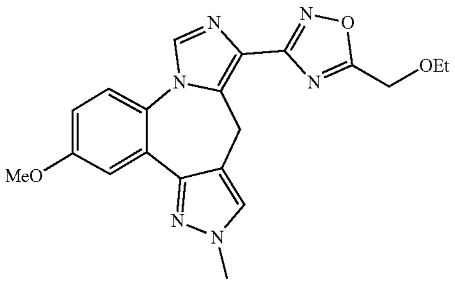 [SMILES: CCOCc1nc(-c2ncn3c2Cc2cn(C)nc2-c2cc(OC)ccc2-3)no1]

Example 67 was prepared analogously as Example 64, using ethoxy acetic acid in the final oxadiazole formation step. MS: [M+1]=393.

Example 67a: Synthesis of Compound 296

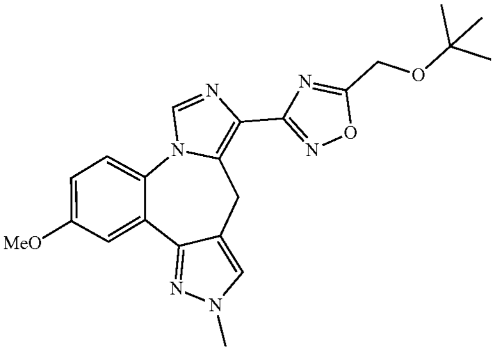 [SMILES: COc1ccc2c(c1)-c1nn(C)cc1Cc1c(-c3noc(COC(C)(C)C)n3)ncn1-2]

Compound 296 was prepared analogously as Example 64, using t-butoxyacetic acid in the final oxadiazole formation step. MS: [M+1]=421.

Example 67b: Synthesis of Compound 342

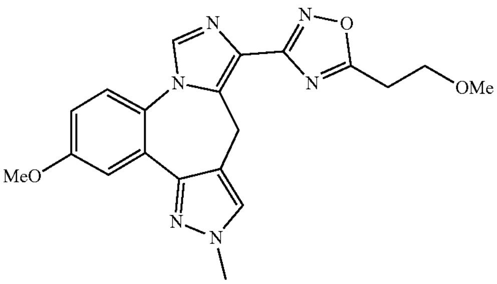 [SMILES: COCCc1nc(-c2ncn3c2Cc2cn(C)nc2-c2cc(OC)ccc2-3)no1]

Compound 342 was prepared analogously as Example 64, using 3-methoxypropanoic acid in the final oxadiazole formation step. MS: [M+1]=393.

Example 67c: Synthesis of Compound 297

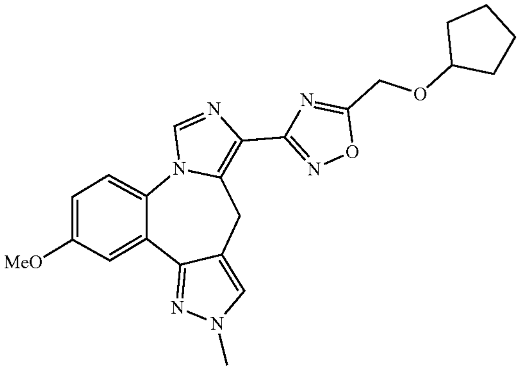 [SMILES: COc1ccc2c(c1)-c1nn(C)cc1Cc1c(-c3noc(COC4CCCC4)n3)ncn1-2]

Compound 297 was prepared analogously as Example 64, using cyclopentoxyacetic acid in the final oxadiazole formation step. MS: [M+1]=433.

Example 67-1: Synthesis of Compound 255

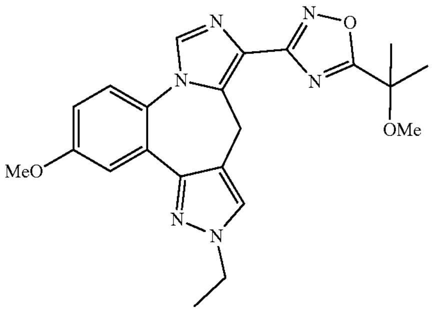 [SMILES: CCn1cc2c(n1)-c1cc(OC)ccc1-n1cnc(-c3noc(C(C)(C)OC)n3)c1C2]

Compound 255 was prepared analogously as Example 64, using iodoethane as the N-alkylating agent in the pyrazole alkylation step (Step 2), and 2-methoxy-2-methyl propanoic acid in the final oxadiazole formation (Step 7). MS: [M+1]=421.

Example 67-2: Synthesis of Compound 202

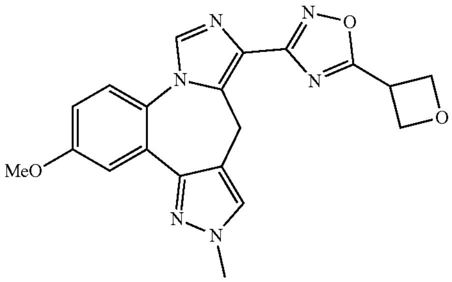 [SMILES: COc1ccc2c(c1)-c1nn(C)cc1Cc1c(-c3noc(C4COC4)n3)ncn1-2]

Compound 202 was prepared analogously as Example 64, using oxetane-3-carboxylic acid in the final oxadiazole formation step. MS: [M+1]=391.

Example 67d: Synthesis of Compound 317

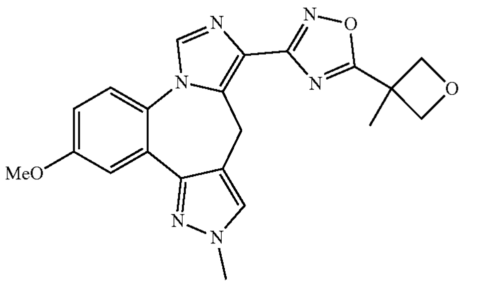 [SMILES: COc1ccc2c(c1)-c1nn(C)cc1Cc1c(-c3noc(C4(C)COC4)n3)ncn1-2]

Compound 317 was prepared analogously as Example 64, using 3-methyloxetane-3-carboxylic acid in the final oxadiazole formation step. MS: [M+1]=405.

Example 67e: Synthesis of Compound 353

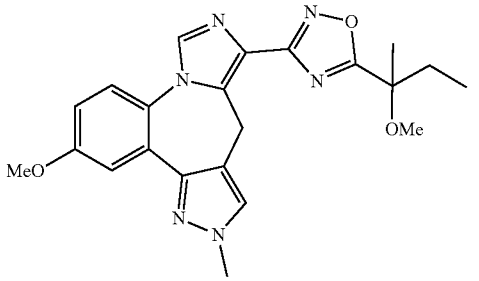 [SMILES: CCC(C)(OC)c1nc(-c2ncn3c2Cc2cn(C)nc2-c2cc(OC)ccc2-3)no1]

Compound 353 was prepared analogously as Example 64, using 2-methoxy-2-methylbutanoic acid in the final oxadiazole formation step. MS: [M+1]=421.

Example 67f: Synthesis of Compound 354

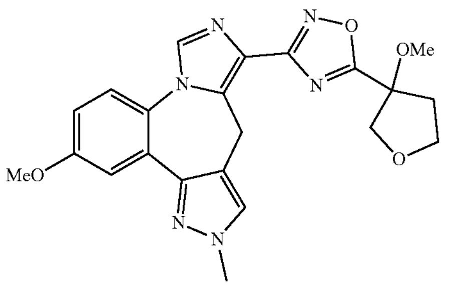 [SMILES: COc1ccc2c(c1)-c1nn(C)cc1Cc1c(-c3noc(C4(OC)CCOC4)n3)ncn1-2]

Compound 354 was prepared analogously as Example 64, using 3-methoxyoxylane-3-carboxylic acid in the final oxadiazole formation step. MS: [M+1]=435.

Example 67g: Synthesis of Compound 355

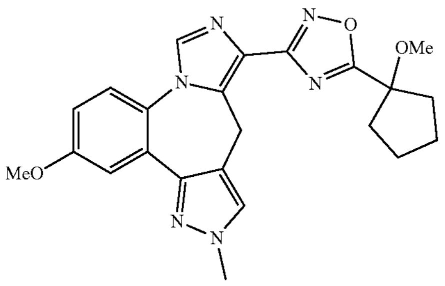 [SMILES: COc1ccc2c(c1)-c1nn(C)cc1Cc1c(-c3noc(C4(OC)CCCC4)n3)ncn1-2]

Compound 355 was prepared analogously as Example 64, using 1-methoxycyclopentane-1-carboxylic acid in the final oxadiazole formation step. MS: [M+1]=433.

Example 67h: Synthesis of Compound 356

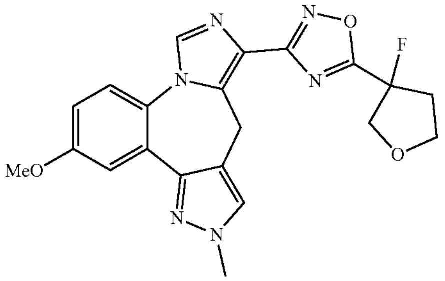 [SMILES: COc1ccc2c(c1)-c1nn(C)cc1Cc1c(-c3noc(C4(F)CCOC4)n3)ncn1-2]

Compound 356 was prepared analogously as Example 64, using 3-fluorooxolane-3-carboxylic acid in the final oxadiazole formation step. MS: [M+1]=423.

Example 67i: Synthesis of Compound 344

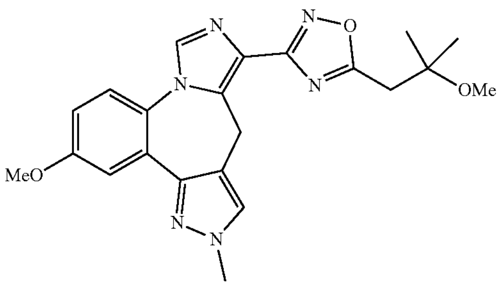 [SMILES: COc1ccc2c(c1)-c1nn(C)cc1Cc1c(-c3noc(CC(C)(C)OC)n3)ncn1-2]

Compound 344 was prepared analogously as Example 64, using 3-methoxy-3-methylbutanoic acid in the final oxadiazole formation step. MS: [M+1]=421.

Example 67j: Synthesis of Compound 323

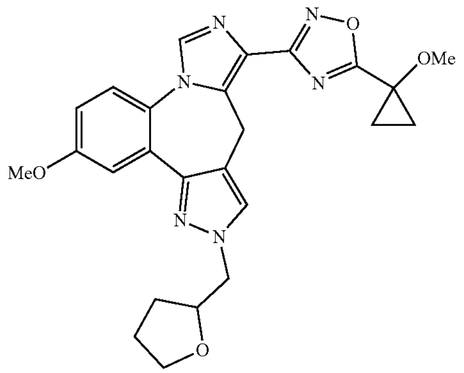 [SMILES: COc1ccc2c(c1)-c1nn(CC3CCCO3)cc1Cc1c(-c3noc(C4(OC)CC4)n3)ncn1-2]

Compound 323 was prepared analogously as Example 64, using tetrahydrofurfuryl bromide as the N-alkylating agent in the pyrazole alkylation step (Step 2), and 1-methoxycyclopropane-1-carboxylic acid in the final oxadiazole formation (Step 7). MS: [M+1]=475.

Example 68: Synthesis of Compound 136

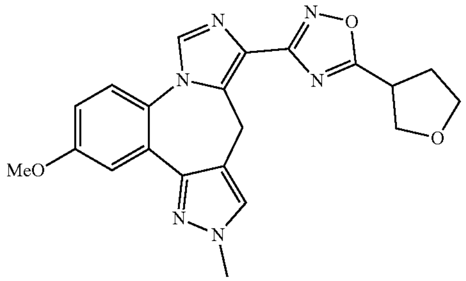 [SMILES: COc1ccc2c(c1)-c1nn(C)cc1Cc1c(-c3noc(C4CCOC4)n3)ncn1-2]

Example 68 was prepared analogously as Example 64, using 3-tetrahydrofuroic acid in the final oxadiazole formation step. MS: [M+1]=405.

Example 68-1: Synthesis of Compound 256

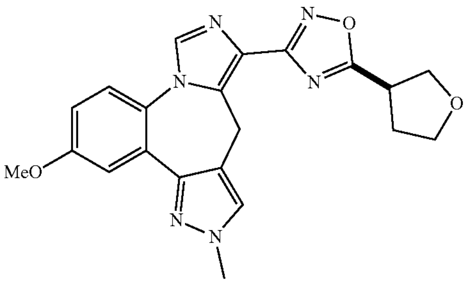

Compound 256 was prepared analogously as Example 68, using (3R)-oxolane-3-carboxylic acid in the oxadiazole formation step. MS: [M+1]=405.

Example 68-2: Synthesis of Compound 257

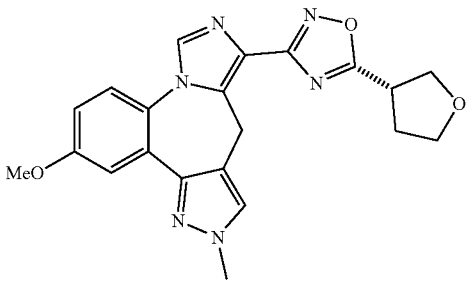

Compound 257 was prepared analogously as Example 68, using (3S)-oxolane-3-carboxylic acid in the oxadiazole formation step. MS: [M+1]=405.

Example 68-3: Synthesis of Compound 258

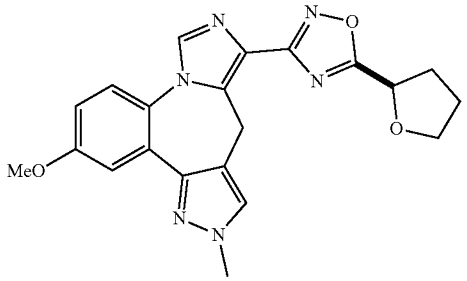

Compound 258 was prepared analogously as Example 68, using (R)-(+)-2-tetrahydrofuroic acid in the oxadiazole formation step. MS: [M+1]=405.

Example 68-4: Synthesis of Compound 259

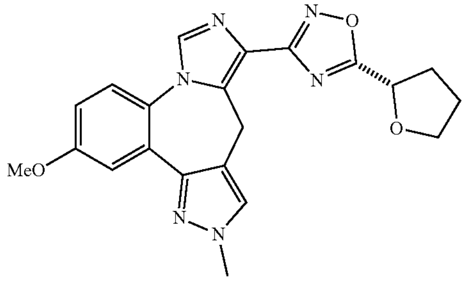

Compound 259 was prepared analogously as Example 68, using (S)-(+)-2-tetrahydrofuroic acid in the oxadiazole formation step. MS: [M+1]=405.

Example 68-5: Synthesis of Compound 254

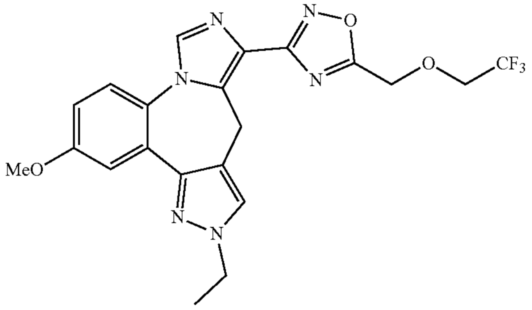 [SMILES: CCn1cc2c(n1)-c1cc(OC)ccc1-n1cnc(-c3noc(COCC(F)(F)F)n3)c1C2]

Compound 254 was prepared analogously as Example 64, using iodoethane as the N-alkylating agent in the pyrazole alkylation step (Step 2), and trifluoroethoxy acetic acid in the final oxadiazole formation (Step 7). MS: [M+1]=461.

Example 68a: Synthesis of Compound 279

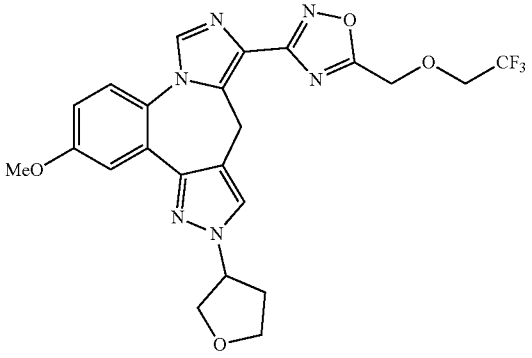 [SMILES: COc1ccc2c(c1)-c1nn(C3CCOC3)cc1Cc1c(-c3noc(COCC(F)(F)F)n3)ncn1-2]

Compound 279 was prepared analogously as Compound 254, using 3-iodotetrahydrofuran as the N-alkylating agent in the pyrazole alkylation step (Step 2). MS: [M+1]=503.

Example 68b: Synthesis of Compound 292

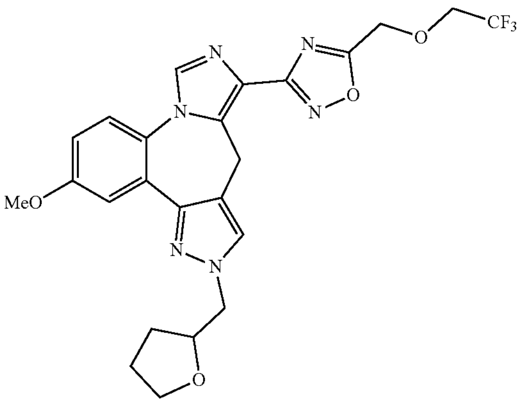 [SMILES: COc1ccc2c(c1)-c1nn(CC3CCCO3)cc1Cc1c(-c3noc(COCC(F)(F)F)n3)ncn1-2]

Compound 292 was prepared analogously as Compound 254, using tetrahydrofurfuryl bromide as the N-alkylating agent in the pyrazole alkylation step. MS: [M+1]=517.

Example 69: Synthesis of Compound 130

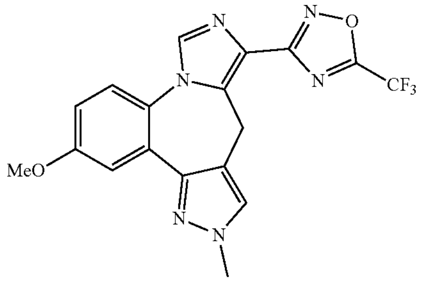 [SMILES: COc1ccc2c(c1)-c1nn(C)cc1Cc1c(-c3noc(C(F)(F)F)n3)ncn1-2]

Example 69 was prepared analogously as Example 63, using trifluoroacetic anhydride in the final oxadiazole formation step. MS: [M+1]=403.

Example 70: Synthesis of Compound 140

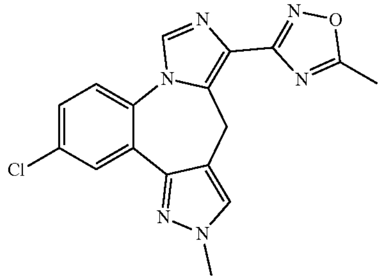 [SMILES: Cc1nc(-c2ncn3c2Cc2cn(C)nc2-c2cc(Cl)ccc2-3)no1]

Example 70 was prepared analogously as Example 63, starting with Intermediate B ($R^1$=Cl). MS: [M+1]=353.

Example 71: Synthesis of Compound 147

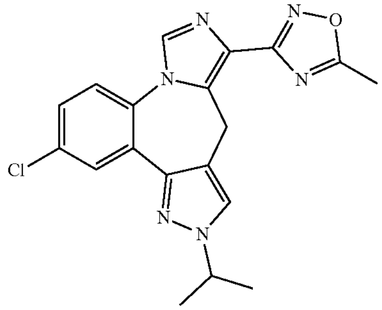 [SMILES: Cc1nc(-c2ncn3c2Cc2cn(C(C)C)nc2-c2cc(Cl)ccc2-3)no1]

Example 71 was prepared analogously as Example 70, using 2-iodopropane as the N-alkylating agent in the pyrazole alkylation step (Step 2). MS: [M+1]=381.

Example 72: Synthesis of Compound 141

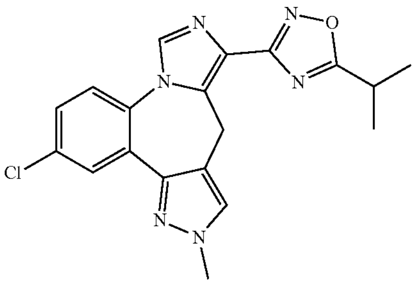 [SMILES: CC(C)c1nc(-c2ncn3c2Cc2cn(C)nc2-c2cc(Cl)ccc2-3)no1]

Example 72 was prepared analogously as Example 64, starting with Intermediate B ($R^1$=Cl), and using isobutyric acid in the final oxadiazole formation step. MS: [M+1]=381.

Example 72-1: Synthesis of Compound 175

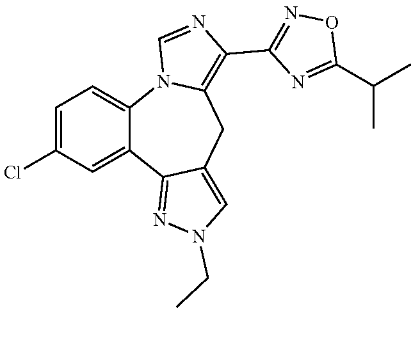 [SMILES: CCn1cc2c(n1)-c1cc(Cl)ccc1-n1cnc(-c3noc(C(C)C)n3)c1C2]

Compound 175 was prepared analogously as Example 72, using iodoethane as the N-alkylating agent in the pyrazole alkylation step. MS: [M+1]=395.

Example 73: Synthesis of Compound 150

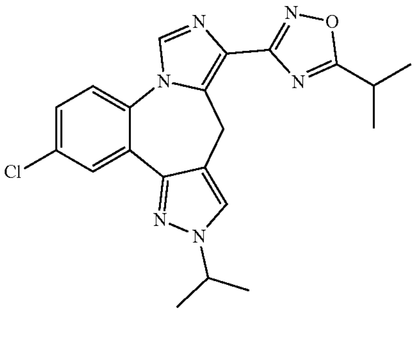 [SMILES: CC(C)c1nc(-c2ncn3c2Cc2cn(C(C)C)nc2-c2cc(Cl)ccc2-3)no1]

Example 73 was prepared analogously as Example 72, using 2-iodopropane as the N-alkylating agent in the pyrazole alkylation step (Step 2). MS: [M+1]=409.

Example 74: Synthesis of Compound 142

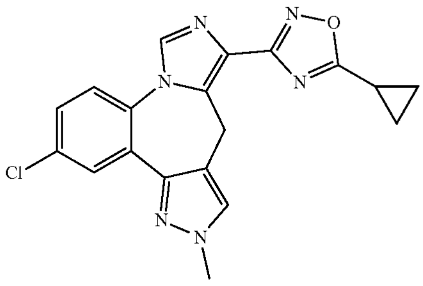 [SMILES: Cn1cc2c(n1)-c1cc(Cl)ccc1-n1cnc(-c3noc(C4CC4)n3)c1C2]

Example 74 was prepared analogously as Example 72, using cyclopropanecarboxylic acid in the final oxadiazole formation step (Step 7). MS: [M+1]=379.

Example 74-1: Synthesis of Compound 176

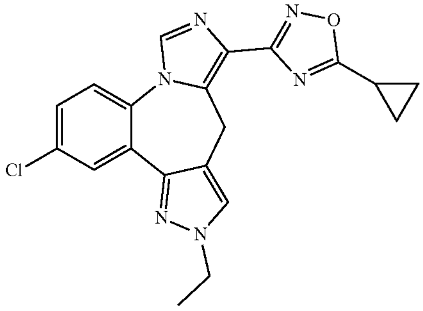 [SMILES: CCn1cc2c(n1)-c1cc(Cl)ccc1-n1cnc(-c3noc(C4CC4)n3)c1C2]

Compound 176 was prepared analogously as Example 74, using iodoethane as the N-alkylating agent in the pyrazole alkylation step. MS: [M+1]=393.

Example 75: Synthesis of Compound 149

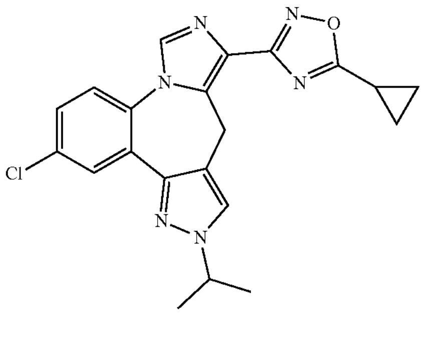 [SMILES: CC(C)n1cc2c(n1)-c1cc(Cl)ccc1-n1cnc(-c3noc(C4CC4)n3)c1C2]

Example 75 was prepared analogously as Example 72, using 2-iodopropane as the N-alkylating agent in the pyrazole alkylation step (Step 2), and cyclopropanecarboxylic acid in the final oxadiazole formation (Step 7). MS: [M+1]=407.

Example 76: Synthesis of Compound 143

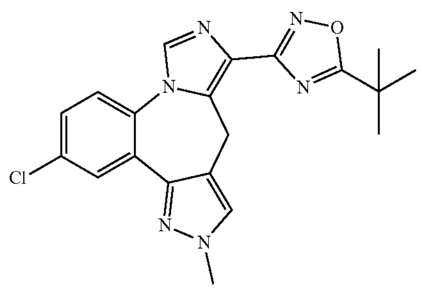 [SMILES: Cn1cc2c(n1)-c1cc(Cl)ccc1-n1cnc(-c3noc(C(C)(C)C)n3)c1C2]

Example 76 was prepared analogously as Example 72, using pivalic acid in the final oxadiazole formation step (Step 7). MS: [M+1]=395.

Example 76-1: Synthesis of Compound 243

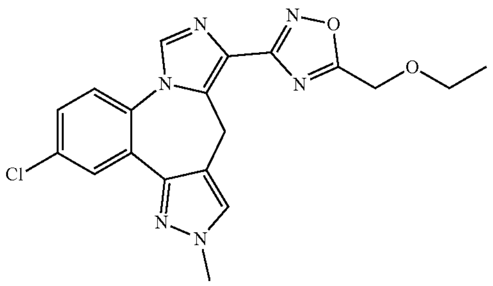 [SMILES: CCOCc1nc(-c2ncn3c2Cc2cn(C)nc2-c2cc(Cl)ccc2-3)no1]

Compound 243 was prepared analogously as Example 72, using ethoxy acetic acid in the oxadiazole formation step. MS: [M+1]=397.

Example 76-2: Synthesis of Compound 211

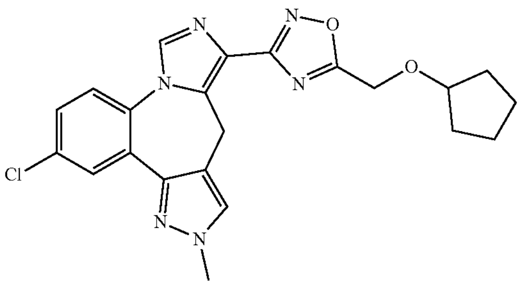 [SMILES: Cn1cc2c(n1)-c1cc(Cl)ccc1-n1cnc(-c3noc(COC4CCCC4)n3)c1C2]

Compound 211 was prepared analogously as Example 72, using cyclopentyloxy acetic acid in the oxadiazole formation step. MS: [M+1]=437.

Example 76-3: Synthesis of Compound 194

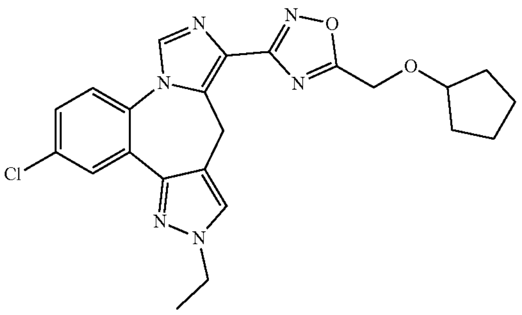 [SMILES: CCn1cc2c(n1)-c1cc(Cl)ccc1-n1cnc(-c3noc(COC4CCCC4)n3)c1C2]

Compound 194 was prepared analogously as Example 72, using iodoethane as the N-alkylating agent in the pyrazole alkylation step (Step 2), and cyclopentyloxy acetic acid in the final oxadiazole formation (Step 7). MS: [M+1]=451.

Example 76-4: Synthesis of Compound 223

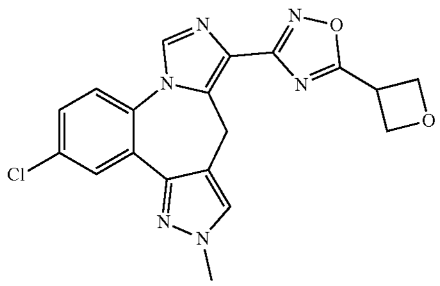 [SMILES: Cn1cc2c(n1)-c1cc(Cl)ccc1-n1cnc(-c3noc(C4COC4)n3)c1C2]

Compound 223 was prepared analogously as Example 72, using oxetane-3-carboxylic acid in the final oxadiazole formation step. MS: [M+1]=395.

Example 76-5: Synthesis of Compound 225

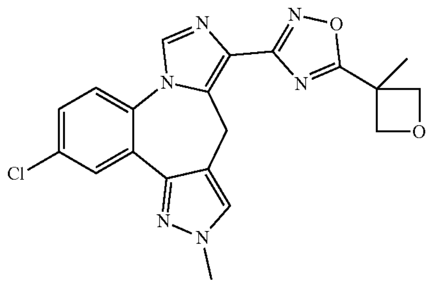 [SMILES: Cn1cc2c(n1)-c1cc(Cl)ccc1-n1cnc(-c3noc(C4(C)COC4)n3)c1C2]

Compound 225 was prepared analogously as Example 72, using 3-methyloxetane-3-carboxylic acid in the final oxadiazole formation step. MS: [M+1]=409.

Example 77: Synthesis of Compound 145

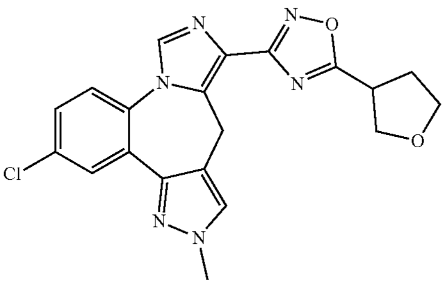 [SMILES: Cn1cc2c(n1)-c1cc(Cl)ccc1-n1cnc(-c3noc(C4CCOC4)n3)c1C2]

Example 77 was prepared analogously as Example 72, using 3-tetrahydrofuroic acid in the final oxadiazole formation step (Step 7). MS: [M+1]=409.

Example 77-1: Synthesis of Compound 214

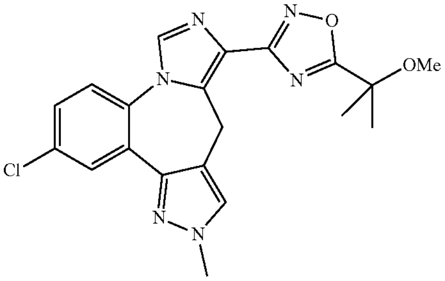 [SMILES: COC(C)(C)c1nc(-c2ncn3c2Cc2cn(C)nc2-c2cc(Cl)ccc2-3)no1]

Compound 214 was prepared analogously as Example 72, using 2-methoxy-2-methylpropanoic acid in the oxadiazole formation step. MS: [M+1]=411.

Example 77-2: Synthesis of Compound 215

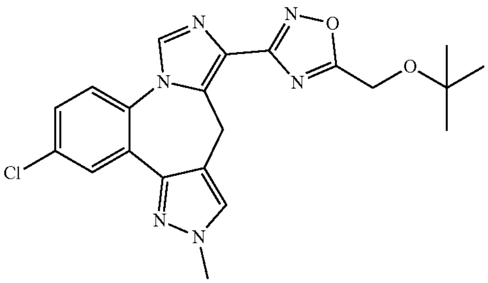 [SMILES: Cn1cc2c(n1)-c1cc(Cl)ccc1-n1cnc(-c3noc(COC(C)(C)C)n3)c1C2]

Compound 215 was prepared analogously as Example 72, using tert-butoxy acetic acid in the oxadiazole formation step. MS: [M+1]=425.

Example 77a: Synthesis of Compound 387

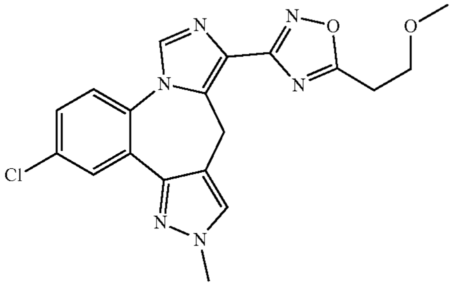 [SMILES: COCCc1nc(-c2ncn3c2Cc2cn(C)nc2-c2cc(Cl)ccc2-3)no1]

Compound 387 was prepared analogously as Example 72, using 3-methoxypropionic acid in the oxadiazole formation step. MS: [M+1]=397.

Example 77-3: Synthesis of Compound 216

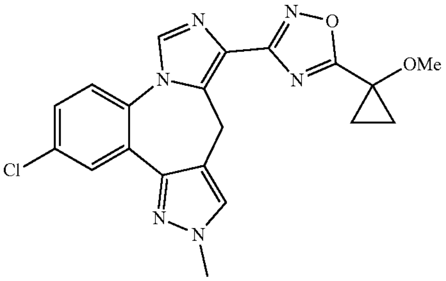 [SMILES: COC1(c2nc(-c3ncn4c3Cc3cn(C)nc3-c3cc(Cl)ccc3-4)no2)CC1]

Compound 216 was prepared analogously as Example 72, using 1-methoxy cyclopropane carboxylic acid in the oxadiazole formation step. MS: [M+1]=409.

Example 77b: Synthesis of Compound 322

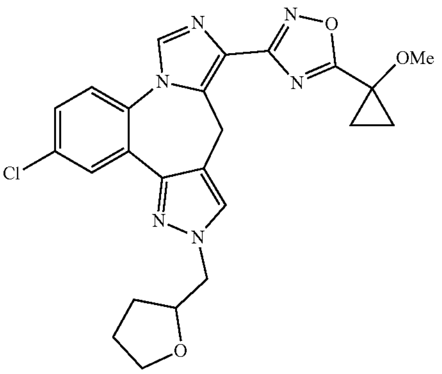 [SMILES: COC1(c2nc(-c3ncn4c3Cc3cn(CC5CCCO5)nc3-c3cc(Cl)ccc3-4)no2)CC1]

Compound 322 was prepared analogously as Compound 216, using tetrahydrofurfuryl bromide in the N-alkylation step. MS: [M+1]=479.

Example 77-4: Synthesis of Compound 213

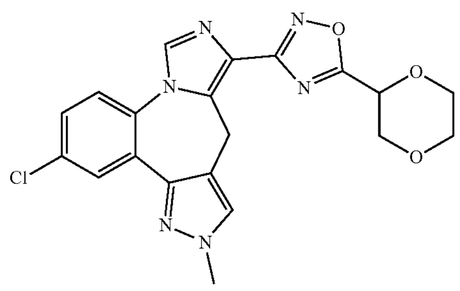 [SMILES: Cn1cc2c(n1)-c1cc(Cl)ccc1-n1cnc(-c3noc(C4COCCO4)n3)c1C2]

Compound 213 was prepared analogously as Example 72, using 1,4-dioxane-2-carboxylic acid in the oxadiazole formation step. MS: [M+1]=425.

Example 77-5: Synthesis of Compound 268

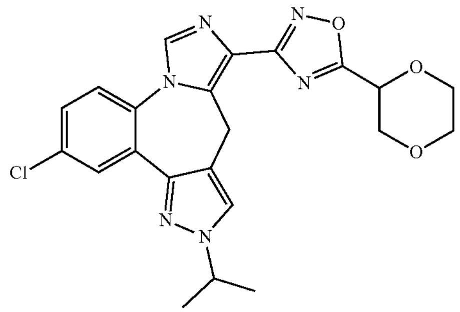 [SMILES: CC(C)n1cc2c(n1)-c1cc(Cl)ccc1-n1cnc(-c3noc(C4COCCO4)n3)c1C2]

Compound 268 was prepared analogously as Example 77-4, using 2-iodopropane as the N-alkylating agent in the pyrazole alkylation step. MS: [M+1]=453.

Example 77-6: Synthesis of Compound 217

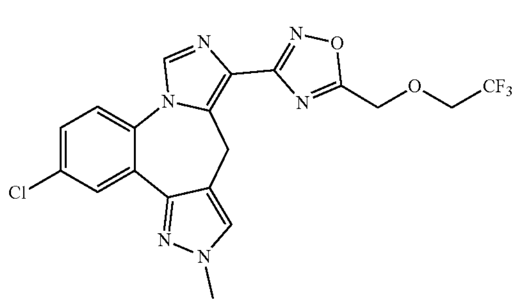 [SMILES: Cn1cc2c(n1)-c1cc(Cl)ccc1-n1cnc(-c3noc(COCC(F)(F)F)n3)c1C2]

Compound 217 was prepared analogously as Example 72, using trifluoroethoxy ethanoic acid in the oxadiazole formation step. MS: [M+1]=451.

Example 77-7: Synthesis of Compound 218

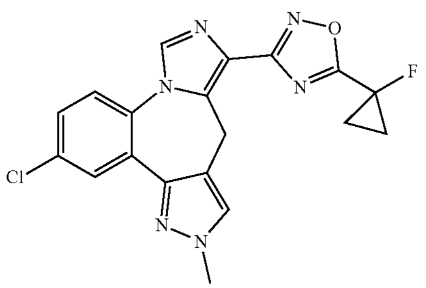 [SMILES: Cn1cc2c(n1)-c1cc(Cl)ccc1-n1cnc(-c3noc(C4(F)CC4)n3)c1C2]

Compound 218 was prepared analogously as Example 72, using 1-fluoro-cyclopropane carboxylic acid in the oxadiazole formation step. MS: [M+1]=397.

Example 78: Synthesis of Compound 144

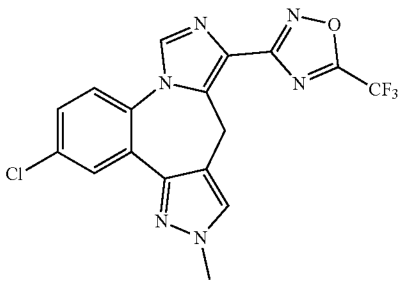 [SMILES: Cn1cc2c(n1)-c1cc(Cl)ccc1-n1cnc(-c3noc(C(F)(F)F)n3)c1C2]

Example 78 was prepared analogously as Example 70, using trifluoroacetic anhydride in the final oxadiazole formation step (Step 7). MS: [M+1]=407.

Example 79: Synthesis of Compound 148

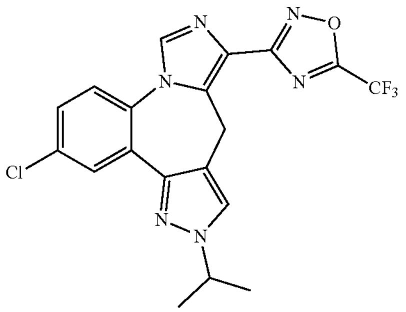 [SMILES: CC(C)n1cc2c(n1)-c1cc(Cl)ccc1-n1cnc(-c3noc(C(F)(F)F)n3)c1C2]

Example 79 was prepared analogously as Example 70, using 2-iodopropane as the N-alkylating agent in the pyrazole alkylation step (Step 2), and trifluoroacetic anhydride in the final oxadiazole formation (Step 7). MS: [M+1]=435.

Example 80: Synthesis of Compound 155

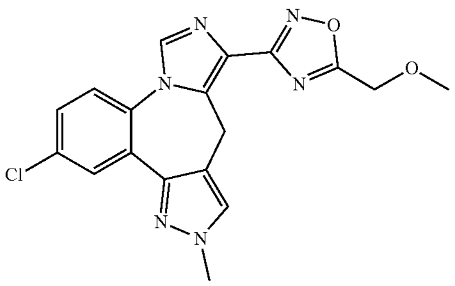 [SMILES: COCc1nc(-c2ncn3c2Cc2cn(C)nc2-c2cc(Cl)ccc2-3)no1]

Example 80 was prepared analogously as Example 70, using methoxy acetic acid in the final oxadiazole formation step (Step 7). MS: [M+1]=383.

Example 81: Synthesis of Compound 156

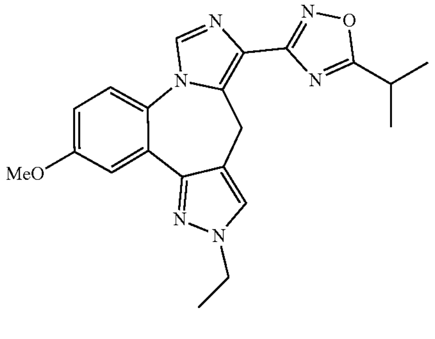 [SMILES: CCn1cc2c(n1)-c1cc(OC)ccc1-n1cnc(-c3noc(C(C)C)n3)c1C2]

Example 81 was prepared analogously as Example 63, using ethyl iodide as the N-alkylating agent in the pyrazole alkylation step (Step 2), and isobutyric acid in the final oxadiazole formation step (Step 7). MS: [M+1]=391.

Example 82: Synthesis of Compound 157

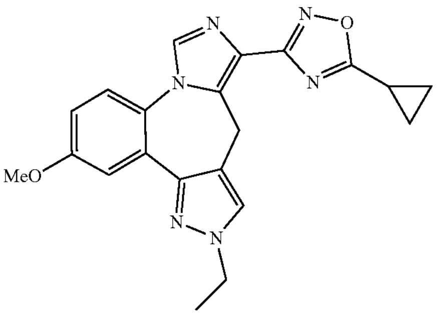 [SMILES: CCn1cc2c(n1)-c1cc(OC)ccc1-n1cnc(-c3noc(C4CC4)n3)c1C2]

Example 82 was prepared analogously as Example 81, using cyclopropanecarboxylic acid in the final oxadiazole formation step (Step 7). MS: [M+1]=389.

Example 83: Synthesis of Compound 158

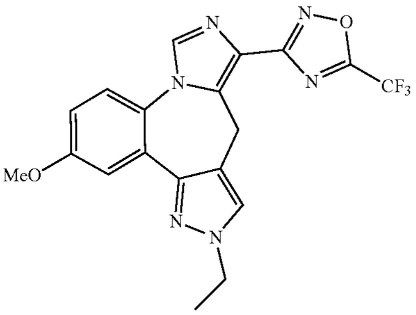 [SMILES: CCn1cc2c(n1)-c1cc(OC)ccc1-n1cnc(-c3noc(C(F)(F)F)n3)c1C2]

Example 83 was prepared analogously as Example 69, using ethyl iodide as the N-alkylating agent in the pyrazole alkylation step (Step 2). MS: [M+1]=417.

Example 83a: Synthesis of Compound 295

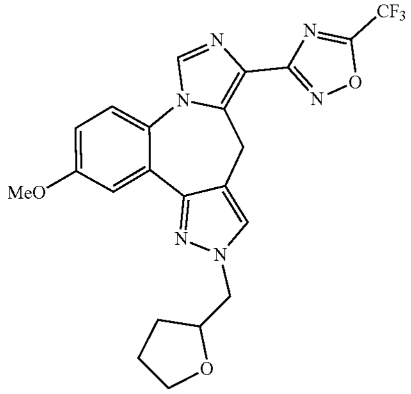 [SMILES: COc1ccc2c(c1)-c1nn(CC3CCCO3)cc1Cc1c(-c3noc(C(F)(F)F)n3)ncn1-2]

Compound 295 was prepared analogously as Example 69, using tetrahydrofurfuryl bromide as the N-alkylating agent in the pyrazole alkylation step (Step 2). MS: [M+1]=473.

Example 83b: Synthesis of Compound 371

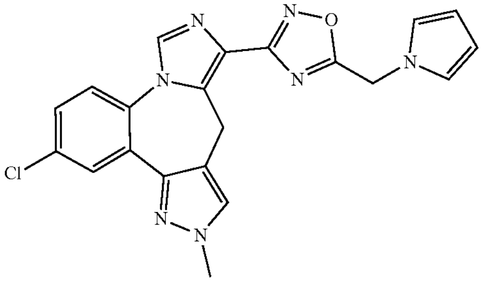 [SMILES: Cn1cc2c(n1)-c1cc(Cl)ccc1-n1cnc(-c3noc(Cn4cccc4)n3)c1C2]

Compound 371 was prepared analogously as Compound 360, starting with Intermediate B ($R_1$=Cl). MS: [M+1]=418.

Example 83c: Synthesis of Compound 372

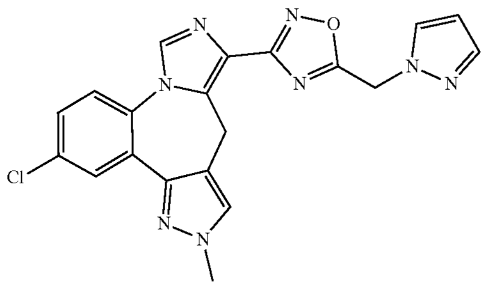 [SMILES: Cn1cc2c(n1)-c1cc(Cl)ccc1-n1cnc(-c3noc(Cn4cccn4)n3)c1C2]

Compound 372 was prepared analogously as Compound 371, using 1-pyrazoleacetic acid in the oxadiazole formation step. MS: [M+1]=419.

Example 83d: Synthesis of Compound 373

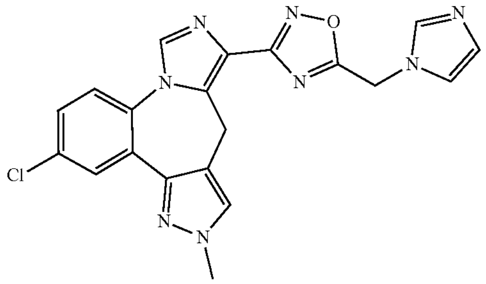 [SMILES: Cn1cc2c(n1)-c1cc(Cl)ccc1-n1cnc(-c3noc(Cn4ccnc4)n3)c1C2]

Compound 373 was prepared analogously as Compound 371, using imidazol-1-ylacetic acid in the oxadiazole formation step. MS: [M+1]=419.

Example 83e: Synthesis of Compound 382

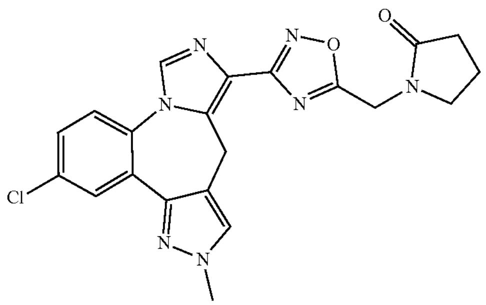 [SMILES: Cn1cc2c(n1)-c1cc(Cl)ccc1-n1cnc(-c3noc(CN4CCCC4=O)n3)c1C2]

Compound 382 was prepared analogously as Compound 371, using 2-oxo-1-pyrrolidineacetic acid in the oxadiazole formation step. MS: [M+1]=436.

Example 83f: Synthesis of Compound 383

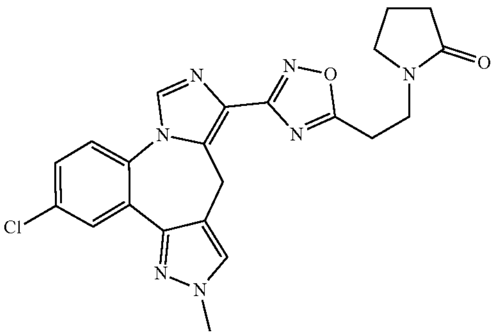 [SMILES: Cn1cc2c(n1)-c1cc(Cl)ccc1-n1cnc(-c3noc(CCN4CCCC4=O)n3)c1C2]

Compound 383 was prepared analogously as Compound 371, using 3-(2-oxopyrrolidin-1-yl)propanoic acid in the oxadiazole formation step. MS: [M+1]=450.

Example 83g: Synthesis of Compound 385

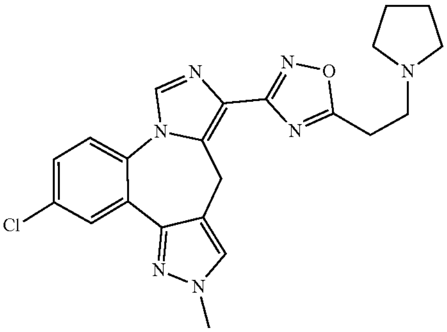 [SMILES: Cn1cc2c(n1)-c1cc(Cl)ccc1-n1cnc(-c3noc(CCN4CCCC4)n3)c1C2]

Compound 385 was prepared analogously as Compound 371, using 3-pyrrolidin-1-yl-propionic acid in the oxadiazole formation step. MS: [M+1]=436.

Example 83h: Synthesis of Compound 365

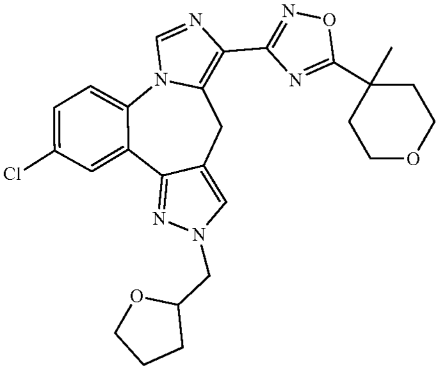 [SMILES: CC1(c2nc(-c3ncn4c3Cc3cn(CC5CCCO5)nc3-c3cc(Cl)ccc3-4)no2)CCOCC1]

Compound 365 was prepared analogously as Compound 371, using tetrahydrofurfuryl bromide as the N-alkylating agent, and 4-methyltetrahydro-2H-pyran-4-carboxylic acid in the final oxadiazole formation step. MS: [M+1]=507.

Scheme 7-B
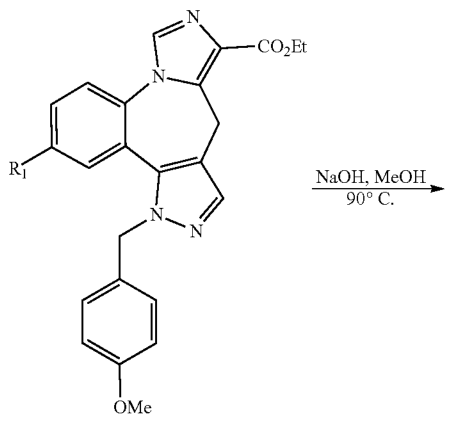
Intermediate B
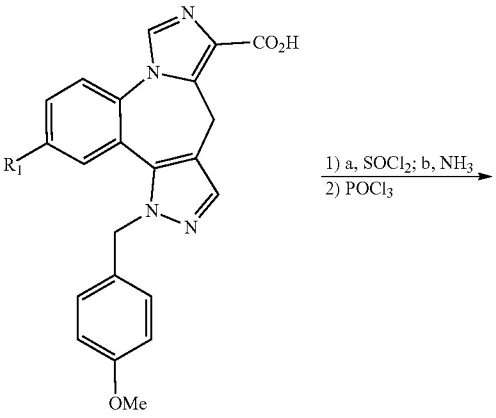
7B.1
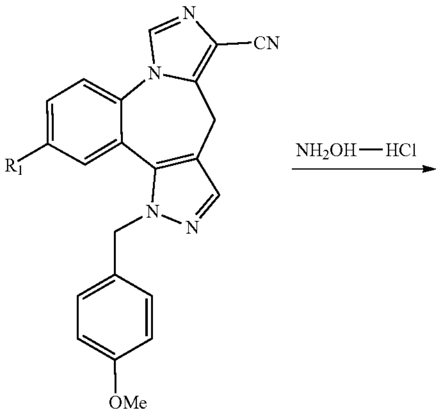
7B. 2
-continued
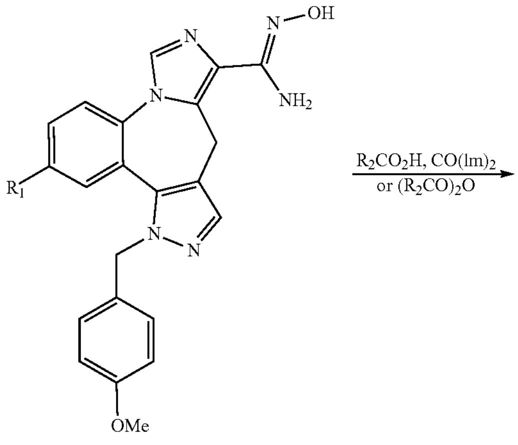
7B.3
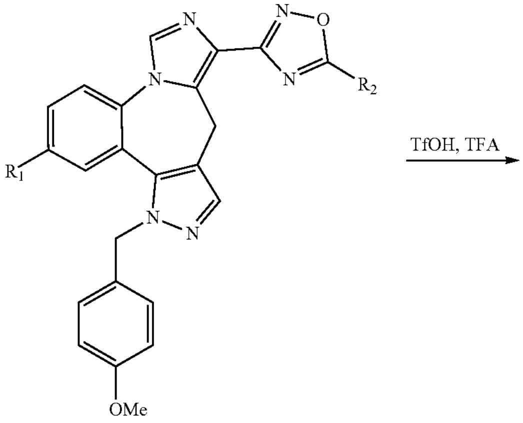
7B.4
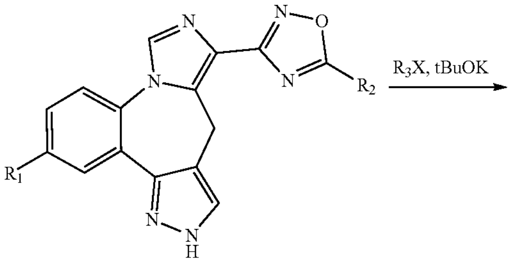
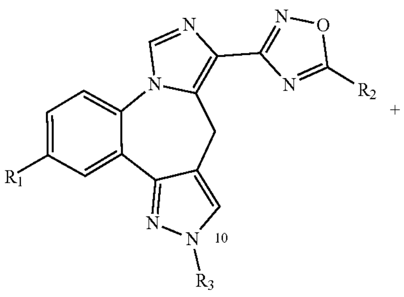
(major isomer)

-continued

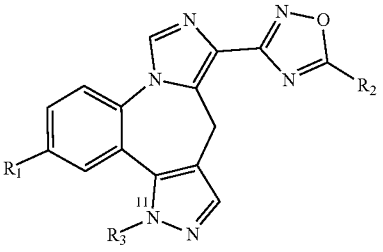

(minor isomer)

| R1 R2 |
|---|
| Ex. 84 Compound 088: OMe, Me |
| Ex. 85 Compound 054: OMe, iPr |
| Ex. 86 Compound 089: OMe, tBu |
| Ex. 86-1 Compound 181: OMe, $(Me)_2CMeO$ |
| Ex. 86-2 Compound 188: OMe, $(CH_2)_2COMe$ |
| Ex. 86-3 Compound 191: OMe, $(CH_2)_2CF$ |
| Ex. 86-4 Compound 174: OMe, $CF3CH_2OCH_2$ |
| Ex. 86-5 Compound 187: OMe, DOX-2-yl |
| Ex. 87 Compound 087: OMe, $CF_3$ |
| Ex. 88 Compound 086: Cl, Me |
| Ex. 89 Compound 084: Cl, iPr |
| Ex. 90 Compound 085: Cl, $CF_3$ |

| | R1 R2 R3 |
|---|---|
| Ex. 91 Compound 109: | OMe, iPr, Me |
| Ex. 92 Compound 114: | OMe, iPr, iPr |
| Ex. 93 Compound 110: | OMe, iPr, $MeO(CH_2)_2$ |
| Ex. 93a Compound 311: | MeO, $(Me)_2COMe$, $MeO(CH_2)_2$ |
| Ex. 93b Compound 343: | MeO, $(Me)_2COMe$, $CF_3O(CH_2)_2$ |
| Ex. 93c Compound 324: | MeO, $CH(CH_2CH_2)_2O$, Me |
| Ex. 93d Compound 318: | MeO, $CH(CH_2CH_2)_2O$, $MeO(CH_2)_2$ |
| Ex. 93e Compound 327: | MeO, $CH(CH_2CH_2)_2O$, $CF_3O(CH_2)_2$ |
| Ex. 93f Compound 340: | MeO, $(CH_2)_2COMe$, Et |
| Ex. 93g Compound 339: | MeO, $(CH_2)_2COMe$, $MeO(CH_2)_2$ |
| Ex. 93h Compound 330: | MeO, $(CH_2)_2COMe$, $CF_3O(CH_2)_2$ |
| Ex. 93i Compound 312: | MeO, $(Me)_2COMe$, OXT-3-yl-$CH_2$ |
| Ex. 93j Compound 333: | MeO, $(Me)_2COMe$, $tBuO(CH_2)_2$ |
| Ex. 93k Compound 293: | MeO, $MeOCH_2$, THF-2-yl-$CH_2$ |
| Ex. 93l Compound 304: | Cl, $MeOCH_2$, THF-2-yl-$CH_2$ |
| Ex. 93m Compound 305: | Cl, DOX-2-yl, THF-2-yl-$CH_2$ |
| Ex. 93n Compound 306: | Cl, $(Me)_2COMe$, THF-2-yl-$CH_2$ |
| Ex. 93o Compound 301: | MeO, $iPrOCH_2$, THF-2-yl-$CH_2$ |
| Ex. 93p Compound 294: | MeO, OXT-3-yl, THF-2-yl-$CH_2$ |
| Ex. 93-1 Compound 183: | OMe, $CF_3CH_2OCH_2$, Me |
| Ex. 93q Compound 313: | OMe, $CF_3CH_2OCH_2$, $MeO(CH_2)_2$ |
| Ex. 93r Compound 314: | OMe, $CF_3CH_2OCH_2$, OXT-3-yl-$CH_2$ |
| Ex. 93-2 Compound 185: | OMe, $(Me)_2COMe$, Me |
| Ex. 93s Compound 341: | OMe, $(Me)_2COEt$, Me |
| Ex. 93t Compound 283: | OMe, $(Me)_2COMe$, THF-2-yl-$CH_2$ |
| Ex. 93u Compound 374: | OMe, $(Me)_2COMe$, THF-3-yl-$CH_2$ |
| Ex. 93-3 Compound 203: | OMe, $(CH_2)_2COMe$, Me |
| Ex. 93v Compound 331: | OMe, $(CH_2)_2COMe$, OXT-3-yl-$CH_2$ |
| Ex. 93-4 Compound 207: | OMe, DOX-2-yl, Me |
| Ex. 93-5 Compound 205: | OMe, $(CH_2)_2CF$, Me |
| Ex. 93-6 Compound 195: | Cl, DOX-2-yl, Et |
| Ex. 93-7 Compound 196: | Cl, $(Me)_2COMe$, Et |
| Ex. 93-8 Compound 197: | Cl, tBuO-$CH_2$, Et |
| Ex. 93w Compound 307: | Cl, iPrO-$CH_2$, THF-2-yl-$CH_2$ |
| Ex. 93x Compound 308: | Cl, THF-3-yl, THF-2-yl-$CH_2$ |
| Ex. 93y Compound 309: | Cl, $CF_3CH_2OCH_2$, THF-2-yl-$CH_2$ |
| Ex. 93z Compound 362: | Cl, $CH(CH_2CH_2)_2O$, THF-2-yl-$CH_2$ |
| Ex. 93-9 Compound 198: | Cl, $(CH_2)_2COMe$, Et |
| Ex. 93-10 Compound 184: | OMe, $CF_3CH_2OCH_2$, Me |
| Ex. 93-11 Compound 186: | OMe, $(Me)_2COMe$, Me |
| Ex. 93-12 Compound 204: | OMe, $(CH_2)_2COMe$, Me |
| Ex. 93-13 Compound 206: | OMe, $(CH_2)_2CF$, Me |

Example 84: Synthesis of Compound 88

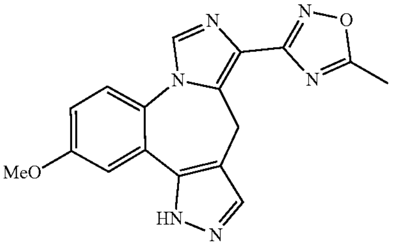 [SMILES: COc1ccc2c(c1)-c1[nH]ncc1Cc1c(-c3noc(C)n3)ncn1-2]

Step 1: Intermediate B ($R_1$=OMe; 594 mg) was treated with NaOH (1N aq.; 3 ml) in MeOH (5 ml) at 90° C. for 2 h, cooled to rt, and acidified to pH 3-4 with dil. HCl. Ppts was collected by filtration, washed with water, and dried to give 511 mg acid 7B.1.

Step 2: The acid 7B.1 (210 mg) was treated with thionyl chloride (1.5 ml) in a pre-heated oil bath of 80° C. for about an hour, cooled to rt, and excess reagent removed in vacuo. Residual thionyl chloride was removed by azeotroping with toluene repeatedly. The resulting crude acid chloride was dissolved in DCM (2 ml) and cooled to 0° C. Ammonia in 1,4-dioxane (0.5 M; 2 ml) was added, and the reaction was allowed to proceed to rt overnight. All solvent was removed in vacuo, and the solid residue was suspended and stirred in sat. $NaHCO_3$ (8 ml) for 2 h. Ppts was collected by filtration, washed with water, and dried to give the crude primary carboxamide as a yellowish solid. This solid was treated with $POCl_3$ (390 mg) in 1,2-dimethoxy ethane (3 ml) at 90° C. for 3 h, cooled to rt, concentrated in vacuo, and further cooled down to 0° C. Sat. $NaHCO_3$ (10 ml) was added, and the aq. mixture was extracted with EtOAc (3×), the combined organic layer was washed with brine, and dried over $MgSO_4$. Filtration and concentration followed by silica gel column chromatography using 0 to 90% EtOAc in hexanes gradient gave 51 mg nitrile 7B.2.

Step 3: Nitrile 7B.2 from above (51 mg) was treated with hydroxylamine hydrochloride (18 mg) in the presence of $K_2CO_3$ (21 mg) in isopropanol (1 ml) and water (0.25 ml) at 80° C. for 2 h, then concentrated to a slurry. Water (5 ml) was added under stirring, and the mixture was cooled to 0° C. Ppts was collected by filtration and washed with water to give 55 mg amide oxime 7B.3.

Step 4: Amide oxime 7B.3 (15.4 mg, 0.0358 mmol) was treated with acetic anhydride (18.3 mg, 0.179 mmol) and triethylamine (18.1 mg, 0.179 mmol) in THE (0.5 ml) at 0° C. for 1 h. THF was then removed and acetic acid (0.1 ml) added, and the reaction mixture was heated at 100° C. for 5 h. Upon cooling, the reaction was treated with sat. $NaHCO_3$, and extracted with EtOAc (3×), the combined extracts washed with brine, and dried over $MgSO_4$. Filtration and solvent removal in vacuo gave the oxadiazole which was treated with trifluoromethane sulfonic acid (21.5 mg) in a mixture of trifluoroacetic acid (0.5 ml) and DCM (0.5 ml) at 45° C. for 20 h. The reaction mixture was concentrated, treated with sat. $NaHCO_3$, and extracted with EtOAc (3×), the combined organic extract was washed with brine and dried over $MgSO_4$. Prep. TLC with 10% MeOH in EtOAc/DCM (1:1) gave 1.5 mg Example 84, Compound 88 as an off-white solid. MS: [M+1]=335.

Example 85: Synthesis of Compound 54

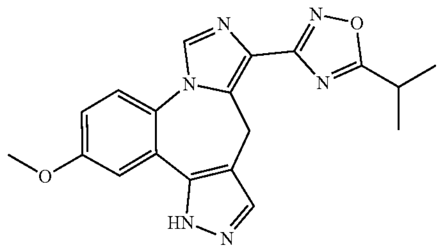 [SMILES: COc1ccc2c(c1)-c1[nH]ncc1Cc1c(-c3noc(C(C)C)n3)ncn1-2]

Example 85 was synthesized analogously as Example 84, using the isobutyric acid/CDI combination (Step 4) as described before (i.e., Example 64 preparation) to make the oxadiazole ring before the final acidic removal of 4-MeOBn protective group. MS: [M+1]=363.

Example 86: Synthesis of Compound 89

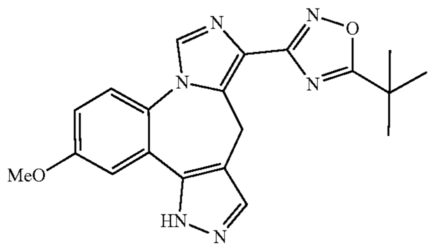 [SMILES: COc1ccc2c(c1)-c1[nH]ncc1Cc1c(-c3noc(C(C)(C)C)n3)ncn1-2]

Example 86 was synthesized analogously as Example 85, using pivalic acid for the construction of the oxadiazole ring in Step 4. MS: [M+1]=377.

Example 86-1: Synthesis of Compound 181

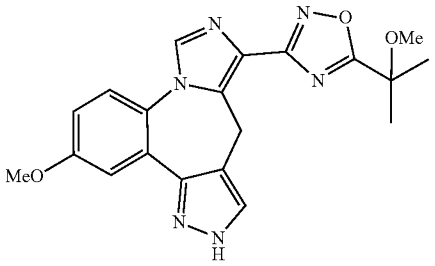 [SMILES: COc1ccc2c(c1)-c1n[nH]cc1Cc1c(-c3noc(C(C)(C)OC)n3)ncn1-2]

Compound 181 was synthesized analogously as Example 85, using 2-methoxy-2-methylpropanoic acid for the construction of the oxadiazole ring in Step 4. MS: [M+1]=393.

Example 86-2: Synthesis of Compound 188

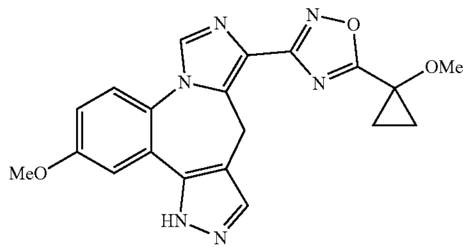 [SMILES: COc1ccc2c(c1)-c1[nH]ncc1Cc1c(-c3noc(C4(OC)CC4)n3)ncn1-2]

Compound 188 was synthesized analogously as Example 85, using 1-methoxy-cyclopropane carboxylic acid for the construction of the oxadiazole ring in Step 4. MS: [M+1] =391.

Example 86-3: Synthesis of Compound 191

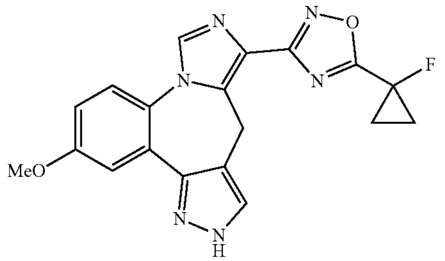 [SMILES: COc1ccc2c(c1)-c1n[nH]cc1Cc1c(-c3noc(C4(F)CC4)n3)ncn1-2]

Compound 191 was synthesized analogously as Example 85, using 1-fluoro-cyclopropane carboxylic acid for the construction of the oxadiazole ring in Step 4. MS: [M+1] =379.

Example 86-4: Synthesis of Compound 174

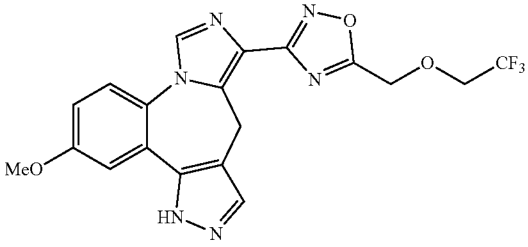 [SMILES: COc1ccc2c(c1)-c1[nH]ncc1Cc1c(-c3noc(COCC(F)(F)F)n3)ncn1-2]

Compound 174 was synthesized analogously as Example 85, using trifluoroethoxy ethanoic acid for the construction of the oxadiazole ring in Step 4. MS: [M+1]=433.

Example 86-5: Synthesis of Compound 187

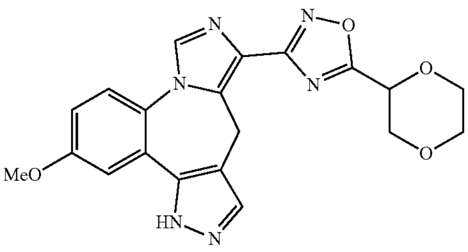 [SMILES: COc1ccc2c(c1)-c1[nH]ncc1Cc1c(-c3noc(C4COCCO4)n3)ncn1-2]

Compound 187 was synthesized analogously as Example 85, using 1,4-dioxane-2-carboxylic acid for the construction of the oxadiazole ring in Step 4. MS: [M+1]=407.

Example 87: Synthesis of Compound 87

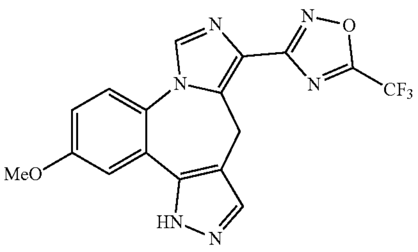 [SMILES: COc1ccc2c(c1)-c1[nH]ncc1Cc1c(-c3noc(C(F)(F)F)n3)ncn1-2]

Example 87 was synthesized analogously as Example 84, using trifluoroacetic anhydride to prepare the oxadiazole ring (Step 4) before the final acidic removal of 4-MeOBn protective group. MS: [M+1]=389.

Example 88: Synthesis of Compound 86

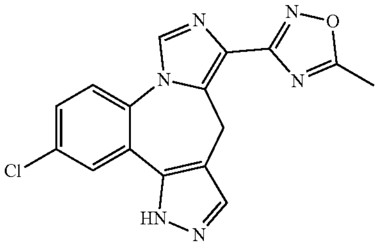 [SMILES: Cc1nc(-c2ncn3c2Cc2cn[nH]c2-c2cc(Cl)ccc2-3)no1]

Example 88 was synthesized analogously as Example 84, starting with Intermediate B ($R_1$=Cl). MS: [M+1]=339.

Example 89: Synthesis of Compound 84

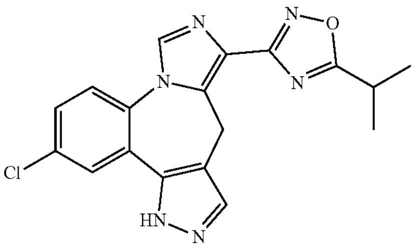 [SMILES: CC(C)c1nc(-c2ncn3c2Cc2cn[nH]c2-c2cc(Cl)ccc2-3)no1]

Example 89 was synthesized analogously as Example 88, using isobutyric acid/CDI combination as described before (i.e., Compound 132 preparation) to make the oxadiazole ring (Step 4) before the final acidic removal of 4-MeOBn protective group. MS: [M+1]=367.

Example 90: Synthesis of Compound 85

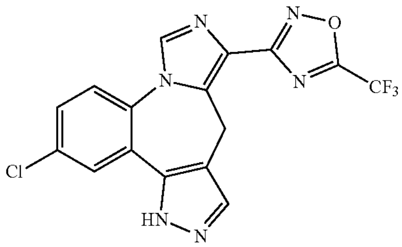 [SMILES: FC(F)(F)c1nc(-c2ncn3c2Cc2cn[nH]c2-c2cc(Cl)ccc2-3)no1]

Example 90 was synthesized analogously as Example 88, using trifluoroacetic anhydride to prepare the oxadiazole ring (Step 4) before the final acidic removal of 4-MeOBn protective group. MS: [M+1]=393.

Example 92: Synthesis of Compound 114

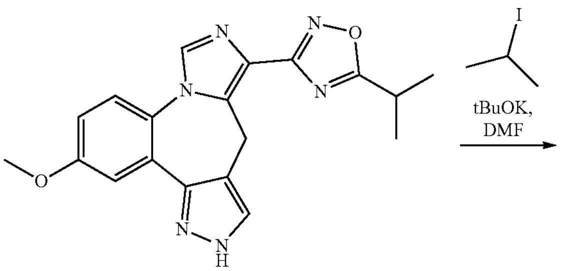

-continued

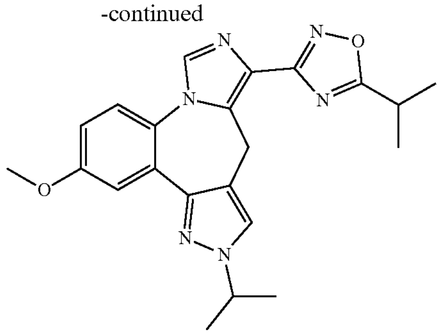

Compound 114
Example 92

To the starting 1H-pyrazole analog (Example 85; 16.5 mg, 0.0455 mmol) and 2-iodopropane (38.7 mg, 0.228 mmol) stirring in DMF (0.25 ml) at 0° C. was added tBuOK (5.6 mg, 0.0500 mmol). After 30 min at 0° C., the reaction mixture was stirred at ambient temperature for 30 min before being heated at 70° C. for 30 min. The reaction mixture was then diluted with EtOAc, washed with sat. $NaHCO_3$, brine, and dried over $MgSO_4$. Prep. TLC (12% MeOH in hexanes/EtOAc=1:1) gave 5.4 mg Example 92, as an off-white solid. MS: [M+1]=405.

Example 91: Synthesis of Compound 109

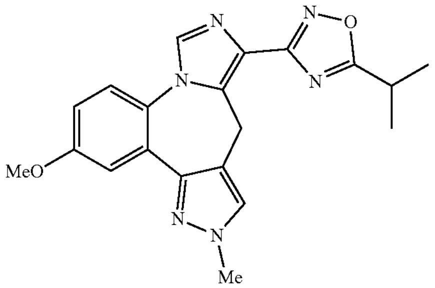 [SMILES: COc1ccc2c(c1)-c1nn(C)cc1Cc1c(-c3noc(C(C)C)n3)ncn1-2]

Example 91 was synthesized analogously as Example 92, using trimethylphenylammonium chloride as the N-alkylating agent in the pyrazole alkylation step. MS: [M+1]=377.

Example 93: Synthesis of Compound 110

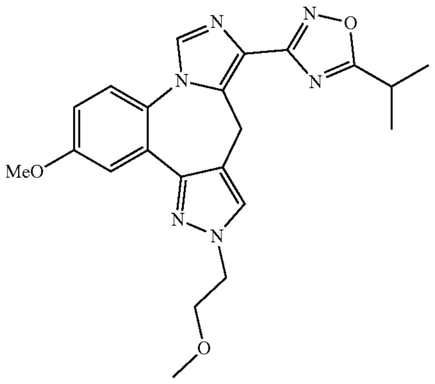 [SMILES: COCCn1cc2c(n1)-c1cc(OC)ccc1-n1cnc(-c3noc(C(C)C)n3)c1C2]

Example 93 was synthesized analogously as Example 92, using methoxyethylbromide as the N-alkylating agent in the pyrazole alkylation step. MS: [M+1]=421.

Example 93a: Synthesis of Compound 311

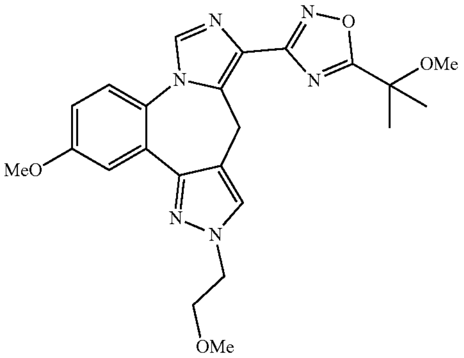 [SMILES: COCCn1cc2c(n1)-c1cc(OC)ccc1-n1cnc(-c3noc(C(C)(C)OC)n3)c1C2]

Compound 311 was synthesized analogously as Compound 110, using 2-methoxy-2-methyl propanoic acid in the oxadiazole formation. MS: [M+1]=451.

Example 93b: Synthesis of Compound 343

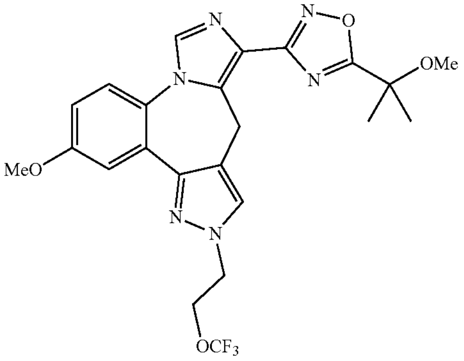 [SMILES: COc1ccc2c(c1)-c1nn(CCOC(F)(F)F)cc1Cc1c(-c3noc(C(C)(C)OC)n3)ncn1-2]

Compound 343 was synthesized analogously as Compound 311, using trifluoromethoxy ethyl bromide for the N-alkylation step. MS: [M+1]=505.

Example 93c: Synthesis of Compound 324

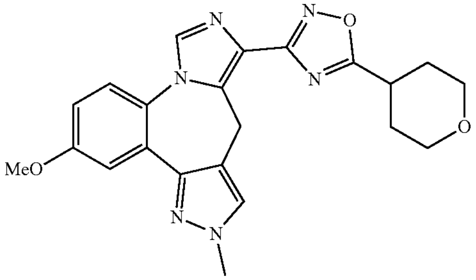 [SMILES: COc1ccc2c(c1)-c1nn(C)cc1Cc1c(-c3noc(C4CCOCC4)n3)ncn1-2]

Compound 324 was synthesized analogously as Compound 109, using tetrahydropyran-4-yl-carboxylic acid in the oxadiazole formation. MS: [M+1]=419.

Example 93d: Synthesis of Compound 318

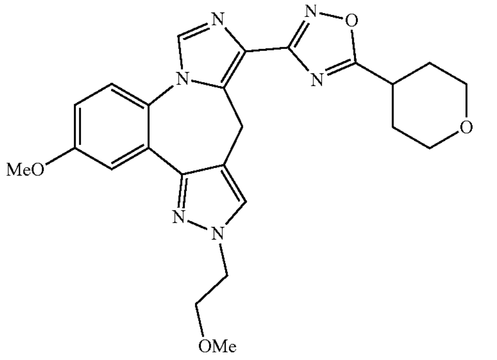 [SMILES: COCCn1cc2c(n1)-c1cc(OC)ccc1-n1cnc(-c3noc(C4CCOCC4)n3)c1C2]

Compound 318 was synthesized analogously as Compound 110, using tetrahydropyran-4-yl-carboxylic acid in the oxadiazole formation. MS: [M+1]=463.

Example 93e: Synthesis of Compound 327

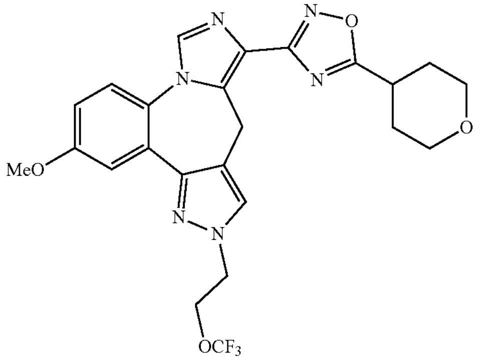 [SMILES: COc1ccc2c(c1)-c1nn(CCOC(F)(F)F)cc1Cc1c(-c3noc(C4CCOCC4)n3)ncn1-2]

Compound 327 was synthesized analogously as Compound 318, using trifluoromethoxy ethyl bromide for the N-alkylation step. MS: [M+1]=517.

Example 93f: Synthesis of Compound 340

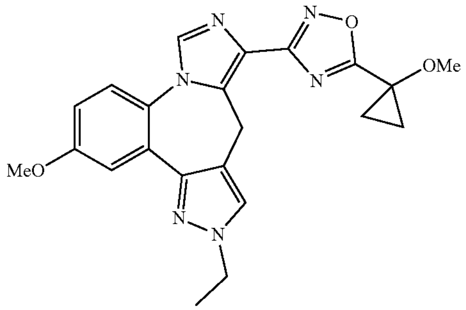 [SMILES: CCn1cc2c(n1)-c1cc(OC)ccc1-n1cnc(-c3noc(C4(OC)CC4)n3)c1C2]

Compound 340 was synthesized analogously as Compound 327, using 1-methoxypropane-1-carboxylic acid in the oxadiazole formation step, and ethyl iodide as the N-alkylating agent in the pyrazole alkylation step. MS: [M+1]=419.

Example 93g: Synthesis of Compound 339

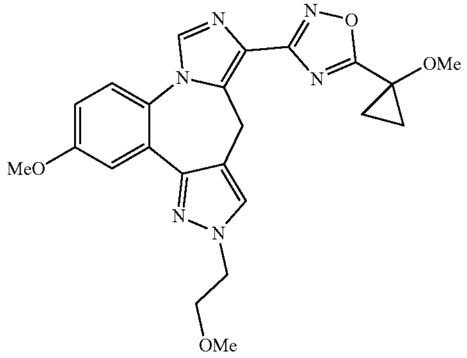 [SMILES: COCCn1cc2c(n1)-c1cc(OC)ccc1-n1cnc(-c3noc(C4(OC)CC4)n3)c1C2]

Compound 339 was synthesized analogously as Compound 327, using 1-methoxypropane-1-carboxylic acid in the oxadiazole formation step, and 2-methoxyethyl bromide as the N-alkylating agent in the pyrazole alkylation step. MS: [M+1]=449.

Example 93h: Synthesis of Compound 330

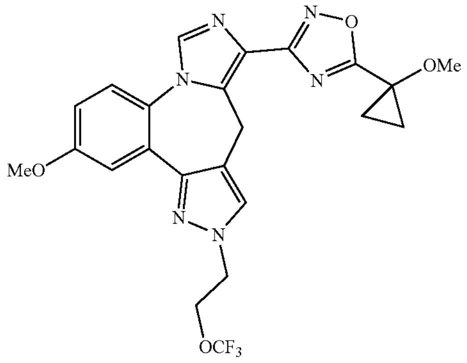 [SMILES: COc1ccc2c(c1)-c1nn(CCOC(F)(F)F)cc1Cc1c(-c3noc(C4(OC)CC4)n3)ncn1-2]

Compound 330 was synthesized analogously as Compound 327, using 1-methoxypropane-1-carboxylic acid to prepare the oxadiazole ring. MS: [M+1]=503.

Example 93i: Synthesis of Compound 312

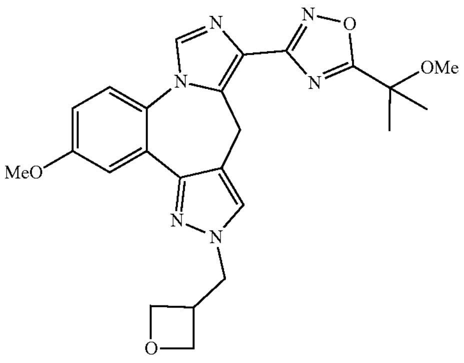 [SMILES: COc1ccc2c(c1)-c1nn(CC3COC3)cc1Cc1c(-c3noc(C(C)(C)OC)n3)ncn1-2]

Compound 312 was synthesized analogously as Compound 311, using toluene-4-sulfonic acid-oxetan-3-yl-methyl ester in the pyrazole N-alkylation steps. MS: [M+1]=463.

Example 93j: Synthesis of Compound 333

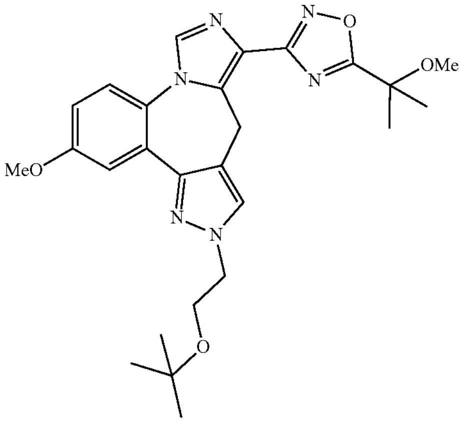 [SMILES: COc1ccc2c(c1)-c1nn(CCOC(C)(C)C)cc1Cc1c(-c3noc(C(C)(C)OC)n3)ncn1-2]

Compound 333 was synthesized analogously as Compound 311, using t-butyl 2-chloroethyl ether in the pyrazole N-alkylation steps. MS: [M+1]=493.

Example 93k: Synthesis of Compound 293

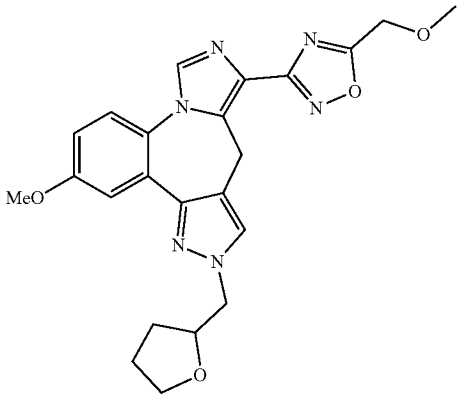 [SMILES: COCc1nc(-c2ncn3c2Cc2cn(CC4CCCO4)nc2-c2cc(OC)ccc2-3)no1]

Compound 293 was synthesized analogously as Compound 110, using methoxyacetic acid in the oxadiazole formation step, and tetrahydrofurfuryl bromide as the N-alkylating agent in the pyrazole alkylation step. MS: [M+1]=449.

Example 93l: Synthesis of Compound 304

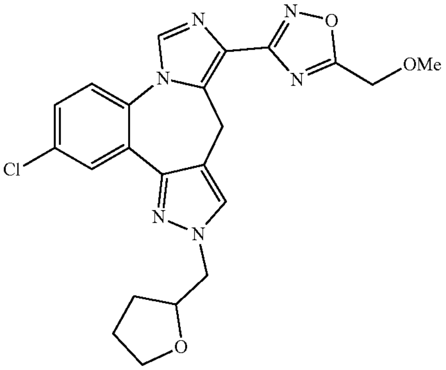 [SMILES: COCc1nc(-c2ncn3c2Cc2cn(CC4CCCO4)nc2-c2cc(Cl)ccc2-3)no1]

Compound 304 was synthesized analogously as Compound 293, starting with Intermediate B ($R_1$=Cl). MS: [M+1]=453.

Example 93m: Synthesis of Compound 305

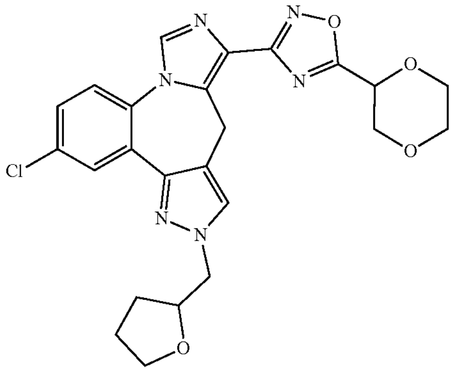 [SMILES: Clc1ccc2c(c1)-c1nn(CC3CCCO3)cc1Cc1c(-c3noc(C4COCCO4)n3)ncn1-2]

Compound 305 was synthesized analogously as Compound 304, using 1,4-dioxane-2-carboxylic acid in the oxadiazole formation step. MS: [M+1]=495.

Example 93n: Synthesis of Compound 306

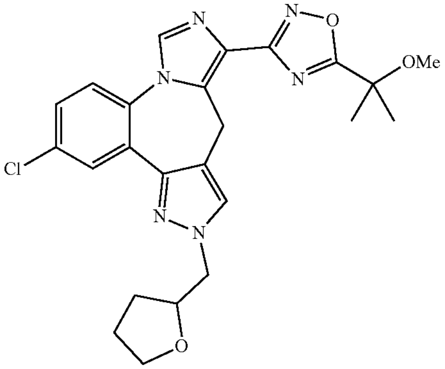 [SMILES: COC(C)(C)c1nc(-c2ncn3c2Cc2cn(CC4CCCO4)nc2-c2cc(Cl)ccc2-3)no1]

Compound 306 was synthesized analogously as Compound 304, using 2-methoxy-2-methylpropanoic acid in the oxadiazole formation step. MS: [M+1]=481.

Example 93o: Synthesis of Compound 301

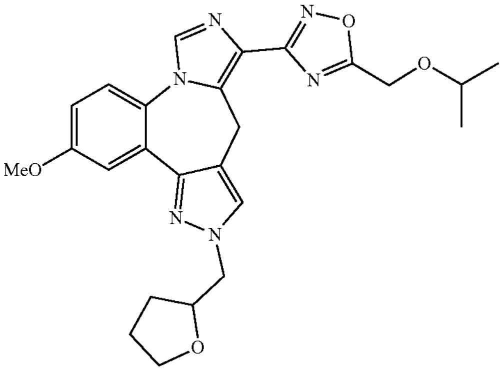 [SMILES: COc1ccc2c(c1)-c1nn(CC3CCCO3)cc1Cc1c(-c3noc(COC(C)C)n3)ncn1-2]

Compound 301 was synthesized analogously as Compound 293, using isopropoxy acetic acid in the oxadiazole formation step. MS: [M+1]=477.

Example 9p: Synthesis of Compound 294

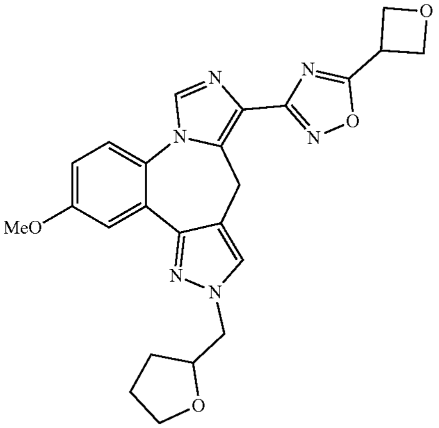 [SMILES: COc1ccc2c(c1)-c1nn(CC3CCCO3)cc1Cc1c(-c3noc(C4COC4)n3)ncn1-2]

Compound 294 was synthesized analogously as Compound 293, using oxetane-3-carboxylic acid in the oxadiazole formation step. MS: [M+1]=461.

Example 93-1 and Example 93-10: Synthesis of Compound 183 and Compound 184

Compound 4183

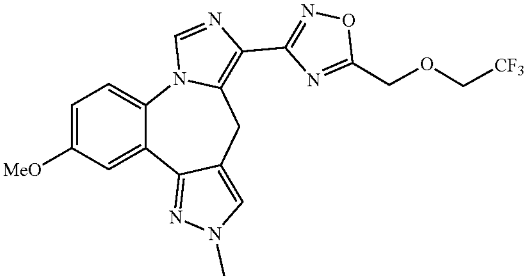

Compound 4184

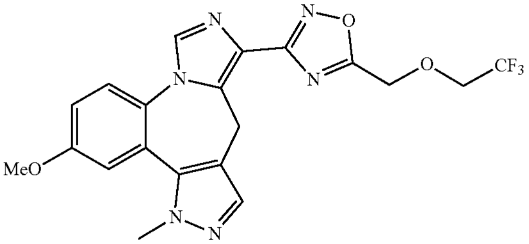

Compound 183 was synthesized analogously as Example 91, using trifluoroethoxy ethanoic acid for the construction of the oxadiazole ring. MS: [M+1]=447.

Also isolated from the preparation was small amount of the N11 minor isomer Example 93-10. MS: [M+1]=447.

Example 93q: Synthesis of Compound 313

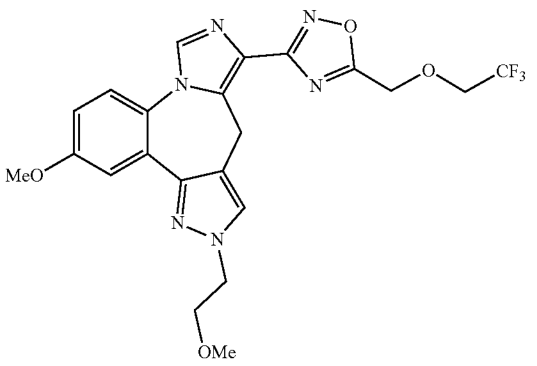 [SMILES: COCCn1cc2c(n1)-c1cc(OC)ccc1-n1cnc(-c3noc(COCC(F)(F)F)n3)c1C2]

Compound 313 was synthesized analogously as Compound 183, using 2-methoxyethyl bromide as the N-alkylating agent in the pyrazole alkylation step. MS: [M+1]=491.

Example 93r: Synthesis of Compound 314

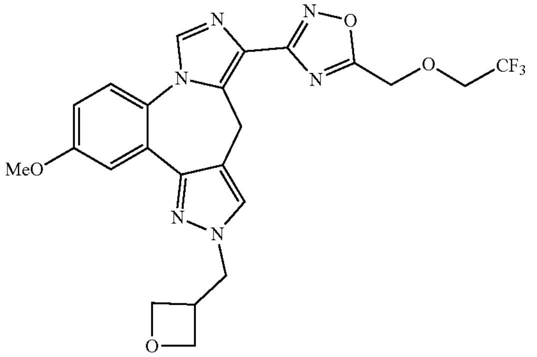 [SMILES: COc1ccc2c(c1)-c1nn(CC3COC3)cc1Cc1c(-c3noc(COCC(F)(F)F)n3)ncn1-2]

Compound 314 was synthesized analogously as Compound 183, using toluene-4-sulfonic acid-oxetan-3-ylmethyl ester in the pyrazole N-alkylation steps. MS: [M+1]=503.

Example 93-2 and Example 93-11: Synthesis of Compound 185 and Compound 186

Compound 185

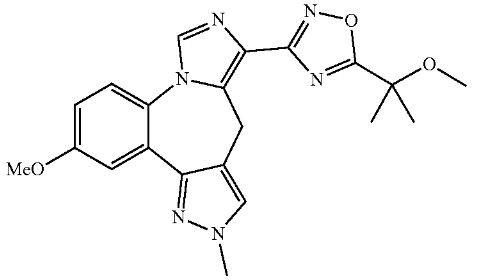

-continued

Compound 186

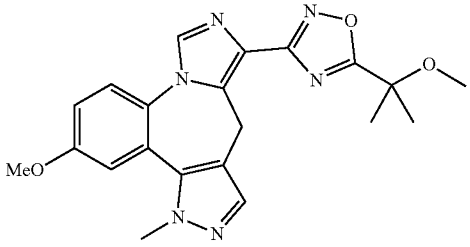

Compound 185 was synthesized analogously as Example 91, using 2-methoxy-2-methylpropanoic acid for the construction of the oxadiazole ring. MS: [M+1]=407.

Also isolated from the preparation was small amount of the N11 minor isomer Example 93-11, Compound 186. MS: [M+1]=407.

Example 93s: Synthesis of Compound 341

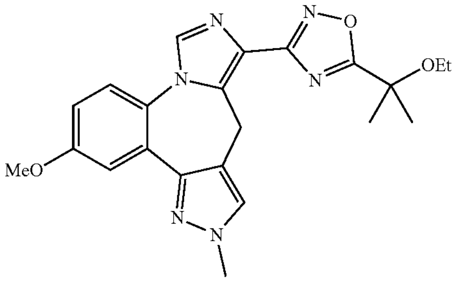 [SMILES: CCOC(C)(C)c1nc(-c2ncn3c2Cc2cn(C)nc2-c2cc(OC)ccc2-3)no1]

Compound 341 was synthesized analogously as Compound 185, using 2-ethoxy-2-methylpropanoic acid in the oxadiazole formation step. MS: [M+1]=421.

Example 93t: Synthesis of Compound 283

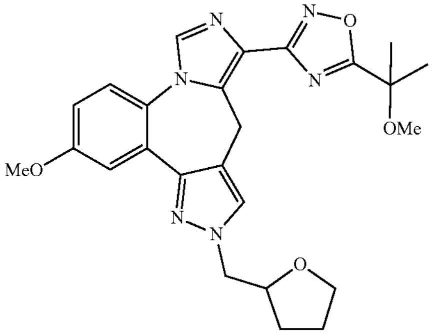 [SMILES: COc1ccc2c(c1)-c1nn(CC3CCCO3)cc1Cc1c(-c3noc(C(C)(C)OC)n3)ncn1-2]

Compound 283 was synthesized analogously as Compound 185, using tetrahydrofurfuryl bromide as the N-alkylating agent. MS: [M+1]=477.

Example 93u: Synthesis of Compound 374

Compound 4374

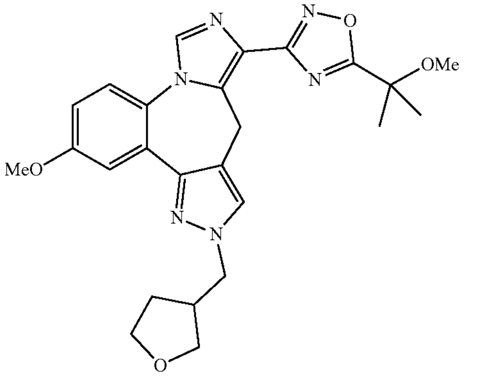

Compound 4375

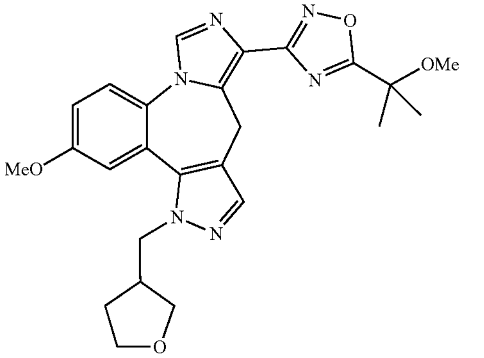

Compound 374 was synthesized analogously as Compound 185, using 3-iodomethyl tetrahydrofurane as the N-alkylating agent. MS: [M+1]=477.

Also isolated from the N-alkylation reaction was the isomer Compound 375. MS: [M+1]=477.

Example 93-3 and Example 93-12: Synthesis of Compound 203 and Compound 204

Compound 203

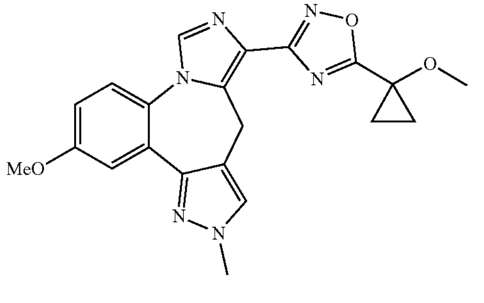

-continued

Compound 204

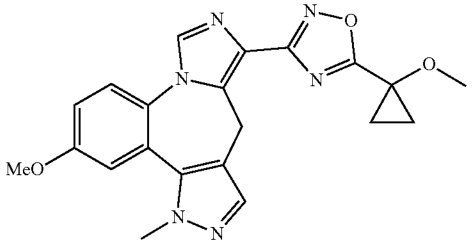

Compound 203 was synthesized analogously as Example 91, using 1-methoxy-cyclopropane carboxylic acid for the construction of the oxadiazole ring. MS: [M+1]=405.

Also isolated from the preparation was small amount of the N11 minor isomer Example 12 Compound 204. MS: [M+1]=405.

Example 93v: Synthesis of Compound 331

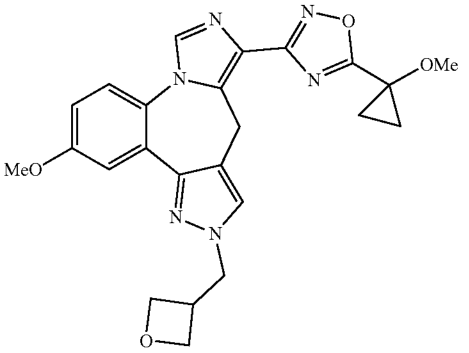 [SMILES: COc1ccc2c(c1)-c1nn(CC3COC3)cc1Cc1c(-c3noc(C4(OC)CC4)n3)ncn1-2]

Compound 331 was synthesized analogously as Compound 203, using toluene-4-sulfonic acid-oxetan-3-yl-methyl ester in the pyrazole N-alkylation steps. MS: [M+1]=461.

Example 93-4: Synthesis of Compound 207

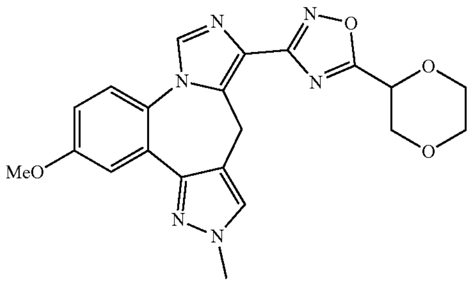 [SMILES: COc1ccc2c(c1)-c1nn(C)cc1Cc1c(-c3noc(C4COCCO4)n3)ncn1-2]

Compound 207 was synthesized analogously as Example 91, using 1,4-dioxane-2-carboxylic acid for the construction of the oxadiazole ring. MS: [M+1]=421.

Example 93-5 and Example 93-13: Synthesis of Compound 205 and Compound 206

Compound 205

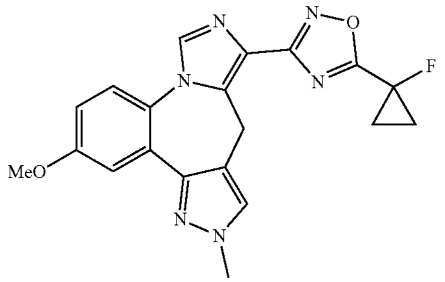

Compound 206

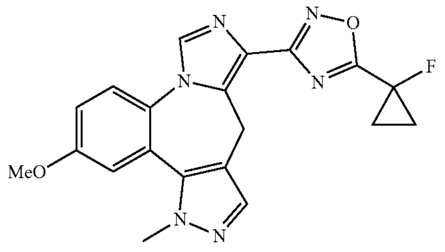

Compound 205 was synthesized analogously as Example 91, using 1-fluoro-cyclopropane carboxylic acid for the construction of the oxadiazole ring. MS: [M+1]=393.

Also isolated from the preparation was small amount of the N11 minor isomer Example 93-13 Compound 206. MS: [M+1]=393.

Example 93-6: Synthesis of Compound 195

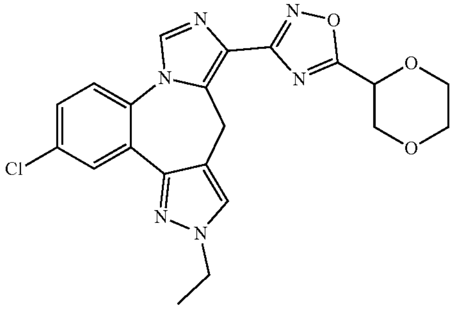 [SMILES: CCn1cc2c(n1)-c1cc(Cl)ccc1-n1cnc(-c3noc(C4COCCO4)n3)c1C2]

Compound 195 was synthesized analogously as Example 91, starting with intermediate B ($R^1$=Cl), using ethyl iodide as the N-alkylating agent in the pyrazole alkylation step, and 1,4-dioxane-2-carboxylic acid in the oxadiazole formation step. MS: [M+1]=439.

Example 93-7: Synthesis of Compound 196

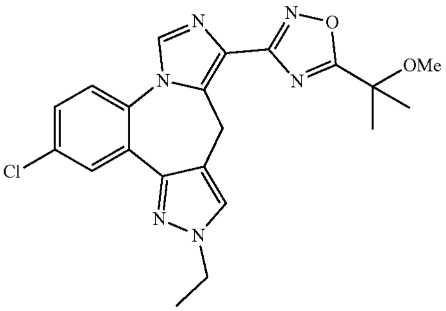 [SMILES: CCn1cc2c(n1)-c1cc(Cl)ccc1-n1cnc(-c3noc(C(C)(C)OC)n3)c1C2]

Compound 196 was synthesized analogously as Example 93-6, using 2-methoxy-2-methyl-propanoic acid in the oxadiazole formation step. MS: [M+1]=425.

Example 93-8: Synthesis of Compound 197

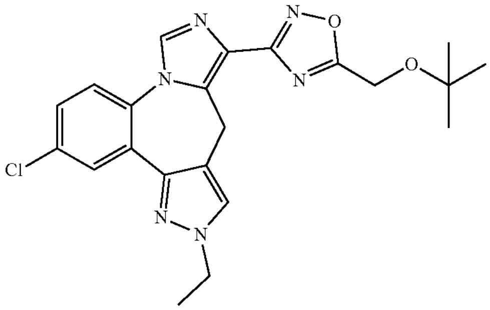 [SMILES: CCn1cc2c(n1)-c1cc(Cl)ccc1-n1cnc(-c3noc(COC(C)(C)C)n3)c1C2]

Compound 197 was synthesized analogously as Example 93-6, using tert-butoxyacetic acid in the oxadiazole formation step. MS: [M+1]=439.

Example 93w: Synthesis of Compound 307

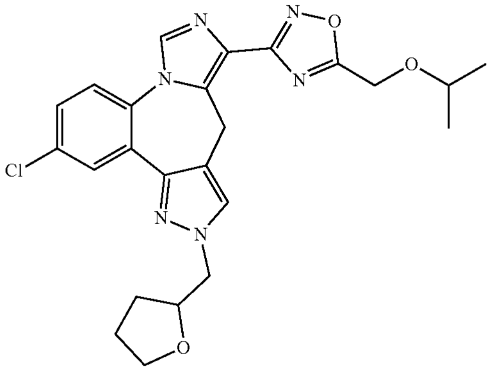 [SMILES: CC(C)OCc1nc(-c2ncn3c2Cc2cn(CC4CCCO4)nc2-c2cc(Cl)ccc2-3)no1]

Compound 307 was synthesized analogously as Compound 197, using tetrahydrofurfuryl bromide as the N-alkylating agent in the pyrazole alkylation step, and isopropoxy acetic acid in the oxadiazole formation step. MS: [M+1]=481.

Example 93x: Synthesis of Compound 308

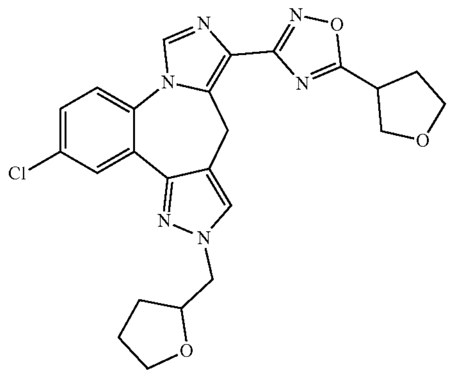 [SMILES: Clc1ccc2c(c1)-c1nn(CC3CCCO3)cc1Cc1c(-c3noc(C4CCOC4)n3)ncn1-2]

Compound 308 was synthesized analogously as Compound 307, using tetrahydro-3-furoic acid in the oxadiazole formation step. MS: [M+1]=479.

Example 93y: Synthesis of Compound 309

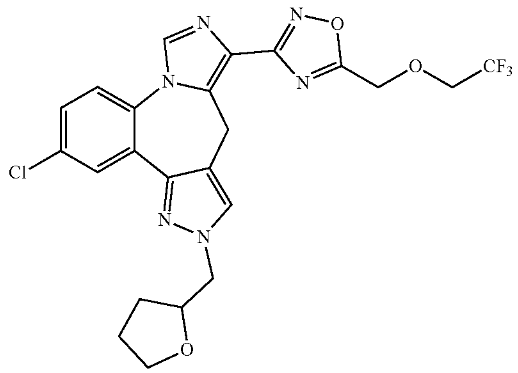 [SMILES: FC(F)(F)COCc1nc(-c2ncn3c2Cc2cn(CC4CCCO4)nc2-c2cc(Cl)ccc2-3)no1]

Compound 309 was synthesized analogously as Compound 307, using trifluoroethoxy acetic acid in the oxadiazole formation step. MS: [M+1]=521.

Example 93z: Synthesis of Compound 362

Compound 362 was synthesized analogously as Compound 307, using trifluoroethoxy acetic acid in the oxadiazole formation step. MS: [M+1]=521.

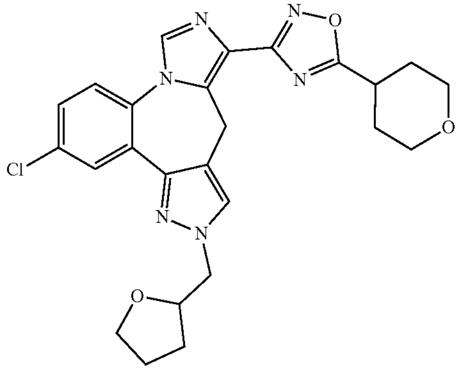 [SMILES: Clc1ccc2c(c1)-c1nn(CC3CCCO3)cc1Cc1c(-c3noc(C4CCOCC4)n3)ncn1-2]

Compound 362 was synthesized analogously as Compound 307, using tetrahydropyran-4-carboxylic acid in the oxadiazole formation step. MS: [M+1]=493.

Example 93-9: Synthesis of Compound 198

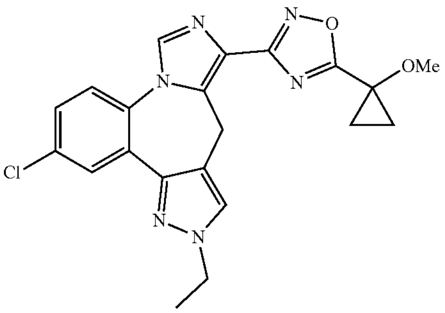 [SMILES: CCn1cc2c(n1)-c1cc(Cl)ccc1-n1cnc(-c3noc(C4(OC)CC4)n3)c1C2]

Compound 198 was synthesized analogously as Example 93-6, using 1-methoxy-cyclopropane carboxylic acid in the oxadiazole formation step. MS: [M+1]=423.

Scheme 8
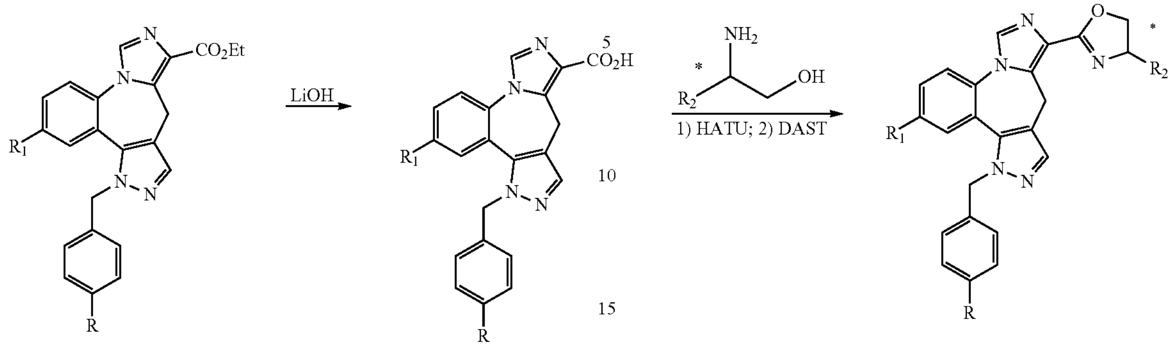
Intermediate B
8.1
R =H
R1 R2
Ex. 94 Compound 05: Cl, Ph (R)
Ex. 95 Compound 06: Cl, Ph (S)
Ex. 96 Compound 12: Cl, Me (R)
Ex. 97 Compound 13: Cl, Me (S)
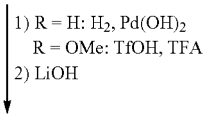
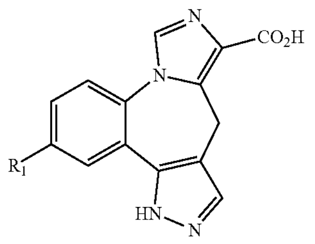
8.2
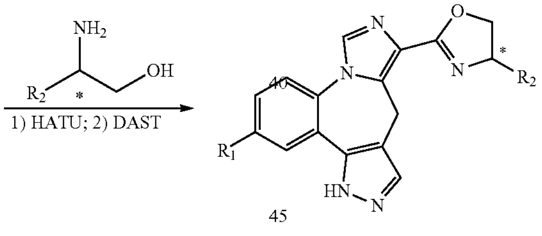
R1 R2
Ex. 98 Compound 15: OMe, Ph (S)
Ex. 99 Compound 14: OMe, Ph (R)
Ex. 100 Compound 24: OMe, 4-Cl-Ph (R)
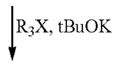
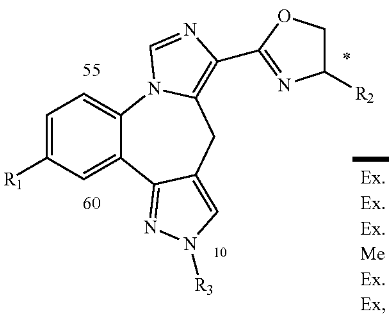
(major isomer)
R1 R2 R3
Ex. 100-1 Compound 177: Cl, iPr (R) Et
Ex. 100-2 Compound 180: Cl, iPr (S), Et
Ex. 100-3 Compound 189: Cl, $MeOCH_2$, Me
Ex. 100-4 Compound 182: Cl, $O(CH_2)_2$, Me
Ex, 100-5 Compound 178: Cl, Ph (R), Et
Ex. 100-6 Compound 179: Cl, Ph (S), Et Example 94: Synthesis of Compound 05

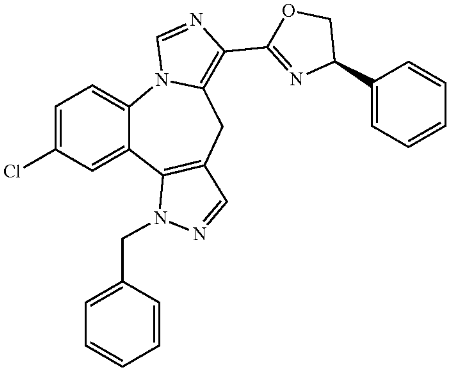 [SMILES: Clc1ccc2c(c1)-c1c(cnn1Cc1ccccc1)Cc1c(C3=N[C@H](c4ccccc4)CO3)ncn1-2]

Step 1: Intermediate B ($R_1$=Cl, R=H; 98.3 mg, 0.235 mmol) was treated with LiOH (22.9 mg, 0.956 mmol) in a mixed-solvent system of THF (1.5 ml), water (1.25 ml) and MeOH (0.25 ml) for 16 h. The reaction mixture was concentrated, acidified to pH 3-4 with dil. HCl, and cooled to 0° C. Ppts was collected by filtration, washed with water and dried to give 82.5 mg carboxylic acid 8.1.

Step 2: Acid 8.1 (9.3 mg, 0.0234 mmol) was treated with HATU (10.0 mg, 0.0263 mmol) and diisopropyl ethylamine (6.0 mg, 0.0468 mmol) in DMF (0.15 ml), (R)-phenylglycinol (3.6 mg, 0.0262 mmol) was added. After 1 h stirring, the reaction mixture was diluted with EtOAc, washed with sat. $NaHCO_3$, brine, and dried over $MgSO_4$. Filtration and solvent removal gave a crude solid adduct that was dissolved in DCM (0.5 ml) and cooled to 0° C., diethylaminosulfur trifluoride (19.2 mg, 0.120 mmol) was added. After 1 h stirring at 0° C., the reaction was quenched with sat. $NaHCO_3$, extracted with EtOAc, the extract washed with brine, and dried over $MgSO_4$. Filtration and concentration followed by prep. TLC using 5% MeOH in EtOAc/DCM (1:1) gave 9.7 mg Example 94, Compound 05. MS: [M+1]=492. $H^1NMR$ ($CDCl_3$) δ 7.68 (1H, s), 7.52-7.27 (12H, m), 7.14 (2H, d, J=8 Hz), 5.56 (1H, d, J=16 Hz), 5.42 (1H, t, J=8 Hz), 5.31 (1H, d, J=16 Hz), 5.08 (1H, m), 4.78 (1H, m), 4.22 (1H, m), and 3.44 (1H, d, J=16 Hz).

Example 95: Synthesis of Compound 06

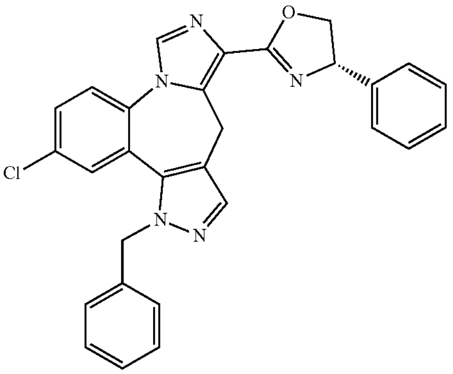 [SMILES: Clc1ccc2c(c1)-c1c(cnn1Cc1ccccc1)Cc1c(C3=N[C@@H](c4ccccc4)CO3)ncn1-2]

Example 95 was prepared analogously as Example 94, using (S)-phenylglycinol to form the oxazoline ring. MS: [M+1]=492.

Example 96: Synthesis of Compound 12

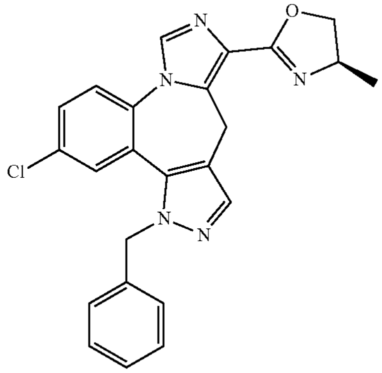 [SMILES: C[C@@H]1COC(c2ncn3c2Cc2cnn(Cc4ccccc4)c2-c2cc(Cl)ccc2-3)=N1]

Example 96 was prepared analogously as Example 94, using (R)-2-aminopropanol to form the oxazoline ring. MS: [M+1]=430.

Example 97: Synthesis of Compound 13

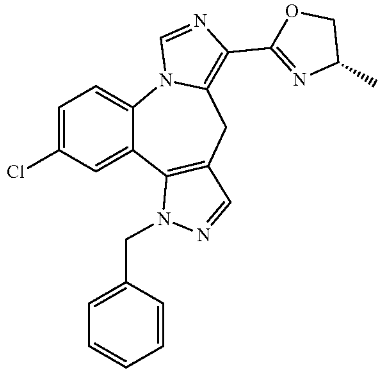 [SMILES: C[C@H]1COC(c2ncn3c2Cc2cnn(Cc4ccccc4)c2-c2cc(Cl)ccc2-3)=N1]

Example 97 was prepared analogously as Example 94, using (S)-2-aminopropanol to form the oxazoline ring. MS: [M+1]=430.

Example 98: Synthesis of Compound 15

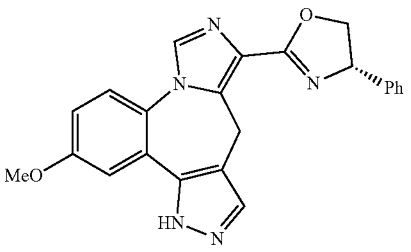 [SMILES: COc1ccc2c(c1)-c1[nH]ncc1Cc1c(C3=N[C@@H](c4ccccc4)CO3)ncn1-2]

Intermediate B ($R_1$=OMe, R=H; 117.8 mg) was stirred with $Pd(OH)_2$ (20% wt on carbon; cat. amount) in the presence of HCl (1N aq.; 0.15 ml) in EtOAc (1 ml) and MeOH (2 ml) under hydrogen atm. for 2 days. Catalyst was removed over Celite and rinsed with 5% MeOH in DCM; solvent of the filtrate was removed in vacuo to give 101.2 mg 1H-pyrazole ester as a yellowish solid.

The ester from above (7.8 mg, 0.0240 mmol) was treated with LiOH (7 mg) in a mixed solvents of THE (0.36 ml), water (0.30 ml) and MeOH (0.03 ml) for 16 h. The reaction mixture was acidified to pH 3-4 with dil. HCl, then all solvents were removed in high vacuum. This crude acid 8.2 (0.0240 mmol) was then treated with HATU (18.2 mg, 0.048 mmol) and diisopropyl ethylamine (12. 4 mg, 0.096 mmol) in DMF (0.15 ml), and (S)-phenylglycinol (4.0 mg, 0.0288 mmol) was added. After 1 h stirring, the reaction mixture was diluted with EtOAc, washed with sat. $NaHCO_3$, brine, and dried over $MgSO_4$. Filtration and solvent removal gave a yellowish solid that was dissolved in DCM (0.3 ml) and cooled to 0° C., diethylaminosulfur trifluoride (11.3 mg, 0.0704 mmol) was added. After 1 h stirring at 0° C., the reaction was quenched with sat. $NaHCO_3$, extracted with EtOAc, the extract washed with brine, and dried over $MgSO_4$. Filtration and concentration followed by prep. TLC using 10% MeOH in EtOAc/DCM (1:1) gave 3.5 mg Example 98 compound 15 as a yellowish filmy solid. MS: [M+1]=398. $H^1NMR$ ($CDCl_3$) δ 7.70 (1H, s), 7.47 (1H, s), 7.43 (2H, m), 7.34-7.27 (5H, m), 7.00 (1H, dd, J=4, 8 Hz), 5.40 (1H, br t, J=8 Hz), 4.75 (1H, br t, J=8 Hz), 4.34 (2H, br s), 4.20 (1H, t, J=8 Hz), and 3.87 (3H, s).

Example 99: Synthesis of Compound 14

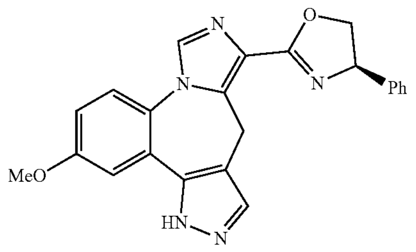 [SMILES: COc1ccc2c(c1)-c1[nH]ncc1Cc1c(C3=N[C@H](c4ccccc4)CO3)ncn1-2]

Example 99 was synthesized analogously as Example 98, using (R)-phenylglycinol to form the oxazoline ring. MS: [M+1]=398.

Example 100: Synthesis of Compound 24

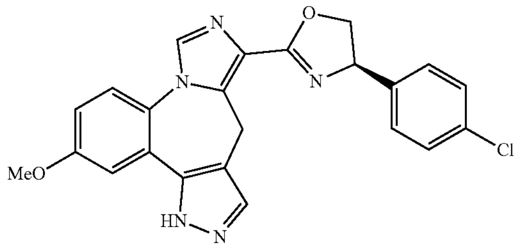 [SMILES: COc1ccc2c(c1)-c1[nH]ncc1Cc1c(C3=N[C@H](c4ccc(Cl)cc4)CO3)ncn1-2]

Example 100 was synthesized analogously as Example 98, using (R)-4-Cl-phenylglycinol to form the oxazoline ring. MS: [M+1]=432.

Example 100-1: Synthesis of Compound 177

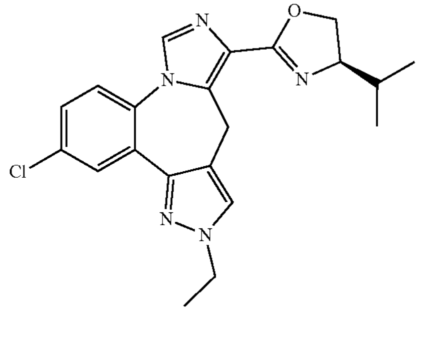 [SMILES: CCn1cc2c(n1)-c1cc(Cl)ccc1-n1cnc(C3=N[C@H](C(C)C)CO3)c1C2]

Compound 177 was synthesized analogously as Example 98, starting with Intermediate B ($R_1$=Cl, R=OMe), using D-valinol for preparing the oxazoline ring, and acidic conditions to remove the 4-MeO benzyl protective group of the pyrazole as described earlier (see examples in Schemes 6, 7-A, and 7-B). Ethylation of the resulting free N—H of the pyrazole was performed using iodoethane as described in any of the previous N-Et reactions (i.e., Compound 104, 248, etc.). MS: [M+1]=396.

Example 100-2: Synthesis of Compound 180

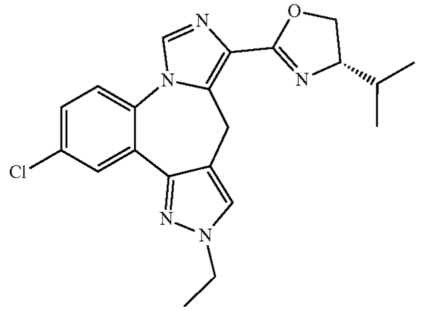 [SMILES: CCn1cc2c(n1)-c1cc(Cl)ccc1-n1cnc(C3=N[C@@H](C(C)C)CO3)c1C2]

Compound 180 was synthesized analogously as Example 100-1, using L-valinol for preparing the oxazoline ring. [M+1]=396.

Example 100-3: Synthesis of Compound 189

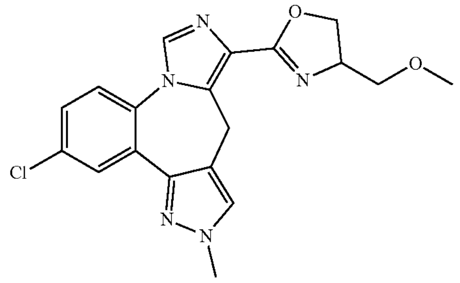 [SMILES: COCC1COC(c2ncn3c2Cc2cn(C)nc2-c2cc(Cl)ccc2-3)=N1]

Compound 189 was synthesized analogously as Example 100-1, using 2-amino-3-methoxypropane-1-ol for preparing the oxazoline ring, and trimethylphenylammonium chloride as the N-alkylating agent in the pyrazole alkylation step. [M+1]=384.

Example 100-4: Synthesis of Compound 182

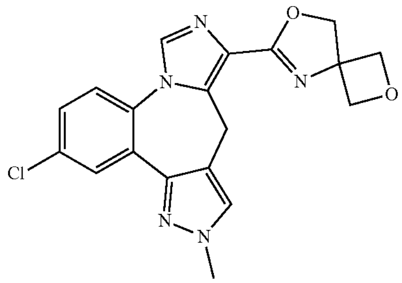 [SMILES: Cn1cc2c(n1)-c1cc(Cl)ccc1-n1cnc(C3=NC4(COC4)CO3)c1C2]

Compound 182 was synthesized analogously as Example 100-1, using (3-amino-oxetan-3-yl)-methanol for preparing the oxazoline ring and trimethylphenylammonium chloride as the N-alkylating agent in the pyrazole alkylation step. [M+1]=382.

Example 100-5: Synthesis of Compound 178

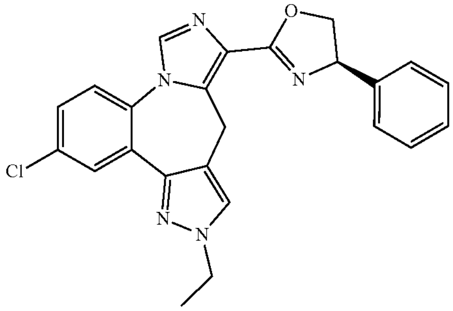 [SMILES: CCn1cc2c(n1)-c1cc(Cl)ccc1-n1cnc(C3=N[C@H](c4ccccc4)CO3)c1C2]

Compound 178 was synthesized analogously as Example 100-1, using (R)-phenylglycinol for preparing the oxazoline ring. [M+1]=430.

Example 100-6: Synthesis of Compound 179

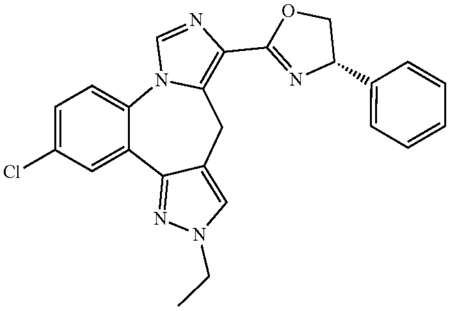 [SMILES: CCn1cc2c(n1)-c1cc(Cl)ccc1-n1cnc(C3=N[C@@H](c4ccccc4)CO3)c1C2]

Compound 179 was synthesized analogously as Example 100-1, using (S)-phenylglycinol for preparing the oxazoline ring. [M+1]=430.

Scheme 9

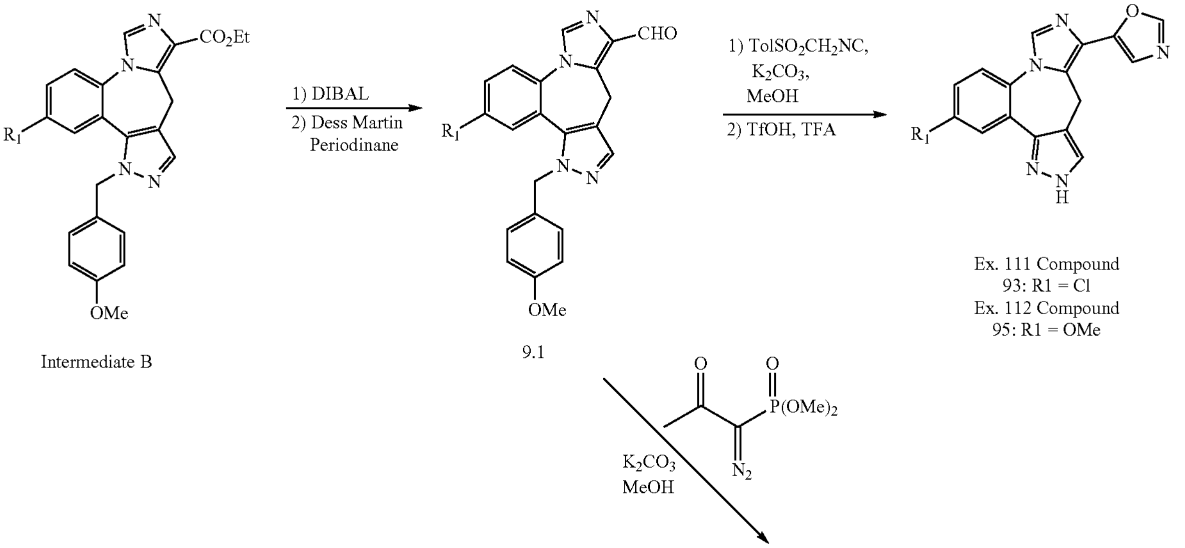

Intermediate B 9.1

Ex. 111 Compound 93: R1 = Cl
Ex. 112 Compound 95: R1 = OMe

-continued
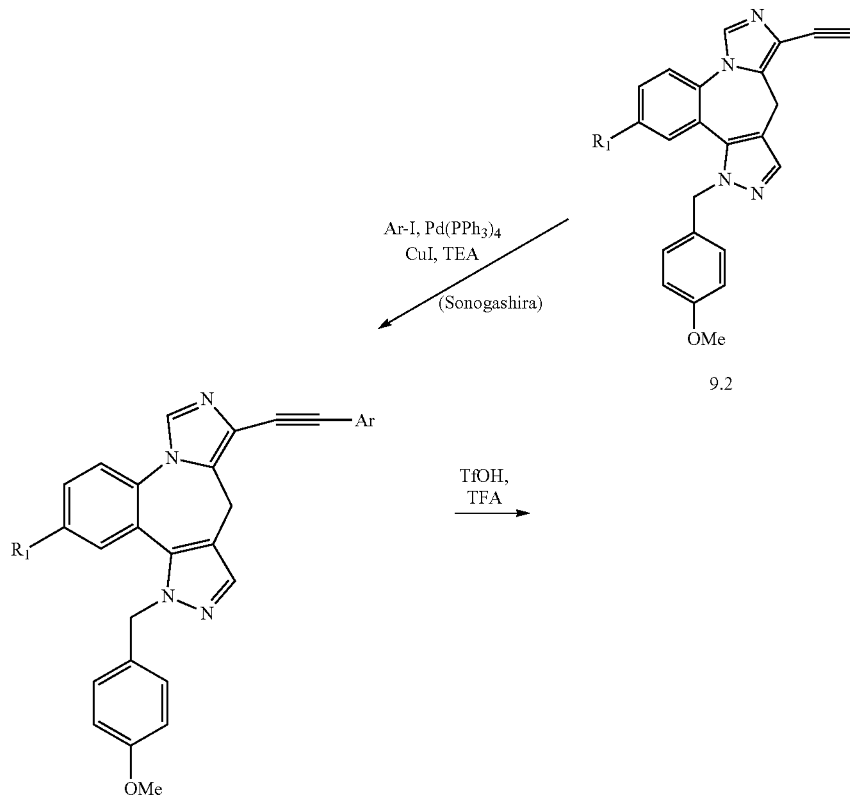
9.2
| | R1 | Ar |
|---|---|---|
| Ex. 101 Compound 36: | OMe, | 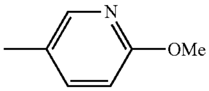 |
| Ex. 102 Compound 37: | OMe, | 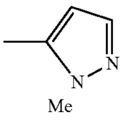 |

-continued

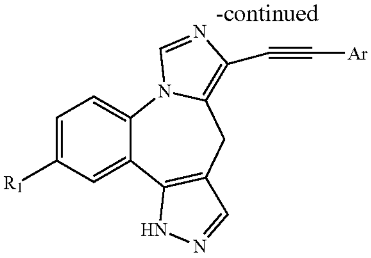

| R1 | Ar | R1 | Ar |
|---|---|---|---|
| Ex. 103 Compound 38: OMe, | 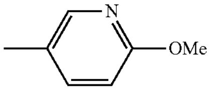 | Ex. 107 Compound 39: OMe, | 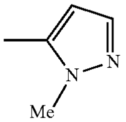 |
| Ex. 104 Compound 90: OMe, | 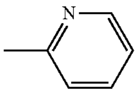 | Ex. 108 Compound 94: Cl, | 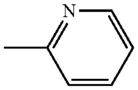 |
| Ex. 105 Compound 53: OMe, | 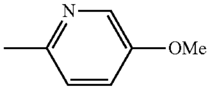 | Ex. 109 Compound 64: Cl, | 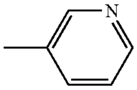 |
| Ex. 106 Compound 91: OMe, | 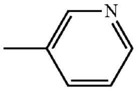 | Ex. 110 Compound 52: Cl, | 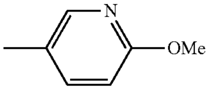 |

Example 101: Synthesis of Compound 36

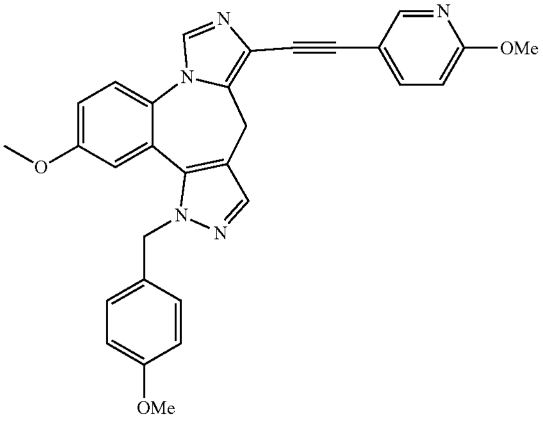 [SMILES: COc1ccc(Cn2ncc3c2-c2cc(OC)ccc2-n2cnc(C#Cc4ccc(OC)nc4)c2C3)cc1]

Step 1: Intermediate B ($R_1$=OMe; 151.2 mg) stirring in THF (1.2 ml) at 0° C. was treated with diisobutylaluminum hydride (2.8 ml; 1M in hexane). The reaction was allowed to proceed to rt overnight, then carefully quenched with potassium sodium tartrate solution (20% aq.; 5 ml) and stirred for 2 h before being diluted with sat. $NaHCO_3$, extracted with EtOAc (3×), the combined organic layer was washed with brine, and dried over $MgSO_4$. Filtration and solvent removal gave 119.4 mg crude alcohol as a yellowish solid.

Step 2: The above obtained alcohol (119.4 mg) was treated with Dess Martin Periodinane (150.0 mg) in DCM (2.5 ml) at rt for 2 h, then sat. $NaHCO_3$ (30 ml) was added and stirred for 30 min. The reaction mixture was extracted with EtOAc/DCM (1:1) repeatedly, and the combined extracts was washed with brine, and dried over $MgSO_4$. Filtration and solvent removal under high vacuum gave 84.1 mg aldehyde 9.1 as a brownish solid.

Step 3: The above obtained aldehyde 9.1 (84.1 mg) was stirred in MeOH (1.3 ml), potassium carbonate (81.0 mg) was added, followed by dimethyl 1-(1-diazo-2-oxopropyl) phosphonate (72.6 mg). After 16 h stirring, the reaction mixture was diluted with sat. $NaHCO_3$, extracted with EtOAc (3×), the combined extract was washed with water, brine, and dried over $MgSO_4$. Filtration and solvent removal in vacuo gave 76.1 mg crude terminal alkyne 9.2 as a brownish foamy solid.

Step 4: The Sonogashira reaction was performed by placing 2-methoxy-5-iodopyridine (62.2 mg, 0.265 mmol) in DMF (1 ml; degassed) under Argon atm., a pre-mixed catalysts of tetrakis(triphenylphosphine)-palladium(0) (20.4 mg, 0.0177 mmol) and CuI (5.0 mg, 0.0265 mmol) was added, and the mixture was stirred at rt for 10 min. The terminal alkyne (35.0 mg, 0.0883 mmol) obtained above was added next, followed by TEA (44.7 mg, 0.441 mmol). The reaction vessel was re-charged with Argon, and the reaction was allowed to proceed overnight. The reaction mixture was diluted with sat. $NaHCO_3$ under stirring, then extracted with EtOAc, the extract washed with brine, and dried over $MgSO_4$. Filtration and concentration followed by prep. TLC using 7% MeOH in EtOAc/DCM (1:1) as eluent gave 19.4 mg of Example 101, compound 36 as a yellowish solid. MS: [M+1]=504. $H^1NMR$ ($CDCl_3$) δ 8.42 (1H, d, J=4 Hz), 7.76 (1H, br d, J=8 Hz), 7.67 (1H, s), 7.62 (1H, s), 7.45 (1H, d, J=8 Hz), 7.10 (2H, d, J=8 Hz), 7.03 (1H, dd, J=4, 8 Hz), 6.94 (1H, d, J=4 Hz), 6.89 (2H, br d, J=8 Hz), 6.77 (1H, d, J=8 Hz), 5.56 (1H, d, J=16 Hz), 5.35 (1H, d, J=16 Hz), 4.20 (1H, d, J=16 Hz), 3.99 (3H, s), 3.81 (3H, s), 3.63 (3H, s), and 3.57 (1H, d, J=16 Hz).

Example 102: Synthesis of Compound 37

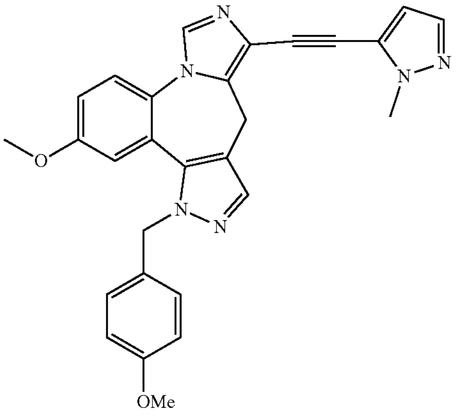 [SMILES: COc1ccc(Cn2ncc3c2-c2cc(OC)ccc2-n2cnc(C#Cc4ccnn4C)c2C3)cc1]

Example 102 was prepared analogously as Example 101, using 5-iodo-1-methyl-1H-pyrazole in the Sonogashira reaction. MS: [M+1]=477.

Example 103: Synthesis of Compound 38

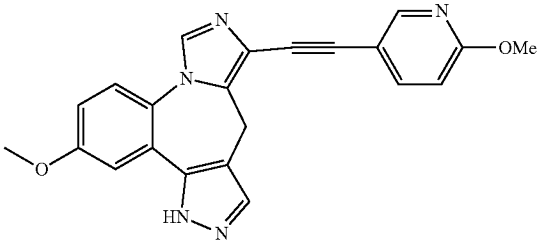 [SMILES: COc1ccc2c(c1)-c1[nH]ncc1Cc1c(C#Cc3ccc(OC)nc3)ncn1-2]

Example 103 was prepared by treating Example 101 (18.2 mg) with trifluoromethane sulfonic acid (15 mg) in a mixture of trifluoroacetic acid (0.36 ml) and DCM (0.36 ml) at rt for 3 days. The reaction mixture was concentrated, treated with sat. $NaHCO_3$, and extracted with EtOAc (3×). The combined organic extract was washed with water, brine, and dried over $MgSO_4$. Filtration and solvent removal followed by prep. TLC using 8% MeOH in EtOAc/DCM (1:1) gave 10.8 mg Example 103 as a yellowish solid. MS: [M+1]=384.

Example 104: Synthesis of Compound 90

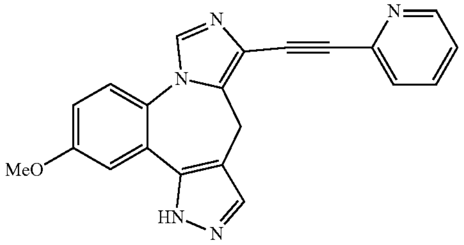 [SMILES: COc1ccc2c(c1)-c1[nH]ncc1Cc1c(C#Cc3ccccn3)ncn1-2]

Example 104 was prepared analogously as Example 103, using 2-iodo-pyridine in the Sonogashira coupling step. MS: [M+1]=354.

Example 105: Synthesis of Compound 53

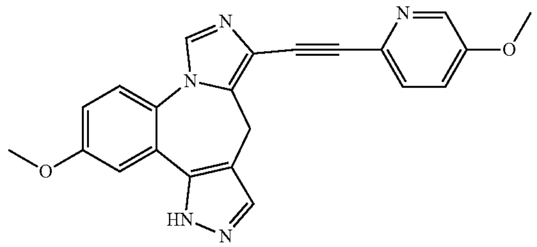

Example 105 was prepared analogously as Example 103, using 2-iodo-5-methoxypyridine in the Sonogashira coupling step. MS: [M+1]=384.

Example 106: Synthesis of Compound 91

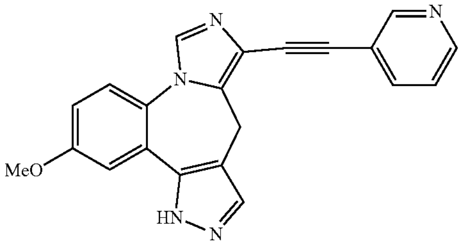 [SMILES: COc1ccc2c(c1)-c1[nH]ncc1Cc1c(C#Cc3cccnc3)ncn1-2]

Example 106 was prepared analogously as Example 103, using 3-iodo-pyridine in the Sonogashira coupling step. MS: [M+1]=354.

Example 107: Synthesis of Compound 39

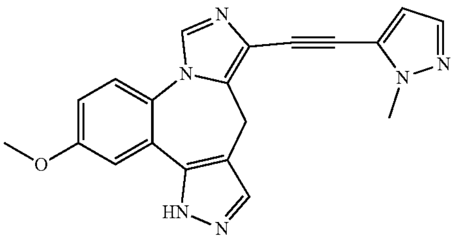 [SMILES: COc1ccc2c(c1)-c1[nH]ncc1Cc1c(C#Cc3ccnn3C)ncn1-2]

Example 107 was prepared analogously as Example 103, using 5-iodo-1-methyl-1H-pyrazole in the Sonogashira coupling step. MS: [M+1]=357.

Example 108: Synthesis of Compound 94

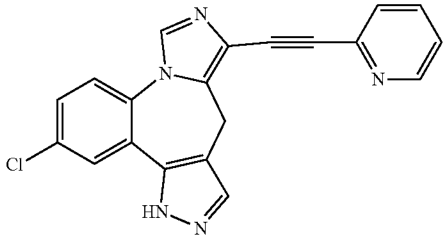 [SMILES: Clc1ccc2c(c1)-c1[nH]ncc1Cc1c(C#Cc3ccccn3)ncn1-2]

Example 108 was prepared analogously as Example 104, starting with Intermediate B (R1=Cl). MS: [M+1]=358.

Example 109: Synthesis of Compound 64

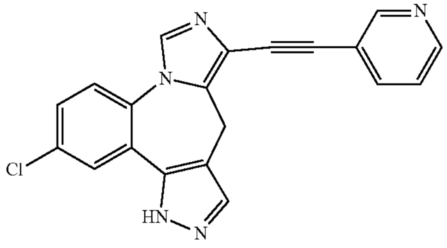 [SMILES: Clc1ccc2c(c1)-c1[nH]ncc1Cc1c(C#Cc3cccnc3)ncn1-2]

Example 109 was prepared analogously as Example 108, using 3-iodo-pyridine in the Sonogashira coupling step. MS: [M+1]=358.

Example 110: Synthesis of Compound 52

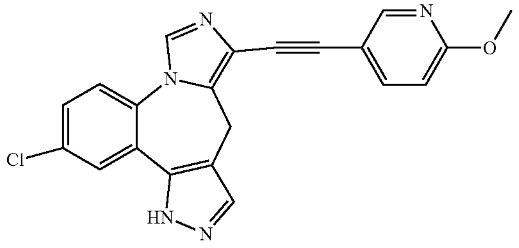 [SMILES: COc1ccc(C#Cc2ncn3c2Cc2cn[nH]c2-c2cc(Cl)ccc2-3)cn1]

Example 110 was prepared analogously as Example 108, using 2-methoxy-5-iodopyridine in the Sonogashira coupling step. MS: [M+1]=388.

Example 111: Synthesis of Compound 93

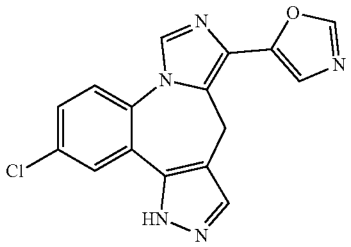 [SMILES: Clc1ccc2c(c1)-c1[nH]ncc1Cc1c(-c3cnco3)ncn1-2]

Aldehyde 9.1 prepared from the Intermediate B (R1=Cl; 15.7 mg, 0.0388 mmol) and p-tosylmethyl isocyanide (9.5 mg, 0.0485 mmol) were stirred in MeOH (0.7 ml), $K_2CO_3$ (10.7 mg, 0.0776 mmol) was added. The reaction mixture was heated at a pre-heated oil bath of 60° C. for 2 h, then cooled and diluted with EtOAc, washed with sat. $NaHCO_3$, brine, and dried over $MgSO_4$. Filtration and concentration followed by prep. TLC using 10% MeOH in EtOAc/DCM (1:1) gave a solid which was treated with trifluoromethane sulfonic acid (24 mg) in a mixture of trifluoroacetic acid (0.5 ml) and DCM (0.5 ml) at 40° C. for 20 h. The reaction mixture was concentrated, treated with sat. $NaHCO_3$, and extracted with EtOAc (3×). The combined organic extract was washed with water, brine, and dried over $MgSO_4$. Filtration and solvent removal followed by prep. TLC using 15% MeOH in EtOAc/DCM (1:1) gave 2.2 mg of Example 111 compound 93 as an off-white solid. MS: [M+1]=324.

Example 112: Synthesis of Compound 95

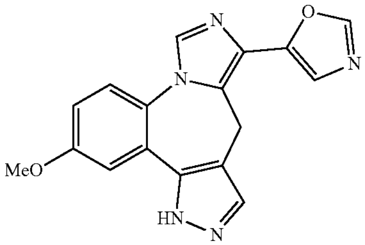 [SMILES: COc1ccc2c(c1)-c1[nH]ncc1Cc1c(-c3cnco3)ncn1-2]

Example 112 was prepared analogously as Example 111, starting with Intermediate B ($R_1$=OMe). MS: [M+1]=320.

Scheme 10
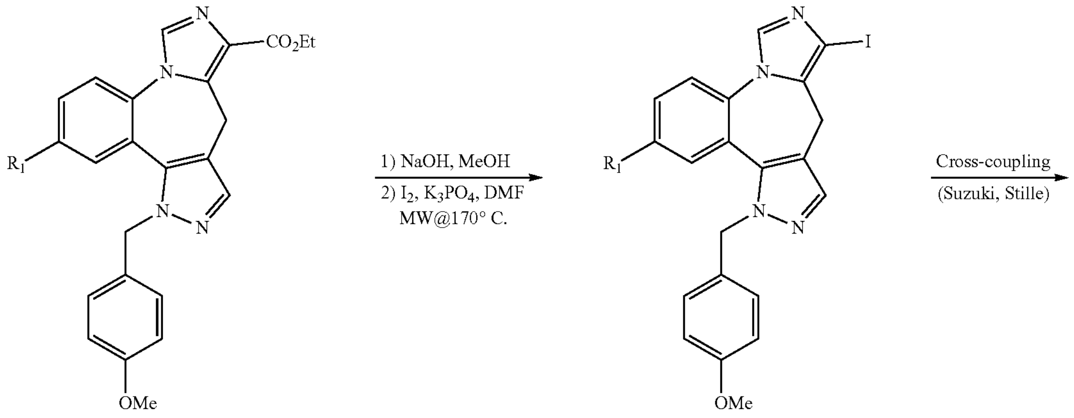
Intermediate B
Intermediate C
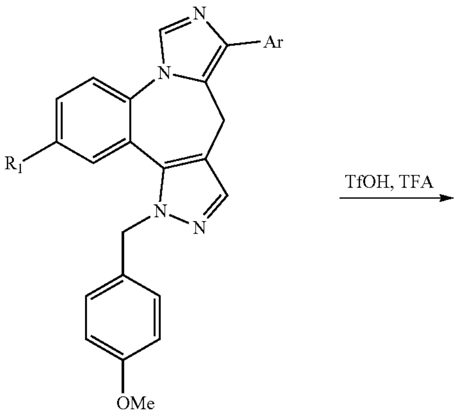
10.1

-continued
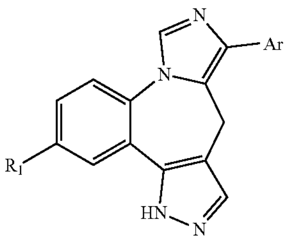
| R1 | Ar | R1 | Ar |
|---|---|---|---|
| Ex. 113 Compound 82: OMe, | 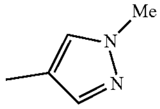 | Ex. 120 Compound 61: Cl, | 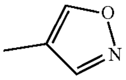 |
| Ex. 114 Compound 81: OMe, | 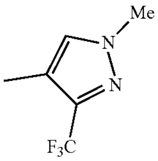 | Ex. 121 Compound 60: Cl, | 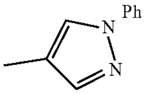 |
| Ex. 115 Compound 70: OMe, | 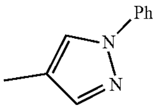 | Ex. 122 Compound 62: Cl, | 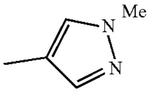 |
| Ex. 116 Compound 72: OMe, | 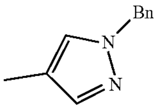 | Ex. 123 Compound 71: OMe, | 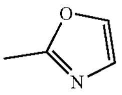 |
| Ex. 117 Compound 78: OMe, | 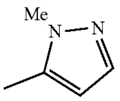 | Ex. 124 Compound 80: OMe, | 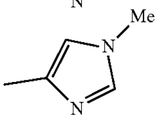 |
| Ex. 118 Compound 79: OMe, | 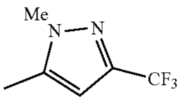 | Ex. 125 Compound 55: Cl, | 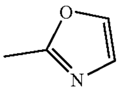 |
| Ex. 119 Compound 74: OMe, | 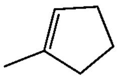 | | |

-continued

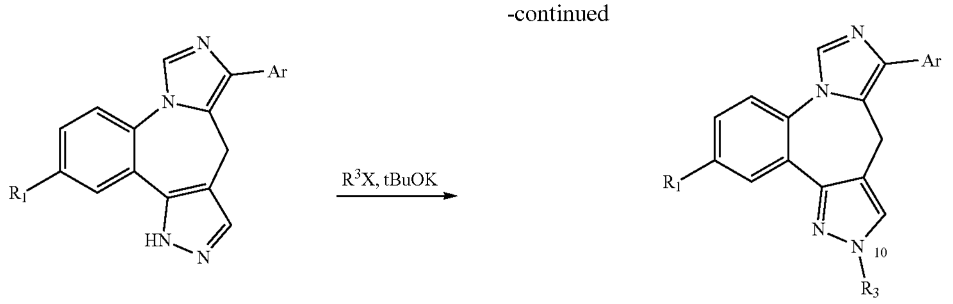

(major isomer)

| R1 | Ar | R3 |
|---|---|---|
| Ex. 126 Compound 76: OMe, | 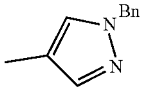 | Bn |
| Ex. 127 Compound 77: OMe, | 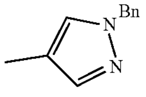 | 2-F Bn |
| Ex. 128 Compound 75: OMe, | 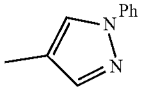 | 2-F Bn |
| Ex. 128-1 Compound 190: Cl, | 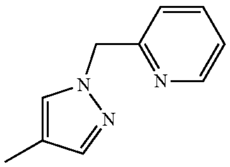 | Me |
| Ex. 128-2 Compound 208: Cl, | 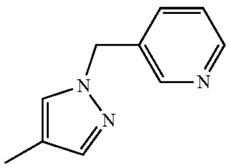 | Me |

Example 113: Synthesis of Compound 82

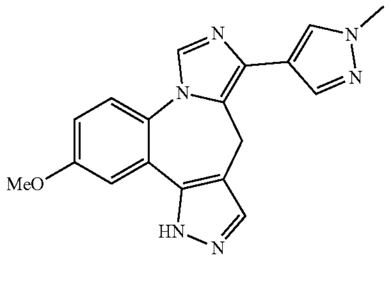 [SMILES: COc1ccc2c(c1)-c1[nH]ncc1Cc1c(-c3cnn(C)c3)ncn1-2]

Step 1: Intermediate B ($R_1$=OMe; 594 mg) was treated with NaOH (1N aq.; 3 ml) in MeOH (5 ml) at 90° C. for 2 h, cooled to rt, and acidified to pH 3-4 with dil. HCl. Ppts was collected by filtration, washed with water, and dried to give 511 mg of carboxylic acid which was used as is.

The acid from above (511 mg) was treated with iodine (1.25 g) in the presence of $K_3PO_4$ (518 mg) in DMF (4 ml) at 170° C. under microwave irradiation conditions for 30 min. The reaction was diluted with EtOAc, washed with water, dil. sodium thiosulfate, brine, and dried over $MgSO_4$. Filtration and concentration followed by silica gel column chromatography using 0 to 100% EtOAc in hexanes gradient gave 413 mg of decarboxylative iodination product Intermediate C as a yellowish solid.

Step 2: The Suzuki cross coupling reaction is followed below: under nitrogen atm., Intermediate C from above (24.0 mg, 0.0482 mmol) was stirred in dioxane (0.4 ml; degassed) and water (0.15 ml; degassed), (1-methyl-1H pyrazole-4-yl)boronic acid HCl (23.5 mg, 0.144 mmol) was added, $K_2CO_3$ (33.3 mg, 0.241 mmol) added next, followed by $PdCl_2(dppf)_2$ 2DCM complex (7.0 mg, 0.0096 mmol). The reaction was purged with $N_2$ gas again before being capped and heated at 120° C. under microwave irradiation conditions for 30 min, then diluted with EtOAc, washed with sat. $NaHCO_3$, brine, dried over $MgSO_4$. Filtration and concentration followed by prep. TLC using 10% MeOH in EtOAc/DCM (1:1) as eluent gave a solid that was treated with trifluoromethane sulfonic acid (14.5 mg) in a mixture of trifluoroacetic acid (0.4 ml) and DCM (0.4 ml) at 40° C. for 20 h. The reaction mixture was concentrated, treated with sat. $NaHCO_3$, and extracted with EtOAc (3×). The combined organic extract was washed with water, brine, and dried over $MgSO_4$. Filtration and solvent removal followed by prep. TLC using 15% MeOH in EtOAc/DCM (1:1) containing trimethylamine (0.1%) as eluent gave 1.3 mg Example 113, compound 82. MS: [M+1]=333.

Example 114: Synthesis of Compound 81

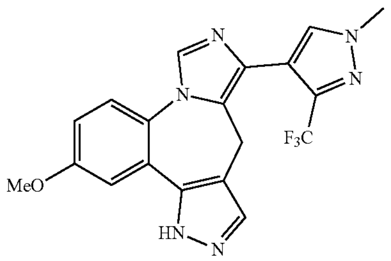 [SMILES: COc1ccc2c(c1)-c1[nH]ncc1Cc1c(-c3cn(C)nc3C(F)(F)F)ncn1-2]

Example 114 was prepared analogously as Example 113, using 1-methyl-3-trifluoromethylpyrazole-4-boronic acid in the Suzuki cross coupling step. MS: [M+1]=401. $H^1NMR$ ($CDCl_3$+ drops $CD_3OD$) δ 7.76 (1H, s), 7.54 (1H, s), 7.45 (1H, d, J=8 Hz), 7.41 (2H, m), 7.00 (1H, dd, J=4, 12 Hz), 3.99 (3H, s), 3.81 (3H, s), and 3.73 (2H, s).

Example 115: Synthesis of Compound 70

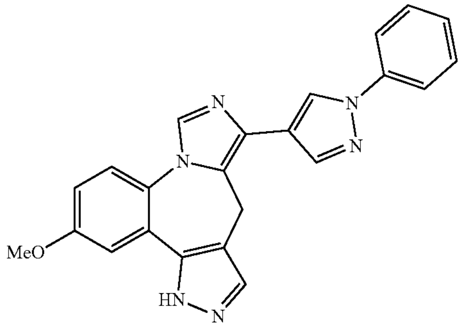 [SMILES: COc1ccc2c(c1)-c1[nH]ncc1Cc1c(-c3cnn(-c4ccccc4)c3)ncn1-2]

Example 115 was prepared analogously as Example 113, using 1-phenylpyrazole-4-boronic acid in the Suzuki cross coupling step. MS: [M+1]=395.

Example 116: Synthesis of Compound 72

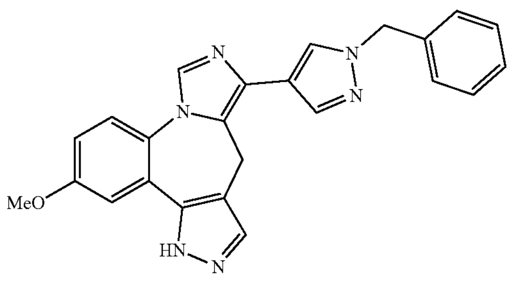 [SMILES: COc1ccc2c(c1)-c1[nH]ncc1Cc1c(-c3cnn(Cc4ccccc4)c3)ncn1-2]

Example 116 was prepared analogously as Example 113, using 1-benzyl-1H-pyrazole-4-boronic acid in the Suzuki cross coupling step. MS: [M+1]=409. $H^1NMR$ ($CDCl_3$) Q 7.76 (1H, s), 7.69 (1H, s), 7.66 (1H, s), 7.37 (3H, m), 7.30-7.22 (6H, m), 6.95 (1H, dd, J=4, 8 Hz), 5.31 (2H, s), 3.87 (2H, s), and 3.78 (3H, s).

Example 117: Synthesis of Compound 78

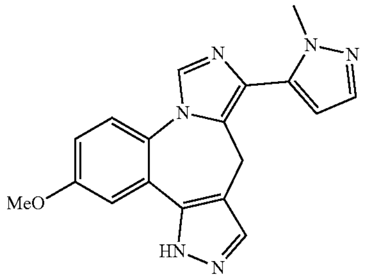 [SMILES: COc1ccc2c(c1)-c1[nH]ncc1Cc1c(-c3ccnn3C)ncn1-2]

Example 117 was prepared analogously as Example 113, using 1-methyl-1H-pyrazole-5-boronic acid in the Suzuki cross coupling step. MS: [M+1]=333.

Example 118: Synthesis of Compound 79

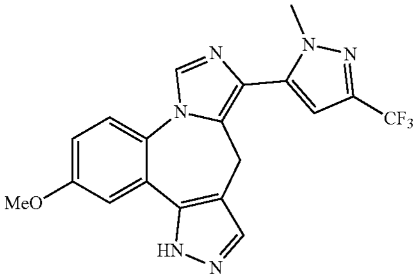 [SMILES: COc1ccc2c(c1)-c1[nH]ncc1Cc1c(-c3cc(C(F)(F)F)nn3C)ncn1-2]

Compound 79 was prepared analogously as Example 113, using 1-methyl-3-trifluoromethylpyrazole-5-boronic acid in the Suzuki cross coupling step. MS: [M+1]=401.

Example 119: Synthesis of Compound 74

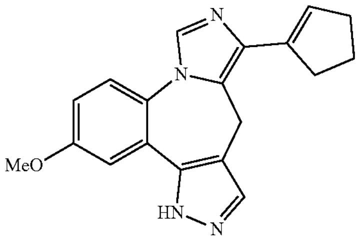 [SMILES: COc1ccc2c(c1)-c1[nH]ncc1Cc1c(C3=CCCC3)ncn1-2]

Example 119 was prepared analogously as Example 113, using cyclopenten-1-yl-boronic acid in the Suzuki cross coupling step. MS: [M+1]=319.

Example 120: Synthesis of Compound 61

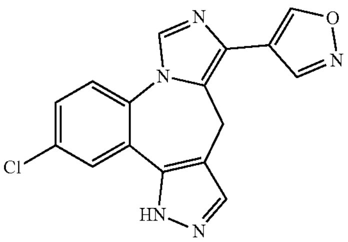 [SMILES: Clc1ccc2c(c1)-c1[nH]ncc1Cc1c(-c3cnoc3)ncn1-2]

Example 120 was prepared analogously as Example 113, starting with Intermediate B ($R_1$=Cl), and using 4-isoxazoleboronic acid pinacol ester in the Suzuki cross coupling step. MS: [M+1]=324.

Example 121: Synthesis of Compound 60

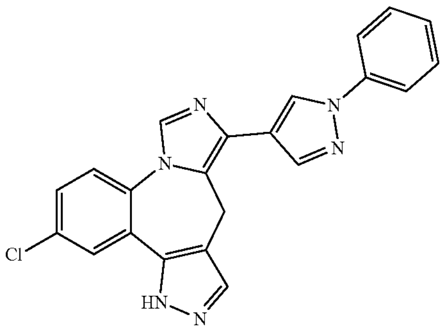 [SMILES: Clc1ccc2c(c1)-c1[nH]ncc1Cc1c(-c3cnn(-c4ccccc4)c3)ncn1-2]

Example 121 was prepared analogously as Example 120, using 1-phenylpyrazole-4-boronic acid in the Suzuki cross coupling step. MS: [M+1]=399.

Example 122: Synthesis of Compound 62

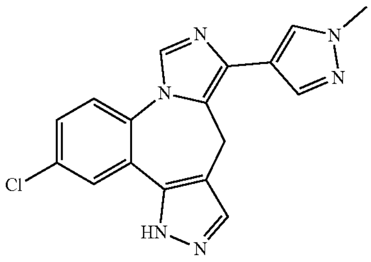 [SMILES: Cn1cc(-c2ncn3c2Cc2cn[nH]c2-c2cc(Cl)ccc2-3)cn1]

Compound 62 was prepared analogously as Example 120, using (1-methyl-1H pyrazole-4-yl)boronic acid HCl in the Suzuki cross coupling step. MS: [M+1]=337.

Example 123: Synthesis of Compound 71

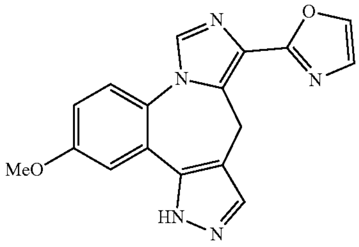 [SMILES: COc1ccc2c(c1)-c1[nH]ncc1Cc1c(-c3ncco3)ncn1-2]

The Stille cross coupling reaction is followed below: Intermediate C ($R_1$=OMe; 52.9 mg, 0.106 mmol) was stirred in dioxane (0.7 ml; degassed) under $N_2$ atm in a sealed tube, 2-(tri-n-butylstannyl)oxazole (114.0 mg, 0.318 mmol) was added, followed by $PdCl_2(dppf)_2$ DCM complex (15.5 mg, 0.0212 mmol). The reaction vessel was purged by nitrogen again before being capped tight and heated at 110° C. for 16 h. Upon cooling, the reaction was diluted with EtOAc, washed with sat. $NaHCO_3$, brine, and dried over $MgSO_4$. Filtration and concentration followed by prep. TLC using 10% MeOH in DCM containing 0.1% triethylamine gave 26.4 mg oxazole adduct which was subjected to acidic removal of the 4-methoxy benzyl group as described previously to give 5.3 mg Example 123, compound 71 as an off-white solid. MS: [M+1]=320. $H^1NMR$ ($CDCl_3$+ drops $CD_3OD$) δ 7.70 (1H, s), 7.67 (1H, s), 7.51 (1H, s), 7.41 (1H, d, J=12 Hz), 7.38 (1H, d, J=4 Hz), 7.17 (1H, s), 6.97 (1H, dd, J=4, 12 Hz), 4.27 (2H, br s), and 3.85 (3H, s).

Example 124: Synthesis of Compound 80

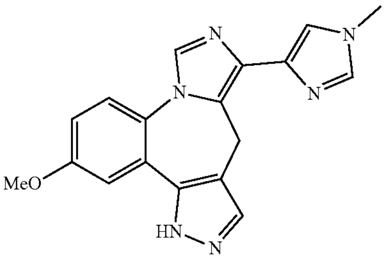 [SMILES: COc1ccc2c(c1)-c1[nH]ncc1Cc1c(-c3cn(C)cn3)ncn1-2]

Example 124 was prepared analogously as Example 123, using N-methyl-4-(tributylstannyl)imidazole in the Stille cross coupling step. MS: [M+1]=333.

Example 125: Synthesis of Compound 55

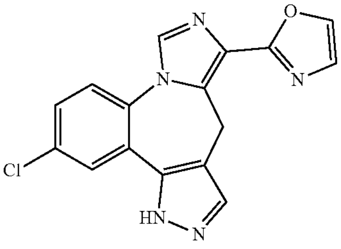 [SMILES: Clc1ccc2c(c1)-c1[nH]ncc1Cc1c(-c3ncco3)ncn1-2]

Example 125 was prepared analogously as Example 123, starting with Intermediate C (R1=Cl). MS: [M+1]=324. $H^1$NMR ($CDCl_3$+ drops $CD_3OD$) δ 7.89 (1H, br s), 7.77 (1H, s), 7.71 (1H, s), 7.58 (1H, s), 7.48 (1H, d, J=8 Hz), 7.43 (1H, dd, J=4, 8 Hz), 7.18 (1H, s), and 4.30 (2H, br s).

Example 126: Synthesis of Compound 76

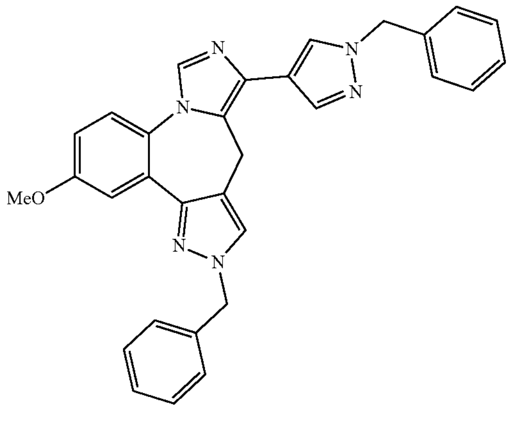 [SMILES: COc1ccc2c(c1)-c1nn(Cc3ccccc3)cc1Cc1c(-c3cnn(Cc4ccccc4)c3)ncn1-2]

Example 126 was synthesized from Example 116, using the same N-alkylation conditions described in Scheme 7-A and Scheme 7-B, with benzyl bromide as the alkylating agent. MS: [M+1]=499. $H^1$ NMR ($CDCl_3$) δ 7.77 (1H, s), 7.72 (1H, s), 7.70 (1H, s), 7.52 (1H, d, J=4 Hz), 7.43-7.35 (7H, m), 7.31-7.27 (4H, m), 7.22 (1H, s), 7.01 (1H, dd, J=4, 12 Hz), 5.36 (2H, s), 5.33 (2H, s), 3.94 (3H, s), and 3.88 (2H, br s).

Example 127: Synthesis of Compound 77

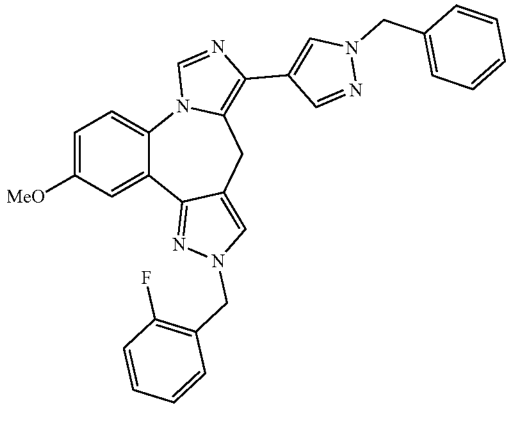 [SMILES: COc1ccc2c(c1)-c1nn(Cc3ccccc3F)cc1Cc1c(-c3cnn(Cc4ccccc4)c3)ncn1-2]

Example 127 was prepared analogously as Example 126, using 2-fluorobenzylbromide as the alkylating agent. MS: [M+1]=517.

Example 128: Synthesis of Compound 75

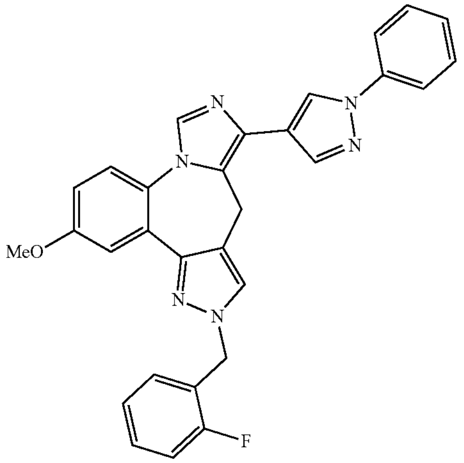 [SMILES: COc1ccc2c(c1)-c1nn(Cc3ccccc3F)cc1Cc1c(-c3cnn(-c4ccccc4)c3)ncn1-2]

Example 128 was synthesized from Example 115, using 2-fluorobenzylbromide as the N-alkylating agent. MS: [M+1]=503. $H^1$ NMR ($CDCl_3$) δ 8.26 (1H, s), 7.98 (1H, s), 7.76 (3H, m), 7.52-7.46 (4H, m), 7.31-7.28 (3H, m), 7.22 (1H, m), 7.12-7.09 (2H, m), 7.03 (1H, dd, J=4, 12 Hz), 5.40 (2H, s), and 3.95 (3H, s).

Example 128-1: Synthesis of Compound 190

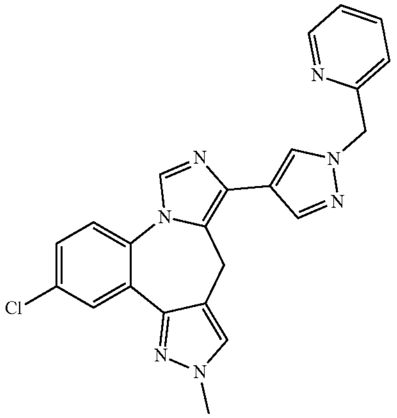 [SMILES: Cn1cc2c(n1)-c1cc(Cl)ccc1-n1cnc(-c3cnn(Cc4ccccn4)c3)c1C2]

Compound 190 was prepared analogously as Example 126, using [1-(pyridin-2-ylmethyl)pyrazol-4-yl]boronic acid in the Suzuki coupling with Intermediate C, and trimethylphenylammonium chloride as the alkylating agent in the final step. MS: [M+1]=428.

Example 128-2: Synthesis of Compound 208
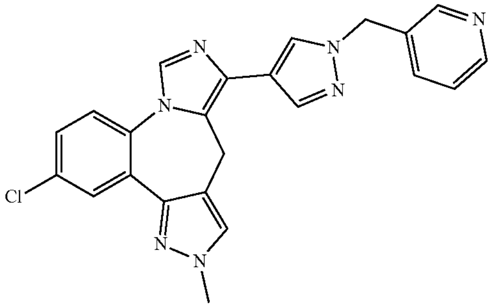 [SMILES: Cn1cc2c(n1)-c1cc(Cl)ccc1-n1cnc(-c3cnn(Cc4cccnc4)c3)c1C2]
Compound 208 was prepared analogously as Example 128-1, using [1-(pyridin-3-ylmethyl)pyrazol-4-yl]boronic acid in the Suzuki coupling with Intermediate C in the cross coupling step. MS: [M+1]=428.
Scheme 10A
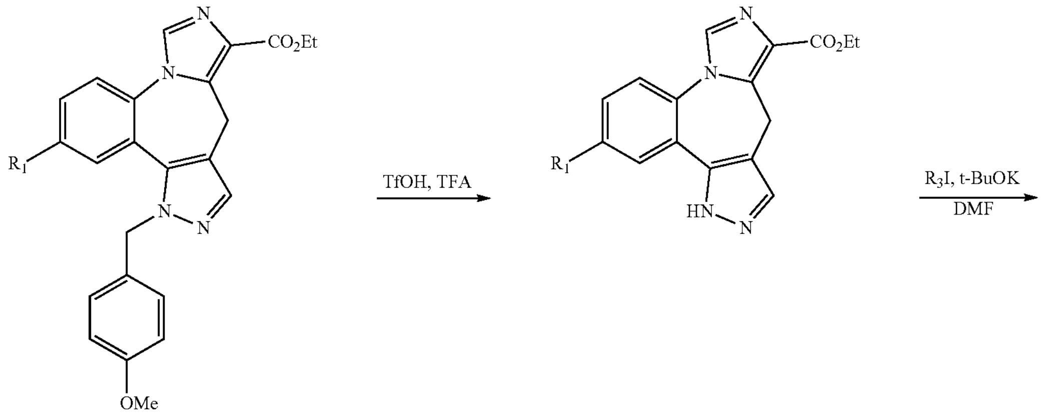
R1 = OMe, Cl
Intermediate B
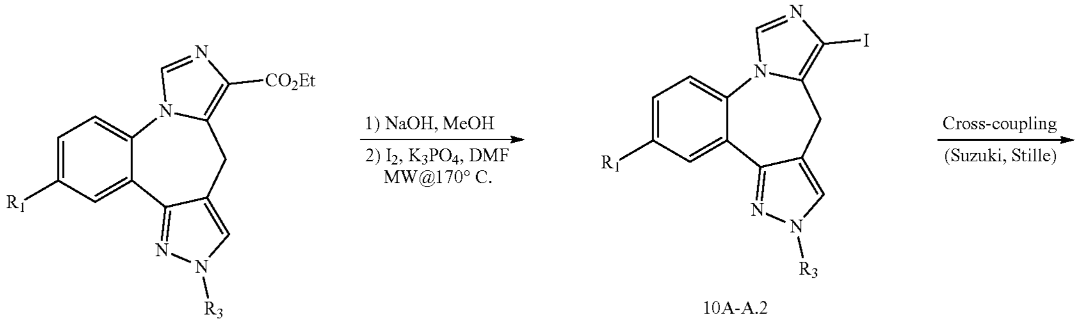
10A-A.1
10A-A.2
(Intermediate C)

-continued
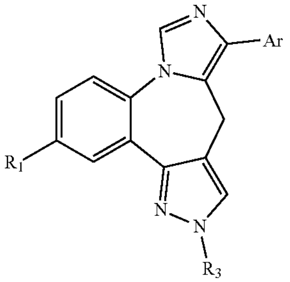
| R1 | R3 | Ar |
|---|---|---|
| Ex.128-3 Compound 221: Cl, Me, | | 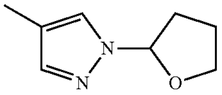 |
| Ex.128-4 Compound 222: Cl, Me, | | 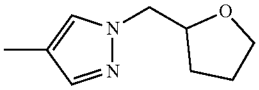 |
| Ex.128a Compound 319: Cl, | 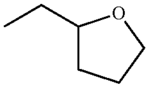 | 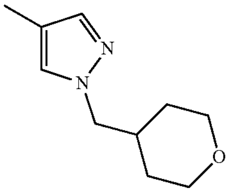 |
| Ex.128b Compound 282: OMe, Me, | | 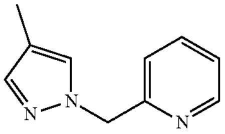 |
| Ex.128c Compound 320: Cl, | 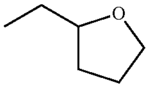 | 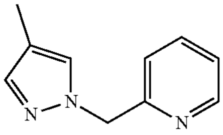 |
| Ex.128d Compound 321: Cl, | 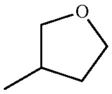 | 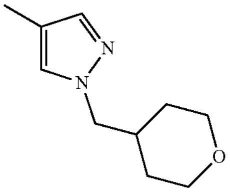 |
| Ex.128e Compound 336: Cl, Me, | | 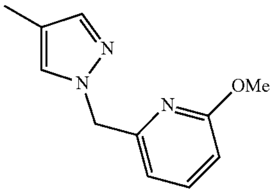 |
| Ex.128f Compound 337: Cl, | 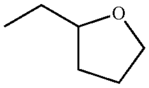 | 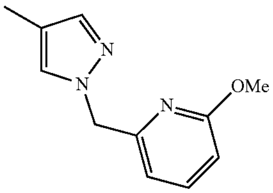 |

-continued

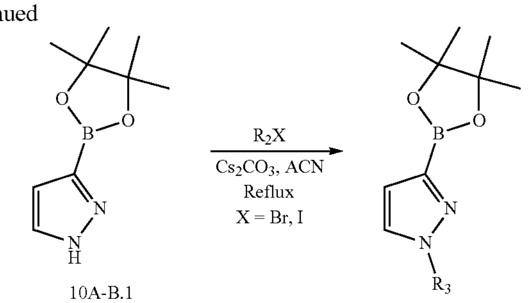

10A-B.1

$R_2$ = 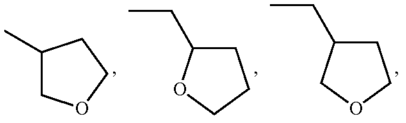 etc.

10A-B.2 10A-B.3 10A-B.4

Example 128-3: Synthesis of Compound 221

Compound 221

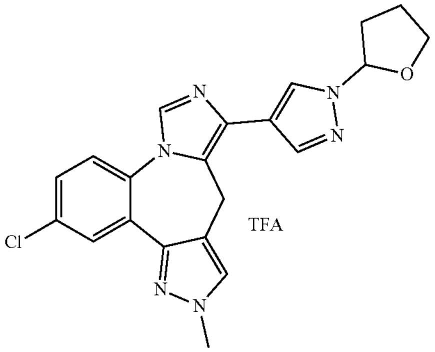

Intermediate B ($R_1$=Cl; 5.0 g, 11.16 mmol) was treated with trifluoromethane sulfonic acid (3.35 g, 22.31 mmol) in a mixture of trifluoroacetic acid (25.0 ml) and DCM (25.0 ml) at 40° C. for 16 h. The reaction mixture was concentrated, treated with sat. $NaHCO_3$ solution to obtain ppts. The ppts were filtered and washed with water. The drying of ppts gave 4.4 g of the deprotection product as a yellowish solid, MS: [M+1]=329.0.

The above obtained product (0.5 g, 1.52 mmol) was dissolved in anhydrous DMF (5.0 mL). The anhydrous t-BuOK (0.21 g, 1.83 mmol) was added at 0° C. temperature, followed by Methyl iodide (0.11 mL, 1.68 mmol). The rxn mixture was stirred at ambient temperature for 16 h. The reaction mixture was diluted with water and extracted with ethyl acetate (15.0 mLx3). The combined organic extract was washed with brine and dried over $MgSO_4$. Filtration and solvent removal followed by silica gel column chromatography using 0 to 100% Ethyl acetate in Hexane gave 0.35 g of 10A-A.1 as a solid product, MS: [M+1]=343.0.

Intermediate 10A-A.1 (0.35 g, 1.0 mmol) solution in MeOH (5.0 mL) was treated with 1.0 N NaOH (2.0 mL, 2.0 mmol) and the rxn mixture was refluxed for 4 h. The rxn mixture was concentrated and pH adjusted with 1.0 M HCl solution to pH 3-4. The solid ppts were collected by filtration, and washed with water and dried to obtain 0.18 g of acid intermediate, MS: [M+1]=315.0.

Intermediate acid (0.17 g, 0.53 mmol), $K_3PO_4$ (0.11 g, 0.53 mmol) and Iodine (0.81 g, 3.11 mmol) solution in Acetonitrile (8.0 mL) were refluxed for 4 h. The reaction mixture was diluted with water and extracted with ethyl acetate (15.0 mLx3). The combined organic extract was washed with aqueous sodium thiosulphate solution and dried over $MgSO_4$. Filtration and solvent removal followed by silica gel column chromatography using 0 to 100% Ethyl acetate in Hexane gave 0.16 g of 10A-A.2 (Intermediate C) as a solid product, MS: [M+1]=396.0.

Intermediate 10A-B.1. (0.05 g, 0.25 mmol), $Cs_2CO_3$ (0.17 g, 0.52 mmol) and 3-iodotetrahydrofuran (0.06 g, 0.31 mmol) solution in Acetonitrile (4.0 mL) were refluxed for 16 h. The reaction mixture was cooled at ambient temperature. Filtration and solvent removal gave 0.068 g of 10A-B.2 as a solid product, MS: [M+1]=265.2

Intermediate 10A-B.1. (0.05 g, 0.25 mmol), $Cs_2CO_3$ (0.17 g, 0.52 mmol) and tetrahydrofurfuryl bromide (0.05 g, 0.31 mmol) solution in Acetonitrile (4.0 mL) were refluxed for 16 h. The reaction mixture was cooled at ambient temperature. Filtration and solvent removal gave 0.072 g of 10A-B.3 as a solid product, MS: [M+1]=265.2

Intermediate 10A-B.4 was prepared analogously as Intermediate XB.1, using 3-(Iodomethyl) tetrahydrofuran in Step 1, MS: [M+1]=265.2.

Intermediate 10A-A.2 (Intermediate C; 0.02 g, 0.051 mmol), Intermediate 10A-B.2 (0.015 g, 0.056 mmol), $Cs_2CO_3$ (0.035 g, 0.11 mmol), X-phos (0.0036 g, 0.008 mmol) and $Pd_2(dba)_3$ (0.0023 g, 0.025 mmol) solution in Dioxane/Water (2.0 mL, 4:1 ratio) were refluxed for 4 h. The reaction mixture was diluted with water and extracted with ethyl acetate (15.0 mLx3). The combined organic extract was washed with brine and dried over $MgSO_4$. Filtration and solvent removal followed by silica gel column chromatography using 0 to 5% MeOH in DCM followed by RP purification using 30 to 80% MeOH gradient in Water (0.1% TFA) gave 0.0075 g of Compound 221 product, MS: [M+1]=407.0.

Example 128-4: Synthesis of Compound 222

Compound 222

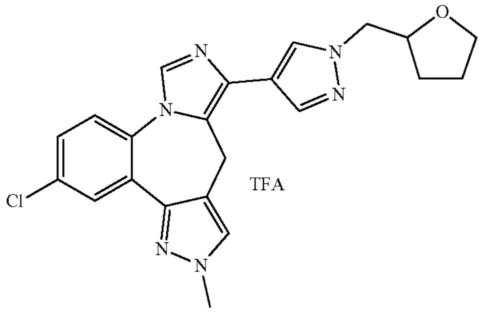

Compound 222 was prepared analogously as Compound 221, using Intermediate 10A-B.3, MS: [M+1]=421.0.

Example 128a: Synthesis of Compound 319

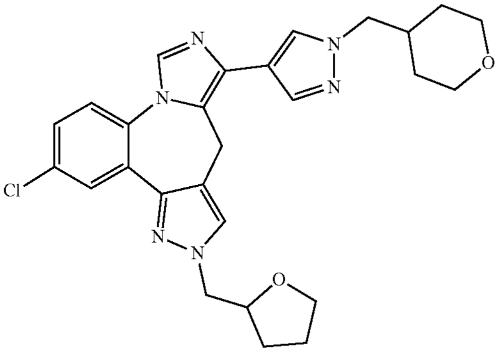 [SMILES: Clc1ccc2c(c1)-c1nn(CC3CCCO3)cc1Cc1c(-c3cnn(CC4CCOCC4)c3)ncn1-2]

Compound 319 was prepared analogously as Compound 221, using tetrahydrofurfuryl bromide as the N-alkylating agent, and 1-(tetrahydro-2H-pyran-4-yl)methyl-1H-pyrazole-4-boronic acid pinacol ester in the Suzuki cross coupling step. MS: [M+1]=506.

Example 128b: Synthesis of Compound 282

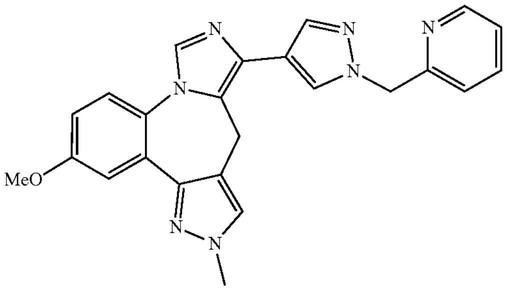 [SMILES: COc1ccc2c(c1)-c1nn(C)cc1Cc1c(-c3cnn(Cc4ccccn4)c3)ncn1-2]

Compound 282 was prepared analogously as Compound 221, starting with Intermediate B ($R_1$=OMe), and using 1-(pyridin-2-ylmethyl)-1H-pyrazole-4-boronic acid pinacol ester in the Suzuki cross coupling step. MS: [M+1]=424.

Example 128c: Synthesis of Compound 320

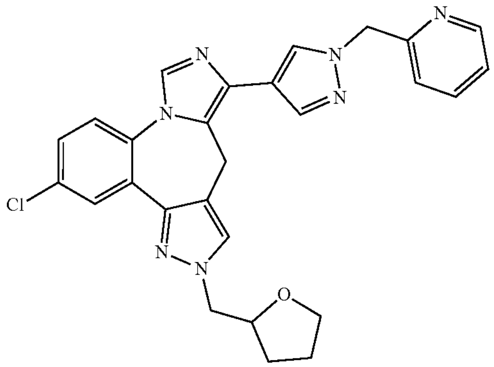 [SMILES: Clc1ccc2c(c1)-c1nn(CC3CCCO3)cc1Cc1c(-c3cnn(Cc4ccccn4)c3)ncn1-2]

Compound 320 was prepared analogously as Compound 319, using 1-(pyridin-2-ylmethyl)-1H-pyrazole-4-boronic acid pinacol ester in the Suzuki cross coupling step. MS: [M+1]=498.

Example 128d: Synthesis of Compound 321

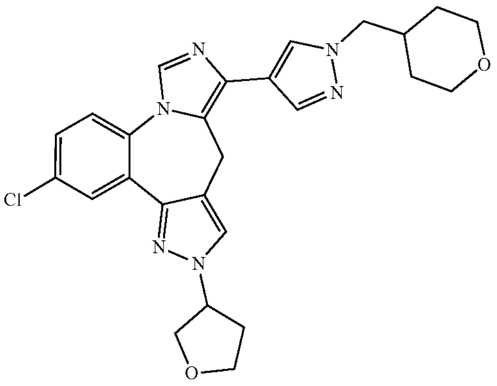 [SMILES: Clc1ccc2c(c1)-c1nn(C3CCOC3)cc1Cc1c(-c3cnn(CC4CCOCC4)c3)ncn1-2]

Compound 321 was prepared analogously as Compound 319, using 3-iodotetrahydrofuran for the N-alkylation. MS: [M+1]=491.

Example 128e: Synthesis of Compound 336

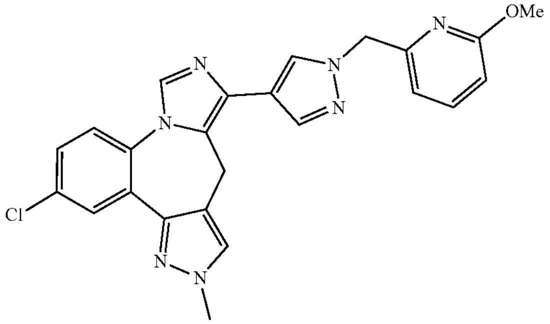 [SMILES: COc1cccc(Cn2cc(-c3ncn4c3Cc3cn(C)nc3-c3cc(Cl)ccc3-4)cn2)n1]

Compound 336 was prepared analogously as Compound 221, using 1-(2-methoxy-pyridin-6-ylmethyl)-1H-pyrazole-4-boronic acid pinacol ester in the Suzuki cross coupling step. MS: [M+1]=458.

Example 128f: Synthesis of Compound 337

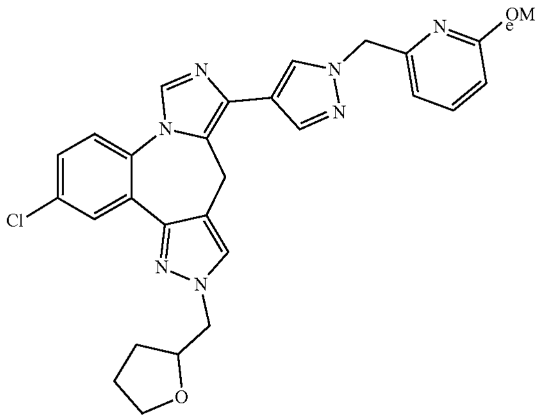 [SMILES: COc1cccc(Cn2cc(-c3ncn4c3Cc3cn(CC5CCCO5)nc3-c3cc(Cl)ccc3-4)cn2)n1]

Compound 337 was prepared analogously as Compound 336, using tetrahydrofurfuryl bromide as the N-alkylating agent. MS: [M+1]=529.

Example 128g: Synthesis of Compound 338

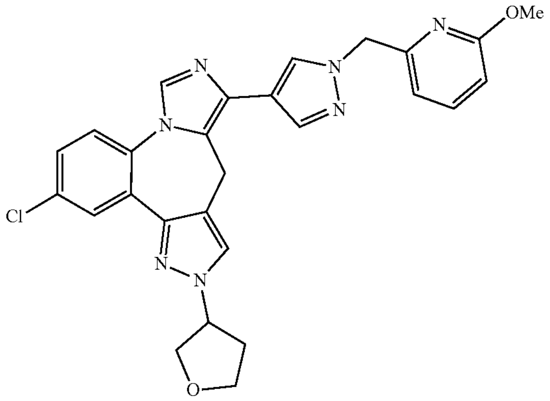 [SMILES: COc1cccc(Cn2cc(-c3ncn4c3Cc3cn(C5CCOC5)nc3-c3cc(Cl)ccc3-4)cn2)n1]

Compound 338 was prepared analogously as Compound 336, using 3-iodotetrahydrofuran as the N-alkylating agent. MS: [M+1]=514.

Scheme 10b

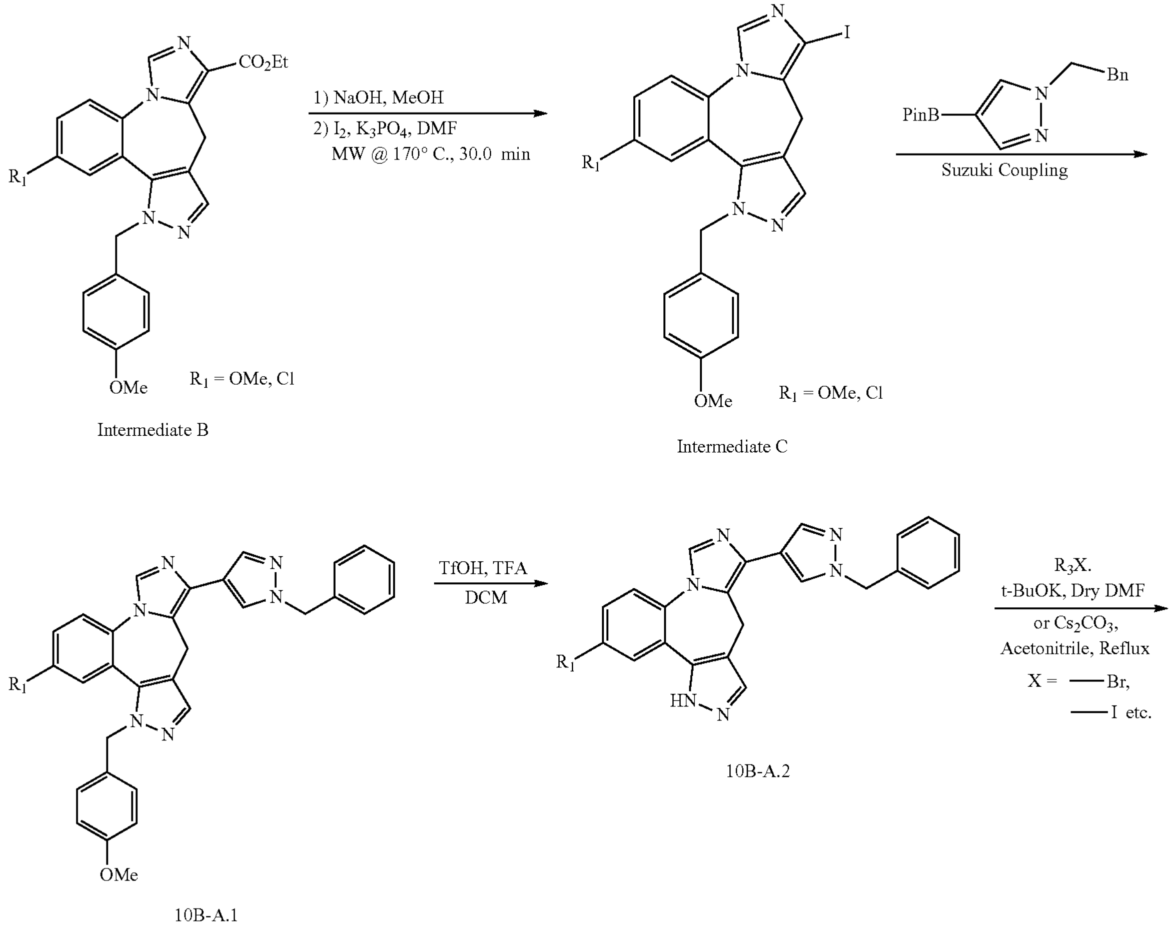

-continued

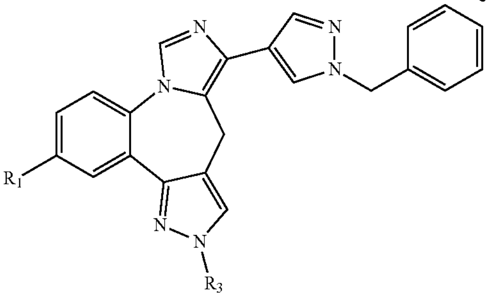

Major

+

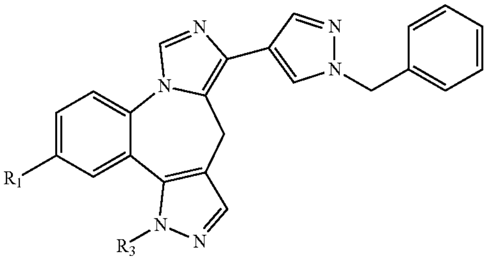

Minor

| $R_1$ $R_3$ | |
|---|---|
| Ex. 128-5 Compound 163: Cl, Me (Major) | |
| Ex. 128-6 Compound 164: Cl, Me (Minor) | |
| Ex 128-7 Compound 165: Cl, iPr (Major) | |
| Ex. 128-8 Compound 229: Cl, | 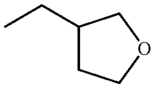 |
| Ex. 128-9 Compound 230: Cl, | 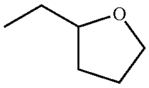 |
| Ex. 128h Compound 274: Cl, | 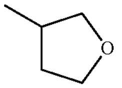 |

Example 128-5 and Example 128-6: Synthesis of Compound 163 and Compound 164

Compound 163

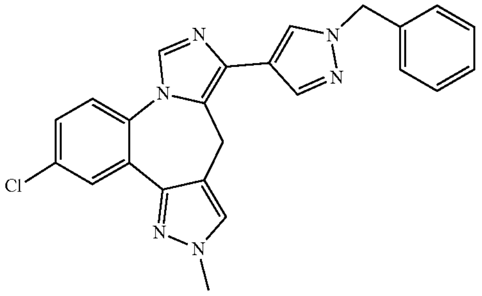

Compound 164

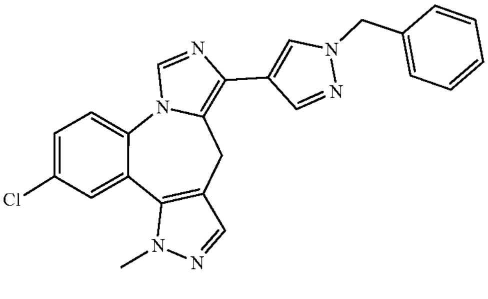

Intermediate B (0.42 g, 0.94 mmol) solution in MeOH (5.0 mL) was treated with 1.0 N NaOH (2.0 mL, 2.0 mmol) and the rxn mixture was refluxed for 4 h. The rxn mixture was concentrated and pH adjusted with 1.0 M HCl solution to pH 3-4. The solid ppts were collected by filtration and washed with water and dried to obtain 0.37 g of acid intermediate, MS: [M+1]=421.2.

Intermediate acid (0.19 g, 0.44 mmol), $K_3PO_4$ (0.19 g, 0.88 mmol) and Iodine (0.45 g, 1.76 mmol) solution in anhydrous DMF (3.0 mL) were heated at 160° C. in Microwave irradiation for 30.0 min. The reaction mixture was diluted with water and extracted with ethyl acetate (15.0 mL×3). The combined organic extract was washed with aqueous sodium thiosulphate solution and dried over $MgSO_4$. Filtration and solvent removal followed by silica gel column chromatography using 0 to 100% Ethyl acetate in Hexane gave 0.31 g of Intermediate C as a solid product, MS: [M+1]=503.1.

Intermediate C (0.065 g, 0.13 mmol), 1-Benzylpyrazole-4-boronic acid, pinacol ester (0.034 g, 0.17 mmol), $K_2CO_3$ (0.053 g, 0.39 mmol), and Pd(dppf)$Cl_2$·DCM (0.021 g, 0.026 mmol) solution in Dioxane/Water (2.0 mL, 4:1 ratio) were heated at 100° C. in Microwave irradiation for 30.0 min. The reaction mixture was diluted with water and extracted with ethyl acetate (10.0 mL×3). The combined organic extract was washed with brine and dried over $MgSO_4$. Filtration and solvent removal followed by silica gel column chromatography using 0 to 100% Ethyl acetate in Hexane gave 0.07 g of 10B-A.1 solid product, MS: [M+1]=533.2.

Intermediate 10B-A.1 (0.07 g, 0.13 mmol) was treated with trifluoromethane sulfonic acid (0.04 g, 0.26 mmol) in a mixture of trifluoroacetic acid (1.0 ml) and DCM (1.0 ml) at 40° C. for 24 h. The reaction mixture was concentrated, treated with sat. $NaHCO_3$ solution to obtain ppts. The ppts were filtered and washed with water. The drying of ppts gave a 0.064 g of 10B-A.2 solid product, MS: [M+1]=413.2.

Intermediate 10B-A.2 (0.02 g, 0.048 mmol) and N,N,N-Trimethylbenzenaminium chloride (0.033 g, 0.19 mmol) were dissolved in anhydrous DMF (2.0 mL). The anhydrous t-BuOK (0.006 g, 0.053 mmol) was added at 0° C. temperature. The rxn mixture was heated at 60° C. for 16 h. The reaction mixture was diluted with water and extracted with ethyl acetate (15.0 mL×3). The combined organic extract was washed with brine and dried over $MgSO_4$. Filtration and solvent removal followed by silica gel column chromatography using 0 to 100% EtOAc in Hexane gave 0.012 g of Compound 163 (Major) and 0.002 g of Compound 164 (Minor) isomer, MS: [M+1]=427.2.

Example 128-7: Synthesis of Compound 165

Compound 165

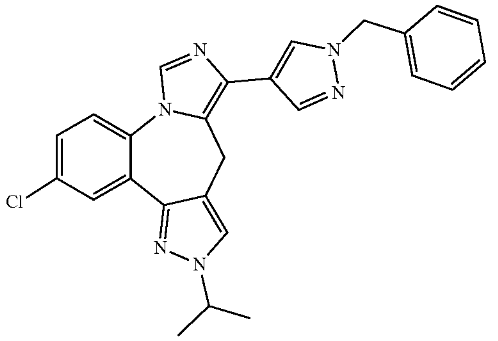

Intermediate 10B-A.2 (0.02 g, 0.05 mmol) solution in anhydrous DMF (2.0 mL) was treated with t-BuOK (0.006 g, 0.05 mmol) at 0° C. The Isopropyl iodide (0.016 g, 0.1 mmol) was added, and reaction mixture was stirred at ambient temperature for 30.0 min and heated at 60° C. for 4 h. The reaction mixture was cooled and diluted with water. The rxn mixture was extracted with ethyl acetate (10.0 mL×3). The combined organic extract was washed with brine and dried over $MgSO_4$. Filtration and solvent removal followed by silica gel column chromatography using 0 to 100% Ethyl acetate in Hexane gave 0.02 g of Compound 165 solid product, MS: [M+1]=455.2.

Example 128-8: Synthesis of Compound 229

Compound 229

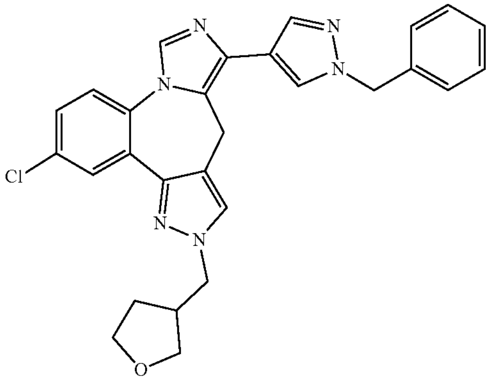

Intermediate 10B-A.2 (0.02 g, 0.05 mmol), $Cs_2CO_3$ (0.03 g, 0.1 mmol) and 3-(Iodomethyl)tetrahydrofuran (0.02 g, 0.1 mmol) solution in Acetonitrile (2.0 mL) were refluxed for 16 h. The reaction mixture was cooled at ambient temperature. Filtration and solvent removal followed by silica gel column chromatography using 0 to 5% MeOH in DCM gave 0.009 g of Compound 229 as a solid product, MS: [M+1]=497.2.

Example 128-9: Synthesis of Compound 230

Compound 230

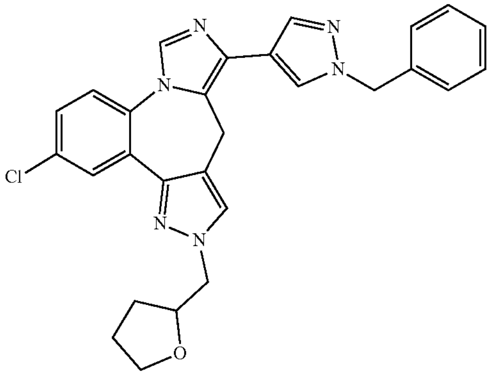

Compound 230 was prepared analogously as Compound 229, using Tetrahydrofurfuryl bromide in Step 4, MS: [M+1]=497.2.

Example 128h: Synthesis of Compound 274

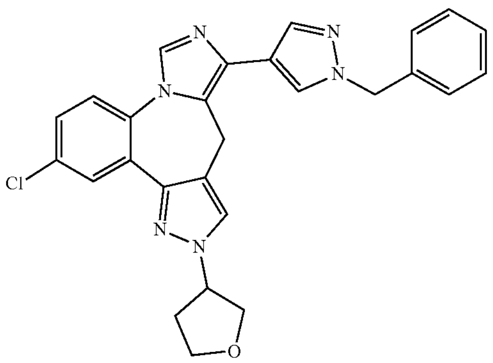 [SMILES: Clc1ccc2c(c1)-c1nn(C3CCOC3)cc1Cc1c(-c3cnn(Cc4ccccc4)c3)ncn1-2]

Compound 274 was prepared analogously as Compound 229, using 3-iodotetrahydrofuran in Step 4, MS: [M+1] =483.

Scheme 10c

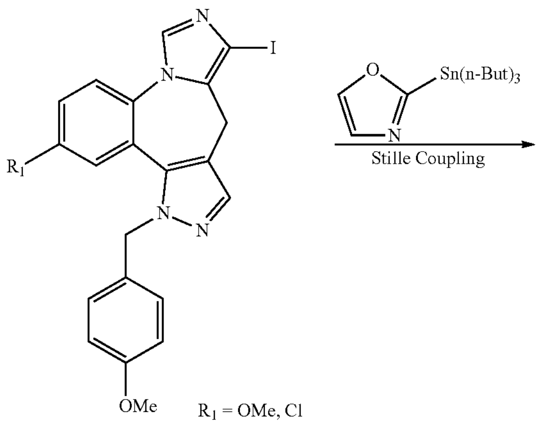

$R_1$ = OMe, Cl

Intermediate C

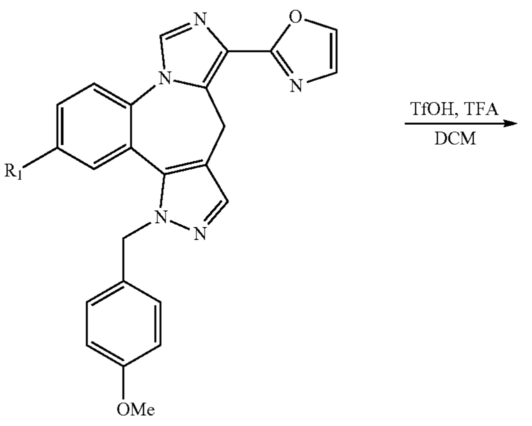

10C-A.1

-continued

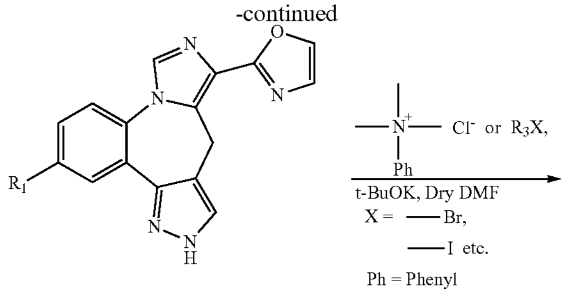

10C-A.2

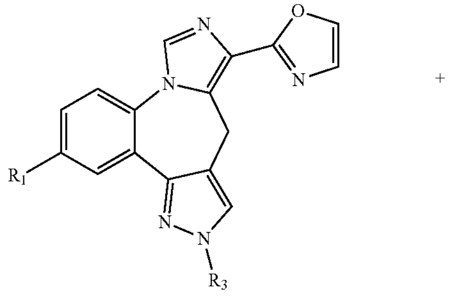

+

Major

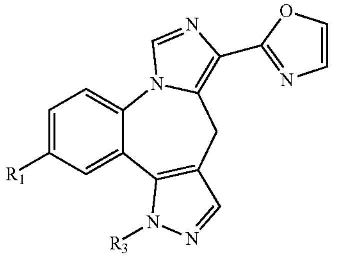

Minor

| $R_1$ $R_3$ |
|---|
| Ex. 128-10 Compound 166: Cl, Me (Major) |
| Ex. 135 Compound 167: Cl, iPr (Major) |
| Ex. 135-1 Compound 172: Cl, 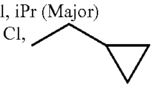 (Major) |

Example 128-10: Synthesis of Compound 166

Compound 166

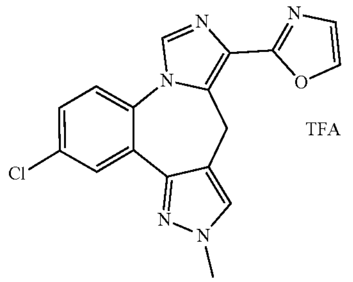

Intermediate C (0.1 g, 0.2 mmol), 2-(Tributylstannyl) oxazole (0.093 g, 0.26 mmol), and $Pd(dppf)Cl_2 \cdot DCM$ (0.033 g, 0.04 mmol) solution in Dioxane (3.0 mL) were heated at 110° C. for 16 h. The reaction mixture was diluted with water and extracted with ethyl acetate (10.0 mL×3). The combined organic extract was washed with brine and dried over $MgSO_4$. Filtration and solvent removal followed by silica gel column chromatography using 0 to 100% Ethyl acetate in Hexane gave 0.071 g of 10C-A.1 solid product, MS: [M+1]=444.1.

Intermediate 10C-A.1 (0.04 g, 0.09 mmol) was treated with trifluoromethane sulfonic acid (0.04 g, 0.3 mmol) in a mixture of trifluoroacetic acid (1.0 ml) and DCM (1.0 ml) at 40° C. for 24 h. The reaction mixture was concentrated, treated with sat. $NaHCO_3$ solution to obtain ppts. The ppts were filtered and washed with water. The drying of ppts gave a 0.036 g of 10C-A.2 solid product, MS: [M+1]=324.1.

Intermediate 10C-A.2 (0.015 g, 0.046 mmol) and N,N,N-Trimethylbenzenaminium chloride (0.032 g, 0.18 mmol) were dissolved in anhydrous DMF (1.0 mL). The anhydrous t-BuOK (0.006 g, 0.055 mmol) was added at 0° C. temperature. The rxn mixture was heated at 60° C. for 16 h. The reaction mixture was diluted with water and extracted with ethyl acetate (15.0 mL×3). The combined organic extract was washed with brine and dried over $MgSO_4$. Filtration and solvent removal followed by RP purification using 10 to 70% MeOH gradient in Water (0.1% TFA) gave 0.0037 g of Compound 166 product, MS: [M+1]=338.1.

Example 135: Synthesis of Compound 167

Compound 167

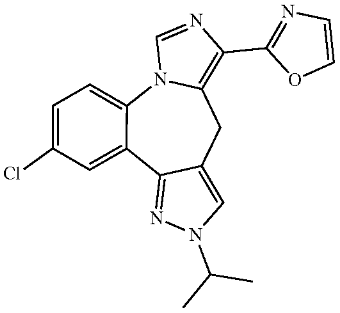

Intermediate 10C-A.2 (0.017 g, 0.05 mmol) solution in anhydrous DMF (2.0 mL) was treated with t-BuOK (0.007 g, 0.06 mmol) at 0° C. The Isopropyl iodide (0.018 g, 0.1 mmol) was added, and reaction mixture was stirred at ambient temperature for 30.0 min and heated at 60° C. for 4 h. The reaction mixture was cooled and diluted with water. The rxn mixture was extracted with ethyl acetate (10.0 mL×3). The combined organic extract was washed with brine and dried over $MgSO_4$. Filtration and solvent removal followed by silica gel column chromatography using 0 to 100% Ethyl acetate in Hexane gave 0.0067 g of Example 135, as a solid product, MS: [M+1]=366.1.

Example 135-1: Synthesis of Compound 172

Compound 172

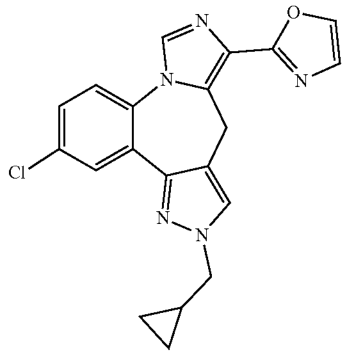

Compound 172 was prepared analogously as Compound 167, using (Iodomethyl)cyclopropane in Step 3, MS: [M+1]=378.1.

Scheme 11

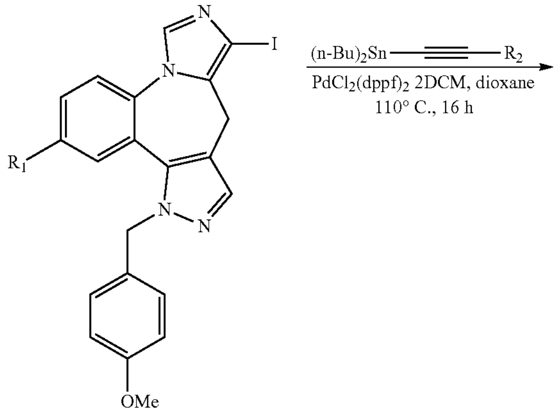

Intermediate C

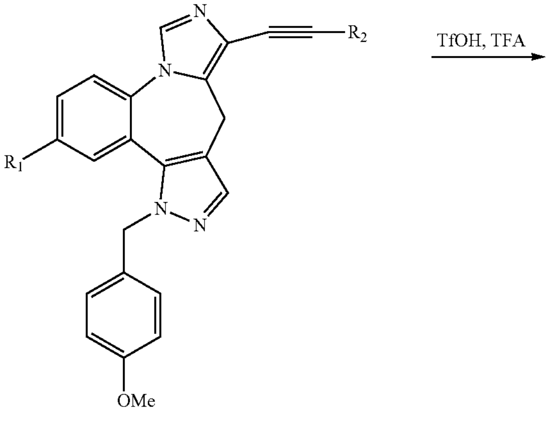

11.1

-continued

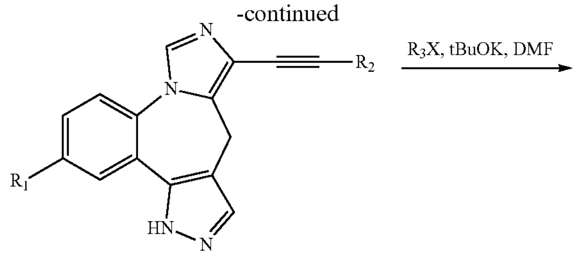

| | R1 | R2 |
|---|---|---|
| Ex. 129 Compound 83: | OMe, | Me |
| Ex. 130 Compound 73: | OMe, | tBu |
| Ex. 131 Compound 65: | Cl, | Me |
| Ex. 132 Compound 63: | Cl, | tBu |

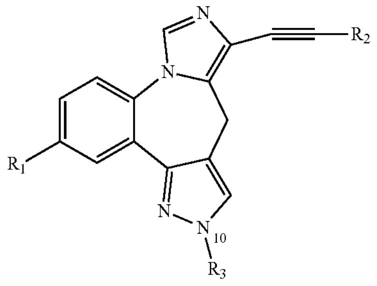

+

(major)

| | R1 | R2 | R3 |
|---|---|---|---|
| Ex. 133 Compound 101: | Cl, | tBu, | Me |
| Ex. 134 Compound 92: | Cl, | tBu, | Bn |

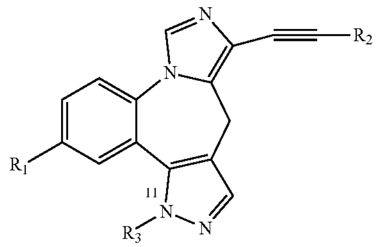

(minor)

| | R1 | R2 | R3 |
|---|---|---|---|
| Ex. 135 Compound 102: | Cl, | tBu, | Me |

Example 129: Synthesis of Compound 83

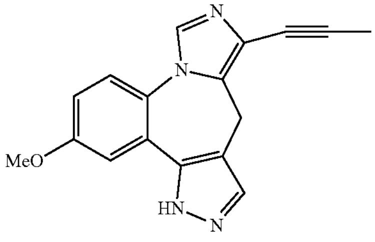 [SMILES: CC#Cc1ncn2c1Cc1cn[nH]c1-c1cc(OC)ccc1-2]

Intermediate C ($R_1$=OMe; 33.6 mg, 0.0674 mmol) was stirred in 1,4-dioxane (0.5 ml; degassed) under $N_2$ atm. in a sealed tube, 1-propynyltributylstannane (66.6 mg, 0.202 mmol) was added, followed by $PdCl_2(dppf)_2$ DCM complex (9.9 mg, 0.0135 mmol). The reaction vessel was purged by nitrogen again before being capped tight and heated at 110° C. for 16 h. Upon cooling, the reaction was diluted with EtOAc, washed with sat. $NaHCO_3$, brine, and dried over $MgSO_4$. Filtration and concentration followed by prep. TLC using 7% MeOH in DCM/EtOAc (1:1) gave the alkyne adduct which was subjected to acidic removal of the 4-methoxy benzyl group as described previously to give 8.3 mg Example 129 compound 83 as an off-white solid. MS: [M+1]=291. $H^1NMR$ ($CDCl_3$) δ 7.62 (1H, s), 7.56 (1H, s), 7.41 (1H, d, J=12 Hz), 7.40 (1H, s), 6.98 (1H, dd, J=4, 12 Hz), 3.89 (2H, s), 3.83 (3H, s), and 2.11 (3H, s).

Example 130: Synthesis of Compound 73

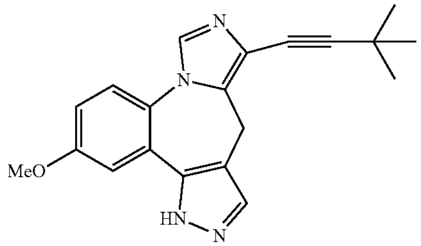 [SMILES: COc1ccc2c(c1)-c1[nH]ncc1Cc1c(C#CC(C)(C)C)ncn1-2]

Example 130 was synthesized analogously as Example 129, using tributyl(3,3-dimethyl-1-butyn-1-yl)stannane in the Sonogashira coupling step. MS: [M+1]=333.

Example 131: Synthesis of Compound 65

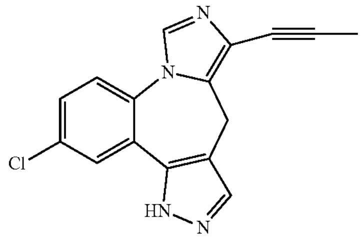 [SMILES: CC#Cc1ncn2c1Cc1cn[nH]c1-c1cc(Cl)ccc1-2]

Example 131 was synthesized analogously as Example 129, starting with Intermediate C ($R^1$=Cl). MS: [M+1]=295. $H^1NMR$ ($CDCl_3$+ drops $CD_3OD$) δ 7.83 (1H, s), 7.55 (1H, s), 7.44 (1H, s), 7.36 (2H, m), 3.79 (2H, s), and 2.01 (3H, s).

Example 132: Synthesis of Compound 63

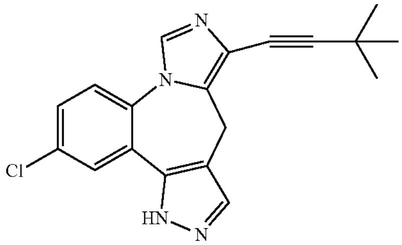 [SMILES: CC(C)(C)C#Cc1ncn2c1Cc1cn[nH]c1-c1cc(Cl)ccc1-2]

Example 132 was synthesized analogously as Example 131, using tributyl(3,3-dimethyl-1-butyn-1-yl)stannane in the Sonogashira coupling step. MS: [M+1]=337.

Example 133 and Example 135: Synthesis of Compound 101 and Compound 102

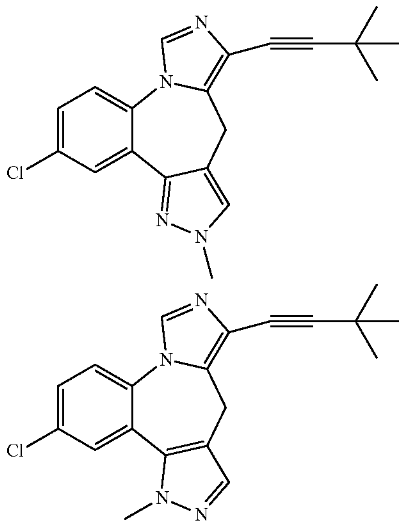

Example 133 was prepared from Example 132, using trimethylphenylammonium chloride as the N-alkylating agent in the pyrazole alkylation step, conditions of which was described previously (i.e. preparation of Example 23 compound 46, Scheme 6, route A). Example 133, compound 101 was isolated as the major isomer, wt: 3.6 mg. MS: [M+1]=351.

Also isolated from this N-methylation reaction was small amount of the minor isomer Example 135 compound 102, wt: 0.9 mg. MS: [M+1]=351.

Example 134: Synthesis of Compound 92

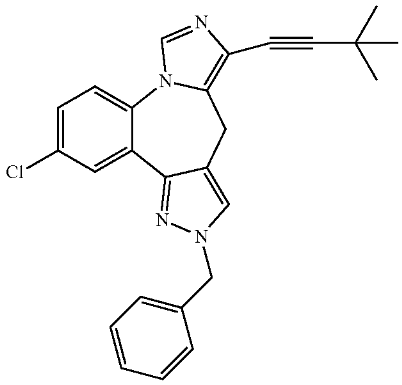 [SMILES: CC(C)(C)C#Cc1ncn2c1Cc1cn(Cc3ccccc3)nc1-c1cc(Cl)ccc1-2]

Example 134 was prepared analogously as Example 133, using benzylbromide as the N-alkylating agent in the pyrazole alkylation step, and Example 134 was isolated as the major isomer. MS: [M+1]=427.

Scheme 12

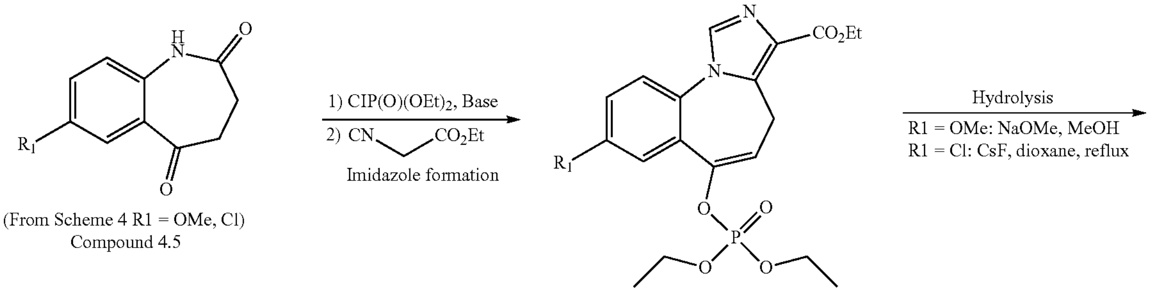

(From Scheme 4 R1 = OMe, Cl)
Compound 4.5

12.1

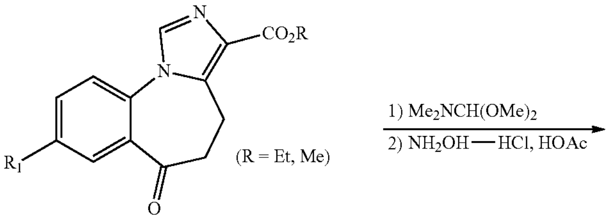

12.2

-continued

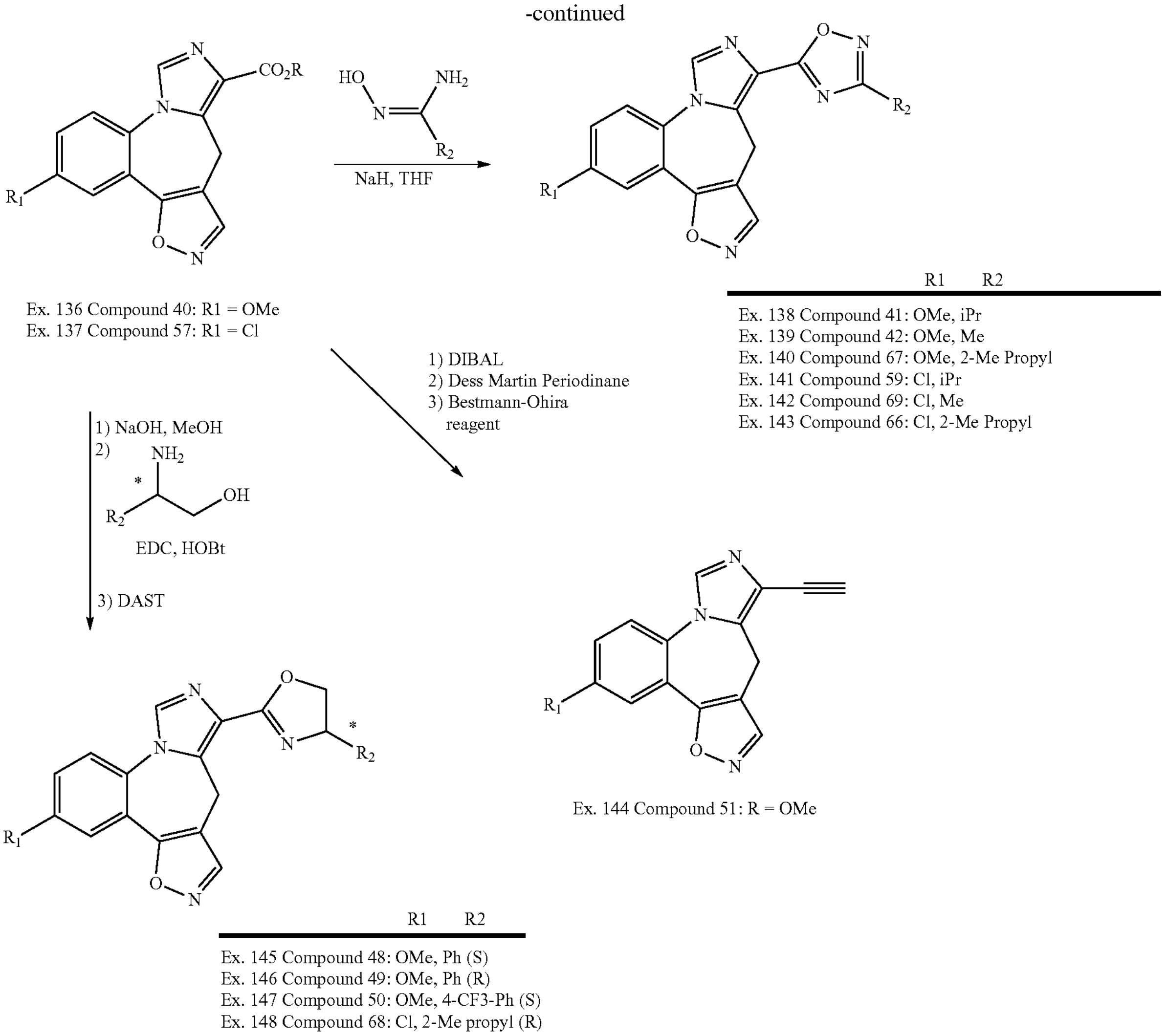

Ex. 136 Compound 40: R1 = OMe
Ex. 137 Compound 57: R1 = Cl

| R1 | R2 |
|---|---|
| Ex. 138 Compound 41: OMe, | iPr |
| Ex. 139 Compound 42: OMe, | Me |
| Ex. 140 Compound 67: OMe, | 2-Me Propyl |
| Ex. 141 Compound 59: Cl, | iPr |
| Ex. 142 Compound 69: Cl, | Me |
| Ex. 143 Compound 66: Cl, | 2-Me Propyl |

Ex. 144 Compound 51: R = OMe

| R1 | R2 |
|---|---|
| Ex. 145 Compound 48: OMe, | Ph (S) |
| Ex. 146 Compound 49: OMe, | Ph (R) |
| Ex. 147 Compound 50: OMe, | 4-CF3-Ph (S) |
| Ex. 148 Compound 68: Cl, | 2-Me propyl (R) |

Example 136: Synthesis of Compound 40

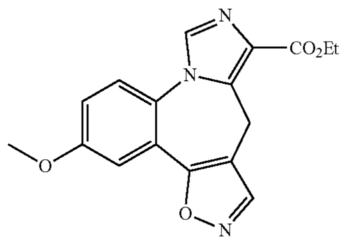 [SMILES: CCOC(=O)c1ncn2c1Cc1cnoc1-c1cc(OC)ccc1-2]

The starting ketone (Scheme 12) 4.5 (7-methoxy-2,3,4,5-tetrahydro-1H-1-benzazepine-2,5-dione) from Scheme 4 ($R_1$=OMe; 1.0 g, 4.87 mmol) was dissolved in mixture of anhydrous THF:DMF (25:5, v/v mL). The rxn mixture was cooled in dry ice bath at −20° C. temperature. The t-BuOK (1.37 g, 12.18 mmol) was added and rxn mixture was stirred at −20° C. for 20.0 min. Diethyl chlorophosphate (1.76 mL, 12.18 mmol) was added at −20° C. and rxn mixture was gradually warmed to ambient temperature with stirring for 2 h. The rxn mixture was cooled back at −30° C. temperature and ethyl isocyanoacetate (1.3 mL, 12.18 mmol) was added. The rxn mixture was further cooled at −78° C. temperature and t-BuOK (1.37 g, 12.18 mmol) was added. The rxn mixture was gradually warmed with stirred at ambient temperature for 3 h. The LCMS data shows product formation m/z 437.2.

The rxn mixture was diluted with water and extracted with Ethyl Acetate. The organic layer was dried over anhydrous sodium sulfate and concentrated under reduced pressure. The residue was purified by ISCO combiflash system, Mobile phase: Ethyl Acetate:Hexane gradient to obtain 1.1 g of the imidazole product 12.1 (Yield 51.8%). MS (ESI) mass calcd. for $C_{20}H_{25}N_2O_7P$, 436.4; m/z found 437.2 $[M+H]^+$.

The imidazole 12.1 from above (1.1 g, 2.52 mmol) was dissolved in anhydrous methanol (10.0 mL) and cooled in ice bath. The 25% w/w sodium methoxide in methanol (1.4 mL, 6.3 mmol) was added dropwise and rxn mixture was gradually warmed with stirring at ambient temperature 3 h. The LCMS data shows mixture of ethyl and methyl ester product formation m/z 301.1 and m z 287.1 respectively. The rxn mixture was concentrated under reduced pressure and diluted with water. The product was extracted with Ethyl Acetate. The organic layer was dried over anhydrous sodium sulfate and concentrated under reduced pressure. The residue was purified by ISCO combiflash system, Mobile phase: Ethyl Acetate:Hexane gradient to obtain 0.18 g of ethyl ester 12.2 (Yield 23.8%), together with 0.12 g of methyl ester 12.2 (Yield 17.2%). MS (ESI) mass calcd. for $C_{16}H_{16}N_2O_4$, 300.31; m/z found 301.1 $[M+H]^+$ for ethyl ester product and MS (ESI) mass calcd. for $C_{15}H_{14}N_2O_4$, 286.28; m/z found 287.1 $[M+H]^+$ for methyl ester product.

The keto imidazole ethyl ester 12.2 isolated from above (0.011 g, 0.035 mmol) was dissolved in anhydrous THE (2.5 mL). The N,N-Dimethylformamide dimethyl acetal (0.023 mL, 0.17 mmol) was added and rxn mixture was refluxed for 6 h. The LCMS data shows intermediate product formation m/z 356 $[M+H]^+$. The rxn mixture was concentrated under reduced pressure. The residue was dissolved in glacial acetic acid (1.5 mL). Hydroxylamine hydrochloride (0.006 g, 0.09 mmol) was added and rxn mixture was heated at 95° C. for 5 h. The LCMS data shows product formation m/z 326.1 $[M+H]^+$. The rxn mixture was concentrated under reduced pressure. The residue was purified by prep-TLC plate, Mobile Phase: Ethyl Acetate:Hexane (60:40 v/v mL) to obtain 5.7 mg of Example 136, compound 40 (Yield 50.1%). MS (ESI) mass calcd. for $C_{17}H_{15}N_3O_4$, 325.32; m/z found 326.1 $[M+H]^+$.

Example 137: Synthesis of Compound 57

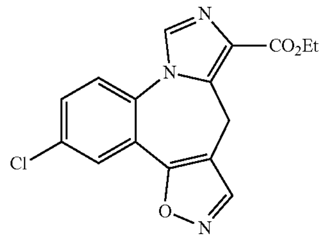 [SMILES: CCOC(=O)c1ncn2c1Cc1cnoc1-c1cc(Cl)ccc1-2]

Example 137 was prepared analogously as Example 136, except using 7-chloro-2,3,4,5-tetrahydro-1H-1-benzazepine-2,5-dione as the starting ketone, and using a different phosphate ester hydrolysis condition detailed here: the phosphate ester of the imidazole (1.0 g, 2.27 mmol) was dissolved in 1,4-Dioxane (8.0 mL). Anhydrous CsF (0.52 g, 3.4 mmol) was added and rxn mixture was heated at 100° C. for 4 h. The LCMS data shows product formation m/z 305.1. The rxn mixture was concentrated under reduced pressure. The residue was purified by ISCO combiflash system, Mobile phase: Ethyl Acetate:Hexane gradient to obtain 0.25 g of product (Yield 36.2%). Remaining steps were performed in the same way as Example 136, compound 40 to give Example 137, compound 57. MS: [M+1]=330.

Example 138: Synthesis of Compound 41

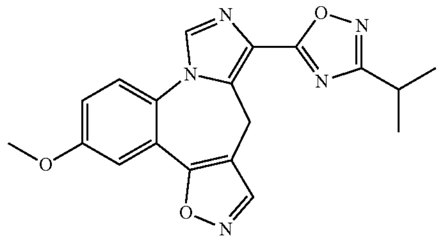 [SMILES: COc1ccc2c(c1)-c1oncc1Cc1c(-c3nc(C(C)C)no3)ncn1-2]

Isobutyramide oxime (0.033 g, 0.32 mmol) was flushed with anhydrous toluene (5.0 mL×3) before use and dissolved in anhydrous THE (2.5 mL). The rxn mixture was cooled in Ice bath and NaH (0.006 g, 0.16 mmol, 60.0% in mineral oil) was added. The rxn mixture was stirred and gradually warmed to ambient temperature for 1 h. Example 136 (0.01 g, 0.03 mmol) was added and rxn mixture was stirred at ambient temperature for 30.0 min and heated at reflux for 2 h. The LCMS data shows product formation m/z 364.2. The rxn mixture was cooled at ambient temperature. The rxn mixture was diluted with water and extracted with Ethyl Acetate. The organic layer was dried over anhydrous sodium sulfate and concentrated under reduced pressure. The residue was purified by prep-TLC plate, Mobile Phase: Ethyl Acetate:Hexane, (80:20 v/v mL) to obtain a 2.3 mg of Example 138 compound 41 (Yield 19.6%). MS (ESI) mass calcd. for $C_{19}H_{17}N_5O_3$, 363.37; m/z found 364.2 $[M+H]^+$.

Example 139: Synthesis of Compound 42

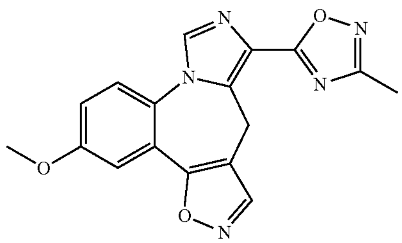

Example 139 was prepared analogously as Example 138, using acetamide oxime in the oxadiazole formation step. MS: [M+1]=336.

Example 140: Synthesis of Compound 67

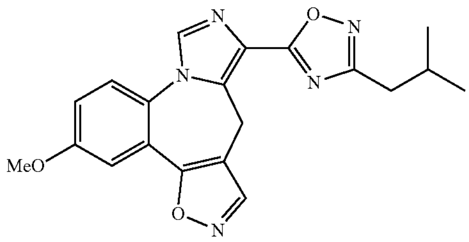 [SMILES: COc1ccc2c(c1)-c1oncc1Cc1c(-c3nc(CC(C)C)no3)ncn1-2]

Example 140 was prepared analogously as Example 138, using N'-Hydroxy-3-methylbutanimidamide in the oxadiazole formation step. MS: [M+1]=378.

Example 141: Synthesis of Compound 59

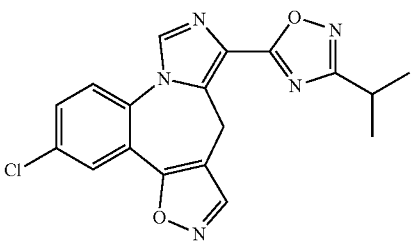 [SMILES: CC(C)c1noc(-c2ncn3c2Cc2cnoc2-c2cc(Cl)ccc2-3)n1]

Example 141 was prepared analogously as Example 138, starting with 7-chloro-2,3,4,5-tetrahydro-1H-1-benzazepine-2,5-dione as the starting ketone. MS: [M+1]=368.

Example 142: Synthesis of Compound 69

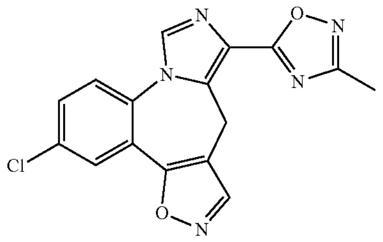 [SMILES: Cc1noc(-c2ncn3c2Cc2cnoc2-c2cc(Cl)ccc2-3)n1]

Example 142 was prepared analogously as Example 141, using acetamide oxime in the oxadiazole formation step. MS: [M+1]=340.

Example 143: Synthesis of Compound 66

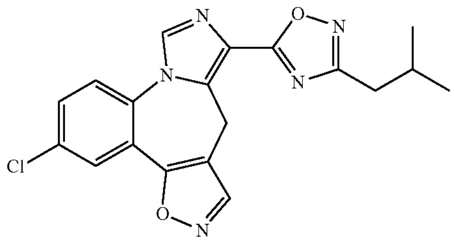 [SMILES: CC(C)Cc1noc(-c2ncn3c2Cc2cnoc2-c2cc(Cl)ccc2-3)n1]

Example 143 was prepared analogously as Example 141, using N'-Hydroxy-3-methylbutanimidamide in the oxadiazole formation step. MS: [M+1]=467.

Example 144: Synthesis of Compound 51

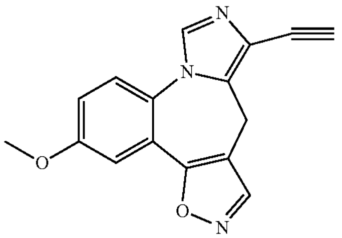 [SMILES: C#Cc1ncn2c1Cc1cnoc1-c1cc(OC)ccc1-2]

Example 136 (0.1 g, 0.32 mmol) was dissolved in anhydrous THF (10.0 mL). The 1.0 M DIBAL in Hexane (1.6 mL, 1.6 mmol) was added dropwise to the rxn mixture at 0° C. The rxn mixture was stirred and gradually warmed to ambient temperature for 3 h. The LCMS data shows product alcohol formation m/z 284.1. The rxn mixture was quenched with methanol (0.5 mL). The rxn mixture was diluted With aq. saturated $NaHCO_3$ solution and filtered over Celite. The residue was washed with Ethyl Acetate (10.0 mL×3). The filtrate was collected and separated the layer. The organic layer was dried over anhydrous sodium sulfate and concentrated under reduced pressure to obtain 67.0 mg of alcohol product (Yield 73.6%). MS (ESI) mass calcd. for $C_{15}H_{13}N_3O_3$, 283.28; m/z found 284.1 $[M+H]^+$.

The alcohol (0.067 g, 0.24 mmol) was dissolved in anhydrous DCM (10.0 mL). The rxn mixture was cooled in ice bath. Dess-Martin periodinane (0.15 g, 0.35 mmol) was added at 0° C. and then stirred and gradually warmed to ambient temperature for 3 h. The LCMS data shows product aldehyde formation m/z 282.1. The rxn mixture was diluted With aq. saturated $NaHCO_3$ solution and extracted with DCM. The organic layer was dried over anhydrous sodium sulfate and concentrated under reduced pressure. The residue was purified by ISCO combiflash system, Mobile phase: Ethyl Acetate:Hexane gradient to obtain 67.0 mg of aldehyde product (Yield Quant.). MS (ESI) mass calcd. for $C_{15}H_{11}N_3O_3$, 281.27; m/z found 282.1 $[M+H]^+$.

The aldehyde (0.067 g, 0.24 mmol) was dissolved in anhydrous methanol (4.0 mL) and to it was added anhydrous $K_2CO_3$ (0.065 g, 0.47 mmol) followed by Bestmann-Ohira reagent (0.053 mL, 0.35 mmol) twice at 12 h interval. The rxn mixture was stirred at ambient temperature for 24 h. The rxn mixture was diluted With aq. saturated NaCl solution. The product was extracted with DCM. The organic layer was dried over anhydrous sodium sulfate and concentrated under reduced pressure. The residue was purified by ISCO combiflash system, Mobile Phase: Ethyl Acetate:Hexane gradient to obtain 11.5 mg of Example 144, compound 51 (Yield 17.5%). MS (ESI) mass calcd. for $C_{16}H_{11}N_3O_2$, 277.28; m/z found 278.1 $[M+H]^+$.

Example 145: Synthesis of Compound 48

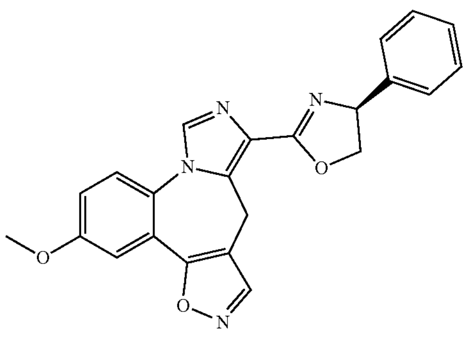 [SMILES: COc1ccc2c(c1)-c1oncc1Cc1c(C3=N[C@@H](c4ccccc4)CO3)ncn1-2]

The methyl ester analog of Example 136, compound 40 (0.12 g, 0.37 mmol; prepared the same way as Example 136, from the corresponding keto imidazole methyl ester) was dissolved in methanol (5.0 mL). Aqueous 1.0 N NaOH solution (1.8 mL, 1.8 mmol) was added and reaction mixture was heated at reflux for 5 h. The LCMS data shows saponification product formation m z 298.0. The rxn mixture was concentrated under reduced pressure and acidified with 1 M aq. HCl solution. The ppts were filtered and dried to obtain 61.3 mg of the acid product (Yield 56.0%). MS (ESI) mass calcd. for $C_{15}H_{11}N_3O_4$, 297.27; m/z found 298.0 $[M+H]^+$.

The carboxylic acid from above (0.03 g, 0.1 mmol) was dissolved in anhydrous DCM (2.5 mL). EDC·HCl (0.04 g, 0.2 mmol) and HOBt·$H_2O$ (0.03 g, 0.2 mmol) were added followed by diisopropylethylamine (0.09 mL, 0.5 mmol and the resultant mixture was stirred at ambient temperature for 15.0 min. (S)-(+)-2-Phenylglycinol (0.03 g, 0.2 mmol) was added and rxn mixture was stirred at ambient temperature for 16 h. The LCMS data shows product amide formation m z 417.2. The rxn mixture was diluted with water and extracted with DCM. The organic layer was dried over anhydrous sodium sulfate and concentrated under reduced pressure. The residue was purified by ISCO combiflash system, Mobile Phase: DCM/Methanol (90:10 v/v mL): DCM gradient to obtain 30.0 mg of the amide product (Yield 72.0%). MS (ESI) mass calcd. for $C_{23}H_{20}N_4O_4$, 416.43; m/z found 417.2 $[M+H]^+$.

The amide from above (0.03 g, 0.07 mmol) was dissolved in anhydrous DCM (2.5 mL). The rxn mixture was cooled in dry Ice bath at −78° C. and DAST (0.019 mL, 0.14 mmol) was added. The rxn mixture was stirred and gradually warmed at 0° C. temperature for 3 h. The LCMS data shows product formation m/z 399.2. The rxn mixture was diluted With aq. saturated $NaHCO_3$ solution and extracted with DCM. The organic layer was dried over anhydrous sodium sulfate and concentrated under reduced pressure. The residue was purified by prep-TLC plate, Mobile Phase: DCM: MeOH (94:06 v/v mL) to obtain 4.4 mg of Example 145, compound 48 (Yield 15.3%). MS (ESI) mass calcd. for $C_{23}H_{18}N_4O_2$, 398.4; m/z found 399.2 $[M+H]^+$.

Example 146: Synthesis of Compound 49

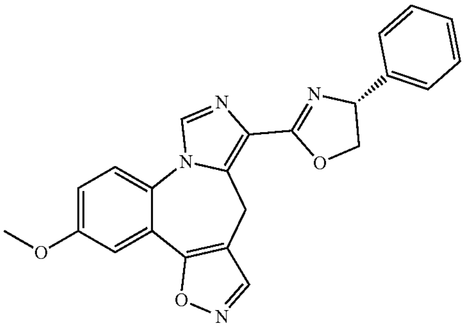 [SMILES: COc1ccc2c(c1)-c1oncc1Cc1c(C3=N[C@H](c4ccccc4)CO3)ncn1-2]

Example 146 was prepared analogously as Example 145, using (R)-(+)-2-phenylglycinol to prepare the oxazoline ring. MS: [M+1]=399.

Example 147: Synthesis of Compound 50

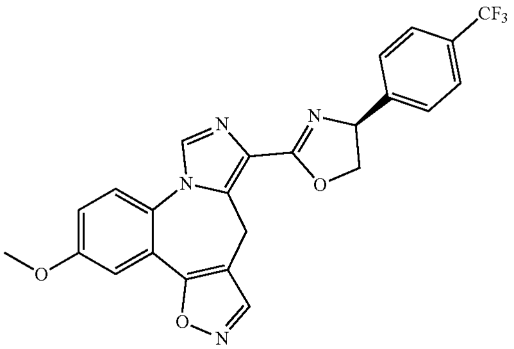 [SMILES: COc1ccc2c(c1)-c1oncc1Cc1c(C3=N[C@@H](c4ccc(C(F)(F)F)cc4)CO3)ncn1-2]

Example 147 was prepared analogously as Example 145, using (S)-(+)-2-amino-2-[p-(trifluoromethyl) phenyl]ethanol hydrochloride to prepare the oxazoline ring. MS: [M+1]=467.

Example 148: Synthesis of Compound 68

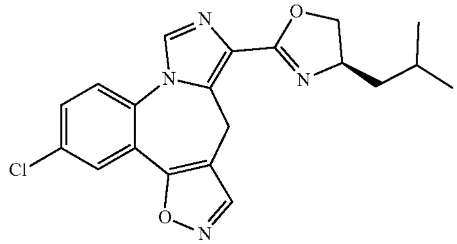 [SMILES: CC(C)C[C@@H]1COC(c2ncn3c2Cc2cnoc2-c2cc(Cl)ccc2-3)=N1]

Example 148 was prepared analogously as Example 145, starting with Example 137, and using (R)-(−)-Leucinol to prepare the oxazoline ring. MS: [M+1]=383.

Scheme 13

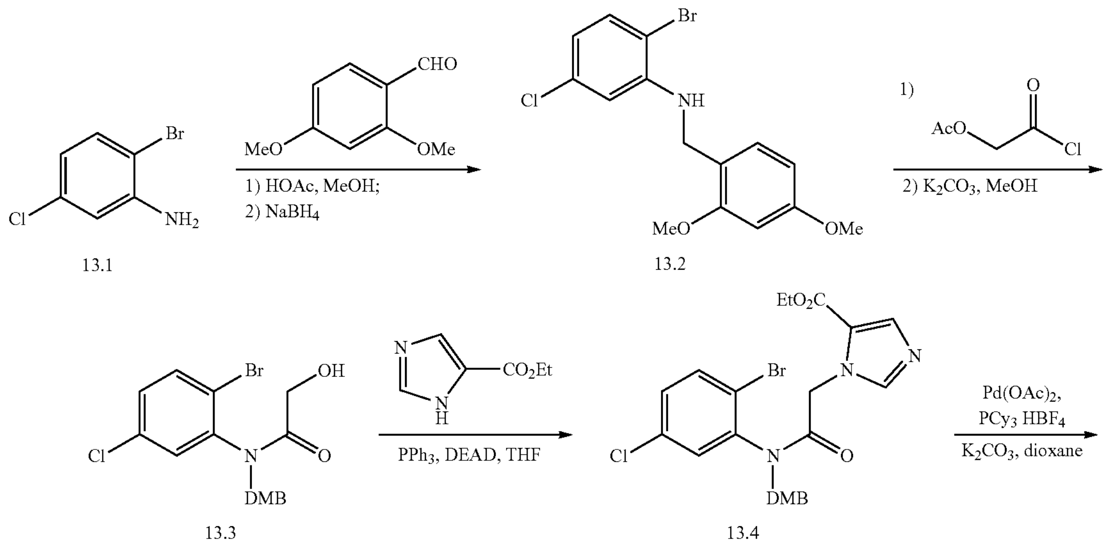

13.1

13.2

13.3

DMB = 2,4-dimethoxybenzyl 13.4

-continued

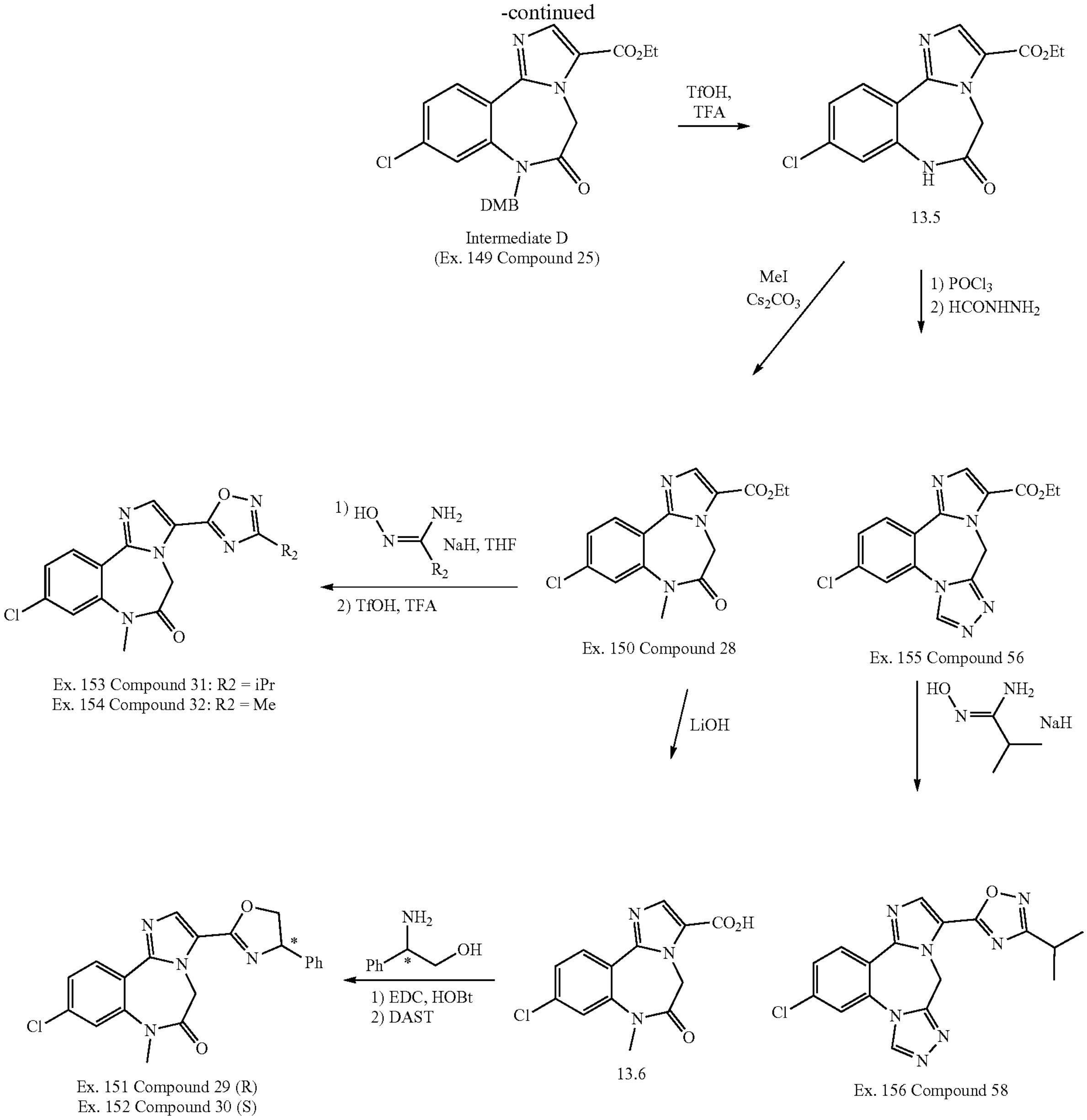

To a solution (Scheme 13) of 2-bromo-5-chloroaniline (13.1) (15.0 g, 72.8 mmol) and 2,4-dimethoxybenzaldehyde (13.3 g, 80.1 mmol) in methanol (150 mL) was added acetic acid (2 mL). After stirred at room temperature for 2 h, the mixture was cooled to 0° C. and followed by the dropwise addition of sodium borohydride (8.2 g, 218.4 mmol). The mixture was stirred at room temperature for 16 h, and concentrated under reduced pressure and the residue was diluted with water and extracted with Ethyl Acetate. The organic layer was dried over anhydrous sodium sulfate and concentrated under reduced pressure. The residue was purified by silica gel chromatography (2-9% Ethyl Acetate in petroleum ether) to obtain crude 13.2 as a white solid 18.0 g (Yield 69.0%).

To a solution of the previously obtained reductive amination product 13.2 (20.0 g, 56.2 mmol) in THF (200 mL) was added triethylamine (6.8 g, 67.4 mmol) and acetoxyacetyl chloride (9.2 g, 67.4 mmol) at 0° C. The mixture was stirred from 0° C. to room temperature for 16 h. The progress of the reaction mixture was monitored by TLC. After completion of the reaction, the mixture was diluted with water and extracted with Ethyl Acetate. The organic layer was washed with brine, dried over anhydrous sodium sulfate and concentrated under reduced pressure. The residue was purified by silica gel chromatography (0-25% Ethyl Acetate in petroleum ether) to obtain amide product as a colorless oil 22.4 g (Yield 87.0%).

To the amide obtained above (22.4 g, 49.1 mmol) in methanol (230 mL) and water (49 mL) was added potassium carbonate (10.2 g, 73.7 mmol). The mixture was stirred at room temperature for 4 h. The progress of the reaction mixture was monitored by TLC. After completion of the reaction, the mixture was concentrated to remove methanol and extracted with water and dichloromethane. The organic layer was dried over anhydrous sodium sulfate and concentrated under reduced pressure to obtain crude hydrolyzed alcohol 13.3 15.6 g (Yield, 76.0%).

A mixture of ethyl 1H-imixazole-4-carboxylate (5.8 g, 41.4 mmol) and triphenylphosphine (29.6 g, 113.0 mmol) in tetrahydrofuran (300 mL) was cooled to −40° C. under nitrogen atmosphere. Then the alcohol from above (15.6 g, 37.7 mmol) was added dropwise, followed by addition of diethyl azodicarboxylate (26.0 g, 113.0 mmol) at −40° C. The mixture was stirred from −40° C. to room temperature for 16 h. The mixture was concentrated under reduced pressure and the residue was purified by silica gel chromatography (9-50% Ethyl Acetate in petroleum ether) to obtain the imidazole adduct 13.4 13.0 g (Yield, 64.0%).

To 13.4 from above (6.7 g, 12.5 mmol), potassium carbonate (3.5 g, 25.0 mmol) and tricyclohexylphosphine tetrafluoroborate (0.56 g, 2.5 mmol) in 1,4-dioxane (70 mL) was added palladium acetate (1.3 g, 2.5 mmol) under nitrogen atmosphere. The mixture was stirred at 120° C. for 16 h. The progress of the reaction mixture was monitored by TLC. After completion of the reaction, the mixture was diluted with water and extracted with Ethyl Acetate. The organic layer was dried over anhydrous sodium sulfate and concentrated under reduced pressure. The residue was purified with silica gel chromatography (4-33% Ethyl Acetate in petroleum ether) to obtain Intermediate D (Example 149, Compound 25) as a brown solid 2.97 g, (Yield 51.0%). MS (ESI) Mass calcd. for $C_{23}H_{22}ClN_3O_5$, 455.89; m/z found 456.20 [M+H]+, $^1H$ NMR (400 MHz, $CDCl_3$): δ 7.89 (s, 1H), 7.83 (d, J=8.4 Hz, 1H), 7.43 (d, J=1.9 Hz, 1H), 7.28 (s, 1H), 6.89 (d, J=8.3 Hz, 1H), 6.31 (dd, J=8.3, 2.3 Hz, 1H), 6.27 (d, J=2.3 Hz, 1H), 6.17 (s, 1H), 5.27 (s, 1H), 4.79 (s, 1H), 4.40 (q, J=7.1 Hz, 2H), 4.35-4.11 (m, 1H), 3.74 (s, 3H), 3.53 (s, 3H), 1.42 (t, J=7.1 Hz, 3H).

Intermediate D (Example 149, Compound 25) (0.25 g, 0.55 mmol) was dissolved in anhydrous DCM (8.0 mL). The rxn mixture was cooled in Ice bath and TFA (0.5 mL, 6.5 mmol) was added followed by Triflic acid (0.12 mL, 0.82 mmol). The rxn mixture was stirred and gradually warmed to ambient temperature for 2 h. The LCMS data shows product formation m z 306.0. The rxn mixture was concentrated under reduced pressure and neutralized with aq. saturated $NaHCO_3$ solution. The ppts were filtered and washed with water (10.0 mLx3) to obtain 0.17 g of debenzylated product 13.5 as a yellowish solid (Yield Quant.). MS (ESI) Mass calcd. for $C_{14}H_{12}ClN_3O_3$, 305.72; m/z found 306.0 [M+H]+.

Example 150: Synthesis of Compound 28

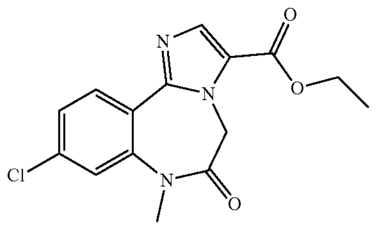 [SMILES: CCOC(=O)c1cnc2n1CC(=O)N(C)c1cc(Cl)ccc1-2]

The debenzylated product 13.5 from above (0.02 g, 0.065 mmol) was dissolved in anhydrous DMF (1.0 mL). $Cs_2CO_3$ (0.04 g, 0.13 mmol) was added followed by methyl iodide (0.05 g, 0.33 mmol). The rxn mixture was stirred at ambient temperature for 16 h. The LCMS data shows methylated product formation m/z 320.0. The rxn mixture was diluted with water and the ppts were filtered. The ppts were dried to obtain 20.0 mg of crude solid product. The crude solid was purified by prep-TLC plate, Mobile Phase: Ethyl Acetate: Hexane (35:65 v/v mL) to obtain 10.0 mg of Example 150, compound 28 (Yield 47.7%). MS (ESI) Mass calcd. for $C_{15}H_{14}ClN_3O_3$, 319.74; m/z found 320.0 $[M+H]^+$.

Example 151: Synthesis of Compound 29

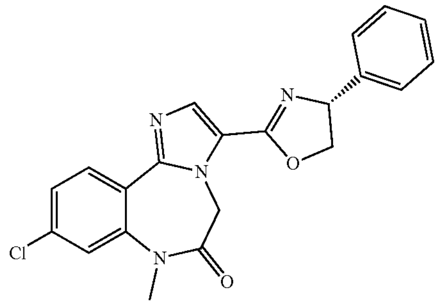 [SMILES: CN1C(=O)Cn2c(C3=N[C@H](c4ccccc4)CO3)cnc2-c2ccc(Cl)cc21]

Example 150, compound 28 (0.1 g, 0.32 mmol) was dissolved in mixture of $THF/H_2O/MeOH$ (2:3:5 v/v mL). Lithium hydroxide (0.02 g, 0.63 mmol) was added and the rxn mixture was stirred at ambient temperature for 4 h. The LCMS data shows hydrolysis product formation m/z 292.0. The rxn mixture was concentrated under reduced pressure and acidified with 1 M aq. HCl solution. The ppts were filtered and dried to obtain 0.1 g of the crude acid 13.6 (Yield Quant.). MS (ESI) Mass calcd. for $C_{13}H_{10}ClN_3O_3$, 291.69; m/z found 292.0 $[M+H]^+$.

The acid 13.6 (0.04 g, 0.14 mmol) was dissolved in anhydrous DCM (3.0 mL). EDC·HCl (0.05 g, 0.27 mmol) and HOBt·$H_2O$ (0.04 g, 0.27 mmol) were added followed by triethylamine (0.1 mL, 0.69 mmol) and the rxn mixture was stirred at ambient temperature for 10.0 min. R-2-Phenylglycinol (0.04 g, 0.27 mmol) was added and rxn mixture was stirred at ambient temperature for 16 h. The LCMS data shows product amide formation m/z 411.0. The rxn mixture was diluted with water and extracted with DCM. The organic layer was dried over anhydrous sodium sulfate and concentrated under reduced pressure. The residue was purified by prep-TLC plate, Mobile Phase: Ethyl Acetate to obtain 16.0 mg of the amide (Yield 28.3%). MS (ESI) Mass calcd. for $C_{21}H_{19}ClN_4O_3$, 410.85; m/z found 411.0 $[M+H]^+$.

The amide (0.017 g, 0.04 mmol) was dissolved in anhydrous DCM (3.0 mL). The rxn mixture was cooled in ice bath and DAST (0.011 mL, 0.08 mmol) was added. The rxn mixture was stirred at ambient temperature for 1 h. The LCMS data shows product formation m/z 393.1. The rxn mixture was diluted with aq. saturated $NaHCO_3$ solution and extracted with DCM. The organic layer was dried over anhydrous sodium sulfate and concentrated under reduced pressure. The residue was purified by prep-TLC plate, Mobile Phase: Ethyl Acetate:Hexane (50:50 v/v mL) to obtain 11.9 mg of Example 151, compound 29 (Yield 73.1%). MS (ESI) Mass calcd. for $C_{12}H_{17}ClN_4O_2$, 392.84; m/z found 393.1 $[M+H]^+$.

Example 152: Synthesis of Compound 30

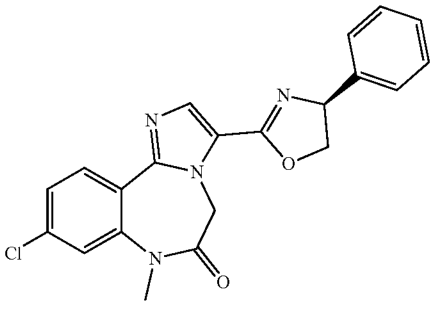 [SMILES: CN1C(=O)Cn2c(C3=N[C@@H](c4ccccc4)CO3)cnc2-c2ccc(Cl)cc21]

Example 152 was prepared analogously as Example 151, using S-2-phenylglycinol to prepare the oxazoline ring. MS: [M+1]=393.

Example 153: Synthesis of Compound 31

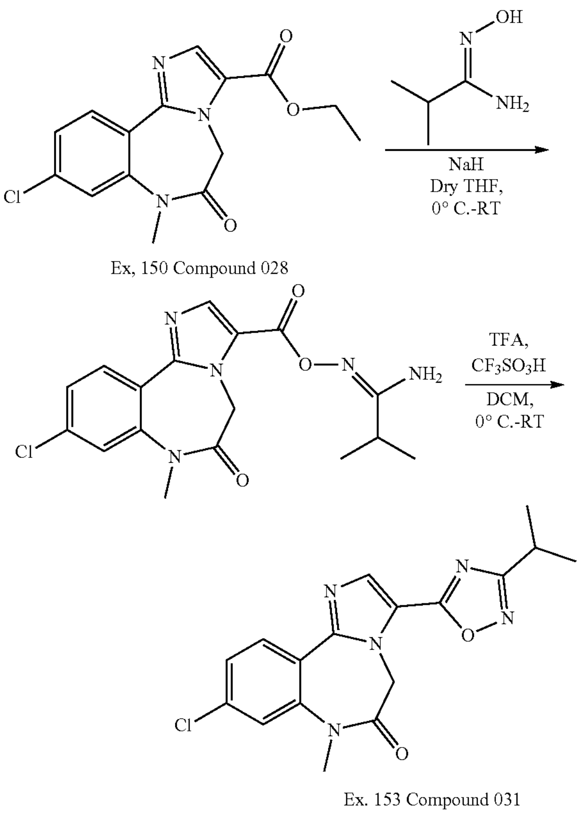

Ex, 150 Compound 028

Ex. 153 Compound 031

Isobutyramide oxime (0.03 g, 0.39 mmol) was flushed with anhydrous toluene (5.0 mL×3) before use and dissolved in anhydrous THF (2.0 mL). The rxn mixture was cooled in Ice bath and NaH (0.03 g, 0.78 mmol, 60.0% in mineral oil) was added. The rxn mixture was stirred and gradually warmed to ambient temperature for 1 h. Example 150, compound 28 (0.025 g, 0.08 mmol) in dry THF (1.0 mL) was added and rxn mixture was stirred at ambient temperature for 2 h. The rxn mixture was diluted with water and extracted with Ethyl Acetate. The organic layer was dried over anhydrous sodium sulfate and concentrated under reduced pressure. The residue was purified by prep-TLC plate, Mobile Phase: DCM:MeOH, (96:04 v/v mL) to obtain a 21.0 mg of the uncyclized intermediate product (Yield 75.1%). This intermediate (0.02 g, 0.05 mmol) was dissolved in anhydrous DCM (3.0 mL). The rxn mixture was cooled in Ice bath and TFA (0.2 mL) was added followed by Triflic acid (0.01 mL, 0.11 mmol). The rxn mixture was stirred and gradually warmed to ambient temperature for 2 h. The LCMS data shows product formation m z 358.0. The rxn mixture was diluted with water and neutralized with aq. saturated $NaHCO_3$ solution. The product was extracted with DCM. The organic layer was dried over anhydrous sodium sulfate and concentrated under reduced pressure. The residue was purified by prep-TLC plate, Mobile Phase: Ethyl Acetate:Hexane (40:60 v/v mL) to obtain 6.0 mg of Example 153, compound 31 (Yield 31.5%). MS (ESI) Mass calcd. for $C_{17}H_{16}ClN_5O_2$, 357.79; m/z found 358.0 $[M+H]^+$.

Example 154: Synthesis of Compound 32

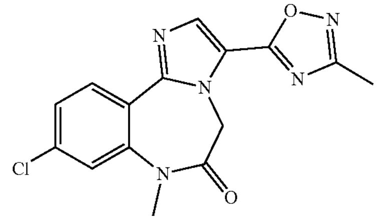 [SMILES: Cc1noc(-c2cnc3n2CC(=O)N(C)c2cc(Cl)ccc2-3)n1]

Example 154 was prepared analogously as Example 153, using acetamide oxime to form the oxadiazole ring. MS: [M+1]=330.

Example 155: Synthesis of Compound 56

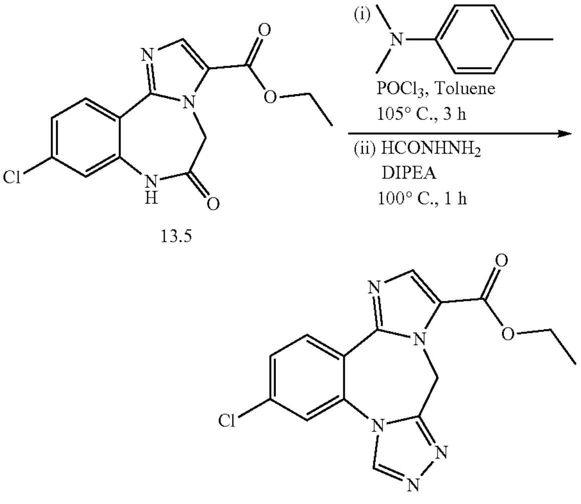

13.5

Ex. 155
Compound 056

The debenzylated ester 13.5 (0.05 g, 0.16 mmol) was suspended in anhydrous toluene (2.5 mL). N,N'-Diimethyl aniline (0.14 mL, 0.98 mmol) was added followed by $POCl_3$ (0.046 mL, 0.49 mmol). The rxn mixture was heated at 100°

C. for 3 h. The LCMS data shows intermediate-chloro imine formation m/z 324.0. The rxn mixture was cooled at ambient temperature. The formic acid hydrazide (0.025 g, 0.41 mmol) was added followed by N,N-diisopropylethylamine (0.17 mL, 0.98 mmol). The rxn mixture was heated at 100° C. for 1 h. The LCMS data shows product formation m/z 330.1. The rxn mixture was concentrated under reduced pressure. The crude product was diluted with water and extracted with Ethyl Acetate. The organic layer was dried over anhydrous sodium sulfate and concentrated under reduced pressure. The residue was purified by ISCO Combi-flash silica gel column, Mobile Phase: Ethyl Acetate:Hexane gradient to obtain 26.0 mg of Example 155, Compound 56 (Yield 48.2%). MS (ESI) Mass calcd. for $C_{15}H_{12}ClN_5O_2$, 329.74; m/z found 330.1 $[M+H]^+$.

Example 156: Synthesis of Compound 58

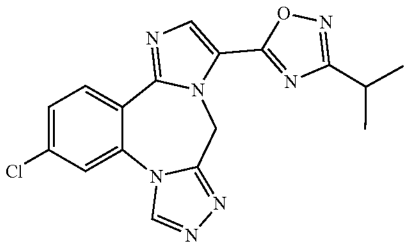 [SMILES: CC(C)c1noc(-c2cnc3n2Cc2nncn2-c2cc(Cl)ccc2-3)n1]

Isobutyramide oxime (0.06 g, 0.61 mmol) was flushed with anhydrous toluene (5.0 mL×3) before use and dissolved in anhydrous THE (2.0 mL). The rxn mixture was cooled in ice bath and NaH (0.01 g, 0.3 mmol, 60.0% in mineral oil) was added. The rxn mixture was stirred and gradually warmed to ambient temperature for 1 h. Example 155, compound 56 (0.02 g, 0.061 mmol) in dry THF (1.0 mL) was added and rxn mixture was stirred at ambient temperature for 1 h. The rxn mixture was heated at reflux for 1 h. The LCMS data shows product formation m z 368.1. The rxn mixture was diluted with water and extracted with Ethyl Acetate. The organic layer was dried over anhydrous sodium sulfate and concentrated under reduced pressure. The residue was purified by ISCO Combi-flash silica gel column, Mobile Phase: Ethyl Acetate:Hexane gradient to obtain 12.1 mg of Example 156, compound 58 (Yield 53.8%). MS (ESI) Mass calcd. for $C_{17}H_{14}ClN_7O$, 367.79; m/z found 368.1 $[M+H]^+$.

Example 157: Synthesis of Compound 26

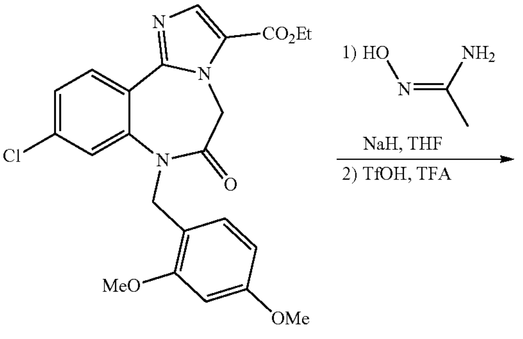

Intermediate D
Ex. 149 Compound 25

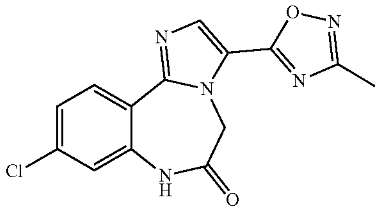

Ex. 157 Compound 26

Acetamide oxime (0.08 g, 1.1 mmol) was flushed with anhydrous Toluene (5.0 mL×3) before use and dissolved in anhydrous THE (2.5 mL). The rxn mixture was cooled in Ice bath and NaH (0.04 g, 1.1 mmol, 60.0% in mineral oil) was added. The rxn mixture was stirred and gradually warmed to ambient temperature for 1 h. The Intermediate D (Example 149, Compound 25) (0.05 g, 0.11 mmol) was added and rxn mixture was stirred at ambient temperature for 30.0 min and heated at reflux for 3 h. The LCMS data shows product formation m/z 484.0. The rxn mixture was cooled at ambient temperature. The rxn mixture was diluted with water and extracted with Ethyl Acetate. The organic layer was dried over anhydrous sodium sulfate and concentrated under reduced pressure. The residue was purified by prep-TLC plate, Mobile Phase: Ethyl Acetate:MeOH, (95:05 v/v mL) to obtain a 36.0 mg of product (Yield 70.4%). MS (ESI) Mass calcd. for $C_{23}H_{20}ClN_5O_4$, 465.89; m/z found 484.0 $[M+H_2O]^+$.

The product previously obtained (0.03 g, 0.06 mmol) was dissolved in anhydrous DCM (3.0 mL). The rxn mixture was cooled in Ice bath and TFA (0.1 mL) was added followed by Triflic acid (0.009 mL, 0.1 mmol). The rxn mixture was stirred and gradually warmed to ambient temperature for 1 h. The LCMS data shows product formation m/z 316.0. The rxn mixture was diluted with water and neutralized with aq. saturated $NaHCO_3$ solution. The product was extracted with DCM. The organic layer was dried over anhydrous sodium sulfate and concentrated under reduced pressure. The residue was purified by prep-TLC plate, Mobile Phase: Ethyl Acetate:Hexane (50:50 v/v mL) to obtain 3.9 mg of Example 157, Compound 26 (Yield 19.1%). MS (ESI) Mass calcd. for $C_{14}H_{10}ClN_5O_2$, 315.71; m/z found 316.0 $[M+H]^+$.

Example 158: Synthesis of Compound 27
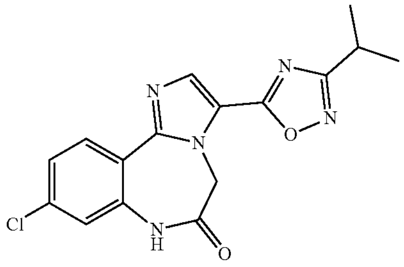 [SMILES: CC(C)c1noc(-c2cnc3n2CC(=O)Nc2cc(Cl)ccc2-3)n1]
Example 158 was analogously prepared as Example 157, using isobutyramide oxime to form the oxadiazole ring. MS: [M+1]=344.
Scheme 14
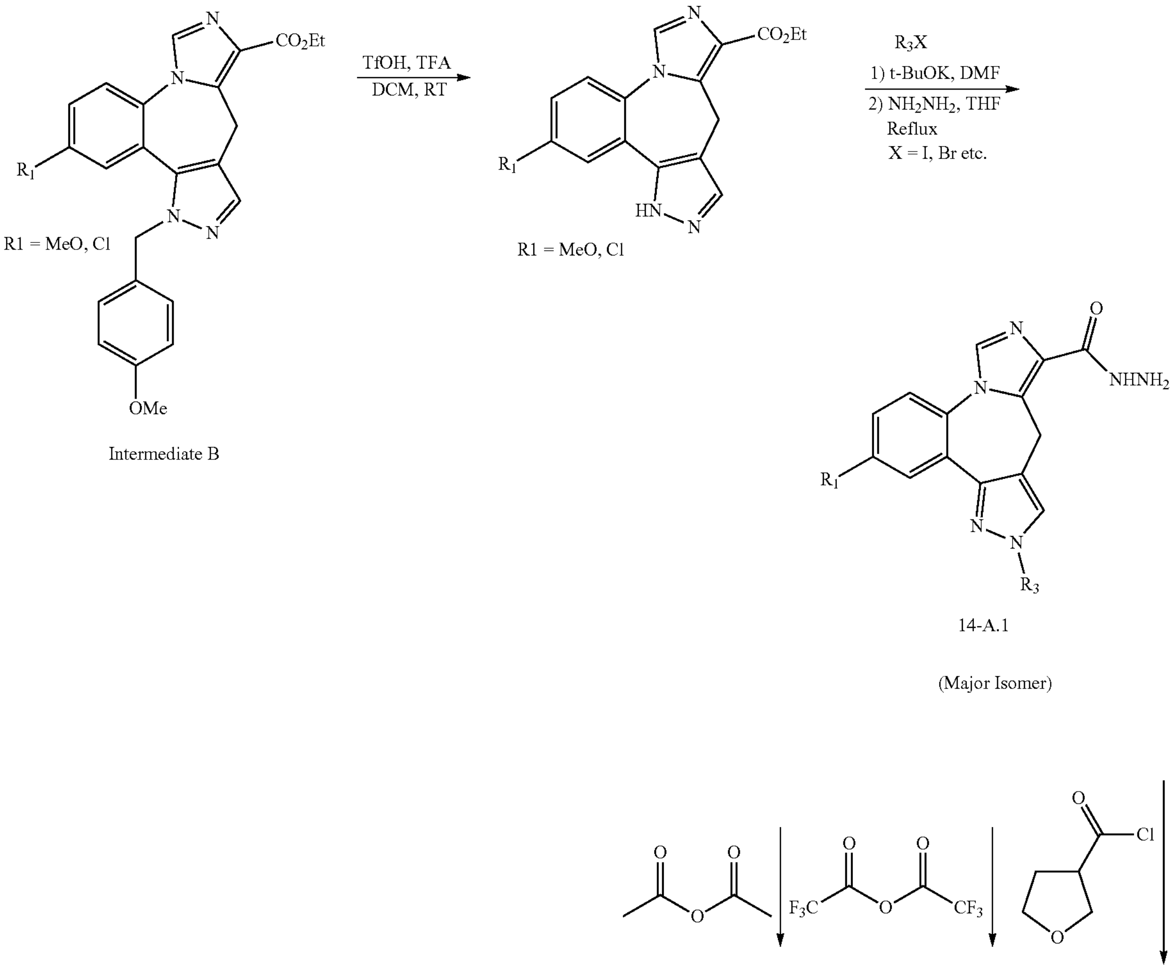
R1 = MeO, Cl
Intermediate B
R1 = MeO, Cl
14-A.1
(Major Isomer)

| $R_1$ $R_2$ | $R_3$ |
|---|---|
| Ex. 159 Compound 209: Cl, Me, | Me |
| Ex. 159a Compound 290: MeO, Me, | Me |
| Ex. 159-1 Compound 210: Cl, $CF_3$, | Me |
| Ex.159b Compound 289: MeO, $CF_3$, | Me |
| Ex. 159c Compound 302: MeO, $CF_3$, | 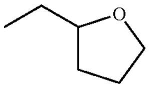 |
| Ex. 159d Compound 334: MeO, $CF_3CH_2OCH_2$, Me | |
| Ex. 159e Compound 303: MeO, $CF_3CH_2OCH_2$, | 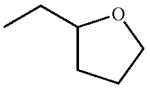 |
| Ex. 159-2 Compound 212: Cl, 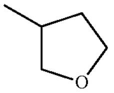 | Me |
| Ex. 159f Compound 219: MeO, 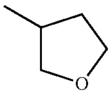 | Me |
| Ex. 159g Compound 325: MeO, 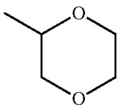 | Me |
| Ex. 159h Compound 326: MeO, $MeOCH_2$, | Me |

-continued

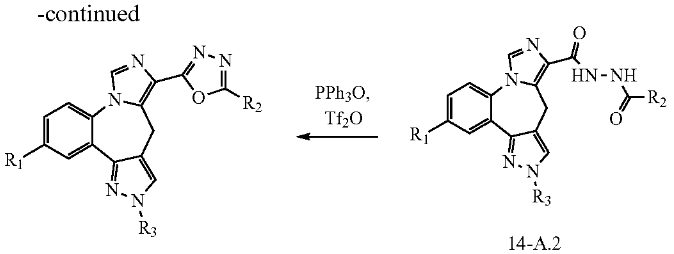

14-A.2

Example 159: Synthesis of Compound 209

Compound 209

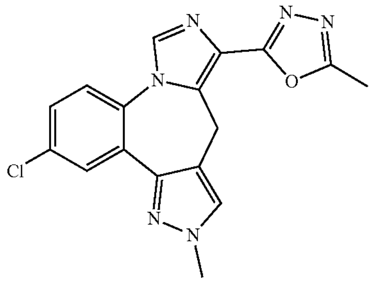

Intermediate B ($R_1$=Cl; 0.6 g, 1.48 mmol) was treated with trifluoromethane sulfonic acid (0.4 g, 3.0 mmol) in a mixture of trifluoroacetic acid (2.0 ml) and DCM (8.0 ml) at rt for 16 h. The reaction mixture was concentrated, treated with sat. $NaHCO_3$ solution to obtain ppts. The ppts were filtered and washed with water. The drying of ppts gave a 0.48 g of deprotection product as a yellowish solid, MS: [M+1]=329.1.

The above obtained pyrazole analog (0.48 g, 1.48 mmol) was dissolved in anhydrous DMF (8.0 mL). The anhydrous t-BuOK (0.28 g, 2.4 mmol) was added at 0° C. temperature, followed by Methyl iodide (0.34 g, 2.2 mmol). The rxn mixture was stirred at ambient temperature for 6 h. The reaction mixture was diluted with water and extracted with ethyl acetate (15.0 mL×3). The combined organic extract was washed with brine and dried over $MgSO_4$. Filtration and solvent removal followed by silica gel column chromatography using 0 to 5% MeOH in DCM gave 0.26 g of the methylated product as a yellowish solid. MS: [M+1]=343.1.

The methylated ester from above (0.25 g, 0.74 mmol) was dissolved in anhydrous THF (5.0 mL). The anhydrous hydrazine (0.1 g, 2.2 mmol) was added and rxn mixture was heated at 90° C. for 4 h. The reaction mixture was cooled at ambient temperature and concentrated under reduced pressure. The rxn mixture was diluted with ice cold water to obtain the ppts. The ppts were filtered and dried to obtain 0.2 g of solid product 14-A.1 MS: [M+1]=329.0.

Intermediate 14-A.1 (0.05 g, 0.14 mmol) was dissolved in anhydrous DCM (3.0 mL). The acetic anhydride (0.05 g, 0.44 mmol) was added followed by triethylamine (0.022 g, 0.22 mmol). The rxn mixture was heated at 40° C. for 30.0 min. The reaction mixture was concentrated and diluted with aq. $NaHCO_3$. The ppts were filtered, washed with ether, and dried to obtain 0.053 g of 14-A.2 as a solid product MS: [M+1]=371.0.

Triflic anhydride (0.05 g, 0.16 mmol) was added slowly to a solution of triphenylphophine oxide (0.09 g, 0.32 mmol) in DCM (2.5 mL) at 0° C. The rxn mixture was stirred at ambient temperature to form ppts. The Intermediate 14-A.2 (0.04 g, 0.11 mmol) was added and rxn mixture stirred at ambient temperature for 16 h. The reaction mixture was diluted with aq. $NaHCO_3$ and extracted with DCM (5.0 mL×3). The combined organic extract was washed with brine and dried over $MgSO_4$. Filtration and solvent removal followed by silica gel column chromatography using 0 to 5% MeOH in DCM gave 0.02 g of product Example 159, Compound 209 MS: [M+1]=353.0.

Example 159a: Synthesis of Compound 290

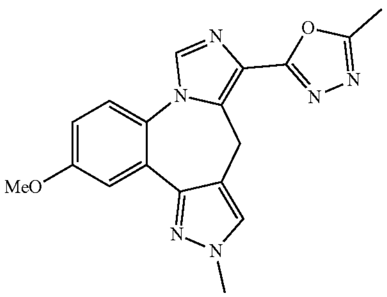 [SMILES: COc1ccc2c(c1)-c1nn(C)cc1Cc1c(-c3nnc(C)o3)ncn1-2]

Compound 290 was prepared analogously as Compound 209, starting with Intermediate B, $R_1$=MeO. MS: [M+1]=349.

Example 159-1: Synthesis of Compound 210

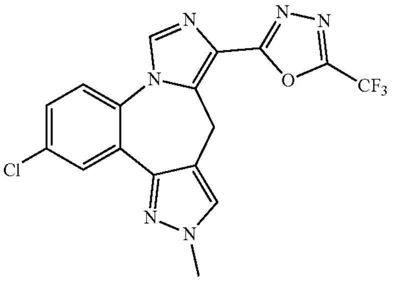

Compound 210

Compound 210 was prepared analogously as Compound 209, using trifluoroacetic anhydride in Step 3 followed by Step 4. MS: [M+1]=407.1.

Example 159b: Synthesis of Compound 289

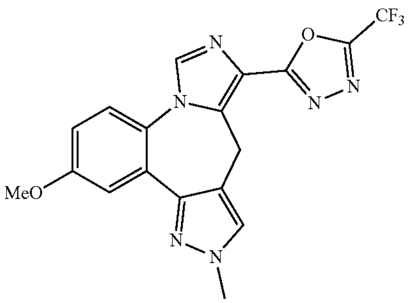 [SMILES: COc1ccc2c(c1)-c1nn(C)cc1Cc1c(-c3nnc(C(F)(F)F)o3)ncn1-2]

Compound 289 was prepared analogously as Compound 210, starting with Intermediate B, $R_1$=MeO. MS: [M+1]=403.

Example 159c: Synthesis of Compound 302

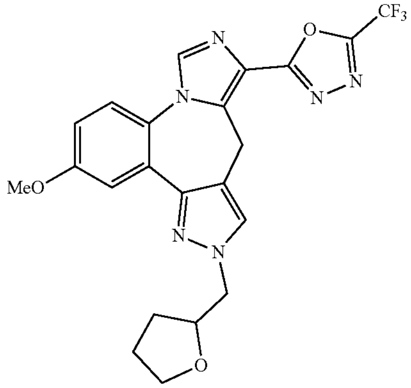 [SMILES: COc1ccc2c(c1)-c1nn(CC3CCCO3)cc1Cc1c(-c3nnc(C(F)(F)F)o3)ncn1-2]

Compound 302 was prepared analogously as Compound 289, using tetrahydrofurfuryl bromide in the N-alkylation step. MS: [M+1]=473.

Example 159d: Synthesis of Compound 334

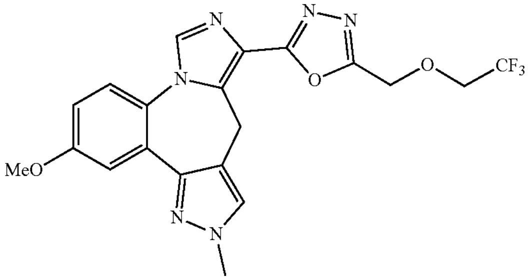 [SMILES: COc1ccc2c(c1)-c1nn(C)cc1Cc1c(-c3nnc(COCC(F)(F)F)o3)ncn1-2]

Compound 334 was prepared analogously as Compound 302, using methyl iodide for N-alkylation, and in-situ generated 2,2,2-trifluoroethoxy acetyl chloride (oxalyl chloride in cat DMF/DCM) for hydrazide acylation in step 4 (Scheme 14) before the final ring closure. MS: [M+1]=447.

Example 159e: Synthesis of Compound 303

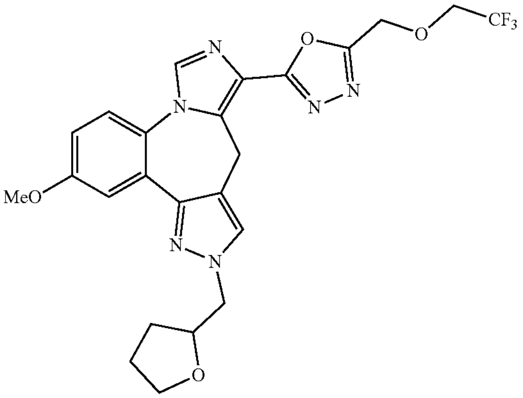 [SMILES: COc1ccc2c(c1)-c1nn(CC3CCCO3)cc1Cc1c(-c3nnc(COCC(F)(F)F)o3)ncn1-2]

Compound 303 was prepared analogously as Compound 302, using in-situ generated 2,2,2-trifluoroethoxy acetyl chloride (oxalyl chloride in cat DMF/DCM) for hydrazide acylation in step 4 (Scheme 14) before the final ring closure. MS: [M+1]=517.

Example 159-2: Synthesis of Compound 212

Compound 212

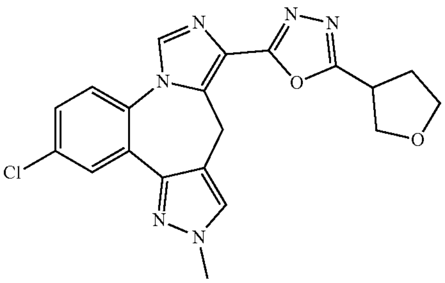

Compound 212 was prepared analogously as Compound 209, using Tetrahydrofuran-3-carbonyl chloride in Step 3 followed by Step 4. The step-4 was performed by $POCl_3$ (3.0 eq.) in acetonitrile (reflux for 1 h) to realize the 1,3,4-oxadiazole ring cyclization, instead of triflic anhydride/triphenylphosphine oxide reagent combo, MS: [M+1]=409.0.

Example 159f: Synthesis of Compound 291

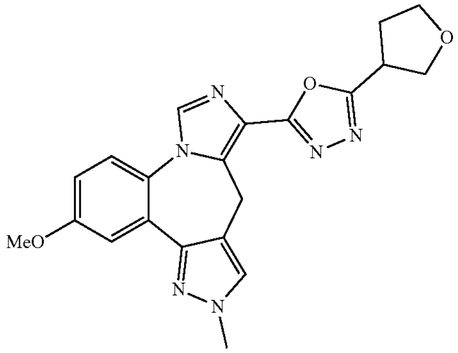 [SMILES: COc1ccc2c(c1)-c1nn(C)cc1Cc1c(-c3nnc(C4CCOC4)o3)ncn1-2]

Compound 291 was prepared analogously as Compound 212, starting with Intermediate B, $R_1$=MeO. MS: [M+1]=405.

Example 159g: Synthesis of Compound 325

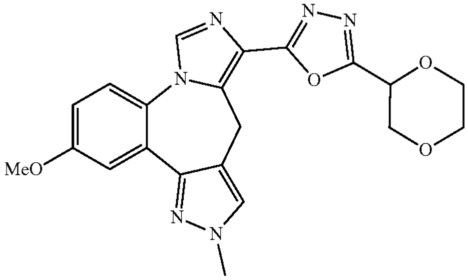 [SMILES: COc1ccc2c(c1)-c1nn(C)cc1Cc1c(-c3nnc(C4COCCO4)o3)ncn1-2]

Compound 325 was prepared analogously as Compound 291, using in-situ generated 1,4-dioxane-2-carbonyl chloride (oxalyl chloride in cat. DMF/DCM) for hydrazide acylation in step 4 (Scheme 14) before the final ring closure. MS: [M+1]=421.

Example 159h: Synthesis of Compound 326

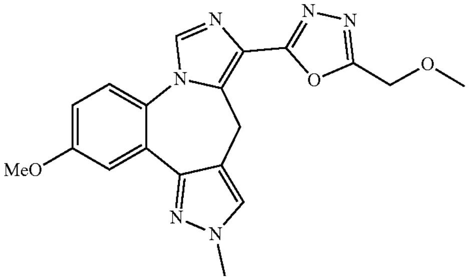 [SMILES: COCc1nnc(-c2ncn3c2Cc2cn(C)nc2-c2cc(OC)ccc2-3)o1]

Compound 326 was prepared analogously as Compound 291, using in-situ generated methoxyacetyl chloride (oxalyl chloride in cat. DMF/DCM) for hydrazide acylation in step 4 (Scheme 14) before the final ring closure. MS: [M+1] =379.

Scheme 15-A

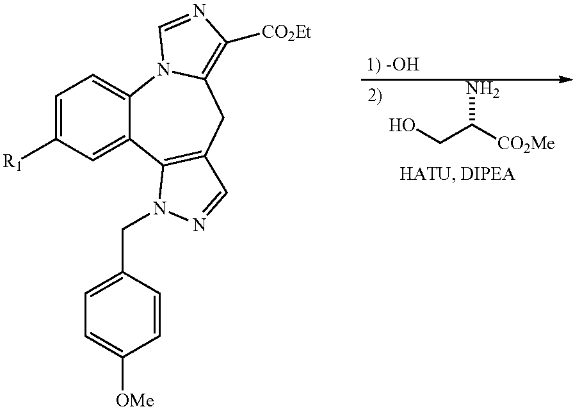

Intermediate B
(R1 = OMe, Cl)

-continued

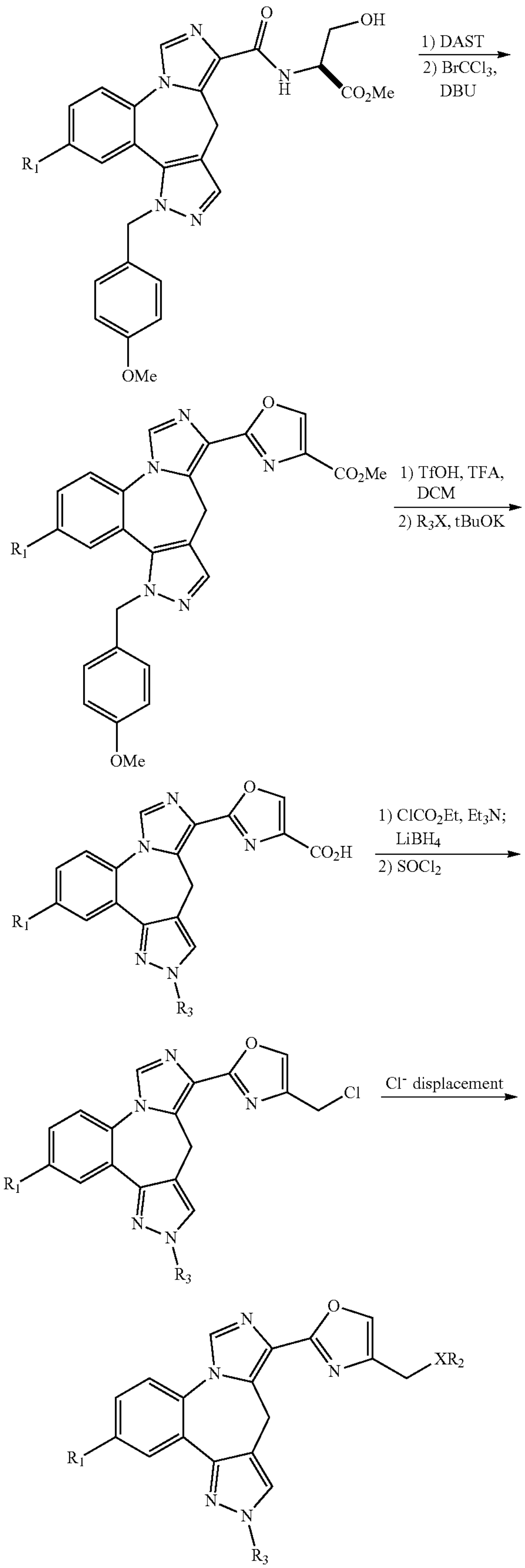

-continued

| R1 XR2 R3 |
|---|
| Ex. 160 Compound 269: OMe, MeO, Me |
| Ex. 160a Compound 284: Cl, MeO, Me |
| Ex. 160-1 Compound 272: OMe, $MeO(CH_2)_2O$, Me |
| Ex. 160b Compound 273: OMe, THF-3-yl-O, Me |
| Ex. 160c Compound 278: Cl, $MeO(CH_2)_2O$, Me |
| Ex. 160d Compound 332: Cl, $(MeOCH_2)_2CHO$, Me |
| Ex. 160e Compound 285: Cl, OXT-3-yl-O, Me |
| Ex. 160f Compound 346: Cl, $O(CH_2CH_2)_2CHO$, Me |
| Ex. 160-2 Compound 270: OMe, $N(CH_2)_4$, Me |
| Ex. 160-3 Compound 271: OMe, $N(CH_2CH_2)_2O$, Me |
| Ex. 160g Compound 380: OMe, $(iPr)_2N$, Me |
| Ex. 160h Compound 276: Cl, $N(CH_2CH_2)_2O$, Me |
| Ex. 160i Compound 277: Cl, $NMe_2$, Me |
| Ex. 160j Compoud 345: Cl, $N(CH_2)_4$, Me |
| Ex. 160k Compound 358: Cl, NMe(Ac), Me |
| Ex. 160l Compound 364: Cl, 2-Prn, Me |
| Ex. 160m Compound 378: OMe, NMe(Ac), Me |
| Ex. 160n Compound 381: OMe, NiPr(Ac), Me |
| Ex. 160o Compound 379: OMe, 2-Prn, Me |

Example 160: Synthesis of Compound 269

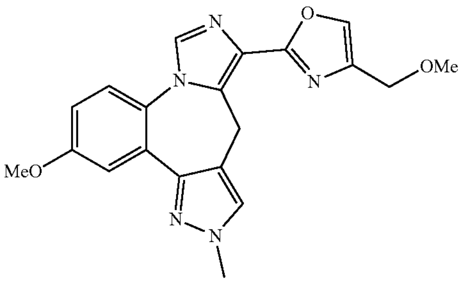 [SMILES: COCc1coc(-c2ncn3c2Cc2cn(C)nc2-c2cc(OC)ccc2-3)n1]

Example 160, Compound 269 was prepared following Scheme 15-A. Intermediate B ($R_1$=OMe; 168.9 mg, 0.380 mmol) was treated with NaOH (1N aq.; 2 ml) in MeOH (2 ml) at 90° C. for 2 hrs, and cooled to RT, acidified to pH 3-4 with dil. HCl. After cooling to 4° C., ppt. was collected by filtration, washed with small amt. of water, and dried to give 151.8 mg (96%) carboxylic acid.

To the acid (230.3 mg, 0.553 mmol) thus obtained from above stirring in DMF (1.5 ml) was added HATU (315.2 mg, 0.829 mmol) and diisopropyl ethylamine (0.290 ml). After 5 min of stirring, serine methyl ester HCl salt (129.0 mg, 0.829 mmol) was added. After 2 hr stirring, the reaction mixture was diluted with EtOAc, washed with sat. $NaHCO_3$, brine, and dried (MgSO4). Filtration and concentration followed by silica gel column chromatography using 0 to 5% MeOH in DCM gradient gave quantitative yield of the amide product as an off-white foam. To this foam stirring in DCM (8 ml) in a salt-ice bath was added diethylaminosulfur trifluoride (202.7 mg, 1.26 mmol). After about 2 hr stirring in ambient temperature, the reaction was cooled in an ice bath, and quenched with sat. $NaHCO_3$ for 30 min, and extracted with EtOAc (2×), washed with brine, and dried over MgSO4. Silica gel column chromatography using 0 to 6% MeOH in DCM gradient gave 218.7 mg (70%) oxazoline product.

To the oxazoline (203.3 mg, 0.407 mmol) stirring in DCM (10 ml) was added $BrCCl_3$ (322.8 mg, 1.63 mmol) and DBU (254.2, 1.67 mmol). The reaction mixture was diluted with EtOAc, washed with sat. $NaHCO_3$, brine, and dried over MgSO4. Silica gel column chromatography of the concentrated filtrate using 0 to 100% EtOAc in hexanes gradient gave 159.0 mg (79%) oxazole product as a waxy solid.

The oxazole from above (159.0 mg) was treated with trifluoroacetic acid (3 ml) and DCM (3 ml) in the presence of trifluoromethane sulfonic acid (192.2 mg) for 4 days. The reaction mixture was concentrated by removing most solvent under reduced pressure, resulting slurry was then treated with a mixture of EtOAc (10 ml) and sat. $NaHCO_3$ (aq.; 10 ml), and stirred for 30 min. PPts was collected by filtration, washed with water, and dried to give 110.2 mg (90%) of the crude deprotection product as a light yellowish solid.

Trimethylphenylammonium chloride was azeotroped three times in toluene before use. Trimethylphenylammonium chloride (320 mg) and the above obtained N—H pyrazole (110.2 mg) was stirred in DMF (1.5 ml) at 0° C., tBuOK (108 mg) was added. After 30 min stirring at 0° C., the reaction was warmed to rt for 2 hrs before being heated at 55° C. for 20 h. Solvent was removed in vacuo, resulting slurry was acidified to pH 3-4 with dil. HCl, then cooled to 4° C. Ppts was collected by filtration, washed with small amt. of cold water, and dried to give 93.5 mg (85%) crude N-methylated pyrazolocarboxylic acid as a greyish solid.

The above obtained acid (93.5 mg) was stirred in THE (1.5 ml) at 0° C., triethylamine (37.6 mg) was added, followed by chloroethylformate (40.4 mg). After 1 hr stirring and still at 0° C., $NaBH_4$ (92 mg) added and the reaction was stirred at ambient temperature for 16 hr. $LiBH_4$ (2M THF; 0.250 ml) was added to the reaction mixture, and stirring continued for 2 hr at rt, then MeOH (0.5 ml) was added for quenching. After 30 min, all solvent was removed, and the mixture was purified by silica gel column chromatography using 0 to 7% MeOH in DCM gradient to give 53.8 mg (60%) product alcohol as a white solid.

To the alcohol from above (5.5 mg, 0.0151 mmol) in DCM (0.15 ml) at 0° C. was added thionyl chloride (4.4 ul; 0.0604 mmol). After 16 hr stirring in ambient temperature, the reaction was quenched with sat. $NaHCO_3$, extracted with EtOAc (3×), washed with brine, and dried over MgSO4. Filtration and solvent removal gave 5.1 mg (88%) of the crude chloride product as an off white solid.

The chloride (5.1 mg, 0.0133 mmol) from above was stirred in anhydrous MeOH (0.15 ml) and THE (0.10 ml) at 0° C., sodium hydride suspended in mineral oil (60%; 20 mg, 0.266 mmol) was added, and the reaction was stirred to rt overnight. The reaction mixture was diluted with EtOAc, washed with sat. $NaHCO_3$, brine, and dried over $MgSO_4$. The product Example 160, Compound 269 was isolated by prep. TLC using 10% MeOH in DCM/EtOAc (1:1) as eluent. Wt: 2.9 mg (58%). MS: [M+1]=378.

Example 160a: Synthesis of Compound 284

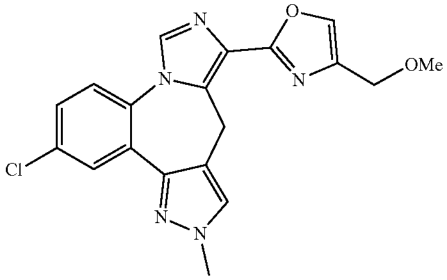 [SMILES: COCc1coc(-c2ncn3c2Cc2cn(C)nc2-c2cc(Cl)ccc2-3)n1]

Compound 284 was prepared analogously as Compound 269, starting with Intermediate B ($R_1$=Cl). MS: [M+1]=382.

Example 160-1: Synthesis of Compound 272

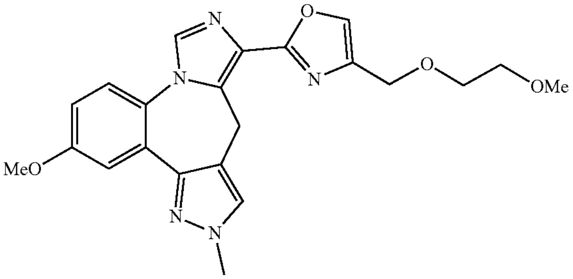 [SMILES: COCCOCc1coc(-c2ncn3c2Cc2cn(C)nc2-c2cc(OC)ccc2-3)n1]

Compound 272 was prepared analogously as Example 160, using 2-methoxyethanol as the nucleophilic agent to displace the chloride in the final step. MS: [M+1]=422.

Example 160b: Synthesis of Compound 273

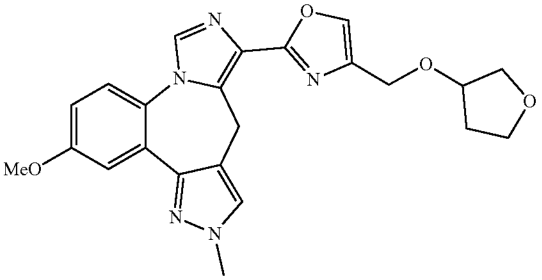 [SMILES: COc1ccc2c(c1)-c1nn(C)cc1Cc1c(-c3nc(COC4CCOC4)co3)ncn1-2]

Compound 273 was prepared analogously as in Example 160, using 3-hydroxytetrahydrofuran as the nucleophilic agent to displace the chloride in the final step. MS: [M+1]=434.

Example 160c: Synthesis of Compound 278

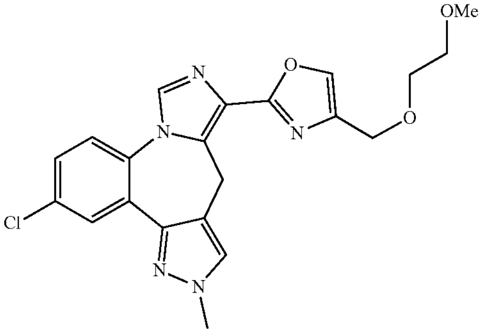 [SMILES: COCCOCc1coc(-c2ncn3c2Cc2cn(C)nc2-c2cc(Cl)ccc2-3)n1]

Compound 278 was prepared analogously as Compound 272, starting with Intermediate B where $R_1$=Cl. MS: [M+1]=426.

Example 160d: Synthesis of Compound 332

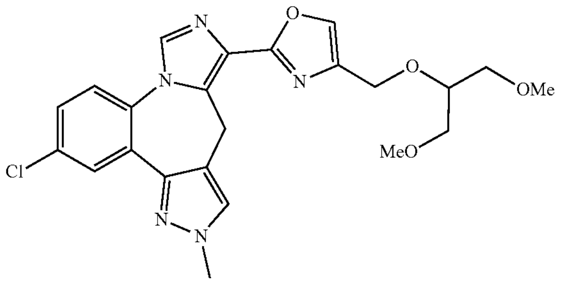 [SMILES: COCC(COC)OCc1coc(-c2ncn3c2Cc2cn(C)nc2-c2cc(Cl)ccc2-3)n1]

Compound 332 was prepared analogously as Compound 278, using 1,3-dimethoxypropan-2-ol as the nucleophilic agent to displace the chloride in the final step. MS: [M+1]=470.

Example 160e: Synthesis of Compound 285

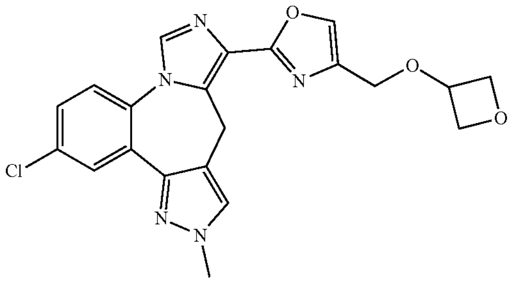 [SMILES: Cn1cc2c(n1)-c1cc(Cl)ccc1-n1cnc(-c3nc(COC4COC4)co3)c1C2]

Compound 285 was prepared analogously as Compound 278, using oxetan-3-ol as the nucleophilic agent to displace the chloride in the final step. MS: [M+1]=424.

Example 160f: Synthesis of Compound 346

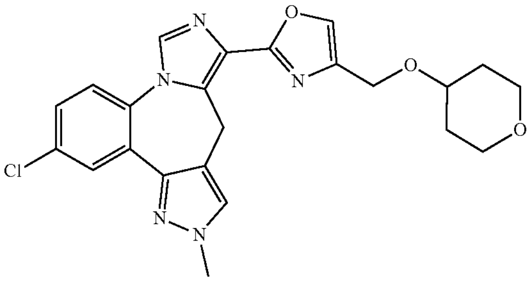 [SMILES: Cn1cc2c(n1)-c1cc(Cl)ccc1-n1cnc(-c3nc(COC4CCOCC4)co3)c1C2]

Compound 346 was prepared analogously as Compound 278, using tetrahydro-pyran-4-ol as the nucleophilic agent to displace the chloride in the final step. MS: [M+1]=452.

Example 160-2: Synthesis of Compound 270

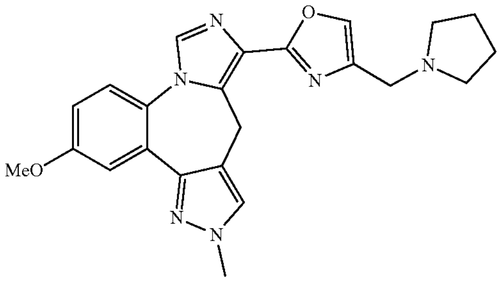 [SMILES: COc1ccc2c(c1)-c1nn(C)cc1Cc1c(-c3nc(CN4CCCC4)co3)ncn1-2]

Compound 270 was prepared similarly as Compound 269 following Scheme 15A except the last step, detailed below:

To the chloride (8.7 mg, 0.0227 mmol) stirring in THE (0.15 ml) at 0° C. was added pyrrolidine (30 ul), and the reaction was allowed to proceed overnight to rt, then diluted with EtOAc, washed with sat. NaHCO3; aq. Layer separated and extracted with EtOAc (2×); the combined EtOAc organic layer was washed with brine, and dried over MgSO4. Prep. TLC using 12% MeOH in DCM containing 0.1% (v/v) triethylamine gave 6.6 mg (69%) desired product as a clear glassy solid. MS: [M+1]=417.

Example 160-3: Synthesis of Compound 271

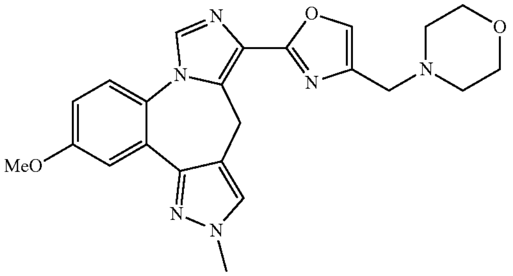 [SMILES: COc1ccc2c(c1)-c1nn(C)cc1Cc1c(-c3nc(CN4CCOCC4)co3)ncn1-2]

Compound 271 was prepared analogously as Example 160-2, using morpholine as the nucleophilic agent to displace the chloride in the final step. MS: [M+1]=433.

Example 160g: Synthesis of Compound 380

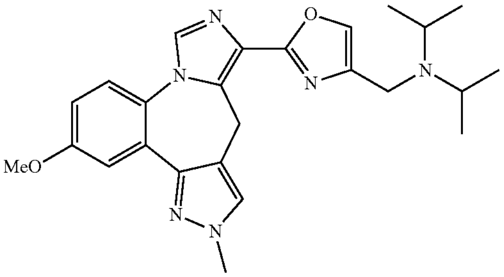 [SMILES: COc1ccc2c(c1)-c1nn(C)cc1Cc1c(-c3nc(CN(C(C)C)C(C)C)co3)ncn1-2]

Compound 380 was prepared analogously as Compound 270, using diisopropyl amine as the nucleophilic agent to displace the chloride in the final step. MS: [M+1]=447.

Example 160h: Synthesis of Compound 276

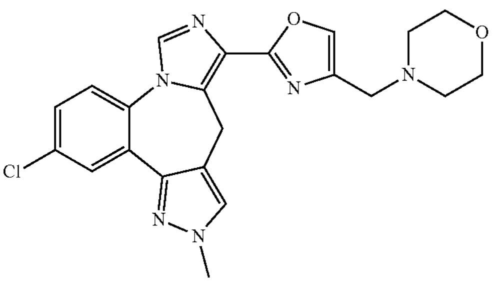 [SMILES: Cn1cc2c(n1)-c1cc(Cl)ccc1-n1cnc(-c3nc(CN4CCOCC4)co3)c1C2]

Compound 276 was prepared analogously as Compound 271, starting with Intermediate B where $R_1$=Cl. MS: [M+1]=437.

Example 160i: Synthesis of Compound 277

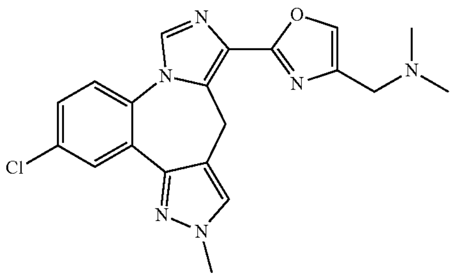 [SMILES: CN(C)Cc1coc(-c2ncn3c2Cc2cn(C)nc2-c2cc(Cl)ccc2-3)n1]

Compound 277 was prepared analogously as Compound 276, using dimethyl amine in THF for the chloride displacement in the final step. MS: [M+1]=395.

Example 160j: Synthesis of Compound 345

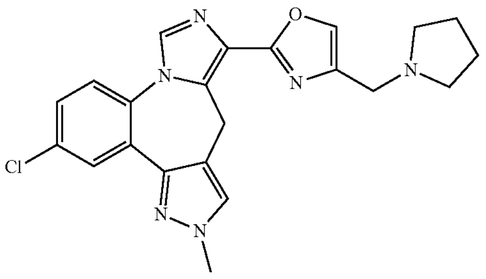 [SMILES: Cn1cc2c(n1)-c1cc(Cl)ccc1-n1cnc(-c3nc(CN4CCCC4)co3)c1C2]

Compound 345 was prepared analogously as Compound 276, using pyrrolidine for the chloride displacement in the final step. MS: [M+1]=421.

Example 160k: Synthesis of Compound 358

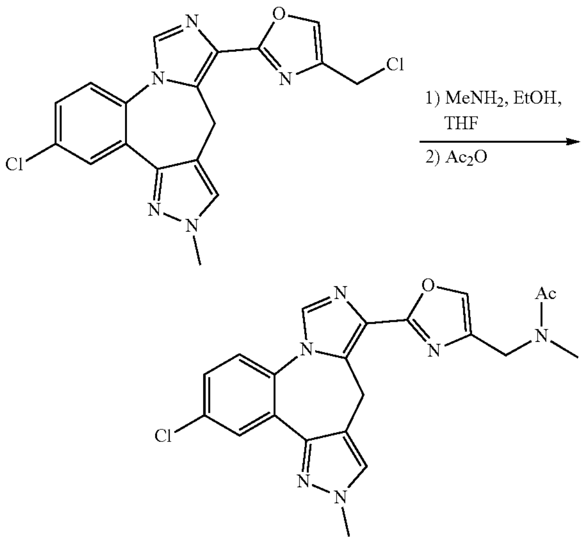

Compound 358 was prepared by amine displacement of the chloride as illustrated in Scheme 15-A, followed by amine acylation as detailed below:

The starting chloride (5.6 mg, 0.0145 mmol) was stirred in THF (0.2 ml) at 0° C., methyl amine in ethanol solution (33%; 1 ml) was added. After overnight stirring at ambient tempt, all solvent was removed in vacuo. Residue was stirred in DCM (0.2 ml) at 0° C., acetic anhydride (0.2 ml) was added. After 2 h stirring, the reaction was quenched with MeOH (1 ml) for 20 min, diluted with EtOAc, washed with sat. $NaHCO_3$, brine, and dried over $MgSO_4$. Prep TLC of the concentrated filtrate with 10% MeOH in hex/EtOAc (1:1) gave 3.4 mg (56%) of the desired product. MS: [M+1]=423.

Example 160l: Synthesis of Compound 378

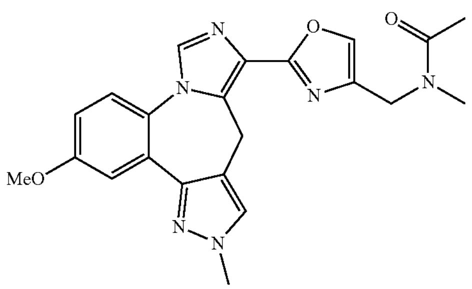 [SMILES: COc1ccc2c(c1)-c1nn(C)cc1Cc1c(-c3nc(CN(C)C(C)=O)co3)ncn1-2]

Compound 378 was prepared analogously as Compound 358, starting with Intermediate B ($R_1$=OMe). MS: [M+1]=419.

Example 160m: Synthesis of Compound 381

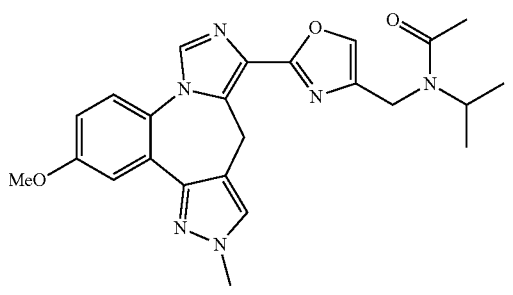 [SMILES: COc1ccc2c(c1)-c1nn(C)cc1Cc1c(-c3nc(CN(C(C)=O)C(C)C)co3)ncn1-2]

Compound 381 was prepared analogously as Compound 378, using isopropyl amine for the displacement of the chloride intermediate before the final acylation. MS: [M+1]=447.

Example 160n: Synthesis of Compound 364

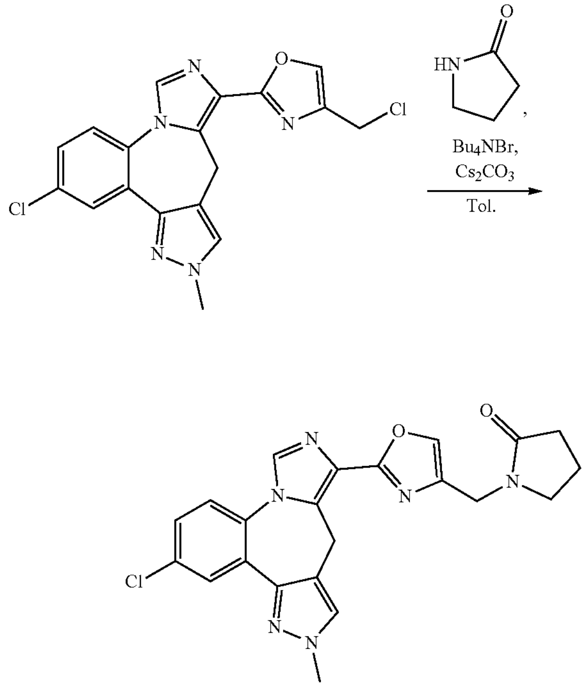

Compound 364 was prepared by chloride displacement as illustrated in Scheme 15-A by 2-pyrrolidinone as detailed below:

To the starting chloride (12.0 mg, 0.0311 mmol) stirring in toluene (0.26 ml) was added 2-pyrrolidinone (26.4 mg, 0.311 mmol), tetrabutylammonium bromide (20.1 mg 0.0622 mmol), and $Cs_2CO_3$ (40.5 mg, 0.124 mmol). The reaction was heated at 60° C. for 20 h, cooled, diluted with EtOAc, washed with sat. $NaHCO_3$, brine, and dried over $MgSO_4$. Prep TLC of the concentrated filtrate with 5% MeOH in DCM repeatedly gave 3.6 mg (27%) of the desired product as a clear filmy solid. MS: [M+1]=435.

Example 160o: Synthesis of Compound 379

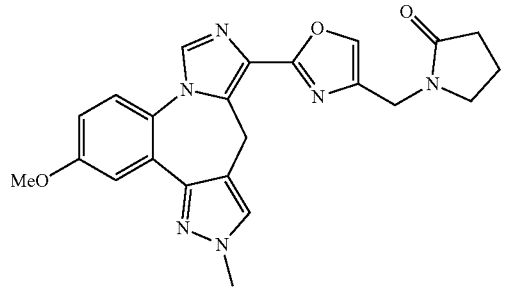 [SMILES: COc1ccc2c(c1)-c1nn(C)cc1Cc1c(-c3nc(CN4CCCC4=O)co3)ncn1-2]

Compound 379 was prepared analogously as Compound 364, starting with Intermediate B ($R_1$=OMe). MS: [M+1]=431.

Scheme 15-B

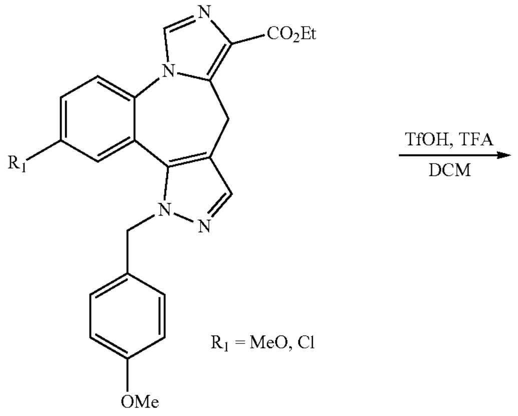

Intermediate B

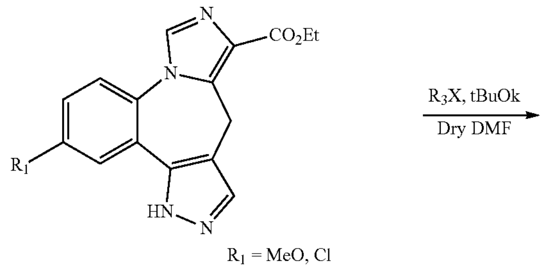

Intermediate C

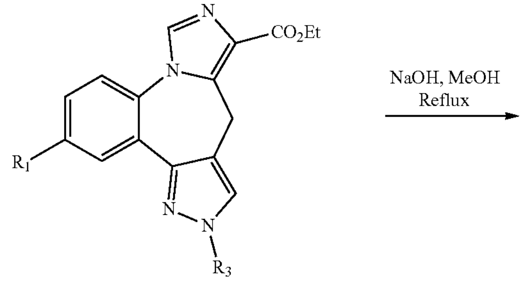

15B-A.1
(major isomer)

-continued

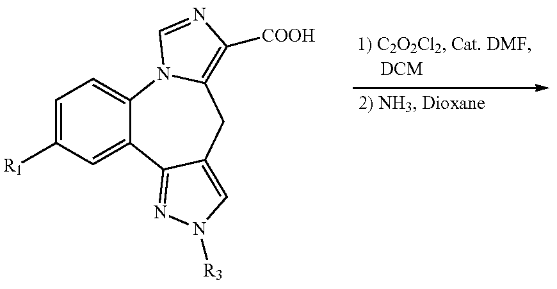

15B-A.2

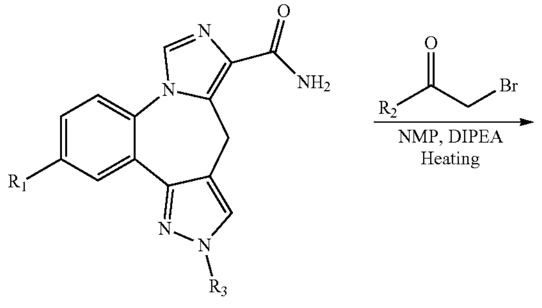

15B-A.3

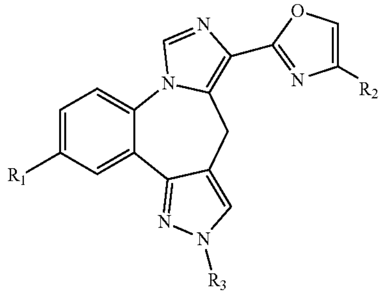

$R_1$ $R_2$ $R_3$

Ex 161 Compound 262: Ome, 2yl-THF, Me

Example 161: Synthesis of Compound 262

Compound 262

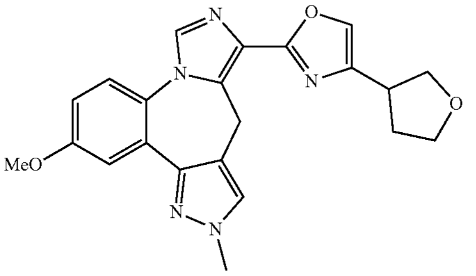

Intermediate B (0.5 g, 1.12 mmol) was treated with trifluoromethane sulfonic acid (0.34 g, 2.25 mmol) in a mixture of trifluoroacetic acid (1.0 ml) and DCM (9.0 ml) at 40° C. for 16 h. The reaction mixture was concentrated, treated with sat. $NaHCO_3$ solution to obtain ppts. The ppts were filtered and washed with water. The drying of ppts gave 0.36 g of Intermediate C as a solid product, MS: [M+1]=325.1.

Intermediate C (0.36 g, 1.13 mmol) was dissolved in anhydrous DMF (6.0 mL). The anhydrous t-BuOK (0.15 g, 1.35 mmol) was added at 0° C. temperature, followed by Methyl iodide (0.16 g, 1.13 mmol). The rxn mixture was stirred at ambient temperature for 4 h. The reaction mixture was diluted with water and extracted with ethyl acetate (15.0 mL×3). The combined organic extract was washed with brine and dried over $MgSO_4$. Filtration and solvent removal followed by silica gel column chromatography using 0 to 100% Ethyl acetate in Hexane gave 0.14 g of 15B-A.1 as a solid product, MS: [M+1]=339.1.

Intermediate 15B-A.1 (0.11 g, 0.33 mmol) solution in anhydrous Methanol (5.0 mL) was treated with 1.0 N NaOH (0.7 mL, 0.65 mmol) and the rxn mixture was refluxed for 4 h. The rxn mixture was concentrated and pH adjusted with 1.0 M HCl solution to obtain the ppts. The solid ppts were washed with water and dried to obtain 0.1 g of 15B-A.2 acid intermediate, MS: [M+1]=311.1.

Intermediate 15B-A.2 (0.03 g, 0.1 mmol) solution in anhydrous DCM (2.5 mL) was treated with Oxalyl chloride (0.015 g, 0.12 mmol) followed by catalytic amount of DMF addition. The rxn mixture was stirred at ambient temperature for 2 h. The rxn mixture was concentrated and diluted with anhydrous DCM (2.0 mL). The rxn mixture was treated with 0.4 M $NH_3$ in Dioxane (1.0 mL) at ambient temperature for 2 h. The rxn mixture was concentrated and diluted with water to obtain ppts. The drying of ppts gave 0.029 g of 15B-A.3 as a solid product, MS: [M+1]=310.1.

Intermediate 15B-A.3 (0.03 g, 0.1 mmol) and 2-bromo-1-(oxolan-3-yl)-ethan-1-one (0.044 g, 0.24 mmol) solution in anhydrous 1-Methyl-2-pyrrolidinone (2.0 mL) was treated with DIPEA (0.025 g, 0.19 mmol). The rxn mixture was heated at 150° C. for 12 h. The rxn mixture was concentrated and the residue was purified by prep-TLC using 0 to 5% MeOH in DCM to obtain 8.7 mg of Example 161, Compound 262 product, MS: [M+1]=404.1.

Scheme 16

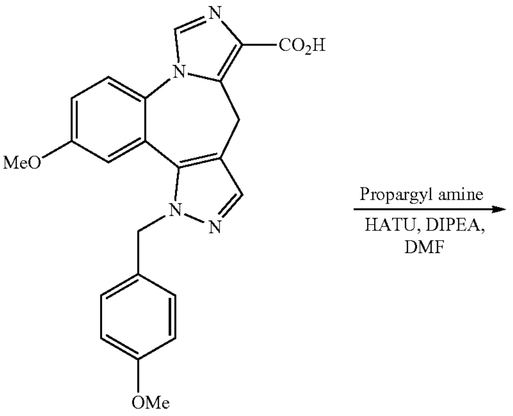

-continued

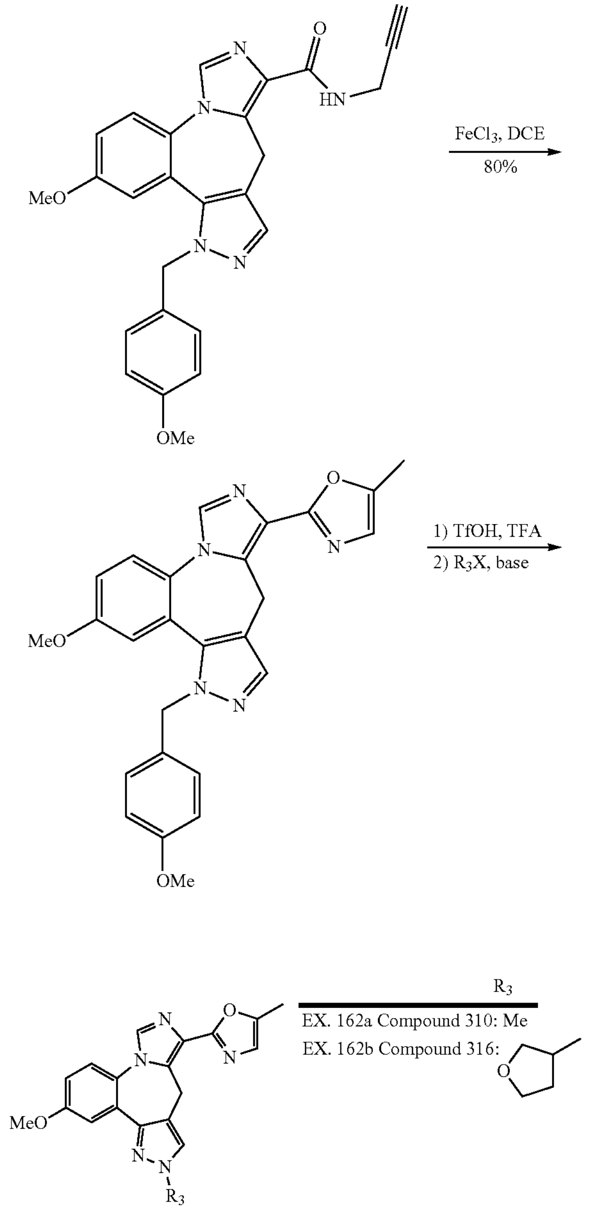

Example 162a: Synthesis of Compound 286

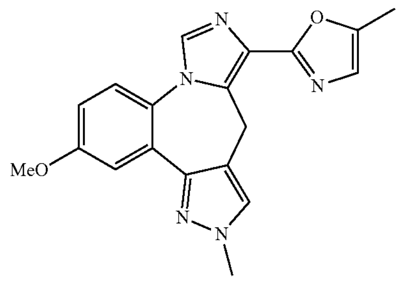 [SMILES: COc1ccc2c(c1)-c1nn(C)cc1Cc1c(-c3ncc(C)o3)ncn1-2]

The starting acid (37.5 mg, 0.090 mmol), obtained from hydrolysis of the Intermediate B ($R_1$=OMe), was stirred in DMF (0.5 ml). HATU (41.1 mg, 0.108 mmol) and diisopropyl ethylamine (47 ul) were added. After 5 min of stirring, propargyl amine (6.0 mg, 0.108 mmol) was added. After 1 hr stirring, the reaction mixture was diluted with EtOAc, washed with sat. $NaHCO_3$, brine, and dried (MgSO4). Filtration and concentration followed by silica gel column chromatography using 0 to 80% EtOAc in hexanes gradient gave 36.7 mg (90%) amide product as a white solid.

To the amide from above (36.7 mg, 0.081 mmol) stirring in dichloroethane (3.0 ml) was added ferric chloride (26.2 mg, 0.162 mmol). The reaction was heated at 80° C. for three hours. Upon cooling, the mixture was diluted with EtOAc, washed with sat. $NaHCO_3$, brine, and dried over $MgSO_4$. Filtration and solvent removal gave 30.8 mg (84%) cyclized product as a brownish clear filmy solid.

The oxazole (30.8 mg, 0.0679 mmol) from above was treated with TfOH (30 ul) and TFA (0.5 ml) at 62° C. for two days. Upon cooling, the reaction mixture was concentrated by removing most TFA in vacuo, and then treated with aq. $NaHCO_3$ (4 ml). The resulting solid chunk was broken up through sonication and stirring, and then cooled to 4° C. The solid ppts was collected by filtration, washed with cold water, and dried to give 35.1 mg (100%) crude product as a greenish solid.

Trimethylphenylammonium chloride (49.5 mg, 0.306 mmol) and the oxazole from above (20.4 mg, 0.0612 mmol) were stirred in DMF (0.3 ml) at 0° C., tBuOK (13.7 mg, 0.122 mmol) was added. After 30 min stirring at 0° C., the reaction was heated at 50° C. for 16 h, quenched with sat. $NaHCO_3$, extracted with EtOAc (3×), the combined extracts washed with brine, and dried over $MgSO_4$. Reverse phase ISCO column purification (20%-80% OMeOH in water elution) gave 4.9 mg (25%) final product as a white solid. MS: [M+1]=348.

Example 162b: Synthesis of Compound 287

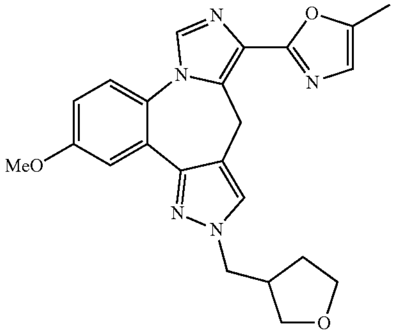 [SMILES: COc1ccc2c(c1)-c1nn(CC3CCOC3)cc1Cc1c(-c3ncc(C)o3)ncn1-2]

Compound 287 was prepared analogously as Compound 286, using 3-iodomethyl tetrahydrofuran for the final N-alkylation. MS: [M+1]=418.

Scheme 17

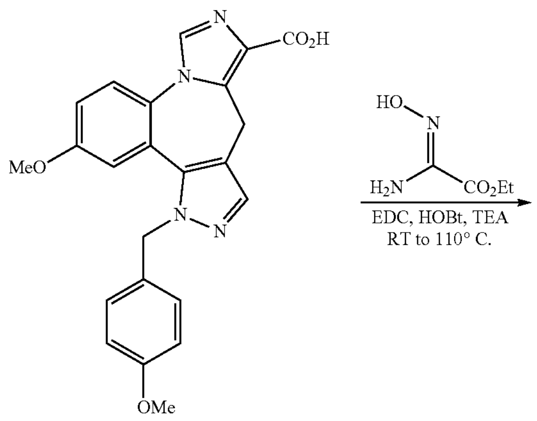

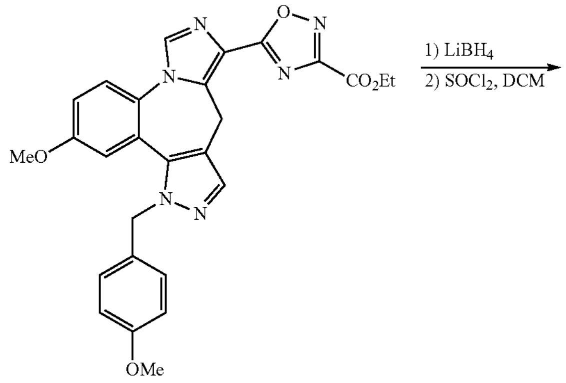

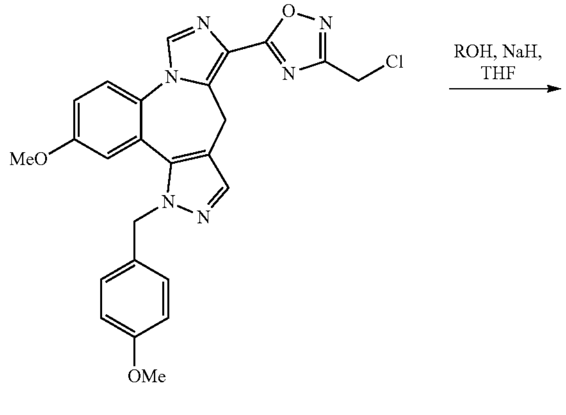

-continued

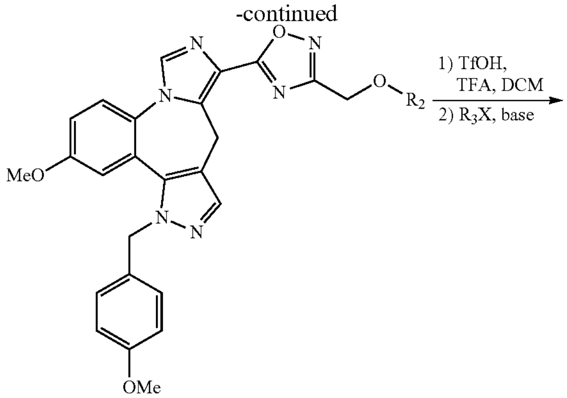

| | | |
|---|---|---|
| EX. 163a Compound 310: | 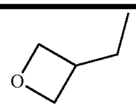 | 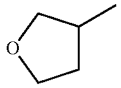 |
| EX. 163b Compound 316: | Me | 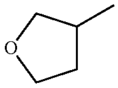 |

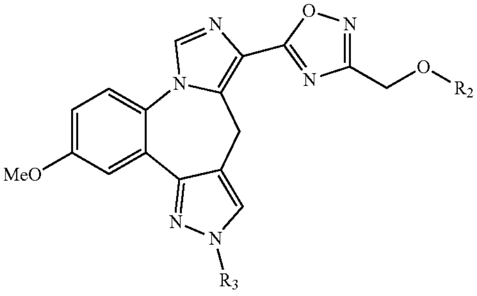

Example 163a: Synthesis of Compound 310

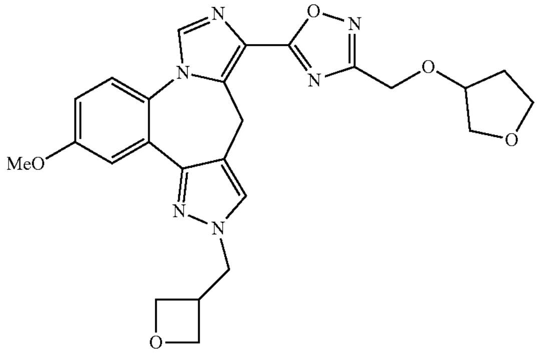 [SMILES: COc1ccc2c(c1)-c1nn(CC3COC3)cc1Cc1c(-c3nc(COC4CCOC4)no3)ncn1-2]

The starting acid (406.2 mg, 0.975 mmol), obtained from hydrolysis of the Intermediate B ($R_1$=OMe), was stirred in a mixture of THF (4 ml) and DCM (4 ml). EDC hydrochloride (373.8 mg, 1.95 mmol), HOBt hydrate (150 mg) and TEA (475 ul) were added. After 5 min of stirring, ethyl 2-amino-2-(hydroxyimino) acetate (219.0 mg, 1.66 mmol) was added. After 16 hr stirring, the reaction was concentrated, toluene (10 ml) and TsOH hydrate (1.1 g) were added, and the reaction mixture was heated at 110° C. for 20 hrs. Upon cooling, the reaction mixture was diluted with EtOAc, washed with sat. $NaHCO_3$, aq. Layer was separated and extracted with EtOAc (3×), the combined EtOAc solution was washed with brine, and dried ($MgSO_4$). Filtration and concentration followed by silica gel column chromatography using 0 to 80% EtOAc in hexanes gradient gave 267.1 mg (53%) ester product as a white solid.

The ester from above (52.2 mg, 0.102 mmol) was treated with $LiBH_4$ (2M THF; 61 ul) in THE (1.1 ml) at 0° C. The reaction was allowed to proceed to RT overnight, then quenched with MeOH (1 ml). All solvent was removed in vacuo and the alcohol product was isolated by $SiO_2$ column chromatography using 0 to 8% MeOH in DCM as eluent gradient. Wt: 40.7 mg (85%).

The alcohol from above (40.7 mg, 0.0865 mmol) was treated with $SOCl_2$ (75 ul) in DCM (1.7 ml) at 0° C. The reaction was allowed to proceed to RT overnight, then all solvent and excess reagent was removed in vacuo. Resulting solid was stirred in THE (1.7 ml) at 0° C., 3-hydroxytetrahydrofuran (280 ul) was added, followed by NaH (60% oil suspension; 350 mg) in batches. After 16 hr stirring at ambient temperature, the reaction was quenched with sat. $NaHCO_3$, extracted with EtOAc (3×), washed with brine, and dried over $MgSO_4$. Filtration and solvent removal the crude ether product which was treated with TfOH (15.3 ul) in gave TFA (0.8 ml) and DCM (0.8 ml) for 72 hrs. Excess solvent and reagent was removed in vacuo, the resulting residue was treated with sat. $NaHCO_3$, extracted with EtOAc (3×), washed with brine, and dried over $MgSO_4$. Filtration and solvent removal gave the crude deprotection product as a yellow solid.

The crude deprotection product from above was stirred in DMF (0.4 ml), toluene-4-sulfonic acid-oxetan-3-yl-methyl ester (41.9 mg, 0.173 mmol) and NaI (13.0 mg, 0.0865 mmol) were added, followed by tBuOK (38.8 mg, 0.346 mmol). After 16 hr stirring at RT, the reaction was heated at 65° C. for 2 hrs, cooled to RT, diluted with EtOAc, washed with sat. $NaHCO_3$, brine, and dried over $MgSO_4$. $SiO_2$ column 10 chromatography (0 to 20% MeOH in hexane/EtOAc 1:1 gradient) followed by prep. TLC with % MeOH in DCM/EtOAc (1:1) solvent system gave 1.3 mg desired product as a white filmy solid. MS: [M+1]=491.

Example 163b: Synthesis of Compound 316

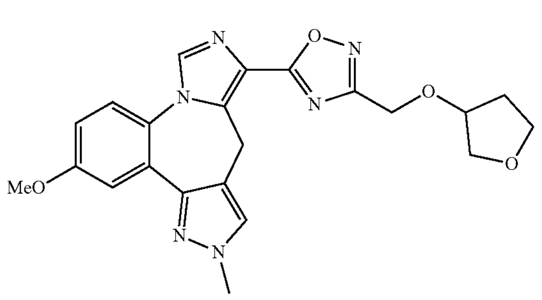 [SMILES: COc1ccc2c(c1)-c1nn(C)cc1Cc1c(-c3nc(COC4CCOC4)no3)ncn1-2]

Compound 316 was prepared analogously as Compound 310, using trimethylphenyl ammonium chloride for the final N-methylation. MS: [M+1]=435.

Scheme 18

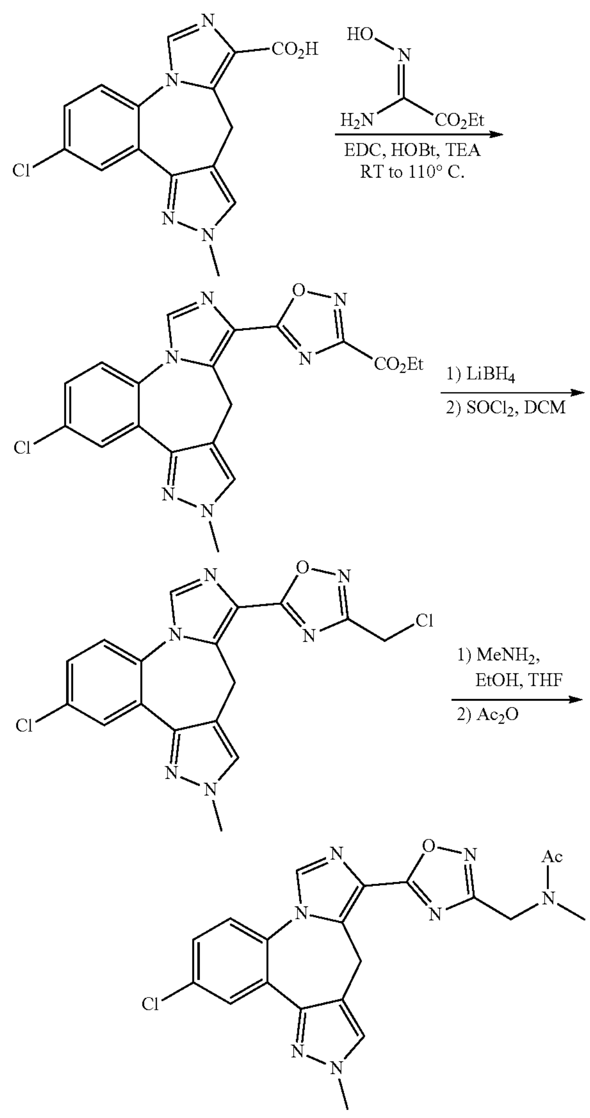

Example 164a: Synthesis of Compound 386

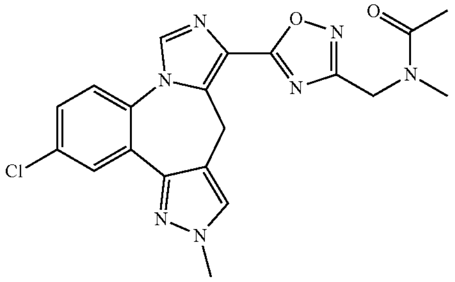 [SMILES: CC(=O)N(C)Cc1noc(-c2ncn3c2Cc2cn(C)nc2-c2cc(Cl)ccc2-3)n1]

Compound 386 was prepared as shown in Scheme 18. The starting acid (62.4 mg, 0.198 mmol), prepared by ester hydrolysis of the intermediate 7A.2 ($R_1$=Cl, $R_3$=Me) in Scheme 7-A, was stirred in a mixture of THE (1.2 ml) and DCM (1.2 ml). EDC hydrochloride (170 mg, 0.891 mmol), HOBt hydrate (30 mg) and TEA (210 ul) were added. After 5 min of stirring, ethyl 2-amino-2-(hydroxyimino) acetate (109.0 mg, 0.832 mmol) was added. After 16 hr stirring, the reaction was concentrated, toluene (7 ml) and TsOH hydrate (188 mg) were added, and the reaction mixture was heated at 110° C. for 20 hrs. Upon cooling, the reaction mixture was diluted with EtOAc, washed with sat. $NaHCO_3$, aq. layer was separated and extracted with EtOAc (3×), the combined EtOAc solution was washed with brine, and dried ($MgSO_4$). Filtration and concentration gave 86.4 mg crude ester product as a yellowish solid.

The ester from above (86.4 mg, 0.210 mmol) was treated with $LiBH_4$ (2M THF; 0.126 ml) in THE (1.2 ml) at 0° C. The reaction was allowed to proceed to RT overnight, then quenched with MeOH (1 ml). All solvent was removed in vacuo and the alcohol product was isolated by $SiO_2$ column chromatography using 0 to 10% MeOH in DCM as eluent gradient. Wt: 23.1 mg (30%).

The alcohol from above (23.1 mg, 0.0626 mmol) was treated with $SOCl_2$ (45 ul) in DCM (1.0 ml) at 0° C. The reaction was allowed to proceed to RT overnight, then all solvent and excess reagent was removed in vacuo. Resulting solid was taken up in EtOAc, washed with sat. $NaHCO_3$, brine, and dried over $MgSO_4$. Upon filtration and solvent removal, 17.8 mg (74%) of the crude chloride product was obtained.

The chloride from above (8.0 mg, 0.0207 mmol) was treated with methyl amine in ethanol solution (33%; 0.51 ml) at 0° C., and the reaction was allowed to proceed to RT overnight, All solvent was removed in vacuo, and the resulting residue was dissolved in DCM (0.3 ml) at 0° C., and treated with acetic anhydride (0.3 ml). After overnight stirring at ambient temperature, the reaction mixture was diluted with EtOAc, washed with sat. $NaHCO_3$, brine, and dried over $MgSO_4$. Filtration and concentration, followed by prep. TLC using 10% MeOH in DCM/EtOAc (1:1) as eluent gave 4.6 mg (52%) desired product as a yellowish solid. MS: [M+1]=424.

Assay Protocols

Example 165: Assessing α5-Containing $GABA_A$ R ($GABA_AR$) Positive Allosteric Modulator Activity Step 1: Establish clones of $GABA_AR$ subunits (α5, β3, γ2, α1, α2 and α3) and prepare the corresponding cRNAs: Human clones of $GABA_A$-R α5, β3, γ2, α1, α2 and α3 subunits are obtained from commercial resources (e.g., OriGene, and Genescript ). These clones are engineered into pRC, pCDM, pcDNA, and pBluescript KSM vector (for oocyte expression) or other equivalent expression vectors. Conventional transfection agents (e.g., FuGene, Lipofectamine 2000, or others) are used to transiently transfect host cells.

Step 2—Functional $GABA_AR$ Assay of α5β3γ2, α1β3γ2, α2β3γ2, and α3β3γ2, subtypes in *Xenopus* oocyte expression system: cRNAs encoding α5, β3, γ2, α1, α2 and α3 subunits are transcribed in vitro using T3 mMESSAGE mMACHINE Kit (Ambion) and injected (in a ratio of α:β:γ=2:2:1 or other optimized conditions) into oocytes freshly prepared from *Xenopus laevis*. After two days of culturing, GABA-gated Cl-currents from oocytes are performed using TEVC setups (Warner Instruments, Inc., Foster City, CA). GABA, benzodiazepine, and diazepam are used as reference compounds to validate the system.

Step 3—Evaluate test compounds for positive allosteric modulator activity on the α5β3γ2 subtype and test off-target activity on the α1 to α3 coupled β3γ2 subtypes when the EC50=5 μM selectivity cut-off is reached: The GABA-gated Cl-current from oocytes are measured in the TEVC setup in the presence of the test compounds. The positive allosteric modulator activity of each the test compounds is tested in a 5-point dose-response assay. The test compounds include some reference compounds (literature EC50 values for the α5β3γ2 subtype are in the range of 3-10 μM). EC50s in the α5β3γ2 subtype are obtained for each compound. If the EC50 in α5β3γ2 is ≤5 μM, then the EC50 of the other three subtypes (a1β2γ2, α2β3γ2, and α3β3γ2) is further determined individually in order to test for selectivity of the compounds in the α5β3γ2 subtype over other subtypes.

Step 4—Evaluate further test compounds on the α5β3γ2 subtype and test off-target activities when the EC50=0.5 μM selectivity cut-off is reached: The second batch of test compounds are tested using the same strategy, but with a lower EC50 cutoff (0.5 μM). Again, the EC50s of the α5β3γ2 subtype for each of the compounds is determined. The α1 to α3 coupled β3γ2 subtypes are tested only if the EC50 for the α5-containing receptor is <0.5 μM.

Example 166: Evaluating Compounds for Binding and Positive Allosteric Modulator Activity on the $GABA_A$ α5 Receptors (A) Binding Activity of Test Compounds on $GABA_AR$ Tissue culture and Membrane Preparation: The binding was performed on Ltk cells stably expressing $GABA_A$ R: αβ1γ2, α2β3γ2, α3β3γ2 and α5β3γ2 (provided by Merck Co., NJ, USA). Cells were seeded in 100 mm culture plates in DMEM/F12 medium containing 10% serum and antibiotics in 5% $CO_2$ and allowed to grow for 1-2 days. $GABA_AR$ expression was then induced by dexamethasone as follows: 0.5 μM for 1 day for α5 containing and 2 μM for 3 days for α1, α2 and α3 containing $GABA_ARs$. After induction, cells were collected by scraping into Dulbecco's Phosphate buffered saline (DPBS, pH 7.4, Invitrogen, Carlsbad, CA, USA) and centrifuged at 150×g for 10 min. The pellet was washed twice by re-suspension and centrifugation. The cell pellets from at least 5 different preps were combined, suspended in the binding assay buffer (50 mM KH2PO4; 1 mM EDTA; 0.2 M KCl, pH 7.4) and membranes prepared by sonication (3-5 times, 30 sec) using Branson Sonifier 150 (G. Heinmann, Germany). Protein content was determined using BCA assay (Bio-Rad Labs, Reinach, Switzerland) with Bovine Serum Albumin (Sigma Aldrich, St. Louis, MO, USA) as the standard. Aliquots were prepared and stored at −20° C. for further use in binding assays.

Ligand Binding: Saturation binding curves were obtained by incubating membranes with increasing concentrations (0.01-8 nM) of [$^3$H]Rol5-1788 (Flumazepil, 75-85 Ci/mmol, PerkinElmer, MA, USA), with nonspecific binding measured in the presence of 10 μM diazepam. Inhibition of [$^3$H]Rol5-1788 binding of the test compounds was performed at concentrations of the radioligand at or lower than the $K_d$ values for α1, α2, α3 and α5 containing $GABA_ARs$ determined from the saturation curves.

All binding assays were performed for 1 h at 4° C. in assay buffer. The total assay volume was 0.5 ml containing 0.2 mg/ml protein for α5 and 0.4 mg/ml for α1, α2, and α3 containing $GABA_AR$ membranes. Incubations were terminated by filtration through GF/B filters using a 24-Cell Harvestor (Brandel, Gaithersburg, MD, USA) followed by 3 washes with ice-cold assay buffer. Filters were transferred to scintillation vials, 5 ml scintillation liquid added, vortex-mixed and kept in dark. Next day, radioactivity was obtained using a scintillation counter (Beckman Coulter, Brea, CA, USA). All assays were performed in triplicate.

Data Analyses: Saturation and inhibition curves were obtained using GraphPad Prism software (GraphPad Software, Inc., CA, USA). The equilibrium dissociation constants ($K_i$ values) of the unlabeled ligand were determined using Cheng-Prusoff equation $K_i=IC_{50}/(1+S/K_d)$, where $IC_{50}$ is the concentration of unlabeled ligand that inhibits 50% of [$^3$H] ligand binding, S is the concentration of radioligand and $K_d$ is the equilibrium dissociation constant of the radioactive ligand. A log range of the compounds (1 nM-10 μM) was used to determine the $K_i$ values which are presented as Mean±SD from triplicate assays.

(B) Positive Allosteric Modulator Activity of Test Compounds on α5β2γ2 Subtype $GABA_AR$ Compounds of the present invention were initially screened at 100 nM for their ability to potentiate an $EC_{20}$ concentration of GABA in oocytes containing $GABA_A$ R (α5β2γ2), using a protocol essentially similar to the one presented above.

On day 1, 1 ng/32 nL of $GABA_A$ α5β2γ2 cDNA was injected into one oocyte. Test starts on day 2. The cDNA injected to the oocytes was a mix of alpha, beta and gamma, their ratio is 1:1:10 (by weight) and the total weight of the mixed 3 subunits to be injected in one oocyte was 1 ng in 32 nl volume. The injected oocytes can also be tested on day 3. In such case, the cDNA amount injected to the oocytes should be reduced by 20%.

Compounds of the present disclosure were tested using the following procedures.

GABA Dose-Response

1). 8 oocytes were placed in 8 chambers of OpusXpress and superfused with Modified Barth's Saline (MBS) at 3 mL/min. Glass electrodes back-filled with 3M KCl (0.5-3 megaohms) were used. Membrane potential of oocytes was voltage-clamped at −60 mV.

2). Average $EC_{20}$ GABA obtained from previous tests were applied for five-six times to stabilize oocytes. Oocytes were washed with MBS for 5-10 min between each GABA applications.

3). Run GABA dose-response to obtain $EC_{20}$ GABA value.

Control Test (Diazepam or Methyl 3,5-Diphenylpyridazine-4-Carboxylate)

1). New oocytes was used to run new test.

2). $EC_{20}$ GABA was applied for five-six times to stabilize oocytes. Oocytes were washed with MBS for 5-10 min between each GABA applications.

3). $EC_{20}$ GABA was applied to obtain current ($I_{GABA}$). Oocytes were washed with MBS for 5-10 min.

4). 1 μM diazepam or methyl 3,5-diphenylpyridazine-4-carboxylate was pre-applied for 40 sec, followed by co-application of 1 μM diazepam or methyl 3,5-diphenylpyridazine-4-carboxylate and $EC_{20}$ GABA to obtain $I_{test}$. $I_{test}$ was divided by $I_{GABA}$ to obtain potentiation (%).

Test Compounds at Multiple Doses

1). Repeat the above steps 1), 2) and 3) in the control test.

2). The first concentration of a test compound was pre-applied for 40 sec followed by co-application of the test compound of the same concentration and $EC_{20}$ GABA to obtain $I_{test}$. Divide $I_{test}$ by $I_{GABA}$ to obtain potentiation (%).

3). Discard all tested oocytes, new oocytes were used and the above steps 1) and 2) were repeated to test second concentration of the same compound. Each oocyte was used for only one concentration test for a single test compound. The steps were repeated for other test compounds.

In some embodiments, the compounds of the present disclosure have a binding affinity (as represented by $K_i$) at α5-containing $GABA_A$Rs of less than 200 nM, less than 180 nM, less than 150 nM, or less than 100 nM. In some embodiments, the compounds of the present disclosure have a binding affinity (as represented by $K_i$) at α5-containing $GABA_A$Rs of less than 50 nM. In some embodiments, the compounds of the present disclosure have a binding affinity (as represented by $K_i$) at α5-containing $GABA_A$Rs of less than 10 nM.

In some embodiments, the compounds of the present disclosure are selective for α5-containing $GABA_A$Rs over α1-containing $GABA_A$Rs. In some embodiments, the compounds of the present disclosure are more than 50-fold, more than 100-fold, more than 500-fold or more than 1000-fold selective for α5-containing $GABA_A$Rs over α1-containing $GABA_A$Rs.

In some embodiments, the compounds of the present disclosure have an $EC_{50}$ at the α5-containing $GABA_A$Rs of less than 500 nM, less than 100 nM or less than 50 nM. In some embodiments, the compounds of the present disclosure have an $EC_{50}$ at the α5-containing $GABA_A$Rs of less than 25 nM.

In some embodiments, the compounds of the present disclosure potentiate α5-containing $GABA_A$Rs for more than 10%, more than 25%, more than 50%, or more than 75% at 100 nM. In some embodiments, the compounds of the present disclosure potentiate α5-containing $GABA_A$Rs for more than 10%, more than 25%, more than 50%, or more than 75% at 1000 nM.

Screening results of the binding and PAM functional activity tests are summarized in Tables 1 and 2 below.

The following Table 1 illustrates the ranges of GABA α5 binding $K_i$'s associated with compounds of this disclosure:

TABLE 1

| GABA α5 Binding Ki Values (nM) | | |
|---|---|---|
| <100 nM | 100-1000 nM | >1000 nM |
| Compound 1, 3, 7, 9, 10, 11, 14, 15, 16, 17, 20, 21, 22, 23, 24, 33, 34, 35, 38, 39, 40, 43, 44, 45, 46, 52, 53, 54, 55, 56, 57, 63, 64, 65, 71, 72, 73, 76, 77, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 166, | Compound 2, 4, 5, 8, 12, 18, 36, 37, 47, 60, 61, 62, 70, 74, 75, 79, 82, 165, 186, 221, 270, 291, 329, 344, 368, 378 | Compound 6, 13, 19, 25, 26, 27, 28, 29, 30, 31, 32, 41, 42, 48, 49, 50, 51, 58, 59, 66, 67, 68, 69, 78, 80, 81, 262 |

TABLE 1-continued

| GABA α5 Binding Ki Values (nM) | | |
|---|---|---|
| <100 nM | 100-1000 nM | >1000 nM |
| 167, 168, 169, 170, 171, 172, 173, 174, 175, 176, 177, 178, 179, 180, 181, 182, 183, 184, 185, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 263, 264, 265, 266, 267, 268, 269, 271, 272, 273, 274, 275, 276, 277, 278, 279, 280, 281, 282, 283, 284, 285, 286, | | |

TABLE 1-continued

| GABA α5 Binding Ki Values (nM) | | |
|---|---|---|
| <100 nM | 100-1000 nM | >1000 nM |
| 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 330, 331, 332, 333, 334, 335, 336, 337, 338, 339, 340, 341, 342, 343, 345, 346, 347, 348, 349, 350, 351, 352, 353, 354, 355, 356, 357, 358, 359, 360, 361, 362, 363, 364, 365, 366, 367, 369, 370, 371, 372, 373, 374, 375, 376, 377, 379, 380, 381, 382, 383, 384, 385, 386, 387, 388 | | |

The following Table 2 illustrates the ranges of GABA α5 functional potentiation associated with compounds of this disclosure:

TABLE 2

| GABA α5 Functional Data | | |
|---|---|---|
| 5-20% @ 100 nM[a,b] | 20-50% @ 100 nM | >50% @ 100 nM |
| Compound 9, 11, 14, 20, 21, 23, 46, 52, 55, 57, 73, 84, 85, 86, 88, 91, 93, 96, 97, 98, 100, 103, 104, 112, 115, 116, 119, 122, 123, 128, 131, 135, 140, 143, 145, 146, 147, 148, 151, 154, 158, 162, 163, 167, 169, 171, 172, 173, 176, 177, 195, 197, 201, 208, 212, 216, 219, 222, 223, 226, 228, 230, 231, 233, 243, 244, 249, 251, 253, 255, 256, 258, 259, 260, 261, 263, 264, 266, 267, 269, 275, 281, 282, 286, 289, 292, 297, 302, 304, 305, 306, 309, 312, 313, 314 | Compound 7, 10, 33, 34, 35, 39, 44, 45, 63, 76, 87, 90, 94, 99, 101, 105, 106, 108, 109, 110, 111, 113, 114, 118, 120, 121, 124, 125, 126, 127, 129, 132, 133, 134, 136, 137, 138, 139, 141, 142, 144, 149, 150, 153, 155, 156, 157, 159, 160, 161, 168, 170, 174, 175, 178, 179, 185, 187, 189, 190, 192, 193, 194, 198, 200, 202, 203, 205, 206, 207, 209, 210, 211, 215, 217, 218, 220, 224, 225, 232, 236, 237, 239, 242, 245, 247, 248, 252, 254, 257, 268, 276, 277, 278, 279, 280, 287, 290, 293, 295, 296, 300, 301, 303, 308, 310, 315 | Compound 54, 64, 130, 181, 183, 184, 188, 213, 214, 250, 278, 283, 284, 285, 288, 294 |

[a]Compounds with potentiation values below 5% are not included in this data set. Those compounds are less useful in the methods of this disclosure.

[b]Compounds with negative potentiation values are NAMs and are not included in this data set. Those compounds are less useful in the methods of this disclosure.

Selected compounds of the present disclosure demonstrate >10-fold binding selectivity for GABA α5 versus GABA α1, GABA α2, or GABA α3. Some compounds of the present disclosure demonstrate over 20-fold, 50-fold, or 100-fold binding selectivity for GABA α5 versus GABA α1, GABA α2, or GABA α3.

The following Tables 3-5 illustrates the ranges of the binding selectivity of the compounds of the present disclosure for GABA α5 versus GABA α1, GABA α2, or GABA α3, respectively:

TABLE 3

| Binding selectivity for GABA α5 versus GABA α1 | | |
|---|---|---|
| 20- to 50-fold[a] | 50- to 100-fold | >100-fold |
| 324, 323, 318, 316, 313, 312, 308, 305, 302, 250, 237, 230, 218, 205, 173, 164, 139, 113, 101, 94, 93, 91, 90, 83, 56, 53, 39 | 321, 319, 317, 307, 304, 300, 299, 283, 282, 260, 256, 254, 253, 252, 236, 231, 212, 210, 203, 188, 187, 181, 177, 176, 174, 171, 169, 168, 167, 156, 154, 153, 138, 135, 131, 130, 129, 128, 126, 117, 115, 104, 103, 100, 99, 97, 96, 92, 89, 64, 57, 46, 24, 23, 10, 9, 1 | 322, 320, 311, 310, 298, 297, 296, 295, 294, 293, 292, 290, 289, 288, 287, 286, 285, 284, 281, 280, 279, 278, 277, 275, 273, 269, 268, 267, 266, 264, 263, 261, 259, 257, 255, 251, 248, 247, 243, 241, 240, 239, 233, 226, 225, 224, 223, 222, 220, 219, 217, 216, 215, 214, 213, 211, 209, 208, 202, 201, 200, 199, 198, 197, 196, 195, 194, 193, 192, 191, 190, 189, 185, 183, 179, 178, 175, 172, 170, 166, 163, 161, 160, 159, 158, 157, 155, 152, 151, 150, 149, 148, 147, 145, 144, 142, 141, 140, 137, 136, 134, 133, 132, 127, 125, 124, 123, 122, 121, 120, 119, 118, 116, 114, 112, 111, 110, 109, 108, 107, 106, 105, 98, 88, 87, 86, 85, 84, 77, 76, 65, 63, 55, 54, 52, 45, 44, 43, 38, 35, 34, 33, 22, 21, 20, 17, 16, 14, 11 |

[a]Compounds with less than 20-fold binding selectivity for GABA α5 versus GABA α1 are not included in this data set. Those compounds are less useful in the methods of this disclosure.

TABLE 4

| Binding selectivity for GABA α5 versus GABA α2 | | |
|---|---|---|
| 20- to 50-fold[a] | 50- to 100-fold | >100-fold |
| 238, 203, 181, 170, 161 | 236, 217, 188, 187, 179, 178, 174, 168, 160, 141, 138, 120, 118, 104, 99, 54, 46, 35, 33 | 239, 220, 202, 189, 185, 183, 175, 157, 156, 155, 153, 150, 149, 142, 137, 136, 135, 134, 133, 132, 130, 129, 127, 126, 125, 124, 121, 119, 114, 111, 110, 109, 108, 106, 105, 98, 87, 76, 64, 63, 45, 44, 34 |

[a]Compounds with less than 20-fold binding selectivity for GABA α5 versus GABA α2 are not included in this data set. Those compounds are less useful in the methods of this disclosure.

TABLE 5

| Binding selectivity for GABA α5 versus GABA α3 | | |
|---|---|---|
| 20- to 50-fold[a] | 50- to 100-fold | >100-fold |
| 181, 170, 168, 161, 160, 141, 139, 129, 127, 118, 104, 99, 63, 54, 46, 44, 34, 33 | 187, 183, 138, 133, 130, 126, 125, 121, 120, 119, 111, 105, 64 | 185, 179, 178, 175, 174, 157, 156, 155, 153, 150, 149, 142, 137, 136, 135, 132, 124, 114, 110, 109, 108, 106, 98, 87, 76 |

[a]Compounds with less than 20-fold binding selectivity for GABA α5 versus GABA α3 are not included this data set. Those compounds are less useful in the methods of this disclosure.

Example 167: Effect of Methyl 3,5-diphenylpyridazine-4-carboxylate in Aged-Impaired (AI) Rats Methyl 3,5-diphenylpyridazine-4-carboxylate, corresponding to compound number 6 in van Niel et al. *J. Med. Chem.* 48:6004-6011 (2005), is a selective α5-containing $GABA_A$ R agonist. It has an α5 in vitro efficacy of +27 ($EC_{20}$). The effect of methyl 3,5-diphenylpyridazine-4-carboxylate in aged-impaired rats was studied using a RAM task. Moreover, receptor occupancy by methyl 3,5-diphenylpyridazine-4-carboxylate in α5-containing $GABA_A$ R was also studied.

(A) Effect of Methyl 3,5-diphenylpyridazine-4-carboxylate in Aged-Impaired Rats Using a Radial Arm Maze (RAM) Behavioral Task The effects of methyl 3,5-diphenylpyridazine-4-carboxylate on the in vivo spatial memory retention of aged-impaired (AI) rats were assessed in a Radial Arm Maze (RAM) behavioral task using vehicle control and four different dosage levels of methyl 3,5-diphenylpyridazine-4-carboxylate (0.1 mg/kg, 0.3 mg/kg, 1 mg/kg and 3 mg/kg, ip). RAM behavioral tasks were performed on eight AI rats. All five treatment conditions (vehicle and four dosage levels) were tested on all eight rats.

The RAM apparatus used consisted of eight equidistantly-spaced arms. An elevated maze arm (7 cm width×75 cm length) projected from each facet of an octagonal center platform (30 cm diameter, 51.5 cm height). Clear side walls on the arms were 10 cm high and were angled at 650 to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided.

The AI rats were initially subjected to a pre-training test (Chappell et al. *Neuropharmacology* 37: 481-487, 1998). The pre-training test consisted of a habituation phase (4 days), a training phase on the standard win-shift task (18 days) and another training phase (14 days) in which a brief delay was imposed between presentation of a subset of arms designated by the experimenter (e.g., 5 arms available and 3 arms blocked) and completion of the eight-arm win-shift task (i.e., with all eight arms available).

In the habituation phase, rats were familiarized to the maze for an 8-minute session on four consecutive days. In each of these sessions, food rewards were scattered on the RAM, initially on the center platform and arms and then progressively confined to the arms. After this habituation phase, a standard training protocol was used, in which a food pellet was located at the end of each arm. Rats received one trial each day for 18 days. Each daily trial terminated when all eight food pellets had been obtained or when either 16 choices were made, or 15 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial "information phase" of the trial. Rats were then removed from the maze for 60 seconds, during which time the barriers on the maze were removed, thus allowing access to all eight arms. Rats were then placed back onto the center platform and allowed to obtain the remaining food rewards during this "retention test" phase of the trial. The identity and configuration of the blocked arms varied across trials.

The number of "errors" the AI rats made during the retention test phase was tracked. An error occurred in the trial if the rats entered an arm from which food had already been retrieved in the pre-delay component of the trial, or if the rat re-visited an arm in the post-delay session that it had already visited.

After completion of the pre-training test, rats were subjected to trials with more extended delay intervals, i.e., a two-hour delay, between the information phase (presentation with some blocked arms) and the retention test (presentation of all arms). During the delay interval, rats remained off to the side of the maze in the testing room, on carts in their individual home cages. AI rats were pretreated 30-40 minutes before daily trials with a one-time shot of the following five conditions: 1) vehicle control—5% dimethyl sulfoxide, 25% polyethylene glycol 300 and 70% distilled water; 2) methyl 3,5-diphenylpyridazine-4-carboxylate at 0.1 mg/kg; 3) methyl 3,5-diphenylpyridazine-4-carboxylate at 0.3 mg/kg; 4) methyl 3,5-diphenylpyridazine-4-carboxylate at 1 mg/kg); and 5) methyl 3,5-diphenylpyridazine-4-carboxylate at 3 mg/kg; through intraperitoneal (i.p.) injection. Injections were given every other day with intervening washout days. Each AI rat was treated with all five conditions within the testing period. To counterbalance any potential bias, drug effect was assessed using ascending-descending dose series, i.e., the dose series was given first in an ascending order and then repeated in a descending order. Therefore, each dose had two determinations.

Parametric statistics (paired t-tests) was used to compare the retention test performance of the AI rats in the two-hour delay version of the RAM task in the context of different doses of methyl 3,5-diphenylpyridazine-4-carboxylate and vehicle control (see FIG. 1). The average numbers of errors that occurred in the trials were significantly fewer with methyl 3,5-diphenylpyridazine-4-carboxylate treatment of 3 mg/kg (average no. of errors±standard error of the mean (SEM)=1.31±0.40) than using vehicle control (average no. of errors±SEM=3.13±0.62). Relative to vehicle control treatment, methyl 3,5-diphenylpyridazine-4-carboxylate significantly improved memory performance at 3 mg/kg ($t(7)=4.233$, $p=0.004$).

The therapeutic dose of 3 mg/kg became ineffective when the AI rats were concurrently treated with 0.3 mg/kg of TB21007, a α5-containing $GABA_A$ R inverse agonist. The average numbers of errors made by rats with the combined TB21007/methyl 3,5-diphenylpyridazine-4-carboxylate treatment (0.3 mg/kg TB21007 with 3 mg/kg methyl 3,5-diphenylpyridazine-4-carboxylate) was 2.88±1.32, and was no different from rats treated with vehicle control (3.13±1.17 average errors). Thus, the effect of methyl 3,5-diphenylpyridazine-4-carboxylate on spatial memory is a $GABA_A$ α5 receptor-dependent effect (see FIG. 1).

(B) Effect of Methyl 3,5-diphenylpyridazine-4-carboxylate on α5-containing $GABA_A$ R Occupancy Animals Adult male Long Evans rats (265-295 g, Charles River, Portage, MI, n=4/group) were used for $GABA_A$α5 receptor occupancy studies. Rats were individually housed in ventilated stainless-steel racks on a 12:12 light/dark cycle. Food and water were available ad libitum. In additional studies to evaluate compound exposures at behaviorally active doses, young or aged Long Evan rats (n=2-4/group) were used for these studies.

Compounds

Ro 15-4513 was used as a receptor occupancy (RO) tracer for $GABA_A$α5 receptor sites in the hippocampus and cerebellum. Ro 15-4513 was chosen as the tracer based on its selectivity for $GABA_A$α5 receptors relative to other alpha subunit containing $GABA_A$ R and because it has been successfully used for $GABA_A$α5 RO studies in animals and humans (see, e.g., Lingford-Hughes et al., *J. Cereb. Blood Flow Metab.* 22:878-89 (2002); Pym et al, *Br. J. Pharmacol.* 146: 817-825 (2005); and Maeda et al., *Synapse* 47: 200-208 (2003)). Ro 15-4513 (1 μg/kg), was dissolved in 25% hydroxyl-propyl beta-cyclodextrin and administered i.v. 20' prior to the RO evaluations. Methyl 3,5-diphenylpyridazine-4-carboxylate (0.1-10 mg/kg) was synthesized by Nox Pharmaceuticals (India) and was dissolved in 25% hydroxyl-propyl beta-cyclodextrin and administered i.v. 15' prior to tracer injection. Compounds were administered in a volume of 0.5 ml/kg except for the highest dose of methyl 3,5-diphenylpyridazine-4-carboxylate (10 mg/kg) which was administered in a volume of 1 ml/kg due to solubility limitations.

Tissue Preparation and Analysis

The rats were sacrificed by cervical dislocation 20' post tracer injection. The whole brain was rapidly removed, and lightly rinsed with sterile water. Trunk blood was collected in EDTA coated eppendorf tubes and stored on wet ice until study completion. Hippocampus and cerebellum were dissected and stored in 1.5 ml eppendorf tubes, and placed on wet ice until tissue extraction. In a drug naïve rat, six cortical brain tissues samples were collected for use in generating blank and standard curve samples.

Acetonitrile containing 0.1% formic acid was added to each sample at a volume of four times the weight of the tissue sample. For the standard curve (0.1-30 ng/g) samples, a calculated volume of standard reduced the volume of acetonitrile. The sample was homogenized (FastPrep-24, Lysing Matrix D; 5.5 m/s, for 60 seconds or 7-8 watts power using sonic probe dismembrator; Fisher Scientific) and centrifuged for 16-minutes at 14,000 rpm. The (100 l) supernatant solution was diluted by 300 μl of sterile water (pH 6.5). This solution was then mixed thoroughly and analyzed via LC/MS/MS for Ro 15-4513 (tracer) and methyl 3,5-diphenylpyridazine-4-carboxylate.

For plasma exposures, blood samples were centrifuged at 14000 rpm for 16 minutes. After centrifuging, 50 ul of supernatant (plasma) from each sample was added to 200 μl of acetonitrile plus 0.1% formic acid. For standard curve (1-1000 ng/ml) samples, a calculated volume of standard reduced the volume of acetonitrile. Samples were sonicated for 5 minutes in an ultrasonic water bath, followed by centrifugation for 30 minutes, at 16000 RPM. 100 ul of supernatant was removed from each sample vial and placed in a new glass auto sample vial, followed by the addition of 300 μl of sterile water (pH 6.5). This solution was then mixed thoroughly and analyzed via LC/MS/MS for methyl 3,5-diphenylpyridazine-4-carboxylate.

Receptor occupancy was determined by the ratio method which compared occupancy in the hippocampus (a region of high $GABA_A\alpha5$ receptor density) with occupancy in the cerebellum (a region with low $GABA_A\alpha5$ receptor density) and additionally by a high dose of the $GABA_A\alpha5$ negative allosteric modulator L-655,708 (10 mg/kg, i.v.) to define full occupancy.

Vehicle administration followed by tracer administration of 1 μg/kg, i.v., of Ro 15-4513 resulted in >5-fold higher levels of Ro 15-4513 in hippocampus (1.93±0.05 ng/g) compared with cerebellum (0.36±0.02 ng/g). Methyl 3,5-diphenylpyridazine-4-carboxylate (0.01-10 mg/kg, i.v.) dose-dependently reduced Ro 15-4513 binding in hippocampus, without affecting cerebellum levels of Ro 15-4513 (FIG. 2) with a dose of 10 mg/kg, i.v., demonstrating >90% occupancy (FIG. 3). Both methods of calculating RO yielding very similar results with ED50 values for methyl 3,5-diphenylpyridazine-4-carboxylate as 1.8 mg/kg or 1.1 mg/kg based on the ratio method or using L-755,608 to define occupancy.

Methyl 3,5-diphenylpyridazine-4-carboxylate exposure was below the quantification limits (BQL) at 0.01 mg/kg, i.v., in both plasma and hippocampus and but was detectable at low levels in hippocampus at 0.1 mg/kg, i.v. (see Table 6). Hippocampal exposure was linear as a 10-fold increase in dose from 0.1 to 1 mg/kg, i.v., resulted in a 12-fold increase in exposure. Increasing the dose from 1 to 10 mg/kg, i.v., only increased the exposure by ~5-fold. Plasma exposure increased 12-fold as the dose increased from 1 to 10 mg/kg, i.v.

TABLE 6

% GABAA α5 Receptor Occupancy by methyl 3,5-diphenylpyridazine-4-carboxylate (0.01-10 mg/kg, i.v.). Hippocampus and Plasma Exposure of methyl 3,5-diphenylpyridazine-4-carboxylate by Treatment Group in young Long Evans rats.

| Dose (mg/kg, i.v.) | % RO (L-655,708 Method) (SEM) | % RO (Ratio Method) (SEM) | Plasma ng/mL (SEM) | Hippocampus ng/g (SEM) |
|---|---|---|---|---|
| 0.01 | 19.2 (11.1) | 15.7 (9.1) | BQL | BQL |
| 0.1 | 16.4 (4.9) | 13.4 (4.0) | BQL | 14.6 (3.5) |
| 1 | 38.5 (11.2) | 31.5 (9.1) | 62.8 (6.1) | 180.0 (10.3) |
| 10 | 110.0 (6.6) | 90.2 (5.4) | 763.5 (85.7) | 947.2 (51.3) |

Additional studies were conducted in aged Long-Evans rats in order to determine the exposures at the behaviorally relevant doses in the cognition studies. Exposure in young Long-Evans rats was also determined to bridge with the receptor occupancy studies that were conducted in young Long-Evans rats. Exposures in young and aged Long-Evans rats were relatively similar (Table 7, FIG. 4). Increasing the dose 3-fold from 1 to 3 mg/kg, ip resulted in a greater than dose-proportional increase in exposure in young and aged rats in both hippocampus and plasma with increases ranging from 4.5 to 6.6-fold.

TABLE 7

Hippocampus and Plasma Exposure of methyl 3,5-diphenylpyridazine-4-carboxylate in Young Long Evans Rats by Treatment Group

| Dose (mg/kg, ip) | Young Hippocampus ng/g (SEM) | Young Plasma ng/mL (SEM) | Aged Hippocampus ng/g (SEM) | Aged Plasma ng/mL (SEM) |
|---|---|---|---|---|
| 1 | 25.9 (1.7) | 20.0 (1.4) | 38.8 (21.7) | 45.2 (29.6) |
| 3 | 129.1 (22.4) | 132.9 (19.5) | 177.5 (19.5) | 196 (18.2) |

In the RO studies, an exposure of 180 ng/g in hippocampus (1 mg/kg, i.v.) represented 32-39% receptor occupancy depending on method used to determine RO. This exposure is comparable to that observed in aged rats at 3 mg/kg, i.p., suggesting that 30-40% RO is required for cognitive efficacy in this model.

These studies demonstrated that methyl 3,5-diphenylpyridazine-4-carboxylate produced dose-dependent increase in $GABA_A$ α5 receptor occupancy. Methyl 3,5-diphenylpyridazine-4-carboxylate also demonstrated good brain exposure with brain/plasma ratios>1. The studies further demonstrated that methyl 3,5-diphenylpyridazine-4-carboxylate was producing its cognitive enhancing effects by positive allosteric modulation at the $GABA_A$ α5 subtype receptor.

Example 168: Effect of Ethyl 3-methoxy-7-methyl-9H-benzo[f]imidazo[1,5-a][1,2,4]triazolo[4,3-d][1,4]diazepine-10-carboxylate in Aged-Impaired (AI) Rats Ethyl 3-methoxy-7-methyl-9H-benzo[f]imidazo[1,5-a][1,2,4]triazolo[4,3-d][1,4]diazepine-10-carboxylate, corresponding to compound number 49 in Achermann et al. *Bioorg. Med. Chem. Lett.*, 19:5746-5752 (2009), is a selective α5-containing $GABA_A$ R agonist.

The effect of ethyl 3-methoxy-7-methyl-9H-benzo[f]imidazo[1,5-a][1,2,4]triazolo[4,3-d][1,4]diazepine-10-carboxylate (compound 49) on the in vivo spatial memory retention of aged-impaired (AI) rats was assessed in a Radial Arm Maze (RAM) behavioral task that is essentially similar to the task as described in Example 168 (A), using vehicle control (25% cyclodextrin, which was tested 3 times: at the beginning, middle and end of ascending/descending series) and six different doses levels (0.1 mg/kg, 0.3 mg/kg, 1 mg/kg, 3 mg/kg, 10 mg/kg and 30 mg/kg, each dose was tested twice) of ethyl 3-methoxy-7-methyl-9H-benzo[f]imidazo[1,5-a][1,2,4]triazolo[4,3-d][1,4]diazepine-10-carboxylate. The same experiment was repeated using the same vehicle control and doses of ethyl 3-methoxy-7-methyl-9H-benzo[f]imidazo[1,5-a][1,2,4]triazolo[4,3-d][1,4]diazepine-10-carboxylate, where the vehicle control was tested 5 times, the 3 mg/kg dose of ethyl 3-methoxy-7-methyl-9H-benzo[f]imidazo[1,5-a][1,2,4]triazolo[4,3-d][1,4]diazepine-10-carboxylate was tested 4 times, and the other doses of ethyl 3-methoxy-7-methyl-9H-benzo[f]imidazo[1,5-a][1,2,4]triazolo[4,3-d][1,4]diazepine-10-carboxylate were tested twice.

Parametric statistics (paired t-tests) was used to compare the retention test performance of the AI rats in the four-hour delay version of the RAM task in the context of different doses of ethyl 3-methoxy-7-methyl-9H-benzo[f]imidazo[1,5-a][1,2,4]triazolo[4,3-d][1,4]diazepine-10-carboxylate and vehicle control (see FIG. 5). Relative to vehicle control treatment, ethyl 3-methoxy-7-methyl-9H-benzo[f]imidazo

[1,5-a][1,2,4]triazolo[4,3-d][1,4]diazepine-10-carboxylate significantly improved memory performance at 3 mg/kg (t(7)=4.13, p=0.004, or t(7)=3.08, p=0.018) and at 10 mg/kg (t(7)=2.82, p=0.026).

The effect of ethyl 3-methoxy-7-methyl-9H-benzo[f]imidazo[1,5-a][1,2,4]triazolo[4,3-d][1,4]diazepine-10-carboxylate on α5-containing $GABA_A$ R occupancy was also studied following a procedure that is essentially similar to the one as described in Example 167(B) (see above). This study demonstrated that ethyl 3-methoxy-7-methyl-9H-benzo[f]imidazo[1,5-a][1,2,4]triazolo[4,3-d][1,4]diazepine-10-carboxylate (0.01-10 mg/kg, i.v.) reduced Ro 15-4513 binding in hippocampus, without affecting cerebellum levels of Ro 15-4513 (FIG. 6) with a dose of 10 mg/kg, i.v., demonstrating >90% occupancy (FIG. 7).

Example 169: Effect of 6,6 dimethyl-3-(3-hydroxypropyl)thio-1-(thiazol-2-yl)-6,7-dihydro-2-benzothiophen-4(5H)-one in Aged-Impaired Rats Using a Morris Water Maze Behavioral Task 6,6 dimethyl-3-(3-hydroxypropyl)thio-1-(thiazol-2-yl)-6,7-dihydro-2-benzothiophen-4(5H)-one, corresponding to compound 44 in Chambers et al. *J. Med. Chem.* 46, 2227-2240 (2003) is a selective α5-containing $GABA_A$ R agonist.

The effects of 6,6 dimethyl-3-(3-hydroxypropyl)thio-1-(thiazol-2-yl)-6,7-dihydro-2-benzothiophen-4(5H)-one on the in vivo spatial memory retention of aged-impaired (AI) rats were assessed in a Morris water maze behavioral task. A water maze is a pool surrounded with a novel set of patterns relative to the maze. The training protocol for the water maze may be based on a modified water maze task that has been shown to be hippocampal-dependent (de Hoz et al., *Eur. J. Neurosci.,* 22:745-54, 2005; Steele and Morris, *Hippocampus* 9:118-36, 1999).

Cognitively impaired aged rats were implanted unilaterally with a cannula into the lateral ventricle. Stereotaxic coordinates were 1.0 mm posterior to bregma, 1.5 mm lateral to midline, and 3.5 mm ventral to the skull surface. After about a week of recovery, the rats were pre-trained in a water maze for 2 days (6 trials per day) to locate a submerged escape platform hidden underneath the surface of the pool, in which the escape platform location varied from day to day. No intracerebroventricular (ICV) infusion was given during pre-training.

After pre-training, rats received ICV infusion of either 100 μg 6,6 dimethyl-3-(3-hydroxypropyl)thio-1-(thiazol-2-yl)-6,7-dihydro-2-benzothiophen-4(5H)-one (n=6) in 5 μl DMSO or vehicle DMSO (n=5) 40 min prior to water maze training and testing. Training consisted of 8 trials per day for 2 days where the hidden escape platform remained in the same location. Rats were given 60 seconds to locate the platform with a 60 seconds inter-trial interval. The rats were given a probe test (120 seconds) 24 hr. after the end of training where the escape platform was removed. During the training, there were 4 blocks, where each block had 4 training trials.

Rats treated with vehicle and 6,6 dimethyl-3-(3-hydroxypropyl)thio-1-(thiazol-2-yl)-6,7-dihydro-2-benzothiophen-4(5H)-one found the escape platform about the same time at the beginning of training (block 1). In this block of training, rats treated with vehicle and 6,6 dimethyl-3-(3-hydroxypropyl)thio-1-(thiazol-2-yl)-6,7-dihydro-2-benzothiophen-4(5H)-one both spent about 24 seconds to find the escape platform. However, rats treated with 6,6 dimethyl-3-(3-hydroxypropyl)thio-1-(thiazol-2-yl)-6,7-dihydro-2-benzothiophen-4(5H)-one were able to find the platform more proficiently (i.e., quicker) at the end of training (block 4) than those treated with vehicle alone. In block 4, rats treated with 6,6 dimethyl-3-(3-hydroxypropyl)thio-1-(thiazol-2-yl)-6,7-dihydro-2-benzothiophen-4(5H)-one spent about 9.6 seconds to find the escape platform, while rats treated with vehicle spent about 19.69 seconds. These results suggest that 6,6 dimethyl-3-(3-hydroxypropyl)thio-1-(thiazol-2-yl)-6,7-dihydro-2-benzothiophen-4(5H)-one improved the learning of the water maze task in rats (see FIG. 8(A)).

During a test trial 24 hr after training, the escape platform was removed. The search/swim pattern of the rats was used to measure whether the rats remember where the escape platform was located during pre-trial training in order to test for the long-term memory of the rats. In this trial, "target annulus" is a designated area 1.5 times the size of the escape platform around the area where the platform was located during pre-trial training. "Opposite annulus" is a control area of the same size as the size of the target annulus, which is located opposite to the target annulus in the pool. If the rats had good long-term memory, they would tend to search in the area surrounding the location where the platform was during the pre-trial training (i.e., the "target" annulus; and not the "opposite" annulus). "Time in annulus" is the amount of time in seconds that the rat spent in the target or opposite annulus area. "Number (#) of crossings" in annulus is the number of times the rat swam across the target or opposite annulus area.

Rats received vehicle spent the same amount of time in the target annulus and opposite annulus, indicating that these rats did not seem to remember where the platform was during the pre-trial training. By contrast, rats treated with 6,6 dimethyl-3-(3-hydroxypropyl)thio-1-(thiazol-2-yl)-6,7-dihydro-2-benzothiophen-4(5H)-one spent significantly more time in the target annulus, and crossed the "target annulus" more often, as compared to the time they spent in, or the number of times they crossed the "opposite annulus". These results show that 6,6 dimethyl-3-(3-hydroxypropyl)thio-1-(thiazol-2-yl)-6,7-dihydro-2-benzothiophen-4(5H)-one improved the long-term memory of rats in the water maze task (see, FIGS. 8(B) and 8(C)).

Compounds of the present disclosure demonstrated positive allosteric modulatory effect on the $GABA_A$ $_{\alpha}5$ receptor (See, e.g., Example 106). These compounds will enhance the effects of GABA at the $GABA_A$ $_{\alpha}5$ receptor. Therefore, compounds of the present disclosure produce cognitive enhancing effects in aged-impaired animals (such as rats), similar to the effects produced by other $GABA_A$ α5 receptor selective agonists, such as methyl 3,5-diphenylpyridazine-4-carboxylate, ethyl 3-methoxy-7-methyl-9H-benzo[f]imidazo[1,5-a][1,2,4]triazolo[4,3-d][1,4]diazepine-10-carboxylate, and 6,6 dimethyl-3-(3-hydroxypropyl)thio-1-(thiazol-2-yl)-6,7-dihydro-2-benzothiophen-4(5H)-one (See, e.g., Examples 165-169).

We claim:

1. A compound having the structure:

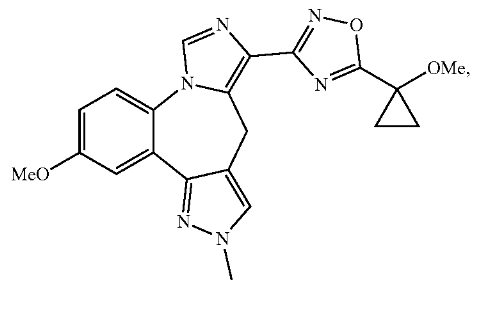 [SMILES: COc1ccc2c(c1)-c1nn(C)cc1Cc1c(-c3noc(C4(OC)CC4)n3)ncn1-2]

or a pharmaceutically acceptable salt thereof.

2. A compound having the structure:

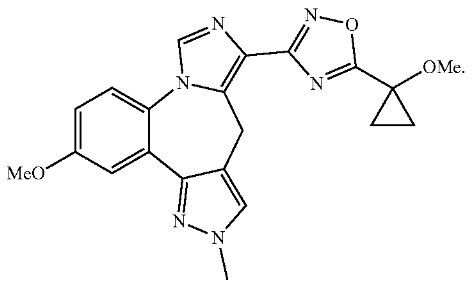 [SMILES: COc1ccc2c(c1)-c1nn(C)cc1Cc1c(-c3noc(C4(OC)CC4)n3)ncn1-2]

3. A pharmaceutically acceptable salt of a compound having the structure:

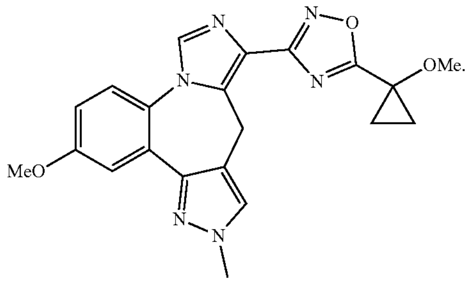 [SMILES: COc1ccc2c(c1)-c1nn(C)cc1Cc1c(-c3noc(C4(OC)CC4)n3)ncn1-2]

4. A pharmaceutical composition comprising the compound, or pharmaceutically acceptable salt thereof, of claim 1 and a pharmaceutically acceptable carrier or excipient.

5. A pharmaceutical composition comprising the compound of claim 2 and a pharmaceutically acceptable carrier or excipient.

6. A pharmaceutical composition comprising the pharmaceutically acceptable salt of a compound of claim 3 and a pharmaceutically acceptable carrier or excipient.

7. A method of treating cognitive impairment associated with a central nervous system (CNS) disorder in a subject in need thereof, wherein the method comprises the step of administering the compound, or pharmaceutically acceptable salt thereof, of claim 1, or administering a pharmaceutical composition comprising that compound, or pharmaceutically acceptable salt thereof, and a pharmaceutically acceptable carrier or excipient.

8. The method of claim 7, wherein the CNS disorder is age-related cognitive impairment, Mild Cognitive Impairment (MCI), dementia, Alzheimer's disease (AD), schizophrenia, bipolar disorder, amyotrophic lateral sclerosis (ALS), post-traumatic stress disorder (PTSD), mental retardation, Parkinson's disease (PD), autism, compulsive behavior, substance addiction, prodromal AD, or a disorder associated with cancer therapy.

9. The method of claim 8, wherein the CNS disorder is age-related cognitive impairment.

10. The method of claim 8, wherein the CNS disorder is Mild Cognitive Impairment (MCI).

11. The method of claim 10, wherein the Mild Cognitive Impairment (MCI) is amnestic MCI (aMCI).

12. The method of claim 8, wherein the CNS disorder is prodromal Alzheimer's disease (AD).

13. The method of claim 8, wherein the CNS disorder is schizophrenia.

14. The method of claim 8, wherein the CNS disorder is Parkinson's disease (PD).

15. A method of treating cognitive impairment associated with a brain cancer in a subject in need thereof, wherein the method comprises the step of administering the compound, or pharmaceutically acceptable salt thereof, of claim 1, or administering a pharmaceutical composition comprising that compound, or pharmaceutically acceptable salt thereof, and a pharmaceutically acceptable carrier or excipient.

16. A method of treating a brain cancer in a subject in need thereof, wherein the method comprises the step of administering the compound, or pharmaceutically acceptable salt thereof, of claim 1, or administering a pharmaceutical composition comprising that compound, or pharmaceutically acceptable salt thereof, and a pharmaceutically acceptable carrier or excipient.

17. A method of treating cognitive impairment associated with a risk factor for cognitive impairment in a subject at risk of said cognitive impairment, wherein the method comprises the step of administering the compound, or pharmaceutically acceptable salt thereof, of claim 1, or administering a pharmaceutical composition comprising that compound, or pharmaceutically acceptable salt thereof, and a pharmaceutically acceptable carrier or excipient.

18. The method of claim 17, wherein the risk factor for cognitive impairment is associated with one or more of: aging; the presence of altered hippocampal functional connectivity in the subject; the presence of one or more genomic variants, mutations, or polymorphs associated with a change in the expression of genes selected from the group consisting of ABCA7, CLU, CR1, PICALM, PLD3, TREM2, and SORL1 in the genome of the subject; the presence of at least one allele of the APOE4 gene in the genome of the subject; or the presence of one or more biofluid biomarkers selected from the group consisting of p-tau, t-tau, and amyloid β in the subject.

19. The method of claim 18, wherein the presence of altered hippocampal functional connectivity in the subject is increased hippocampal functional connectivity.

* * * * *